United States Patent
Bayliss et al.

(10) Patent No.: US 8,383,620 B2
(45) Date of Patent: *Feb. 26, 2013

(54) PHOSPHOINOSITIDE 3-KINASE INHIBITOR COMPOUNDS AND METHODS OF USE

(75) Inventors: Tracy Bayliss, Basel (CH); Irina Chuckowree, Basel (CH); Adrian Folkes, Basel (CH); Sally Oxenford, Basel (CH); Nan Chi Wan, Basel (CH); Georgette Castanedo, South San Francisco, CA (US); Richard Goldsmith, South San Francisco, CA (US); Janet Gunzner, South San Francisco, CA (US); Tim Heffron, South San Francisco, CA (US); Simon Mathieu, South San Francisco, CA (US); Alan Olivero, South San Francisco, CA (US); Steven Staben, South San Francisco, CA (US); Daniel P. Sutherlin, South San Francisco, CA (US); Bing-Yan Zhu, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/978,106

(22) Filed: Dec. 23, 2010

(65) Prior Publication Data

US 2011/0097349 A1     Apr. 28, 2011

Related U.S. Application Data

(62) Division of application No. 11/951,203, filed on Dec. 5, 2007, now Pat. No. 7,888,352.

(60) Provisional application No. 60/873,448, filed on Dec. 7, 2006, provisional application No. 60/977,257, filed on Oct. 3, 2007.

(51) Int. Cl.
   *A61K 31/535*     (2006.01)
(52) U.S. Cl. ................................... 514/234.5
(58) Field of Classification Search ................ 514/234.5
   See application file for complete search history.

(56) References Cited

U.S. PATENT DOCUMENTS

| | | | |
|---|---|---|---|
| 3,475,429 A | 10/1969 | Woitun et al. | |
| 3,661,908 A | 5/1972 | Woitun et al. | |
| 3,763,156 A | 10/1973 | Woitun et al. | |
| 3,838,121 A | 9/1974 | Woitun et at | |
| 3,888,851 A | 6/1975 | Narr et al. | |
| 4,007,187 A | 2/1977 | Fauran et al. | |
| 4,146,716 A | 3/1979 | Cox et al. | |
| 4,196,207 A | 4/1980 | Webber | |
| 5,075,305 A | 12/1991 | Hobbs et al. | |
| 6,187,777 B1 | 2/2001 | Norman et al. | |
| 6,608,053 B2 | 8/2003 | Hayakawa et al. | |
| 6,838,457 B2 | 1/2005 | Hayakawa et al. | |
| 7,037,915 B2 | 5/2006 | Hayakawa et al. | |
| 7,173,029 B2 | 2/2007 | Hayakawa et al. | |
| 7,888,352 B2 | 2/2011 | Bayliss et al. | |
| 2003/0236271 A1 | 12/2003 | Hayakawa et al. | |
| 2006/0229306 A1 | 10/2006 | Terricabras Belart et al. | |
| 2007/0037805 A1 | 2/2007 | Hayakawa et al. | |
| 2007/0249587 A1 | 10/2007 | Yonetoku et al. | |
| 2008/0039459 A1 | 2/2008 | Folkes et al. | |
| 2008/0076758 A1 | 3/2008 | Folkes et al. | |
| 2008/0076768 A1 | 3/2008 | Chuckowree et al. | |
| 2008/0207611 A1 | 8/2008 | Shuttleworth et al. | |
| 2008/0269210 A1 | 10/2008 | Castanedo et al. | |

FOREIGN PATENT DOCUMENTS

| | | |
|---|---|---|
| DE | 1959403 A1 | 6/1971 |
| DE | 2050814 A1 | 4/1972 |
| EP | 1277738 | 1/2003 |
| GB | 1393161 | 5/1975 |
| WO | WO 2006/046031 | 5/2006 |

(Continued)

OTHER PUBLICATIONS

Briel et al., "Selective Nucleophilic Replacement of the Benzylsulfanyl Group in 2,4-Disulfanyl-Substituted Thieno[2,3-D]Pyrimidin-6-Carboxylic Acid Derivatives by Secondary Amines", *Journal of Heterocyclic Chemistry* 42(5), 841-846, 2005.

(Continued)

*Primary Examiner* — Rebecca Anderson
(74) *Attorney, Agent, or Firm* — Viksnins Harris & Padys PLLP

(57) ABSTRACT

Compounds of Formulas Ia-d where X is S or O, mor is a morpholine group, and $R^3$ is a monocyclic heteroaryl group, and including stereoisomers, geometric isomers, tautomers, solvates, metabolites and pharmaceutically acceptable salts thereof, are useful for modulating the activity of lipid kinases including PI3K, and for treating disorders such as cancer mediated by lipid kinases. Methods of using compounds of Formula Ia-d for in vitro, in situ, and in vivo diagnosis, prevention or treatment of such disorders in mammalian cells, or associated pathological conditions, are disclosed.

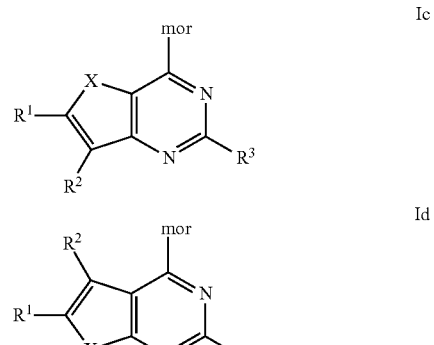

20 Claims, No Drawings

FOREIGN PATENT DOCUMENTS

| WO | WO 2006/046035 | 5/2006 |
|---|---|---|
| WO | WO 2006/046040 | 5/2006 |
| WO | WO 2007/122410 | 11/2007 |
| WO | WO 2007/127175 | 11/2007 |
| WO | WO 2007/127183 | 11/2007 |
| WO | WO 2007/132171 | 11/2007 |

OTHER PUBLICATIONS

International Search Report, PCT/US2007/086543, Apr. 2, 2008.
Written Opinion of the International Searching Authority, PCT/US2007/086543, Apr. 2, 2008.
Bourguignon et al., "No. 152.-Syntheses de thieno[2,3-d]pyrimidines substituees en 2 et 4", *Bull. de la Societe Chimique de France*, 3/4, 815-819, 1975 (English translation provided).
"No. 152.-Synthesis of thieno[2,3-d]pyrimidines substituted at 2 and 4" English translation of: (Bourguignon et al., "No. 152.-Syntheses de thieno[2,3-d]pyrimidines substituees en 2 et 4", *Bull. de la Societe Chimique de France*, 3/4, 815-819, 1975).
Bourguignon et al., "No. 465.-Syntheses de thieno[2,3-d]pyrimidines substituees en 2 et 4 Ii", *Bull. de la Societe Chimique de France*, 11/12, 2483-2487, 1975 (English translation provided).
"No. 465—Syntheses of 2- and 4-substituted thieno[2,3-d]pyrimidines II" coversheet and pp. 1-14 English translation of: (Bourguignon et al., "No. 465.-Syntheses de thieno[2,3-d]pyrimidines substituees en 2 et 4 II", *Bull. de la Societe Chimique de France*, 11/12, 2483-2487, 1975).
Database Chemcats [online] Chemical Abstracts Service, Columbus Ohio, US, X002481877, Database accession No. 2038647104, Sep. 6, 2007.
Database Chemcats [online] Chemical Abstracts Service, Columbus Ohio, US, XP002481878, Database accession No. 2038019439, Sep. 6, 2007.
Database Chemcats [online] Chemical Abstracts Service, Columbus Ohio, US, XP002481879, Database accession No. 2038018435, Sep. 6, 2007.
Database Chemcats [online] Chemical Abstracts Service, Columbus Ohio, US, XP002481880, Database accession No. 2031400284, Sep. 6, 2007.
Database Chemcats [online] Chemical Abstracts Service, Columbus Ohio, US, XP002481881, Database accession No. 2031384736, Sep. 6, 2007.
Database Chemcats [online] Chemical Abstracts Service, Columbus Ohio, US, XP002481882, Database accession No. 2026153101, Sep. 6, 2007.
Bachman et al., "The *PIK3CA* gene is mutated with high frequency in human breast cancers", *Cancer Biology & Therapy*, 3(8), 772-775, Aug. 2004.
Berge et al., "Pharmaceutical Salts", *Journal of Pharmaceutical Sciences*, 66(1), 1-19, Jan. 1977.
C. Garcia-Echeverria et al., "Drug discovery approaches targeting the PI3/Akt pathway in cancer", *Oncogene*, 27, 5511-5526, 2008.
Kang et al., "Phosphatidylinositol 3-kinase mutations identified in human cancer are oncogenic", *PNAS*, 102(3), 802-807, Jan. 18, 2005.
Raynaud et al., "Biological properties of potent inhibitors of class I phophatidylinositide 3-kinases: from PI-103 through PI-540, Pi-620 to the oral agent GDC-0941", *Mol. Cancer Ther.*, 8(7), 1725-1738, Jul. 2009.
Samuels et al., "High frequency of mutations of the *PIK3CA* gene in human cancers", *Science*, 304, 554, Apr. 23, 2004.
Shayesteh et al., "*PIK3CA* is implicated as an oncogene in ovarian cancer", *Nature Genetics*, 21, 99-102, Jan. 1999.
Workman et al., "Drugging the PI3 kinome", *Nature Biotechnology*, 24(7), 794-796, Jul. 2006.
Yap et al., "Targeting the PI3K-AKT-mTOR pathway: progress, pitfalls, and promises", *Current Opinion in Pharmacology*, 8, 393-412, 2008.
Peeyush K. Lala et al., "Role of nitric oxide in tumor progression: Lessons from experimental tumors", *Cancer and Metastasis Reviews*, 17(1), 91-106, 1998.
T.R. Golub et al., "Molecular Classification of Cancer: Class Discovery and Class Prediction by Gene Expression Monitoring", *Science*, vol. 286, 531-537, 1999.
Stephen R. Byrn et al., "Solid-State Chemistry of Drugs", *Second Edition*, 233-247, 1999.
Sutherlin, "The discovery of the class I PI3K/mTOR Kinase inhibitor GDC-0980 for the treatment of cancer", Department of Discovery Chemistry, Genentech Inc., *AACR 102$^{nd}$ Annual Meeting, Educational Session: From Chemistry to the Clinic: Pathways for Drug Discover and Development, Part 2: Optimizing Drug Discovery: Insights on an Important Process*, 19 pages, 2011.

PHOSPHOINOSITIDE 3-KINASE INHIBITOR COMPOUNDS AND METHODS OF USE

CROSS REFERENCE TO RELATED APPLICATIONS

This application is a divisional application of U.S. application Ser. No. 11/951,203, filed Dec. 5, 2007, now U.S. Pat. No. 7,888,352; and claims the benefit of priority under 35 USC §119(e) of U.S. Provisional Application No. 60/873,448 filed Dec. 7, 2006 and of U.S. Provisional Application No. 60/977,257 filed Oct. 3, 2007, all of which are incorporated by reference in entirety.

The invention claimed herein was made as a result of activities undertaken within the scope of a joint research agreement between Piramed Limited and Genentech, Inc.

FIELD OF THE INVENTION

The invention relates generally to compounds with anti-cancer activity and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol (hereinafter abbreviated as "PI") is one of a number of phospholipids found in cell membranes. In recent years it has become clear that PI plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The main PI3-kinase isoform in cancer is the Class I PI3-kinase, p110 α (alpha) (U.S. Pat. Nos. 5,824,492; 5,846,824; 6,274,327). Other isoforms are implicated in cardiovascular and immune-inflammatory disease (Workman P (2004) Biochem Soc Trans 32:393-396; Patel et al (2004) Proceedings of the American Association of Cancer Research (Abstract LB-247) 95th Annual Meeting, March 27-31, Orlando, Fla., USA; Ahmadi K and Waterfield M D (2004) Encyclopedia of Biological Chemistry (Lennarz W J, Lane M D eds) Elsevier/Academic Press).

The PI3 kinase/Akt/PTEN pathway is an attractive target for cancer drug development since such agents would be expected to inhibit proliferation, reverse the repression of apoptosis and surmount resistance to cytotoxic agents in cancer cells. PI3 kinase inhibitors have been reported (Yaguchi et al (2006) Jour. of the Nat. Cancer Inst. 98(8):545-556; U.S. Pat. Nos. 7,173,029; 7,037,915; 6,608,056; 6,608,053; 6,838,457; 6,770,641; 6,653,320; 6,403,588; 6,703,414; WO 97/15658; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070).

Certain thienopyrimidine compounds have p110 alpha binding, PI3 kinase inhibitory activity and inhibit the growth of cancer cells (WO 2006/046031; WO 2006/046035; WO 2006/046040; WO 2007/122410; WO 2007/127183; WO 2007/127175; U.S. Ser. No. 11/789,423, "PHARMACEUTICAL COMPOUNDS", Chuckowree et al, Filing Date 24 Apr. 2007; and U.S. Ser. No. 60/873,422, "PHOSPHOINOSITIDE 3-KINASE INHIBITOR COMPOUNDS AND METHODS OF USE", Castanedo et al, Filing Date 7 Dec. 2006).

SUMMARY OF THE INVENTION

The invention relates generally to 2-monocyclic heteroaryl, 4-morpholino substituted thienopyrimidine and furanopyrimidine compounds with anti-cancer activity, and more specifically with PI3 kinase inhibitory activity. Certain hyperproliferative disorders are characterized by the modulation of PI3 kinase function, for example by mutations or overexpression of the proteins. Accordingly, the compounds of the invention may be useful in the treatment of hyperproliferative disorders such as cancer. The compounds may inhibit tumor growth in mammals and may be useful for treating human cancer patients.

The invention also relates to methods of using the compounds for in vitro, in situ, and in vivo diagnosis or treatment of mammalian cells, organisms, or associated pathological conditions.

More specifically, one aspect of the invention provides 2-monocyclic heteroaryl, 4-morpholino substituted thienopyrimidine (X=S) and furanopyrimidine (X=O) compounds of Formulas Ia and Ib:

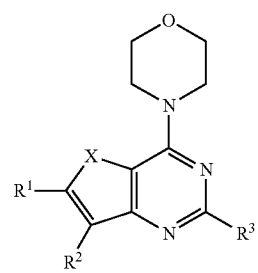

Ia

Ib

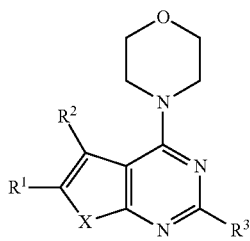

and Formulas Ic and Id:

Ic

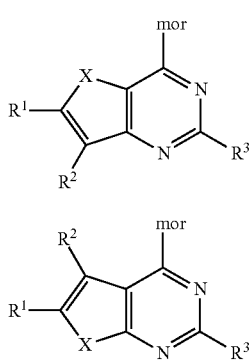

Id and stereoisomers, geometric isomers, tautomers, solvates, metabolites, and pharmaceutically acceptable salts thereof. Groups $R^1$, $R^2$, $R^3$, and mor are as defined herein.

Another aspect of the invention provides a pharmaceutical composition comprising a thienopyrimidine or furanopyrimidine compound of Formula Ia-d and a pharmaceutically acceptable carrier. The pharmaceutical composition may further comprise one or more additional therapeutic agents selected from anti-proliferative agents, anti-inflammatory agents, immunomodulatory agents, neurotropic factors, agents for treating cardiovascular disease, agents for treating liver disease, anti-viral agents, agents for treating blood disorders, agents for treating diabetes, and agents for treating immunodeficiency disorders.

Another aspect of the invention provides methods of inhibiting PI3 kinase activity, comprising contacting a PI3 kinase with an effective inhibitory amount of a compound of Formula Ia-d, or a stereoisomer, geometric isomer, tautomer, solvate, metabolite, or pharmaceutically acceptable salt or prodrug thereof.

Another aspect of the invention provides methods of preventing or treating a disease or disorder modulated by PI3 kinases, comprising administering to a mammal in need of such treatment an effective amount of a compound of Formula Ia-d, or a stereoisomer, geometric isomer, tautomer, solvate, metabolite, or pharmaceutically acceptable salt or prodrug thereof. Examples of such diseases, conditions and disorders include, but are not limited to, hyperproliferative disorders (e.g., cancer, including melanoma and other cancers of the skin), neurodegeneration, cardiac hypertrophy, pain, migraine, neurotraumatic diseases, stroke, diabetes, hepatomegaly, cardiovascular disease, Alzheimer's disease, cystic fibrosis, viral diseases, autoimmune diseases, atherosclerosis, restenosis, psoriasis, allergic disorders, inflammation, neurological disorders, hormone-related diseases, conditions associated with organ transplantation, immunodeficiency disorders, destructive bone disorders, hyperproliferative disorders, infectious diseases, conditions associated with cell death, thrombin-induced platelet aggregation, chronic myelogenous leukemia (CML), liver disease, pathologic immune conditions involving T cell activation, and CNS disorders.

Another aspect of the invention provides methods of preventing or treating a hyperproliferative disorder, comprising administering to a mammal in need of such treatment an effective amount of a compound of Formula Ia-d, or a stereoisomer, geometric isomer, tautomer, solvate, metabolite, or pharmaceutically acceptable salt or prodrug thereof, alone or in combination with one or more additional compounds having anti-hyperproliferative properties.

In a further aspect the present invention provides a method of using a compound of this invention to treat a disease or condition modulated by PI3 kinase in a mammal.

An additional aspect of the invention is the use of a compound of this invention in the preparation of a medicament for the treatment or prevention of a disease or condition modulated by PI3 kinase in a mammal.

Another aspect of the invention includes kits comprising a compound of Formula Ia-d, or a stereoisomer, geometric isomer, tautomer, solvate, metabolite, or pharmaceutically acceptable salt or prodrug thereof, a container, and optionally a package insert or label indicating a treatment.

Another aspect of the invention includes methods of preparing, methods of separating, and methods of purifying compounds of Formula Ia-d.

Another aspect of the invention includes novel intermediates useful for preparing Formula Ia-d compounds.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

The terms "alkyl" or "alk" as used herein refer to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—$C\equiv CH$), propynyl (propargyl, —$CH_2C\equiv CH$), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. The term "heterocycle" includes heterocycloalkoxy. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "monocyclic heteroaryl" (MoHy) refers to a five- or six-membered, unsubstituted or substituted, monocyclic heteroaryl radical which contains 1, 2, 3 or 4 ring heteroatoms independently selected from N, O and S. The monocyclic heteroaryl may be attached to the C-2 position of the pyrimidine ring according to Formulas Ia-d at any carbon (carbon-linked), or nitrogen (nitrogen-linked) atom of the monocyclic heteroaryl $R^3$ group. Monocyclic heteroaryl radicals include, but are not limited to: 2-pyridyl, 3-pyridyl, 4-pyridyl, 3-isoxazolyl, 4-isoxazolyl, 5-isoxazolyl, 2-imidazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, 2-furanyl, 3-furanyl, 2-thienyl, 3-thienyl, 3-triazolyl, 1-triazolyl, 5-tetrazolyl, 1-tetrazolyl, and 2-tetrazolyl. Monocyclic heteroaryls are optionally substituted independently with one or more substituents described herein.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic.

For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafarnib (SCH 66336), sorafenib (NEXAVAR, Bayer Labs), and gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The term "prodrug" as used in this application refers to a precursor or derivative form of a compound of the invention that may be less cytotoxic to cells compared to the parent compound or drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug (such as the PI3 kinase inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention" and "compounds of Formula Ia-d" include compounds of Formulas Ia-d and stereoisomers, geometric isomers, tautomers, solvates, metabolites, and pharmaceutically acceptable salts and prodrugs thereof.

The term "mammal" includes, but is not limited to, humans, mice, rats, guinea pigs, monkeys, dogs, cats, horses, cows, pigs, and sheep.

PI3 Kinase Inhibitor Compounds

The present invention provides 4-morpholino thienopyrimidine and furanopyrimidine compounds, and pharmaceutical formulations thereof, which are potentially useful in the treatment of diseases, conditions and/or disorders modulated by PI3 kinases. More specifically, the present invention provides compounds of Formulas Ia and Ib.

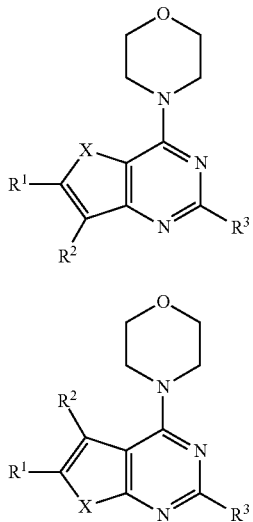

and stereoisomers, geometric isomers, tautomers, solvates, metabolites, and pharmaceutically acceptable salts thereof, wherein:

X is O or S;
$R^1$ is a group of formula:

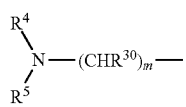

$R^2$ is selected from H, F, Cl, Br, I, and $C_1$-$C_6$ alkyl;

$R^3$ is a monocyclic heteroaryl group selected from pyridyl, isoxazolyl, imidazolyl, pyrazolyl, pyrrolyl, thiazolyl, pyridazinyl, pyrimidinyl, pyrazinyl, oxazolyl, furanyl, thienyl, triazolyl, tetrazolyl, where the monocyclic heteroaryl group is optionally substituted with one or more groups selected from F, Cl, Br, I, —CN, —$NR^{10}R^{11}$, —$OR^{10}$, —C(O)$R^{10}$, —$NR^{10}$C(O)$R^{11}$, —N(C(O)$R^{11}$)$_2$, —$NR^{10}$C(O)$NR^{10}R^{11}$, —$NR^{12}$S(O)$_2R^{10}$, —C(=O)$OR^{10}$, —C(=O)$NR^{10}R^{11}$, $C_1$-$C_{12}$ alkyl and ($C_1$-$C_{12}$ alkyl)-$OR^{10}$;

$R^4$ and $R^5$ form, together with the N atom to which they are attached, a group selected from piperazine, piperidine, pyrrolidine, oxazolidinone, morpholine, thiomorpholine, diazepan and 2,5-diaza-bicyclo[2,2,1]-heptane, which group is optionally substituted with one or more groups independently selected from F, Cl, Br, I, —CN, $CF_3$, —$NO_2$, oxo, —C(=Y)$R^{10}$, —C(=Y)$OR^{10}$, —C(=Y)$NR^{10}R^{11}$, —($CR^{14}R^{15}$)$_n$$NR^{10}R^{11}$, —($CR^{14}R^{15}$)$_n$$NR^{12}SO_2R^{10}$, —($CR^{14}R^{15}$)$_n$$OR^{10}$, —$NR^{10}R^{11}$, —$NR^{12}$C(=Y)$R^{10}$, —$NR^{12}$C(=Y)$OR^{11}$, —$NR^{12}$C(=Y)$NR^{10}R^{11}$, —$NR^{12}SO_2R^{10}$, =$NR^{12}$, $OR^{10}$, —OC(=Y)$R^{10}$, —OC(=Y)$OR^{10}$, —OC(=Y)$NR^{10}R^{11}$, —OS(O)$_2$(O$R^{10}$), —OP(=Y)(O$R^{10}$)(O$R^{11}$), —OP(O$R^{10}$)(O$R^{11}$), S$R^{10}$, —S(O)$R^{10}$, —S(O)$_2R^{10}$, —S(O)$_2$—($C_1$-$C_6$ alkyl)-S(O)$_2R^{10}$, —S(O)$_2$$NR^{10}R^{11}$, —S(O)(O$R^{10}$), —S(O)$_2$(O$R^{10}$), —SC(=Y)$R^{10}$, —SC(=Y)$OR^{10}$, —SC(=Y)$NR^{10}R^{11}$, optionally substituted $C_1$-$C_{12}$ alkyl, optionally substituted $C_2$-$C_8$ alkenyl, optionally substituted $C_2$-$C_8$ alkynyl, optionally substituted $C_3$-$C_{12}$ carbocyclyl, optionally substituted $C_2$-$C_{20}$ heterocyclyl, optionally substituted $C_6$-$C_{20}$ aryl, and optionally substituted $C_1$-$C_{20}$ heteroaryl;

or one of $R^4$ and $R^5$ is $C_1$-$C_6$ alkyl, —($C_1$-$C_6$ alkyl)$_q$-($C_2$-$C_{20}$) heterocyclyl, or —($C_1$-$C_6$ alkyl)$_q$-$OR^{10}$ and the other is a piperazine, piperidine, pyrrolidine, sulfonylpyran or -(alk)$_q$-($C_2$-$C_{20}$) heterocyclyl group, wherein said piperazine, piperidine, pyrrolidine, sulfonylpyran or heterocyclyl is unsubstituted or substituted by $C_1$-$C_6$ alkyl, —($C_1$-$C_6$ alkyl)$_q$-$OR^{10}$ or —S(O)$_2R^{10}$;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a $C_3$-$C_{20}$ heterocyclic ring optionally containing one or more additional ring atoms selected from N, O or S, wherein said heterocyclic ring is optionally substituted with one or more groups independently selected from oxo, (CH$_2$)$_n$OR$^{10}$, NR$^{10}R^{11}$, CF$_3$, F, Cl, Br, I, SO$_2R^{10}$, C(=O)$R^{10}$, $NR^{12}$C(=Y)$R^{11}$, C(=Y)$NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —(CH$_2$)$_n$-aryl, or $R^{14}$ and $R^{15}$ together with the atoms to which they are attached form a saturated or partially unsaturated $C_3$-$C_{12}$ carbocyclic ring, $R^{30}$ is H or $C_1$-$C_6$ alkyl;
Y is O, S, or $NR^{12}$;
each q is independently 0 or 1;
m is 0 or 1;
r is 0 or 1.

The present invention also provides compounds of Formulas Ic and Id:

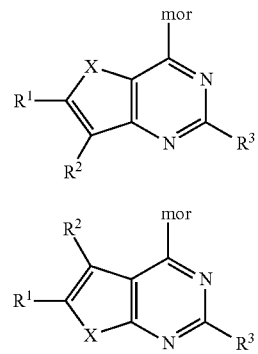

and stereoisomers, geometric isomers, tautomers, solvates, metabolites, and pharmaceutically acceptable salts thereof, wherein:

X is O or S;
$R^1$ is a group of formula:

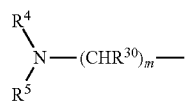

$R^2$ is selected from H, F, Cl, Br, I, $C_6$-$C_{20}$ aryl, $C_1$-$C_{20}$ heteroaryl, $C_1$-$C_6$ alkyl, $C_2$-$C_8$ alkenyl, and $C_2$-$C_8$ alkynyl;

$R^3$ is a monocyclic heteroaryl group selected from pyridyl, isoxazolyl, imidazolyl, pyrazolyl, pyrrolyl, thiazolyl, pyridazinyl, pyrimidinyl, pyrazinyl, oxazolyl, furanyl, thienyl, triazolyl, tetrazolyl, where the monocyclic heteroaryl group is optionally substituted with one or more groups selected from F, Cl, Br, I, —CN, —NR$^{10}$R$^{11}$, —OR$^{10}$, —C(O)R$^{10}$, —NR$^{10}$C(O)R$^{11}$, —N(C(O)R$^{11}$)$_2$, —NR$^{10}$C(O)NR$^{10}$R$^{11}$, —NR$^{12}$SO$_2$R$^{10}$, —NO$_2$, —SR$^{10}$, —C(=O)R$^{10}$, —C(=O)NR$^{10}$R$^{11}$, C$_6$-C$_{20}$ aryl, C$_1$-C$_{12}$ alkyl and (C$_1$-C$_{12}$ alkyl)-OR$^{10}$;

$R^4$ and $R^5$ form, together with the N atom to which they are attached, a group selected from piperazine, piperidine, pyrrolidine, oxazolidinone, morpholine, thiomorpholine, diazepan and 2,5-diaza-bicyclo[2,2,1]-heptane, which group is optionally substituted with one or more groups independently selected from F, Cl, Br, I, —CN, CF$_3$, —NO$_2$, oxo, —C(=Y)R$^{10}$, —C(=Y)OR$^{10}$, —C(=Y)NR$^{10}$R$^{11}$, —(CR$^{14}$R$^{15}$)$_n$NR$^{10}$R$^{11}$, —(CR$^{14}$R$^{15}$)$_n$NR$^{12}$SO$_2$R$^{10}$, —(CR$^{14}$R$^{15}$)$_n$OR$^{10}$, —NR$^{10}$R$^{11}$, —NR$^{12}$C(=Y)R$^{10}$, —NR$^{12}$C(=Y)OR$^{11}$, —NR$^{12}$C(=Y)NR$^{10}$R$^{11}$, —NR$^{12}$SO$_2$R$^{10}$, =NR$^{12}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), —SR$^{10}$, —S(O)R$^{10}$, —S(O)$_2$—(C$_1$-C$_6$ alkyl)-S(O)$_2$R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl;

or one of R$^4$ and R$^5$ is C$_1$-C$_6$ alkyl, —(C$_1$-C$_6$ alkyl)$_q$-(C$_2$-C$_{20}$) heterocyclyl, or —(C$_1$-C$_6$ alkyl)$_q$-OR$^{10}$ and the other is a piperazine, piperidine, pyrrolidine, sulfonylpyran, —(C$_1$-C$_6$ alkyl)-(C$_2$-C$_{20}$) heterocyclyl group, or —(C$_1$-C$_6$ alkyl)-(C$_1$-C$_{20}$) heteroaryl group, wherein said piperazine, piperidine, pyrrolidine, sulfonylpyran, heterocyclyl, or heteroaryl group is unsubstituted or substituted by C$_1$-C$_6$ alkyl, —(C$_1$-C$_6$ alkyl)$_q$-OR$^{10}$ or —S(O)$_2$R$^{10}$;

R$^{10}$, R$^{11}$ and R$^{12}$ are independently H, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl, or R$^{10}$ and R$^{11}$ together with the nitrogen to which they are attached optionally form a C$_3$-C$_{20}$ heterocyclic ring optionally containing one or more additional ring atoms selected from N, O or S, wherein said heterocyclic ring is optionally substituted with one or more groups independently selected from oxo, (CH$_2$)$_n$OR$^{10}$, NR$^{10}$R$^{11}$, CF$_3$, F, Cl, Br, I, SO$_2$R$^{10}$, C(=O)R$^{10}$, NR$^{12}$C(=Y)R$^{11}$, C(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl and C$_1$-C$_{20}$ heteroaryl;

R$^{14}$ and R$^{15}$ are independently selected from H, C$_1$-C$_{12}$ alkyl, or —(CH$_2$)$_n$-aryl, or R$^{14}$ and R$^{15}$ together with the atoms to which they are attached form a saturated or partially unsaturated C$_3$-C$_{12}$ carbocyclic ring, R$^{14}$ is H or C$_1$-C$_6$ alkyl;

mor is a morpholine group optionally substituted with one or more groups selected from F, Cl, Br, I, —C(C$_1$-C$_6$ alkyl)$_2$NR$^{10}$R$^{11}$, —(CR$^{14}$R$^{15}$)$_n$NR$^{10}$R$^{11}$, —C(R$^{14}$R$^{15}$)$_n$NR$^{12}$C(=Y)R$^{10}$, —(CR$^{14}$R$^{15}$)$_n$NR$^{12}$S(O)$_2$R$^{10}$, —CH(OR$^{10}$)R$^{10}$, —(CR$^{14}$R$^{15}$)$_n$OR$^{10}$, —(CR$^{14}$R$^{15}$)$_n$S(O)$_2$R$^{10}$, —(CR$^{14}$R$^{15}$)$_n$S(O)$_2$NR$^{10}$R$^{11}$, —C(=Y)R$^{10}$, —C(=Y)OR$^{10}$, —C(=Y)NR$^{10}$R$^{11}$, —C(=Y)NR$^{12}$OR$^{10}$, —C(=O)NR$^{12}$S(O)$_2$R$^{10}$, —C(=O)NR$^{12}$(CR$^{14}$R$^{15}$), NR$^{10}$R$^{11}$, —NO$_2$, —NR$^{10}$R$^{11}$, —NR$^{12}$C(=Y)R$^{11}$, —NR$^{12}$C(=Y)OR$^{11}$, —NR$^{12}$C(=Y)NR$^{10}$R$^{11}$, —NR$^{12}$S(O)$_2$R$^{10}$, —NR$^{12}$SO$_2$NR$^{10}$R$^{11}$, —S(O)$_2$R$^{10}$, —S(O)$_2$NR$^{10}$R$^{11}$, —SC(=Y)R$^{10}$, —SC(=Y)OR$^{10}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl;

where said alkyl, alkenyl, alkynyl, carbocyclyl, heterocyclyl, aryl and heteroaryl are optionally substituted with one or more groups independently selected from F, Cl, Br, I, —CN, CF$_3$, —NO$_2$, oxo, —C(=Y)R$^{10}$, —C(=Y)OR$^{10}$, —C(=Y)NR$^{10}$R$^{11}$, —(CR$^{14}$R$^{15}$)$_n$NR$^{10}$R$^{11}$, —(CR$^{14}$R$^{15}$)$_n$NR$^{12}$SO$_2$R$^{10}$, —(CR$^{14}$R$^{15}$)$_n$OR$^{10}$, —NR$^{10}$R$^{11}$, —NR$^{12}$C(=Y)R$^{10}$, —NR$^{12}$C(=Y)OR$^{11}$, —NR$^{12}$C(=Y)NR$^{10}$R$^{11}$, —NR$^{12}$SO$_2$R$^{10}$, —NR$^{12}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, optionally substituted C$_1$-C$_{12}$ alkyl, optionally substituted C$_2$-C$_8$ alkenyl, optionally substituted C$_2$-C$_8$ alkynyl, optionally substituted C$_3$-C$_{12}$ carbocyclyl, optionally substituted C$_2$-C$_{20}$ heterocyclyl, optionally substituted C$_6$-C$_{20}$ aryl, and optionally substituted C$_1$-C$_{20}$ heteroaryl;

Y is O, S, or NR$^{12}$;

each q is independently 0 or 1;

m is 0 or 1; and n is 1, 2, 3, 4, 5, or 6;

with the provisos that:

when in Formula (Ic) mor is unsubstituted morpholino, X is S, R$^1$ is a (4-methylsulfonylpiperazin-1-yl)methyl group and R$^2$ is H, then R$^3$ is not a group selected from imidazolyl which is unsubstituted or substituted with one CH$_3$ group, pyrimidinyl which is unsubstituted and pyridinyl which is unsubstituted or substituted with one F group;

when in Formula (Ic) mor is unsubstituted morpholino, X is S, R$^1$ is a (4-methylpiperazin-1-yl)methyl group and R$^2$ is H, then R$^3$ is not a group selected from pyrazolyl which is unsubstituted and pyridinyl which is substituted by one OH group; and when in Formula (Id) mor is unsubstituted morpholino, X is S, R$^1$ is a (4-methylsulfonylpiperazin-1-yl)methyl group and R$^2$ is H, then R$^3$ is not a group selected from pyridinyl which is unsubstituted and pyrimidinyl which is unsubstituted or substituted by one —OCH$_3$ or —N(CH$_3$)$_2$ group.

Formula Ia-d compounds are regioisomers, i.e. differ by the placement of atom X in the thienopyrimidine (X=sulfur) or furanopyrimidine (X=oxygen) ring system. Parent molecules of Formula Ia-d compounds are:

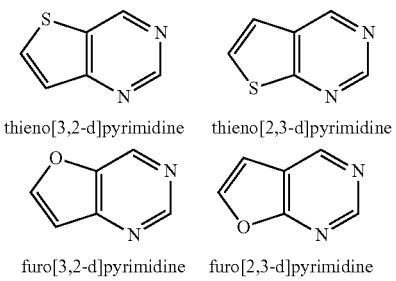

thieno[3,2-d]pyrimidine    thieno[2,3-d]pyrimidine furo[3,2-d]pyrimidine    furo[2,3-d]pyrimidine Compounds of the invention thus include both regioisomers of each of the 4-morpholino thienopyrimidine and 4-morpholino furanopyrimidine compounds, and the substituted forms as described by R$^1$, R$^2$, and R$^3$ herein:

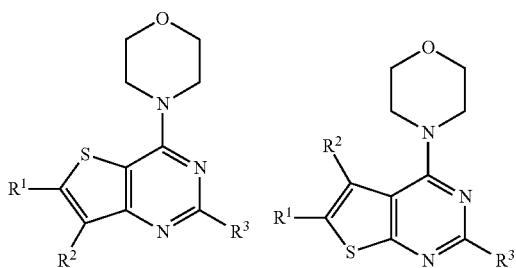

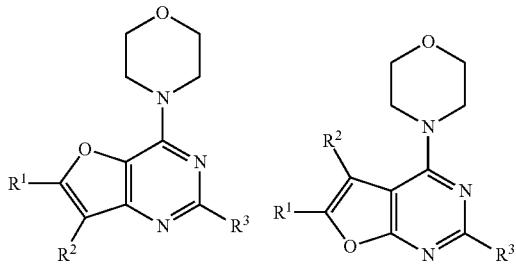

In certain embodiments, mor is selected from the structures:

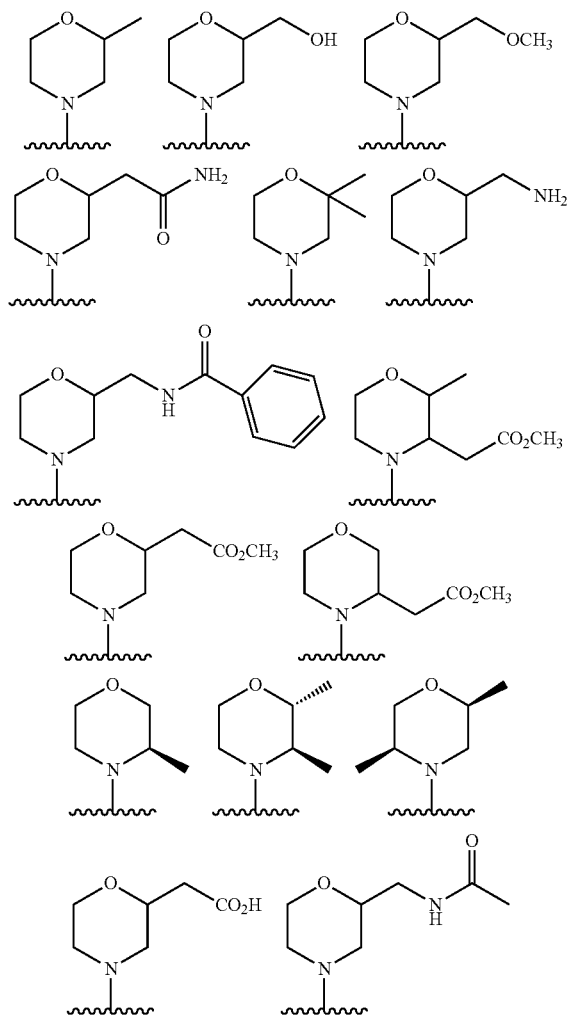

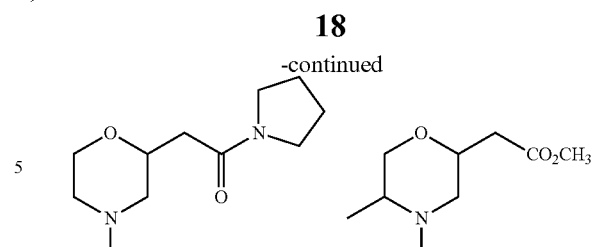

where the wavy line indicates the attachment to the 4-position of the pyrimidine ring.

In certain embodiments, $R^1$ is selected from the groups:

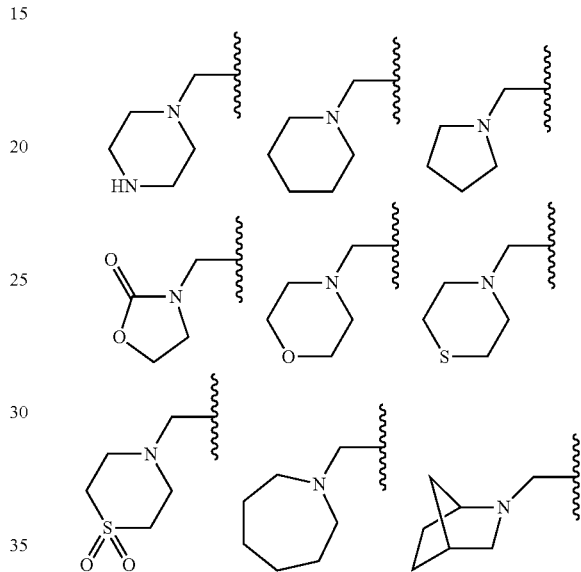

where $R^1$ is unsubstituted or substituted with one or more groups independently selected from F, Cl, Br, I, CN, $CF_3$, $-NO_2$, oxo, $-C(=Y)R^{10}$, $-C(=Y)OR^{10}$, $-C(=Y)NR^{10}R^{11}$, $-(CR^{14}R^{15})_nNR^{10}R^{11}$, $-(CR^{14}R^{15})_nNR^{12}SO_2R^{10}$, $-(CR^{14}R^{15})_nOR^{10}$, $-NR^{10}R^{11}$, $-NR^{12}C(=Y)R^{10}$, $-NR^{12}C(=Y)OR^{11}$, $-NR^{12}C(=Y)NR^{10}R^{11}$, $-NR^{12}SO_2R^{10}$, $=NR^{12}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})(OR^{11})$, $SR^{10}$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, optionally substituted $C_1$-$C_{12}$ alkyl, optionally substituted $C_2$-$C_8$ alkenyl, optionally substituted $C_2$-$C_8$ alkynyl, optionally substituted $C_3$-$C_{12}$ carbocyclyl, optionally substituted $C_2$-$C_{20}$ heterocyclyl, optionally substituted $C_6$-$C_{20}$ aryl, optionally substituted $C_1$-$C_{20}$ heteroaryl.

In certain embodiments, $R^1$ is selected from the groups:

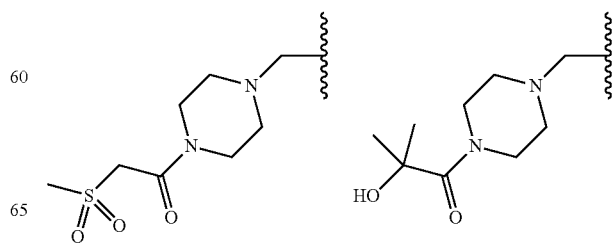

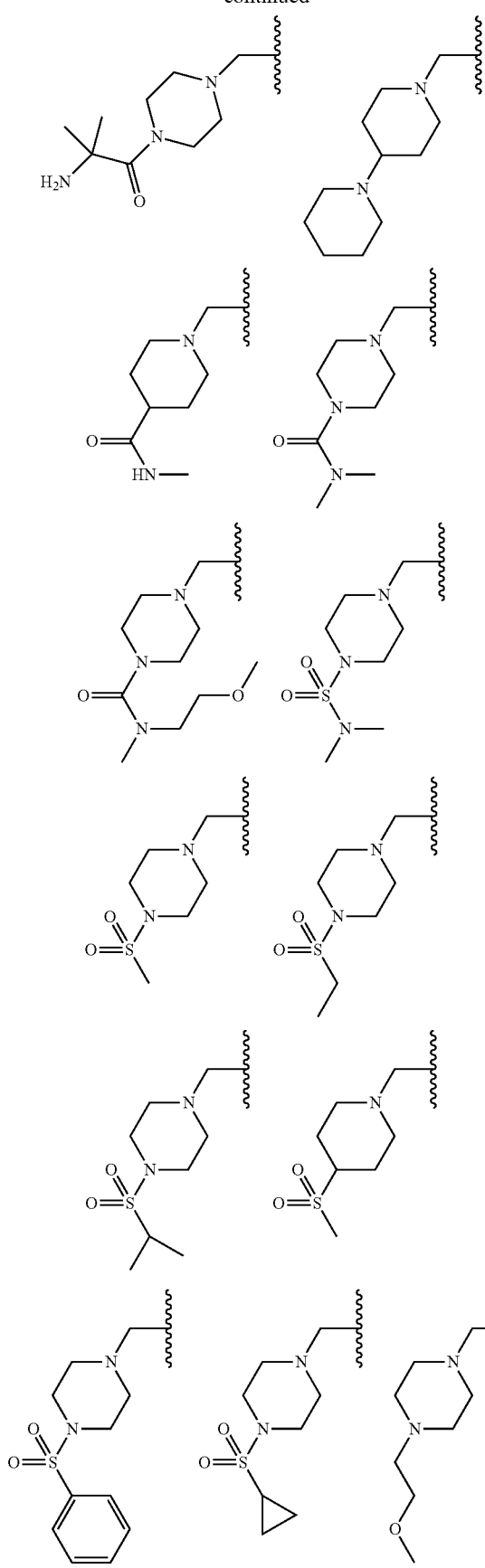

-continued
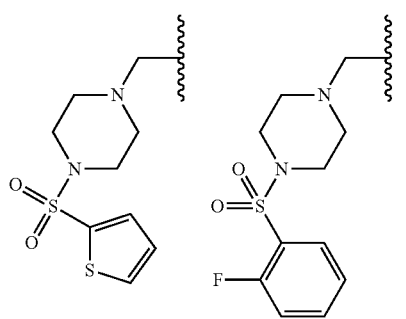
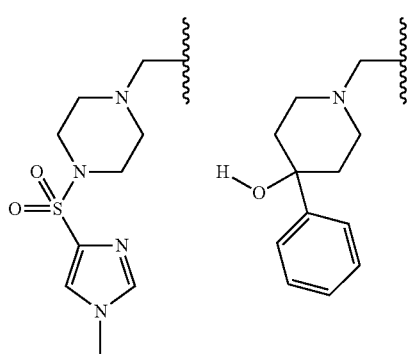
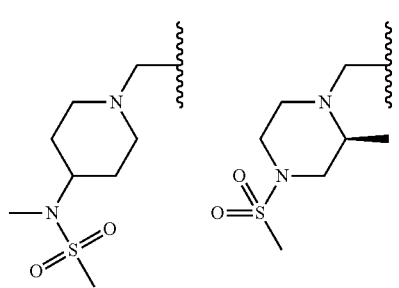
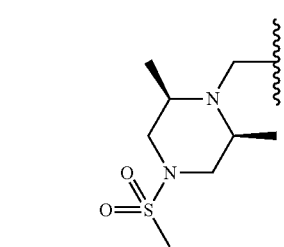
In certain embodiments, R¹ is selected from the groups:
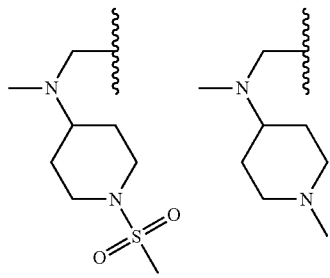
In certain embodiments, R² is H or CH₃.
In certain embodiments, R³ is selected from the structures:
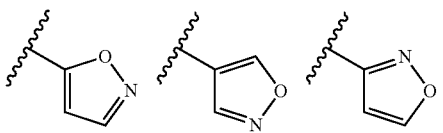
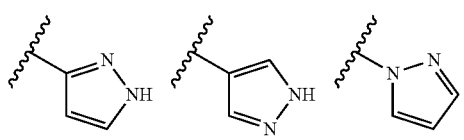
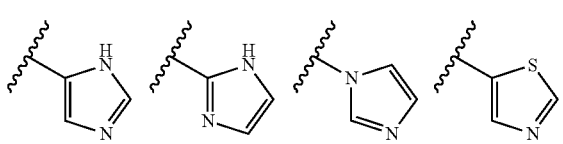
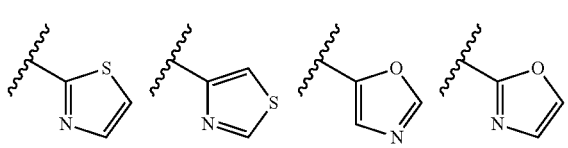
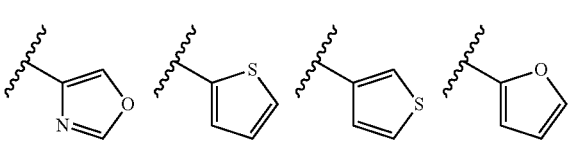
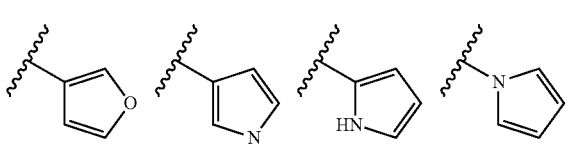
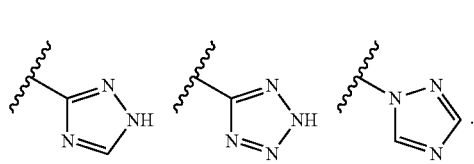
In certain embodiments, R³ is selected from the structures:
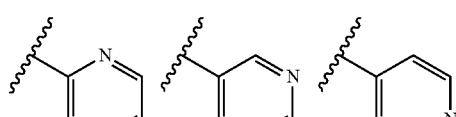
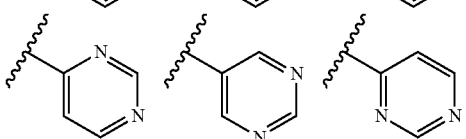
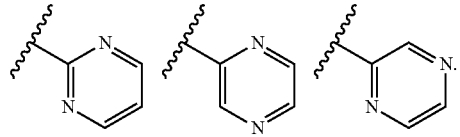

In certain embodiments, $R^3$ is selected from the structures:

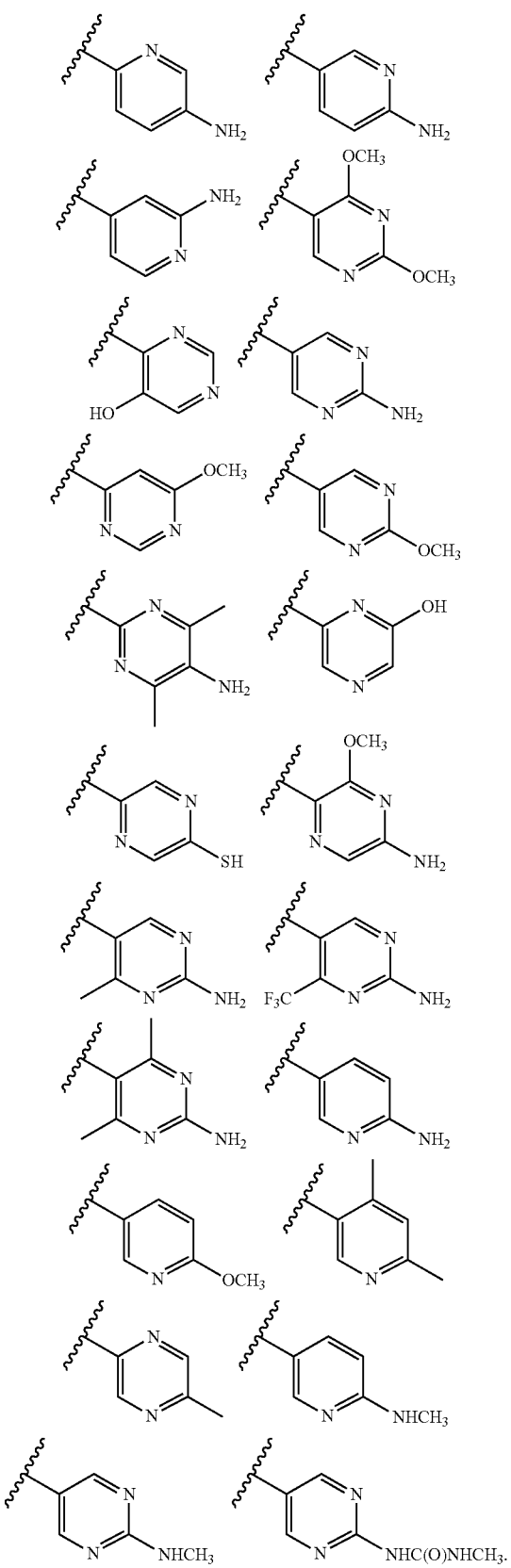

In certain embodiments, the monocyclic heteroaryl group is substituted with one or more groups selected from F, —$NH_2$, —$NHCH_3$, —OH, —$OCH_3$, —$C(O)CH_3$, —$NHC(O)CH_3$, —$N(C(O)CH_3)_2$, —$NHC(O)NH_2$, —$CO_2H$, —CHO, —$CH_2OH$, —$C(=O)NHCH_3$, —$C(=O)NH_2$, and —$CH_3$.

In certain embodiments, the compounds of the invention exclude 6-((4-methylsulfonylpiperazin-1-yl)methyl)-4-morpholino-2-(pyrimidin-5-yl)thieno[2,3-d]pyrimidine; 2-(1H-imidazol-1-yl)-6-((4-methylsulfonylpiperazin-1-yl)methyl)-4-morpholinothieno[3,2-d]pyrimidine; 5-(6-((4-methylpiperazin-1-yl)methyl)-4-morpholinothieno[3,2-d]pyrimidin-2-yl)pyridin-3-ol; 6-((4-methylpiperazin-1-yl)methyl)-4-morpholino-2-(1H-pyrazol-4-yl)thieno[3,2-d]pyrimidine; 6-((4-methylsulfonylpiperazin-1-yl)methyl)-4-morpholino-2-(pyrimidin-5-yl)thieno[3,2-d]pyrimidine; 2-(6-fluoropyridin-3-yl)-6-((4-methylsulfonylpiperazin-1-yl)methyl)-4-morpholinothieno[3,2-d]pyrimidine; 2-(2-fluoropyridin-3-yl)-6-((4-methylsulfonylpiperazin-1-yl)methyl)-4-morpholinothieno[3,2-d]pyrimidine; 6-(4-Methanesulfonyl-piperazin-1-ylmethyl)-2-(2-methoxy-pyrimidin-5-yl)-4-morpholin-4-yl-thieno[2,3-d]pyrimidine; {5-[6-(4-Methanesulfonyl-piperazin-1-ylmethyl)-4-morpholin-4-yl-thieno[2,3-d]pyrimidin-2-yl]-pyrimidin-2-yl}-dimethyl-amine; 6-(4-Methanesulfonyl-piperazin-1-ylmethyl)-4-morpholin-4-yl-2-pyridin-3-yl-thieno[3,2-d]pyrimidine; 6-(4-Methanesulfonyl-piperazin-1-ylmethyl)-4-morpholin-4-yl-2-pyridin-3-yl-thieno[2,3-d]pyrimidine; and 6-(4-Methanesulfonyl-piperazin-1-ylmethyl)-2-(2-methyl-imidazol-1-yl)-4-morpholin-4-yl-thieno[3,2-d]pyrimidine; as well as and stereoisomers, geometric isomers, tautomers, solvates, metabolites, and pharmaceutically acceptable salts thereof.

In certain embodiments the invention provides compounds of formulas Ia and Ib as well as and stereoisomers, geometric isomers, tautomers, solvates, metabolites, and pharmaceutically acceptable salts thereof with the provisos that:
(i) when in formula (Ia) X is S, $R^1$ is a (4-methylsulfonylpiperazin-1-yl)methyl group and $R^2$ is H, then $R^3$ is not a group selected from imidazolyl which is unsubstituted or substituted with one —$CH_3$ group, pyrimidinyl which is unsubstituted and pyridinyl which is unsubstituted or substituted with one F group;
(ii) when in formula (Ia) X is S, $R^1$ is a (4-methylpiperazin-1-yl)methyl group and $R^2$ is H, then $R^3$ is not a group selected from pyrazolyl which is unsubstituted and pyridinyl which is substituted by one OH group; and
(iii) when in formula (Ib) X is S, $R^1$ is a (4-methylsulfonylpiperazin-1-yl)methyl group and $R^2$ is H, then $R^3$ is not a group selected from pyridinyl which is unsubstituted and pyrimidinyl which is unsubstituted or substituted by one —$OCH_3$ or —$N(CH_3)_2$ group.

The Formula Ia-d compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a Formula Ia-d compound incorporates a double bond or a fused ring, the cis- and trans-forms, as well as mixtures thereof, are embraced within the scope of the invention. Both the single positional isomers and mixture of positional isomers are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^{3}H$ and $^{14}C$) are useful in compound and/or substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Preparation of Formula Ia-d Compounds

Thienopyrimidine and furanopyrimidine compounds of Formula Ia-d may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967- 1999 ed.), or *Beilsteins Handbuch der organischen Chemie*, 4, Aufl. ed. Springer-Verlag, Berlin, including supplements (also available via the Beilstein online database).

In certain embodiments, compounds of Formula Ia-d may be readily prepared using procedures well-known to prepare thiophenes, furans, pyrimidines (U.S. Pat. Nos. 6,608,053; 6,492,383; 6,232,320; 6,187,777; 3,763,156; 3,661,908; 3,475,429; 5,075,305; US 2003/220365; GB 1393161; WO 93/13664); and other heterocycles, which are described in: Comprehensive Heterocyclic Chemistry, Editors Katritzky and Rees, Pergamon Press, 1984.

Compounds of Formula Ia-d may be prepared singly or as compound libraries comprising at least 2, for example 5 to 1,000 compounds, or 10 to 100 compounds. Libraries of compounds of Formula Ia-d may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, Schemes 1-4 show general methods for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing compounds of Formulas Ia-d, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

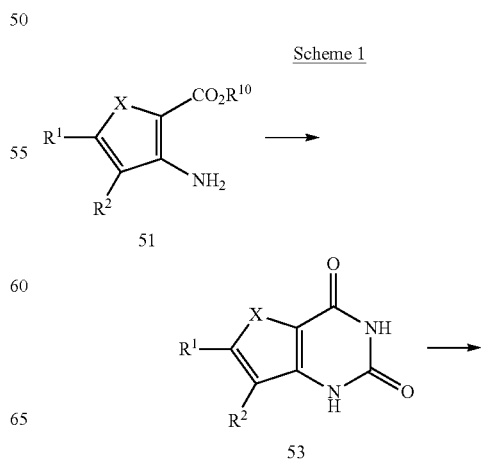

Scheme 1

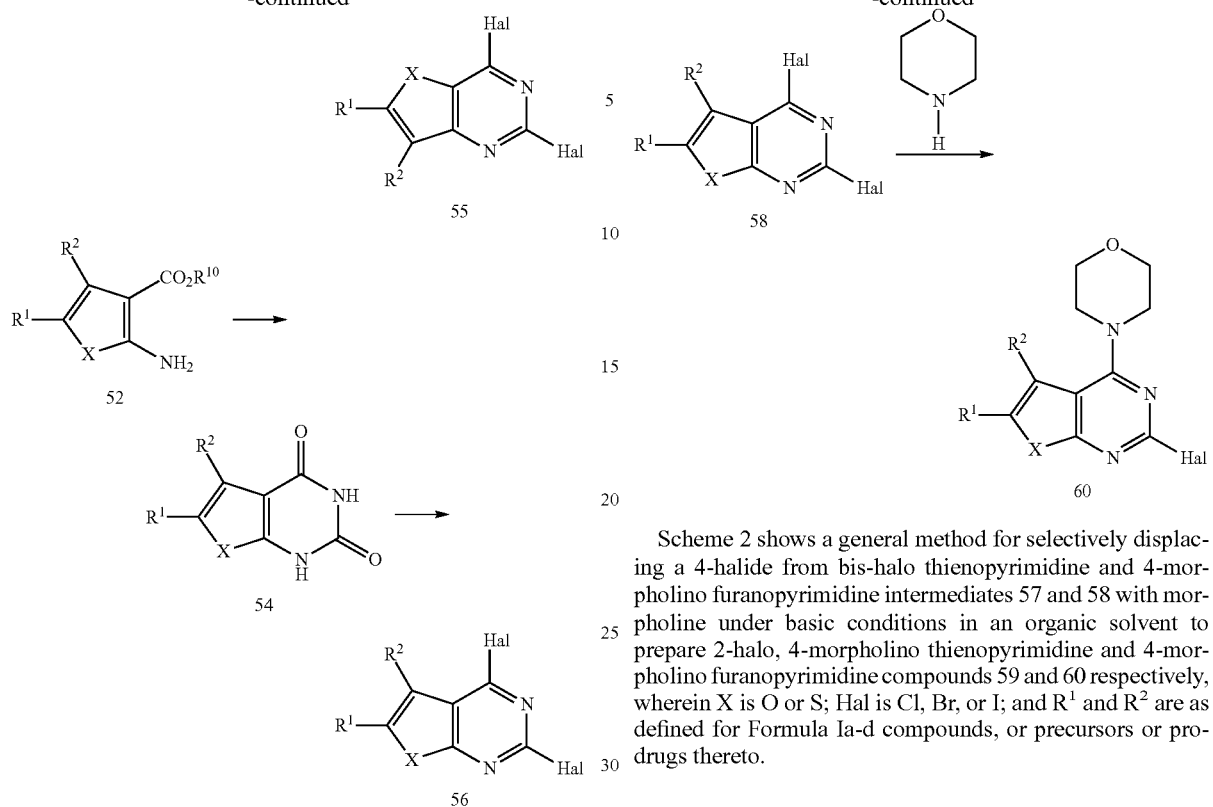

Scheme 1 shows a general method for preparation of the thienopyrimidine and furanopyrimidine intermediates 55 and 56 from 2-carboxyester, 3-amino thiophene (X=S) and furan (X=O), and 2-amino, 3-carboxy ester thiophene (X=S) and furan (X=O) reagents, respectively 51 and 52, wherein X is O or S; Hal is Cl, Br, or I; and $R^1$, $R^2$, and $R^{10}$ are as defined for Formula Ia-d compounds, or precursors or prodrugs thereto.

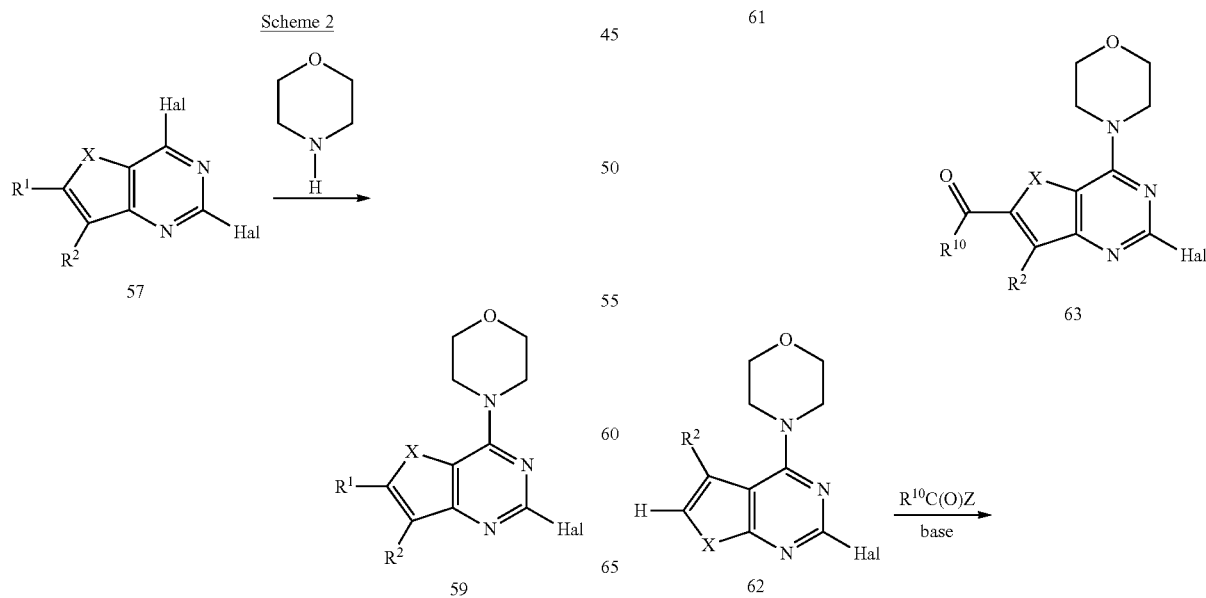

Scheme 2 shows a general method for selectively displacing a 4-halide from bis-halo thienopyrimidine and 4-morpholino furanopyrimidine intermediates 57 and 58 with morpholine under basic conditions in an organic solvent to prepare 2-halo, 4-morpholino thienopyrimidine and 4-morpholino furanopyrimidine compounds 59 and 60 respectively, wherein X is O or S; Hal is Cl, Br, or I; and $R^1$ and $R^2$ are as defined for Formula Ia-d compounds, or precursors or prodrugs thereto.

-continued

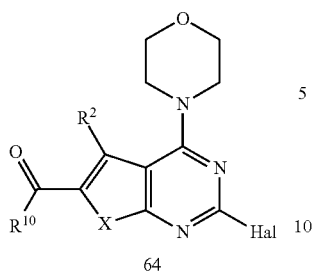
64

-continued

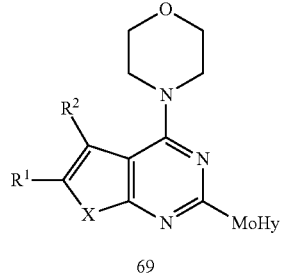
69

Scheme 3 shows a general method for derivatizing the 6-position of 2-halo, 4-morpholino, 6-hydrogen thienopyrimidine and 4-morpholino furanopyrimidine compounds 61 and 62 where $R^1$ is H. Treating 61 or 62 with a lithiating reagent to remove the 6 position proton, followed by adding an acylating reagent $R^{10}C(O)Z$ where Z is a leaving group, such as halide, NHS ester, carboxylate, or dialkylamino, gives 2-halo, 4-morpholino, 6-acyl thienopyrimidine and 4-morpholino furanopyrimidine compounds 63 and 64, wherein X is O or S; Hal is Cl, Br, or I; and $R^2$ and $R^{10}$ are as defined for Formula Ia-d compounds, or precursors or prodrugs thereto. An example of $R^{10}C(O)Z$ to prepare 6-formyl compounds ($R^{10}$=H) is N,N'-dimethylformamide (DMF).

Scheme 4

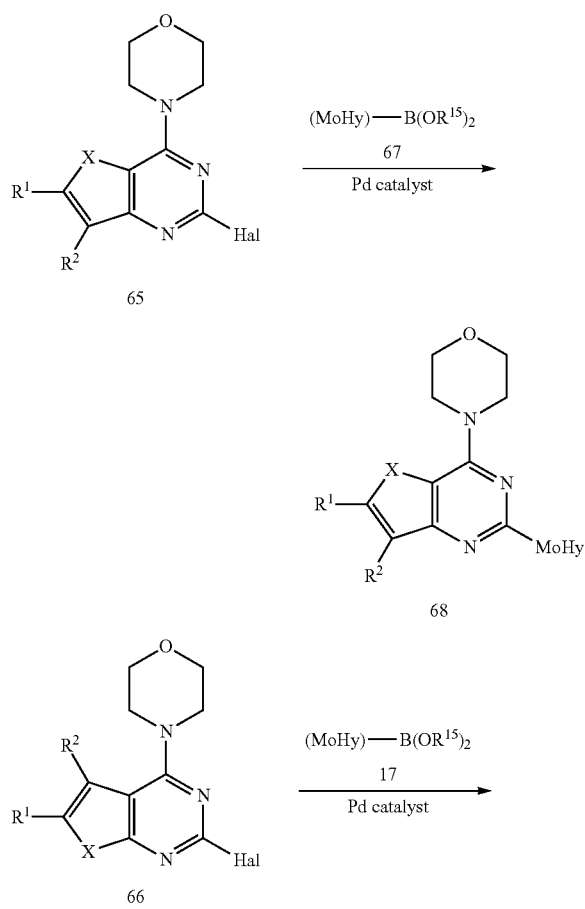

Scheme 4 shows a general method for Suzuki-type coupling of a 2-halo pyrimidine intermediate (65 and 66) with a monocyclic heteroaryl boronate acid ($R^{15}$=H) or ester ($R^{15}$=alkyl) reagent 67 to prepare the 2-monocyclic heteroaryl (MoHy), 4-morpholino thienopyrimidine and 4-morpholino furanopyrimidine compounds (68 and 69) of Formulas Ia and Ib wherein X is O or S; Hal is Cl, Br, or I; and $R^1$ and $R^2$ are as defined for Formula Ia and Ib compounds, or precursors or prodrugs thereto. For reviews of the Suzuki reaction, see: Miyaura et al. (1995) Chem. Rev. 95:2457-2483; Suzuki, A. (1999) J. Organomet. Chem. 576:147-168; Suzuki, A. in Metal-Catalyzed Cross-Coupling Reactions, Diederich, F., Stang, P. J., Eds., VCH, Weinheim, Del. (1998), pp 49-97. The palladium catalyst may be any that is typically used for Suzuki-type cross-couplings, such as $PdCl_2(PPh_3)_2$, $Pd(PPh_3)_4$, $Pd(OAc)_2$, $PdCl_2(dppf)$-DCM, $Pd_2(dba)_3$/Pt-$Bu)_3$ (Owens et al (2003) Bioorganic & Med. Chem. Letters 13:4143-4145; Molander et al (2002) Organic Letters 4(11): 1867-1870; U.S. Pat. No. 6,448,433).

Methods of Separation

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem., (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Biological Evaluation

Determination of the activity of PI3 kinase activity of a compound of Formula Ia-d is possible by a number of direct and indirect detection methods. Certain exemplary compounds described herein were assayed for their PI3K binding activity (Example 347) and in vitro activity against tumor cells (Example 348). The range of PI3K binding activities was less than 1 nM (nanomolar) to about 10 μM (micromolar). Certain exemplary compounds of the invention had PI3K binding activity $IC_{50}$ values less than 10 nM. Certain compounds of the invention had tumor cell-based activity $IC_{50}$ values less than 100 nM.

The cytotoxic or cytostatic activity of Formula Ia-d exemplary compounds was measured by: establishing a proliferating mammalian tumor cell line in a cell culture medium, adding a Formula Ia-d compound, culturing the cells for a period from about 6 hours to about 5 days; and measuring cell viability (Example 348). Cell-based in vitro assays were used to measure viability, i.e. proliferation ($IC_{50}$), cytotoxicity ($EC_{50}$), and induction of apoptosis (caspase activation).

The in vitro potency of Formula Ia-d exemplary compounds was measured by the cell proliferation assay, CellTiter-Glo® Luminescent Cell Viability Assay, commercially available from Promega Corp., Madison, Wis. (Example 348). This homogeneous assay method is based on the recombinant expression of *Coleoptera* luciferase (U.S. Pat. Nos. 5,583,024; 5,674,713; 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay an be used with various multiwell formats, e.g. 96 or 384 well format. Data can be recorded by luminometer or CCD camera imaging device. The luminescence output is presented as relative light units (RLU), measured over time.

The anti-proliferative effects of Formula Ia-d exemplary compounds were measured by the CellTiter-Glo® Assay (Example 348) against several tumor cell lines, including PC3, Detroit 562, and MDAMB361.1. $EC_{50}$ values were established for the tested compounds. The range of in vitro cell potency activities was about 100 nM to about 10 μM.

Certain ADME properties were measured for certain exemplary compounds by assays including: Caco-2 Permeability (Example 349), Hepatocyte Clearance (Example 350), Cytochrome P450 Inhibition (Example 351), Cytochrome P450 Induction (Example 352), Plasma Protein Binding (Example 353), and hERG channel blockage (Example 354).

Exemplary Formula Ia-d compounds No. 101-318 in Table 1 and No. 319-429 in Table 2, which were made according to the methods of this invention, have the following structures and their corresponding names (ChemDraw Ultra, Version 9.0.1, CambridgeSoft Corp., Cambridge Mass.) in Tables 1 and 2.

TABLE 1

| Compound | Structure | Name |
|---|---|---|
| 101 | 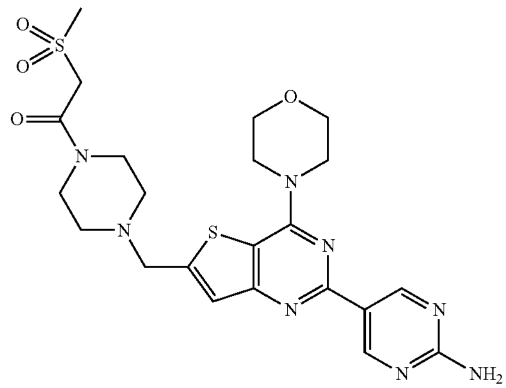 [SMILES: CS(=O)(=O)CC(=O)N1CCN(Cc2cc3nc(-c4cnc(N)nc4)nc(N4CCOCC4)c3s2)CC1] | 1-(4-((2-(2-aminopyrimidin-5-yl)-4-morpholinothieno[3,2-d]pyrimidin-6-yl)methyl)piperazin-1-yl)-2-(methylsulfonyl)ethanone |
| 102 | 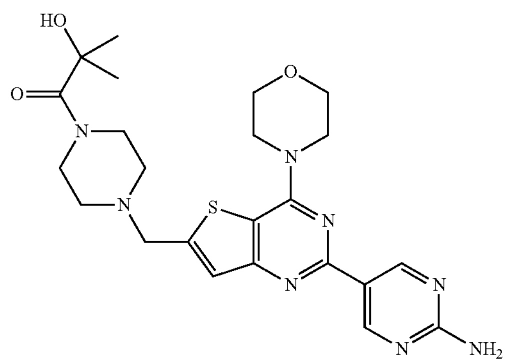 [SMILES: CC(C)(O)C(=O)N1CCN(Cc2cc3nc(-c4cnc(N)nc4)nc(N4CCOCC4)c3s2)CC1] | 1-(4-((2-(2-aminopyrimidin-5-yl)-4-morpholinothieno[3,2-d]pyrimidin-6-yl)methyl)piperazin-1-yl)-2-hydroxy-2-methylpropan-1-one |
| 103 | 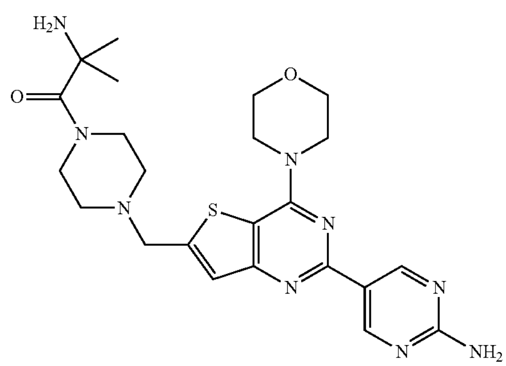 [SMILES: CC(C)(N)C(=O)N1CCN(Cc2cc3nc(-c4cnc(N)nc4)nc(N4CCOCC4)c3s2)CC1] | 2-amino-1-(4-((2-(2-aminopyrimidin-5-yl)-4-morpholinothieno[3,2-d]pyrimidin-6-yl)methyl)piperazin-1-yl)-2-methylpropan-1-one |
| 104 | 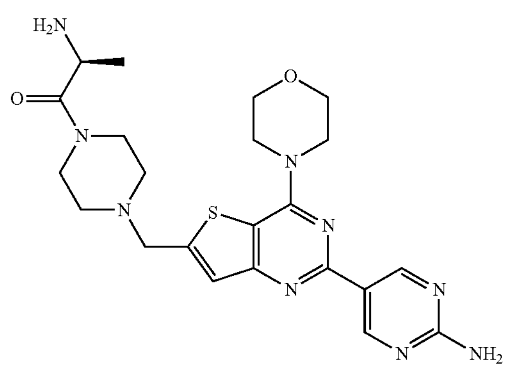 [SMILES: C[C@H](N)C(=O)N1CCN(Cc2cc3nc(-c4cnc(N)nc4)nc(N4CCOCC4)c3s2)CC1] | (S)-2-amino-1-(4-((2-(2-aminopyrimidin-5-yl)-4-morpholinothieno[3,2-d]pyrimidin-6-yl)methyl)piperazin-1-yl)propan-1-one |

TABLE 1-continued

| Compound | Structure | Name |
| --- | --- | --- |
| 105 | 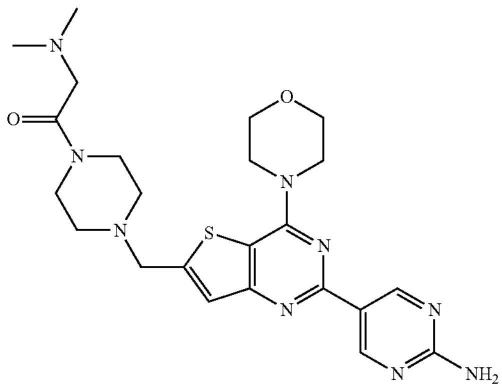 [SMILES: CN(C)CC(=O)N1CCN(Cc2cc3nc(-c4cnc(N)nc4)nc(N4CCOCC4)c3s2)CC1] | 1-(4-((2-(2-aminopyrimidin-5-yl)-4-morpholinothieno[3,2-d]pyrimidin-6-yl)methyl)piperazin-1-yl)-2-(dimethylamino)ethanone |
| 106 | 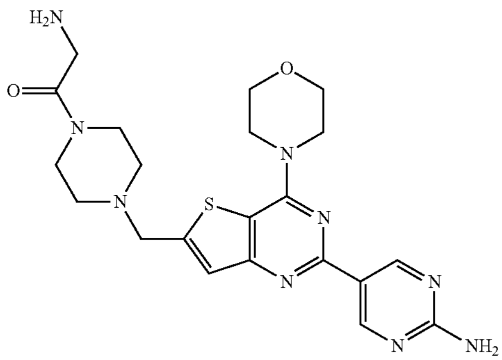 [SMILES: NCC(=O)N1CCN(Cc2cc3nc(-c4cnc(N)nc4)nc(N4CCOCC4)c3s2)CC1] | 2-amino-1-(4-((2-(2-aminopyrimidin-5-yl)-4-morpholinothieno[3,2-d]pyrimidin-6-yl)methyl)piperazin-1-yl)ethanone |
| 107 | 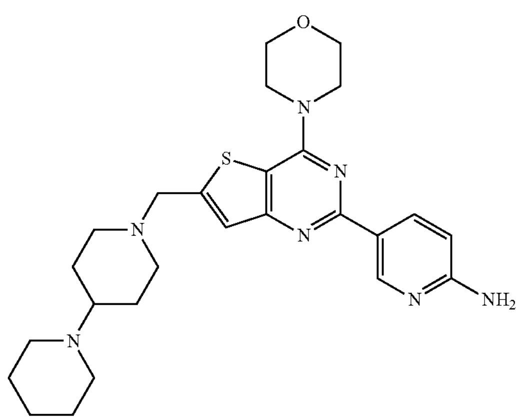 [SMILES: Nc1ccc(-c2nc(N3CCOCC3)c3sc(CN4CCC(N5CCCCC5)CC4)cc3n2)cn1] | 5-(4-morpholino-6-((4-(piperidin-1-yl)piperidin-1-yl)methyl)thieno[3,2-d]pyrimidin-2-yl)pyridin-2-amine |
| 108 | 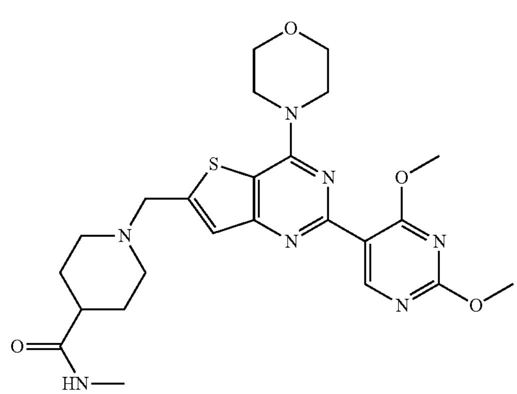 [SMILES: CNC(=O)C1CCN(Cc2cc3nc(-c4cnc(OC)nc4OC)nc(N4CCOCC4)c3s2)CC1] | 1-((2-(2,4-dimethoxypyrimidin-5-yl)-4-morpholinothieno[3,2-d]pyrimidin-6-yl)methyl)-N-methylpiperidine-4-carboxamide |

TABLE 1-continued

| Compound | Structure | Name |
|---|---|---|
| 109 | 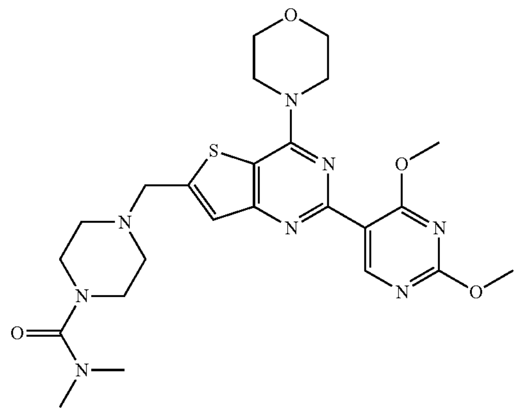 [SMILES: COc1ncc(-c2nc(N3CCOCC3)c3sc(CN4CCN(C(=O)N(C)C)CC4)cc3n2)c(OC)n1] | 4-((2-(2,4-dimethoxypyrimidin-5-yl)-4-morpholinothieno[3,2-d]pyrimidin-6-yl)methyl)-N,N-dimethylpiperazine-1-carboxamide |
| 110 | 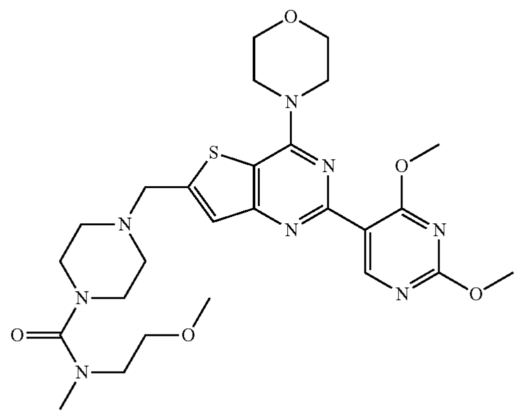 [SMILES: COCCN(C)C(=O)N1CCN(Cc2cc3nc(-c4cnc(OC)nc4OC)nc(N4CCOCC4)c3s2)CC1] | N-(2-methoxyethyl)-4-((2-(2,4-dimethoxypyrimidin-5-yl)-4-morpholinothieno[3,2-d]pyrimidin-6-yl)methyl)-N-methylpiperazine-1-carboxamide |
| 111 | 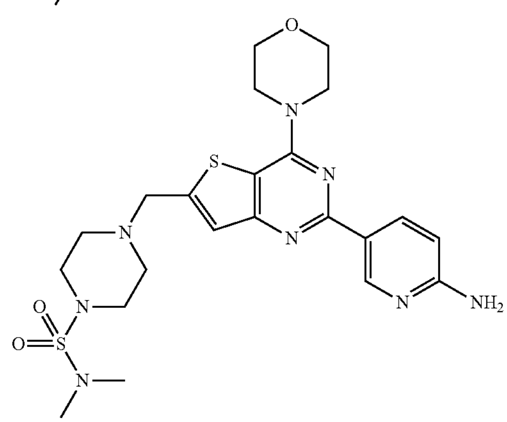 | 5-(4-morpholino-6-((4-N-dimethylaminosulfonylpiperazin-1-yl)methyl)thieno[3,2-d]pyrimidin-2-yl)pyridin-2-amine |
| 112 | 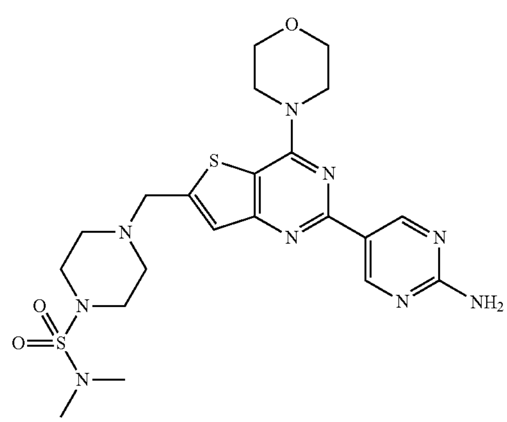 | 5-(4-morpholino-6-((4-N-dimethylaminosulfonylpiperazin-1-yl)methyl)thieno[3,2-d]pyrimidin-2-yl)pyrimidin-2-amine |

TABLE 1-continued

| Compound | Structure | Name |
|---|---|---|
| 113 | 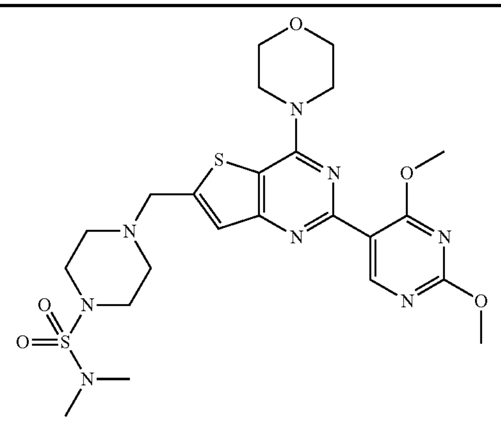 | 2-(2,4-dimethoxypyrimidin-5-yl)-4-morpholino-6-((4-N-dimethylaminosulfonylpiperazin-1-yl)methyl)thieno[3,2-d]pyrimidine |
| 114 | 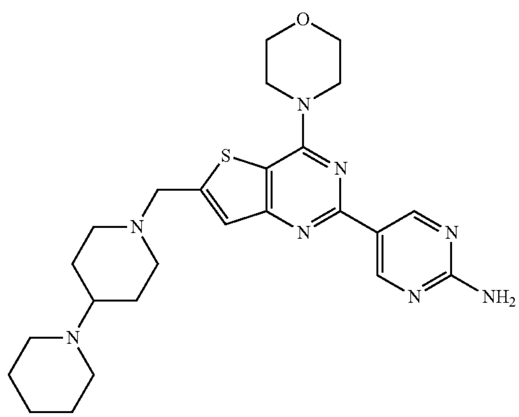 [SMILES: Nc1ncc(-c2nc(N3CCOCC3)c3sc(CN4CCC(N5CCCCC5)CC4)cc3n2)cn1] | 5-(4-morpholino-6-((4-(piperidin-1-yl)piperidin-1-yl)methyl)thieno[3,2-d]pyrimidin-2-yl)pyrimidin-2-amine |
| 115 | 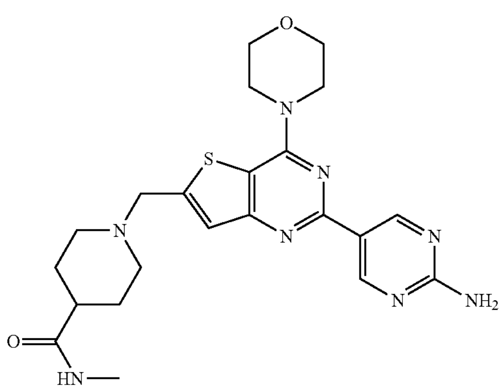 [SMILES: CNC(=O)C1CCN(Cc2cc3nc(-c4cnc(N)nc4)nc(N4CCOCC4)c3s2)CC1] | 1-((2-(2-aminopyrimidin-5-yl)-4-morpholinothieno[3,2-d]pyrimidin-6-yl)methyl)-N-methylpiperidine-4-carboxamide |
| 116 | 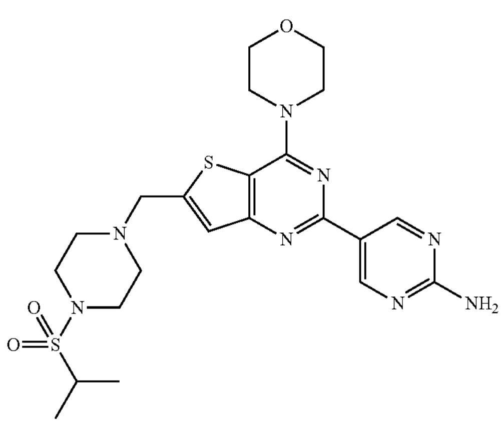 [SMILES: CC(C)S(=O)(=O)N1CCN(Cc2cc3nc(-c4cnc(N)nc4)nc(N4CCOCC4)c3s2)CC1] | 5-(4-morpholino-6-((4-N-isopropylsulfonylpiperazin-1-yl)methyl)thieno[3,2-d]pyrimidin-2-yl)pyrimidin-2-amine |

TABLE 1-continued

| Compound | Structure | Name |
|---|---|---|
| 117 | 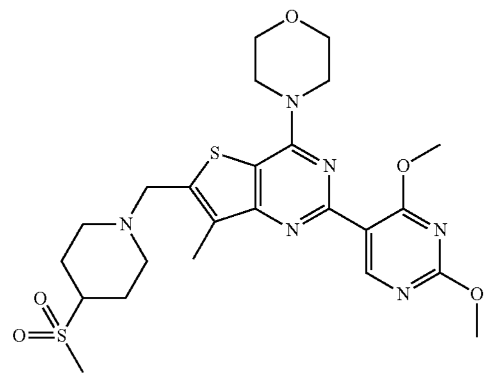 [SMILES: COc1ncc(-c2nc(N3CCOCC3)c3sc(CN4CCC(S(C)(=O)=O)CC4)c(C)c3n2)c(OC)n1] | 2-(2,4-dimethoxypyrimidin-5-yl)-7-methyl-6-((4-(methylsulfonyl)piperidin-1-yl)methyl)-4-morpholinothieno[3,2-d]pyrimidine |
| 118 | 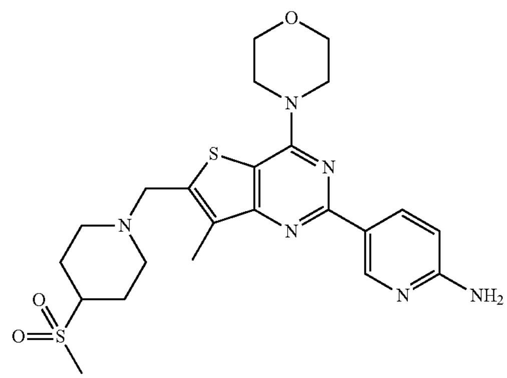 [SMILES: Cc1c(CN2CCC(S(C)(=O)=O)CC2)sc2c(N3CCOCC3)nc(-c3ccc(N)nc3)nc12] | 5-(7-methyl-6-((4-(methylsulfonyl)piperidin-1-yl)methyl)-4-morpholinothieno[3,2-d]pyrimidin-2-yl)pyridin-2-amine |
| 119 | 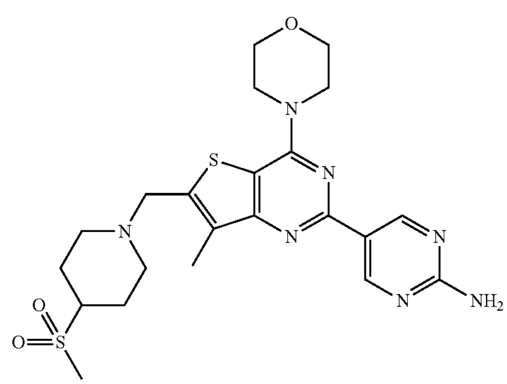 [SMILES: Cc1c(CN2CCC(S(C)(=O)=O)CC2)sc2c(N3CCOCC3)nc(-c3cnc(N)nc3)nc12] | 5-(7-methyl-6-((4-(methylsulfonyl)piperidin-1-yl)methyl)-4-morpholinothieno[3,2-d]pyrimidin-2-yl)pyrimidin-2-amine |
| 120 | 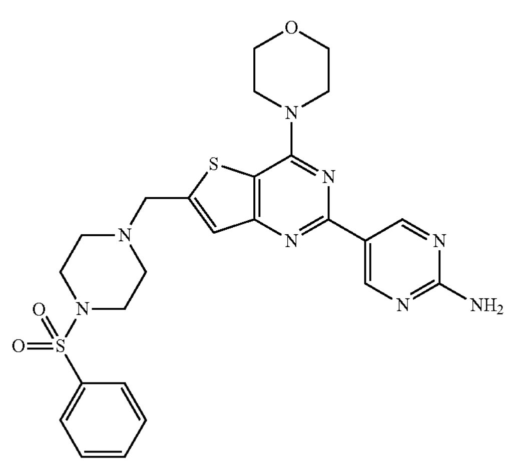 [SMILES: Nc1ncc(-c2nc(N3CCOCC3)c3sc(CN4CCN(S(=O)(=O)c5ccccc5)CC4)cc3n2)cn1] | 5-(4-morpholino-6-((4-N-phenylsulfonylpiperazin-1-yl)methyl)thieno[3,2-d]pyrimidin-2-yl)pyrimidin-2-amine |

TABLE 1-continued

| Compound | Structure | Name |
|---|---|---|
| 121 | 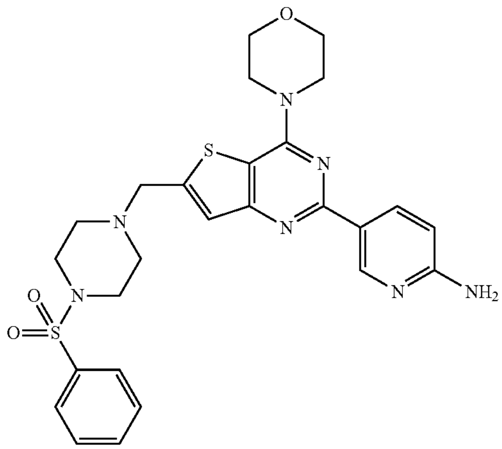 [SMILES: Nc1ccc(-c2nc(N3CCOCC3)c3sc(CN4CCN(S(=O)(=O)c5ccccc5)CC4)cc3n2)cn1] | 5-(4-morpholino-6-((piperazin-1-yl)methyl)thieno[3,2-d]pyrimidin-2-yl)pyridin-2-amine |
| 122 | 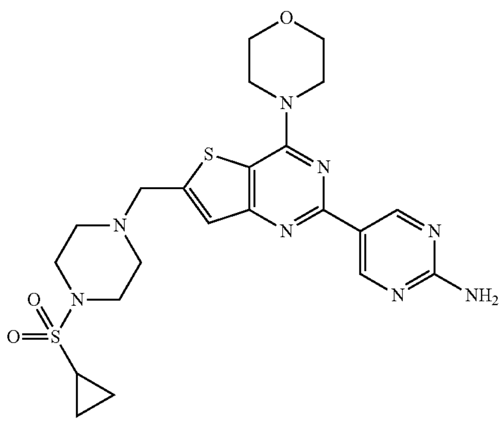 [SMILES: Nc1ncc(-c2nc(N3CCOCC3)c3sc(CN4CCN(S(=O)(=O)C5CC5)CC4)cc3n2)cn1] | 5-(4-morpholino-6-((4-N-cyclopropylsulfonylpiperazin-1-yl)methyl)thieno[3,2-d]pyrimidin-2-yl)pyrimidin-2-amine |
| 123 | 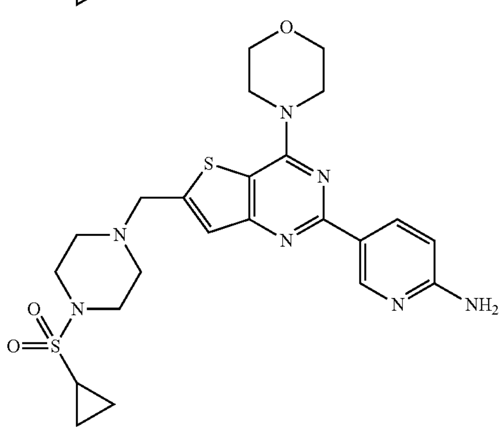 | 5-(4-morpholino-6-((4-N-cyclopropylsulfonylpiperazin-1-yl)methyl)thieno[3,2-d]pyrimidin-2-yl)pyridin-2-amine |
| 124 | 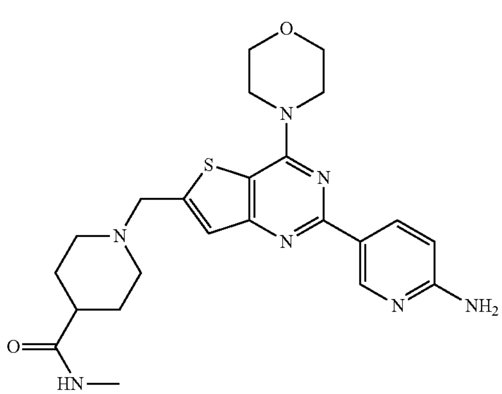 [SMILES: CNC(=O)C1CCN(Cc2cc3nc(-c4ccc(N)nc4)nc(N4CCOCC4)c3s2)CC1] | 1-((2-(6-aminopyridin-3-yl)-4-morpholinothieno[3,2-d]pyrimidin-6-yl)methyl)-N-methylpiperidine-4-carboxamide |

TABLE 1-continued

| Compound | Structure | Name |
|---|---|---|
| 125 | 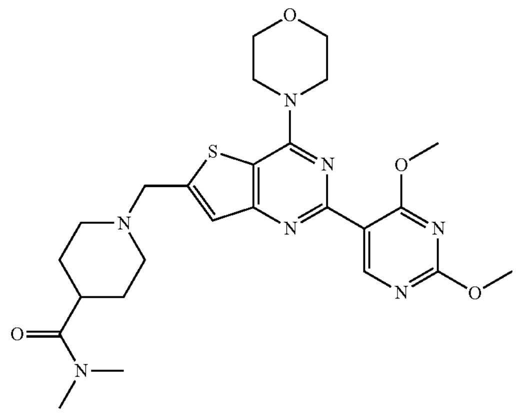 [SMILES: COc1ncc(-c2nc(N3CCOCC3)c3sc(CN4CCC(C(=O)N(C)C)CC4)cc3n2)c(OC)n1] | 1-((2-(2,4-dimethoxypyrimidin-5-yl)-4-morpholinothieno[3,2-d]pyrimidin-6-yl)methyl)-N,N-dimethylpiperidine-4-carboxamide |
| 126 | 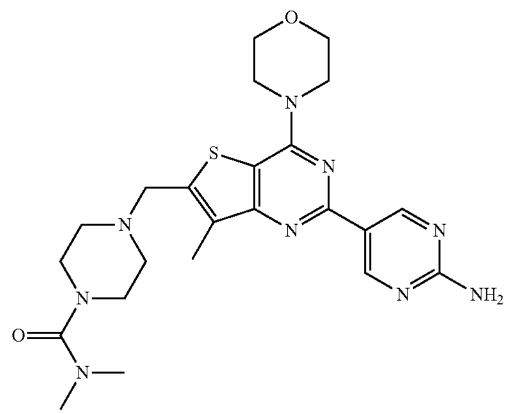 [SMILES: Cc1c(CN2CCN(C(=O)N(C)C)CC2)sc2c(N3CCOCC3)nc(-c3cnc(N)nc3)nc12] | 4-((2-(2-aminopyrimidin-5-yl)-7-methyl-4-morpholinothieno[3,2-d]pyrimidin-6-yl)methyl)-N,N-dimethylpiperazine-1-carboxamide |
| 127 | 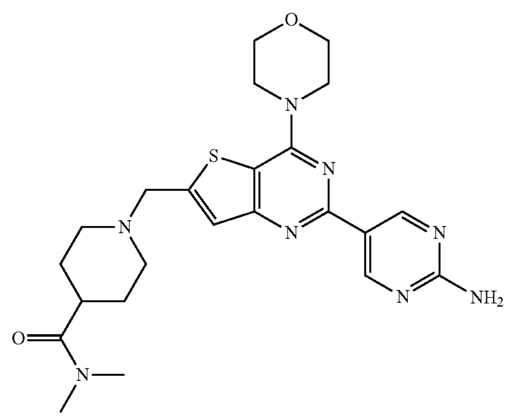 [SMILES: CN(C)C(=O)C1CCN(Cc2cc3nc(-c4cnc(N)nc4)nc(N4CCOCC4)c3s2)CC1] | 1-((2-(2-aminopyrimidin-5-yl)-4-morpholinothieno[3,2-d]pyrimidin-6-yl)methyl)-N,N-dimethylpiperidine-4-carboxamide |
| 128 | 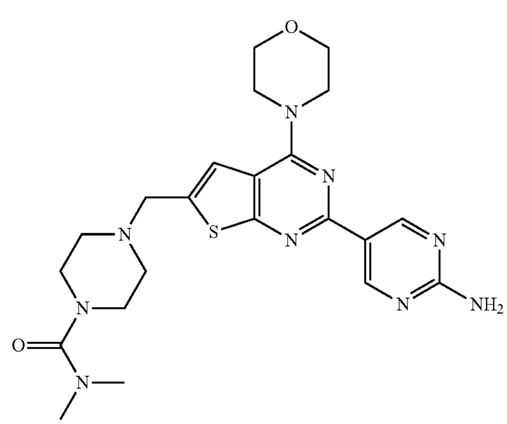 [SMILES: CN(C)C(=O)N1CCN(Cc2cc3c(N4CCOCC4)nc(-c4cnc(N)nc4)nc3s2)CC1] | 4-((2-(2-aminopyrimidin-5-yl)-4-morpholinothieno[2,3-d]pyrimidin-6-yl)methyl)-N,N-dimethylpiperazine-1-carboxamide |

TABLE 1-continued

| Compound | Structure | Name |
|---|---|---|
| 129 | 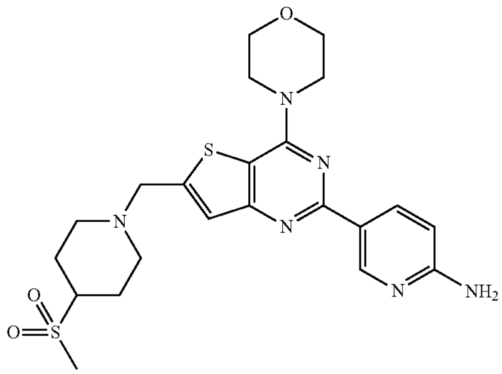 [SMILES: CS(=O)(=O)C1CCN(Cc2cc3nc(-c4ccc(N)nc4)nc(N4CCOCC4)c3s2)CC1] | 5-(6-((4-(methylsulfonyl)piperidin-1-yl)methyl)-4-morpholinothieno[3,2-d]pyrimidin-2-yl)pyridin-2-amine |
| 1300 | 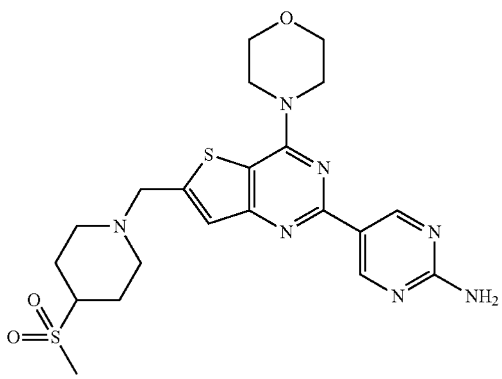 [SMILES: CS(=O)(=O)C1CCN(Cc2cc3nc(-c4cnc(N)nc4)nc(N4CCOCC4)c3s2)CC1] | 5-(6-((4-(methylsulfonyl)piperidin-1-yl)methyl)-4-morpholinothieno[3,2-d]pyrimidin-2-yl)pyrimidin-2-amine |
| 131 | 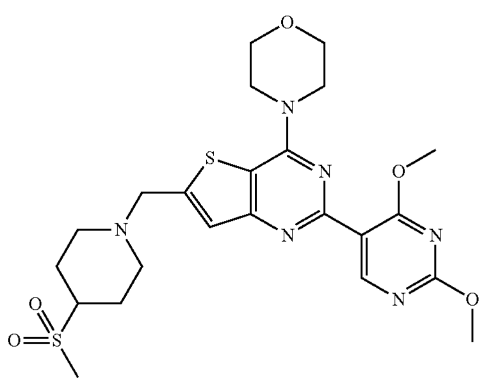 [SMILES: COc1ncc(-c2nc(N3CCOCC3)c3sc(CN4CCC(S(C)(=O)=O)CC4)cc3n2)c(OC)n1] | 2-(2,4-dimethoxypyrimidin-5-yl)-6-((4-(methylsulfonyl)piperidin-1-yl)methyl)-4-morpholinothieno[3,2-d]pyrimidine |
| 132 | 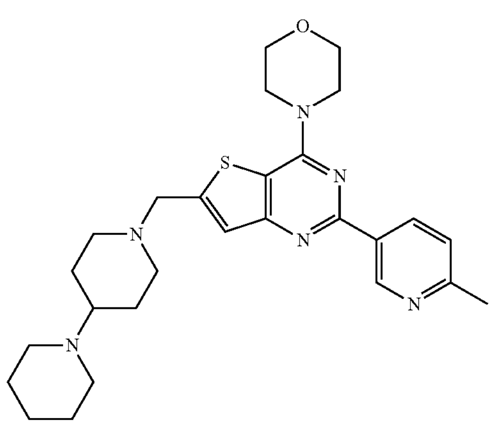 [SMILES: Cc1ccc(-c2nc(N3CCOCC3)c3sc(CN4CCC(N5CCCCC5)CC4)cc3n2)cn1] | 2-(6-methylpyridin-3-yl)-4-morpholino-6-((4-(piperidin-1-yl)piperidin-1-yl)methyl)thieno[3,2-d]pyrimidine |

TABLE 1-continued

| Compound | Structure | Name |
|---|---|---|
| 133 | 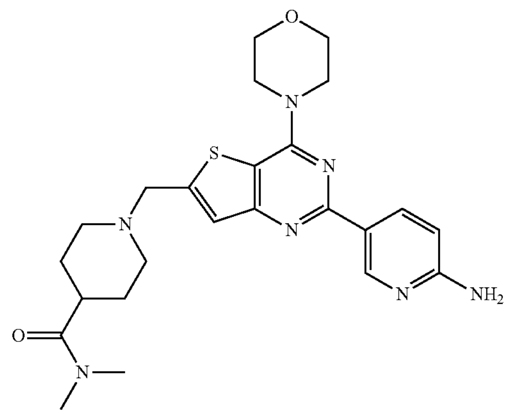 | 1-((2-(6-aminopyridin-3-yl)-4-morpholinothieno[3,2-d]pyrimidin-6-yl)methyl)-N,N-dimethylpiperidine-4-carboxamide |
| 134 | 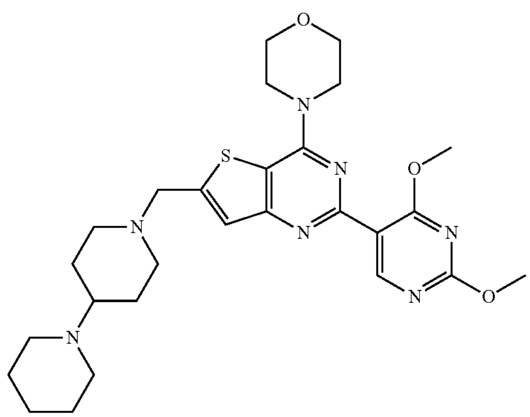 [SMILES: COc1ncc(-c2nc(N3CCOCC3)c3sc(CN4CCC(N5CCCCC5)CC4)cc3n2)c(OC)n1] | 2-(2,4-dimethoxypyrimidin-5-yl)-4-morpholino-6-((4-(piperidin-1-yl)piperidin-1-yl)methyl)thieno(3,2-d]pyrimidine |
| 135 | 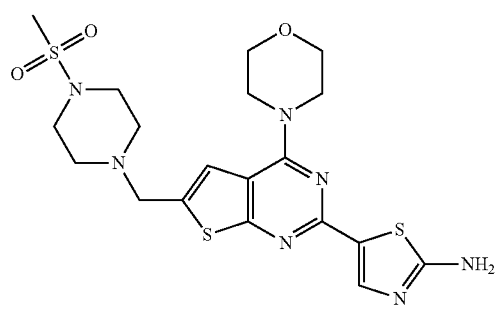 [SMILES: CS(=O)(=O)N1CCN(Cc2cc3c(N4CCOCC4)nc(-c4cnc(N)s4)nc3s2)CC1] | 5-(4-morpholino-6-((4-N-methylsulfonylpiperazin-1-yl)methyl)thieno[2,3-d]pyrimidin-2-yl)thiazol-2-amine |
| 136 | 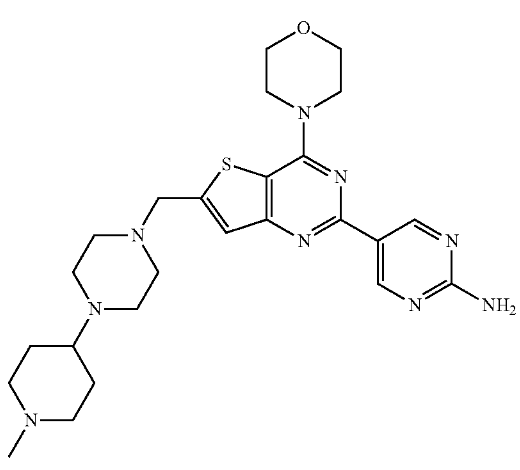 [SMILES: CN1CCC(N2CCN(Cc3cc4nc(-c5cnc(N)nc5)nc(N5CCOCC5)c4s3)CC2)CC1] | 5-(6-((4-(1-methylpiperidin-4-yl)piperazin-1-yl)methyl)-4-morpholinothieno[3,2-d]pyrimidin-2-yl)pyrimidin-2-amine |

TABLE 1-continued

| Compound | Structure | Name |
| --- | --- | --- |
| 137 | 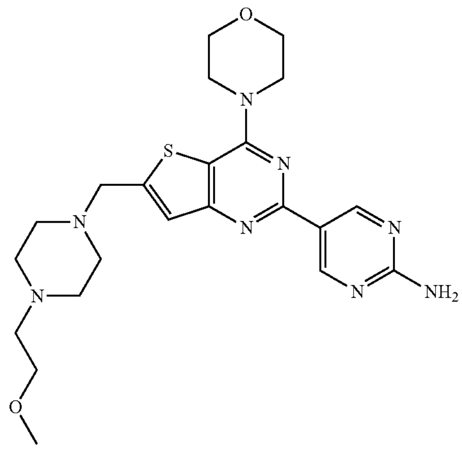 [SMILES: COCCN1CCN(Cc2cc3nc(-c4cnc(N)nc4)nc(N4CCOCC4)c3s2)CC1] | 5-(6-((4-(2-methoxyethyl)piperazin-1-yl)methyl)-4-morpholinothieno[3,2-d]pyrimidin-2-yl)pyrimidin-2-amine |
| 138 | 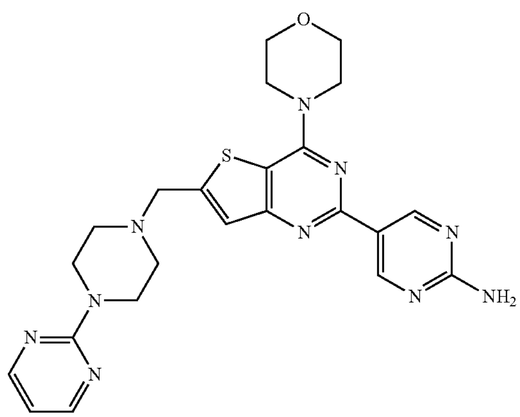 [SMILES: Nc1ncc(-c2nc(N3CCOCC3)c3sc(CN4CCN(c5ncccn5)CC4)cc3n2)cn1] | 5-(4-morpholino-6-((4-(pyrimidin-2-yl)piperazin-1-yl)methyl)thieno[3,2-d]pyrimidin-2-yl)pyrimidin-2-amine |
| 139 | 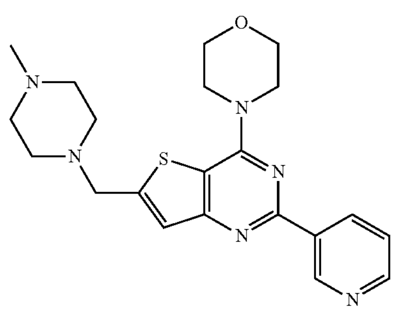 [SMILES: CN1CCN(Cc2cc3nc(-c4cccnc4)nc(N4CCOCC4)c3s2)CC1] | 6-((4-methylpiperazin-1-yl)methyl)-4-morpholino-2-(pyridin-3-yl)thieno[3,2-d]pyrimidine |
| 140 | 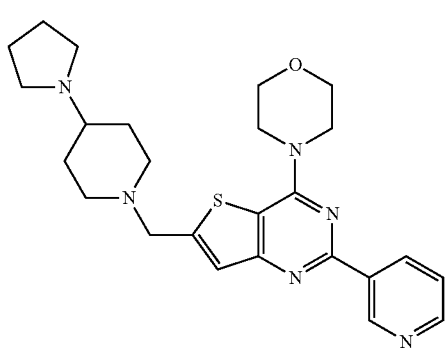 [SMILES: c1cncc(-c2nc(N3CCOCC3)c3sc(CN4CCC(N5CCCC5)CC4)cc3n2)c1] | 4-morpholino-2-(pyridin-3-yl)-6-((4-(pyrrolidin-1-yl)piperidin-1-yl)methyl)thieno[3,2-d]pyrimidine |

TABLE 1-continued

| Compound | Structure | Name |
|---|---|---|
| 141 | 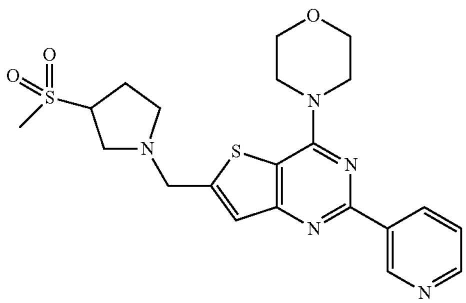 [SMILES: CS(=O)(=O)C1CCN(Cc2cc3nc(-c4cccnc4)nc(N4CCOCC4)c3s2)C1] | 6-((3-(methylsulfonyl)pyrrolidin-1-yl)methyl)-4-morpholino-2-(pyridin-3-yl)thieno[3,2-d]pyrimidine |
| 142 | 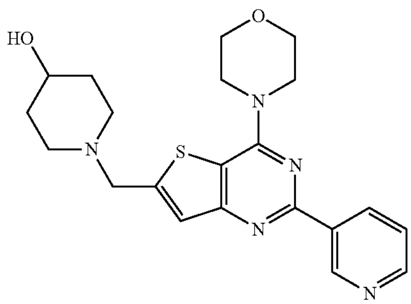 [SMILES: OC1CCN(Cc2cc3nc(-c4cccnc4)nc(N4CCOCC4)c3s2)CC1] | 1-((4-morpholino-2-(pyridin-3-yl)thieno[3,2-d]pyrimidin-6-yl)methyl)piperidin-4-ol |
| 143 | 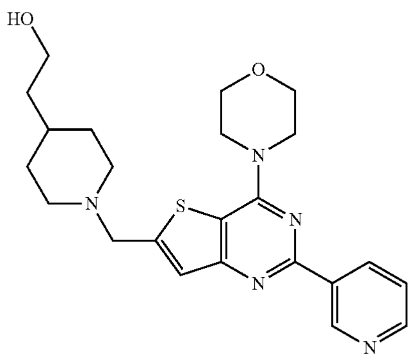 [SMILES: OCCC1CCN(Cc2cc3nc(-c4cccnc4)nc(N4CCOCC4)c3s2)CC1] | 2-(1-((4-morpholino-2-(pyridin-3-yl)thieno[3,2-d]pyrimidin-6-yl)methyl)piperidin-4-yl)ethanol |
| 144 | 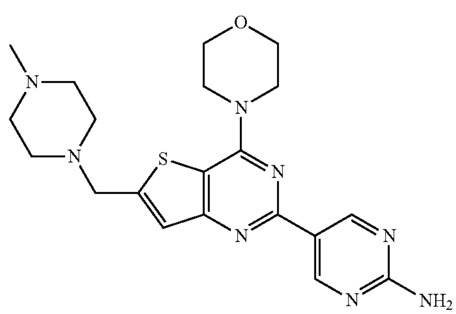 [SMILES: CN1CCN(Cc2cc3nc(-c4cnc(N)nc4)nc(N4CCOCC4)c3s2)CC1] | 5-(6-((4-methylpiperazin-1-yl)methyl)-4-morpholinothieno[3,2-d]pyrimidin-2-yl)pyrimidin-2-amine |
| 145 | 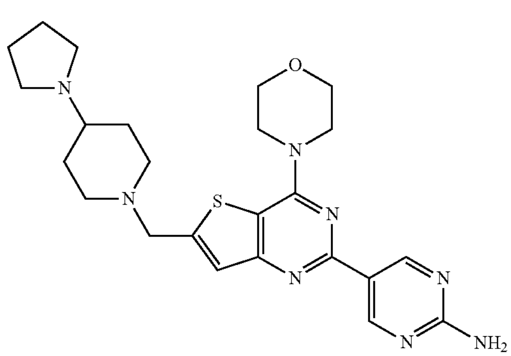 [SMILES: Nc1ncc(-c2nc(N3CCOCC3)c3sc(CN4CCC(N5CCCC5)CC4)cc3n2)cn1] | 5-(4-morpholino-6-((4-(pyrrolidin-1-yl)piperidin-1-yl)methyl)thieno[3,2-d]pyrimidin-2-yl)pyrimidin-2-amine |

TABLE 1-continued

| Compound | Structure | Name |
|---|---|---|
| 146 | 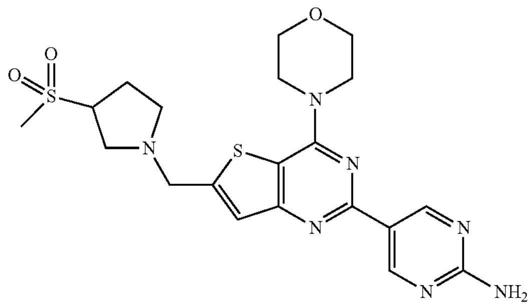 [SMILES: CS(=O)(=O)C1CCN(Cc2cc3nc(-c4cnc(N)nc4)nc(N4CCOCC4)c3s2)C1] | 5-(6-((3-(methylsulfonyl)pyrrolidin-1-yl)methyl)-4-morpholinothieno[3,2-d]pyrimidin-2-yl)pyrimidin-2-amine |
| 147 | 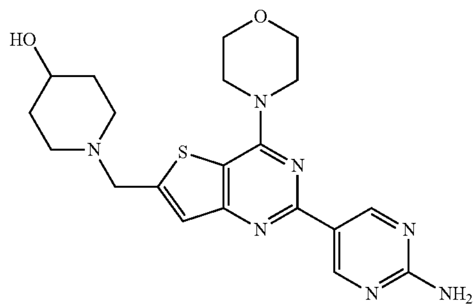 [SMILES: Nc1ncc(-c2nc(N3CCOCC3)c3sc(CN4CCC(O)CC4)cc3n2)cn1] | 1-((2-(2-aminopyrimidin-5-yl)-4-morpholinothieno[3,2-d]pyrimidin-6-yl)methyl)piperidin-4-ol |
| 148 | 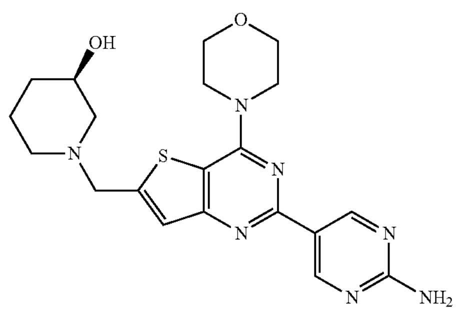 [SMILES: Nc1ncc(-c2nc(N3CCOCC3)c3sc(CN4CCC[C@@H](O)C4)cc3n2)cn1] | (R)-1-((2-(2-aminopyrimidin-5-yl)-4-morpholinothieno[3,2-d]pyrimidin-6-yl)methyl)piperidin-3-ol |
| 149 | 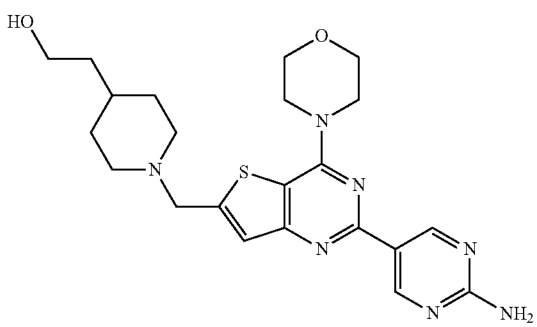 [SMILES: Nc1ncc(-c2nc(N3CCOCC3)c3sc(CN4CCC(CCO)CC4)cc3n2)cn1] | 2-(1-((2-(2-aminopyrimidin-5-yl)-4-morpholinothieno[3,2-d]pyrimidin-6-yl)methyl)piperidin-4-yl)ethanol |
| 150 | 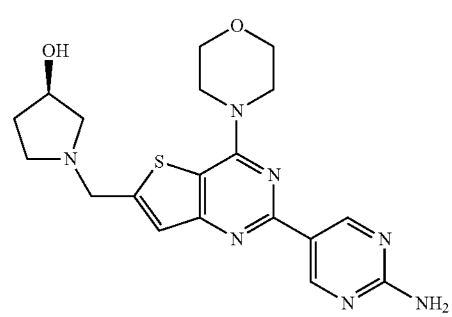 [SMILES: Nc1ncc(-c2nc(N3CCOCC3)c3sc(CN4CC[C@@H](O)C4)cc3n2)cn1] | (R)-1-((2-(2-aminopyrimidin-5-yl)-4-morpholinothieno[3,2-d]pyrimidin-6-yl)methyl)pyrrolidin-3-ol |

TABLE 1-continued

| Compound | Structure | Name |
|---|---|---|
| 151 | 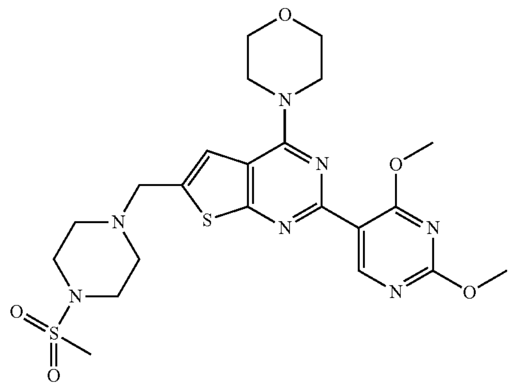 [SMILES: COc1ncc(-c2nc(N3CCOCC3)c3cc(CN4CCN(S(C)(=O)=O)CC4)sc3n2)c(OC)n1] | 2-(2,4-dimethoxypyrimidin-5-yl)-4-morpholino-6-((4-N-methylsulfonylpiperazin-1-yl)methyl)thieno[2,3-d]pyrimidine |
| 152 | 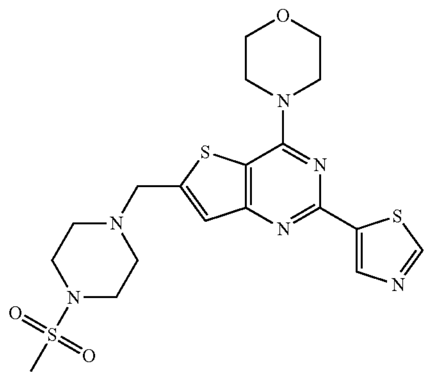 [SMILES: CS(=O)(=O)N1CCN(Cc2cc3nc(-c4cncs4)nc(N4CCOCC4)c3s2)CC1] | 4-morpholino-6-((4-N-methylsulfonylpiperazin-1-yl)methyl)-2-(thiazol-5-yl)thieno[3,2-d]pyrimidine |
| 153 | 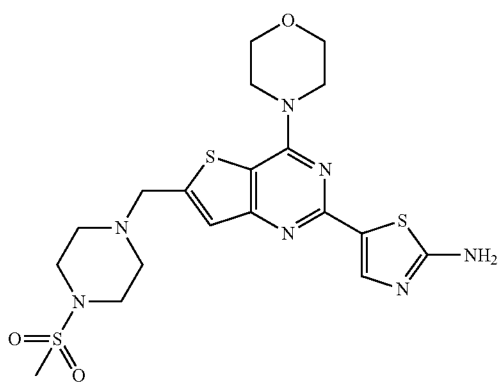 [SMILES: CS(=O)(=O)N1CCN(Cc2cc3nc(-c4cnc(N)s4)nc(N4CCOCC4)c3s2)CC1] | 5-(4-morpholino-6-((4-N-methylsulfonylpiperazin-1-yl)methyl)thieno[3,2-d]pyrimidin-2-yl)thiazol-2-amine |
| 154 | 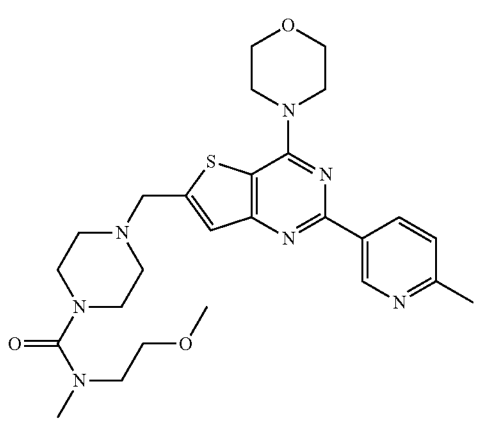 [SMILES: COCCN(C)C(=O)N1CCN(Cc2cc3nc(-c4ccc(C)nc4)nc(N4CCOCC4)c3s2)CC1] | N-(2-methoxyethyl)-N-methyl-4-((2-(6-methylpyridin-3-yl)-4-morpholinothieno[3,2-d]pyrimidin-6-yl)methyl)piperazine-1-carboxamide |

TABLE 1-continued

| Compound | Structure | Name |
|---|---|---|
| 155 | 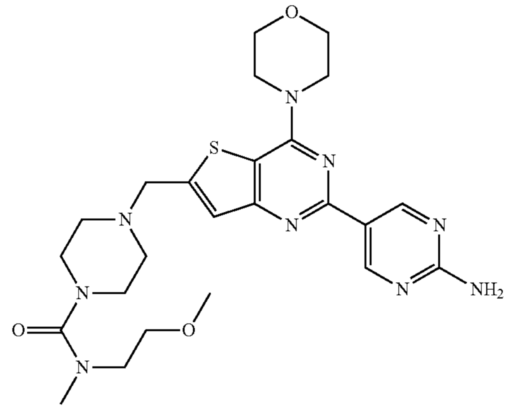 [SMILES: COCCN(C)C(=O)N1CCN(Cc2cc3nc(-c4cnc(N)nc4)nc(N4CCOCC4)c3s2)CC1] | 4-((2-(2-aminopyrimidin-5-yl)-4-morpholinothieno[3,2-d]pyrimidin-6-yl)methyl)-N-(2-methoxyethyl)-N-methylpiperazine-1-carboxamide |
| 156 | 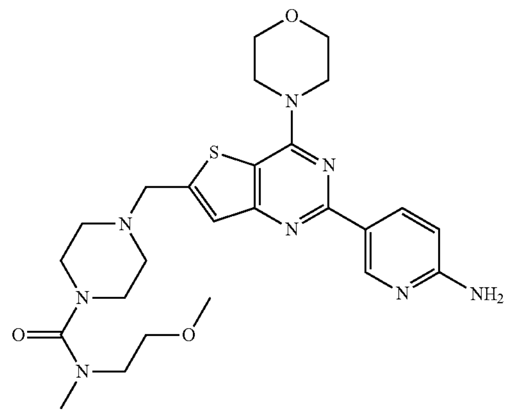 [SMILES: COCCN(C)C(=O)N1CCN(Cc2cc3nc(-c4ccc(N)nc4)nc(N4CCOCC4)c3s2)CC1] | 4-((2-(6-aminopyridin-3-yl)-4-morpholinothieno[3,2-d]pyrimidin-6-yl)methyl)-N-(2-methoxyethyl)-N-methylpiperazine-1-carboxamide |
| 157 | 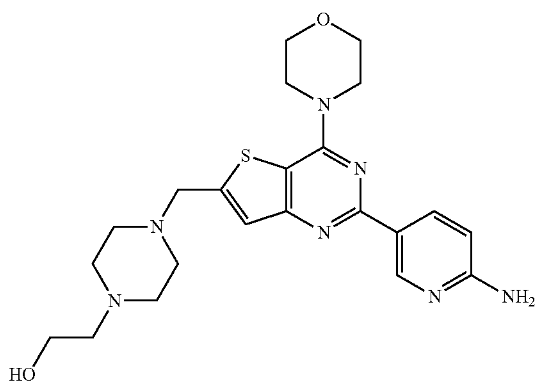 [SMILES: Nc1ccc(-c2nc(N3CCOCC3)c3sc(CN4CCN(CCO)CC4)cc3n2)cn1] | 2-(4-((2-(6-aminopyridin-3-yl)-4-morpholinothieno[3,2-d]pyrimidin-6-yl)methyl)piperazin-1-yl)ethanol |
| 158 | 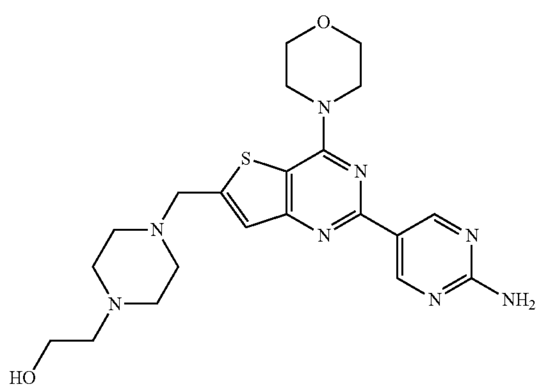 [SMILES: Nc1ncc(-c2nc(N3CCOCC3)c3sc(CN4CCN(CCO)CC4)cc3n2)cn1] | 2-(4-((2-(2-aminopyrimidin-5-yl)-4-morpholinothieno[3,2-d]pyrimidin-6-yl)methyl)piperazin-1-yl)ethanol |

TABLE 1-continued

| Compound | Structure | Name |
|---|---|---|
| 159 | 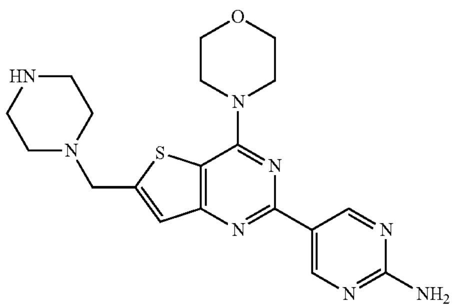 [SMILES: Nc1ncc(-c2nc(N3CCOCC3)c3sc(CN4CCNCC4)cc3n2)cn1] | 5-(4-morpholino-6-((piperazin-1-yl)methyl)thieno[3,2-d]pyrimidin-2-yl)pyrimidin-2-amine |
| 160 | 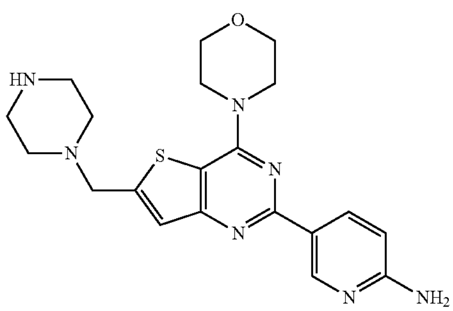 [SMILES: Nc1ccc(-c2nc(N3CCOCC3)c3sc(CN4CCNCC4)cc3n2)cn1] | 5-(4-morpholino-6-((piperazin-1-yl)methyl)thieno[3,2-d]pyrimidin-2-yl)pyridin-2-amine |
| 161 | 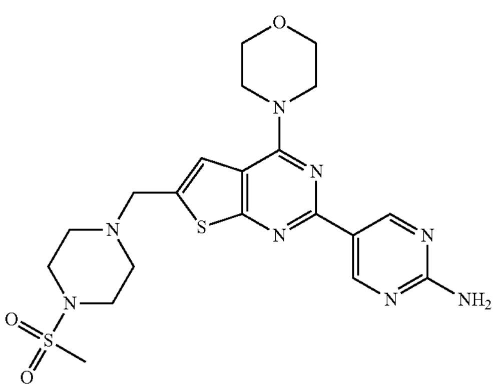 [SMILES: CS(=O)(=O)N1CCN(Cc2cc3c(N4CCOCC4)nc(-c4cnc(N)nc4)nc3s2)CC1] | 5-(4-morpholino-6-((4-N-methylsulfonylpiperazin-1-yl)methyl)thieno[2,3-d]pyrimidin-2-yl)pyrimidin-2-amine |
| 162 | 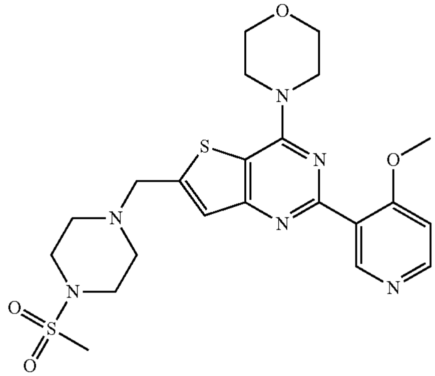 [SMILES: COc1ccncc1-c1nc(N2CCOCC2)c2sc(CN3CCN(S(C)(=O)=O)CC3)cc2n1] | 2-(4-methoxypyridin-3-yl)-4-morpholino-6-((4-N-methylsulfonylpiperazin-1-yl)methyl)thieno[3,2-d]pyrimidine |

TABLE 1-continued

| Compound | Structure | Name |
|---|---|---|
| 163 | 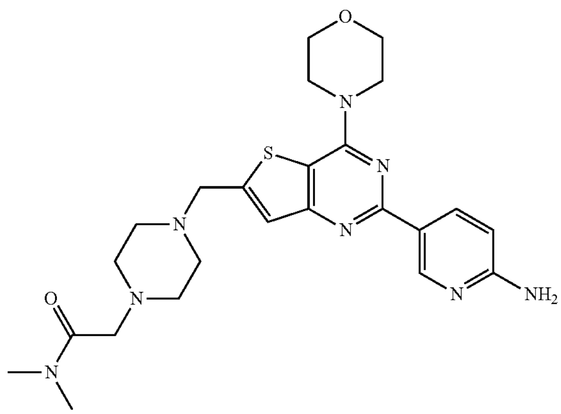 [SMILES: CN(C)C(=O)CN1CCN(Cc2cc3nc(-c4ccc(N)nc4)nc(N4CCOCC4)c3s2)CC1] | 2-(4-((2-(6-aminopyridin-3-yl)-4-morpholinothieno[3,2-d]pyrimidin-6-yl)methyl)piperazin-1-yl)-N,N-dimethylacetamide |
| 164 | 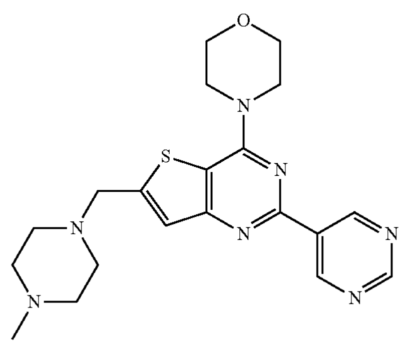 [SMILES: CN1CCN(Cc2cc3nc(-c4cncnc4)nc(N4CCOCC4)c3s2)CC1] | 6-((4-methylpiperazin-1-yl)methyl)-4-morpholino-2-(pyrimidin-5-yl)thieno[3,2-d]pyrimidine |
| 165 | 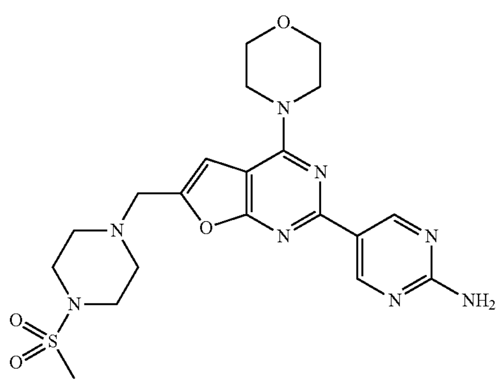 [SMILES: CS(=O)(=O)N1CCN(Cc2cc3c(N4CCOCC4)nc(-c4cnc(N)nc4)nc3o2)CC1] | 5-(4-morpholino-6-((4-N-methylsulfonylpiperazin-1-yl)methyl)furo[2,3-d]pyrimidin-2-yl)pyrimidin-2-amine |
| 166 | 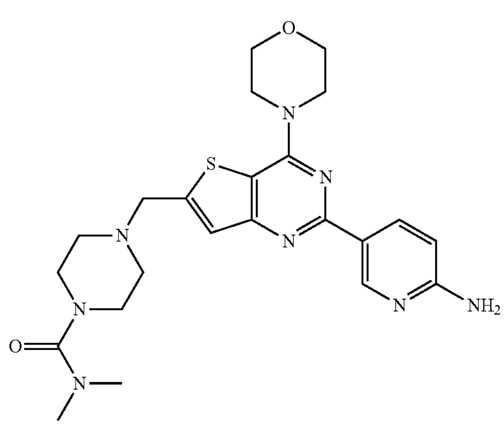 | 4-((2-(6-aminopyridin-3-yl)-4-morpholinothieno[3,2-d]pyrimidin-6-yl)methyl)-N,N-dimethylpiperazine-1-carboxamide |

TABLE 1-continued

| Compound | Structure | Name |
|---|---|---|
| 167 | 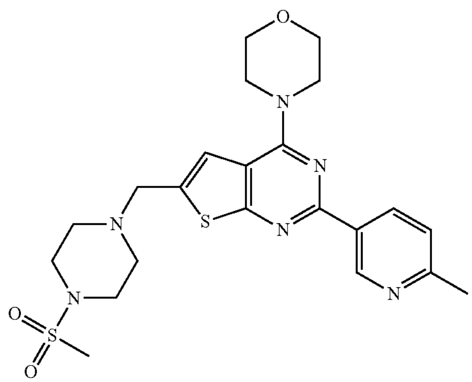 [SMILES: Cc1ccc(-c2nc(N3CCOCC3)c3cc(CN4CCN(S(C)(=O)=O)CC4)sc3n2)cn1] | 2-(6-methylpyridin-3-yl)-4-morpholino-6-((4-N-methylsulfonylpiperazin-1-yl)methyl)thieno[2,3-d]pyrimidine |
| 168 | 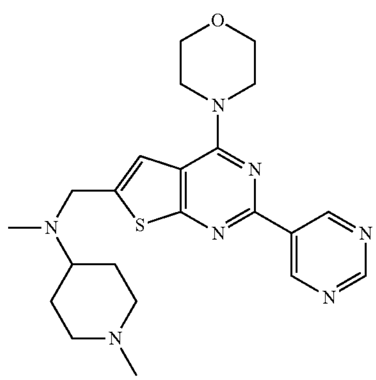 [SMILES: CN1CCC(N(C)Cc2cc3c(N4CCOCC4)nc(-c4cncnc4)nc3s2)CC1] | N,1-dimethyl-N-((4-morpholino-2-(pyrimidin-5-yl)thieno[2,3-d]pyrimidin-6-yl)methyl)piperidin-4-amine |
| 169 | 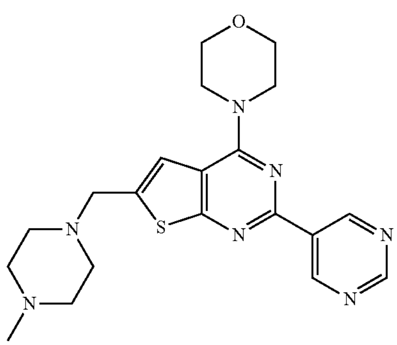 [SMILES: CN1CCN(Cc2cc3c(N4CCOCC4)nc(-c4cncnc4)nc3s2)CC1] | 6-((4-methylpiperazin-1-yl)methyl)-4-morpholino-2-(pyrimidin-5-yl)thieno[2,3-d]pyrimidine |
| 170 | 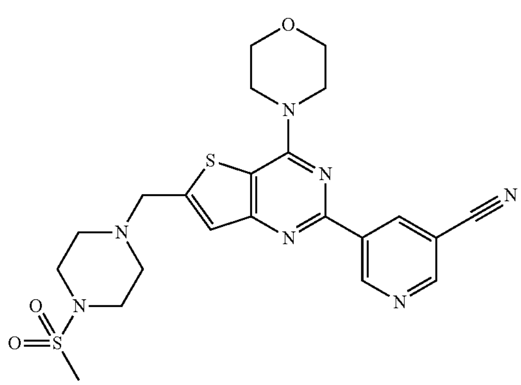 [SMILES: CS(=O)(=O)N1CCN(Cc2cc3nc(-c4cncc(C#N)c4)nc(N4CCOCC4)c3s2)CC1] | 5-(4-morpholino-6-((piperazin-1-yl)methyl)thieno[3,2-d]pyrimidin-2-yl)pyridine-3-carbonitrile |

TABLE 1-continued
| Compound | Structure | Name |
|---|---|---|
| 171 | 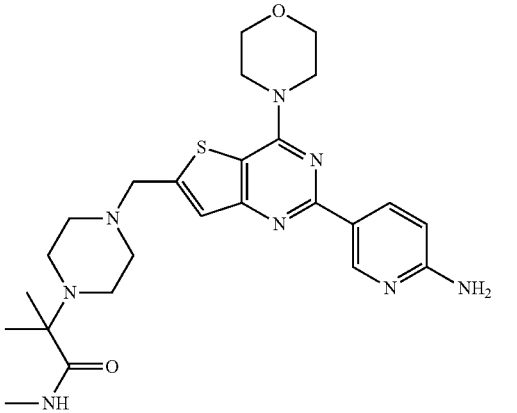 [SMILES: CNC(=O)C(C)(C)N1CCN(Cc2cc3nc(-c4ccc(N)nc4)nc(N4CCOCC4)c3s2)CC1] | 2-(4-((2-(6-aminopyridin-3-yl)-4-morpholinothieno[3,2-d]pyrimidin-6-yl)methyl)piperazin-1-yl)-N,2-dimethylpropanamide |
| 172 | 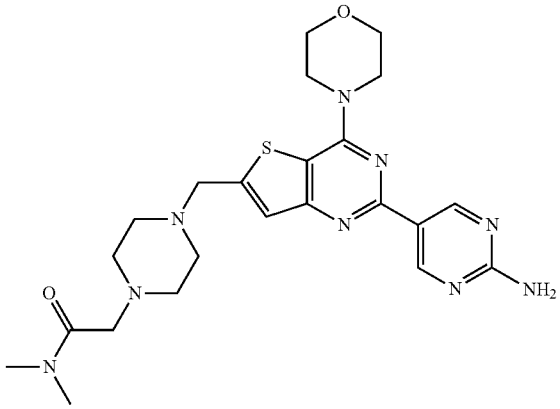 [SMILES: CN(C)C(=O)CN1CCN(Cc2cc3nc(-c4cnc(N)nc4)nc(N4CCOCC4)c3s2)CC1] | 2-(4-((2-(2-aminopyrimidin-5-yl)-4-morpholinothieno[3,2-d]pyrimidin-6-yl)methyl)piperazin-1-yl)-N,N-dimethylacetamide |
| 173 | 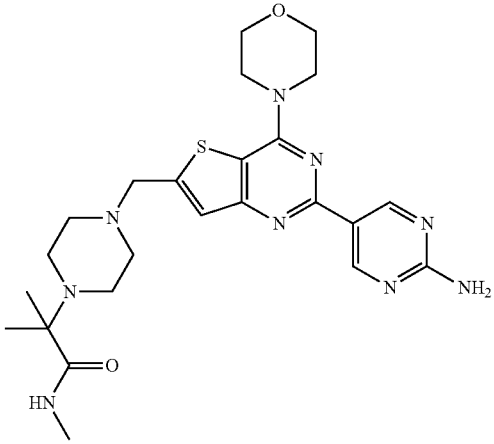 [SMILES: CNC(=O)C(C)(C)N1CCN(Cc2cc3nc(-c4cnc(N)nc4)nc(N4CCOCC4)c3s2)CC1] | 2-(4-((2-(2-aminopyrimidin-5-yl)-4-morpholinothieno[3,2-d]pyrimidin-6-yl)methyl)piperazin-1-yl)-N,2-dimethylpropanamide |

TABLE 1-continued

| Compound | Structure | Name |
| --- | --- | --- |
| 174 | 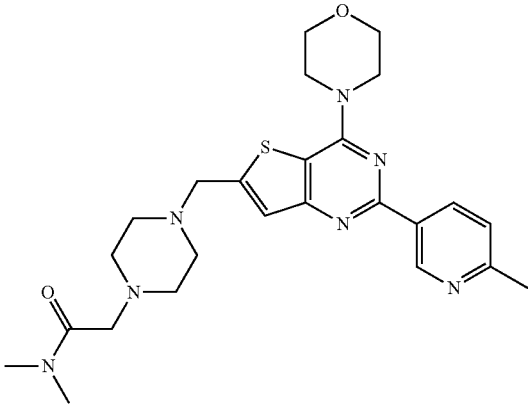 | N,N-dimethyl-2-(4-((2-(6-methylpyridin-3-yl)-4-morpholinothieno[3,2-d]pyrimidin-6-yl)methyl)piperazin-1-yl)acetamide |
| 175 | 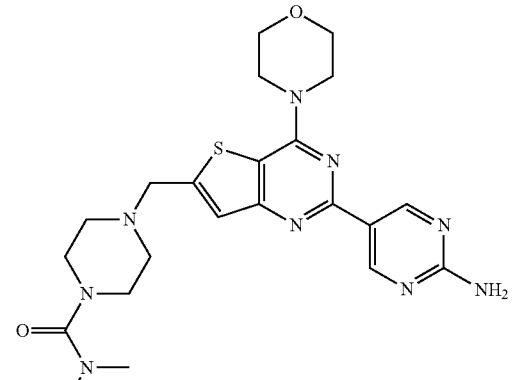 | 4-((2-(2-aminopyrimidin-5-yl)-4-morpholinothieno[3,2-d]pyrimidin-6-yl)methyl)-N,N-dimethylpiperazine-1-carboxamide |
| 176 | 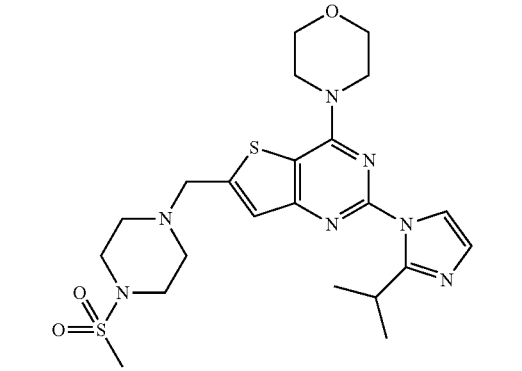 [SMILES: CC(C)c1nccn1-c1nc(N2CCOCC2)c2sc(CN3CCN(S(C)(=O)=O)CC3)cc2n1] | 2-(2-isopropyl-1H-imidazol-1-yl)-4-morpholino-6-((piperazin-1-yl)methyl)thieno[3,2-d]pyrimidine |
| 177 | 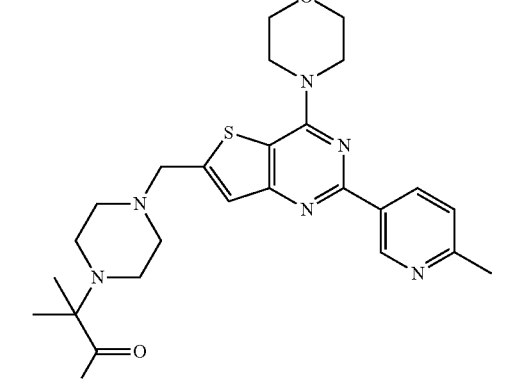 | N,2-dimethyl-2-(4-((2-(6-methylpyridin-3-yl)-4-morpholinothieno[3,2-d]pyrimidin-6-yl)methyl)piperazin-1-yl)propanamide |

TABLE 1-continued

| Compound | Structure | Name |
|---|---|---|
| 178 | 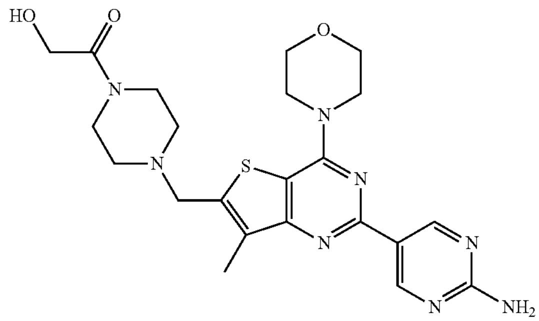 [SMILES: Cc1c(CN2CCN(C(=O)CO)CC2)sc2c(N3CCOCC3)nc(-c3cnc(N)nc3)nc12] | 1-(4-((2-(2-aminopyrimidin-5-yl)-7-methyl-4-morpholinothieno[3,2-d]pyrimidin-6-yl)methyl)piperazin-1-yl)-2-hydroxyethanone |
| 179 | 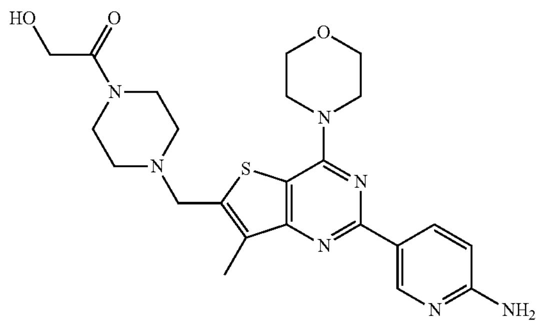 [SMILES: Cc1c(CN2CCN(C(=O)CO)CC2)sc2c(N3CCOCC3)nc(-c3ccc(N)nc3)nc12] | 1-(4-((2-(6-aminopyridin-3-yl)-7-methyl-4-morpholinothieno[3,2-d]pyrimidin-6-yl)methyl)piperazin-1-yl)-2-hydroxyethanone |
| 180 | 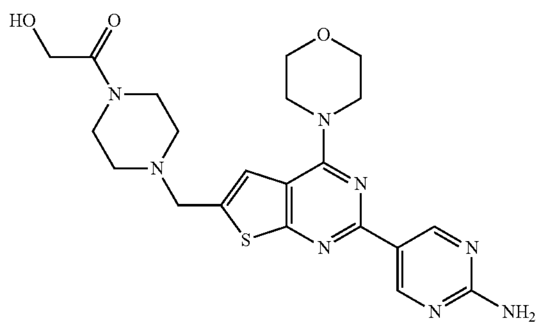 [SMILES: Nc1ncc(-c2nc(N3CCOCC3)c3cc(CN4CCN(C(=O)CO)CC4)sc3n2)cn1] | 1-(4-((2-(2-aminopyrimidin-5-yl)-4-morpholinothieno[2,3-d]pyrimidin-6-yl)methyl)piperazin-1-yl)-2-hydroxyethanone |
| 181 | 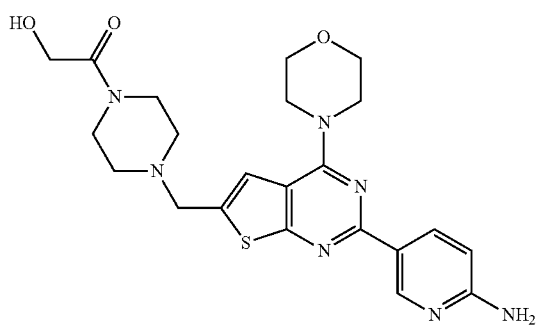 [SMILES: Nc1ccc(-c2nc(N3CCOCC3)c3cc(CN4CCN(C(=O)CO)CC4)sc3n2)cn1] | 1-(4-((2-(6-aminopyridin-3-yl)-4-morpholinothieno[2,3-d]pyrimidin-6-yl)methyl)piperazin-1-yl)-2-hydroxyethanone |
| 182 | 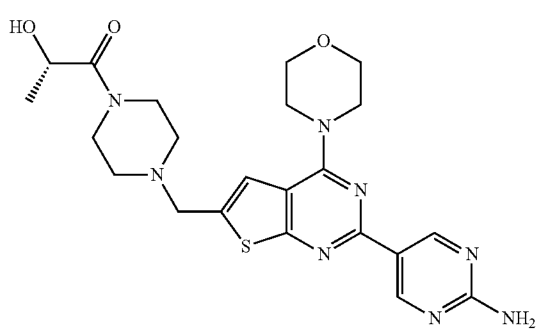 [SMILES: C[C@H](O)C(=O)N1CCN(Cc2cc3c(N4CCOCC4)nc(-c4cnc(N)nc4)nc3s2)CC1] | (S)-1-(4-((2-(2-aminopyrimidin-5-yl)-4-morpholinothieno[2,3-d]pyrimidin-6-yl)methyl)piperazin-1-yl)-2-hydroxypropan-1-one |

TABLE 1-continued

| Compound | Structure | Name |
|---|---|---|
| 183 | 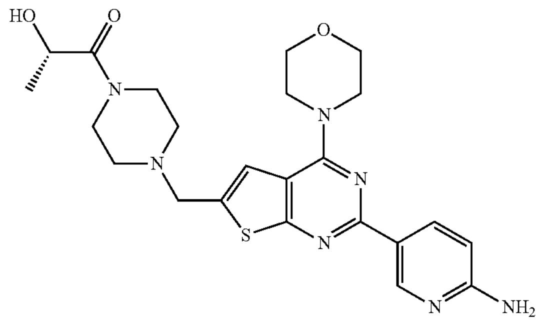 [SMILES: C[C@H](O)C(=O)N1CCN(Cc2cc3c(N4CCOCC4)nc(-c4ccc(N)nc4)nc3s2)CC1] | (S)-1-(4-((2-(6-aminopyridin-3-yl)-4-morpholinothieno[2,3-d]pyrimidin-6-yl)methyl)piperazin-1-yl)-2-hydroxypropan-1-one |
| 184 | 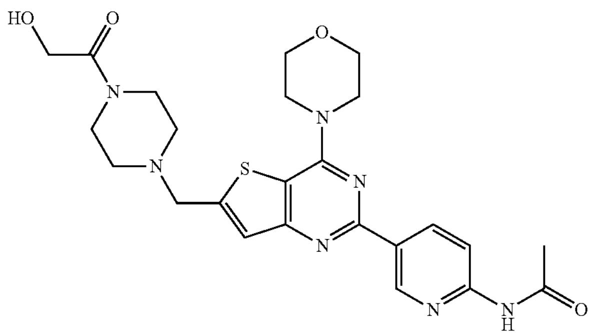 [SMILES: CC(=O)Nc1ccc(-c2nc(N3CCOCC3)c3sc(CN4CCN(C(=O)CO)CC4)cc3n2)cn1] | N-(5-(6-((4-(2-hydroxyacetyl)piperazin-1-yl)methyl)-4-morpholinothieno[3,2-d]pyrimidin-2-yl)pyridin-2-yl)acetamide |
| 185 | 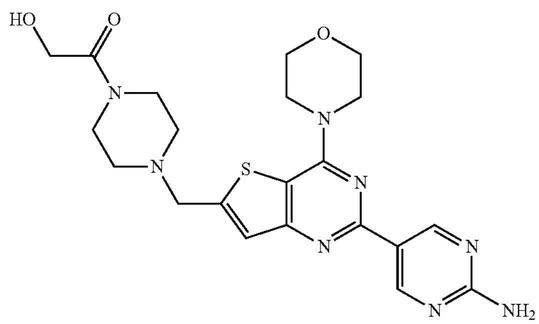 [SMILES: Nc1ncc(-c2nc(N3CCOCC3)c3sc(CN4CCN(C(=O)CO)CC4)cc3n2)cn1] | 1-(4-((2-(2-aminopyrimidin-5-yl)-4-morpholinothieno[3,2-d]pyrimidin-6-yl)methyl)piperazin-1-yl)-2-hydroxyethanone |
| 186 | 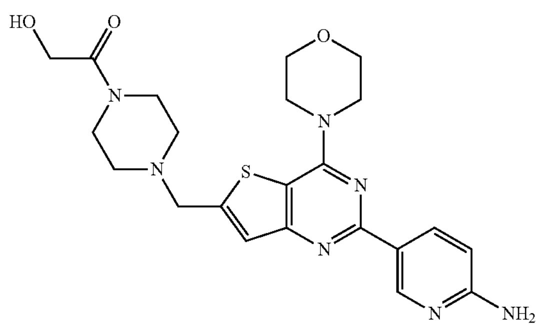 [SMILES: Nc1ccc(-c2nc(N3CCOCC3)c3sc(CN4CCN(C(=O)CO)CC4)cc3n2)cn1] | 1-(4-((2-(6-aminopyridin-3-yl)-4-morpholinothieno[3,2-d]pyrimidin-6-yl)methyl)piperazin-1-yl)-2-hydroxyethanone |
| 187 | 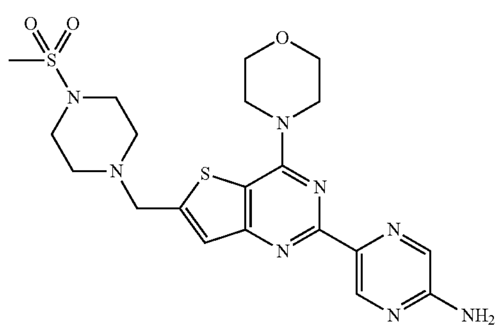 [SMILES: CS(=O)(=O)N1CCN(Cc2cc3nc(-c4cnc(N)cn4)nc(N4CCOCC4)c3s2)CC1] | 5-(4-morpholino-6-((piperazin-1-yl)methyl)thieno[3,2-d]pyrimidin-2-yl)pyrazin-2-amine |

TABLE 1-continued

| Compound | Structure | Name |
|---|---|---|
| 188 | 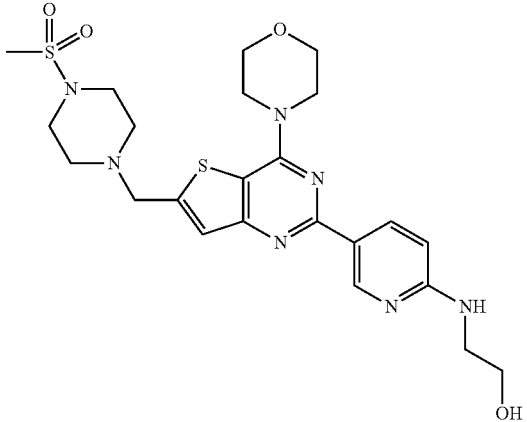 [SMILES: CS(=O)(=O)N1CCN(Cc2cc3nc(-c4ccc(NCCO)nc4)nc(N4CCOCC4)c3s2)CC1] | 2-(5-(4-morpholino-6-((piperazin-1-yl)methyl)thieno[3,2-d]pyrimidin-2-yl)pyridin-2-ylamino)ethanol |
| 189 | 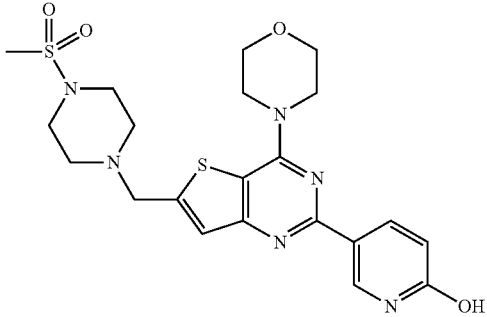 [SMILES: CS(=O)(=O)N1CCN(Cc2cc3nc(-c4ccc(O)nc4)nc(N4CCOCC4)c3s2)CC1] | 5-(4-morpholino-6-((4-N-methylsulfonylpiperazin-1-yl)methyl)thieno[3,2-d]pyrimidin-2-yl)pyridin-2-ol |
| 190 | 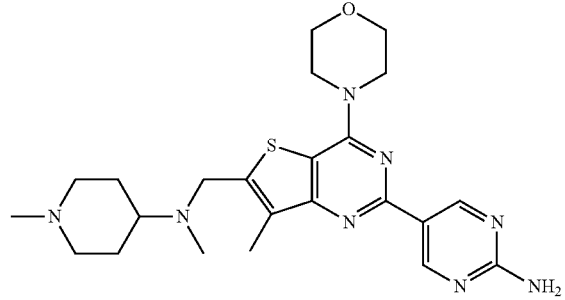 | 5-(6-((1-methylpiperidin-4-yl-N-methylamino)methyl)-7-methyl-4-morpholinothieno[3,2-d]pyrimidin-2-yl)pyrimidin-2-amine |
| 191 | 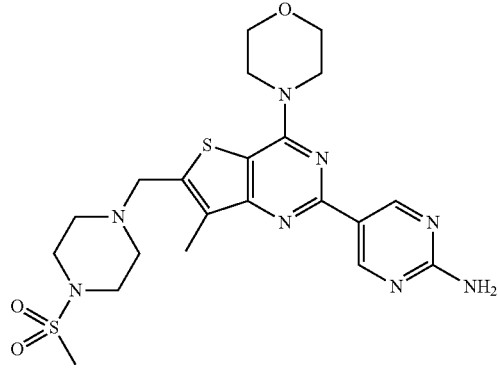 [SMILES: Cc1c(CN2CCN(S(C)(=O)=O)CC2)sc2c(N3CCOCC3)nc(-c3cnc(N)nc3)nc12] | 5-(7-methyl-4-morpholino-6-((4-N-methylsulfonylpiperazin-1-yl)methyl)thieno[3,2-d]pyrimidin-2-yl)pyrimidin-2-amine |

TABLE 1-continued

| Compound | Structure | Name |
|---|---|---|
| 192 | 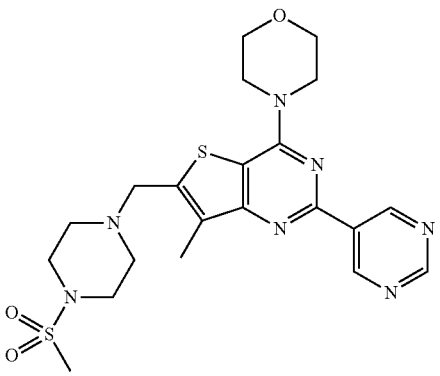 [SMILES: Cc1c(CN2CCN(S(C)(=O)=O)CC2)sc2c(N3CCOCC3)nc(-c3cncnc3)nc12] | 7-methyl-4-morpholino-6-((4-N-methylsulfonylpiperazin-1-yl)methyl)-2-(pyrimidin-5-yl)thieno[3,2-d]pyrimidine |
| 193 | 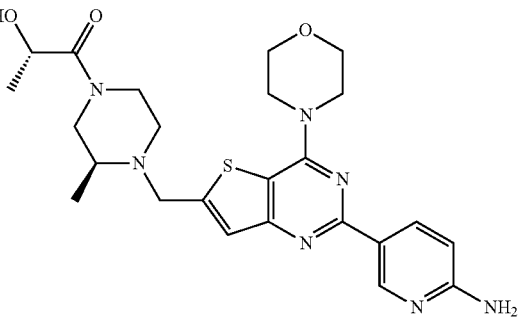 | (S)-1-((S)-4-((2-(6-aminopyridin-3-yl)-4-morpholinothieno[3,2-d]pyrimidin-6-yl)methyl)-3-methylpiperazin-1-yl)-2-hydroxypropan-1-one |
| 194 | 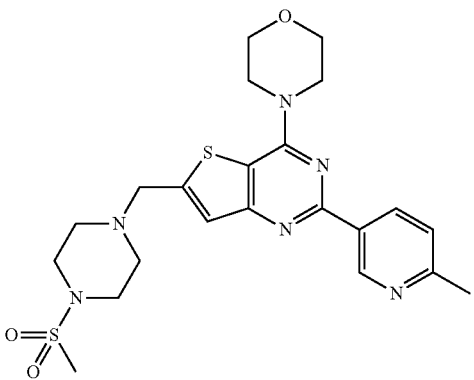 [SMILES: Cc1ccc(-c2nc(N3CCOCC3)c3sc(CN4CCN(S(C)(=O)=O)CC4)cc3n2)cn1] | 2-(6-methylpyridin-3-yl)-4-morpholino-6-((4-N-methylsulfonylpiperazin-1-yl)methyl)thieno[3,2-d]pyrimidine |
| 195 | 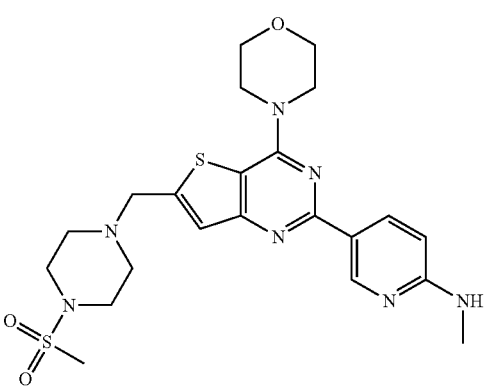 [SMILES: CNc1ccc(-c2nc(N3CCOCC3)c3sc(CN4CCN(S(C)(=O)=O)CC4)cc3n2)cn1] | N-methyl-5-(4-morpholino-6-((4-N-methylsulfonylpiperazin-1-yl)methyl)thieno[3,2-d]pyrimidin-2-yl)pyridin-2-amine |

TABLE 1-continued

| Compound | Structure | Name |
|---|---|---|
| 196 | 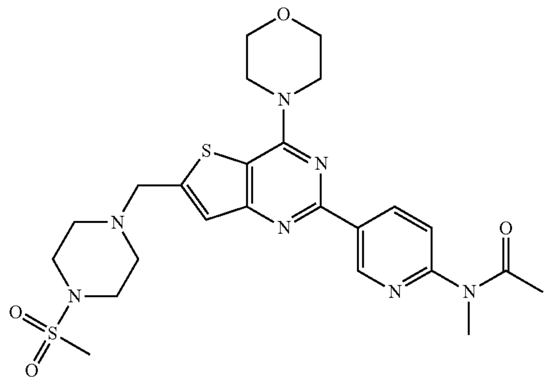 [SMILES: CC(=O)N(C)c1ccc(-c2nc(N3CCOCC3)c3sc(CN4CCN(S(C)(=O)=O)CC4)cc3n2)cn1] | N-methyl-N-(5-(4-morpholino-6-((piperazin-1-yl)methyl)thieno[3,2-d]pyrimidin-2-yl)pyridin-2-yl)acetamide |
| 197 | 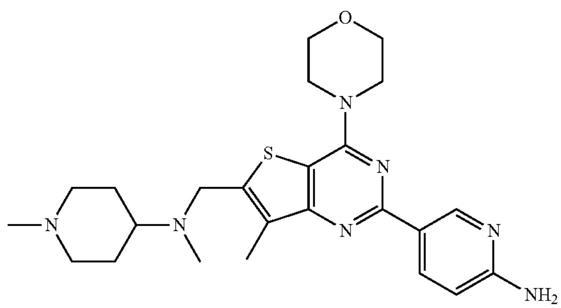 [SMILES: Cc1c(CN(C)C2CCN(C)CC2)sc2c(N3CCOCC3)nc(-c3ccc(N)nc3)nc12] | 5-(6-((1-methylpiperidin-4-ylamino)N-methylaminomethyl)-7-methyl-4-morpholinothieno[3,2-d]pyrimidin-2-yl)pyridin-2-amine |
| 198 | 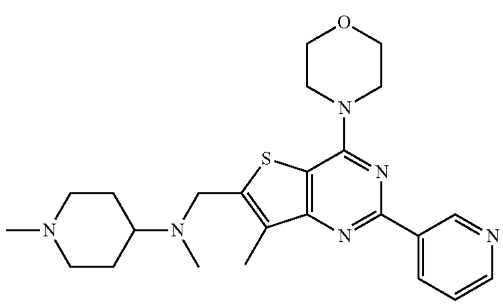 [SMILES: Cc1c(CN(C)C2CCN(C)CC2)sc2c(N3CCOCC3)nc(-c3cccnc3)nc12] | N,1-dimethyl-N-((7-methyl-4-morpholino-2-(pyridin-3-yl)thieno[3,2-d]pyrimidin-6-yl)methyl)piperidin-4-amine |
| 199 | 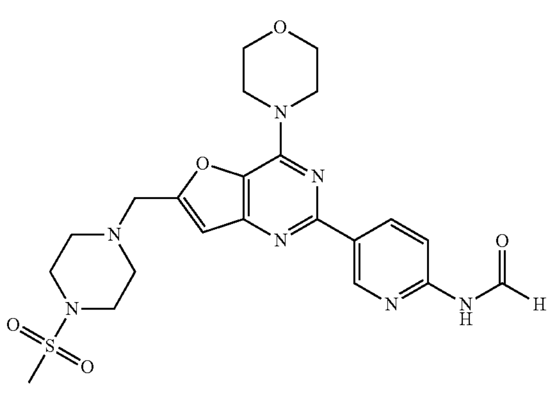 [SMILES: CS(=O)(=O)N1CCN(Cc2cc3nc(-c4ccc(NC=O)nc4)nc(N4CCOCC4)c3o2)CC1] | N-(5-(4-morpholino-6-((4-N-methylsulfonylpiperazin-1-yl)methyl)furo[3,2-d]pyrimidin-2-yl)pyridin-2-yl)formamide |

TABLE 1-continued

| Compound | Structure | Name |
|---|---|---|
| 200 | 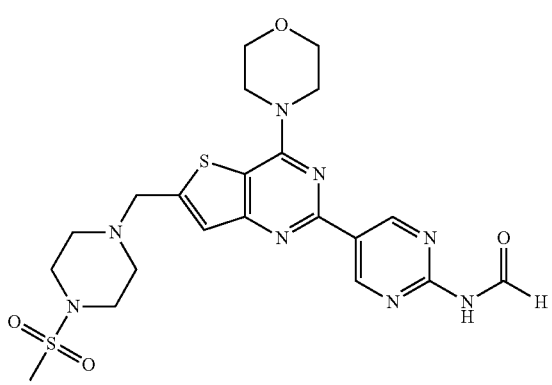 [SMILES: CS(=O)(=O)N1CCN(Cc2cc3nc(-c4cnc(NC=O)nc4)nc(N4CCOCC4)c3s2)CC1] | N-(5-(4-morpholino-6-((4-N-methylsulfonylpiperazin-1-yl)methyl)thieno[3,2-d]pyrimidin-2-yl)pyrimidin-2-yl)formamide |
| 201 | 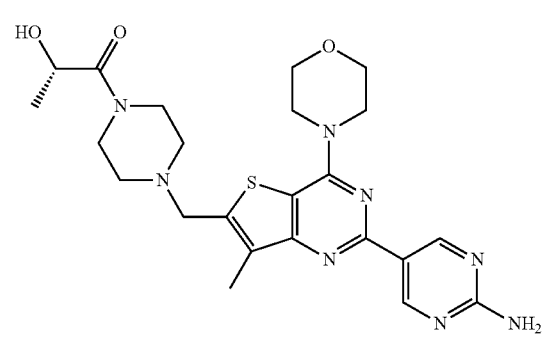 | (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one |
| 202 | 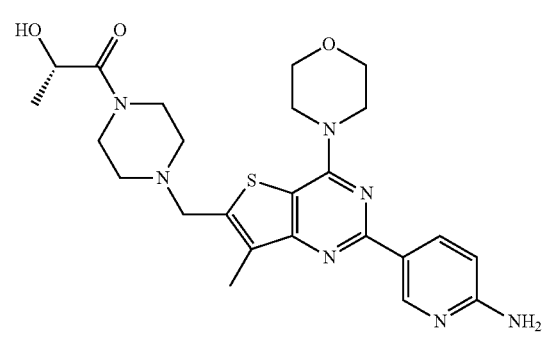 [SMILES: Cc1c(CN2CCN(C(=O)[C@H](C)O)CC2)sc2c(N3CCOCC3)nc(-c3ccc(N)nc3)nc12] | (S)-1-(4-((2-(6-aminopyridin-3-yl)-7-methyl-4-morpholinothieno[3,2-d]pyrimidin-6-yl)methyl)piperazin-1-yl)-2-hydroxypropan-1-one |
| 203 | 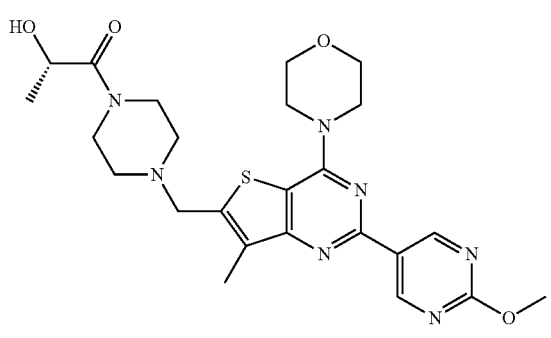 [SMILES: COc1ncc(-c2nc(N3CCOCC3)c3sc(CN4CCN(C(=O)[C@H](C)O)CC4)c(C)c3n2)cn1] | (S)-2-hydroxy-1-(4-((2-(2-methoxypyrimidin-5-yl)-7-methyl-4-morpholinothieno[3,2-d]pyrimidin-6-yl)methyl)piperazin-1-yl)propan-1-one |

TABLE 1-continued

| Compound | Structure | Name |
|---|---|---|
| 204 | 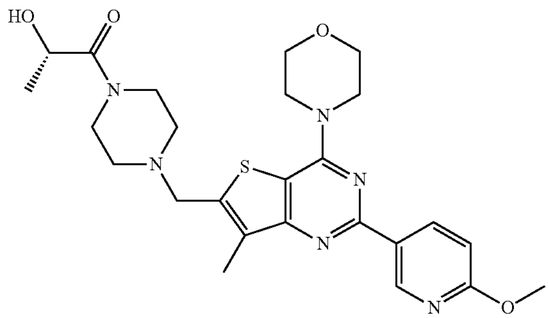 [SMILES: COc1ccc(-c2nc(N3CCOCC3)c3sc(CN4CCN(C(=O)[C@H](C)O)CC4)c(C)c3n2)cn1] | (S)-2-hydroxy-1-(4-((2-(6-methoxypyridin-3-yl)-7-methyl-4-morpholinothieno[3,2-d]pyrimidin-6-yl)methyl)piperazin-1-yl)propan-1-one |
| 205 | 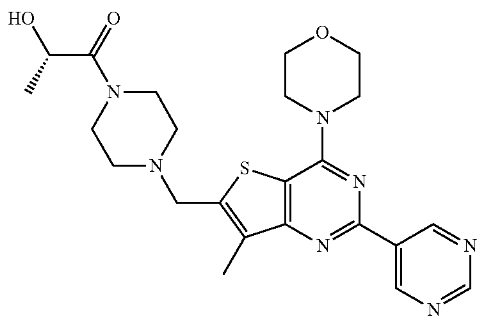 [SMILES: Cc1c(CN2CCN(C(=O)[C@H](C)O)CC2)sc2c(N3CCOCC3)nc(-c3cncnc3)nc12] | (S)-2-hydroxy-1-(4-((7-methyl-4-morpholino-2-(pyrimidin-5-yl)thieno[3,2-d]pyrimidin-6-yl)methyl)piperazin-1-yl)propan-1-one |
| 206 | 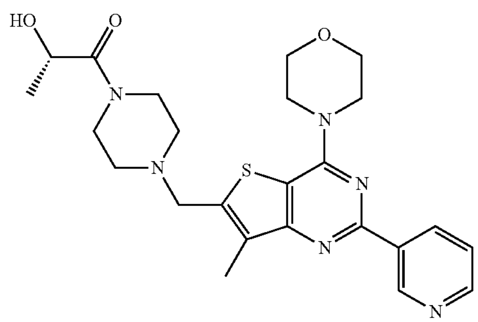 [SMILES: Cc1c(CN2CCN(C(=O)[C@H](C)O)CC2)sc2c(N3CCOCC3)nc(-c3cccnc3)nc12] | (S)-2-hydroxy-1-(4-((7-methyl-4-morpholino-2-(pyridin-3-yl)thieno[3,2-d]pyrimidin-6-yl)methyl)piperazin-1-yl)propan-1-one |
| 207 | 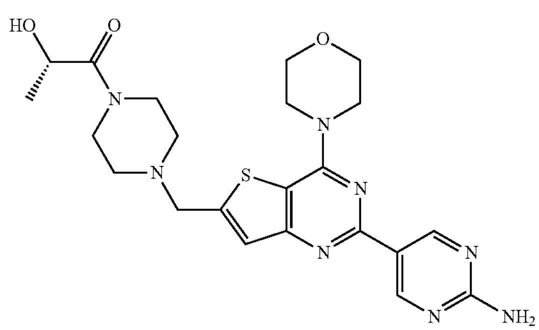 [SMILES: C[C@H](O)C(=O)N1CCN(Cc2cc3nc(-c4cnc(N)nc4)nc(N4CCOCC4)c3s2)CC1] | (S)-1-(4-((2-(2-aminopyrimidin-5-yl)-4-morpholinothieno[3,2-d]pyrimidin-6-yl)methyl)piperazin-1-yl)-2-hydroxypropan-1-one |
| 208 | 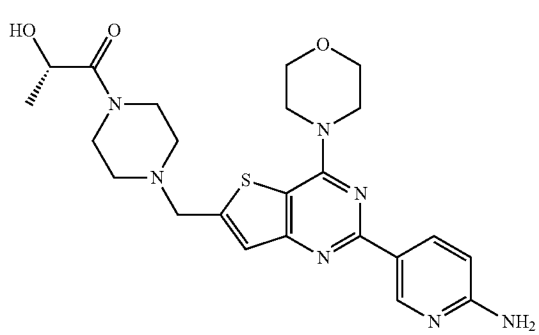 [SMILES: C[C@H](O)C(=O)N1CCN(Cc2cc3nc(-c4ccc(N)nc4)nc(N4CCOCC4)c3s2)CC1] | (S)-1-(4-((2-(6-aminopyridin-3-yl)-4-morpholinothieno[3,2-d]pyrimidin-6-yl)methyl)piperazin-1-yl)-2-hydroxypropan-1-one |

TABLE 1-continued

| Compound | Structure | Name |
|---|---|---|
| 209 | 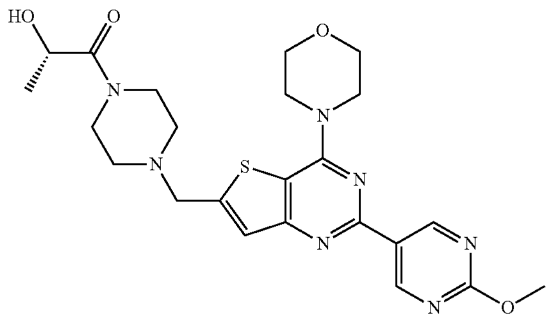 [SMILES: COc1ncc(-c2nc(N3CCOCC3)c3sc(CN4CCN(C(=O)[C@H](C)O)CC4)cc3n2)cn1] | (S)-2-hydroxy-1-(4-((2-(2-methoxypyrimidin-5-yl)-4-morpholinothieno[3,2-d]pyrimidin-6-yl)methyl)piperazin-1-yl)propan-1-one |
| 210 | 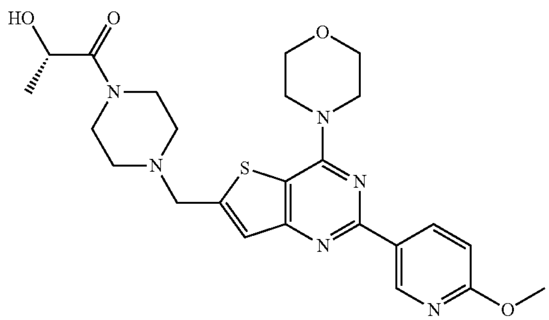 [SMILES: COc1ccc(-c2nc(N3CCOCC3)c3sc(CN4CCN(C(=O)[C@H](C)O)CC4)cc3n2)cn1] | (S)-2-hydroxy-1-(4-((2-(6-methoxypyridin-3-yl)-4-morpholinothieno[3,2-d]pyrimidin-6-yl)methyl)piperazin-1-yl)propan-1-one |
| 211 | 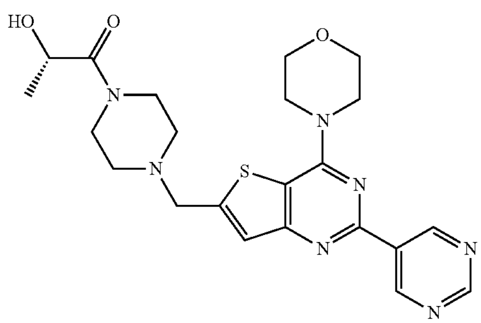 [SMILES: C[C@H](O)C(=O)N1CCN(Cc2cc3nc(-c4cncnc4)nc(N4CCOCC4)c3s2)CC1] | (S)-2-hydroxy-1-(4-((4-morpholino-2-(pyrimidin-5-yl)thieno[3,2-d]pyrimidin-6-yl)methyl)piperazin-1-yl)propan-1-one |
| 212 | 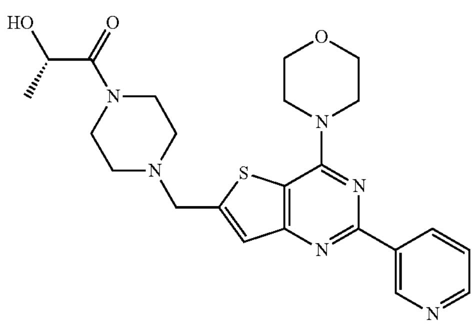 [SMILES: C[C@H](O)C(=O)N1CCN(Cc2cc3nc(-c4cccnc4)nc(N4CCOCC4)c3s2)CC1] | (S)-2-hydroxy-1-(4-((4-morpholino-2-(pyridin-3-yl)thieno[3,2-d]pyrimidin-6-yl)methyl)piperazin-1-yl)propan-1-one |
| 213 | 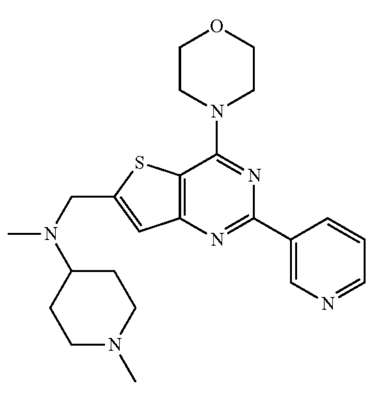 [SMILES: CN1CCC(N(C)Cc2cc3nc(-c4cccnc4)nc(N4CCOCC4)c3s2)CC1] | N,1-dimethyl-N-((4-morpholino-2-(pyridin-3-yl)thieno[3,2-d]pyrimidin-6-yl)methyl)piperidin-4-amine |

TABLE 1-continued

| Compound | Structure | Name |
|---|---|---|
| 214 | 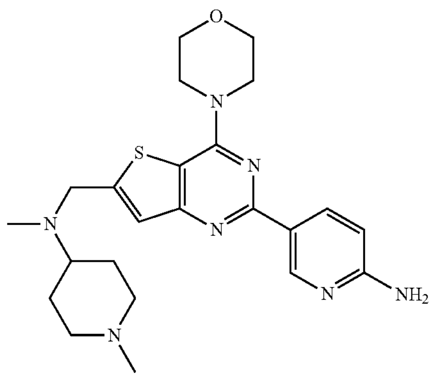 [SMILES: CN1CCC(N(C)Cc2cc3nc(-c4ccc(N)nc4)nc(N4CCOCC4)c3s2)CC1] | N,1-dimethyl-N-((4-morpholino-2-(6-aminopyridin-3-yl)thieno[3,2-d]pyrimidin-6-yl)methyl)piperidin-4-amine |
| 215 | 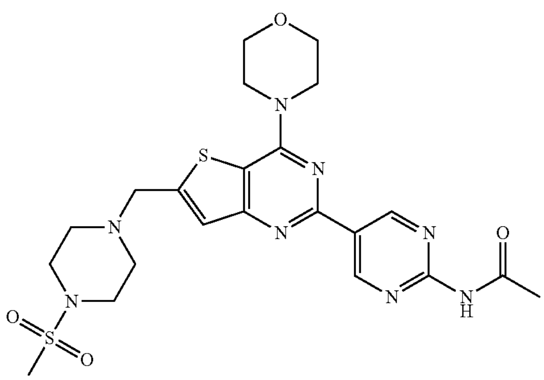 [SMILES: CC(=O)Nc1ncc(-c2nc(N3CCOCC3)c3sc(CN4CCN(S(C)(=O)=O)CC4)cc3n2)cn1] | N-(5-(4-morpholino-6-((4-N-methylsulfonylpiperazin-1-yl)methyl)thieno[3,2-d]pyrimidin-2-yl)pyrimidin-2-yl)acetamide |
| 216 | 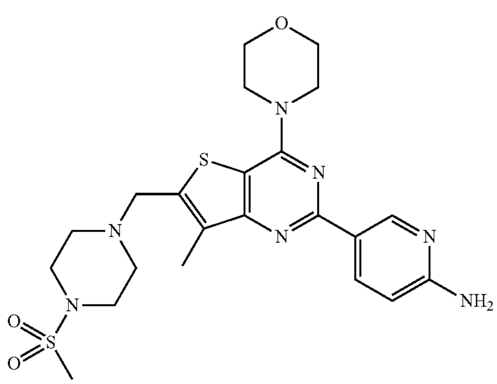 [SMILES: Cc1c(CN2CCN(S(C)(=O)=O)CC2)sc2c(N3CCOCC3)nc(-c3ccc(N)nc3)nc12] | 5-(6-((4-N-methylsulfonylpiperazin-1-yl)methyl)-7-methyl-4-morpholinothieno[3,2-d]pyrimidin-2-yl)pyridin-2-amine |
| 217 | 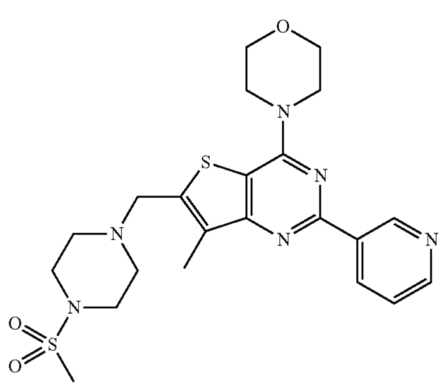 [SMILES: Cc1c(CN2CCN(S(C)(=O)=O)CC2)sc2c(N3CCOCC3)nc(-c3cccnc3)nc12] | 7-methyl-4-morpholino-6-((4-N-methylsulfonylpiperazin-1-yl)methyl)-2-(pyridin-3-yl)thieno[3,2-d]pyrimidine |

TABLE 1-continued

| Compound | Structure | Name |
|---|---|---|
| 218 | 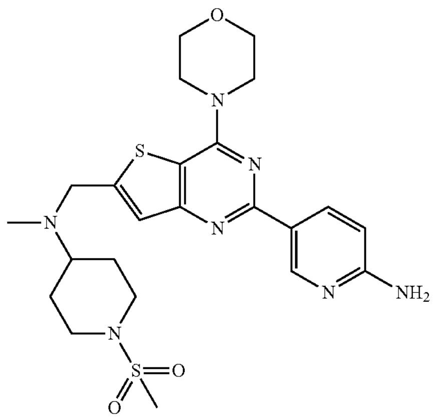 [SMILES: CN(Cc1cc2nc(-c3ccc(N)nc3)nc(N3CCOCC3)c2s1)C1CCN(S(C)(=O)=O)CC1] | N-((2-(2-aminopyridin-5-yl)-4-morpholinothieno[3,2-d]pyrimidin-6-yl)methyl)-N-methyl(N-1-methylsulfonyl)piperidin-4-amine |
| 219 | 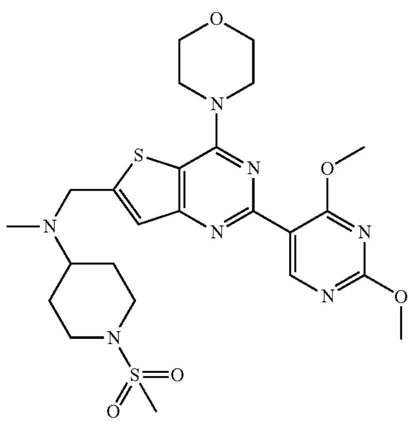 | N-((2-(2,4-dimethoxypyrimidin-5-yl)-4-morpholinothieno[3,2-d]pyrimidin-6-yl)methyl)-N-methyl(N-1-methylsulfonyl)piperidin-4-amine |
| 220 | 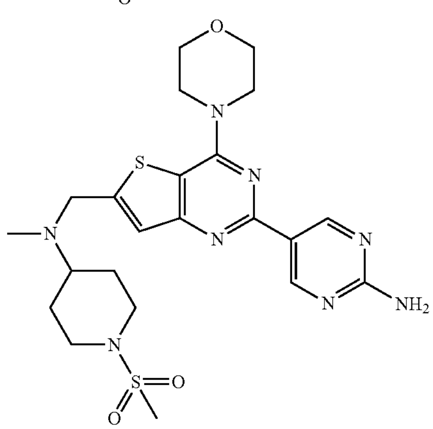 | N-((2-(2-aminopyrimidin-5-yl)-4-morpholinothieno[3,2-d]pyrimidin-6-yl)methyl)-N-methyl(N-1-methylsulfonyl)piperidin-4-amine |
| 221 | 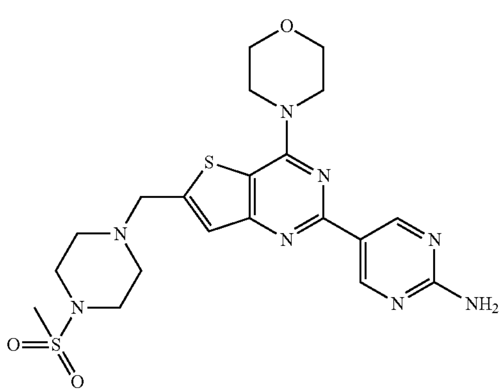 [SMILES: CS(=O)(=O)N1CCN(Cc2cc3nc(-c4cnc(N)nc4)nc(N4CCOCC4)c3s2)CC1] | 5-(4-morpholino-6-((4-N-methylsulfonylpiperazin-1-yl)methyl)thieno[3,2-d]pyrimidin-2-yl)pyrimidin-2-amine |

TABLE 1-continued

| Compound | Structure | Name |
|---|---|---|
| 222 | 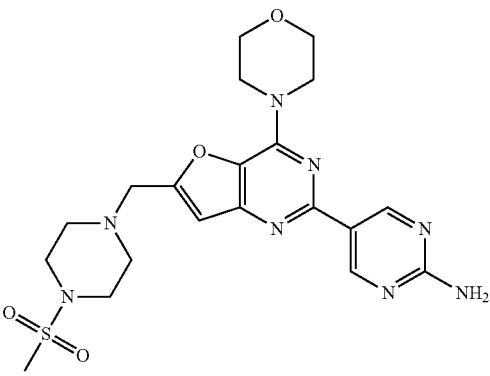 [SMILES: CS(=O)(=O)N1CCN(Cc2cc3nc(-c4cnc(N)nc4)nc(N4CCOCC4)c3o2)CC1] | 5-(4-morpholino-6-((4-N-methylsulfonylpiperazin-1-yl)methyl)furo[3,2-d]pyrimidin-2-yl)pyrimidin-2-amine |
| 223 | 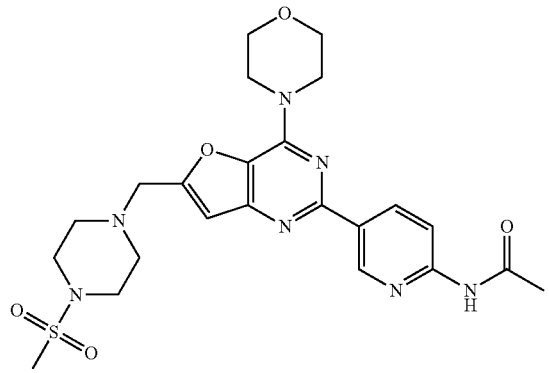 [SMILES: CC(=O)Nc1ccc(-c2nc(N3CCOCC3)c3oc(CN4CCN(S(C)(=O)=O)CC4)cc3n2)cn1] | N-(5-(4-morpholino-6-((4-N-methylsulfonylpiperazin-1-yl)methyl)furo[3,2-d]pyrimidin-2-yl)pyridin-2-yl)acetamide |
| 224 | 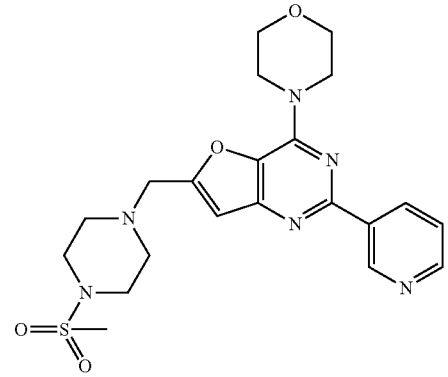 [SMILES: CS(=O)(=O)N1CCN(Cc2cc3nc(-c4cccnc4)nc(N4CCOCC4)c3o2)CC1] | 4-morpholino-6-((4-N-methylsulfonylpiperazin-1-yl)methyl)-2-(pyridin-3-yl)furo[3,2-d]pyrimidine |
| 225 | 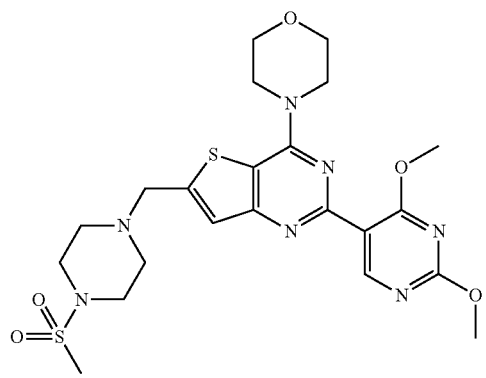 | 2-(2,4-dimethoxypyrimidin-5-yl)-4-morpholino-6-((4-N-methylsulfonylpiperazin-1-yl)methyl)thieno[3,2-d]pyrimidine |

TABLE 1-continued

| Compound | Structure | Name |
|---|---|---|
| 226 | 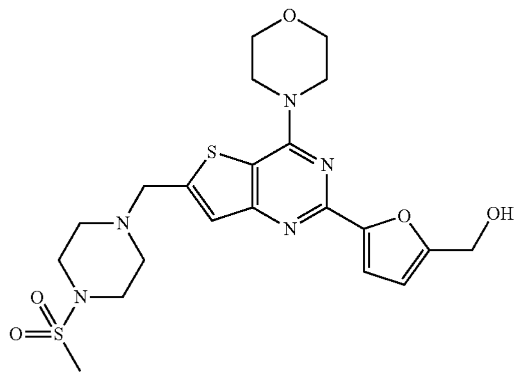 [SMILES: CS(=O)(=O)N1CCN(Cc2cc3nc(-c4ccc(CO)o4)nc(N4CCOCC4)c3s2)CC1] | (5-(4-morpholino-6-((4-N-methylsulfonylpiperazin-1-yl)methyl)thieno[3,2-d]pyrimidin-2-yl)furan-2-yl)methanol |
| 227 | 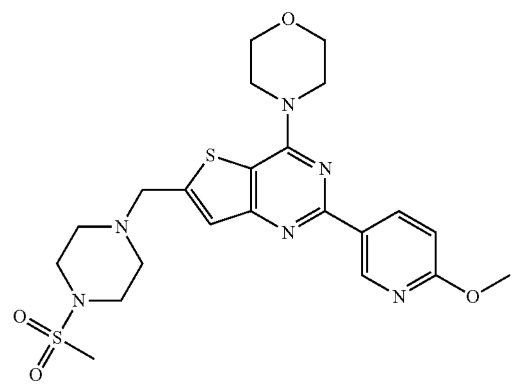 [SMILES: COc1ccc(-c2nc(N3CCOCC3)c3sc(CN4CCN(S(C)(=O)=O)CC4)cc3n2)cn1] | 2-(6-methoxypyridin-3-yl)-4-morpholino-6-((piperazin-1-yl)methyl)thieno[3,2-d]pyrimidine |
| 228 | 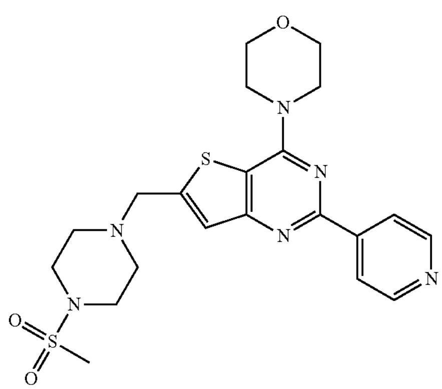 [SMILES: CS(=O)(=O)N1CCN(Cc2cc3nc(-c4ccncc4)nc(N4CCOCC4)c3s2)CC1] | 4-morpholino-6-((piperazin-1-yl)methyl)-2-(4-N-methylpyridin-4-yl)thieno[3,2-d]pyrimidine |
| 229 | 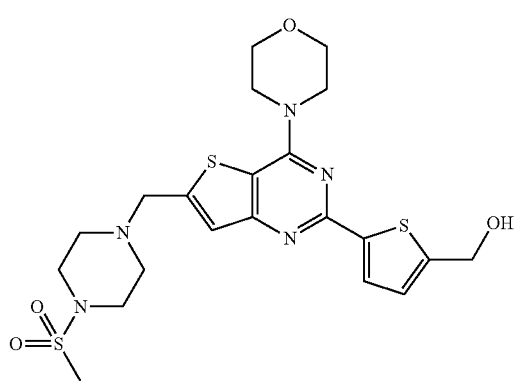 | (5-(4-morpholino-6-((4-N-methylsulfonylpiperazin-1-yl)methyl)thieno[3,2-d]pyrimidin-2-yl)thiophen-2-yl)methanol |

TABLE 1-continued

| Compound | Structure | Name |
| --- | --- | --- |
| 230 | 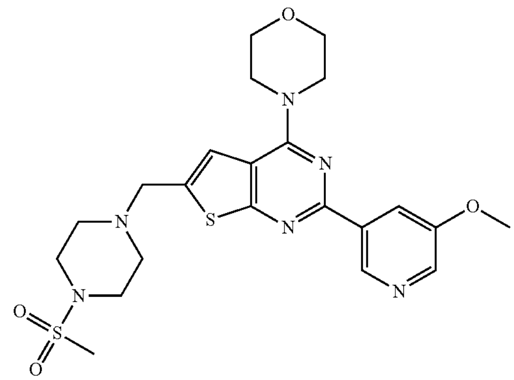 [SMILES: COc1cncc(-c2nc(N3CCOCC3)c3cc(CN4CCN(S(C)(=O)=O)CC4)sc3n2)c1] | 2-(5-methoxypyridin-3-yl)-4-morpholino-6-((4-N-methylsulfonylpiperazin-1-yl)methyl)thieno[2,3-d]pyrimidine |
| 231 | 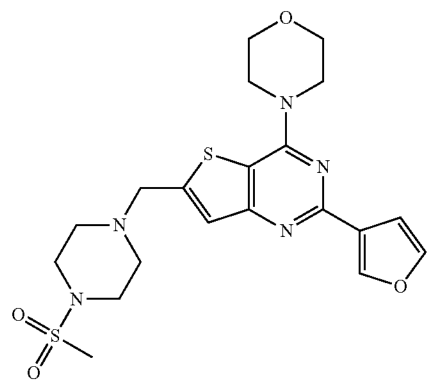 [SMILES: CS(=O)(=O)N1CCN(Cc2cc3nc(-c4ccoc4)nc(N4CCOCC4)c3s2)CC1] | 2-(furan-3-yl)-4-morpholino-6-((4-N-methylsulfonylpiperazin-1-yl)methyl)thieno[3,2-d]pyrimidine |
| 232 | 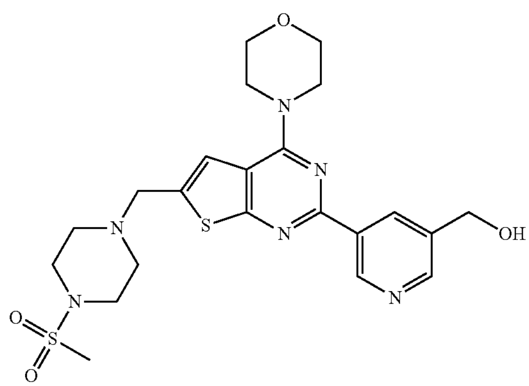 [SMILES: CS(=O)(=O)N1CCN(Cc2cc3c(N4CCOCC4)nc(-c4cncc(CO)c4)nc3s2)CC1] | (5-(4-morpholino-6-((4-N-methylsulfonylpiperazin-1-yl)methyl)thieno[2,3-d]pyrimidin-2-yl)pyridin-3-yl)methanol |
| 233 | 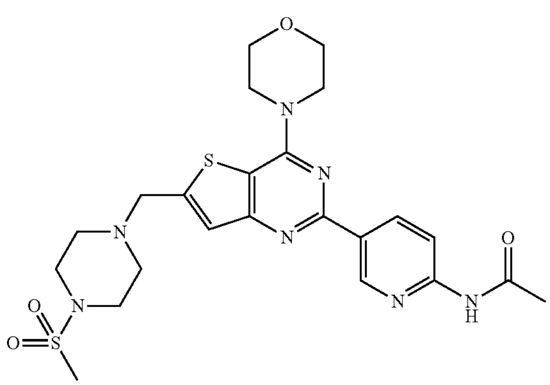 [SMILES: CC(=O)Nc1ccc(-c2nc(N3CCOCC3)c3sc(CN4CCN(S(C)(=O)=O)CC4)cc3n2)cn1] | N-(5-(4-morpholino-6-((4-N-methylsulfonylpiperazin-1-yl)methyl)thieno[3,2-d]pyrimidin-2-yl)pyridin-2-yl)acetamide |

TABLE 1-continued

| Compound | Structure | Name |
|---|---|---|
| 234 | 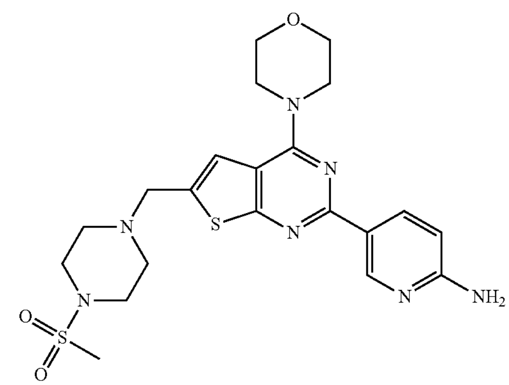 [SMILES: CS(=O)(=O)N1CCN(Cc2cc3c(N4CCOCC4)nc(-c4ccc(N)nc4)nc3s2)CC1] | 5-(4-morpholino-6-((4-N-methylsulfonylpiperazin-1-yl)methyl)thieno[2,3-d]pyrimidin-2-yl)pyridin-2-amine |
| 235 | 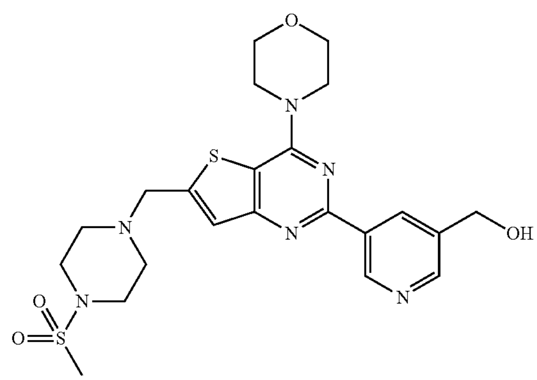 [SMILES: CS(=O)(=O)N1CCN(Cc2cc3nc(-c4cncc(CO)c4)nc(N4CCOCC4)c3s2)CC1] | (5-(4-morpholino-6-((4-N-methylsulfonylpiperazin-1-yl)methyl)thieno[3,2-d]pyrimidin-2-yl)pyridin-3-yl)methanol |
| 236 | 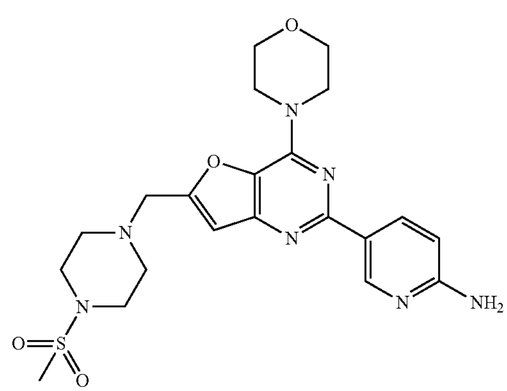 [SMILES: CS(=O)(=O)N1CCN(Cc2cc3nc(-c4ccc(N)nc4)nc(N4CCOCC4)c3o2)CC1] | 5-(4-morpholino-6-((4-N-methylsulfonylpiperazin-1-yl)methyl)furo[3,2-d]pyrimidin-2-yl)pyridin-2-amine |
| 237 | 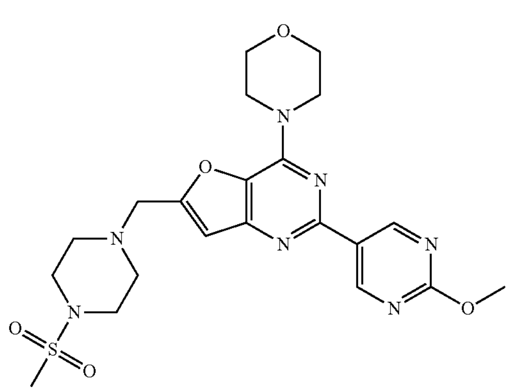 [SMILES: COc1ncc(-c2nc(N3CCOCC3)c3oc(CN4CCN(S(C)(=O)=O)CC4)cc3n2)cn1] | 2-(2-methoxypyrimidin-5-yl)-4-morpholino-6-((4-N-methylsulfonylpiperazin-1-yl)methyl)furo[3,2-d]pyrimidine |

TABLE 1-continued

| Compound | Structure | Name |
|---|---|---|
| 238 | 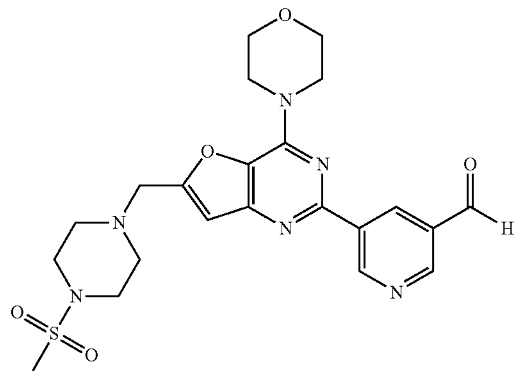 [SMILES: CS(=O)(=O)N1CCN(Cc2cc3nc(-c4cncc(C=O)c4)nc(N4CCOCC4)c3o2)CC1] | 5-(4-morpholino-6-((4-N-methylsulfonylpiperazin-1-yl)methyl)furo[3,2-d]pyrimidin-2-yl)pyridine-3-carbaldehyde |
| 239 | 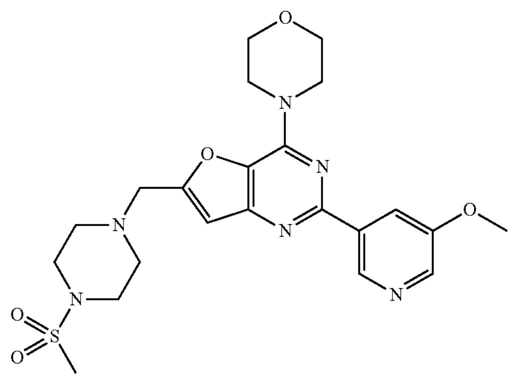 [SMILES: COc1cncc(-c2nc(N3CCOCC3)c3oc(CN4CCN(S(C)(=O)=O)CC4)cc3n2)c1] | 2-(5-methoxypyridin-3-yl)-4-morpholino-6-((4-N-methylsulfonylpiperazin-1-yl)methyl)furo[3,2-d]pyrimidine |
| 240 | 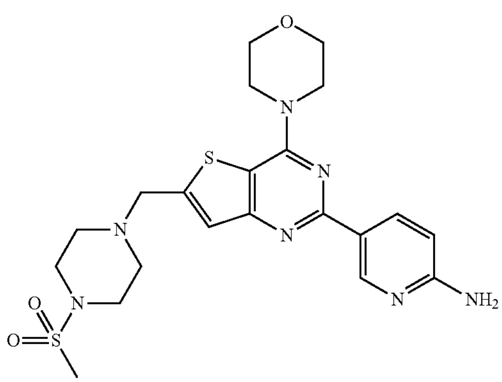 | 5-(4-morpholino-6-((4-N-methylsulfonylpiperazin-1-yl)methyl)thieno[3,2-d]pyrimidin-2-yl)pyridin-2-amine |
| 241 | 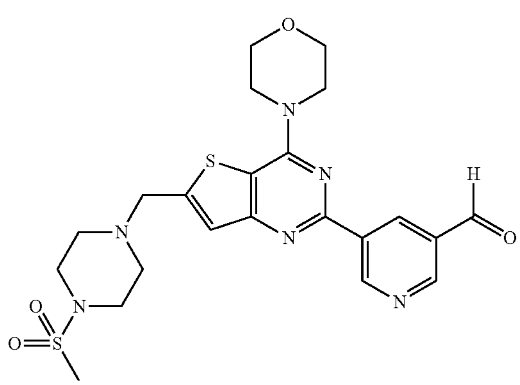 [SMILES: CS(=O)(=O)N1CCN(Cc2cc3nc(-c4cncc(C=O)c4)nc(N4CCOCC4)c3s2)CC1] | 5-(4-morpholino-6-((4-N-methylsulfonylpiperazin-1-yl)methyl)thieno[3,2-d]pyrimidin-2-yl)pyridine-3-carbaldehyde |

TABLE 1-continued

| Compound | Structure | Name |
|---|---|---|
| 242 | | |
| 243 | 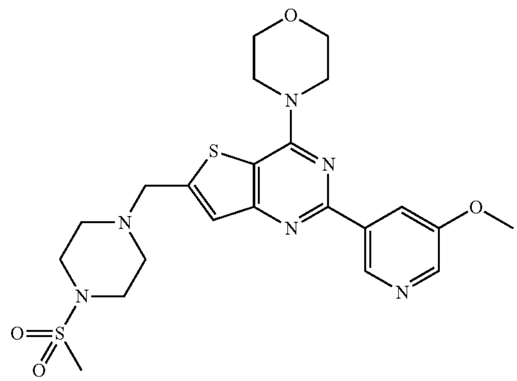 [SMILES: COc1cncc(-c2nc(N3CCOCC3)c3sc(CN4CCN(S(C)(=O)=O)CC4)cc3n2)c1] | 2-(5-methoxypyridin-3-yl)-4-morpholino-6-((4-N-methylsulfonylpiperazin-1-yl)methyl)thieno[3,2-d]pyrimidine |
| 244 | 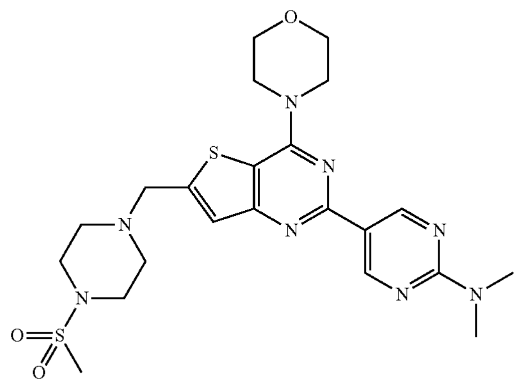 [SMILES: CN(C)c1ncc(-c2nc(N3CCOCC3)c3sc(CN4CCN(S(C)(=O)=O)CC4)cc3n2)cn1] | N,N-dimethyl-5-(4-morpholino-6-((4-N-methylsulfonylpiperazin-1-yl)methyl)thieno[3,2-d]pyrimidin-2-yl)pyrimidin-2-amine |
| 245 | 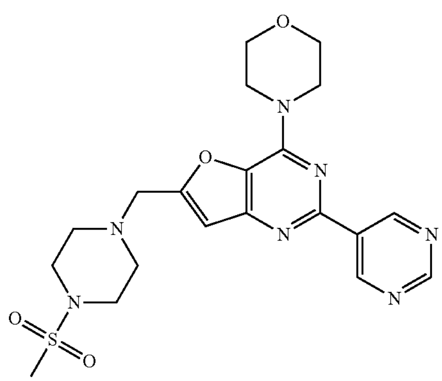 [SMILES: CS(=O)(=O)N1CCN(Cc2cc3nc(-c4cncnc4)nc(N4CCOCC4)c3o2)CC1] | 4-morpholino-6-((4-N-methylsulfonylpiperazin-1-yl)methyl)-2-(pyrimidin-5-yl)furo[3,2-d]pyrimidine |
| 246 | 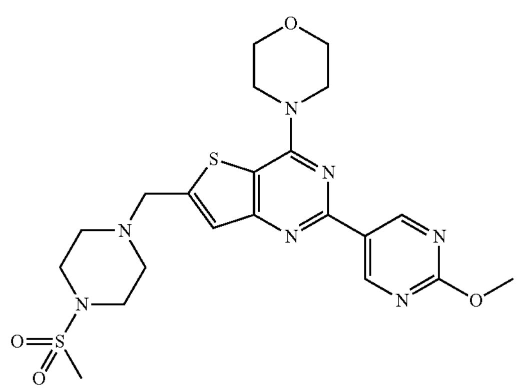 [SMILES: COc1ncc(-c2nc(N3CCOCC3)c3sc(CN4CCN(S(C)(=O)=O)CC4)cc3n2)cn1] | 2-(2-methoxypyrimidin-5-yl)-4-morpholino-6-((4-N-methylsulfonylpiperazin-1-yl)methyl)thieno[3,2-d]pyrimidine |

TABLE 1-continued

| Compound | Structure | Name |
|---|---|---|
| 247 | 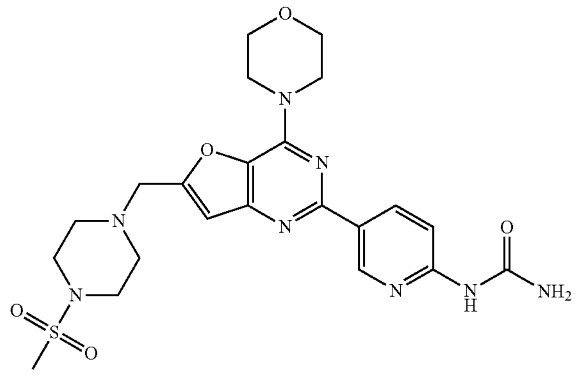 [SMILES: CS(=O)(=O)N1CCN(Cc2cc3nc(-c4ccc(NC(N)=O)nc4)nc(N4CCOCC4)c3o2)CC1] | 1-(5-(4-morpholino-6-((4-N-methylsulfonylpiperazin-1-yl)methyl)furo[3,2-d]pyrimidin-2-yl)pyridin-2-yl)urea |
| 257 | 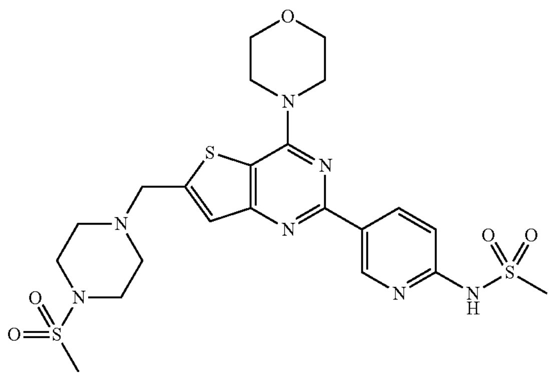 [SMILES: CS(=O)(=O)Nc1ccc(-c2nc(N3CCOCC3)c3sc(CN4CCN(S(C)(=O)=O)CC4)cc3n2)cn1] | 5-(4-morpholino-6-((4-N-methylsulfonylpiperazin-1-yl)methyl)thieno[3,2-d]pyrimidin-2-yl)pyridin-2-methylsulfonylamine |
| 258 | 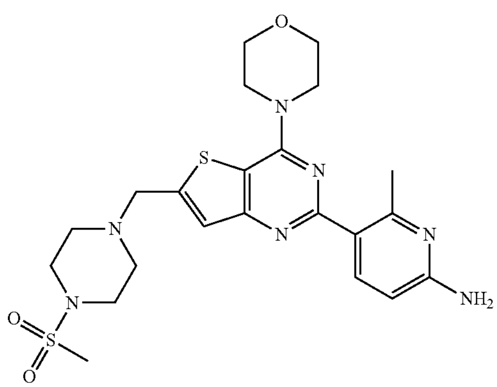 [SMILES: Cc1nc(N)ccc1-c1nc(N2CCOCC2)c2sc(CN3CCN(S(C)(=O)=O)CC3)cc2n1] | 6-methyl-5-(4-morpholino-6-((4-N-methylsulfonylpiperazin-1-yl)methyl)thieno[3,2-d]pyrimidin-2-yl)pyridin-2-amine |
| 259 | 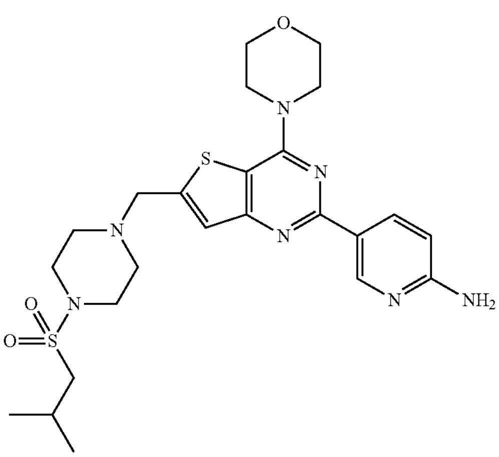 [SMILES: CC(C)CS(=O)(=O)N1CCN(Cc2cc3nc(-c4ccc(N)nc4)nc(N4CCOCC4)c3s2)CC1] | 5-(4-morpholino-6-((4-N-isobutylsulfonylpiperazin-1-yl)methyl)thieno[3,2-d]pyrimidin-2-yl)pyridin-2-amine |

TABLE 1-continued

| Compound | Structure | Name |
|---|---|---|
| 260 | 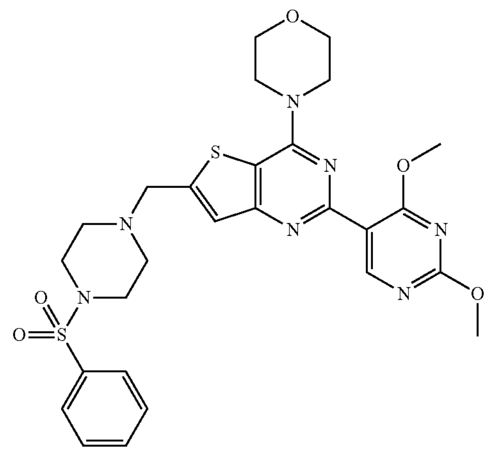 [SMILES: COc1ncc(-c2nc(N3CCOCC3)c3sc(CN4CCN(S(=O)(=O)c5ccccc5)CC4)cc3n2)c(OC)n1] | 2-(2,4-dimethoxypyrimidin-5-yl)-4-morpholino-6-((4-N-phenylsulfonylpiperazin-1-yl)methyl)thieno[3,2-d]pyrimidine |
| 261 | 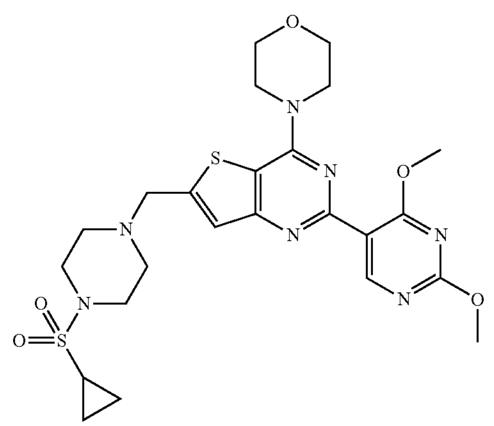 [SMILES: COc1ncc(-c2nc(N3CCOCC3)c3sc(CN4CCN(S(=O)(=O)C5CC5)CC4)cc3n2)c(OC)n1] | 2-(2,4-dimethoxypyrimidin-5-yl)-4-morpholino-6-((4-N-cyclopropylsulfonylpiperazin-1-yl)methyl)thieno[3,2-d]pyrimidine |
| 262 | 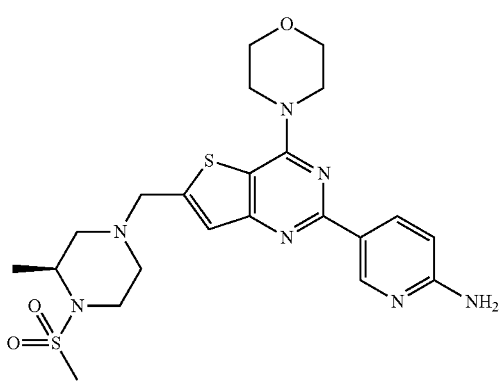 [SMILES: C[C@H]1CN(Cc2cc3nc(-c4ccc(N)nc4)nc(N4CCOCC4)c3s2)CCN1S(C)(=O)=O] | 5-(6-(((S)-3-methyl-(4-N-methylsulfonyl)piperazin-1-yl)methyl)-4-morpholinothieno[3,2-d]pyrimidin-2-yl)pyridin-2-amine |
| 263 | 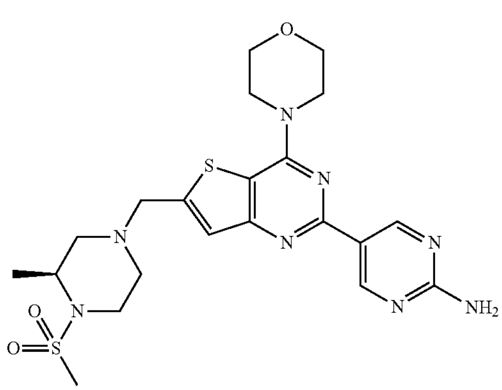 [SMILES: C[C@H]1CN(Cc2cc3nc(-c4cnc(N)nc4)nc(N4CCOCC4)c3s2)CCN1S(C)(=O)=O] | 5-(6-(((S)-3-methyl-(4-N-methylsulfonyl)piperazin-1-yl)methyl)-4-morpholinothieno[3,2-d]pyrimidin-2-yl)pyrimidin-2-amine |

TABLE 1-continued

| Compound | Structure | Name |
|---|---|---|
| 264 | 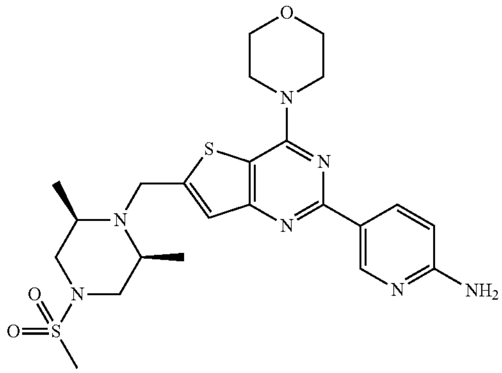 [SMILES: C[C@@H]1CN(S(C)(=O)=O)C[C@H](C)N1Cc1cc2nc(-c3ccc(N)nc3)nc(N3CCOCC3)c2s1] | 5-(6-(((2R,6S)-2,6-dimethyl-(4-N-methylsulfonyl)piperazin-1-yl)methyl)-4-morpholinothieno[3,2-d]pyrimidin-2-yl)pyridin-2-amine |
| 265 | 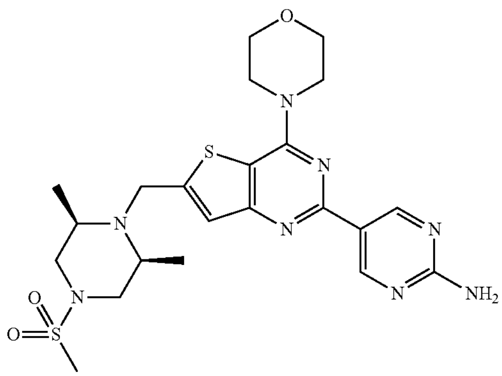 [SMILES: C[C@@H]1CN(S(C)(=O)=O)C[C@H](C)N1Cc1cc2nc(-c3cnc(N)nc3)nc(N3CCOCC3)c2s1] | 5-(6-(((2R,6S)-2,6-dimethyl-(4-N-methylsulfonyl)piperazin-1-yl)methyl)-4-morpholinothieno[3,2-d]pyrimidin-2-yl)pyrimidin-2-amine |
| 266 | 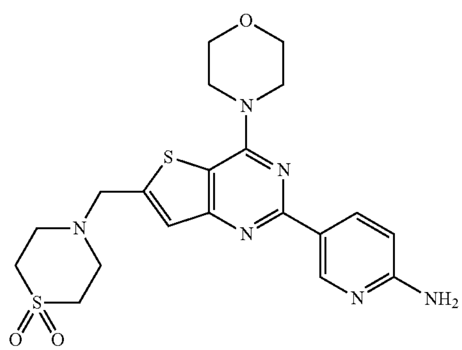 [SMILES: Nc1ccc(-c2nc(N3CCOCC3)c3sc(CN4CCS(=O)(=O)CC4)cc3n2)cn1] | 5-(4-morpholino-6-((1-O,O-S-thiomorpholin-4-yl)methyl)thieno[3,2-d]pyrimidin-2-yl)pyridin-2-amine |
| 267 | 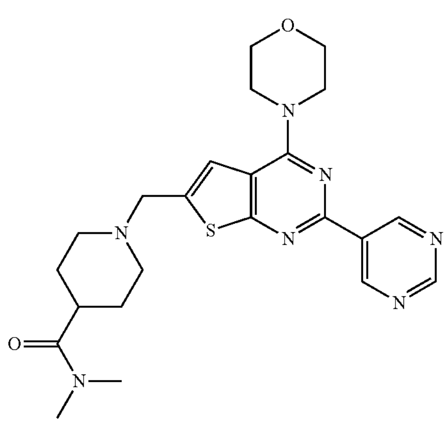 [SMILES: CN(C)C(=O)C1CCN(Cc2cc3c(N4CCOCC4)nc(-c4cncnc4)nc3s2)CC1] | N,N-dimethyl-1-((4-morpholino-2-(pyrimidin-5-yl)thieno[2,3-d]pyrimidin-6-yl)methyl)piperidine-4-carboxamide |

TABLE 1-continued

| Compound | Structure | Name |
|---|---|---|
| 268 | 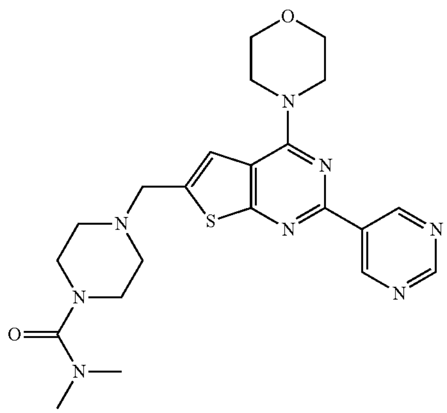 [SMILES: CN(C)C(=O)N1CCN(Cc2cc3c(N4CCOCC4)nc(-c4cncnc4)nc3s2)CC1] | N,N-dimethyl-4-((4-morpholino-2-(pyrimidin-5-yl)thieno[2,3-d]pyrimidin-6-yl)methyl)piperazine-1-carboxamide |
| 269 | 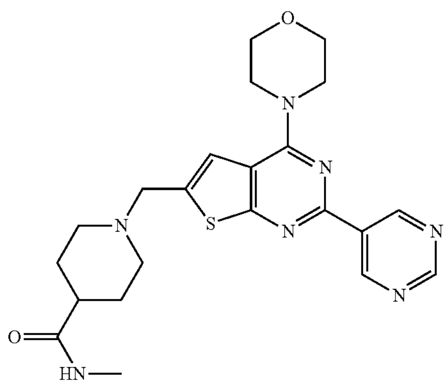 [SMILES: CNC(=O)C1CCN(Cc2cc3c(N4CCOCC4)nc(-c4cncnc4)nc3s2)CC1] | N-methyl-1-((4-morpholino-2-(pyrimidin-5-yl)thieno[2,3-d]pyrimidin-6-yl)methyl)piperidine-4-carboxamide |
| 270 | 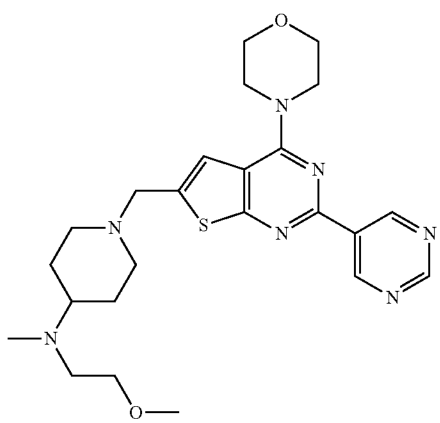 [SMILES: COCCN(C)C1CCN(Cc2cc3c(N4CCOCC4)nc(-c4cncnc4)nc3s2)CC1] | N-(2-methoxyethyl)-N-methyl-1-((4-morpholino-2-(pyrimidin-5-yl)thieno[2,3-d]pyrimidin-6-yl)methyl)piperidin-4-amine |
| 271 | 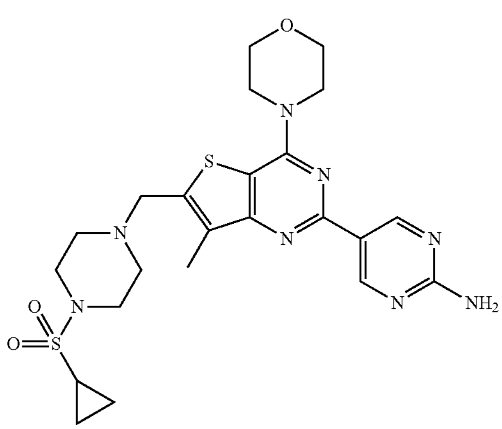 [SMILES: Cc1c(CN2CCN(S(=O)(=O)C3CC3)CC2)sc2c(N3CCOCC3)nc(-c3cnc(N)nc3)nc12] | 5-(7-methyl-4-morpholino-6-((4-N-cyclopropylsulfonylpiperazin-1-yl)methyl)thieno[3,2-d]pyrimidin-2-yl)pyrimidin-2-amine |

TABLE 1-continued

| Compound | Structure | Name |
| --- | --- | --- |
| 272 | 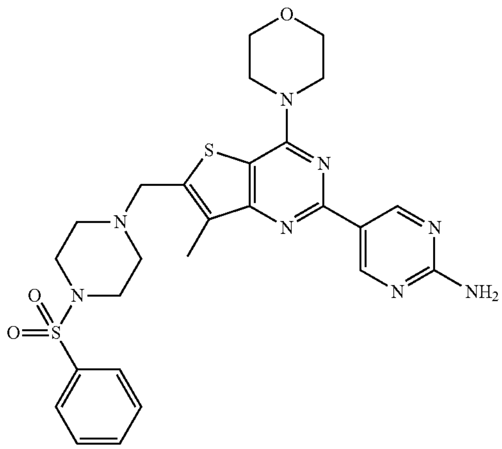 [SMILES: Cc1c(CN2CCN(S(=O)(=O)c3ccccc3)CC2)sc2c(N3CCOCC3)nc(-c3cnc(N)nc3)nc12] | 5-(7-methyl-4-morpholino-6-((4-N-phenylsulfonylpiperazin-1-yl)methyl)thieno[3,2-d]pyrimidin-2-yl)pyrimidin-2-amine |
| 273 | 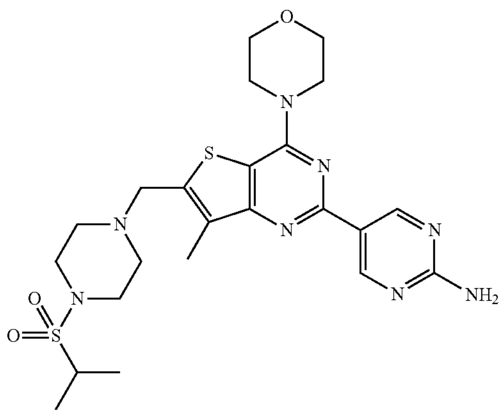 [SMILES: Cc1c(CN2CCN(S(=O)(=O)C(C)C)CC2)sc2c(N3CCOCC3)nc(-c3cnc(N)nc3)nc12] | 5-(7-methyl-4-morpholino-6-((4-N-isopropylsulfonylpiperazin-1-yl)methyl)thieno[3,2-d]pyrimidin-2-yl)pyrimidin-2-amine |
| 274 | 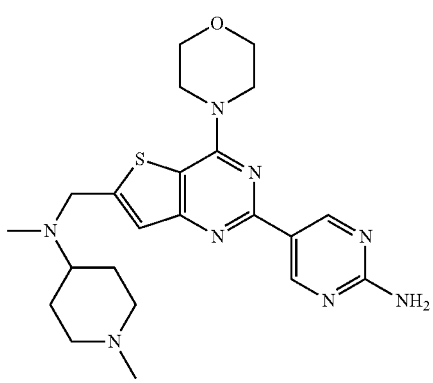 [SMILES: CN1CCC(N(C)Cc2cc3nc(-c4cnc(N)nc4)nc(N4CCOCC4)c3s2)CC1] | N,1-dimethyl-N-((4-morpholino-2-(pyrimidin-5-yl)thieno[3,2-d]-2-amino-pyrimidin-6-yl)methyl)piperidin-4-amine |
| 275 | 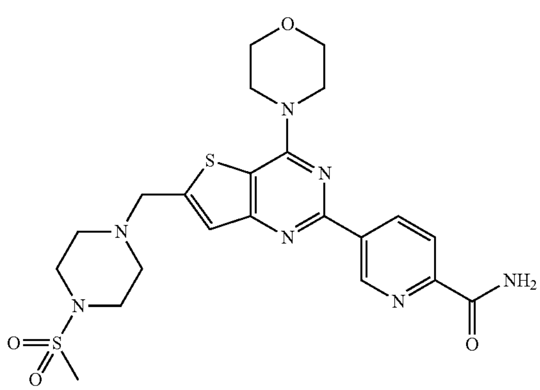 [SMILES: CS(=O)(=O)N1CCN(Cc2cc3nc(-c4ccc(C(N)=O)nc4)nc(N4CCOCC4)c3s2)CC1] | 5-(4-morpholino-6-((4-N-methylsulfonylpiperazin-1-yl)methyl)thieno[3,2-d]pyrimidin-2-yl)pyridine-2-carboxamide |

TABLE 1-continued

| Compound | Structure | Name |
|---|---|---|
| 276 | 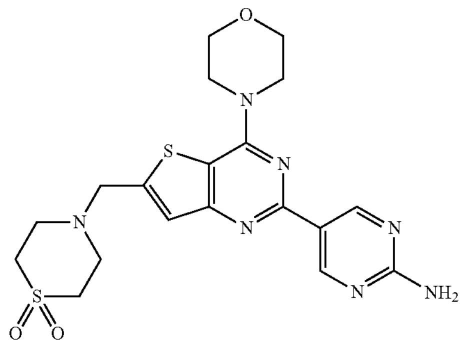 [SMILES: Nc1ncc(-c2nc(N3CCOCC3)c3sc(CN4CCS(=O)(=O)CC4)cc3n2)cn1] | 5-(4-morpholino-6-((1-O,O-S-thiomorpholin-4-yl)methyl)thieno[3,2-d]pyrimidin-2-yl)pyrimidin-2-amine |
| 277 | 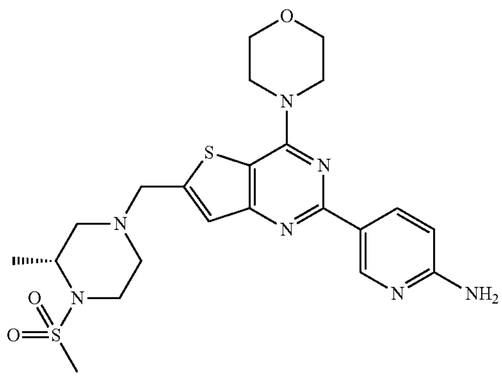 [SMILES: C[C@@H]1CN(Cc2cc3nc(-c4ccc(N)nc4)nc(N4CCOCC4)c3s2)CCN1S(C)(=O)=O] | 5-(6-(((R)-3-methyl-(4-N-methylsulfonyl)piperazin-1-yl)methyl)-4-morpholinothieno[3,2-d]pyrimidin-2-yl)pyridin-2-amine |
| 278 | 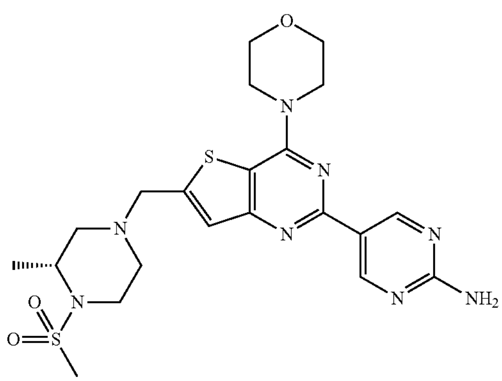 [SMILES: C[C@@H]1CN(Cc2cc3nc(-c4cnc(N)nc4)nc(N4CCOCC4)c3s2)CCN1S(C)(=O)=O] | 5-(6-(((R)-3-methyl-(4-N-methylsulfonyl)piperazin-1-yl)methyl)-4-morpholinothieno[3,2-d]pyrimidin-2-yl)pyrimidin-2-amine |
| 279 | 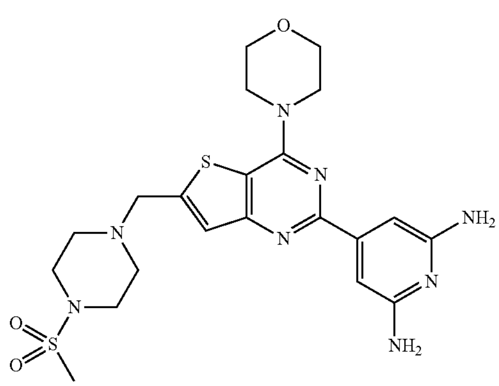 [SMILES: CS(=O)(=O)N1CCN(Cc2cc3nc(-c4cc(N)nc(N)c4)nc(N4CCOCC4)c3s2)CC1] | 4-(4-morpholino-6-((4-N-methylsulfonylpiperazin-1-yl)methyl)thieno[3,2-d]pyrimidin-2-yl)pyridine-2,6-diamine |

TABLE 1-continued

| Compound | Structure | Name |
|---|---|---|
| 280 | 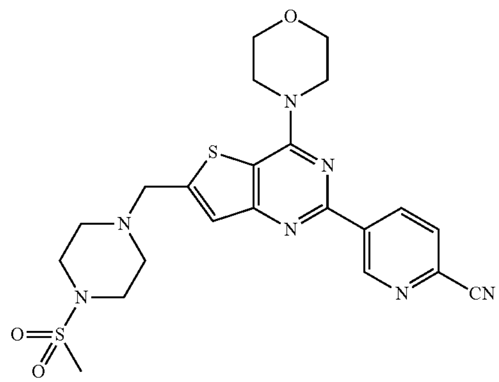 [SMILES: CS(=O)(=O)N1CCN(Cc2cc3nc(-c4ccc(C#N)nc4)nc(N4CCOCC4)c3s2)CC1] | 5-(4-morpholino-6-((4-N-methylsulfonylpiperazin-1-yl)methyl)thieno[3,2-d]pyrimidin-2-yl)pyridine-2-carbonitrile |
| 281 | 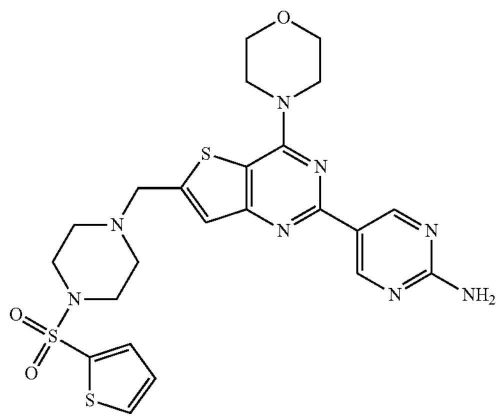 [SMILES: Nc1ncc(-c2nc(N3CCOCC3)c3sc(CN4CCN(S(=O)(=O)c5cccs5)CC4)cc3n2)cn1] | 5-(4-morpholino-6-((4-N-(thiophen-2-yl)sulfonyl)piperazin-1-yl)methyl)thieno[3,2-d]pyrimidin-2-yl)pyrimidin-2-amine |
| 282 | 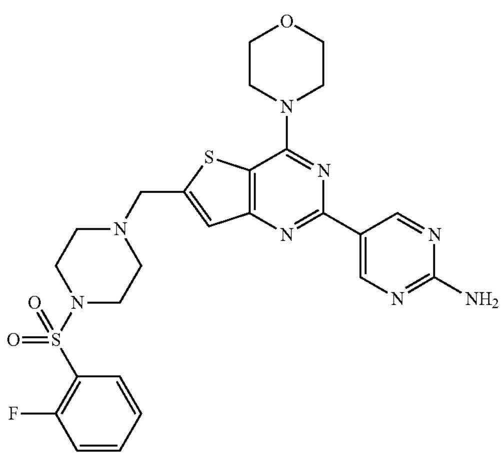 [SMILES: Nc1ncc(-c2nc(N3CCOCC3)c3sc(CN4CCN(S(=O)(=O)c5ccccc5F)CC4)cc3n2)cn1] | 5-(4-morpholino-6-((4-N-2-fluorophenylsulfonylpiperazin-1-yl)methyl)thieno[3,2-d]pyrimidin-2-yl)pyrimidin-2-amine |
| 283 | 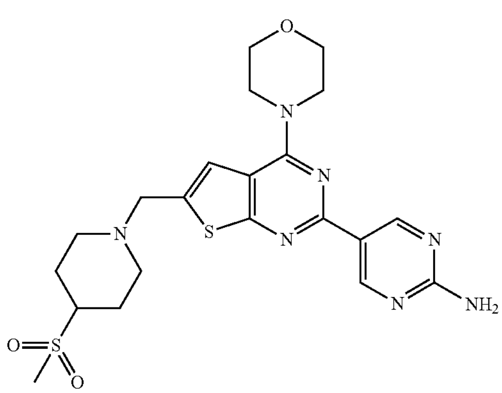 [SMILES: CS(=O)(=O)C1CCN(Cc2cc3c(N4CCOCC4)nc(-c4cnc(N)nc4)nc3s2)CC1] | 5-(6-((4-(methylsulfonyl)piperidin-1-yl)methyl)-4-morpholinothieno[2,3-d]pyrimidin-2-yl)pyrimidin-2-amine |

TABLE 1-continued

| Compound | Structure | Name |
|---|---|---|
| 284 | 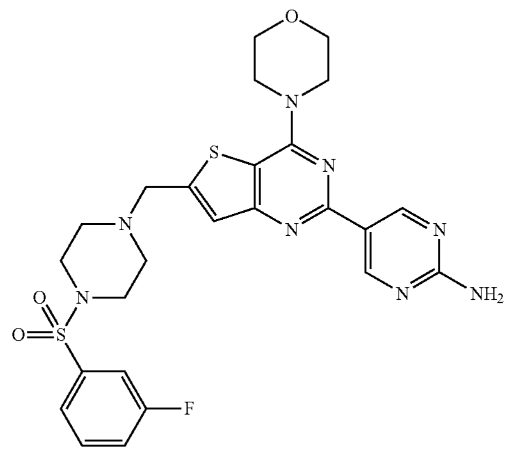 [SMILES: Nc1ncc(-c2nc(N3CCOCC3)c3sc(CN4CCN(S(=O)(=O)c5cccc(F)c5)CC4)cc3n2)cn1] | 5-(4-morpholino-6-((4-N-3-fluorophenylsulfonylpiperazin-1-yl)methyl)thieno[3,2-d]pyrimidin-2-yl)pyrimidin-2-amine |
| 285 | 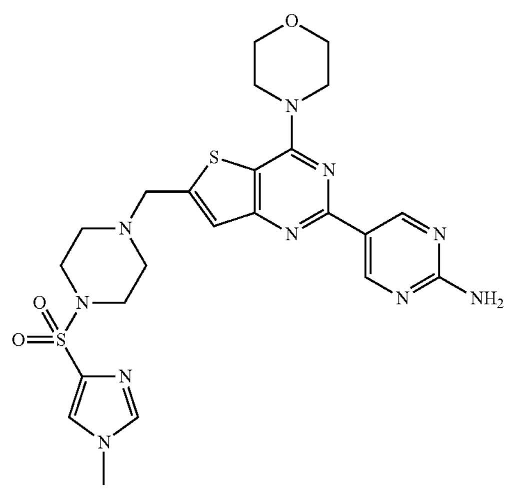 [SMILES: Cn1cnc(S(=O)(=O)N2CCN(Cc3cc4nc(-c5cnc(N)nc5)nc(N5CCOCC5)c4s3)CC2)c1] | 5-(4-morpholino-6-((4-N-(1-methylimidazol-4-yl)piperazin-1-yl)methyl)thieno[3,2-d]pyrimidin-2-yl)pyrimidin-2-amine |
| 286 | 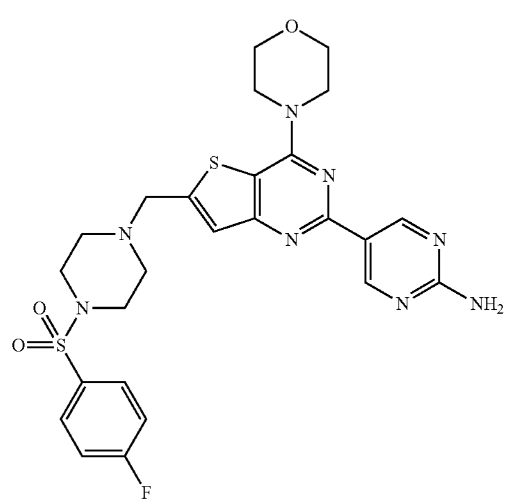 [SMILES: Nc1ncc(-c2nc(N3CCOCC3)c3sc(CN4CCN(S(=O)(=O)c5ccc(F)cc5)CC4)cc3n2)cn1] | 5-(4-morpholino-6-((4-N-4-fluorophenylsulfonylpiperazin-1-yl)methyl)thieno[3,2-d]pyrimidin-2-yl)pyrimidin-2-amine |

TABLE 1-continued

| Compound | Structure | Name |
|---|---|---|
| 287 | 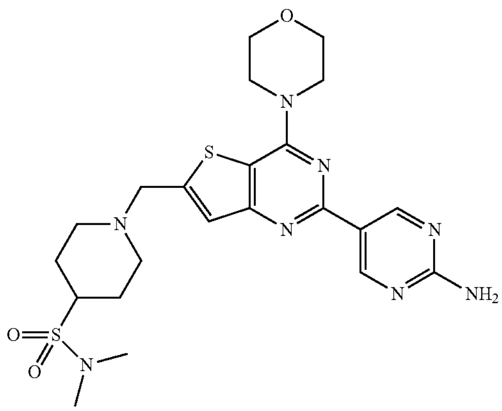 [SMILES: CN(C)S(=O)(=O)C1CCN(Cc2cc3nc(-c4cnc(N)nc4)nc(N4CCOCC4)c3s2)CC1] | 5-(4-morpholino-6-((4-(dimethylaminosulfonyl)piperidin-1-yl)methyl)thieno[3,2-d]pyrimidin-2-yl)pyrimidin-2-amine |
| 288 | 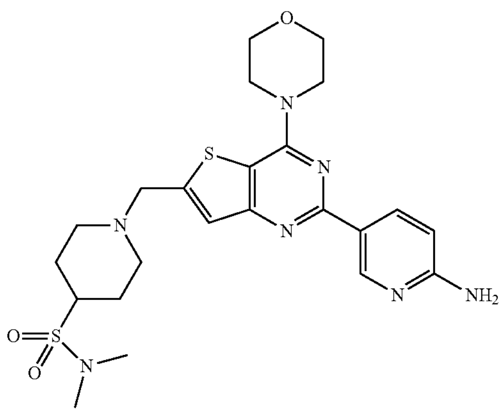 [SMILES: CN(C)S(=O)(=O)C1CCN(Cc2cc3nc(-c4ccc(N)nc4)nc(N4CCOCC4)c3s2)CC1] | 5-(4-morpholino-6-((4-(dimethylaminosulfonyl)piperidin-1-yl)methyl)thieno[3,2-d]pyrimidin-2-yl)pyridin-2-amine |
| 289 | 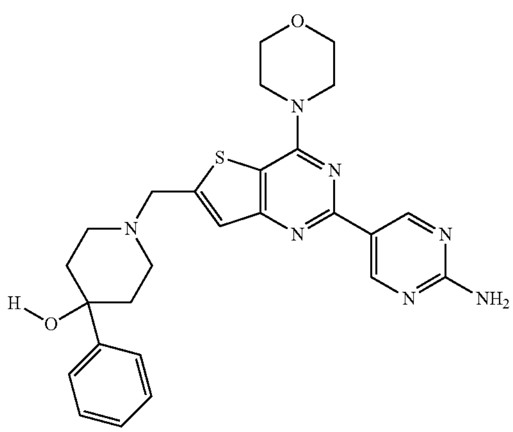 [SMILES: Nc1ncc(-c2nc(N3CCOCC3)c3sc(CN4CCC(O)(c5ccccc5)CC4)cc3n2)cn1] | 1-((2-(2-aminopyrimidin-5-yl)-4-morpholinothieno[3,2-d]pyrimidin-6-yl)methyl)-4-phenylpiperidin-4-ol |
| 290 | 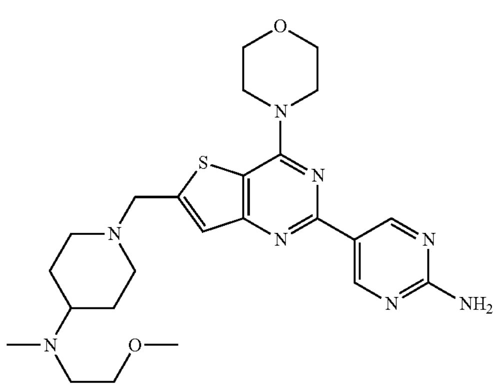 [SMILES: COCCN(C)C1CCN(Cc2cc3nc(-c4cnc(N)nc4)nc(N4CCOCC4)c3s2)CC1] | 5-(6-((4-(N-(2-methoxyethyl)-N-methylamino)piperidin-1-yl)methyl)-4-morpholinothieno[3,2-d]pyrimidin-2-yl)pyrimidin-2-amine |

TABLE 1-continued

| Compound | Structure | Name |
|---|---|---|
| 291 | 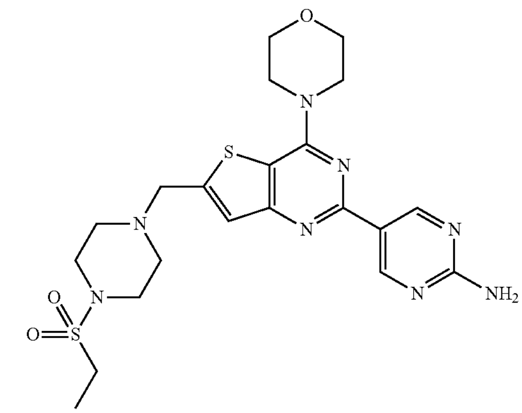 | 5-(4-morpholino-6-((4-N-ethylsulfonylpiperazin-1-yl)methyl)thieno[3,2-d]pyrimidin-2-yl)pyrimidin-2-amine |
| 292 | 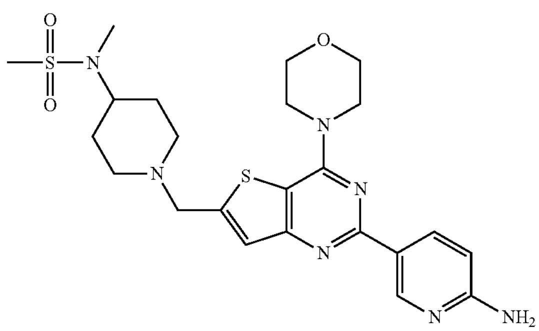 [SMILES: CN(C1CCN(Cc2cc3nc(-c4ccc(N)nc4)nc(N4CCOCC4)c3s2)CC1)S(C)(=O)=O] | 5-(6-((4-(N-methyl,N-methylsulfonylamino)piperidin-1-yl)methyl)-4-morpholinothieno[3,2-d]pyrimidin-2-yl)pyridin-2-amine |
| 293 | 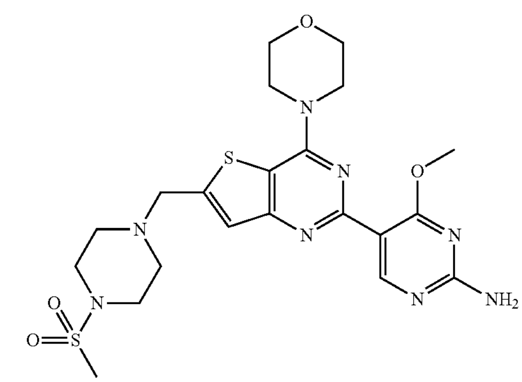 [SMILES: COc1nc(N)ncc1-c1nc(N2CCOCC2)c2sc(CN3CCN(S(C)(=O)=O)CC3)cc2n1] | 4-methoxy-5-(4-morpholino-6-((4-N-methylsulfonylpiperazin-1-yl)methyl)thieno[3,2-d]pyrimidin-2-yl)pyrimidin-2-amine |
| 294 | 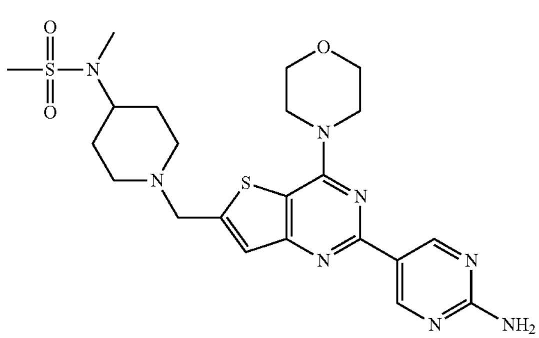 [SMILES: CN(C1CCN(Cc2cc3nc(-c4cnc(N)nc4)nc(N4CCOCC4)c3s2)CC1)S(C)(=O)=O] | 5-(6-((4-(N-methyl,N-methylsulfonylamino)piperidin-1-yl)methyl)-4-morpholinothieno[3,2-d]pyrimidin-2-yl)pyrimidin-2-amine |

| Compound | Structure | Name |
|---|---|---|
| 295 | 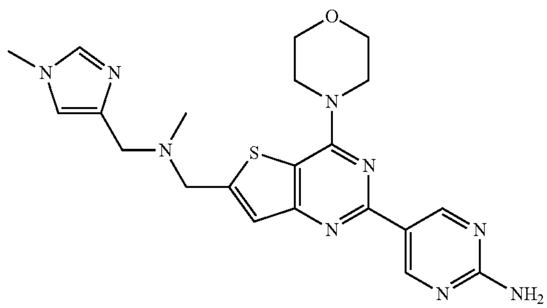 [SMILES: CN(Cc1cn(C)cn1)Cc1cc2nc(-c3cnc(N)nc3)nc(N3CCOCC3)c2s1] | 5-(6-((methyl((1-methyl-1H-imidazol-4-yl)methyl)amino)methyl)-4-morpholinothieno[3,2-d]pyrimidin-2-yl)pyrimidin-2-amine |
| 296 | 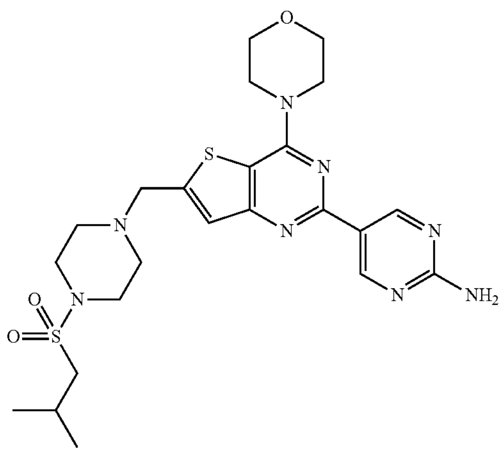 [SMILES: CC(C)CS(=O)(=O)N1CCN(Cc2cc3nc(-c4cnc(N)nc4)nc(N4CCOCC4)c3s2)CC1] | 5-(4-morpholino-6-((4-N-isobutyrylsulfonylpiperazin-1-yl)methyl)thieno[3,2-d]pyrimidin-2-yl)pyrimidin-2-amine |
| 297 | 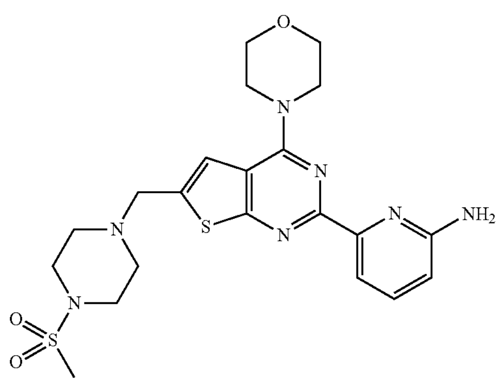 [SMILES: CS(=O)(=O)N1CCN(Cc2cc3c(N4CCOCC4)nc(-c4cccc(N)n4)nc3s2)CC1] | 6-(4-morpholino-6-((4-N-methylsulfonylpiperazin-1-yl)methyl)thieno[2,3-d]pyrimidin-2-yl)pyridin-2-amine |
| 298 | 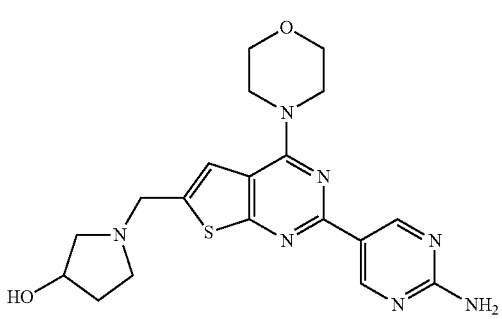 [SMILES: Nc1ncc(-c2nc(N3CCOCC3)c3cc(CN4CCC(O)C4)sc3n2)cn1] | 1-((2-(2-aminopyrimidin-5-yl)-4-morpholinothieno[2,3-d]pyrimidin-6-yl)methyl)pyrrolidin-3-ol |

TABLE 1-continued

| Compound | Structure | Name |
|---|---|---|
| 299 | 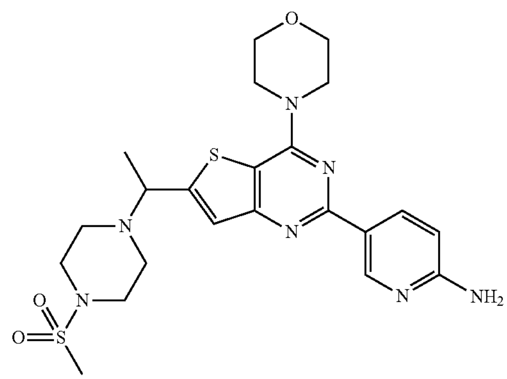 | 5-(4-morpholino-6-(1-(4-N-methylsulfonylpiperazin-1-yl)ethyl)thieno[3,2-d]pyrimidin-2-yl)pyridin-2-amine |
| 300 | 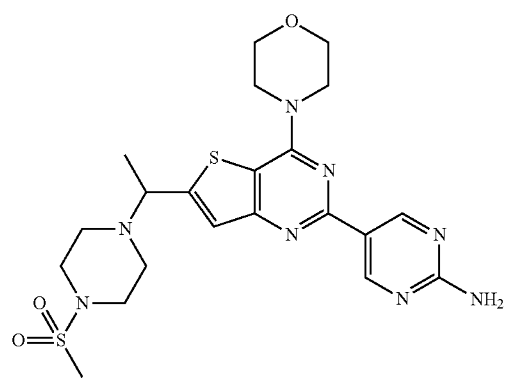 [SMILES: CC(c1cc2nc(-c3cnc(N)nc3)nc(N3CCOCC3)c2s1)N1CCN(S(C)(=O)=O)CC1] | 5-(4-morpholino-6-(1-(4-N-methylsulfonylpiperazin-1-yl)ethyl)thieno[3,2-d]pyrimidin-2-yl)pyrimidin-2-amine |
| 301 | 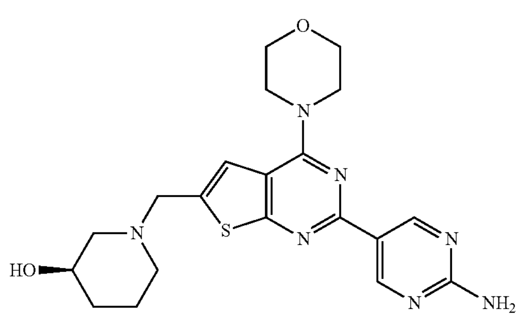 [SMILES: Nc1ncc(-c2nc(N3CCOCC3)c3cc(CN4CCC[C@@H](O)C4)sc3n2)cn1] | (R)-1-((2-(2-aminopyrimidin-5-yl)-4-morpholinothieno[2,3-d]pyrimidin-6-yl)methyl)piperidin-3-ol |
| 302 | 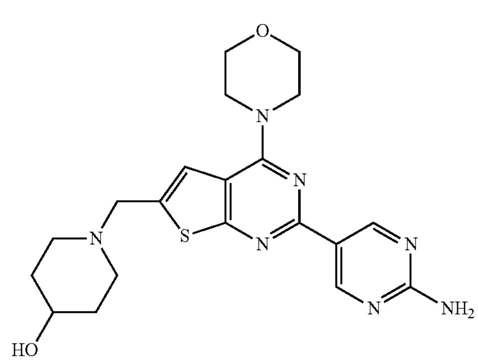 [SMILES: Nc1ncc(-c2nc(N3CCOCC3)c3cc(CN4CCC(O)CC4)sc3n2)cn1] | 1-((2-(2-aminopyrimidin-5-yl)-4-morpholinothieno[2,3-d]pyrimidin-6-yl)methyl)piperidin-4-ol |

TABLE 1-continued

| Compound | Structure | Name |
|---|---|---|
| 303 | 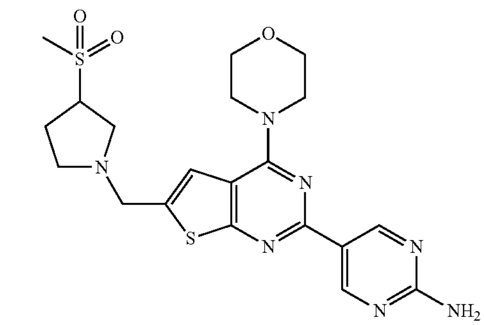 [SMILES: CS(=O)(=O)C1CCN(Cc2cc3c(N4CCOCC4)nc(-c4cnc(N)nc4)nc3s2)C1] | 5-(6-((3-(methylsulfonyl)pyrrolidin-1-yl)methyl)-4-morpholinothieno[2,3-d]pyrimidin-2-yl)pyrimidin-2-amine |
| 304 | 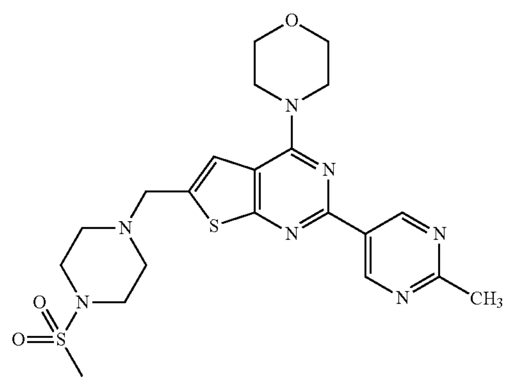 [SMILES: Cc1ncc(-c2nc(N3CCOCC3)c3cc(CN4CCN(S(C)(=O)=O)CC4)sc3n2)cn1] | 2-(2-methylpyrimidin-5-yl)-morpholino-6-(4-N-methylsulfonyl(piperazin-1-yl)methyl)thieno[2,3-d]pyrimidine |
| 305 | 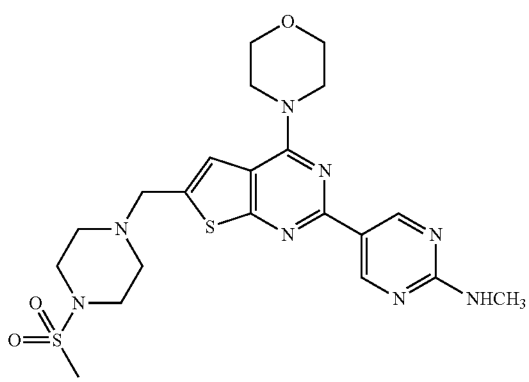 [SMILES: CNc1ncc(-c2nc(N3CCOCC3)c3cc(CN4CCN(S(C)(=O)=O)CC4)sc3n2)cn1] | 2-(2-methylaminopyrimidin-5-yl)-morpholino-6-(4-N-methylsulfonyl(piperazin-1-yl)methyl)thieno[2,3-d]pyrimidine |
| 306 | 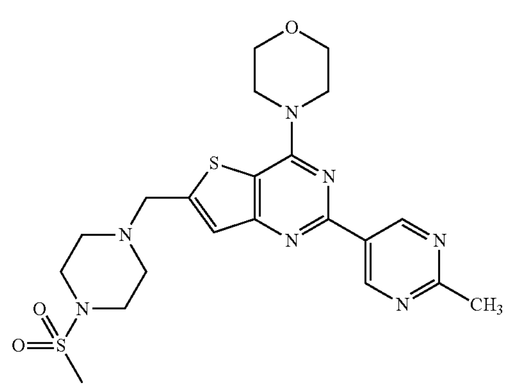 [SMILES: Cc1ncc(-c2nc(N3CCOCC3)c3sc(CN4CCN(S(C)(=O)=O)CC4)cc3n2)cn1] | 2-(2-methylpyrimidin-5-yl)-4-morpholino-6-(4-N-methylsulfonyl(piperazin-1-yl)methyl)thieno[3,2-d]pyrimidine |

TABLE 1-continued

| Compound | Structure | Name |
|---|---|---|
| 307 | 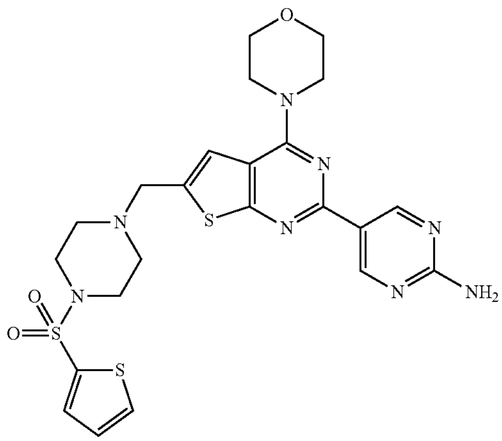 [SMILES: Nc1ncc(-c2nc(N3CCOCC3)c3cc(CN4CCN(S(=O)(=O)c5cccs5)CC4)sc3n2)cn1] | 5-(4-morpholino-6-(4-N-(thiophen-2-yl)sulfonyl(piperazin-1-yl)methyl)thieno[2,3-d]pyrimidin-2-yl)pyrimidin-2-amine |
| 308 | 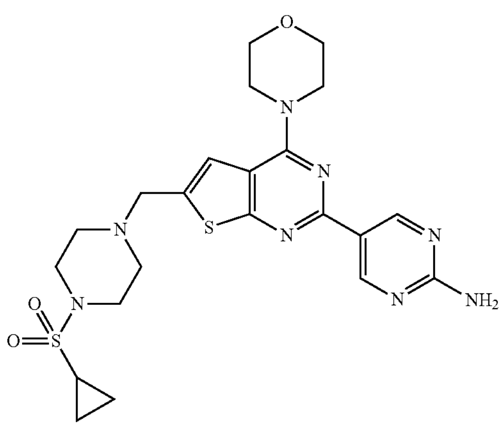 [SMILES: Nc1ncc(-c2nc(N3CCOCC3)c3cc(CN4CCN(S(=O)(=O)C5CC5)CC4)sc3n2)cn1] | 5-(4-morpholino-6-((4-N-cyclopropylsulfonylpiperazin-1-yl)methyl)thieno[2,3-d]pyrimidin-2-yl)pyrimidin-2-amine |
| 309 | 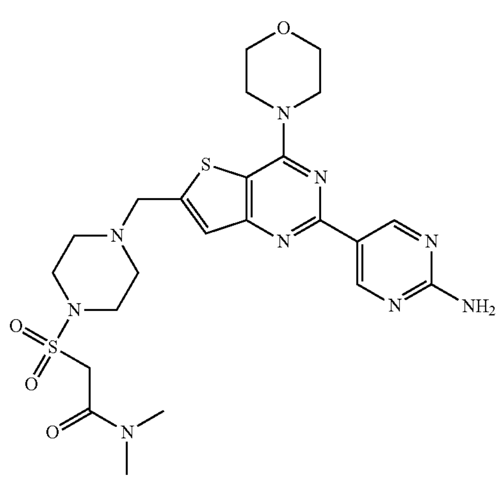 [SMILES: CN(C)C(=O)CS(=O)(=O)N1CCN(Cc2cc3nc(-c4cnc(N)nc4)nc(N4CCOCC4)c3s2)CC1] | 2-(1-((2-(2-aminopyrimidin-5-yl)-4-morpholinothieno[3,2-d]pyrimidin-6-yl)methyl)piperidin-4-ylsulfonyl)-N,N-dimethylacetamide |

TABLE 1-continued
| Compound | Structure | Name |
|---|---|---|
| 310 | 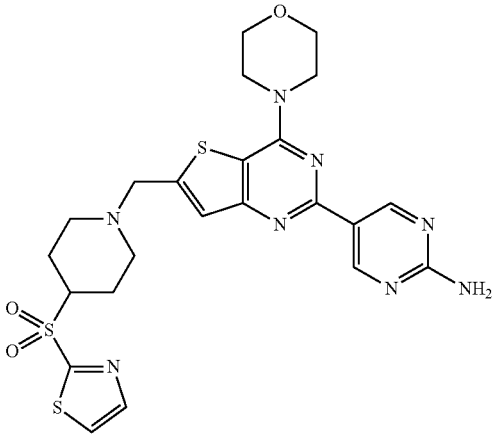 [SMILES: Nc1ncc(-c2nc(N3CCOCC3)c3sc(CN4CCC(S(=O)(=O)c5nccs5)CC4)cc3n2)cn1] | 5-(4-morpholino-6-((4-(thiazol-2-ylsulfonyl)piperidin-1-yl)methyl)thieno[3,2-d]pyrimidin-2-yl)pyrimidin-2-amine |
| 311 | 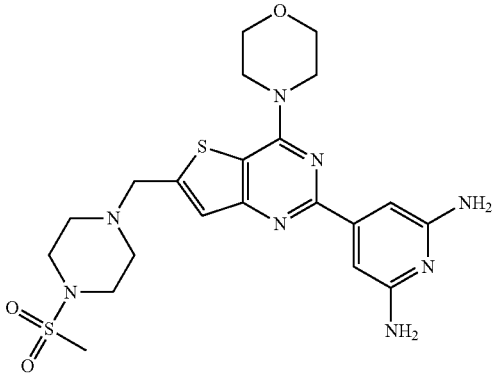 [SMILES: CS(=O)(=O)N1CCN(Cc2cc3nc(-c4cc(N)nc(N)c4)nc(N4CCOCC4)c3s2)CC1] | 4-(4-morpholino-6-((4-N-methylsulfonylpiperazin-1-yl)methyl)thieno[3,2-d]pyrimidin-2-yl)pyridine-2,6-diamine |
| 312 | 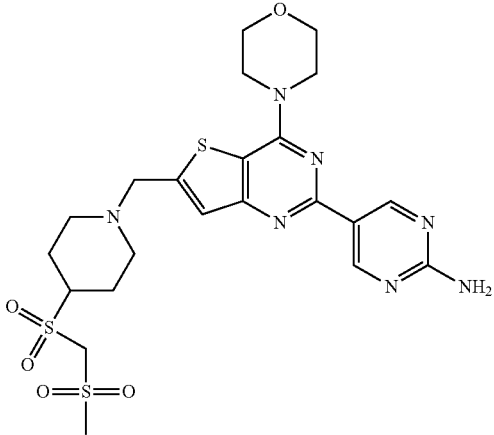 [SMILES: CS(=O)(=O)CS(=O)(=O)C1CCN(Cc2cc3nc(-c4cnc(N)nc4)nc(N4CCOCC4)c3s2)CC1] | 5-(6-((4-((methylsulfonyl)methylsulfonyl)piperidin-1-yl)methyl)-4-morpholinothieno[3,2-d]pyrimidin-2-yl)pyrimidin-2-amine |

TABLE 1-continued

| Compound | Structure | Name |
|---|---|---|
| 313 | 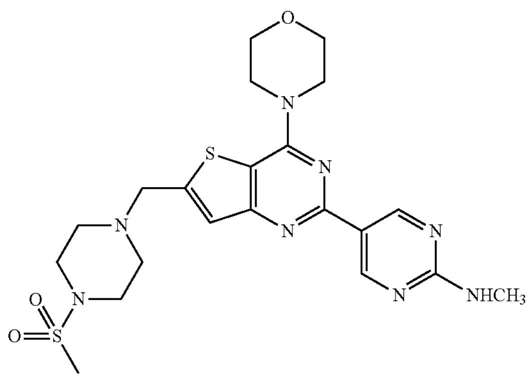 [SMILES: CNc1ncc(-c2nc(N3CCOCC3)c3sc(CN4CCN(S(C)(=O)=O)CC4)cc3n2)cn1] | 2-(2-methylaminopyrimidin-5-yl)-morpholino-6-(4-N-methylsulfonyl(piperazin-1-yl)methyl)thieno[3,2-d]pyrimidine |
| 314 | 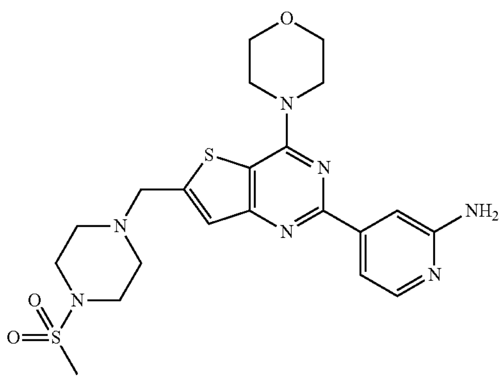 [SMILES: CS(=O)(=O)N1CCN(Cc2cc3nc(-c4ccnc(N)c4)nc(N4CCOCC4)c3s2)CC1] | 4-(4-morpholino-6-((4-N-methylsulfonylpiperazin-1-yl)methyl)thieno[3,2-d]pyrimidin-2-yl)pyridin-2-amine |
| 315 | 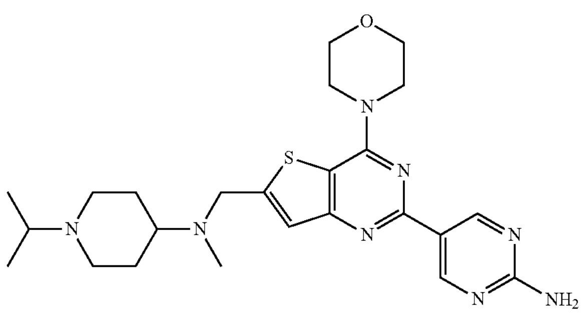 [SMILES: CC(C)N1CCC(N(C)Cc2cc3nc(-c4cnc(N)nc4)nc(N4CCOCC4)c3s2)CC1] | N-((2-(2-aminopyrimidin-5-yl)-4-morpholinothieno[3,2-d]pyrimidin-6-yl)methyl)-N-methyl(N-1-isopropyl)piperidin-4-amine |
| 316 | 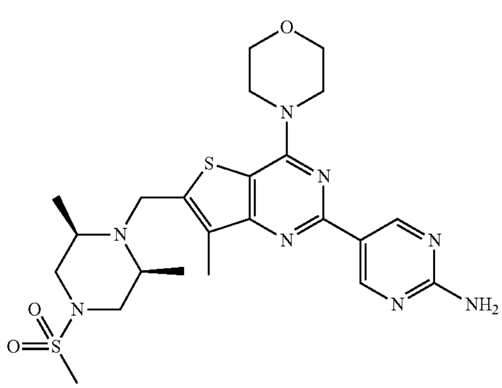 [SMILES: Cc1c(CN2[C@H](C)CN(S(C)(=O)=O)C[C@@H]2C)sc2c(N3CCOCC3)nc(-c3cnc(N)nc3)nc12] | 5-(7-methyl-6-(((2R,6S)-2,6-dimethyl-(4-N-methylsulfonyl)piperazin-1-yl)methyl)-4-morpholinothieno[3,2-d]pyrimidin-2-yl)pyrimidin-2-amine |

TABLE 1-continued

| Compound | Structure | Name |
|---|---|---|
| 317 | 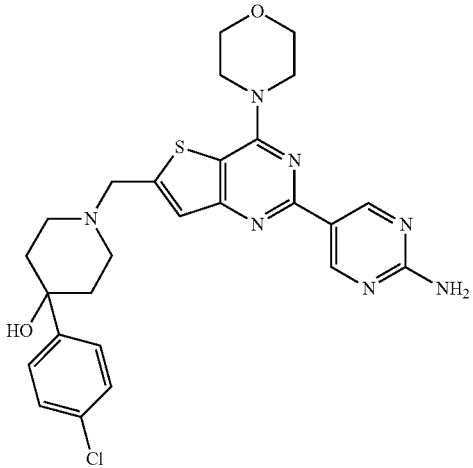 [SMILES: Nc1ncc(-c2nc(N3CCOCC3)c3sc(CN4CCC(O)(c5ccc(Cl)cc5)CC4)cc3n2)cn1] | 1-((2-(2-aminopyrimidin-5-yl)-4-morpholinothieno[3,2-d]pyrimidin-6-yl)methyl)-4-(4-chlorophenyl)piperidin-4-ol |
| 318 | 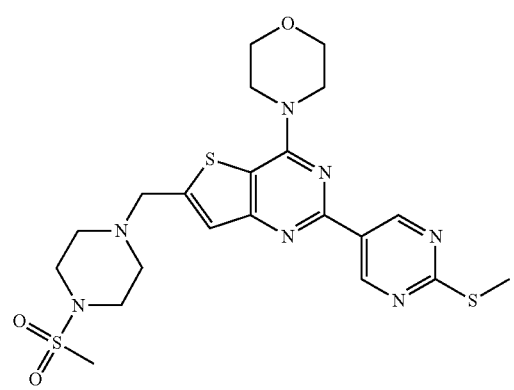 [SMILES: CSc1ncc(-c2nc(N3CCOCC3)c3sc(CN4CCN(S(C)(=O)=O)CC4)cc3n2)cn1] | 2-(2-(methylthio)pyrimidin-5-yl)-4-morpholino-6-((4-N-methylsulfonylpiperazin-1-yl)methyl)thieno[3,2-d]pyrimidine |

TABLE 2

| Compound | Structure | Name |
|---|---|---|
| 319 | 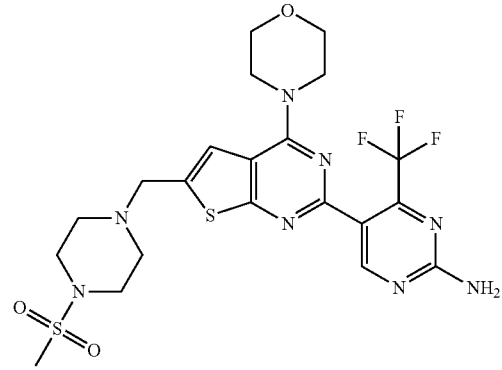 [SMILES: CS(=O)(=O)N1CCN(Cc2cc3c(N4CCOCC4)nc(-c4cnc(N)nc4C(F)(F)F)nc3s2)CC1] | 5-(6-((4-(methylsulfonyl)piperazin-1-yl)methyl)-4-morpholinothieno[2,3-d]pyrimidin-2-yl)-4-(trifluoromethyl)pyrimidin-2-amine |

TABLE 2-continued

| Compound | Structure | Name |
|---|---|---|
| 320 | 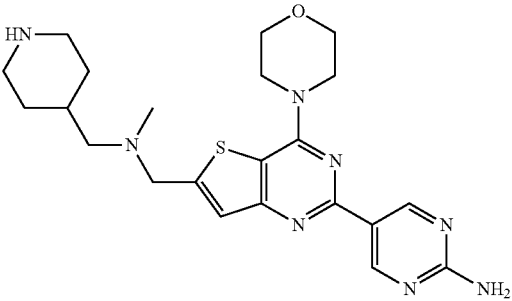 [SMILES: CN(Cc1cc2nc(-c3cnc(N)nc3)nc(N3CCOCC3)c2s1)CC1CCNCC1] | 5-(6-((methyl(piperidin-4-ylmethyl)amino)methyl)-4-morpholinothieno[3,2-d]pyrimidin-2-yl)pyrimidin-2-amine |
| 321 | 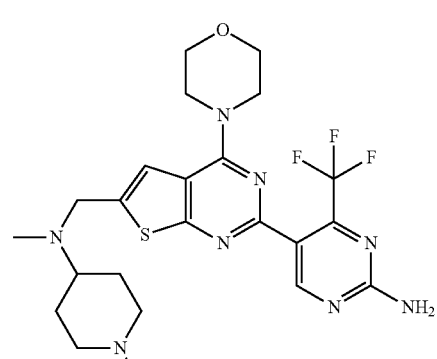 | 5-(6-((methyl(1-methylpiperidin-4-yl)amino)methyl)-4-morpholinothieno[2,3-d]pyrimidin-2-yl)-4-(trifluoromethyl)pyrimidin-2-amine |
| 322 | 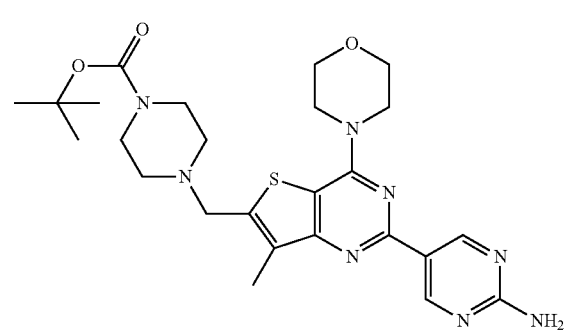 [SMILES: Cc1c(CN2CCN(C(=O)OC(C)(C)C)CC2)sc2c(N3CCOCC3)nc(-c3cnc(N)nc3)nc12] | tert-butyl 4-((2-(2-aminopyrimidin-5-yl)-7-methyl-4-morpholinothieno[3,2-d]pyrimidin-6-yl)methyl)piperazine-1-carboxylate |
| 323 | 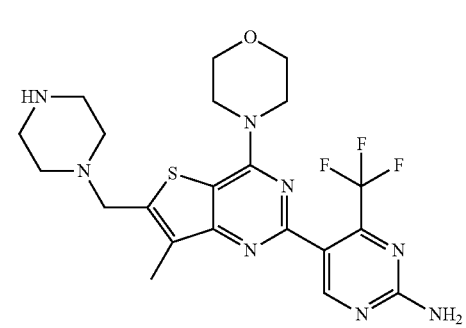 [SMILES: Cc1c(CN2CCNCC2)sc2c(N3CCOCC3)nc(-c3cnc(N)nc3C(F)(F)F)nc12] | 5-(7-methyl-4-morpholino-6-(piperazin-1-ylmethyl)thieno[3,2-d]pyrimidin-2-yl)-4-(trifluoromethyl)pyrimidin-2-amine |

TABLE 2-continued

| Compound | Structure | Name |
|---|---|---|
| 324 | 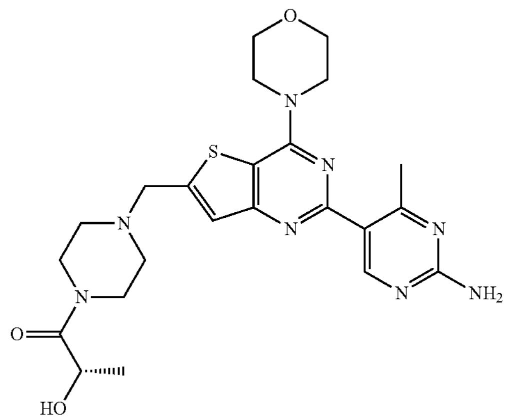 [SMILES: Cc1nc(N)ncc1-c1nc(N2CCOCC2)c2sc(CN3CCN(C(=O)[C@H](C)O)CC3)cc2n1] | (S)-1-(4-((2-(2-amino-4-methylpyrimidin-5-yl)-4-morpholinothieno[3,2-d]pyrimidin-6-yl)methyl)piperazin-1-yl)-2-hydroxypropan-1-one |
| 325 | 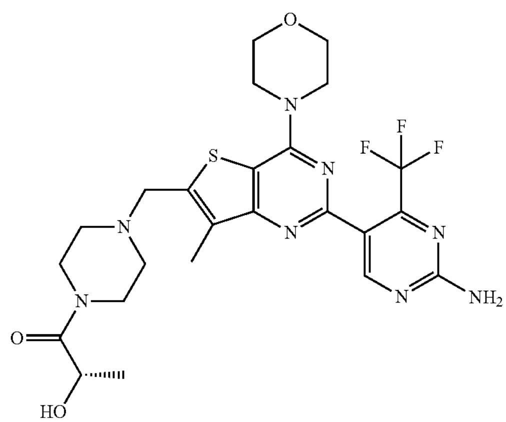 [SMILES: Cc1c(CN2CCN(C(=O)[C@H](C)O)CC2)sc2c(N3CCOCC3)nc(-c3cnc(N)nc3C(F)(F)F)nc12] | (S)-1-(4-((2-(2-amino-4-(trifluoromethyl)pyrimidin-5-yl)-7-methyl-4-morpholinothieno[3,2-d]pyrimidin-6-yl)methyl)piperazin-1-yl)-2-hydroxypropan-1-one |
| 326 | 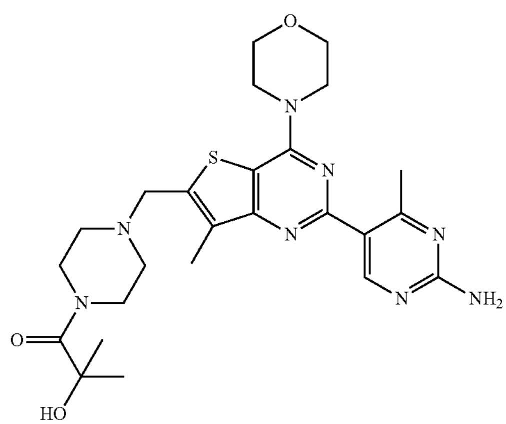 [SMILES: Cc1nc(N)ncc1-c1nc(N2CCOCC2)c2sc(CN3CCN(C(=O)C(C)(C)O)CC3)c(C)c2n1] | 1-(4-((2-(2-amino-4-methylpyrimidin-5-yl)-7-methyl-4-morpholinothieno[3,2-d]pyrimidin-6-yl)methyl)piperazin-1-yl)-2-hydroxy-2-methylpropan-1-one |
| 327 | 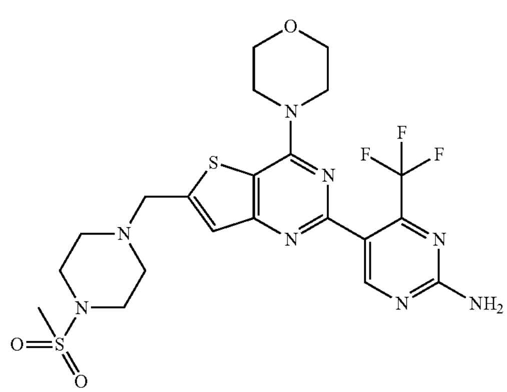 [SMILES: CS(=O)(=O)N1CCN(Cc2cc3nc(-c4cnc(N)nc4C(F)(F)F)nc(N4CCOCC4)c3s2)CC1] | 5-(6-((4-(methylsulfonyl)piperazin-1-yl)methyl)-4-morpholinothieno[3,2-d]pyrimidin-2-yl)-4-(trifluoromethyl)pyrimidin-2-amine |

TABLE 2-continued

| Compound | Structure | Name |
|---|---|---|
| 328 | 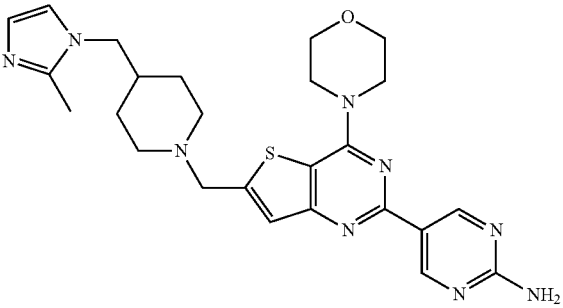 [SMILES: Cc1nccn1CC1CCN(Cc2cc3nc(-c4cnc(N)nc4)nc(N4CCOCC4)c3s2)CC1] | 5-(6-((4-((2-methyl-1H-imidazol-1-yl)methyl)piperidin-1-yl)methyl)-4-morpholinothieno[3,2-d]pyrimidin-2-yl)pyrimidin-2-amine |
| 329 | 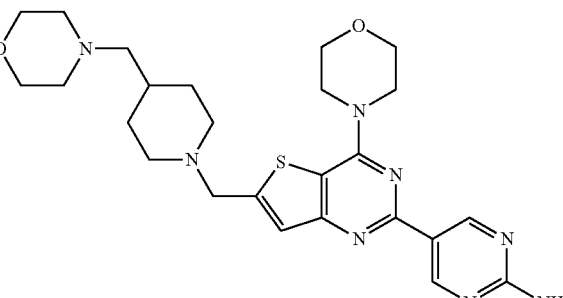 | 5-(4-morpholino-6-((4-(morpholinomethyl)piperidin-1-yl)methyl)thieno[3,2-d]pyrimidin-2-yl)pyrimidin-2-amine |
| 330 | 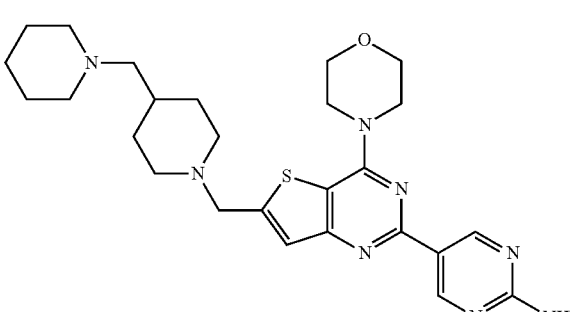 | 5-(4-morpholino-6-((4-(piperidin-1-ylmethyl)piperidin-1-yl)methyl)thieno[3,2-d]pyrimidin-2-yl)pyrimidin-2-amine |
| 331 | 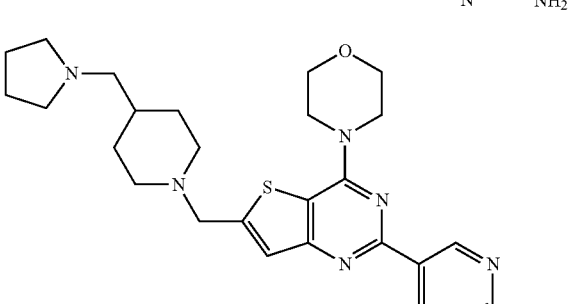 | 5-(4-morpholino-6-((4-(pyrrolidin-1-ylmethyl)piperidin-1-yl)methyl)thieno[3,2-d]pyrimidin-2-yl)pyrimidin-2-amine |
| 332 | 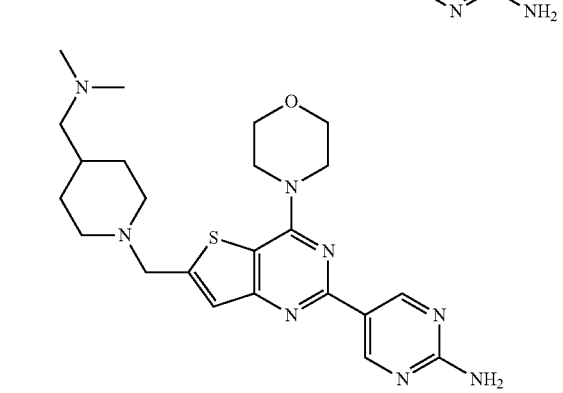 | 5-(6-((4-((dimethylamino)methyl)piperidin-1-yl)methyl)-4-morpholinothieno[3,2-d]pyrimidin-2-yl)pyrimidin-2-amine |

TABLE 2-continued

| Compound | Structure | Name |
|---|---|---|
| 333 | 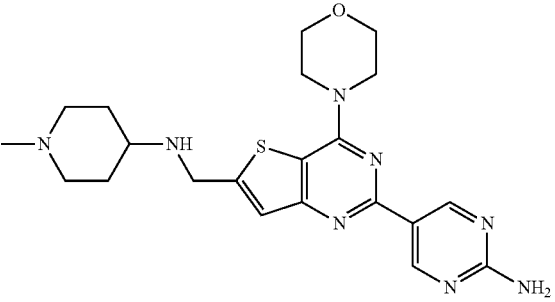 [SMILES: CN1CCC(NCc2cc3nc(-c4cnc(N)nc4)nc(N4CCOCC4)c3s2)CC1] | 5-(6-((1-methylpiperidin-4-ylamino)methyl)-4-morpholinothieno[3,2-d]pyrimidin-2-yl)pyrimidin-2-amine |
| 334 | 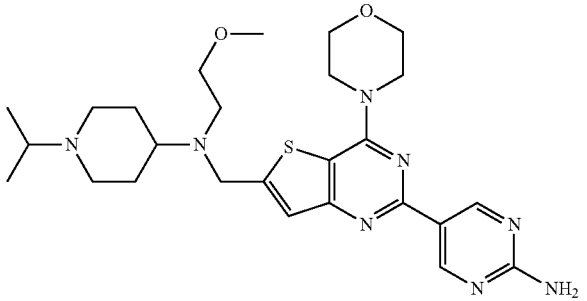 [SMILES: COCCN(Cc1cc2nc(-c3cnc(N)nc3)nc(N3CCOCC3)c2s1)C1CCN(C(C)C)CC1] | 5-(6-(((1-isopropylpiperidin-4-yl)(2-methoxyethyl)amino)methyl)-4-morpholinothieno[3,2-d]pyrimidin-2-yl)pyrimidin-2-amine |
| 335 | 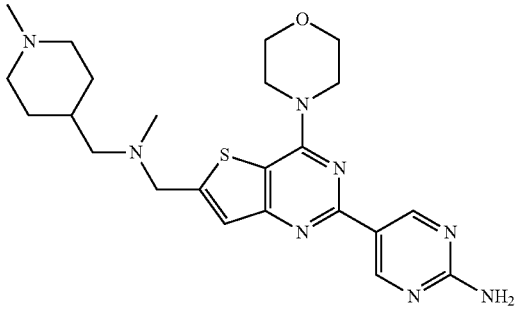 [SMILES: CN1CCC(CN(C)Cc2cc3nc(-c4cnc(N)nc4)nc(N4CCOCC4)c3s2)CC1] | 5-(6-((methyl((1-methylpiperidin-4-yl)methyl)amino)methyl)-4-morpholinothieno[3,2-d]pyrimidin-2-yl)pyrimidin-2-amine |
| 336 | 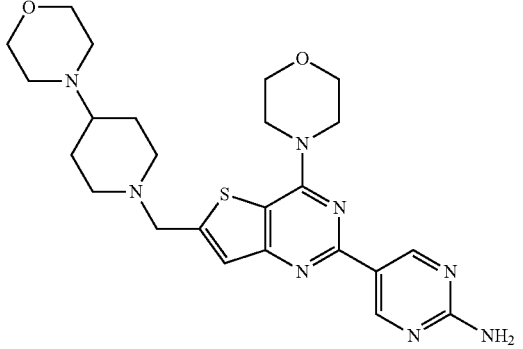 [SMILES: Nc1ncc(-c2nc(N3CCOCC3)c3sc(CN4CCC(N5CCOCC5)CC4)cc3n2)cn1] | 5-(4-morpholino-6-((4-morpholinopiperidin-1-yl)methyl)thieno[3,2-d]pyrimidin-2-yl)pyrimidin-2-amine |
| 337 | 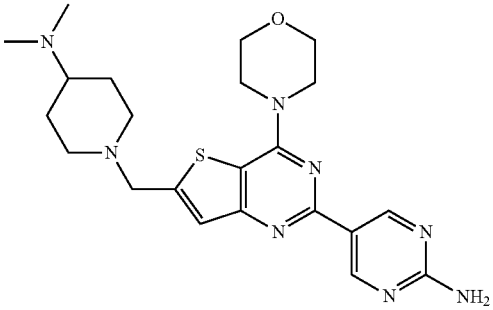 [SMILES: CN(C)C1CCN(Cc2cc3nc(-c4cnc(N)nc4)nc(N4CCOCC4)c3s2)CC1] | 5-(6-((4-(dimethylamino)piperidin-1-yl)methyl)-4-morpholinothieno[3,2-d]pyrimidin-2-yl)pyrimidin-2-amine |

TABLE 2-continued

| Compound | Structure | Name |
|---|---|---|
| 338 | 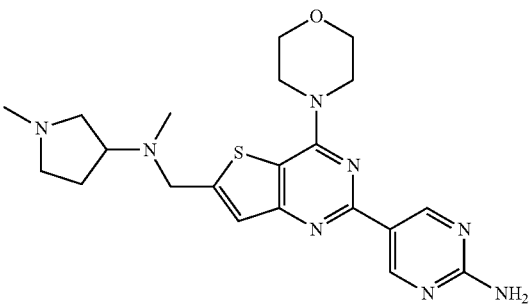 [SMILES: CN1CCC(N(C)Cc2cc3nc(-c4cnc(N)nc4)nc(N4CCOCC4)c3s2)C1] | 5-(6-((methyl(1-methylpyrrolidin-3-yl)amino)methyl)-4-morpholinothieno[3,2-d]pyrimidin-2-yl)pyrimidin-2-amine |
| 339 | 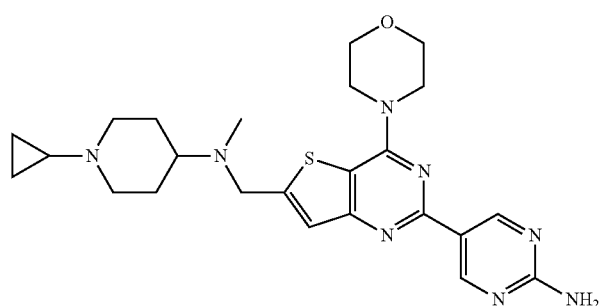 | 5-(6-(((1-cyclopropylpiperidin-4-yl)(methyl)amino)methyl)-4-morpholinothieno[3,2-d]pyrimidin-2-yl)pyrimidin-2-amine |
| 340 | 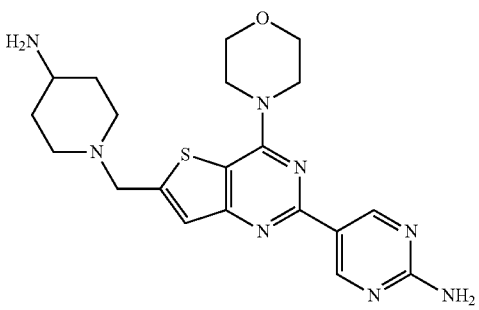 [SMILES: Nc1ncc(-c2nc(N3CCOCC3)c3sc(CN4CCC(N)CC4)cc3n2)cn1] | 5-(6-((4-aminopiperidin-1-yl)methyl)-4-morpholinothieno[3,2-d]pyrimidin-2-yl)pyrimidin-2-amine |
| 341 | 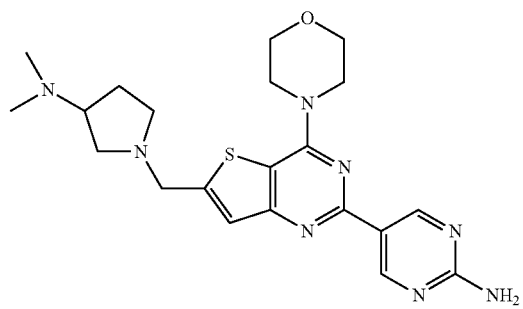 [SMILES: CN(C)C1CCN(Cc2cc3nc(-c4cnc(N)nc4)nc(N4CCOCC4)c3s2)C1] | 5-(6-((3-(dimethylamino)pyrrolidin-1-yl)methyl)-4-morpholinothieno[3,2-d]pyrimidin-2-yl)pyrimidin-2-amine |
| 342 | 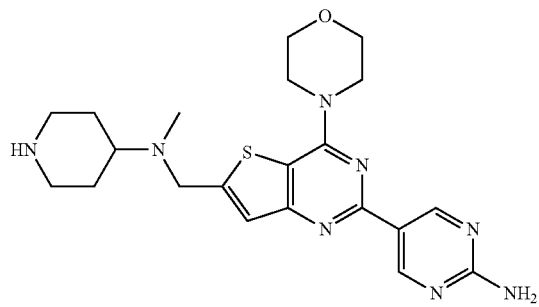 [SMILES: CN(Cc1cc2nc(-c3cnc(N)nc3)nc(N3CCOCC3)c2s1)C1CCNCC1] | 5-(6-((methyl(piperidin-4-yl)amino)methyl)-4-morpholinothieno[3,2-d]pyrimidin-2-yl)pyrimidin-2-amine |

TABLE 2-continued

| Compound | Structure | Name |
| --- | --- | --- |
| 343 | 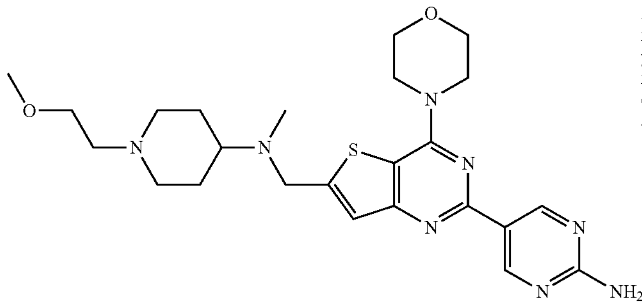 [SMILES: COCCN1CCC(N(C)Cc2cc3nc(-c4cnc(N)nc4)nc(N4CCOCC4)c3s2)CC1] | 5-(6-(((1-(2-methoxyethyl)piperidin-4-yl)(methyl)amino)methyl)-4-morpholinothieno[3,2-d]pyrimidin-2-yl)pyrimidin-2-amine |
| 344 | 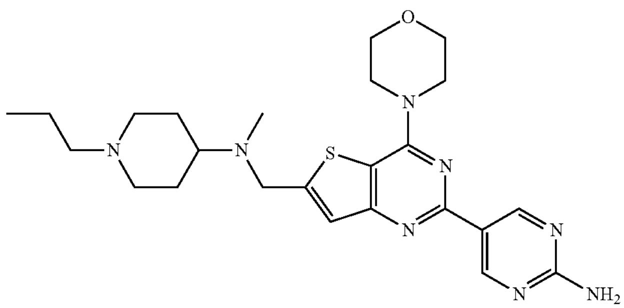 [SMILES: CCCN1CCC(N(C)Cc2cc3nc(-c4cnc(N)nc4)nc(N4CCOCC4)c3s2)CC1] | 5-(6-((methyl(1-propylpiperidin-4-yl)amino)methyl)-4-morpholinothieno[3,2-d]pyrimidin-2-yl)pyrimidin-2-amine |
| 345 | 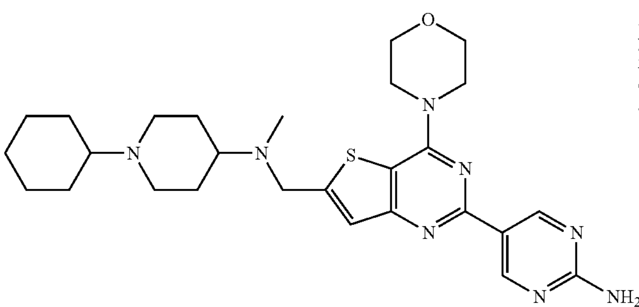 [SMILES: CN(Cc1cc2nc(-c3cnc(N)nc3)nc(N3CCOCC3)c2s1)C1CCN(C2CCCCC2)CC1] | 5-(6-(((1-cyclohexylpiperidin-4-yl)(methyl)amino)methyl)-4-morpholinothieno[3,2-d]pyrimidin-2-yl)pyrimidin-2-amine |
| 346 | 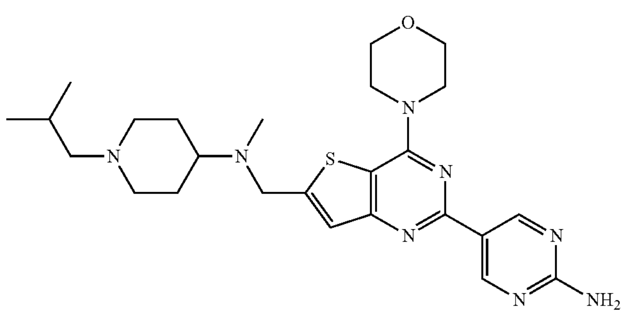 [SMILES: CC(C)CN1CCC(N(C)Cc2cc3nc(-c4cnc(N)nc4)nc(N4CCOCC4)c3s2)CC1] | 5-(6-(((1-isobutylpiperidin-4-yl)(methyl)amino)methyl)-4-morpholinothieno[3,2-d]pyrimidin-2-yl)pyrimidin-2-amine |
| 347 | 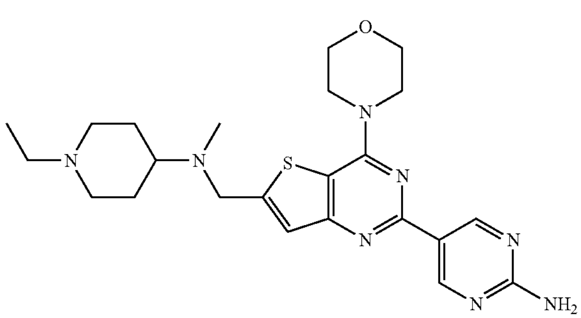 [SMILES: CCN1CCC(N(C)Cc2cc3nc(-c4cnc(N)nc4)nc(N4CCOCC4)c3s2)CC1] | 5-(6-(((1-ethylpiperidin-4-yl)(methyl)amino)methyl)-4-morpholinothieno[3,2-d]pyrimidin-2-yl)pyrimidin-2-amine |

TABLE 2-continued

| Compound | Structure | Name |
|---|---|---|
| 348 | 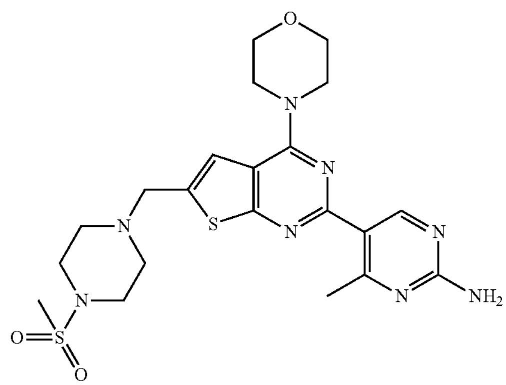 [SMILES: Cc1nc(N)ncc1-c1nc(N2CCOCC2)c2cc(CN3CCN(S(C)(=O)=O)CC3)sc2n1] | 4-methyl-5-(6-((4-(methylsulfonyl)piperazin-1-yl)methyl)-4-morpholinothieno[2,3-d]pyrimidin-2-yl)pyrimidin-2-amine |
| 349 | 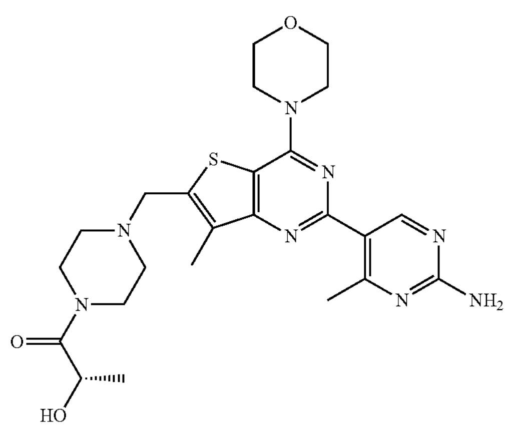 [SMILES: Cc1nc(N)ncc1-c1nc(N2CCOCC2)c2sc(CN3CCN(C(=O)[C@H](C)O)CC3)c(C)c2n1] | (S)-1-(4-((2-(2-amino-4-methylpyrimidin-5-yl)-7-methyl-4-morpholinothieno[3,2-d]pyrimidin-6-yl)methyl)piperazin-1-yl)-2-hydroxypropan-1-one |
| 350 | 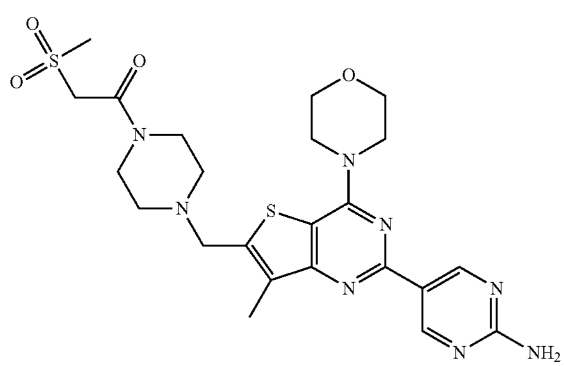 [SMILES: Cc1c(CN2CCN(C(=O)CS(C)(=O)=O)CC2)sc2c(N3CCOCC3)nc(-c3cnc(N)nc3)nc12] | 1-(4-((2-(2-aminopyrimidin-5-yl)-7-methyl-4-morpholinothieno[3,2-d]pyrimidin-6-yl)methyl)piperazin-1-yl)-2-(methylsulfonyl)ethanone |
| 351 | 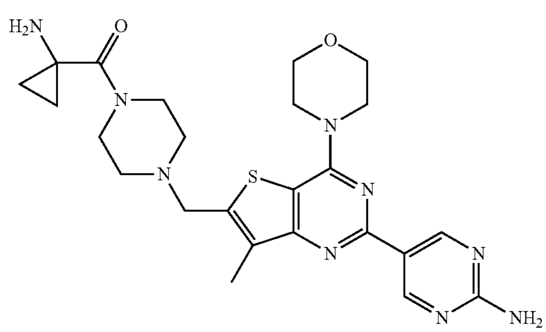 [SMILES: Cc1c(CN2CCN(C(=O)C3(N)CC3)CC2)sc2c(N3CCOCC3)nc(-c3cnc(N)nc3)nc12] | (1-aminocyclopropyl)(4-((2-(2-aminopyrimidin-5-yl)-7-methyl-4-morpholinothieno[3,2-d]pyrimidin-6-yl)methyl)piperazin-1-yl)methanone |

TABLE 2-continued

| Compound | Structure | Name |
|---|---|---|
| 352 | 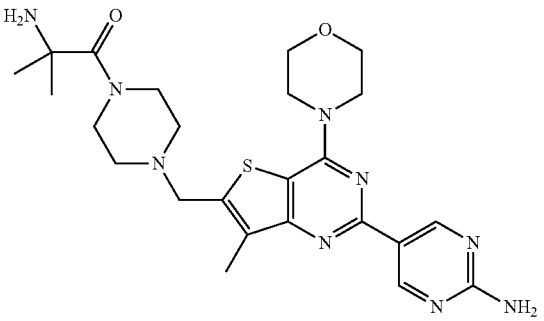 [SMILES: Cc1c(CN2CCN(C(=O)C(C)(C)N)CC2)sc2c(N3CCOCC3)nc(-c3cnc(N)nc3)nc12] | 2-amino-1-(4-((2-(2-aminopyrimidin-5-yl)-7-methyl-4-morpholinothieno[3,2-d]pyrimidin-6-yl)methyl)piperazin-1-yl)-2-methylpropan-1-one |
| 353 | 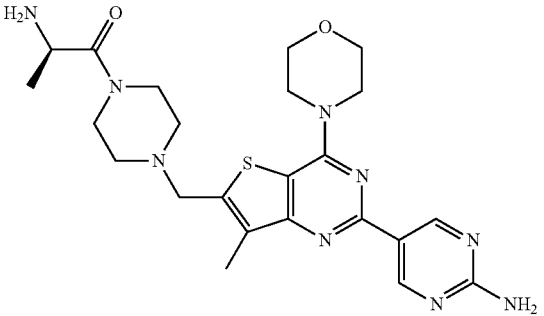 [SMILES: Cc1c(CN2CCN(C(=O)[C@@H](C)N)CC2)sc2c(N3CCOCC3)nc(-c3cnc(N)nc3)nc12] | (R)-2-amino-1-(4-((2-(2-aminopyrimidin-5-yl)-7-methyl-4-morpholinothieno[3,2-d]pyrimidin-6-yl)methyl)piperazin-1-yl)propan-1-one |
| 354 | 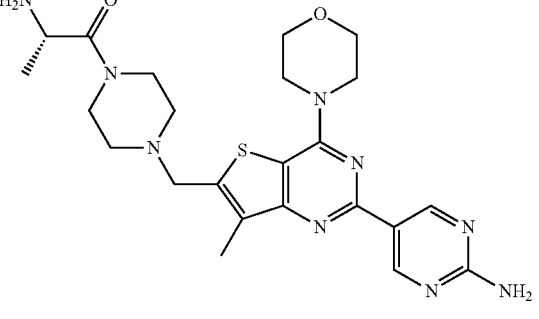 | (S)-2-amino-1-(4-((2-(2-aminopyrimidin-5-yl)-7-methyl-4-morpholinothieno[3,2-d]pyrimidin-6-yl)methyl)piperazin-1-yl)propan-1-one |
| 355 | 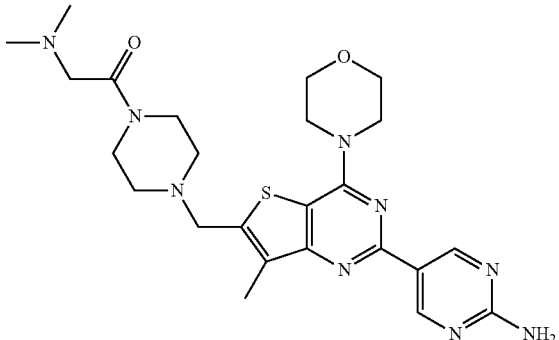 | 1-(4-((2-(2-aminopyrimidin-5-yl)-7-methyl-4-morpholinothieno[3,2-d]pyrimidin-6-yl)methyl)piperazin-1-yl)-2-(dimethylamino)ethanone |
| 356 | 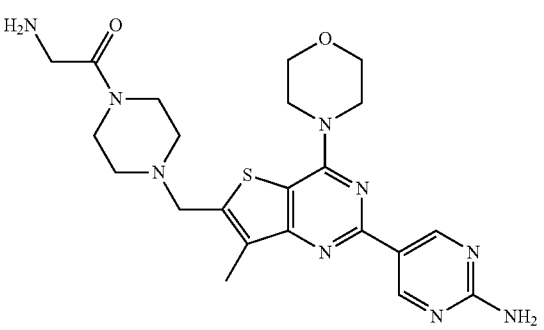 [SMILES: Cc1c(CN2CCN(C(=O)CN)CC2)sc2c(N3CCOCC3)nc(-c3cnc(N)nc3)nc12] | 2-amino-1-(4-((2-(2-aminopyrimidin-5-yl)-7-methyl-4-morpholinothieno[3,2-d]pyrimidin-6-yl)methyl)piperazin-1-yl)ethanone |

TABLE 2-continued

| Compound | Structure | Name |
|---|---|---|
| 357 | 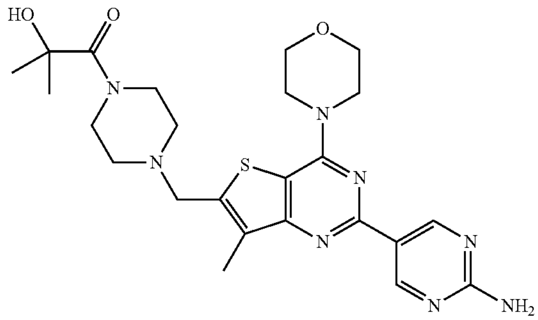 [SMILES: Cc1c(CN2CCN(C(=O)C(C)(C)O)CC2)sc2c(N3CCOCC3)nc(-c3cnc(N)nc3)nc12] | 1-(4-((2-(2-aminopyrimidin-5-yl)-7-methyl-4-morpholinothieno[3,2-d]pyrimidin-6-yl)methyl)piperazin-1-yl)-2-hydroxy-2-methylpropan-1-one |
| 358 | 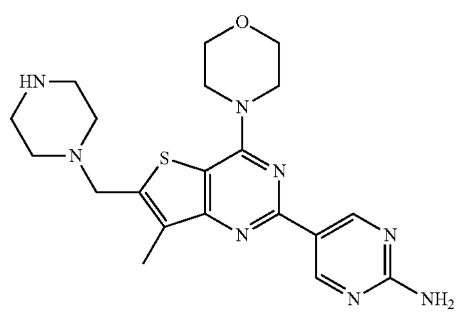 [SMILES: Cc1c(CN2CCNCC2)sc2c(N3CCOCC3)nc(-c3cnc(N)nc3)nc12] | 5-(7-methyl-4-morpholino-6-(piperazin-1-ylmethyl)thieno[3,2-d]pyrimidin-2-yl)pyrimidin-2-amine |
| 359 | 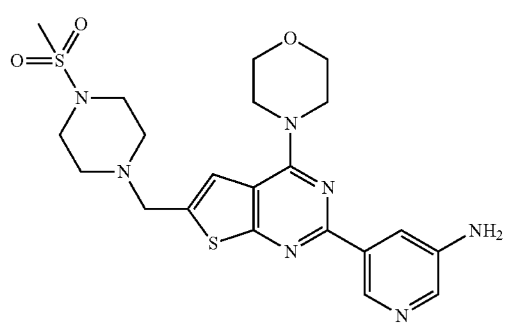 [SMILES: CS(=O)(=O)N1CCN(Cc2cc3c(N4CCOCC4)nc(-c4cncc(N)c4)nc3s2)CC1] | 5-(6-((4-(methylsulfonyl)piperazin-1-yl)methyl)-4-morpholinothieno[2,3-d]pyrimidin-2-yl)pyridin-3-amine |
| 360 | 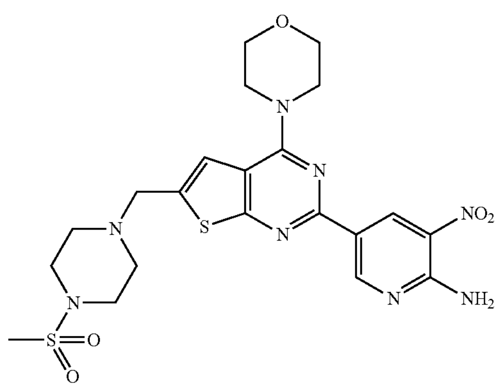 [SMILES: CS(=O)(=O)N1CCN(Cc2cc3c(N4CCOCC4)nc(-c4cnc(N)c([N+](=O)[O-])c4)nc3s2)CC1] | 5-(6-((4-(methylsulfonyl)piperazin-1-yl)methyl)-4-morpholinothieno[2,3-d]pyrimidin-2-yl)-3-nitropyridin-2-amine |

TABLE 2-continued

| Compound | Structure | Name |
|---|---|---|
| 361 | 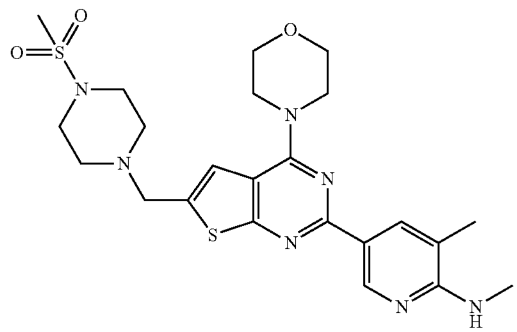 [SMILES: CNc1ncc(-c2nc(N3CCOCC3)c3cc(CN4CCN(S(C)(=O)=O)CC4)sc3n2)cc1C] | N,3-dimethyl-5-(6-((4-(methylsulfonyl)piperazin-1-yl)methyl)-4-morpholinothieno[2,3-d]pyrimidin-2-yl)pyridin-2-amine |
| 362 | 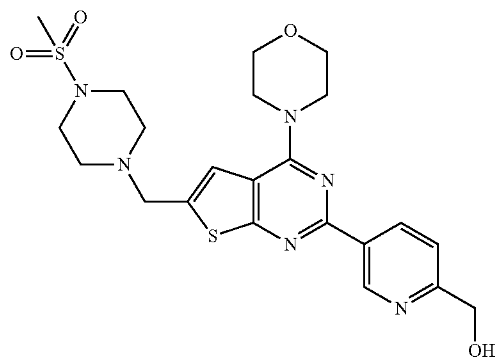 [SMILES: CS(=O)(=O)N1CCN(Cc2cc3c(N4CCOCC4)nc(-c4ccc(CO)nc4)nc3s2)CC1] | (5-(6-((4-(methylsulfonyl)piperazin-1-yl)methyl)-4-morpholinothieno[2,3-d]pyrimidin-2-yl)pyridin-2-yl)methanol |
| 363 | 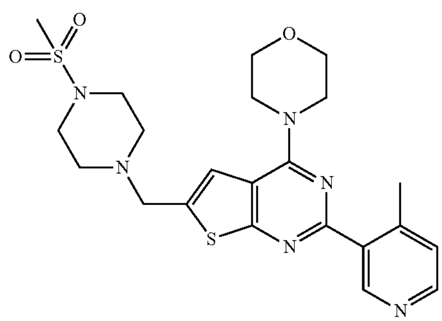 [SMILES: Cc1ccncc1-c1nc(N2CCOCC2)c2cc(CN3CCN(S(C)(=O)=O)CC3)sc2n1] | 4-(2-(4-methylpyridin-3-yl)-6-((4-(methylsulfonyl)piperazin-1-yl)methyl)thieno[2,3-d]pyrimidin-4-yl)morpholine |
| 364 | 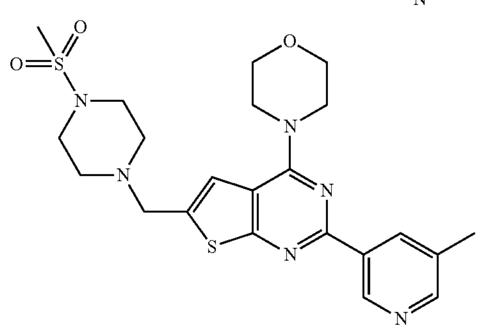 | 4-(2-(5-methylpyridin-3-yl)-6-((4-(methylsulfonyl)piperazin-1-yl)methyl)thieno[2,3-d]pyrimidin-4-yl)morpholine |
| 365 | 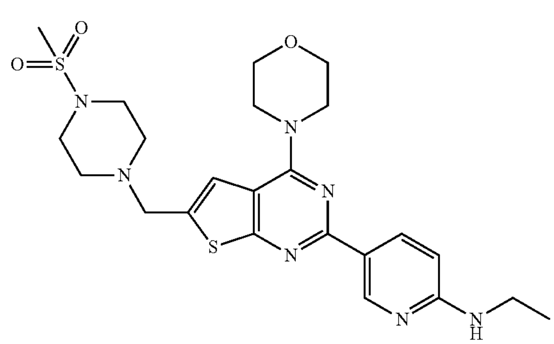 [SMILES: CCNc1ccc(-c2nc(N3CCOCC3)c3cc(CN4CCN(S(C)(=O)=O)CC4)sc3n2)cn1] | N-ethyl-5-(6-((4-(methylsulfonyl)piperazin-1-yl)methyl)-4-morpholinothieno[2,3-d]pyrimidin-2-yl)pyridin-2-amine |

TABLE 2-continued

| Compound | Structure | Name |
|---|---|---|
| 366 | 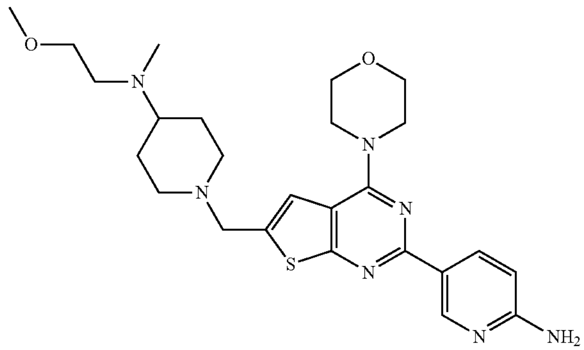 [SMILES: COCCN(C)C1CCN(Cc2cc3c(N4CCOCC4)nc(-c4ccc(N)nc4)nc3s2)CC1] | 5-(6-((4-((2-methoxyethyl)(methyl)amino)piperidin-1-yl)methyl)-4-morpholinothieno[2,3-d]pyrimidin-2-yl)pyridin-2-amine |
| 367 | 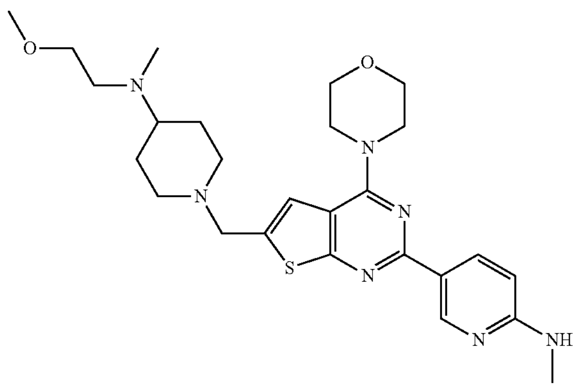 | 5-(6-((4-((2-methoxyethyl)(methyl)amino)piperidin-1-yl)methyl)-4-morpholinothieno[2,3-d]pyrimidin-2-yl)-N-methylpyridin-2-amine |
| 368 | 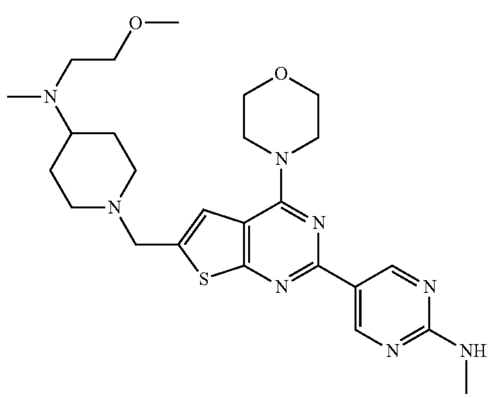 | 5-(6-((4-((2-methoxyethyl)(methyl)amino)piperidin-1-yl)methyl)-4-morpholinothieno[2,3-d]pyrimidin-2-yl)-N-methylpyrimidin-2-amine |
| 369 | 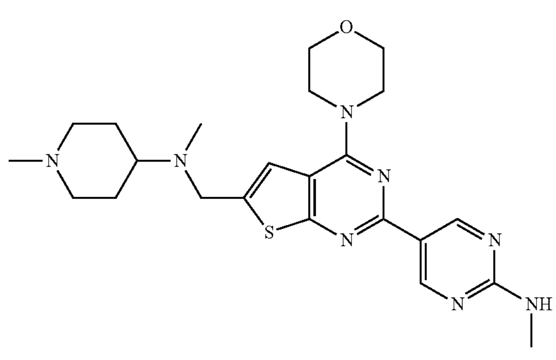 | N-methyl-5-(6-((methyl(1-methylpiperidin-4-yl)amino)methyl)-4-morpholinothieno[2,3-d]pyrimidin-2-yl)pyrimidin-2-amine |

TABLE 2-continued

| Compound | Structure | Name |
|---|---|---|
| 370 | 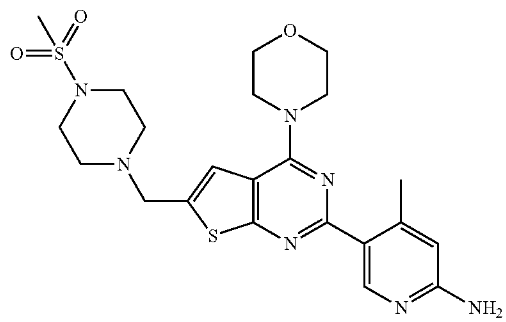 [SMILES: Cc1cc(N)ncc1-c1nc(N2CCOCC2)c2cc(CN3CCN(S(C)(=O)=O)CC3)sc2n1] | 4-methyl-5-(6-((4-(methylsulfonyl)piperazin-1-yl)methyl)-4-morpholinothieno[2,3-d]pyrimidin-2-yl)pyridin-2-amine |
| 371 | 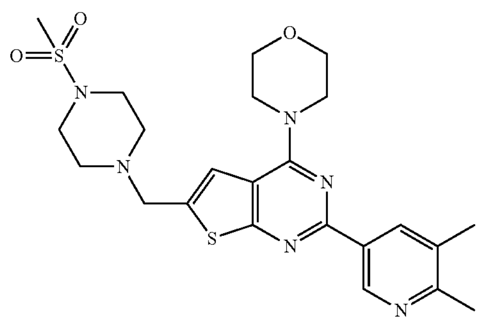 [SMILES: Cc1cc(-c2nc(N3CCOCC3)c3cc(CN4CCN(S(C)(=O)=O)CC4)sc3n2)cnc1C] | 4-(2-(5,6-dimethylpyridin-3-yl)-6-((4-(methylsulfonyl)piperazin-1-yl)methyl)thieno[2,3-d]pyrimidin-4-yl)morpholine |
| 372 | 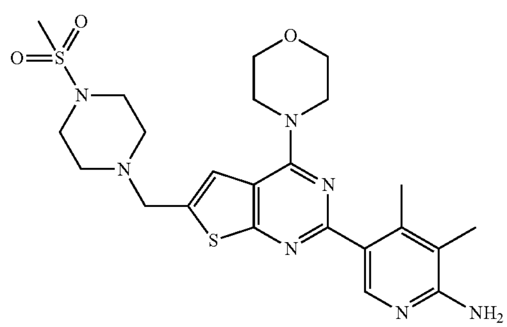 [SMILES: Cc1c(-c2nc(N3CCOCC3)c3cc(CN4CCN(S(C)(=O)=O)CC4)sc3n2)cnc(N)c1C] | 3,4-dimethyl-5-(6-((4-(methylsulfonyl)piperazin-1-yl)methyl)-4-morpholinothieno[2,3-d]pyrimidin-2-yl)pyridin-2-amine |
| 373 | 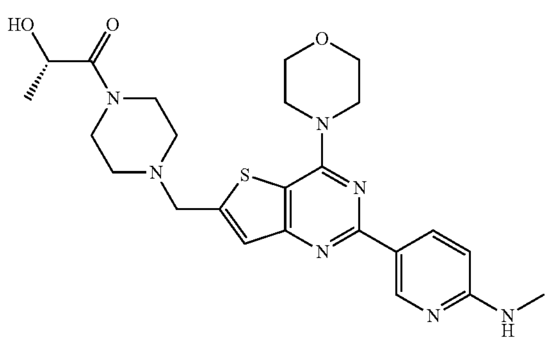 [SMILES: CNc1ccc(-c2nc(N3CCOCC3)c3sc(CN4CCN(C(=O)[C@H](C)O)CC4)cc3n2)cn1] | (S)-2-hydroxy-1-(4-((2-(6-(methylamino)pyridin-3-yl)-4-morpholinothieno[3,2-d]pyrimidin-6-yl)methyl)piperazin-1-yl)propan-1-one |
| 374 | 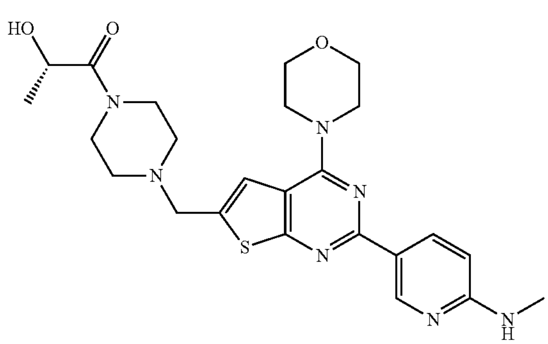 [SMILES: CNc1ccc(-c2nc(N3CCOCC3)c3cc(CN4CCN(C(=O)[C@H](C)O)CC4)sc3n2)cn1] | (S)-2-hydroxy-1-(4-((2-(6-(methylamino)pyridin-3-yl)-4-morpholinothieno[2,3-d]pyrimidin-6-yl)methyl)piperazin-1-yl)propan-1-one |

| Compound | Structure | Name |
| --- | --- | --- |
| 375 | 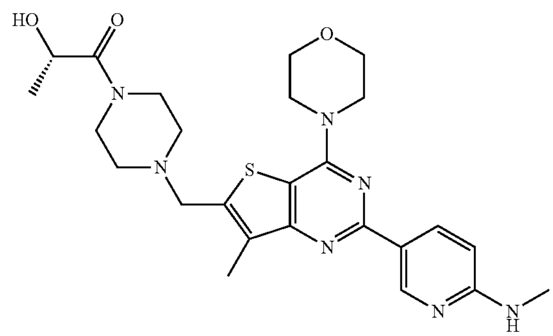 [SMILES: CNc1ccc(-c2nc(N3CCOCC3)c3sc(CN4CCN(C(=O)[C@H](C)O)CC4)c(C)c3n2)cn1] | (S)-2-hydroxy-1-(4-((7-methyl-2-(6-(methylamino)pyridin-3-yl)-4-morpholinothieno[3,2-d]pyrimidin-6-yl)methyl)piperazin-1-yl)propan-1-one |
| 376 | 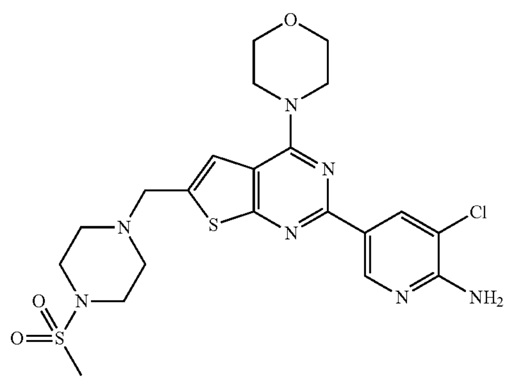 [SMILES: CS(=O)(=O)N1CCN(Cc2cc3c(N4CCOCC4)nc(-c4cnc(N)c(Cl)c4)nc3s2)CC1] | 3-chloro-5-(6-((4-(methylsulfonyl)piperazin-1-yl)methyl)-4-morpholinothieno[2,3-d]pyrimidin-2-yl)pyridin-2-amine |
| 377 | 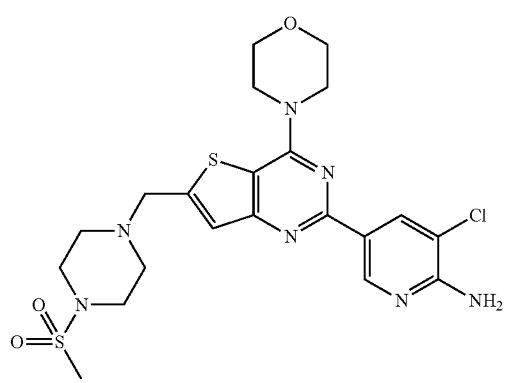 [SMILES: CS(=O)(=O)N1CCN(Cc2cc3nc(-c4cnc(N)c(Cl)c4)nc(N4CCOCC4)c3s2)CC1] | 3-chloro-5-(6-((4-(methylsulfonyl)piperazin-1-yl)methyl)-4-morpholinothieno[3,2-d]pyrimidin-2-yl)pyridin-2-amine |
| 378 | 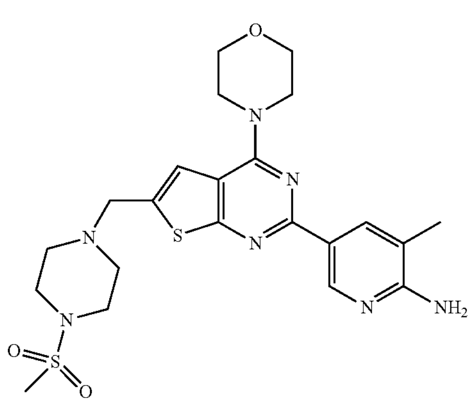 [SMILES: Cc1cc(-c2nc(N3CCOCC3)c3cc(CN4CCN(S(C)(=O)=O)CC4)sc3n2)cnc1N] | 3-methyl-5-(6-((4-(methylsulfonyl)piperazin-1-yl)methyl)-4-morpholinothieno[2,3-d]pyrimidin-2-yl)pyridin-2-amine |

TABLE 2-continued

| Compound | Structure | Name |
|---|---|---|
| 379 | 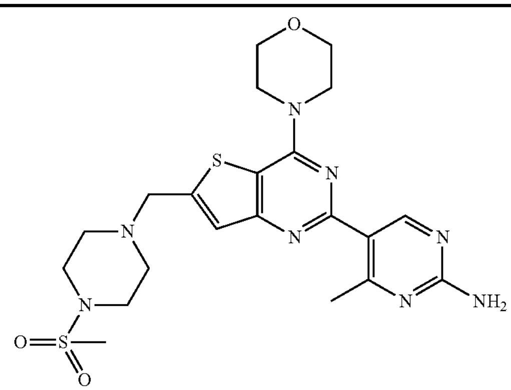 | 4-methyl-5-(6-((4-(methylsulfonyl)piperazin-1-yl)methyl)-4-morpholinothieno[3,2-d]pyrimidin-2-yl)pyrimidin-2-amine |
| 380 | 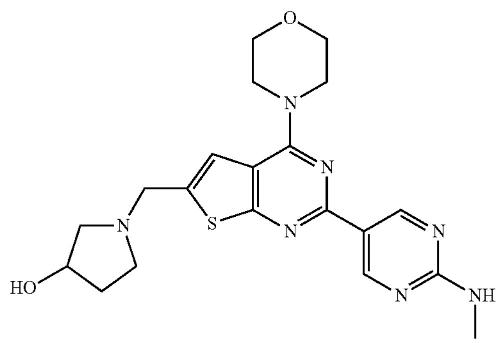 [SMILES: CNc1ncc(-c2nc(N3CCOCC3)c3cc(CN4CCC(O)C4)sc3n2)cn1] | 1-((2-(2-(methylamino)pyrimidin-5-yl)-4-morpholinothieno[2,3-d]pyrimidin-6-yl)methyl)pyrrolidin-3-ol |
| 381 | 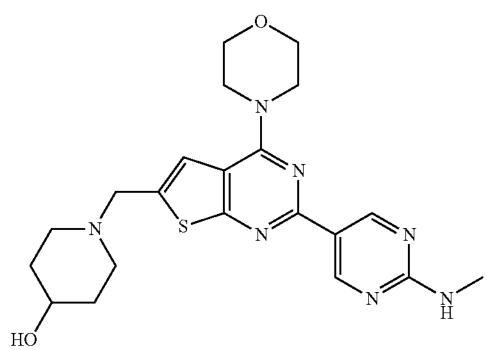 [SMILES: CNc1ncc(-c2nc(N3CCOCC3)c3cc(CN4CCC(O)CC4)sc3n2)cn1] | 1-((2-(2-(methylamino)pyrimidin-5-yl)-4-morpholinothieno[2,3-d]pyrimidin-6-yl)methyl)piperidin-4-ol |
| 382 | 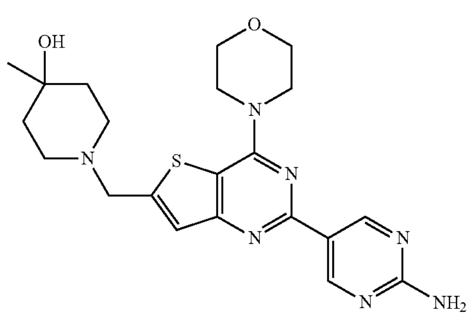 [SMILES: CC1(O)CCN(Cc2cc3nc(-c4cnc(N)nc4)nc(N4CCOCC4)c3s2)CC1] | 1-((2-(2-aminopyrimidin-5-yl)-4-morpholinothieno[3,2-d]pyrimidin-6-yl)methyl)-4-methylpiperidin-4-ol |

TABLE 2-continued

| Compound | Structure | Name |
|---|---|---|
| 383 | 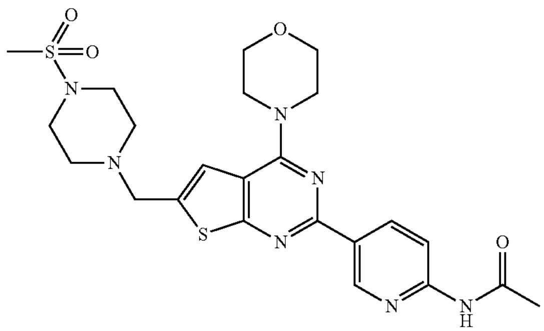 [SMILES: CC(=O)Nc1ccc(-c2nc(N3CCOCC3)c3cc(CN4CCN(S(C)(=O)=O)CC4)sc3n2)cn1] | N-(5-(6-((4-(methylsulfonyl)piperazin-1-yl)methyl)-4-morpholinothieno[2,3-d]pyrimidin-2-yl)pyridin-2-yl)acetamide |
| 384 | 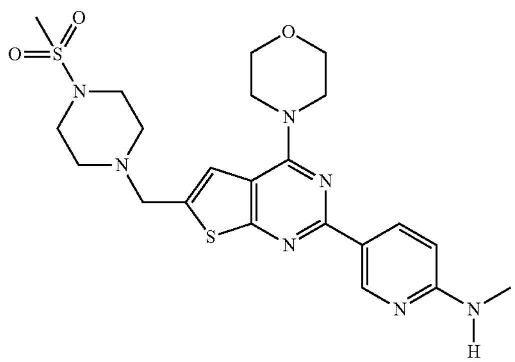 [SMILES: CNc1ccc(-c2nc(N3CCOCC3)c3cc(CN4CCN(S(C)(=O)=O)CC4)sc3n2)cn1] | N-methyl-5-(6-((4-(methylsulfonyl)piperazin-1-yl)methyl)-4-morpholinothieno[2,3-d]pyrimidin-2-yl)pyridin-2-amine |
| 385 | 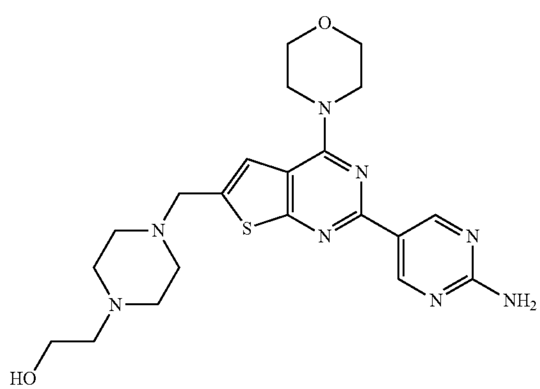 [SMILES: Nc1ncc(-c2nc(N3CCOCC3)c3cc(CN4CCN(CCO)CC4)sc3n2)cn1] | 2-(4-((2-(2-aminopyrimidin-5-yl)-4-morpholinothieno[2,3-d]pyrimidin-6-yl)methyl)piperazin-1-yl)ethanol |
| 386 | 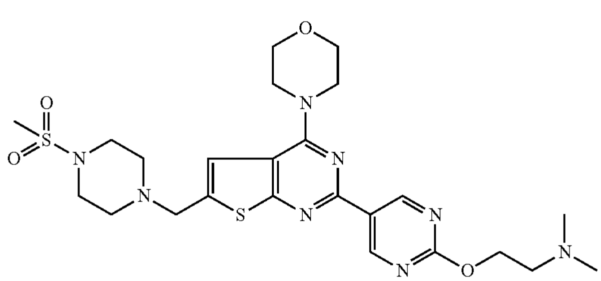 [SMILES: CN(C)CCOc1ncc(-c2nc(N3CCOCC3)c3cc(CN4CCN(S(C)(=O)=O)CC4)sc3n2)cn1] | N,N-dimethyl-2-(5-(6-((4-(methylsulfonyl)piperazin-1-yl)methyl)-4-morpholinothieno[2,3-d]pyrimidin-2-yl)pyrimidin-2-yloxy)ethanamine |

TABLE 2-continued

| Compound | Structure | Name |
|---|---|---|
| 387 | 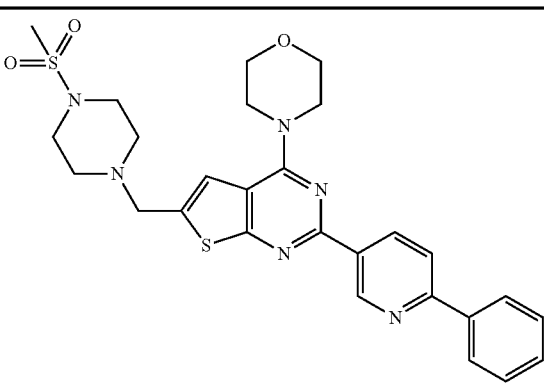 | 4-(6-((4-(methylsulfonyl)piperazin-1-yl)methyl)-2-(6-phenylpyridin-3-yl)thieno[2,3-d]pyrimidin-4-yl)morpholine |
| 388 | 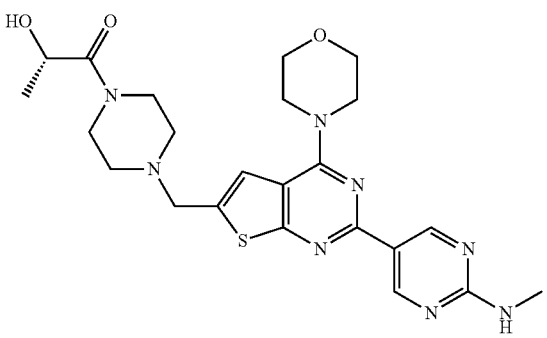 [SMILES: CNc1ncc(-c2nc(N3CCOCC3)c3cc(CN4CCN(C(=O)[C@H](C)O)CC4)sc3n2)cn1] | (S)-2-hydroxy-1-(4-((2-(2-(methylamino)pyrimidin-5-yl)-4-morpholinothieno[2,3-d]pyrimidin-6-yl)methyl)piperazin-1-yl)propan-1-one |
| 389 | 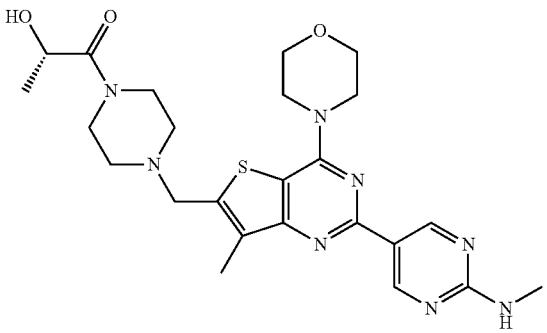 [SMILES: CNc1ncc(-c2nc(N3CCOCC3)c3sc(CN4CCN(C(=O)[C@H](C)O)CC4)c(C)c3n2)cn1] | (S)-2-hydroxy-1-(4-((7-methyl-2-(2-(methylamino)pyrimidin-5-yl)-4-morpholinothieno[3,2-d]pyrimidin-6-yl)methyl)piperazin-1-yl)propan-1-one |
| 390 | 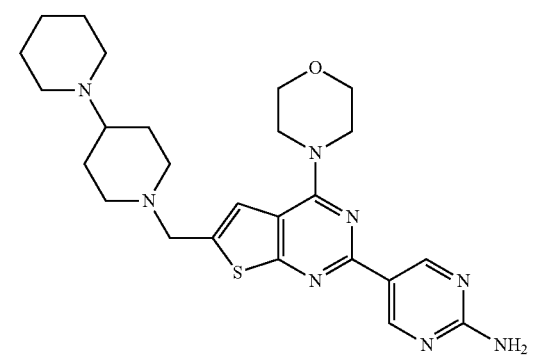 [SMILES: Nc1ncc(-c2nc(N3CCOCC3)c3cc(CN4CCC(N5CCCCC5)CC4)sc3n2)cn1] | 5-(6-(1,4'-bipiperidin-1'-ylmethyl)-4-morpholinothieno[2,3-d]pyrimidin-2-yl)pyrimidin-2-amine |

TABLE 2-continued

| Compound | Structure | Name |
|---|---|---|
| 391 | 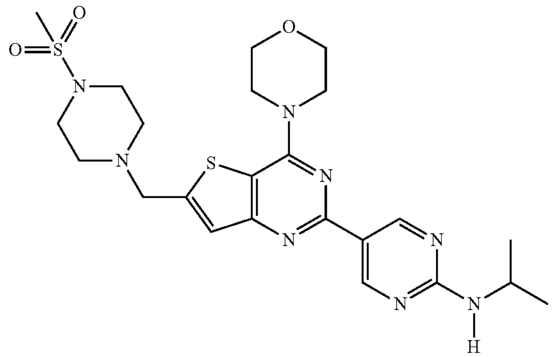 [SMILES: CC(C)Nc1ncc(-c2nc(N3CCOCC3)c3sc(CN4CCN(S(C)(=O)=O)CC4)cc3n2)cn1] | N-isopropyl-5-(6-((4-(methylsulfonyl)piperazin-1-yl)methyl)-4-morpholinothieno[3,2-d]pyrimidin-2-yl)pyrimidin-2-amine |
| 392 | 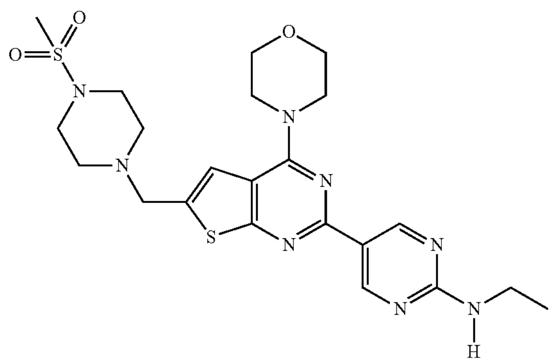 [SMILES: CCNc1ncc(-c2nc(N3CCOCC3)c3cc(CN4CCN(S(C)(=O)=O)CC4)sc3n2)cn1] | N-ethyl-5-(6-((4-(methylsulfonyl)piperazin-1-yl)methyl)-4-morpholinothieno[2,3-d]pyrimidin-2-yl)pyrimidin-2-amine |
| 393 | 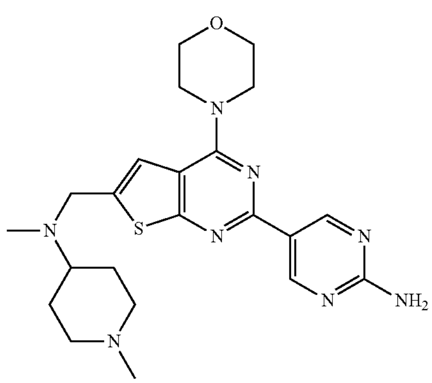 [SMILES: CN1CCC(N(C)Cc2cc3c(N4CCOCC4)nc(-c4cnc(N)nc4)nc3s2)CC1] | 5-(6-((methyl(1-methylpiperidin-4-yl)amino)methyl)-4-morpholinothieno[2,3-d]pyrimidin-2-yl)pyrimidin-2-amine |
| 394 | 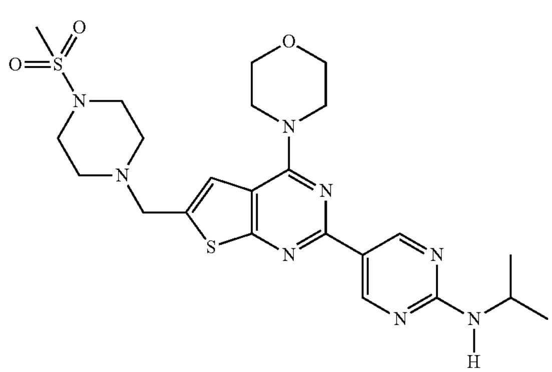 [SMILES: CC(C)Nc1ncc(-c2nc(N3CCOCC3)c3cc(CN4CCN(S(C)(=O)=O)CC4)sc3n2)cn1] | N-isopropyl-5-(6-((4-(methylsulfonyl)piperazin-1-yl)methyl)-4-morpholinothieno[2,3-d]pyrimidin-2-yl)pyrimidin-2-amine |

TABLE 2-continued

| Compound | Structure | Name |
|---|---|---|
| 395 | 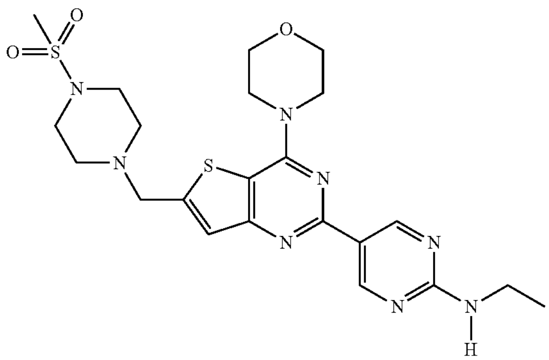 [SMILES: CCNc1ncc(-c2nc(N3CCOCC3)c3sc(CN4CCN(S(C)(=O)=O)CC4)cc3n2)cn1] | N-ethyl-5-(6-((4-(methylsulfonyl)piperazin-1-yl)methyl)-4-morpholinothieno[3,2-d]pyrimidin-2-yl)pyrimidin-2-amine |
| 396 | 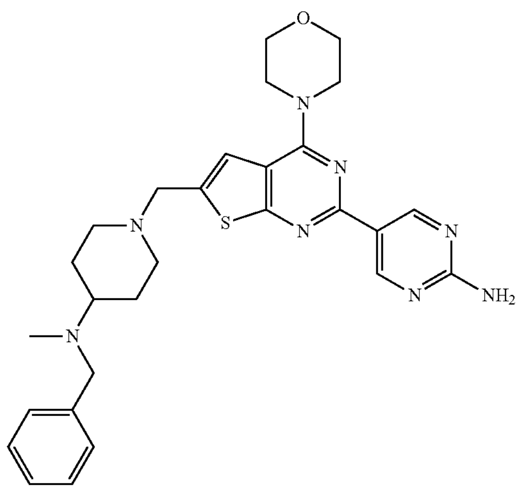 [SMILES: CN(Cc1ccccc1)C1CCN(Cc2cc3c(N4CCOCC4)nc(-c4cnc(N)nc4)nc3s2)CC1] | 5-(6-((4-(benzyl(methyl)amino)piperidin-1-yl)methyl)-4-morpholinothieno[2,3-d]pyrimidin-2-yl)pyrimidin-2-amine |
| 397 | 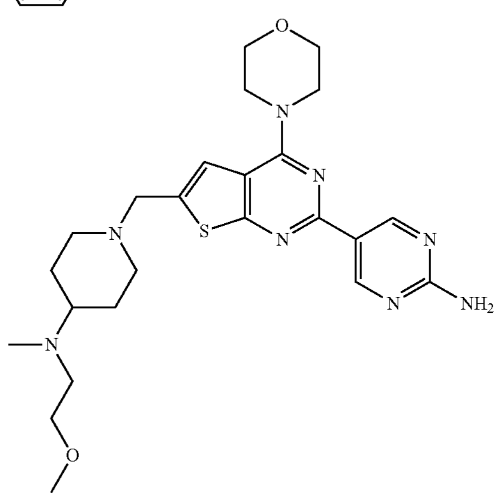 | 5-(6-((4-((2-methoxyethyl)(methyl)amino)piperidin-1-yl)methyl)-4-morpholinothieno[2,3-d]pyrimidin-2-yl)pyrimidin-2-amine |
| 398 | 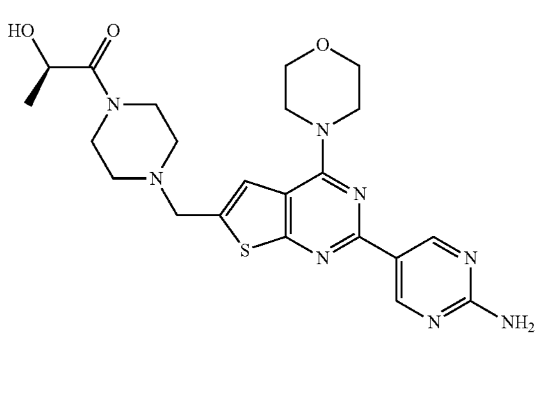 [SMILES: C[C@@H](O)C(=O)N1CCN(Cc2cc3c(N4CCOCC4)nc(-c4cnc(N)nc4)nc3s2)CC1] | (R)-1-(4-((2-(2-aminopyrimidin-5-yl)-4-morpholinothieno[2,3-d]pyrimidin-6-yl)methyl)piperazin-1-yl)-2-hydroxypropan-1-one |

| Compound | Structure | Name |
|---|---|---|
| 399 | 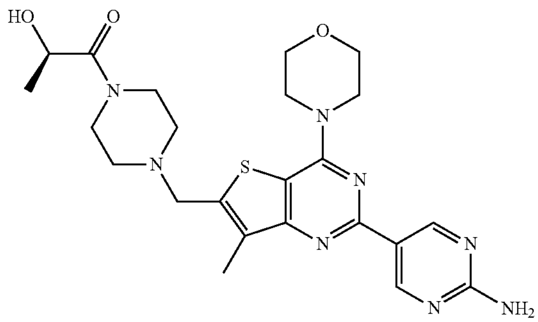 [SMILES: Cc1c(CN2CCN(C(=O)[C@@H](C)O)CC2)sc2c(N3CCOCC3)nc(-c3cnc(N)nc3)nc12] | (R)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one |
| 400 | 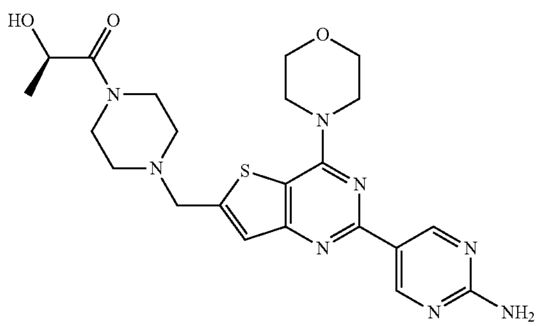 [SMILES: C[C@@H](O)C(=O)N1CCN(Cc2cc3nc(-c4cnc(N)nc4)nc(N4CCOCC4)c3s2)CC1] | (R)-1-(4-((2-(2-aminopyrimidin-5-yl)-4-morpholinothieno[3,2-d]pyrimidin-6-yl)methyl)piperazin-1-yl)-2-hydroxypropan-1-one |
| 401 | 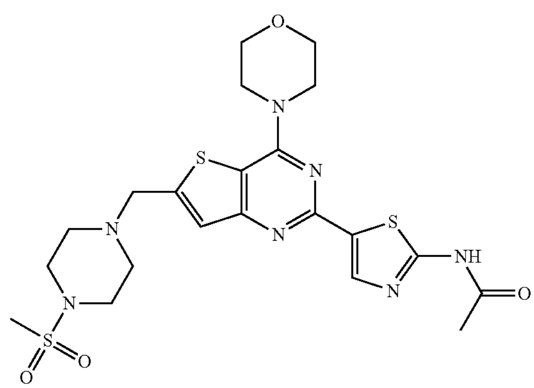 [SMILES: CC(=O)Nc1ncc(-c2nc(N3CCOCC3)c3sc(CN4CCN(S(C)(=O)=O)CC4)cc3n2)s1] | N-(5-(6-((4-(methylsulfonyl)piperazin-1-yl)methyl)-4-morpholinothieno[3,2-d]pyrimidin-2-yl)thiazol-2-yl)acetamide |
| 402 | 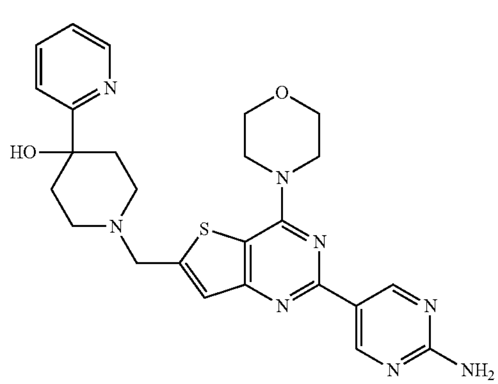 [SMILES: Nc1ncc(-c2nc(N3CCOCC3)c3sc(CN4CCC(O)(c5ccccn5)CC4)cc3n2)cn1] | 1-((2-(2-aminopyrimidin-5-yl)-4-morpholinothieno[3,2-d]pyrimidin-6-yl)methyl)-4-(pyridin-2-yl)piperidin-4-ol |

TABLE 2-continued

| Compound | Structure | Name |
|---|---|---|
| 403 | 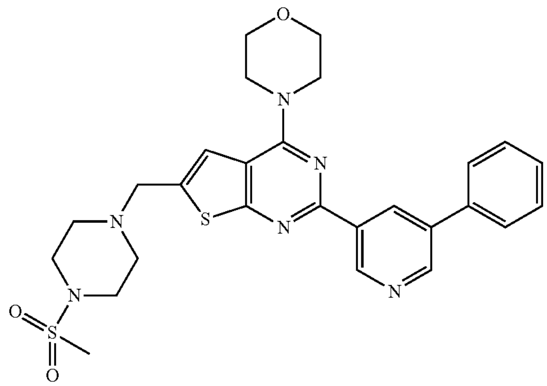 [SMILES: CS(=O)(=O)N1CCN(Cc2cc3c(N4CCOCC4)nc(-c4cncc(-c5ccccc5)c4)nc3s2)CC1] | 4-(6-((4-(methylsulfonyl)piperazin-1-yl)methyl)-2-(5-phenylpyridin-3-yl)thieno[2,3-d]pyrimidin-4-yl)morpholine |
| 404 | 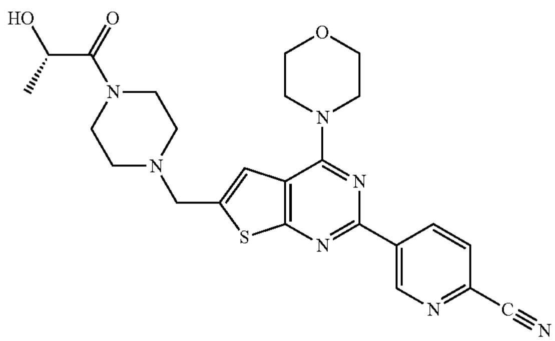 [SMILES: C[C@H](O)C(=O)N1CCN(Cc2cc3c(N4CCOCC4)nc(-c4ccc(C#N)nc4)nc3s2)CC1] | (S)-5-(6-((4-(2-hydroxypropanoyl)piperazin-1-yl)methyl)-4-morpholinothieno[2,3-d]pyrimidin-2-yl)picolinonitrile |
| 405 | 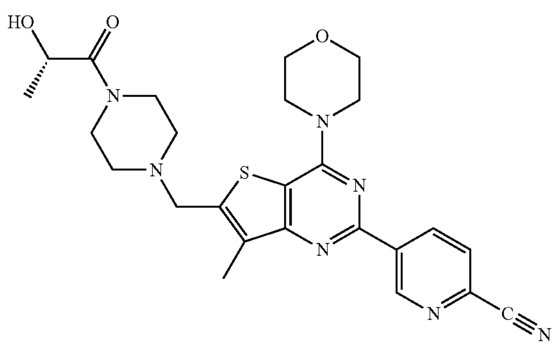 [SMILES: Cc1c(CN2CCN(C(=O)[C@H](C)O)CC2)sc2c(N3CCOCC3)nc(-c3ccc(C#N)nc3)nc12] | (S)-5-(6-((4-(2-hydroxypropanoyl)piperazin-1-yl)methyl)-7-methyl-4-morpholinothieno[3,2-d]pyrimidin-2-yl)picolinonitrile |
| 406 | 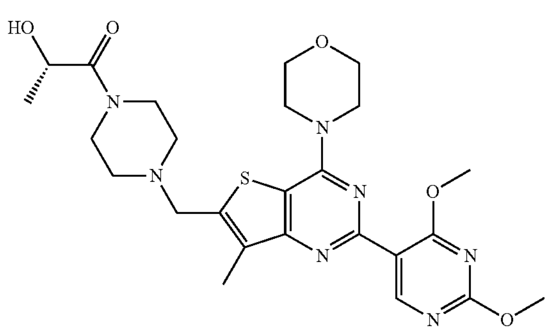 [SMILES: COc1ncc(-c2nc(N3CCOCC3)c3sc(CN4CCN(C(=O)[C@H](C)O)CC4)c(C)c3n2)c(OC)n1] | (S)-1-(4-((2-(2,4-dimethoxypyrimidin-5-yl)-7-methyl-4-morpholinothieno[3,2-d]pyrimidin-6-yl)methyl)piperazin-1-yl)-2-hydroxypropan-1-one |

| Compound | Structure | Name |
|---|---|---|
| 407 | 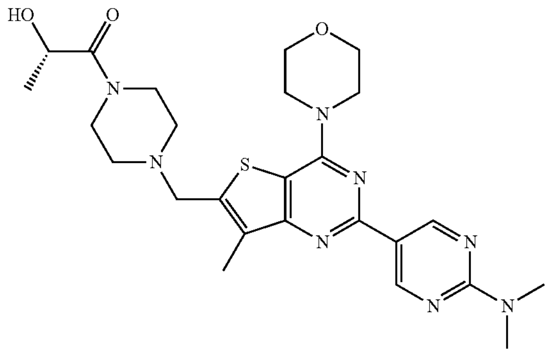 [SMILES: Cc1c(CN2CCN(C(=O)[C@H](C)O)CC2)sc2c(N3CCOCC3)nc(-c3cnc(N(C)C)nc3)nc12] | (S)-1-(4-((2-(2-(dimethylamino)pyrimidin-5-yl)-7-methyl-4-morpholinothieno[3,2-d]pyrimidin-6-yl)methyl)piperazin-1-yl)-2-hydroxypropan-1-one |
| 408 | 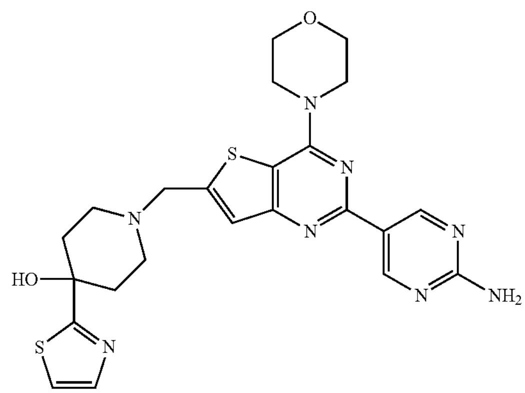 [SMILES: Nc1ncc(-c2nc(N3CCOCC3)c3sc(CN4CCC(O)(c5nccs5)CC4)cc3n2)cn1] | 1-((2-(2-aminopyrimidin-5-yl)-4-morpholinothieno[3,2-d]pyrimidin-6-yl)methyl)-4-(thiazol-2-yl)piperidin-4-ol |
| 409 | 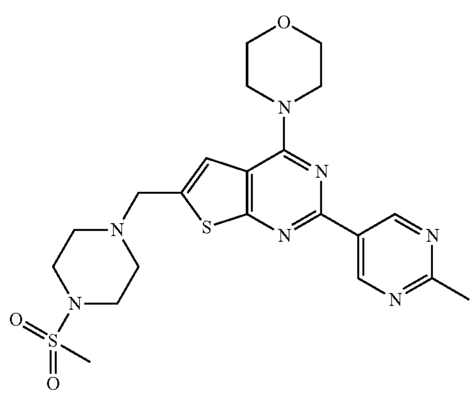 [SMILES: Cc1ncc(-c2nc(N3CCOCC3)c3cc(CN4CCN(S(C)(=O)=O)CC4)sc3n2)cn1] | 4-(2-(2-methylpyrimidin-5-yl)-6-((4-(methylsulfonyl)piperazin-1-yl)methyl)thieno[2,3-d]pyrimidin-4-yl)morpholine |
| 410 | 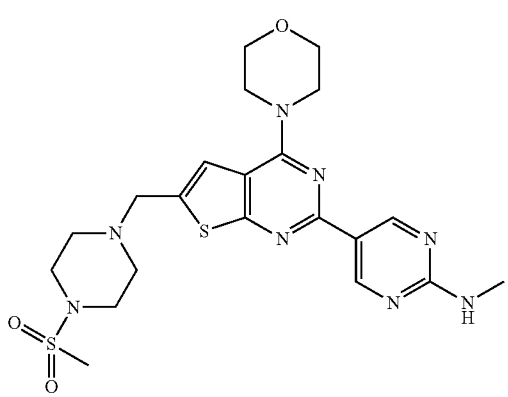 [SMILES: CNc1ncc(-c2nc(N3CCOCC3)c3cc(CN4CCN(S(C)(=O)=O)CC4)sc3n2)cn1] | N-methyl-5-(6-((4-(methylsulfonyl)piperazin-1-yl)methyl)-4-morpholinothieno[2,3-d]pyrimidin-2-yl)pyrimidin-2-amine |

TABLE 2-continued

| Compound | Structure | Name |
|---|---|---|
| 411 | 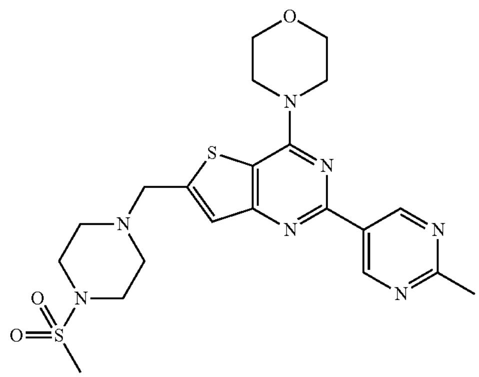 [SMILES: Cc1ncc(-c2nc(N3CCOCC3)c3sc(CN4CCN(S(C)(=O)=O)CC4)cc3n2)cn1] | 4-(2-(2-methylpyrimidin-5-yl)-6-((4-(methylsulfonyl)piperazin-1-yl)methyl)thieno[3,2-d]pyrimidin-4-yl)morpholine |
| 412 | 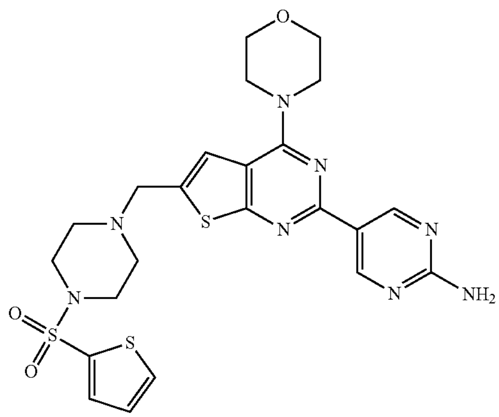 [SMILES: Nc1ncc(-c2nc(N3CCOCC3)c3cc(CN4CCN(S(=O)(=O)c5cccs5)CC4)sc3n2)cn1] | 5-(4-morpholino-6-((4-(thiophen-2-ylsulfonyl)piperazin-1-yl)methyl)thieno[2,3-d]pyrimidin-2-yl)pyrimidin-2-amine |
| 413 | 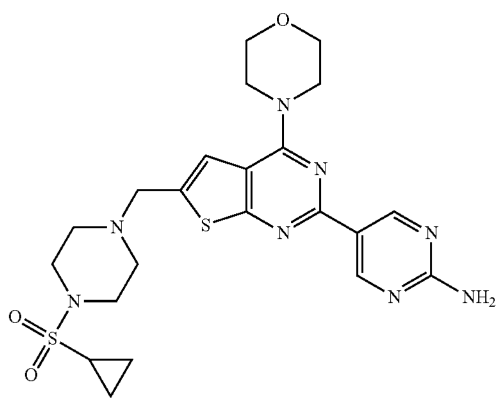 [SMILES: Nc1ncc(-c2nc(N3CCOCC3)c3cc(CN4CCN(S(=O)(=O)C5CC5)CC4)sc3n2)cn1] | 5-(6-((4-(cyclopropylsulfonyl)piperazin-1-yl)methyl)-4-morpholinothieno[2,3-d]pyrimidin-2-yl)pyrimidin-2-amine |
| 414 | 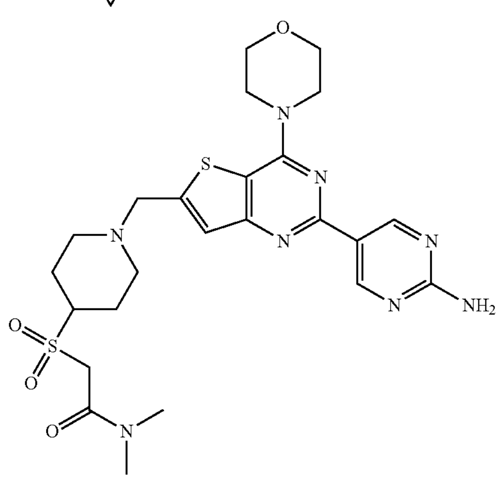 | 2-(1-((2-(2-aminopyrimidin-5-yl)-4-morpholinothieno[3,2-d]pyrimidin-6-yl)methy)piperidin-4-ylsulfonyl)-N,N-dimethylacetamide |

TABLE 2-continued

| Compound | Structure | Name |
|---|---|---|
| 415 | 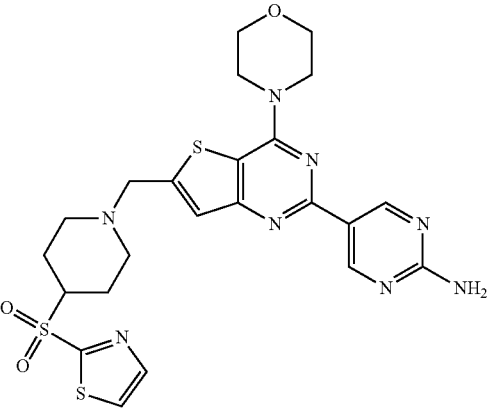 [SMILES: Nc1ncc(-c2nc(N3CCOCC3)c3sc(CN4CCC(S(=O)(=O)c5nccs5)CC4)cc3n2)cn1] | 5-(4-morpholino-6-((4-(thiazol-2-ylsulfonyl)piperidin-1-yl)methyl)thieno[3,2-d]pyrimidin-2-yl)pyrimidin-2-amine |
| 416 | 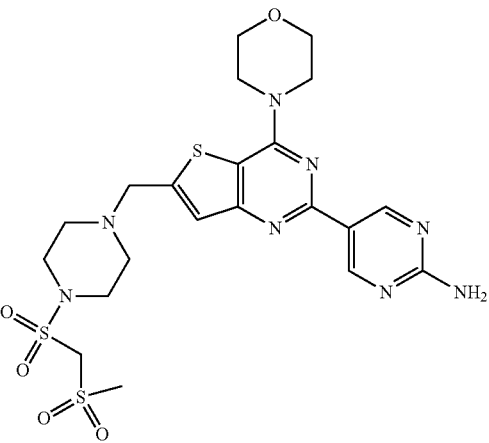 [SMILES: CS(=O)(=O)CS(=O)(=O)N1CCN(Cc2cc3nc(-c4cnc(N)nc4)nc(N4CCOCC4)c3s2)CC1] | 5-(6-((4-(methylsulfonylmethylsulfonyl)piperazin-1-yl)methyl)-4-morpholinothieno[3,2-d]pyrimidin-2-yl)pyrimidin-2-amine |
| 417 | 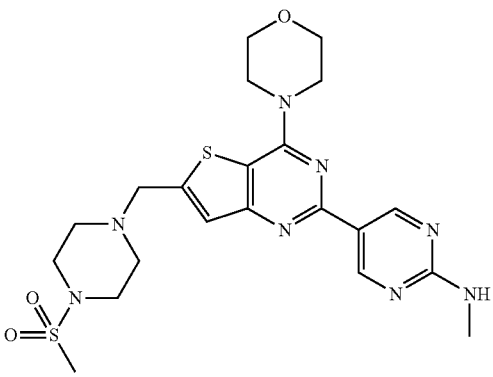 [SMILES: CNc1ncc(-c2nc(N3CCOCC3)c3sc(CN4CCN(S(C)(=O)=O)CC4)cc3n2)cn1] | N-methyl-5-(6-((4-(methylsulfonyl)piperazin-1-yl)methyl)-4-morpholinothieno[3,2-d]pyrimidin-2-yl)pyrimidin-2-amine |
| 418 | 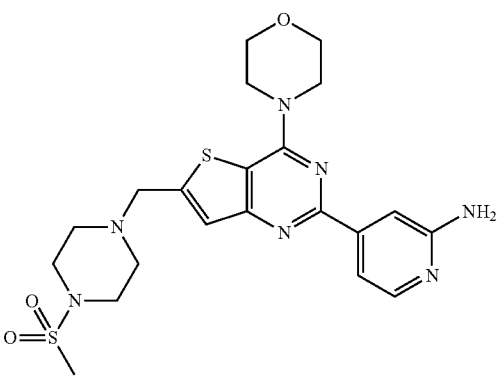 [SMILES: CS(=O)(=O)N1CCN(Cc2cc3nc(-c4ccnc(N)c4)nc(N4CCOCC4)c3s2)CC1] | 4-(6-((4-(methylsulfonyl)piperazin-1-yl)methyl)-4-morpholinothieno[3,2-d]pyrimidin-2-yl)pyridin-2-amine |

TABLE 2-continued

| Compound | Structure | Name |
|---|---|---|
| 419 | 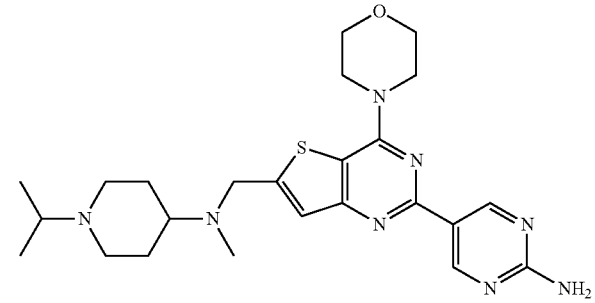 [SMILES: CC(C)N1CCC(N(C)Cc2cc3nc(-c4cnc(N)nc4)nc(N4CCOCC4)c3s2)CC1] | 5-(6-(((1-isopropylpiperidin-4-yl)(methyl)amino)methyl)-4-morpholinothieno[3,2-d]pyrimidin-2-yl)pyrimidin-2-amine |
| 420 | 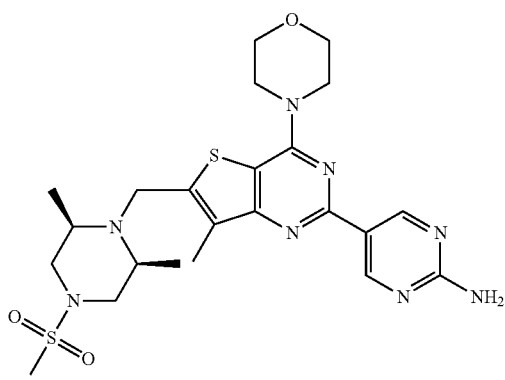 [SMILES: Cc1c(CN2[C@H](C)CN(S(C)(=O)=O)C[C@@H]2C)sc2c(N3CCOCC3)nc(-c3cnc(N)nc3)nc12] | 5-(6-(((2R,6S)-2,6-dimethyl-4-(methylsulfonyl)piperazin-1-yl)methyl)-7-methyl-4-morpholinothieno[3,2-d]pyrimidin-2-yl)pyrimidin-2-amine |
| 421 | 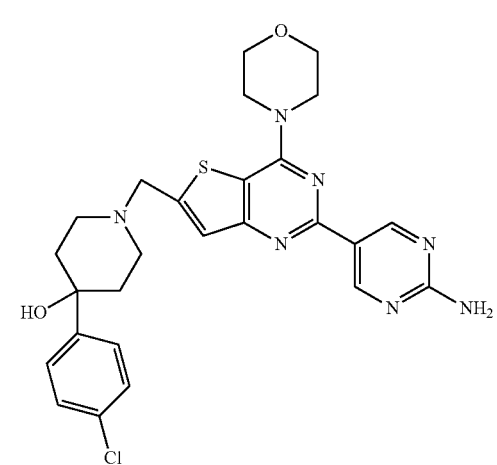 [SMILES: Nc1ncc(-c2nc(N3CCOCC3)c3sc(CN4CCC(O)(c5ccc(Cl)cc5)CC4)cc3n2)cn1] | 1-((2-(2-aminopyrimidin-5-yl)-4-morpholinothieno[3,2-d]pyrimidin-6-yl)methyl)-4-(4-chlorophenyl)piperidin-4-ol |
| 422 | 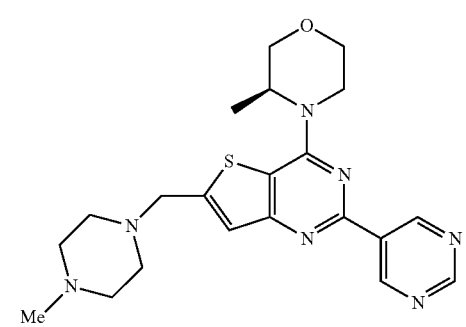 [SMILES: C[C@H]1COCCN1c1nc(-c2cncnc2)nc2cc(CN3CCN(C)CC3)sc12] | (S)-3-methyl-4-(6-((4-methylpiperazin-1-yl)methyl)-2-(pyrimidin-5-yl)thieno[3,2-d]pyrimidin-4-yl)morpholine |

TABLE 2-continued

| Compound | Structure | Name |
|---|---|---|
| 423 | 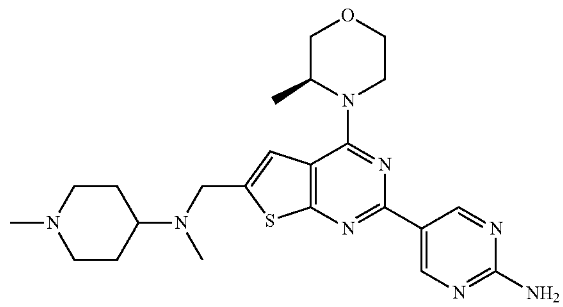 [SMILES: C[C@H]1COCCN1c1nc(-c2cnc(N)nc2)nc2sc(CN(C)C3CCN(C)CC3)cc12] | (S)-5-(6-((methyl(1-methylpiperidin-4-yl)amino)methyl)-4-(3-methylmorpholino)thieno[2,3-d]pyrimidin-2-yl)pyrimidin-2-amine |
| 424 | 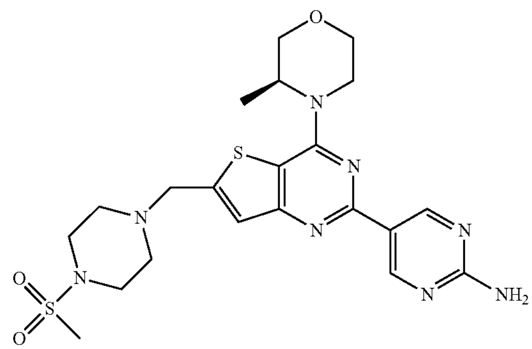 [SMILES: C[C@H]1COCCN1c1nc(-c2cnc(N)nc2)nc2cc(CN3CCN(S(C)(=O)=O)CC3)sc12] | (S)-5-(4-(3-methylmorpholino)-6-((4-(methylsulfonyl)piperazin-1-yl)methyl)thieno[3,2-d]pyrimidin-2-yl)pyrimidin-2-amine |
| 425 | 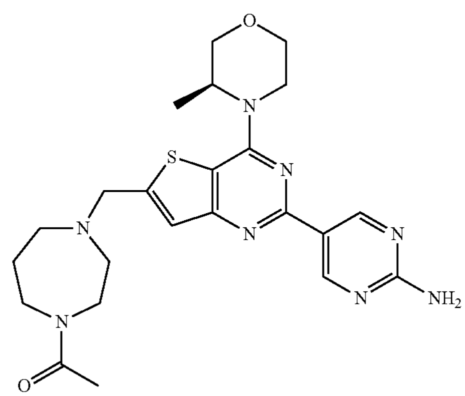 [SMILES: CC(=O)N1CCCN(Cc2cc3nc(-c4cnc(N)nc4)nc(N4CCOC[C@@H]4C)c3s2)CC1] | (S)-1-(4-((2-(2-aminopyrimidin-5-yl)-4-(3-methylmorpholino)thieno[3,2-d]pyrimidin-6-yl)methyl)-1,4-diazepan-1-yl)ethanone |
| 426 | | 5-(6-((methyl(pyridin-4-ylmethyl)amino)methyl)-4-morpholinothieno[3,2-d]pyrimidin-2-yl)pyrimidin-2-amine |
| 427 | | 5-(6-((methyl(pyridin-3-ylmethyl)amino)methyl)-4-morpholinothieno[3,2-d]pyrimidin-2-yl)pyrimidin-2-amine |

TABLE 2-continued

| Compound | Structure | Name |
|---|---|---|
| 428 | | 5-(6-((methyl(pyridin-2-ylmethyl)amino)methyl)-4-morpholinothieno[3,2-d]pyrimidin-2-yl)pyrimidin-2-amine |
| 429 | 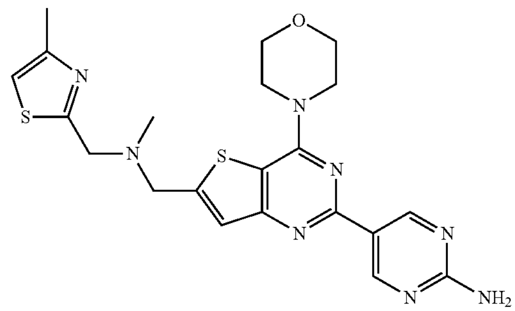 [SMILES: Cc1csc(CN(C)Cc2cc3nc(-c4cnc(N)nc4)nc(N4CCOCC4)c3s2)n1] | 5-(6-((methyl((4-methylthiazol-2-yl)methyl)amino)methyl)-4-morpholinothieno[3,2-d]pyrimidin-2-yl)pyrimidin-2-amine |

Administration of Compounds of Formula Ia-d

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula Ia-d compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula Ia-d Compounds

Compounds of the present invention are useful for treating diseases, conditions and/or disorders including, but not limited to, those characterized by over expression of lipid kinases, e.g. PI3 kinase. Accordingly, another aspect of this invention includes methods of treating or preventing diseases or conditions that can be treated or prevented by inhibiting lipid kinases, including PI3. In one embodiment, the method comprises administering to a mammal in need thereof a therapeutically effective amount of a compound of Formula Ia-d, or a stereoisomer, geometric isomer, tautomer, solvate, metabolite, or pharmaceutically acceptable salt or prodrug thereof.

Diseases and conditions treatable according to the methods of this invention include, but are not limited to, cancer, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient. In one embodiment, a human patient is treated with a compound of Formula Ia-d and a pharmaceutically acceptable carrier, adjuvant, or vehicle, wherein said compound of Formula Ia-d is present in an amount to detectably inhibit PI3 kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Cardiovascular diseases which can be treated according to the methods of this invention include, but are not limited to, restenosis, cardiomegaly, atherosclerosis, myocardial infarction, and congestive heart failure.

Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Inflammatory diseases which can be treated according to the methods of this invention include, but are not limited to, rheumatoid arthritis, psoriasis, contact dermatitis, and delayed hypersensitivity reactions.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula Ia-d having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula Ia-d may be prepared. Suitable examples of sustained-release preparations include semipermeable matrices of solid hydrophobic polymers containing a compound of Formula Ia-d, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula Ia-d suitable for oral administration may be prepared as discrete units such as pills, capsules, cachets or tablets each containing a predetermined amount of a compound of Formula Ia-d.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula Ia-d intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula Ia-d compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula Ia-d may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formulas Ia-d may be employed alone or in combination with other therapeutic agents for the treatment of a disease or disorder described herein, such as a hyperproliferative disorder (e.g., cancer). In certain embodiments, a compound of Formula Ia-d is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula Ia-d such that they do not adversely affect each other. Such compounds are suitably present in combination in amounts that are effective for the purpose intended. In one embodiment, a composition of this invention comprises a compound of Formula Ia-d, or a stereoisomer, geometric isomer, tautomer, solvate, metabolite, or pharmaceutically acceptable salt or prodrug thereof, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula Ia-d, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula Ia-d, or a stereoisomer, geometric isomer, tautomer, solvate, metabolite, or pharmaceutically acceptable salt or prodrug thereof, and the use of at least one other cancer treatment method. The amounts of the compound(s) of Formula Ia-d and the other pharmaceutically active chemotherapeutic agent(s) and the relative timings of administration will be selected in order to achieve the desired combined therapeutic effect.

Metabolites of Compounds of Formulas Ia-d

Also falling within the scope of this invention are the in vivo metabolic products of Formulas Ia-d described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formulas Ia-d, including compounds produced by a process comprising contacting a compound of this invention with a mammal for a period of time sufficient to yield a metabolic product thereof.

Metabolite products typically are identified by preparing a radiolabelled (e.g., $^{14}C$ or $^3H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Prodrugs of Formula Ia-d Compounds

In addition to compounds of Formulas Ia-d, the invention also includes pharmaceutically acceptable prodrugs of such compounds. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of Formula Ia-d can be derivatized as an amide or alkyl ester. As another example, compounds of this invention comprising free hydroxy groups may be derivatized as prodrugs by converting the hydroxy group into a group such as, but not limited to, a phosphate ester, hemisuccinate, dimethylaminoacetate, or phosphoryloxymethyloxycarbonyl group, as outlined in Advanced Drug Delivery Reviews, (1996) 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_1-C_6)$alkanoyloxymethyl, $1-((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(OH)_2$, —$P(O)(O(C_1-C_6)alkyl)_2$ or glycosyl (the radical resulting from the removal of a hydroxyl group of the hemiacetal form of a carbohydrate).

For additional examples of prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "*Design and Application of Prodrugs*," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Articles of Manufacture

In another embodiment of the invention, an article of manufacture, or "kit", containing materials useful for the treatment of the diseases and disorders described above is provided. In one embodiment, the kit comprises a container comprising a compound of Formula Ia-d, or a stereoisomer, geometric isomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula Ia-d or a formulation thereof which is effective for treating the condition and may have a sterile access port (for example, the container may be an intravenous solution bag or a vial having a stopper pierceable by a hypodermic injection needle). At least one active agent in the composition is a compound of Formula Ia-d. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula Ia-d can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula Ia-d and, if present, the second pharmaceutical formulation. For example, if the kit comprises a first composition comprising a compound of Formula Ia-d and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula Ia-d, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula Ia-d contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula Ia-d and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

General Preparative Procedures
General Procedure A Suzuki Coupling:

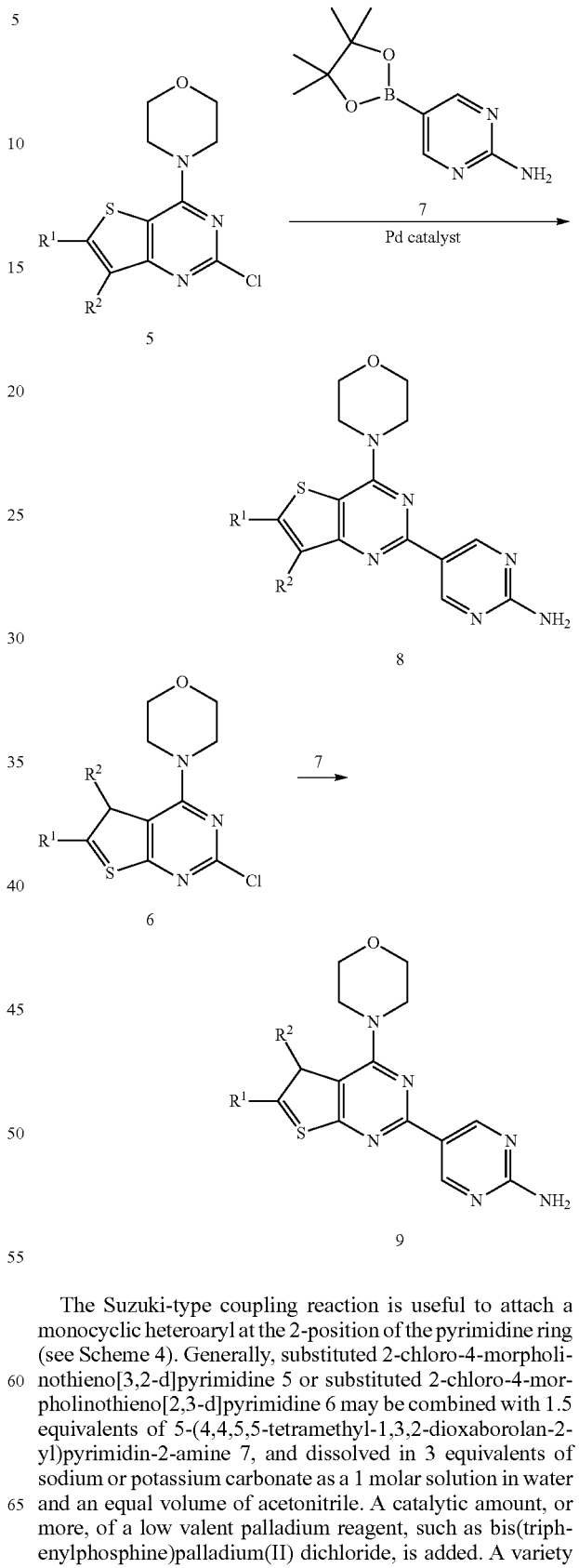

The Suzuki-type coupling reaction is useful to attach a monocyclic heteroaryl at the 2-position of the pyrimidine ring (see Scheme 4). Generally, substituted 2-chloro-4-morpholinothieno[3,2-d]pyrimidine 5 or substituted 2-chloro-4-morpholinothieno[2,3-d]pyrimidine 6 may be combined with 1.5 equivalents of 5-(4,4,5,5-tetramethyl-1,3,2-dioxaborolan-2-yl)pyrimidin-2-amine 7, and dissolved in 3 equivalents of sodium or potassium carbonate as a 1 molar solution in water and an equal volume of acetonitrile. A catalytic amount, or more, of a low valent palladium reagent, such as bis(triphenylphosphine)palladium(II) dichloride, is added. A variety of boronic acids or boronic esters can be used in place of the pinacol boronic ester indicated. Also alternatively, the nitrogen of the pyrimidin-2-amine may be protected, for example with a tetrahydropyranyl group. In some cases potassium acetate was used in place of sodium carbonate to adjust the pH of the aqueous layer. The reaction was then heated, for example to about 100-150° C. under pressure in a Biotage Optimizer microwave reactor (Biotage, Inc.) for 10 to 30 minutes. The contents are extracted with ethyl acetate, or another organic solvent. After evaporation of the organic layer the product, 8 or 9, may be purified on silica or by reverse phase HPLC.

General Procedure B-1 Amide Coupling:

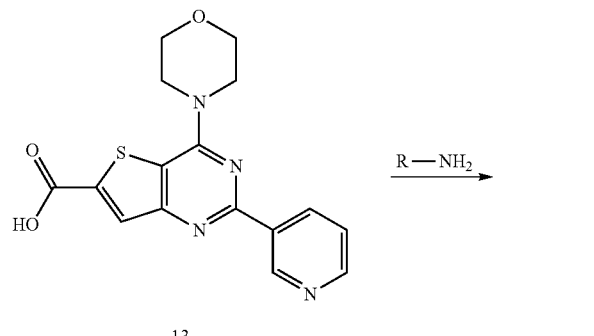

[2,3-d]pyrimidine-6-carboxylic acid 14 is treated with 1.5 eq HATU, 3 eq of an alkylamine (R—NH$_2$) and 3 eq of DIPEA in DMF to approximately 0.1 M concentration. The reaction is stirred until complete and extracted in ethylacetate with saturated bicarbonate solution one time. The organic layer is dried, filtered and concentrated to yield the crude intermediate. This intermediate is purified via reverse phase HPLC to yield product 15 or 16.

General Procedure B-2 Amide Coupling:

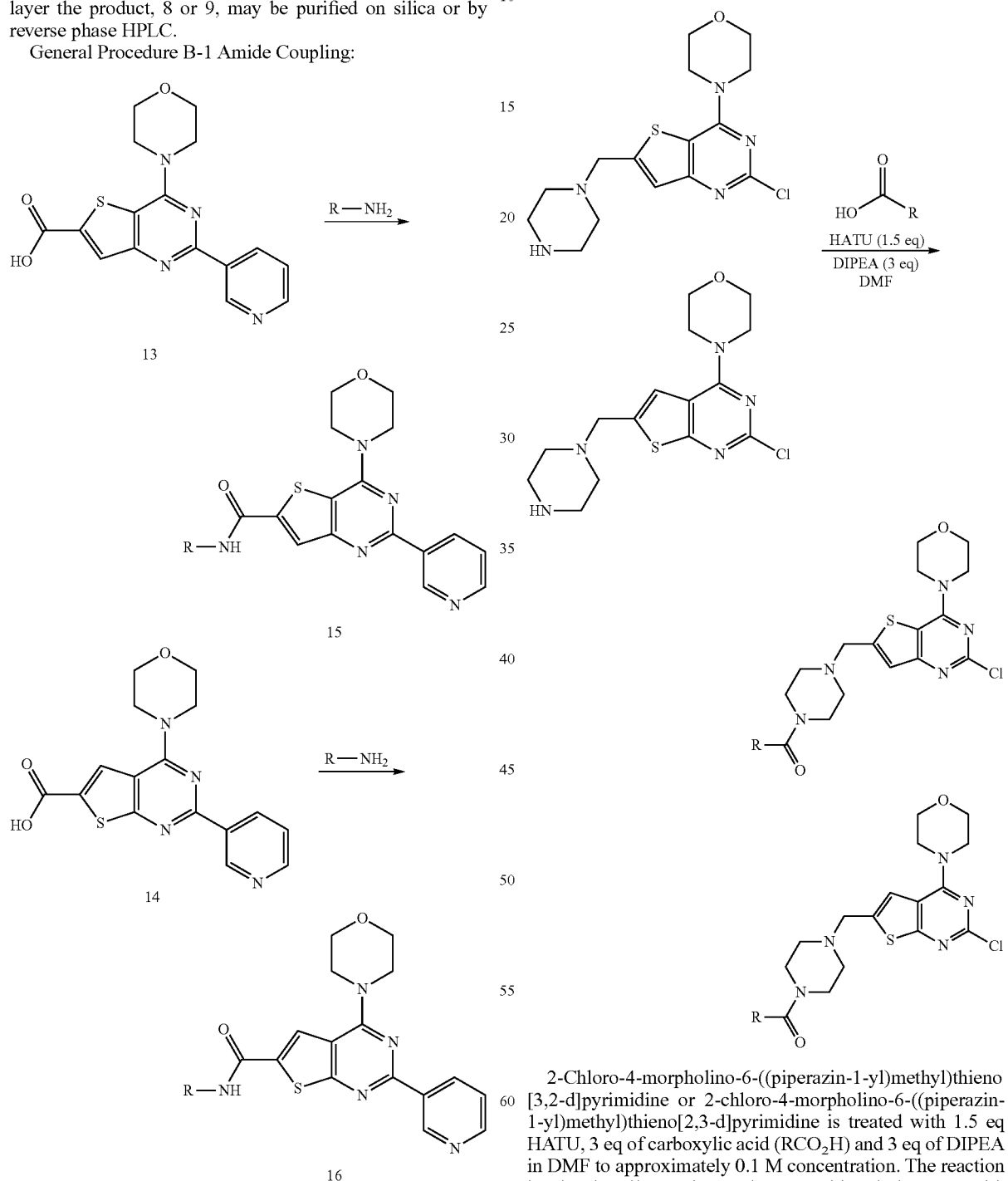

2-Chloro-4-morpholino-6-((piperazin-1-yl)methyl)thieno[3,2-d]pyrimidine or 2-chloro-4-morpholino-6-((piperazin-1-yl)methyl)thieno[2,3-d]pyrimidine is treated with 1.5 eq HATU, 3 eq of carboxylic acid (RCO$_2$H) and 3 eq of DIPEA in DMF to approximately 0.1 M concentration. The reaction is stirred until complete and extracted in ethyl acetate with saturated bicarbonate solution one time. The organic layer is dried, filtered and concentrated to yield the crude intermediate.

4-Morpholino-2-(pyridin-3-yl)thieno[3,2-d]pyrimidine-6-carboxylic acid 13 or 4-morpholino-2-(pyridin-3-yl)thieno

General Procedure B-3 Reductive Amination:

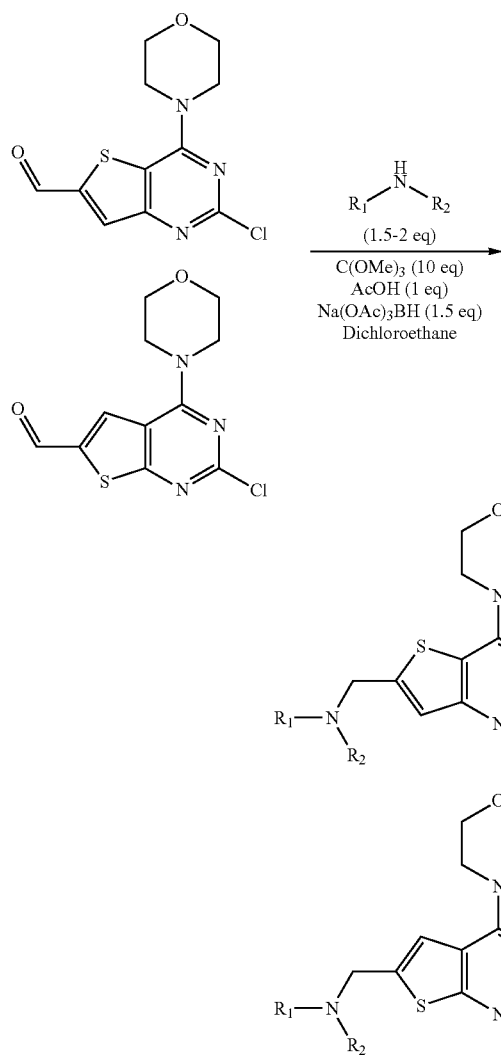

2-Chloro-4-morpholinothieno[3,2-d]pyrimidine-6-carbaldehyde 10 or 2-chloro-4-morpholinothieno[2,3-d]pyrimidine-6-carbaldehyde was dissolved to a 0.2 M concentration in dichloroethane. To this solution was added 1.5 to 2.0 equivalents of an amine ($R^1R^2NH$), 10 equivalents of trimethylorthoformate, and 1 equivalent of acetic acid. The mixture was allowed to stir for 2-6 hours prior to adding 1.5 equivalents of sodium triacetoxyborohydride. Following 12 to 16 hours of stirring the reaction was poured into saturated sodium bicarbonate and extracted several times with ethyl acetate. This intermediate was either purified on silica gel or used crude in the next reaction.

For example, a mixture of 2-chloro-4-morpholin-4-yl-thieno[3,2-d]pyrimidine-6-carbaldehyde 10 (3.5 g), 1-BOC-piperazine (2.76 g) and trimethylorthoformate (4.05 mL) was stirred in 1,2-dichloroethane (300 mL) for 1 hr at room temperature. To this was added sodium triacetoxyborohydride (3.92 g) and the reaction mixture was stirred for 24 hours at room temperature. The mixture was then quenched with brine, extracted with dichloromethane, dried ($MgSO_4$) and the solvent removed in vacuo. The residue was purified using flash chromatography to yield 4-(2-chloro-4-morpholin-4-yl-thieno[3,2-d]pyrimidin-6-ylmethyl)-piperazine-1-carboxylic acid tert-butyl ester (3.4 g). Treatment with HCl in dichloromethane/methanol yielded 2-chloro-4-morpholin-4-yl-6-piperazin-1-ylmethyl-thieno[3,2-d]pyrimidine.

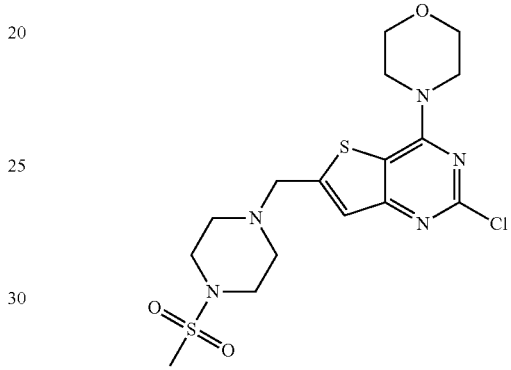

For example, N—BOC-piperazine and methanesulfonyl chloride were reacted together in dichloromethane and triethylamine to yield 4-methanesulfonyl-piperazine-1-carboxylic acid tert-butyl ester. Cleavage of the BOC protecting group using HCl (2M) in dichloromethane yielded 1-methanesulfonyl-piperazine. HCl salt. A mixture of 2-chloro-4-morpholin-4-yl-thieno[3,2-d]pyrimidine-6-carbaldehyde 10 (1.00 g), 1-methanesulfonyl-piperazine (750 mg) and trimethylorthoformate (3.80 mL) was stirred in 1,2-dichloroethane (30 mL) for 6 hrs at room temperature. To this was added sodium triacetoxyborohydride (900 mg) and the reaction mixture was stirred for 24 hours at room temperature. The mixture was then quenched with brine, extracted with dichloromethane, dried ($MgSO_4$) and the solvent removed in vacuo. The residue was triturated with hot ethyl acetate to yield 2-chloro-6-((4-methylsulfonylpiperazin-1-yl)methyl)-4-morpholinothieno[3,2-d]pyrimidine as a white solid (1.01 g).

General Procedure B-4 Reductive Amination:

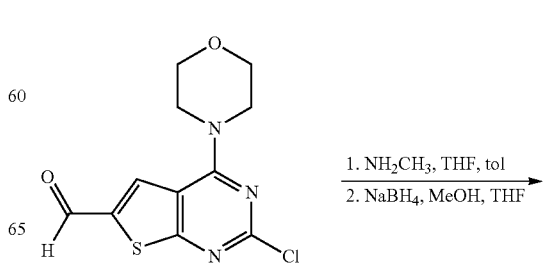

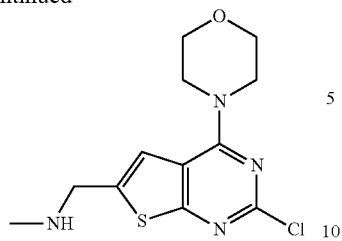

To 2-chloro-4-morpholinothieno[2,3-d]pyrimidine-6-carbaldehyde (2.0 g) in 50 mL toluene and 50 mL THF was added 20 mL of 40% methylamine in H$_2$O. The reaction mixture was stirred at room temp under N$_2$ for 24 hours. The solvents were removed in vacuo and the residue was dissolved in 50 mL MeOH and 50 mL THF and the NaBH$_4$ added portion-wise. This reaction mixture was stirred at room temp under N$_2$ for 24 hours and complete reaction was confirmed by LCMS. The solvents were removed in vacuo and the crude product purified by flash chromatography (EtOAc/EtOH) to give 1.12 g (2-chloro-4-morpholinothieno[2,3-d]pyrimidin-6-yl)-N-methylmethanamine (53% yield). MS (Q1) 300 (M+).

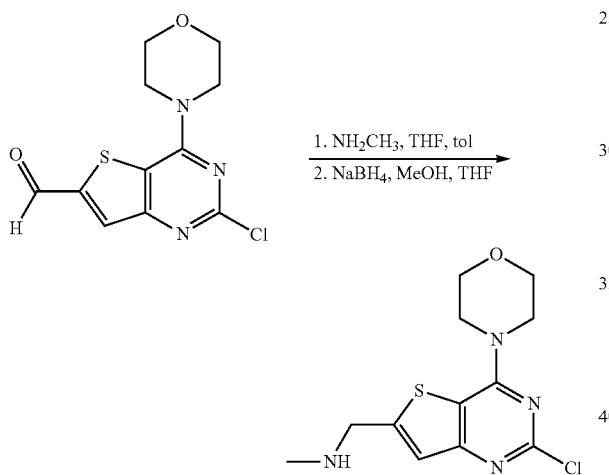

2-Chloro-4-morpholinothieno[3,2-d]pyrimidine-6-carbaldehyde 10 (2.0 g) was dissolved in 50 mL toluene and 50 mL THF followed by the addition of 20 mL of 40% methylamine in H$_2$O. The reaction mixture was stirred at room temp under N$_2$ for 24 hours. The solvents were removed in vacuo and the residue was dissolved in 50 mL MeOH and 50 mL THF and the NaBH$_4$ added portion-wise. This reaction mixture was stirred at room temp under N$_2$ for 24 hours and complete reaction was confirmed by LCMS. The solvents were removed in vacuo and the crude product purified by flash chromatography (EtOAc/EtOH) to give 1.12 g (2-chloro-4-morpholinothieno[3,2-d]pyrimidin-6-yl)-N-methylmethanamine (53% yield). MS (Q1) 300 (M+).

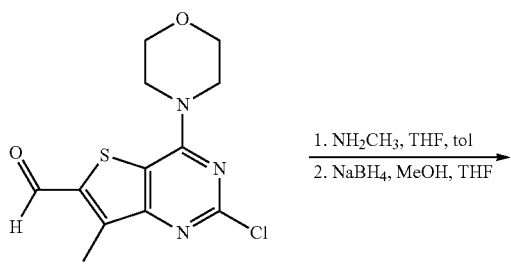

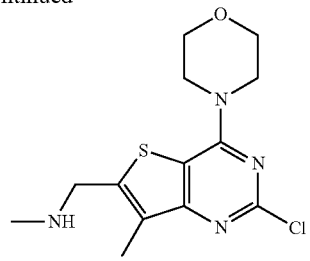

2-Chloro-7-methyl-4-morpholinothieno-[3,2-d]pyrimidine-6-carbaldehyde was dissolved in 20 mL toluene and 20 mL THF followed by the addition of 15 mL 40% methylamine in H$_2$O and the reaction was stirred for 24 hours. The reaction mixture was concentrated in vacuo and the residue dissolved in 30 mL MeOH and 30 mL THF followed by the addition of NaBH$_4$. The reaction was stirred at room temp for at least 24 hours and product formation was confirmed by LCMS. The solvents were removed in vacuo and the crude product purified by flash chromatography to give 2.53 g of (2-chloro-7-methyl-4-morpholinothieno[3,2-d]pyrimidin-6-yl)-N-methylmethanamine. (70% yield) MS (Q1) 314 (M)+

General procedure D-2 Aldehyde Synthesis

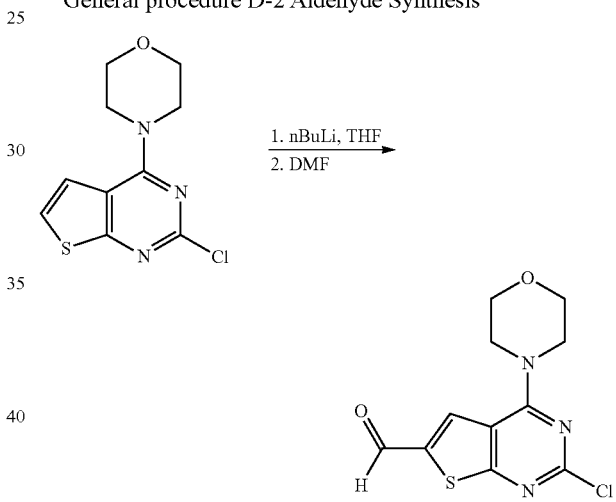

To a suspension of 2-chloro-4-morpholinothieno[2,3-d]pyrimidine (1.75 g, 6.85 mmol) in dry THF (40 mL) at −78° C. was added a 2.5M solution of n-butyllithium (nBuLi) in hexane (3.3 mL, 1.2 eq.). After stirring for 1 h, dry DMF (796 µL, 1.5 eq.) was added. The reaction mixture was stirred for 1 h at −78° C. and then warmed slowly to room temperature. After a further 2 h at room temperature the reaction mixture was poured onto ice/water yielding a yellow precipitate. This was collected by filtration and air-dried to yield 2-chloro-4-morpholinothieno[2,3-d]pyrimidine-6-carbaldehyde (1.50 g) MS (Q1) 284 (M+).

General procedure D-3 2-Iodo Synthesis

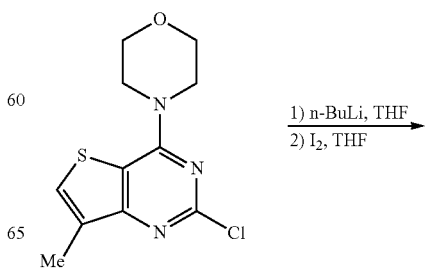

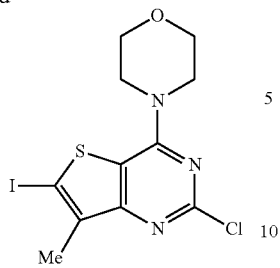

To a solution of 2-chloro-7-methyl-4-morpholinothieno[3,2-d]pyrimidine (3.0 g, 11.1 mmol; prepared according to the procedure for the synthesis of 2-chloro-4-morpholin-4-yl-thieno[3,2-d]pyrimidine but commencing with 3-amino-4-methyl-thiophene-2-carboxylic acid ethyl ester) in THF (60 mL) at −78° C. was added n-BuLi (8.9 mL, 2.5 M in Et$_2$O). The resulting slurry was warmed to −40° C. and stirred 50 min. The reaction mixture was then cooled to −78° C. and a solution of I$_2$ (5.6 g, 22.2 mmol) in THF (30 mL) was added. The solution was warmed to room temperature and stirred 5 h. The reaction was quenched by the addition of water. The organic layer was separated and the aqueous layer was extracted with CH$_2$Cl$_2$. The combined organics were washed with saturated aqueous Na$_2$S$_2$O$_3$, dried over Na$_2$SO$_4$, filtered, and concentrated in vacuo to provide 2-chloro-6-iodo-7-methyl-4-morpholinothieno[3,2-d]pyrimidine (3.8 g, 84% yield).

General Procedure E Removal of t-butoxylcarbonyl (BOC) Group

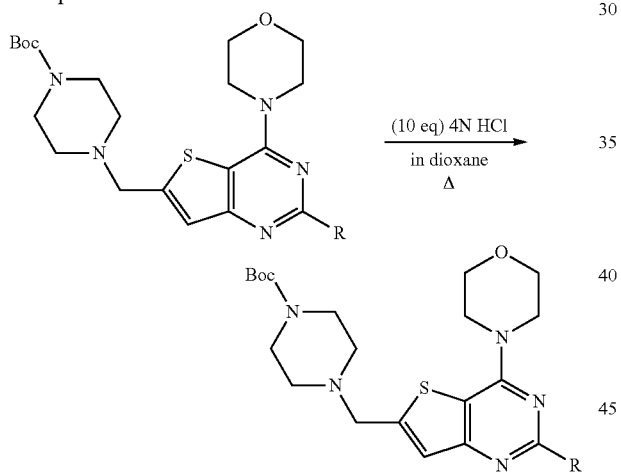

Ten or more equivalents of 4N HCl in Dioxane, with or without dichloromethane as a co-solvent, are added to the starting material (general scheme shown above but similar scaffolds also used). Heating up to 40° C. for several hours is occasionally required to remove the boc group. The reaction is concentrated to dryness and may be used crude in subsequent reactions.

General Procedure G Amide Coupling Reaction

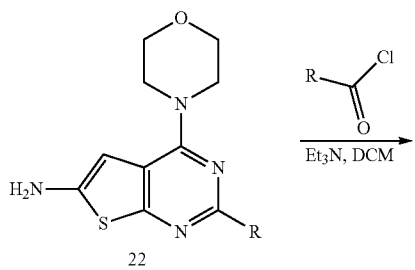

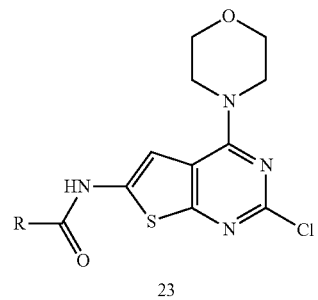

2-Chloro-4-morpholinothieno[3,2-d]pyrimidin-6-amine 22 (1 eq), acid chloride (1.5~2 eq) and triethylamine (2 eq) in dichloromethane was stirred. The reaction was monitored by LC/MS until complete. The mixture was evaporated to give the crude amide 23, which was directly used for the next step reaction without purification.

General Procedure K 6-Aminoalkyl Acylation and 2-Suzuki Coupling

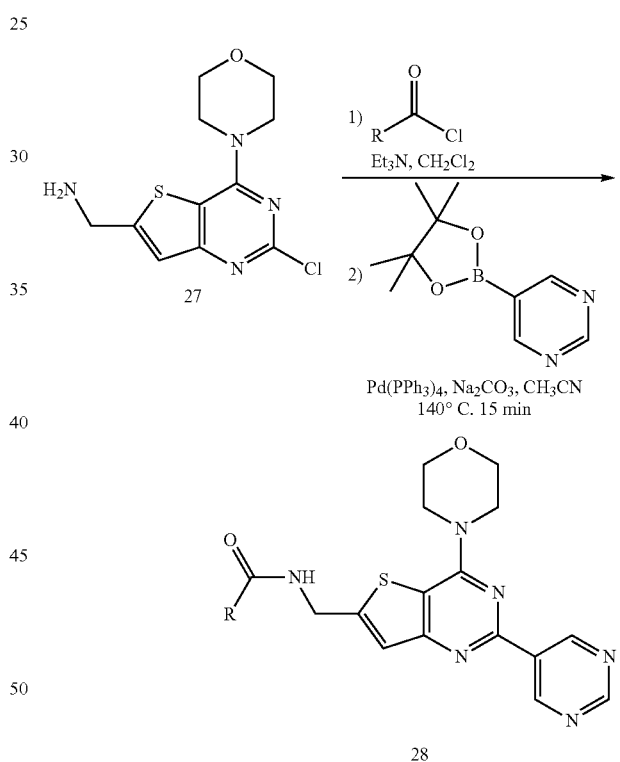

To a solution of 2-chloro-4-morpholinothieno[3,2-d]pyrimidin-6-yl)methanamine 27 (50 mg, 0.2 mmol) in CH$_2$Cl$_2$ (4 mL) was added Et$_3$N (84 µL, 0.6 mmol) and the appropriate acid chloride or HCl salt thereof (0.3 mmol). The reaction stirred 18-48 hr at room temperature before being quenched with water. The aqueous layer was extracted with EtOAc. The combined organics were dried over Na$_2$SO$_4$ and concentrated in vacuo. The 2-chloro crude product was coupled with 5-(4,4,5,5-tetramethyl-1,3,2-dioxaborolan-2-yl)pyrimidine and tetrakis triphenylphosphine palladium catalyst according to General Procedure A to give 28 which was purified by reversed phase HPLC purification.

EXAMPLES

The chemical reactions in the Examples described may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the Examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters). $^1$H NMR spectra were recorded on a Varian instrument operating at 400 MHz. $^1$H NMR spectra were obtained in deuterated CDCl$_3$, d$_6$-DMSO, CH$_3$OD or d$_6$-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

2,4-Dichloro-thieno[3,2-d]pyrimidine 3

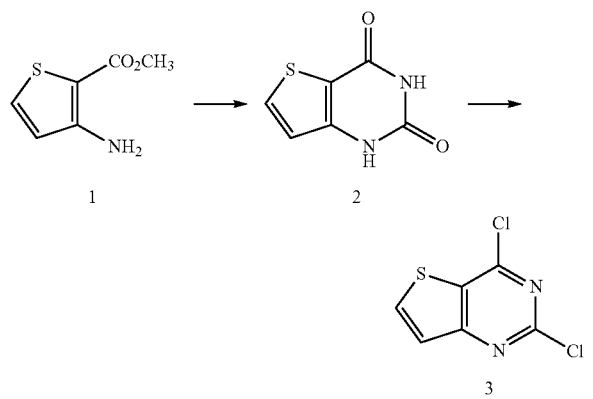

A mixture of methyl 3-amino-2-thiophenecarboxylate 1 (13.48 g, 85.85 mmol) and urea (29.75 g, 5 eq.) was heated at 190° C. for 2 hours. The hot reaction mixture was poured onto sodium hydroxide solution and any insoluble material was removed by filtration. The mixture was then acidified (HCl, 2N) to yield 1H-thieno[3,2-d]pyrimidine-2,4-dione 2 as a white precipitate, which was collected by filtration and air dried (9.49 g, 66%). 1H NMR 400 MHz, d$_6$-DMSO) 6.90 (1H, d, J=5.2 Hz), 8.10 (1H, d, J=5.2 Hz), 11.60-11.10 (2H, br s).

A mixture of 1H-thieno[3,2-d]pyrimidine-2,4-dione 2 (9.49 g, 56.49 mmol) and phosphorous oxychloride (150 mL) was heated at reflux for 6 h. The reaction mixture was then cooled and poured onto ice/water with vigorous stirring yielding a precipitate. The mixture was then filtered to yield 2,4-dichloro-thieno[3,2-d]pyrimidine 3 as a white solid (8.68 g, 75%). $^1$H NMR (400 MHz, CDCl$_3$) 7.56 (1H, d, J=5.5 Hz), 8.13 (1H, d, J=5.5 Hz).

Example 2

2-Chloro-4-morpholin-4-yl-thieno[3,2-d]pyrimidine 4

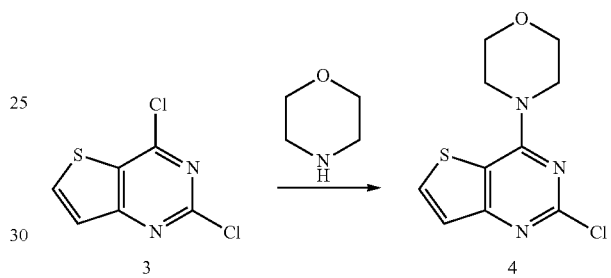

A mixture of 2,4-dichloro-thieno[3,2-d]pyrimidine 3, (8.68 g, 42.34 mmol), morpholine (8.11 mL, 2.2 eq.) and MeOH (150 mL) was stirred at room temperature for 1 h. The reaction mixture was then filtered, washed with water and MeOH, to yield 2-chloro-4-morpholin-4-yl-thieno[3,2-d]pyrimidine 4 as a white solid (11.04 g, 100%). $^1$H NMR (400 MHz, d$_6$-DMSO) 3.74 (4H, t, J=4.9 Hz), 3.90 (4H, t, J=4.9 Hz), 7.40 (1H, d, J=5.6 Hz), 8.30 (1H, d, J=5.6 Hz).

Example 3

2-Chloro-4-morpholin-4-yl-thieno[3,2-d]pyrimidine-6-carbaldehyde 10

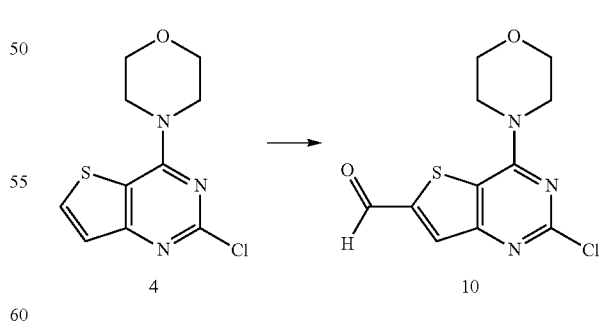

To a suspension of 2-chloro-4-morpholin-4-yl-thieno[3,2-d]pyrimidine 4 (1.75 g, 6.85 mmol) in dry THF (40 mL) at −78° C. was added a 2.5M solution of n-butyllithium (nBuLi) in hexane (3.3 mL, 1.2 eq.). After stirring for 1 h, dry DMF (796 μL, 1.5 eq.) was added. The reaction mixture was stirred for 1 h at −78° C. and then warmed slowly to room temperature. After a further 2 h at room temperature the reaction mixture poured onto ice/water yielding a yellow precipitate. This was collected by filtration and air-dried to yield 2-chloro-4-morpholin-4-yl-thieno[3,2-d]pyrimidine-6-carbaldehyde 10 (1.50 g, 77%). ¹H NMR (400 MHz, d₆-DMSO) 3.76 (4H, t, J=4.9), 3.95 (4H, t, J=4.9), 8.28 (1H, s), 10.20 (1H, s).

Example 4

(2-Chloro-4-morpholinothieno[3,2-d]pyrimidin-6-yl)methanol 29

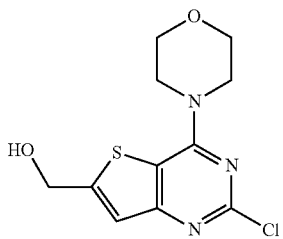

A solution of 2-chloro-4-morpholinothieno[3,2-d]pyrimidine-6-carbaldehyde 10 (Example 3, General Procedure B-3, 1.0 g, 3.5 mmol) in MeOH (30 mL) at 0° C. was treated with NaBH₄ (0.1 g, 3.5 mmol). The solution was allowed to warm to room temperature and stirred 15 min. The reaction mixture was quenched with a mixture of a saturated solution of sodium bicarbonate and water (1:1, v/v). The aqueous solution was extracted with EtOAc. The combined organic layers were dried over Na₂SO₄ and concentrated in vacuo. The crude material 29 required no further purification (0.9 g, 90%). MS (Q1) 286 (M)+

Example 5

6-(Bromomethyl)-2-chloro-4-morpholinothieno[3,2-d]pyrimidine 30

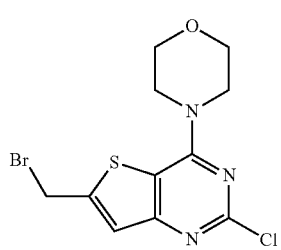

To a solution of (2-chloro-4-morpholinothieno[3,2-d]pyrimidin-6-yl)methanol 29 (100 mg, 0.4 mmol) in benzene (3.0 mL) at 0° C. was added PBr₃ (30 µL, 0.4 mmol). The reaction was heated at reflux for 1 hour. After cooling to room temperature the reaction was quenched by the addition of water. The aqueous layer was extracted with EtOAc. The combined organics were dried over Na₂SO₄ and concentrated in vacuo. The crude product 30 did not require further purification (115 mg, 94%). MS (Q1) 350 (M)+

Example 6

2-((2-Chloro-4-morpholinothieno[3,2-d]pyrimidin-6-yl)methyl)isoindoline-1,3-dione 31

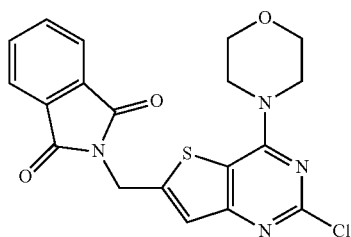

To a solution of 6-(bromomethyl)-2-chloro-4-morpholinothieno[3,2-d]pyrimidine 30 (0.3 g, 0.9 mmol) in DMF (10 mL) was added K₂CO₃ (0.2 g, 1.3 mmol), and phthalimide (0.1 g, 0.9 mmol). The resulting solution stirred 20 h at room temperature. The reaction was concentrated in vacuo and diluted with water (10 mL). The heterogeneous mixture was filtered to afford 2-((2-chloro-4-morpholinothieno[3,2-d]pyrimidin-6-yl)methyl)isoindoline-1,3-dione 31 (0.3 g, 75%). MS (Q1) 415 (M)+

Example 7

(2-Chloro-4-morpholinothieno[3,2-d]pyrimidin-6-yl)methanamine 27

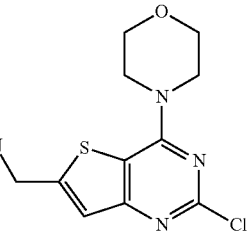

To a solution of 2-((2-chloro-4-morpholinothieno[3,2-d]pyrimidin-6-yl)methyl)isoindoline-1,3-dione 31 (100 mg, 0.24 mmol) in MeOH (7 mL) was added H₂NNH₂.H₂O (24 µL, 0.48 mmol). The reaction was heated at reflux for 1 h. After cooling to room temperature the reaction was quenched with water (10 mL) and extracted with EtOAc. The combined organics were dried over Na₂SO₄ and concentrated in vacuo to afford (2-chloro-4-morpholinothieno[3,2-d]pyrimidin-6-yl)methanamine 27 (0.05 g, 73%). MS (Q1) 285 (M)+

Example 8

2-Chloro-6-iodo-4-morpholinothieno[3,2-d]pyrimidine 19

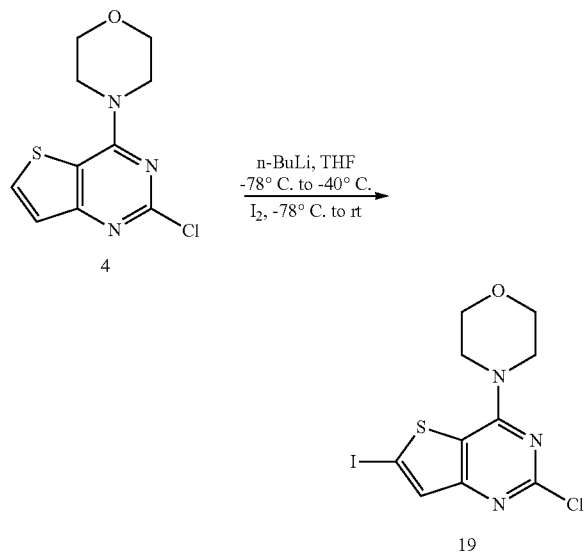

Following the procedures in U.S. Pat. No. 6,492,383, 2.5 M of n-Butylithium (9.4 mL, 22.48 mmol) in hexane solution was added to a mixture of 2-chloro-4-morpholinothieno[3,2-d]pyrimidine 4 (3.0 g, 11.74 mmol) in 60 mL of THF at −78° C. The reaction mixture was allowed to warm to −40° C. and stirred for 30 min. A solution of iodine (6.0 g, 23.48 mmol) in 10 mL of THF was added dropwise. After the addition was completed. The reaction mixture was brought to room temperature and stirred for 2 h. The mixture was quenched by diluting with dichloromethane and extracting with $H_2O$ (2×100 mL). The organic layer was washed with $Na_2S_2O_3$ (2×100 mL), $H_2O$ (2×100 mL), dried over $MgSO_4$, filtered and evaporated to afford 2-chloro-6-iodo-4-morpholinothieno[3,2-d]pyrimidine 19 (3.4 g, 75%).

Example 9

Tert-butyl furan-3-ylcarbamate 32

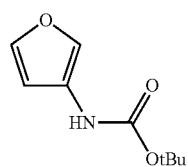

3-Furoic acid (5.60 g, 1.0 eq) was dissolved in tert-butanol (200 ml) and treated with triethylamine (10 ml, 1.4 eq) and diphenyl phosphoryl azide (12 ml, 1.1 eq). Mixture was heated at reflux for 18 h. Reaction mixture was cooled to room temperature, then concentrated to 50 ml and poured into saturated aq. $NaHCO_3$. Mixture was stirred at 0° C. for 2 h. Solid was collected by filtration and dried under high vacuum. The crude reaction mixture was purified by flash chromatography to yield tert-butyl furan-3-ylcarbamate 32 (6.95 g, 76%): $^1$H NMR (CDCl$_3$, 400 MHz) δ 7.71 (bs, 1H), 7.27 (m, 1H), 6.27 (bs, 1H), 6.20 (bs, 1H), 1.50 (s, 9H); MS (Q1) 184 (M)$^+$.

Example 10

Tert-butyl 2-(methoxycarbonyl)furan-3-ylcarbamate 33

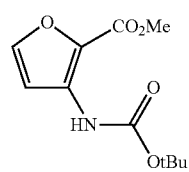

To a solution of tert-butyl furan-3-ylcarbamate 32 (1.7 g, 1.0 eq) in THF (50 ml) at −30° C. was added TMEDA (1.75 ml, 1.3 eq) followed by 1.6M solution of n-butyllithium (8.4 ml, 2.25 eq, 1.6M in hexanes). Reaction mixture was allowed to warm up to 0° C. and stirred for 1 h, before being cooled back to −30° C. Dimethyl carbonate (2.4 ml, 3.0 eq) was quickly added, before the reaction mixture was allowed to warm up to room temperature for 1 hr. Reaction mixture was quenched with 2M HCl, followed by addition of saturated aq. NaCl. Mixture was extracted with ethyl acetate. The combined organic extracts were dried with $Na_2SO_4$ and concentrated. The crude reaction mixture was purified by flash chromatography to yield tert-butyl 2-(methoxycarbonyl)furan-3-ylcarbamate 33 (1.14 g, 51%): MS (Q1) 242 (M)$^+$.

Example 11

Methyl 3-aminofuran-2-carboxylate 34

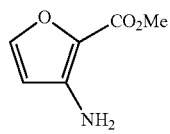

Tert-butyl 2-(methoxycarbonyl)furan-3-ylcarbamate 33 (1.14 g, 1.0 eq) was dissolved in dichloromethane (8 ml) and treated with trifluoroacetic acid (5 ml). Reaction mixture was stirred at room temperature for 3 h, and was then concentrated. Residue was dissolved in dichloromethane and washed with saturated aq. $NaHCO_3$. The organic layer was dried ($Na_2SO_4$) and concentrated Mixture was extracted with ethyl acetate. The combined organic extracts were dried with $Na_2SO_4$ and concentrated. The crude reaction mixture was purified by flash chromatography to yield methyl 3-aminofuran-2-carboxylate 34 (574 mg, 86%): MS (Q1) 142 (M)$^+$.

Example 12

Ethyl 3-ureidofuran-2-carboxylate 35

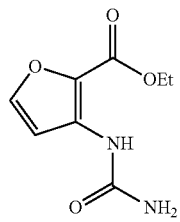

To a solution of methyl 3-aminofuran-2-carboxylate 34 (100 mg, 1.0 eq) in dichloromethane (3 ml) at −78° C. was added chlorosulfonyl isocyanate (0.09 ml, 1.4 eq) dropwise. The reaction was slowly warmed to room temperature and stirred for 40 minutes. Reaction was concentrated. To the residue was added 6N HCl (3.5 ml) and mixture was heated to 100° C. for 20 minutes. Reaction mixture was allowed to cool down to room temperature, and was neutralized with saturated aq. $NaHCO_3$. Solid was collected by filtration to yield ethyl 3-ureidofuran-2-carboxylate 35 (120 mg, 92%) as a beige solid which was used in the next reaction without further purification.

Example 13

Furo[3,2-d]pyrimidine-2,4-diol 36

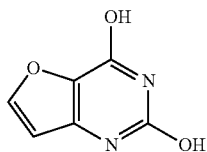

Ethyl 3-ureidofuran-2-carboxylate 35 (120 mg, 1.0 eq) was suspended in methanol (6 ml) and treated with 1.5 M NaOH (1.5 ml). Reaction mixture was heated to reflux for 90 minutes. Reaction mixture was allowed to cool down to room temperature, and was acidified with 6N HCl up to pH 3. Mixture was concentrated. Methanol was added to residue and solid was filtered and dried at 95° C. under high vacuum for 24 h to yield furo[3,2-d]pyrimidine-2,4-diol 36 (90 mg, 91%) which was used in the next reaction without further purification.

Example 14

2,4-Dichlorofuro[3,2-d]pyrimidine 37

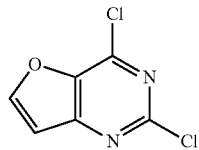

Furo[3,2-d]pyrimidine-2,4-diol 36 (39 mg, 1.0 eq) was dissolved in $POCl_3$ (1.8 ml). Mixture was cooled to −40° C. and N,N-diisopropylethylamine (0.45 ml) wad slowly added. Reaction mixture was then heated to reflux for 48 h, then cooled to room temperature Reaction mixture was poured into ice/water. Mixture was extracted with ethyl acetate. The combined organic layers were washed with saturated aq. $NaHCO_3$, dried ($Na_2SO_4$) and concentrated to yield 2,4-dichlorofuro[3,2-d]pyrimidine 37 (23 mg, 48%) which was used in the next reaction without further purification.

Example 15

2-Chloro-4-morpholinofuro[3,2-d]pyrimidine 38

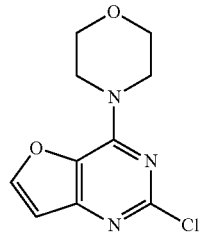

2,4-Dichlorofuro[3,2-d]pyrimidine 37 (23 mg, 1.0 eq) was suspended in methanol (1.7 ml) and treated with morpholine (0.09 ml, 4.0 eq). Reaction mixture was stirred at room temperature for 2 h, before being quenched with saturated aq. $NaHCO_3$. Mixture was extracted with dichloromethane. The combined organic layers were dried ($Na_2SO_4$) and concentrated to yield 2-chloro-4-morpholinofuro[3,2-d]pyrimidine 38 (14 mg, 48%) which was used in the next reaction without further purification.

Example 16

2-Chloro-4-morpholinofuro[3,2-d]pyrimidine-6-carbaldehyde 39

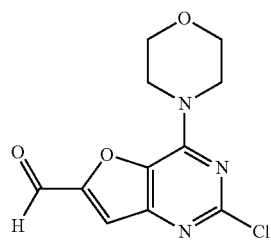

To a solution of 2-chloro-4-morpholinofuro[3,2-d]pyrimidine 38 (40 mg, 1.0 eq) dissolved in THF (1.7 ml) at −78° C. was added 1.6M solution of n-butyllithium (0.14 ml, 1.3 eq, 1.6M in hexanes). Reaction mixture was stirred at −78° C. for 30 minutes. DMF (0.05 ml, 4.0 eq) was added and reaction mixture was allowed to slowly warm up to room temperature and stirred for 90 minutes. Reaction mixture was quenched with water, and extracted with dichloromethane. The combined organic layers were dried ($Na_2SO_4$) and concentrated. The crude reaction mixture was purified by flash chromatography to yield 2-chloro-4-morpholinofuro[3,2-d]pyrimidine-6-carbaldehyde 39 (22 mg, 50%): $^1H$ NMR ($CDCl_3$, 400 MHz) δ 9.92 (s, 1H), 7.48 (s, 1H), 4.12 (m, 4H), 3.86 (dd, 4H); MS (Q1) 268 (M)$^+$.

Example 17

2-Chloro-6-iodo-4-morpholinofuro[3,2-d]pyrimidine 45

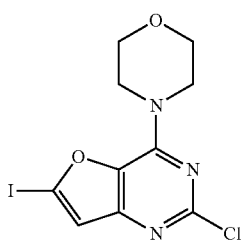

To a solution of 2-chloro-4-morpholinofuro[3,2-d]pyrimidine 38 (50 mg, 1.0 eq) dissolved in THF (2.1 ml) at −78° C. was added 1.6M solution of n-butyllithium (0.17 ml, 1.3 eq, 1.6M in hexanes). Reaction mixture was stirred at −78° C. for 30 minutes. A solution of iodine (159 mg, 3.0 eq) in THF (0.6 ml) was added and reaction mixture was allowed to slowly warm up to room temperature and stirred for 45 minutes. The reaction mixture was quenched with saturated aq. $Na_2S_2O_3$, and extracted with dichloromethane. The combined organic layers were dried ($Na_2SO_4$) and concentrated. The crude reaction mixture was purified by flash chromatography to yield 2-chloro-6-iodo-4-morpholinofuro[3,2-d]pyrimidine 45 (63 mg, 83%): MS (Q1) 366 (M)+.

Example 18

1-(4-((2-(2-aminopyrimidin-5-yl)-4-morpholinothieno[3,2-d]pyrimidin-6-yl)methyl)piperazin-1-yl)-2-(methylsulfonyl)ethanone 101

2-Chloro-4-morpholinothieno[3,2-d]pyrimidine-6-carbaldehyde 10 from Example 3 (4.17 g) was converted via General Procedure B-3 to yield 5.67 g of tert-butyl 4-((2-chloro-4-morpholinothieno[3,2-d]pyrimidin-6-yl)methyl)piperazine-1-carboxylate. Tert-butyl 4-((2-chloro-4-morpholinothieno[3,2-d]pyrimidin-6-yl)methyl)piperazine-1-carboxylate (1 g) was reacted with 5-(4,4,5,5-tetramethyl-1,3,2-dioxaborolan-2-yl)pyrimidin-2-amine via General Procedure A to give 1.02 g of tert-butyl 4-((2-(2-aminopyrimidin-5-yl)-4-morpholinothieno[3,2-d]pyrimidin-6-yl)methyl)piperazine-1-carboxylate. This intermediate was then converted to the HCl salt of 5-(4-morpholino-6-((piperazin-1-yl)methyl)thieno[3,2-d]pyrimidin-2-yl)pyrimidin-2-amine via General Procedure D.

The HCl salt of 5-(4-morpholino-6-((piperazin-1-yl)methyl)thieno[3,2-d]pyrimidin-2-yl)pyrimidin-2-amine (100 mg) was then reacted with methanesulfonylacetic acid via General Procedure B to generate 56 mg of 101. MS (Q1) 533.2 (M)+.

Example 19

1-(4-((2-(2-aminopyrimidin-5-yl)-4-morpholinothieno[3,2-d]pyrimidin-6-yl)methyl)piperazin-1-yl)-2-hydroxy-2-methylpropan-1-one 102

The HCl salt of 5-(4-morpholino-6-((piperazin-1-yl)methyl)thieno[3,2-d]pyrimidin-2-yl)pyrimidin-2-amine (100 mg) was reacted with 2-hydroxyisobutyric Acid via General Procedure B to generate 40.6 mg of 102. MS (Q1) 499.3 (M)+.

Example 20

2-amino-1-(4-((2-(2-aminopyrimidin-5-yl)-4-morpholinothieno[3,2-d]pyrimidin-6-yl)methyl)piperazin-1-yl)-2-methylpropan-1-one 103

The HCl salt of 5-(4-morpholino-6-((piperazin-1-yl)methyl)thieno[3,2-d]pyrimidin-2-yl)pyrimidin-2-amine (100 mg) was reacted with Boc-2-aminoisobutyric Acid via General Procedure B followed by Boc removal with TFA to generate 28.8 mg of 103 after purification. MS (Q1) 498.3 (M)+.

Example 21

(S)-2-amino-1-(4-((2-(2-aminopyrimidin-5-yl)-4-morpholinothieno[3,2-d]pyrimidin-6-yl)methyl)piperazin-1-yl)propan-1-one 104

The HCl salt of 5-(4-morpholino-6-((piperazin-1-yl)methyl)thieno[3,2-d]pyrimidin-2-yl)pyrimidin-2-amine (100 mg) was reacted with Boc-alanine via General Procedure B followed by Boc removal with TFA to generate 30.9 mg of 104 after purification. MS (Q1) 484.3 (M)+.

Example 22

1-(4-((2-(2-aminopyrimidin-5-yl)-4-morpholinothieno[3,2-d]pyrimidin-6-yl)methyl)piperazin-1-yl)-2-(dimethylamino)ethanone The HCl salt of 5-(4-morpholino-6-((piperazin-1-yl)methyl)thieno[3,2-d]pyrimidin-2-yl)pyrimidin-2-amine (100 mg) was reacted with N,N-dimethylglycine via General Procedure B to generate 38.3 mg of 105. MS (Q1) 498.3 (M)+.

Example 23

2-amino-1-(4-((2-(2-aminopyrimidin-5-yl)-4-morpholinothieno[3,2-d]pyrimidin-6-yl)methyl)piperazin-1-yl)ethanone 106

The HCl salt of 5-(4-morpholino-6-((piperazin-1-yl)methyl)thieno[3,2-d]pyrimidin-2-yl)pyrimidin-2-amine (100 mg) was reacted with Boc-glycine via General Procedure B followed by Boc removal with TFA to generate 44 mg of 106 after purification. MS (Q1) 470.2 (M)+.

Example 24

5-(4-morpholino-6-((4-(piperidin-1-yl)piperidin-1-yl)methyl)thieno[3,2-d]pyrimidin-2-yl)pyridin-2-amine 107

2-Chloro-4-morpholin-4-yl-thieno[3,2-d]pyrimidine-6-carbaldehyde 10 from Example 3 and 4-piperidinopiperidine were reacted using General Procedure B-3 to give 1'-(2-chloro-4-morpholin-4-yl-thieno[3,2-d]pyrimidin-6-ylmethyl)-[1,4']bipiperidinyl, which was reacted with 5-(4,4,5,5-tetramethyl-[1,3,2]dioxaborolan-2-yl)-pyridin-2-ylamine in General Procedure A. Purification on silica yielded 107. NMR (CDCl$_3$): 1.46 (m, 2H, CH2), 1.61-1.68 (m, 6H, 6×CH), 1.82-1.85 (m, 2H, 2×CH), 2.09-2.14 (m, 2H, CH2), 2.30 (m, H, CH), 2.54 (m, 4H, 4×CH), 3.04-3.07 (m, 2H, 2×CH), 3.81 (s, 2H, CH2), 3.89-3.91 (m, 4H, 2×CH2), 4.04-4.06 (m, 4H, 2×CH2), 4.64 (sbr, 2H, NH2), 6.58 (d, H, ArH, J=8.59 Hz), 7.26 (s, H, ArH), 8.47 (dd, H, ArH, J=8.58 Hz, 2.25 Hz), 9.16 (d, H, ArH, J=1.86 Hz). MS: (ESI+): MH+=494.32

Example 25

1-((2-(2,4-dimethoxypyrimidin-5-yl)-4-morpholinothieno[3,2-d]pyrimidin-6-yl)methyl)-N-methylpiperidine-4-carboxamide 108

To a stirring solution of BOC-isonipecotic acid (400 mg) in N,N-dimethylformamide (4 mL) was added 1,1'-carbonyldiimidazole (560 mg). The reaction mixture was stirred overnight and then methylamine hydrochloride (280 mg) and triethylamine (0.48 mL) were added. After 5 hours the reaction mixture was diluted with ethyl acetate, washed with water, dried (MgSO$_4$) and the solvent removed in vacuo. Treatment with HCl yielded piperidine-4-carboxylic acid methylamide, which was isolated as the hydrochloride salt.

Reaction between 2-chloro-4-morpholin-4-yl-thieno[3,2-d]pyrimidine-6-carbaldehyde 10 from Example 3 and piperidine-4-carboxylic acid methylamide, using General Procedure B-3 yielded 1-(2-chloro-4-morpholin-4-yl-thieno[3,2-d]pyrimidin-6-ylmethyl)-piperidine-4-carboxylic acid methylamide.

1-(2-Chloro-4-morpholin-4-yl-thieno[3,2-d]pyrimidin-6-ylmethyl)-piperidine-4-carboxylic acid methylamide was reacted with 2,4-dimethoxy-5-(4,4,5,5-tetramethyl-[1,3,2]dioxaborolan-2-yl)-pyrimidine in General Procedure A. Purification on silica yielded 108. NMR (CDCl$_3$): 1.84-1.89 (m, 4H, 2×CH2), 2.10-2.18 (m, 3H, CH2+CH), 2.84 (d, 3H, CH3, J=4.8 Hz), 3.03-3.06 (m, 2H, CH2), 3.83 (s, 2H, CH2), 3.88-3.90 (m, 4H, 2×CH2), 4.02-4.05 (m, 4H, 2×CH2), 4.08 (s, 3H, CH3), 4.11 (s, 3H, CH3), 5.47 (sbr, H, NH), 7.30 (s, H, ArH), 8.93 (s, H, ArH). MS: (ESI+): MH+=514.27

Example 26

4-((2-(2,4-dimethoxypyrimidin-5-yl)-4-morpholinothieno[3,2-d]pyrimidin-6-yl)methyl)-N,N-dimethylpiperazine-1-carboxamide 109

To a solution of 1-BOC-piperazine (867 mg) in dry tetrahydrofuran (8 mL) was added triethylamine (0.97 mL) followed by dimethylcarbamoyl chloride (0.51 mL). After stirring for 24 hours the reaction mixture was then diluted with dichloromethane, washed with brine, dried (MgSO$_4$) and the solvent removed in vacuo to yield 4-dimethylcarbamoyl-piperazine-1-carboxylic acid tert-butyl ester (940 mg). Treatment of this compound with HCl in dichloromethane/methanol yielded piperazine-1-carboxylic acid dimethylamide.

Reaction between 2-chloro-4-morpholin-4-yl-thieno[3,2-d]pyrimidine-6-carbaldehyde 10 from Example 3 and piperazine-1-carboxylic acid dimethylamide using General Procedure Z yielded 4-(2-chloro-4-morpholin-4-yl-thieno[3,2-d]pyrimidin-6-ylmethyl)-piperazine-1-carboxylic acid dimethylamide.

4-(2-Chloro-4-morpholin-4-yl-thieno[3,2-d]pyrimidin-6-ylmethyl)-piperazine-1-carboxylic acid dimethylamide was reacted with 2,4-dimethoxy-5-(4,4,5,5-tetramethyl-[1,3,2]dioxaborolan-2-yl)-pyrimidine in General Procedure A. Purification on silica yielded 109. NMR (CDCl$_3$): 2.48-2.51 (m, 4H, 2×CH2), 2.76 (s, 6H, 2×CH3), 3.21-3.24 (m, 4H, 2×CH2), 3.77-3.80 (m, 4H, 2×CH2), 3.93-3.96 (m, 4H, 2×CH2), 3.99 (s, 3H, CH3), 4.01 (s, 3H, CH3), 7.25 (s, H, ArH), 8.83 (s, H, ArH). MS: (ESI+): MH+=529.35

Example 27

N-(2-methoxyethyl)-4-((2-(2,4-dimethoxypyrimidin-5-yl)-4-morpholinothieno[3,2-d]pyrimidin-6-yl)methyl)-N-methylpiperazine-1-carboxamide To N—BOC-piperazine (500 mg) in dichloromethane (5 mL) and triethylamine (0.41 ml) was added 4-nitrophenyl chloroformate (541 mg). After 1 hour the reaction mixture was diluted with dichloromethane, washed with brine, dried (MgSO$_4$) and the solvent removed in vacuo to yield piperazine-1,4-dicarboxylic acid tert-butyl ester 4-nitro-phenyl ester (940 mg).

To piperazine-1,4-dicarboxylic acid tert-butyl ester 4-nitro-phenyl ester (500 mg) in tetrahydrofuran (5 ml) was added N-(2-methoxyethyl)methylamine (254 mg) and the reaction mixture was heated to reflux for 24 hours. The reaction mixture was reduced in vacuo and purified using flash chromatography to yield 4-[(2-methoxy-ethyl)-methyl-carbamoyl]-piperazine-1-carboxylic acid tert-butyl ester (304 mg). Treatment of this compound with HCl in dichloromethane/methanol yielded piperazine-1-carboxylic acid (2-methoxy-ethyl)-methyl-amide, which was isolated as the hydrochloride salt.

Reaction between 2-chloro-4-morpholin-4-yl-thieno[3,2-d]pyrimidine-6-carbaldehyde 10 from Example 3 and piperazine-1-carboxylic acid (2-methoxy-ethyl)-methyl-amide using General Procedure B-3 yielded 4-(2-Chloro-4-morpholin-4-yl-thieno[3,2-d]pyrimidin-6-ylmethyl)-piperazine-1-carboxylic acid (2-methoxy-ethyl)-methyl-amide.

4-(2-Chloro-4-morpholin-4-yl-thieno[3,2-d]pyrimidin-6-ylmethyl)-piperazine-1-carboxylic acid (2-methoxy-ethyl)-methyl-amide was reacted with 2,4-dimethoxy-5-(4,4,5,5-tetramethyl-[1,3,2]dioxaborolan-2-yl)-pyrimidine in General Procedure A. Purification on silica yielded 110. NMR (CDCl$_3$): 2.48-2.50 (m, 4H, 2×CH2), 2.83 (s, 3H, CH3), 3.21-3.23 (m, 4H, 2×CH2), 3.26 (s, 3H, CH3), 3.29-3.32 (m, 2H, CH2), 3.45-3.48 (m, 2H, CH2), 3.76-3.80 (m, 6H, 3×CH2), 3.93-3.95 (m, 4H, 2×CH2), 3.99 (s, 3H, CH3), 4.02 (s, 3H, CH3), 7.19 (s, H, ArH), 8.85 (s, H, ArH). MS: (ESI+): MH+=573.35

Example 28

5-(4-morpholino-6-((4-N-dimethylaminosulfonylpiperazin-1-yl)methyl)thieno[3,2-d]pyrimidin-2-yl)pyridin-2-amine 111

Piperazine-1-sulfonic acid dimethylamide was reacted with 10 in General Procedure B-3. Purification on silica yielded 4-(2-chloro-4-morpholin-4-yl-thieno[3,2-d]pyrimidin-6-ylmethyl)-piperazine-1-sulfonic acid dimethylamide.

4-(2-Chloro-4-morpholin-4-yl-thieno[3,2-d]pyrimidin-6-ylmethyl)-piperazine-1-sulfonic acid dimethylamide was reacted with 2-amino-5-(4,4,5,5-tetramethyl-1,3,2-dioxaborolan-2-yl)pyridine in General Procedure A. Purification on silica yielded 111. NMR (CDCl$_3$): 2.50-2.54 (4H, m, CH$_2$), 2.74 (6H, s, Me), 3.21-3.24 (4H, m, CH$_2$), 3.75 (2 H, s, CH$_2$), 3.78-3.82 (4H, m, CH$_2$), 3.95-3.98 (4H, m, CH$_2$), 4.58 (2H, br s, NH$_2$), 6.50 (1 H, d, J 8.6, Ar), 7.17 (1H, s, Ar), 8.38 (1H, dd, J 8.6 and 1.8, Ar) and 9.12 (1H, d, J 1.8, Ar). MS: (ESI+): MH+=519.34.

Example 29

5-(4-morpholino-6-((4-N-dimethylaminosulfonylpiperazin-1-yl)methyl)thieno[3,2-d]pyrimidin-2-yl)pyrimidin-2-amine 4-(2-Chloro-4-morpholin-4-yl-thieno[3,2-d]pyrimidin-6-ylmethyl)-piperazine-1-sulfonic acid dimethylamide (Example 28) was reacted with 2-aminopyrimidine-5-boronic acid pinacol ester in General Procedure A. Purification on silica yielded 112. NMR (CDCl$_3$): 2.51-2.55 (4H, m CH$_2$), 2.75 (6H, s, Me), 3.22-3.25 (4H, m, CH$_2$), 3.77 (2H, s, CH$_2$), 3.78-3.82 (4H, m, CH$_2$), 3.94-3.97 (4H, m, CH$_2$), 5.14 (2H, br s, NH$_2$), 7.20 (1H, s, Ar) and 9.20 (2H, s, Ar). MS: (ESI+): MH+=520.34.

Example 30

2-(2,4-dimethoxypyrimidin-5-yl)-4-morpholino-6-((4-N-dimethylaminosulfonylpiperazin-1-yl)methyl)thieno[3,2-d]pyrimidine 113

4-(2-Chloro-4-morpholin-4-yl-thieno[3,2-d]pyrimidin-6-ylmethyl)-piperazine-1-sulfonic acid dimethylamide (Example 28) was reacted with 2,4-dimethoxypyrimidine-5-boronic acid in General Procedure A. Purification on silica yielded 113. NMR (CDCl$_3$): 2.50-2.53 (4H, m, CH$_2$), 2.75 (6H, s, Me), 3.21-3.24 (4H, m, CH$_2$), 3.68-3.71 (6H, m, CH$_2$), 3.94-3.98 (4H, m, CH$_2$), 4.01 (3H, s, Me), 4.04 (3H, s, Me), 7.20 (1H, s, Ar) and 8.87 (1H, s, Ar). MS: (ESI+): MH+=565.44

Example 31

5-(4-morpholino-6-((4-(piperidin-1-yl)piperidin-1-yl)methyl)thieno[3,2-d]pyrimidin-2-yl)pyrimidin-2-amine 114

1'-(2-Chloro-4-morpholin-4-yl-thieno[3,2-d]pyrimidin-6-ylmethyl)-[1,4']bipiperidinyl (Example 24) was reacted with 5-(4,4,5,5-tetramethyl-[1,3,2]dioxaborolan-2-yl)-pyrimidin-2-ylamine in General Procedure A. Purification on silica yielded 114. NMR (CDCl$_3$): 1.50 (m, 2H, CH2), 1.58-1.70 (m, 6H, 3×CH2), 1.80 (m, 2H, CH2), 2.12 (m, 2H, CH2), 2.30 (m, H, CH), 2.53 (m, 4H, 2×CH2), 3.05 (m, 2H, CH2), 3.82 (s, 2H, CH2), 3.89-3.91 (m, 4H, 2×CH2), 4.03-4.06 (m, 4H, 2×CH2), 5.23 (sbr, 2H, NH2), 7.26 (s, H, ArH), 9.30 (s, 2H, 2×ArH). MS: (ESI+): MH+=495.49

Example 32

1-((2-(2-aminopyrimidin-5-yl)-4-morpholinothieno[3,2-d]pyrimidin-6-yl)methyl)-N-methylpiperidine-4-carboxamide 115

1-(2-Chloro-4-morpholin-4-yl-thieno[3,2-d]pyrimidin-6-ylmethyl)-piperidine-4-carboxylic acid methylamide (Example 25) was reacted with 5-(4,4,5,5-tetramethyl-[1,3,2]dioxaborolan-2-yl)-pyrimidin-2-ylamine in General Procedure A. Purification on silica yielded 115. NMR (CDCl$_3$): 1.85-1.89 (m, 4H, 2×CH2), 2.08-2.18 (m, 3H, CH2+CH), 2.84 (d, 3H, CH3, J=4.8 Hz), 3.04 (m, 2H, CH2), 3.83 (s, 2H, CH2), 3.90-3.92 (m, 4H, 2×CH2), 4.04-4.06 (m, 4H, 2×CH2), 5.22 (s, 2H, NH2), 5.45 (sbr, H, NH), 7.26 (s, H, ArH), 9.30 (s, 2H, 2×ArH). MS: (ESI+): MH+=469.27

Example 33

5-(4-morpholino-6-((4-N-isopropylsulfonylpiperazin-1-yl)methyl)thieno[3,2-d]pyrimidin-2-yl)pyrimidin-2-amine 116

A mixture of 2-chloro-4-morpholin-4-yl-6-piperazin-1-ylmethyl-thieno[3,2-d]pyrimidine from General Procedure B-3 (500 mg), isopropylsulfonyl chloride (0.26 mL) and triethylamine (0.57 mL) in dichloromethane (5 mL) was stirred at room temperature. After stirring for 24 hours, standard work-up yielded 2-chloro-4-morpholin-4-yl-6-[4-(propane-2-sulfonyl)-piperazin-1-ylmethyl]-thieno[3,2-d]pyrimidine.

2-Chloro-4-morpholin-4-yl-6-[4-(propane-2-sulfonyl)-piperazin-1-ylmethyl]-thieno[3,2-d]pyrimidine was reacted with 2-aminopyrimidine-5-boronic acid pinacol ester using General Procedure A. Purification on silica yielded 116. (400 MHz, CDCl3): 1.28 (6H, d (J=6.85), CH3), 2.54-2.56 (4H, m, CH2), 3.12 (1H, m, CH), 3.34-3.37 (4H, m, CH2), 3.79 (2H, s, CH2), 3.80-3.82 (4H, m, CH2), 3.94-3.97 (4H, m, CH2), 5.13 (2H, b, NH2), 7.21 (1H, s, ar), 9.21 (2H, s, ar). (M+H)+ 519.27

Example 34

2-(2,4-dimethoxypyrimidin-5-yl)-7-methyl-6-((4-(methylsulfonyl)piperidin-1-yl)methyl)-4-morpholinothieno[3,2-d]pyrimidine 117

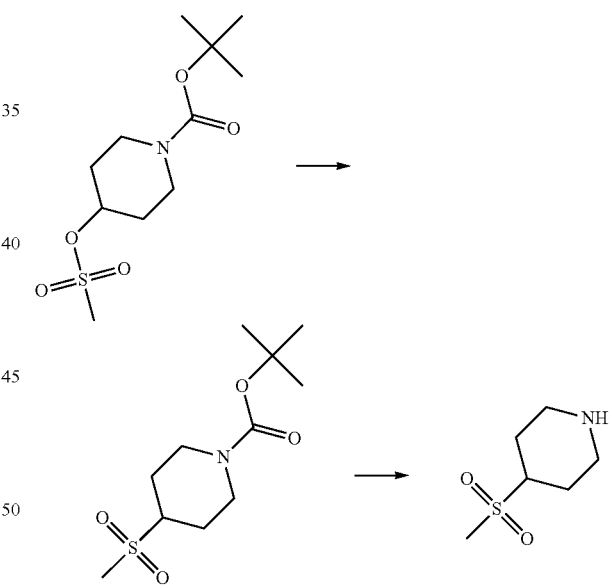

A mixture of 4-methanesulfonyloxy-piperidine-1-carboxylic acid tert-butyl ester (1.015 g), sodium thiomethoxide (635 mg) was heated to 80° C. in dimethylformamide (10 mL). After 4 h, the reaction mixture was diluted with water, extracted with ethyl acetate, dried (MgSO$_4$), filtered and concentrated in vacuo and then purified by flash chromatography to give 4-methylsulfanyl-piperidine-1-carboxylic acid tert-butyl ester (600 mg). To a solution of 4-methylsulfanyl-piperidine-1-carboxylic acid tert-butyl ester (600 mg) in chloroform (15 mL) was added mCPBA (1.46 g). After stirring for 2 days, the reaction mixture was diluted with dichloromethane, washed with sodium bicarbonate solution, dried (MgSO$_4$) and the solvent removed in vacuo to yield 4-methanesulfonyl-piperidine-1-carboxylic acid tert-butyl ester (505 mg) as a white solid. Treatment of this compound with HCl in dichloromethane/methanol yielded 4-(methylsulfonyl)piperidine, which was isolated as the hydrochloride salt.

4-Methanesulfonyl-piperidine HCl salt was reacted with 2-chloro-4-(tetrahydro-2H-pyran-4-yl)-7-methylthieno[3,2-d]pyrimidine-6-carbaldehyde following General Procedure B-3 to give 2-chloro-6-(4-methanesulfonyl-piperidin-1-ylmethyl)-4-morpholin-4-yl-thieno[3,2-d]pyrimidine.

2-Chloro-6-(4-methanesulfonyl-piperidin-1-ylmethyl)-4-morpholin-4-yl-thieno[3,2-d]pyrimidine (described below) was reacted with 2,4-dimethoxypyrimidine-5-boronic acid in General Procedure A. Purification on silica and ether trituration gave 117. NMR (CDCl3): 1.87-1.94 (2H, m), 2.5-2.09 (4H, m), 2.34 (3H, s), 2.78 (3H, s), 2.77-2.80 (1H, m), 3.10-3.13 (2H, br d), 3.74 (2H, s), 3.80-3.83 (4H, m), 3.94-3.97 (4H, m), 4.08 (3H, s), 4.11 (3H, s), 9.03 (1H, s). MS (ESI+): MH+ 549.44

Example 35

5-(7-methyl-6-((4-(methylsulfonyl)piperidin-1-yl)methyl)-4-morpholinothieno[3,2-d]pyrimidin-2-yl)pyridin-2-amine 118

2-Chloro-6-(4-methanesulfonyl-piperidin-1-ylmethyl)-4-morpholin-4-yl-thieno[3,2-d]pyrimidine (Example 34) was reacted with 2-amino-pyridine-5-boronic acid pinacol ester in General Procedure A. Purification on silica and ether trituration gave 118. NMR (CDCl$_3$): 1.87-1.94 (2H, m), 2.5-2.09 (4H, m), 2.34 (3H, s), 2.78 (3H, s), 2.77-2.80 (1H, m), 3.10-3.13 (2H, br d), 3.74 (2H, s), 3.80-3.83 (4H, m), 3.94-3.97 (4H, m), 4.60 (2H, br), 6.58 (1H, d, J=8.5), 8.53 (1H, d, J=8.5), 9.22 (1H, s). MS (ESI+): MH+ 503.33

Example 36

5-(7-methyl-6-((4-(methylsulfonyl)piperidin-1-yl)methyl)-4-morpholinothieno[3,2-d]pyrimidin-2-yl)pyrimidin-2-amine 119

2-Chloro-6-(4-methanesulfonyl-piperidin-1-ylmethyl)-4-morpholin-4-yl-thieno[3,2-d]pyrimidine (Example 34) was reacted with 2-amino-pyrimidine-5-boronic acid pinacol ester in General Procedure A. Purification on silica and ether trituration gave 119. NMR (CDCl3): 1.87-1.94 (2H, m), 2.5-2.09 (4H, m), 2.34 (3H, s), 2.78 (3H, s), 2.77-2.80 (1H, m), 3.10-3.13 (2H, br d), 3.74 (2H, s), 3.80-3.83 (4H, m), 3.94-3.97 (4H, m), 5.12 (2H, br), 9.25 (2H, s). MS (ESI+): MH+ 504.32

Example 37

5-(4-morpholino-6-((4-N-phenylsulfonylpiperazin-1-yl)methyl)thieno[3,2-d]pyrimidin-2-yl)pyrimidin-2-amine 120

A mixture of 2-chloro-4-morpholin-4-yl-6-piperazin-1-ylmethyl-thieno[3,2-d]pyrimidine from General Procedure B-3 (500 mg), benzenesulfonyl chloride (0.30 mL) and triethylamine (0.57 mL) in dichloromethane (5 mL) was stirred at room temperature. After stirring for 24 hours, standard work-up yielded 6-(4-benzenesulfonyl-piperazin-1-ylmethyl)-2-chloro-4-morpholin-4-yl-thieno[3,2-d]pyrimidine.

6-(4-Benzenesulfonyl-piperazin-1-ylmethyl)-2-chloro-4-morpholin-4-yl-thieno[3,2-d]pyrimidine was reacted with 2-aminopyrimidine-5-boronic acid pinacol ester using General Procedure A. Purification on silica yielded 120. (400 MHz, CDCl3): 2.56-2.58 (4H, m, CH2), 3.04 (4H, m, CH2), 3.74 (2H, s, CH2), 3.76-3.79 (4H, m, CH2), 3.90-3.92 (4H, m, CH2), 7.18 (1H, s, ar), 7.47-7.51 (1H, d (J=7.36), ar), 7.55 (1H, d (J=7.36), ar), 7.71 (2H, d (J=7.07), ar), 9.19 (2H, s, ar). (M+H)+ 553.29

Example 38

5-(4-morpholino-6-((piperazin-1-yl)methyl)thieno[3,2-d]pyrimidin-2-yl)pyridin-2-amine 121

6-(4-Benzenesulfonyl-piperazin-1-ylmethyl)-2-chloro-4-morpholin-4-yl-thieno[3,2-d]pyrimidine following General Procedure B-3 was reacted with 2-aminopyridine-5-boronic acid pinacol ester using General Procedure A. Purification on silica yielded 121. (400 MHz, CDCl3): 2.65-2.67 (4H, m, CH2), 3.13 (4H, m, CH2), 3.82 (2H, s, CH2), 3.85-3.88 (4H, m, CH2), 3.99-4.02 (4H, m, CH2), 4.63 (211, b, NH2), 6.57 (1H, dd (J=8.62, 0.62), ar), 7.27 (1H, s, ar), 7.58-7.60 (2H, m, ar), 7.63-7.67 (1H, m, ar), 7.80 (2H, d (J=7.07), ar), 8.46 (1H, dd (J=8.59-2.26), ar), 9.16 (1H, d (J=1.66), ar). (M+H)+ 552.34

Example 39

5-(4-morpholino-6-((4-N-cyclopropylsulfonylpiperazin-1-yl)methyl)thieno[3,2-d]pyrimidin-2-yl)pyrimidin-2-amine 122

A mixture of 2-chloro-4-morpholin-4-yl-6-piperazin-1-ylmethyl-thieno[3,2-d]pyrimidine following General Procedure B-3 (500 mg), cyclopropanesulfonyl chloride (0.24 mL) and triethylamine (0.57 mL) in dichloromethane (5 mL) was stirred at room temperature. After stirring for 24 hours, standard work-up yielded 2-chloro-6-(4-cyclopropanesulfonyl-piperazin-1-ylmethyl)-4-morpholin-4-yl-thieno[3,2-d]pyrimidine.

2-Chloro-6-(4-cyclopropanesulfonyl-piperazin-1-ylmethyl)-4-morpholin-4-yl-thieno[3,2-d]pyrimidine was reacted with 2-aminopyrimidine-5-boronic acid pinacol ester using General Procedure A. Purification on silica yielded 122. (400 MHz, CDCl3): 0.92-0.94 (2H, m, CH2), 1.11-1.12 (2H, m, CH2), 2.21 (1H, m, CH), 2.58-2.61 (4H, m, CH2), 3.29-3.32 (4H, m, CH2), 3.80-3.82 (6H, m, CH2), 3.94-3.97 (4H, m, CH2), 5.13 (2H, b, NH2), 7.23 (1H, s, ar), 9.21 (2H, s, ar). (M+H)+ 517.35

Example 40

5-(4-morpholino-6-((4-N-cyclopropylsulfonylpiperazin-1-yl)methyl)thieno[3,2-d]pyrimidin-2-yl)pyridin-2-amine 123

2-Chloro-6-(4-cyclopropanesulfonyl-piperazin-1-ylmethyl)-4-morpholin-4-yl-thieno[3,2-d]pyrimidine (Example 39) following General Procedure B-3 was reacted with 2-aminopyridine-5-boronic acid pinacol ester using General Procedure A. Purification on silica yielded 123. (400 MHz, CDCl3): 0.91-0.94 (2H, m, CH2), 1.10-1.12 (2H, m, CH2), 2.20 (1H, m, CH), 2.58-2.60 (4H, m, CH2), 3.29-3.31 (4H, m, CH2), 3.79-3.82 (6H, m, CH2), 3.94-3.97 (4H, m, CH2), 4.55 (1H, b, NH2), 6.47 (1H, d (J=0.62), ar), 7.22 (1H, s, ar), 8.38 (1H, dd (J=8.89, 2.27), ar), 9.08 (1H, dd (J=2.20, 0.49), ar). (M+H)+ 516.37

Example 41

1-((2-(6-aminopyridin-3-yl)-4-morpholinothieno[3,2-d]pyrimidin-6-yl)methyl)-N-methylpiperidine-4-carboxamide 124

1-(2-Chloro-4-morpholin-4-yl-thieno[3,2-d]pyrimidin-6-ylmethyl)-piperidine-4-carboxylic acid methylamide, prepared following General Procedure B-3, was reacted with 5-(4,4,5,5-tetramethyl-[1,3,2]dioxaborolan-2-yl)-pyridin-2-ylamine by General Procedure A. Purification on silica yielded 124. NMR (CDCl$_3$): 1.85-1.87 (m, 4H, 2×CH2), 2.10-2.18 (m, 3H, CH2+CH), 2.85 (d, 3H, Ch3, J=4.8 Hz), 3.03-3.06 (m, 2H, CH2), 3.82 (s, 2H, CH2), 3.89-3.92 (m, 4H, 2×CH2), 4.04-4.06 (m, 4H, 2×CH2), 4.63 (sbr, 2H, NH2), 5.46 (sbr, H, NH), 6.58 (d, H, ArH, J=8.59 Hz), 7.26 (s, H, ArH), 8.48 (dd, H, ArH, J=2.2 Hz, 8.58 Hz), 9.17 (d, H, ArH, J=2.03 Hz). MS: (ESI+): MH+=468.37

Example 42

1-((2-(2,4-dimethoxypyrimidin-5-yl)-4-morpholinothieno[3,2-d]pyrimidin-6-yl)methyl)-N,N-dimethylpiperidine-4-carboxamide 125

To a stirring solution of BOC-isonipecotic acid (400 mg) in N,N-dimethylformamide (4 mL) was added 1,1'-carbonyldiimidazole (560 mg). The reaction mixture was stirred overnight and then dimethylamine hydrochloride (280 mg) and triethylamine (0.48 mL) were added. After 5 hours the reaction mixture was diluted with ethyl acetate, washed with water, dried (MgSO$_4$) and the solvent removed in vacuo to yield 4-dimethylcarbamoyl-piperidine-1-carboxylic acid tert-butyl ester. Removal of the BOC group with HCl yielded piperidine-4-carboxylic acid dimethylamide, which was isolated as the hydrochloride salt.

Reaction between 2-chloro-4-morpholin-4-yl-thieno[3,2-d]pyrimidine-6-carbaldehyde 10 (Example 3) and piperidine-4-carboxylic acid dimethylamide using General Procedure B-3 yielded 1-(2-chloro-4-morpholin-4-yl-thieno[3,2-d]pyrimidin-6-ylmethyl)-piperidine-4-carboxylic acid dimethylamide.

1-(2-Chloro-4-morpholin-4-yl-thieno[3,2-d]pyrimidin-6-ylmethyl)-piperidine-4-carboxylic acid dimethylamide was reacted with 2,4-dimethoxy-5-(4,4,5,5-tetramethyl-[1,3,2]dioxaborolan-2-yl)-pyrimidine in General Procedure A. Purification on silica yielded 125. NMR (CDCl$_3$): 1.74 (m, 2H, CH2), 2.02 (m, 2H, CH2), 2.17 (m, 2H, CH2), 2.55 (m, H, CH), 2.97 (s, 3H, CH3), 3.04-3.07 (m+s, 5H, CH2+CH3), 3.84 (s, 2H, CH2), 3.88-3.90 (m, 4H, 2×CH2), 4.03-4.05 (m, 4H, 2×CH2), 4.08 (s, 3H, CH3), 4.11 (s, 3H, CH3), 7.30 (s, H, ArH), 8.93 (s, H, ArH). MS: (ESI+): MH+=528.45

Example 43

4-((2-(2-aminopyrimidin-5-yl)-7-methyl-4-morpholinothieno[3,2-d]pyrimidin-6-yl)methyl)-N,N-dimethylpiperazine-1-carboxamide 126

Reaction between 2-chloro-7-methyl-4-morpholin-4-yl-thieno[3,2-d]pyrimidine-6-carbaldehyde and piperazine-1-carboxylic acid dimethylamide (Example 26) using General Procedure B-3 yielded 4-(2-chloro-7-methyl-4-morpholin-4-yl-thieno[3,2-d]pyrimidin-6-ylmethyl)-piperazine-1-carboxylic acid dimethylamide.

4-(2-Chloro-7-methyl-4-morpholin-4-yl-thieno[3,2-d]pyrimidin-6-ylmethyl)-piperazine-1-carboxylic acid dimethylamide was reacted with 5-(4,4,5,5-tetramethyl-[1,3,2]dioxaborolan-2-yl)-pyrimidin-2-ylamine in General Procedure A. Purification on silica yielded 126. NMR (CDCl$_3$): 2.44 (s, 3H, CH3), 2.56-2.60 (m, 4H, 2×CH2), 2.85 (s, 6H, 2×CH3), 3.31-3.33 (m, 4H, 2×CH2), 3.83 (s, 2H, CH2), 3.88-3.91 (m, 4H, 2×CH2), 4.03-4.05 (m, 4H, 2×CH2), 5.22 (sbr, 2H, NH2), 9.35 (s, 2H, 2×ArH). MS: (ESI+): MH+=498.32

Example 44

1-((2-(2-aminopyrimidin-5-yl)-4-morpholinothieno[3,2-d]pyrimidin-6-yl)methyl)-N,N-dimethylpiperidine-4-carboxamide 127

1-(2-Chloro-4-morpholin-4-yl-thieno[3,2-d]pyrimidin-6-ylmethyl)-piperidine-4-carboxylic acid dimethylamide (Example 43) was reacted with 5-(4,4,5,5-tetramethyl-[1,3,2]dioxaborolan-2-yl)-pyrimidin-2-ylamine in General Procedure A. Purification on silica yielded 127. NMR (CDCl$_3$): 1.85-1.88 (m, 2H, CH2), 2.07-2.18 (m, 2H, CH2), 2.30-2.35 (m, 2H, CH2), 2.66-2.72 (m, H, CH), 3.11 (s, 3H, CH3), 3.19-3.21 (m+s, 5H, CH2+CH3), 3.98 (s, 2H, CH2), 4.04-4.06 (m, 4H, 2×CH2), 4.18-4.21 (m, 4H, 2×CH2), 5.36 (sbr, 2H, NH2), 7.40 (s, H, ArH), 9.44 (s, 2H, 2×ArH). MS: (ESI+): MH+=483.33

Example 45

4-((2-(2-aminopyrimidin-5-yl)-4-morpholinothieno[2,3-d]pyrimidin-6-yl)methyl)-N,N-dimethylpiperazine-1-carboxamide 128

Reaction between 2-chloro-4-morpholin-4-yl-thieno[2,3-d]pyrimidine-6-carbaldehyde (General Procedure D-2) and piperazine-1-carboxylic acid dimethylamide using General Procedure B-3 yielded 4-(2-chloro-4-morpholin-4-yl-thieno[2,3-d]pyrimidin-6-ylmethyl)-piperazine-1-carboxylic acid dimethylamide.

4-(2-Chloro-4-morpholin-4-yl-thieno[2,3-d]pyrimidin-6-ylmethyl)-piperazine-1-carboxylic acid dimethylamide was reacted with 5-(4,4,5,5-tetramethyl-[1,3,2]dioxaborolan-2-yl)-pyrimidin-2-ylamine in General Procedure A. Purification on silica yielded 128. NMR (CDCl$_3$): 2.55 (m, 4H, 2×CH2), 2.84 (s, 6H, 2×CH3), 3.32 (m, 4H, 2×CH2), 3.79 (s, 2H, CH2), 3.89-3.91 (m, 4H, 2×CH2), 3.95-3.97 (m, 4H, 2×CH2), 5.24 (sbr, 2H, NH2), 7.14 (s, H, ArH), 9.30 (s, 2H, 2×ArH). MS: (ESI+): MH+=484.31

Example 46

5-(6-((4-(methylsulfonyl)piperidin-1-yl)methyl)-4-morpholinothieno[3,2-d]pyrimidin-2-yl)pyridin-2-amine 129

A mixture of 4-methanesulfonyloxy-piperidine-1-carboxylic acid tert-butyl ester (1.015 g), sodium thiomethoxide (635 mg) was heated to 80° C. in dimethylformamide (10 mL). After 4 h, the reaction mixture was diluted with water, extracted with ethyl acetate, dried (MgSO$_4$), filtered and concentrated in vacuo and then purified by flash chromatography to give 4-methylsulfanyl-piperidine-1-carboxylic acid tert-butyl ester (600 mg). To a solution of 4-methylsulfanyl-piperidine-1-carboxylic acid tert-butyl ester (600 mg) in chloroform (15 mL) was added mCPBA (1.46 g). After stirring for 2 days, the reaction mixture was diluted with dichloromethane, washed with sodium bicarbonate solution, dried (MgSO$_4$) and the solvent removed in vacuo to yield 4-methanesulfonyl-piperidine-1-carboxylic acid tert-butyl ester (505 mg) as a white solid. Treatment of this compound with HCl in dichloromethane/methanol yielded 4-methanesulfonyl-piperidine, which was isolated as the hydrochloride salt.

4-Methanesulfonyl-piperidine hydrochloride salt was reacted with 2-chloro-4-morpholin-4-yl-thieno[3,2-d]pyrimidine-6-carbaldehyde 10 following General Procedure B-3. Purification on silica yielded 2-chloro-6-(4-methanesulfonyl-piperidin-1-ylmethyl)-4-morpholin-4-yl-thieno[3,2-d]pyrimidine.

2-Chloro-6-(4-methanesulfonyl-piperidin-1-ylmethyl)-4-morpholin-4-yl-thieno[3,2-d]pyrimidine was reacted with 2-amino-5-(4,4,5,5-tetramethyl-1,3,2-dioxaborolan-2-yl) pyridine in General Procedure A. Purification on silica yielded 129. NMR (MeOD): 1.72-1.90 (2H, m), 2.05-2.10 (2H, M), 2.60 (3H, s, Me), 2.85-2.88 (1H, m), 3.08-3.14 (2H, m), 3.30-3.33 (2H, m), 3.80 (2H, s, CH$_2$), 3.83-3.87 (4H, m, CH$_2$), 3.94-3.98 (4H, m, CH$_2$), 6.53 (1H, d, J 8.5, Ar), 7.19 (1H, s, Ar), 8.32 (1H, dd, J 8.5 and 1.8, Ar) and 8.92 (1H, d, J 1.8, Ar). MS: (ESI+): MH+=489.27

Example 47

5-(6-((4-(methylsulfonyl)piperidin-1-yl)methyl)-4-morpholinothieno[3,2-d]pyrimidin-2-yl)pyrimidin-2-amine 130

2-Chloro-6-(4-methanesulfonyl-piperidin-1-ylmethyl)-4-morpholin-4-yl-thieno[3,2-d]pyrimidine, prepared following Example 46, was reacted with 2-aminopyrimidine-5-boronic acid pinacol ester via General Procedure A. Purification on silica yielded 130. NMR (DMSO): 1.61-1.68 (2H, m), 2.01-2.08 (2H, m), 2.12-2.18 (2H, m), 2.94 (3H, s, Me), 3.02-3.11 (3H, m), 3.76-3.80 (4H, m, CH$_2$), 3.89 (2H, s, CH$_2$), 3.96-3.99 (4H, m, CH$_2$), 7.02 (2H, s, NH$_2$), 7.32 (1H, s, Ar) and 9.10 (2H, s, Ar). MS: (ESI+): MH+=490.34

Example 48

2-(2,4-dimethoxypyrimidin-5-yl)-6-((4-(methylsulfonyl)piperidin-1-yl)methyl)-4-morpholinothieno[3,2-d]pyrimidine 131

2-Chloro-6-(4-methanesulfonyl-piperidin-1-ylmethyl)-4-morpholin-4-yl-thieno[3,2-d]pyrimidine, prepared following Example 46, was reacted with 2,4-dimethoxypyrimidine-5-boronic acid in General Procedure A. Purification on silica yielded 131. NMR (CDCl3): 1.96-2.04 (2H, m), 2.18-2.26 (4H, m), 2.84-2.91 (1H, m), 2.86 (3H, s, Me), 3.12-3.20 (2H, m), 3.82 (2H, s, CH$_2$), 3.84-3.90 (4H, m, CH$_2$), 3.98-4.02 (4H, m, CH$_2$), 4.04 (3H, s, Me), 4.08 (3H, s, Me), 7.32 (1H, s, Ar) and 8.94 (1H, s, Ar). MS: (ESI+): MH+=535.39

Example 49

2-(6-methylpyridin-3-yl)-4-morpholino-6-((4-(piperidin-1-yl)piperidin-1-yl)methyl)thieno[3,2-d]pyrimidine 132

1'-(2-Chloro-4-morpholin-4-yl-thieno[3,2-d]pyrimidin-6-ylmethyl)-[1,4']bipiperidinyl (Example 24) was reacted with 2-methyl-5-(4,4,5,5-tetramethyl-[1,3,2]dioxaborolan-2-yl)-pyridine in General Procedure A. Purification on silica yielded 132. NMR (CDCl$_3$): 1.62 m, 10H, 5×CH2), 1.70 (m, 2H, CH2), 2.13 (t, 2H, CH2, J=11.07 Hz), 2.36 (m, H, CH), 2.58 (m, 2H, CH2), 2.66 (s, 3H, CH3), 3.06 (d, 2H, CH2, J=11.5 Hz), 3.83 (s. 2H, CH2), 3.90-3.92 (m, 4H, 2×CH2), 4.06-4.08 (m, 4H, 2×CH2), 7.25 (d, H, ArH, J=8.1 Hz), 7.31 (s, H, ArH), 8.58 (dd, H, ArH, J=2.14 Hz, 8.09 Hz), 9.52 (d, H, ArH, J=1.9 Hz). MS: (ESI+): MH+=493.45

Example 50

1-((2-(6-aminopyridin-3-yl)-4-morpholinothieno[3,2-d]pyrimidin-6-yl)methyl)-N,N-dimethylpiperidine-4-carboxamide 133

1-(2-Chloro-4-morpholin-4-yl-thieno[3,2-d]pyrimidin-6-ylmethyl)-piperidine-4-carboxylic acid dimethylamide (Example 45) was reacted with 5-(4,4,5,5-tetramethyl-[1,3,2]dioxaborolan-2-yl)-pyridin-2-ylamine in General Procedure A. Purification on silica yielded 133. NMR (CDCl$_3$): 1.70-1.73 (m, 2H, CH2), 1.91-2.01 (m, 2H, CH2), 2.14-2.20 9 m, 2H, CH2), 2.52-2.54 (m, H, CH), 2.97 (s, 3H, CH3), 3.05-3.07 (m, 5H, CH3+CH2), 3.84 (s, 2H, CH2), 3.90-3.92 (m, 4H, 2×CH2), 4.04-4.06 (m, 4H, 2×CH2), 4.63 (sbr, 2H, NH2), 6.57 (d, H, ArH, J=8.6 Hz), 7.26 (s, H, ArH), 8.47 (dd, H, ArH, J=2.27 Hz, 8.59 Hz), 9.16 (d, H, ArH, J=1.74 Hz). MS: (ESI+): MH+=482.36

Example 51

2-(2,4-dimethoxypyrimidin-5-yl)-4-morpholino-6-((4-(piperidin-1-yl)piperidin-1-yl)methyl)thieno[3,2-d]pyrimidine 134

1'-(2-Chloro-4-morpholin-4-yl-thieno[3,2-d]pyrimidin-6-ylmethyl)-[1,4']bipiperidinyl (Example 24) was reacted with 2,4-dimethoxy-5-(4,4,5,5-tetramethyl-[1,3,2]dioxaborolan-2-yl)-pyrimidine in General Procedure A. Purification on silica yielded 134. NMR (CDCl$_3$): 1.46 (m, 2H, CH2), 1.60-1.69 (m, 6H, 3×CH2), 1.83 (m, 2H, Ch2), 2.12 (t, 2H, CH2, J=10.91 Hz), 2.28 (m, H, CH), 2.53 (m, 4H, 2×CH2), 3.04 (d, 2H, CH2, J=11 Hz), 3.82 (s, 2H, CH2), 3.87-3.89 (m, 4H, 2×CH2), 4.02-4.04 (m, 4H, 2×CH2), 4.08 (s, 3H, CH3), 4.11 (s, 3H, CH3), 7.30 (s, H, ArH), 8.93 (s, H, ArH). MS: (ESI+): MH+=540.51

Example 52

5-(4-morpholino-6-((4-N-methylsulfonylpiperazin-1-yl)methyl)thieno[2,3-d]pyrimidin-2-yl)thiazol-2-amine 135

A suspension of 2-chloro-6-(4-methanesulfonyl-piperidin-1-ylmethyl)-4-morpholin-4-yl-thieno[2,3-d]pyrimidine, prepared via General Procedure B-3 (180 mg, 0.42 mmol), (5-tributylstannyl-thiazol-2-yl)-carbamic acid tert-butyl ester (306 mg, 0.625 mmol), and Pd(PPh$_3$)$_4$ (24 mg, 0.021 mmol) in anhydrous DMA was heated in a microwave at 150° C. for 10 mins. The crude reaction was loaded onto a preconditioned SCX cartridge, washing the cartridge with methanol and dichloromethane before eluting with 7N ammonia in methanol to give crude material. This was purified by on silica using 10% methanol in ethyl acetate as the eluent to give 135 as a white solid (63 mg, 30%). NMR (DMSO, 400 MHz), 2.52-2.55 (4H, m), 2.88 (3H, s), 3.13-3.18 (4H, m), 3.74-3.85 (10H, m), 7.37 (2H, s), 7.47 (1H, s), 7.75 (1H, s). MS: (ESI+): MH+=496

Example 53

5-(6-((4-(1-methylpiperidin-4-yl)piperazin-1-yl)methyl)-4-morpholinothieno[3,2-d]pyrimidin-2-yl)pyrimidin-2-amine 136

To a solution of 2-chloro-4-morpholinothieno[3,2-d]pyrimidine-6-carbaldehyde (150 mg, 0.5 mmol) in 1,2-dichloroethane (2.5 mL) was added 1-(N-methylpiperidin-4-yl-methyl)piperazine (150 mg, 0.7 mmol) and AcOH (30 µL, 0.5 mmol). After stirring 10 min at room temperature, Na(OAc)$_3$BH (130 mg, 0.6 mmol) was added and the resulting mixture stirred overnight. The reaction was quenched by the addition of saturated aqueous NaHCO$_3$ and the organic layer was separated. The aqueous layer was extracted with CH$_2$Cl$_2$ and the combined organics were dried over Na$_2$SO$_4$, filtered, and concentrated in vacuo. The resulting crude mixture was coupled following General Procedure A with 5-(4,4,5,5-tetramethyl-1,3,2-dioxaborolan-2-yl)pyrimidin-2-amine to provide 136 after reverse phase HPLC purification (8 mg). MS (Q1) 510 (M)+.

Example 54

5-(6-((4-(2-methoxyethyl)piperazin-1-yl)methyl)-4-morpholinothieno[3,2-d]pyrimidin-2-yl)pyrimidin-2-amine 137

To a solution of 2-chloro-4-morpholinothieno[3,2-d]pyrimidine-6-carbaldehyde (150 mg, 0.5 mmol) in 1,2-dichloroethane (2.5 mL) was added 1-(2-methoxyethyl)piperazine (110 µL, 0.7 mmol) and AcOH (30 pit, 0.5 mmol). After stirring 10 min at room temperature, Na(OAc)$_3$BH (130 mg, 0.6 mmol) was added and the resulting mixture stirred overnight. The reaction was quenched by the addition of saturated aqueous NaHCO$_3$ and the organic layer was separated. The aqueous layer was extracted with CH$_2$Cl$_2$ and the combined organics were dried over Na$_2$SO$_4$, filtered, and concentrated in vacuo. The resulting crude mixture was coupled using General Procedure A with 5-(4,4,5,5-tetramethyl-1,3,2-dioxaborolan-2-yl)pyrimidin-2-amine to provide 137 after reverse phase HPLC purification (43 mg). MS (Q1) 471 (M)+.

Example 55

5-(4-morpholino-6-((4-(pyrimidin-2-yl)piperazin-1-yl)methyl)thieno[3,2-d]pyrimidin-2-yl)pyrimidin-2-amine 138

To a solution of 2-chloro-4-morpholinothieno[3,2-d]pyrimidine-6-carbaldehyde (150 mg, 0.5 mmol) in 1,2-dichloroethane (2.5 mL) was added 1-(2-pyrimidyl)piperazine (110 µL, 0.7 mmol) and AcOH (30 µL, 0.5 mmol). After stirring 10 min at room temperature, Na(OAc)$_3$BH (130 mg, 0.6 mmol) was added and the resulting mixture stirred overnight. The reaction was quenched by the addition of saturated aqueous NaHCO$_3$ and the organic layer was separated. The aqueous layer was extracted with CH$_2$Cl$_2$ and the combined organics were dried over Na$_2$SO$_4$, filtered, and concentrated in vacuo. The resulting crude mixture was coupled using General Procedure A with 5-(4,4,5,5-tetramethyl-1,3,2-dioxaborolan-2-yl)pyrimidin 2-amine to provide 138 after reverse phase HPLC purification (5 mg). MS (Q1) 491 (M)+.

Example 56

6-((4-methylpiperazin-1-yl)methyl)-4-morpholino-2-(pyridin-3-yl)thieno[3,2-d]pyrimidine 139

2-Chloro-4-morpholinothieno[3,2-d]pyrimidine-6-carbaldehyde 10 from Example 3 (100 mg) was reacted with N-methylpiperazine following the protocol in General Procedure C. One half of the crude material was then used with pyridine-3-boronic acid in General Procedure A to give 139 following reversed phase HPLC purification. MS (Q1) 411 (M)+.

Example 57

4-morpholino-2-(pyridin-3-yl)-6-((4-(pyrrolidin-1-yl)piperidin-1-yl)methyl)thieno[3,2-d]pyrimidine 140

2-Chloro-4-morpholinothieno[3,2-d]pyrimidine-6-carbaldehyde 10 from Example 3 (100 mg) was reacted with 2-(pyrrolidin-1-yl)piperidine following the protocol in General Procedure C. One half of the crude material was then used with pyridine-3-boronic acid in General Procedure A to give 12 mg of 140 following reversed phase HPLC purification. MS (Q1) 465 (M)+.

Example 58

6-((3-(methylsulfonyl)pyrrolidin-1-yl)methyl)-4-morpholino-2-(pyridin-3-yl)thieno[3,2-d]pyrimidine 141

2-Chloro-4-morpholinothieno[3,2-d]pyrimidine-6-carbaldehyde 10 from Example 3 (100 mg) was reacted with 3-(methanesulfonyl)pyrrolidine following the protocol in General Procedure C. One half of the crude material was then used with pyridine-3-boronic acid in General Procedure A to give 47 mg of 141 following reversed phase HPLC purification. MS (Q1) 460 (M)+.

Example 59

1-((4-morpholino-2-(pyridin-3-yl)thieno[3,2-d]pyrimidin-6-yl)methyl)piperidin-4-ol 142

2-Chloro-4-morpholinothieno[3,2-d]pyrimidine-6-carbaldehyde 10 from Example 3 (100 mg) was reacted with 4-hydroxypiperidine following the protocol in General Procedure C. One half of the crude material was then used with pyridine-3-boronic acid in General Procedure A to give 24 mg of 142 following reversed phase HPLC purification. MS (Q1) 412 (M)+.

Example 60

2-(1-((4-morpholino-2-(pyridin-3-yl)thieno[3,2-d]pyrimidin-6-yl)methyl)piperidin-4-yl)ethanol 143

2-Chloro-4-morpholinothieno[3,2-d]pyrimidine-6-carbaldehyde 10 from Example 3 (100 mg) was reacted with 2-(piperidin-4-yl)ethanol following the protocol in General Procedure C. One half of the crude material was then used with pyridine-3-boronic acid in General Procedure A to give 42 mg of 143 following reversed phase HPLC purification. MS (Q1) 440 (M)+.

Example 61

5-(6-((4-methylpiperazin-1-yl)methyl)-4-morpholinothieno[3,2-d]pyrimidin-2-yl)pyrimidin-2-amine 144

2-Chloro-4-morpholinothieno[3,2-d]pyrimidine-6-carbaldehyde 10 from Example 3 (100 mg) was reacted with 100 mg of 2-chloro-4-morpholinothieno[3,2-d]pyrimidine-6-carbaldehyde was used along with N-methylpiperazine following the protocol in General Procedure C. One half of the crude material was then used in General Procedure A to give 4 mg of 144 following reversed phase HPLC purification. MS (Q1) 427 (M)+.

Example 62

5-(4-morpholino-6-((4-(pyrrolidin-1-yl)piperidin-1-yl)methyl)thieno[3,2-d]pyrimidin-2-yl)pyrimidin-2-amine 145

2-Chloro-4-morpholinothieno[3,2-d]pyrimidine-6-carbaldehyde 10 from Example 3 (100 mg) was reacted with 2-(pyrrolidin-1-yl)piperidine following the protocol in General Procedure C. One half of the crude material was then used in General Procedure A to give 1 mg of 145 following reversed phase HPLC purification. MS (Q1) 481 (M)+.

Example 63

5-(6-((3-(methylsulfonyl)pyrrolidin-1-yl)methyl)-4-morpholinothieno[3,2-d]pyrimidin-2-yl)pyrimidin-2-amine 146

2-Chloro-4-morpholinothieno[3,2-d]pyrimidine-6-carbaldehyde 10 from Example 3 (100 mg) was reacted with 3-(methanesulfonyl)pyrrolidine following the protocol in General Procedure C. One half of the crude material was then used in General Procedure A to give 32 mg of 146 following reversed phase HPLC purification. MS (Q1) 476 (M)+.

Example 64

1-((2-(2-aminopyrimidin-5-yl)-4-morpholinothieno[3,2-d]pyrimidin-6-yl)methyl)piperidin-4-ol 147

2-Chloro-4-morpholinothieno[3,2-d]pyrimidine-6-carbaldehyde 10 from Example 3 (100 mg) was reacted with 4-hydroxypiperidine following the protocol in General Procedure C. One half of the crude material was then used in General Procedure A to give 9 mg of 147 following reversed phase HPLC purification. MS (Q1) 428 (M)+.

Example 65

(R)-1-((2-(2-aminopyrimidin-5-yl)-4-morpholinothieno[3,2-d]pyrimidin-6-yl)methyl)piperidin-3-ol 148

2-Chloro-4-morpholinothieno[3,2-d]pyrimidine-6-carbaldehyde 10 from Example 3 (50 mg) was reacted with 3-(R)-hydroxypiperidine following the protocol in General Procedure C. The crude material was then used in General Procedure A to give 25 mg of 148 following reversed phase HPLC purification. MS (Q1) 428 (M)+.

Example 66

2-(1-((2-(2-aminopyrimidin-5-yl)-4-morpholinothieno[3,2-d]pyrimidin-6-yl)methyl)piperidin-4-yl)ethanol 149

2-Chloro-4-morpholinothieno[3,2-d]pyrimidine-6-carbaldehyde 10 from Example 3 (100 mg) was reacted with 2-(piperidin-4-yl)ethanol following the protocol in General Procedure C. One half of the crude material was then used in General Procedure A to give 25 mg of 149 following reversed phase HPLC purification. MS (Q1) 456 (M)+.

Example 67

(R)-1-((2-(2-aminopyrimidin-5-yl)-4-morpholinothieno[3,2-d]pyrimidin-6-yl)methyl)pyrrolidin-3-ol 150

2-Chloro-4-morpholinothieno[3,2-d]pyrimidine-6-carbaldehyde 10 from Example 3 (100 mg) was reacted with 3-(S)-hydroxypyrrolidine following the protocol in General Procedure C. The crude material was then used following General Procedure A to give 8 mg of 150 following reversed phase HPLC purification. MS (Q1) 414 (M)+.

Example 68

2-(2,4-dimethoxypyrimidin-5-yl)-4-morpholino-6-((4-N-methylsulfonylpiperazin-1-yl)methyl)thieno[2,3-d]pyrimidine 151

2-Chloro-6-(4-methanesulfonyl-piperidin-1-ylmethyl)-4-morpholin-4-yl-thieno[2,3-d]pyrimidine, prepared via General Procedure B-3, was reacted with 2,4-dimethoxypyrimidine-5-boronic acid in General Procedure A. Purification on silica yielded 151. NMR (CDCl$_3$): 2.62-2.69 (4H, m), 2.80 (3H, s, Me), 3.28-3.32 (4H, m), 3.81 (2H, s, CH$_2$), 3.87-3.92 (4H, m, CH$_2$), 3.94-3.98 (4H, m, CH$_2$), 4.08 (3H, s, Me), 4.11 (3H, s, Me), 7.17 (1H, s, Ar) and 8.98 (1H, s, Ar). MS: (ESI+): MH+=536.20

Example 69

4-morpholino-6-((4-N-methylsulfonylpiperazin-1-yl)methyl)-2-(thiazol-5-yl)thieno[3,2-d]pyrimidine 152

A suspension of 2-chloro-6-(4-methanesulfonyl-piperazin-1-ylmethyl)-4-morpholin-4-yl-thieno[3,2-d]pyrimidine, prepared via General Procedure B-3, (144 mg, 0.33 mmol), 5-tributylstannanyl-thiazole (187 mg, 0.5 mmol), and Pd(PPh$_3$)$_4$ (19 mg, 0.017 mmol) in anhydrous DMA was heated in a microwave at 150° C. for 10 mins. The crude reaction was loaded onto a preconditioned SCX cartridge, washing the cartridge with methanol and dichloromethane before eluting with 7N ammonia in methanol to give crude material. This was purified by on silica using 5% methanol in ethyl acetate as the eluent to give 152 as an off-white solid (80 mg, 50%). NMR (CDCl$_3$, 400 MHz), 2.68-2.72 (4H, m), 2.83 (3H, s), 3.32-3.36 (4H, m), 3.88-3.93 (6H, m), 4.03-4.06 (4H, m), 7.32 (1H, s), 8.67 (1H, m), 8.84 (1H, s). MS: (ESI+): MH+=481

Example 70

5-(4-morpholino-6-((4-N-methylsulfonylpiperazin-1-yl)methyl)thieno[3,2-d]pyrimidin-2-yl)thiazol-2-amine 153

A suspension of 2-chloro-6-(4-methanesulfonyl-piperazin-1-ylmethyl)-4-morpholin-4-yl-thieno[3,2-d]pyrimidine, prepared via General Procedure B-3, (201 mg, 0.465 mmol), (5-tributylstannyl-thiazol-2-yl)-carbamic acid tert-butyl ester (341 mg, 0.7 mmol), and Pd(PPh$_3$)$_4$ (27 mg, 0.023 mmol) in anhydrous DMA was heated in a microwave at 150° C. for 10 mins. Ethyl acetate/water extraction and purification on silica using 10% methanol in ethyl acetate as the eluent to give 153 as an off-white solid (84 mg, 36%). NMR (MeOD), 2.68-2.72 (4H, m), 2.88 (3H, s), 3.26-3.31 (4H, m), 3.83-3.87 (4H, m), 3.95 (2H, s), 3.99-4.03 (4H, m), 4.65 (2H, br s), 7.25 (1H, s), 7.82 (1H, s). MS: (ESI+): MH+ 496

Example 71

N-(2-methoxyethyl)-N-methyl-4-((2-(6-methylpyridin-3-yl)-4-morpholinothieno[3,2-d]pyrimidin-6-yl)methyl)piperazine-1-carboxamide 154

4-(2-Chloro-4-morpholin-4-yl-thieno[3,2-d]pyrimidin-6-ylmethyl)-piperazine-1-carboxylic acid (2-methoxy-ethyl)-methyl-amide (Example 27) was reacted with 2-methyl-5-(4,4,5,5-tetramethyl-[1,3,2]dioxaborolan-2-yl)-pyridine via General Procedure A. Purification on silica yielded 154. NMR (CDCl$_3$): 2.58-2.60 (m, 4H, 2×CH2), 2.65 (s, 3H, CH3), 2.92 (s, 3H, CH3), 3.31-3.33 (m, 4H, 2×CH2), 3.36 (s, 3H, CH3), 3.38-3.41 (m, 4H, 2×CH2), 3.55-3.58 (m, 4H, 2×CH2), 3.87 (s, 2H, CH2), 3.90-3.92 (m, 4H, 2×CH2), 4.06-4.09 (m, 4H, 2×CH2), 7.26 (d, H, ArH, J=8.13 Hz), 7.33 (s, H, ArH), 58.58 (dd, H, ArH, J=8.07 Hz), 9.52 (d, H, ArH, J=1.86 Hz). MS: (ESI+): MH+ 526.45

Example 72

4-((2-(2-aminopyrimidin-5-yl)-4-morpholinothieno[3,2-d]pyrimidin-6-yl)methyl)-N-(2-methoxyethyl)-N-methylpiperazine-1-carboxamide 155

4-(2-Chloro-4-morpholin-4-yl-thieno[3,2-d]pyrimidin-6-ylmethyl)-piperazine-1-carboxylic acid (2-methoxy-ethyl)-methyl-amide (Example 27) was reacted with 5-(4,4,5,5-tetramethyl-[1,3,2]dioxaborolan-2-yl)-pyrimidin-2-ylamine via General Procedure A. Purification on silica yielded 155. NMR (CDCl$_3$): 2.57-2.60 (m, 4H, 2×CH2), 2.92 (s, 3H, CH3), 3.31-3.33 (m, 4H, 2×CH2), 3.36 (s, 3H, CH3), 3.38-3.41 (m, 4H, 2×CH2), 3.55-3.57 (m, 4H, 2×CH2), 3.86 (s, 2H, CH2), 3.89-3.92 (m, 4H, 2×CH2), 4.04-4.06 (m, 4H, 2×CH2), 5.28 (sbr, 2H, NH2), 7.29 (s, H, ArH), 7.33 (s, H, ArH), 9.29 (s, 2H, 2×ArH). MS: (ESI+): MH+ 528.44

Example 73

4-((2-(6-aminopyridin-3-yl)-4-morpholinothieno[3,2-d]pyrimidin-6-yl)methyl)-N-(2-methoxyethyl)-N-methylpiperazine-1-carboxamide 156

4-(2-Chloro-4-morpholin-4-yl-thieno[3,2-d]pyrimidin-6-ylmethyl)-piperazine-1-carboxylic acid (2-methoxy-ethyl)-methyl-amide (Example 27) was reacted with 5-(4,4,5,5-tetramethyl-[1,3,2]dioxaborolan-2-yl)-pyridin-2-ylamine in General Procedure A. Purification on silica yielded 156. NMR (CDCl$_3$): 2.57-2.59 (m, 4H, 2×CH2), 2.92 (s, 3H, CH3), 3.30-3.32 (m, 4H, 2×CH2), 3.36 (s, 3H, CH3), 3.38-3.41 (m, 4H, 2×CH2), 3.55-3.58 (m, 4H, 2×CH2), 3.85 (s, 2H, CH2), 3.89-3.91 (m, 4H, 2×CH2), 4.04-4.06 (m, 4H, 2×CH2), 4.67 (sbr, 2H, NH2), 6.58 (d, H, ArH, J=8.64 Hz), 7.29 (s, H, ArH), 8.48 (dd, H, ArH, J=2.2 Hz, 8.6 Hz), 9.17 (d, H, ArH, J=2.02 Hz). MS: (ESI+): MH+ 527.49

Example 74

2-(4-((2-(6-aminopyridin-3-yl)-4-morpholinothieno[3,2-d]pyrimidin-6-yl)methyl)piperazin-1-yl)ethanol 157

To a solution of 2-chloro-4-morpholinothieno[3,2-d]pyrimidine-6-carbaldehyde (1.3 g, 4.6 mmol) in 1,2-dichloroethane (45 mL) was added 1-(2-hydroxyethyl)piperazine (0.8 mL, 6.4 mmol) and AcOH (260 µL, 4.6 mmol). After stirring 10 min at room temperature, Na(OAc)$_3$BH (1.2 g, 5.5 mmol) was added and the resulting mixture stirred overnight. The reaction was quenched by the addition of saturated aqueous NaHCO$_3$ and the organic layer was separated. The aqueous layer was extracted with CH$_2$Cl$_2$ and the combined organics were dried over Na$_2$SO$_4$, filtered, and concentrated in vacuo. A portion (0.4 mmol) of the crude intermediate was coupled using General Procedure A with 5-(4,4,5,5-tetramethyl-1,3,2-dioxaborolan-2-yl)pyridin-2-amine to provide 157 after reverse phase HPLC purification (21 mg). MS (Q1) 456 (M)+.

Example 75

2-(4-((2-(2-aminopyrimidin-5-yl)-4-morpholinothieno[3,2-d]pyrimidin-6-yl)methyl)piperazin-1-yl)ethanol 158

To a solution of 2-chloro-4-morpholinothieno[3,2-d]pyrimidine-6-carbaldehyde (1.3 g, 4.6 mmol) in 1,2-dichloroethane (45 mL) was added 1-(2-hydroxyethyl)piperazine (0.8 mL, 6.4 mmol) and AcOH (260 µL, 4.6 mmol). After stirring 10 min at room temperature, Na(OAc)$_3$BH (1.2 g, 5.5 mmol) was added and the resulting mixture stirred overnight. The reaction was quenched by the addition of saturated aqueous NaHCO$_3$ and the organic layer was separated. The aqueous layer was extracted with CH$_2$Cl$_2$ and the combined organics were dried over Na$_2$SO$_4$, filtered, and concentrated in vacuo. A portion (0.4 mmol) of the crude intermediate was coupled following General Procedure A with 5-(4,4,5,5-tetramethyl-1,3,2-dioxaborolan-2-yl)pyrimidin-2-amine to provide 158 after reverse phase HPLC purification (15 mg). MS (Q1) 457 (M)$^+$.

Example 76

5-(4-morpholino-6-((piperazin-1-yl)methyl)thieno[3,2-d]pyrimidin-2-yl)pyrimidin-2-amine 159

2-Chloro-6-((4-Boc-piperazin-1-yl)methyl)-4-morpholinothieno[3,2-d]pyrimidine (200 mg) was reacted with 5-(4,4,5,5-tetramethyl-1,3,2-dioxaborolan-2-yl)pyrimidin-2-amine 7 following General Procedure A followed by Boc removal with 1N HCl in dioxane to generate 159 after reversed phase HPLC purification. MS (Q1) 413 (M)+.

Example 77

5-(4-morpholino-6-((piperazin-1-yl)methyl)thieno[3,2-d]pyrimidin-2-yl)pyridin-2-amine 160

2-Chloro-6-((4-Boc-piperazin-1-yl)methyl)-4-morpholinothieno[3,2-d]pyrimidine (200 mg) was used in General Procedure A followed by Boc removal with 1N HCl in dioxane to generate 36 mg of 160 after reversed phase HPLC purification. MS (Q1) 372 (M)+.

Example 78

5-(4-morpholino-6-((4-N-methylsulfonylpiperazin-1-yl)methyl)thieno[2,3-d]pyrimidin-2-yl)pyrimidin-2-amine 161

2-Chloro-6-(4-methanesulfonyl-piperidin-1-ylmethyl)-4-morpholin-4-yl-thieno[2,3-d]pyrimidine, prepared via General Procedure B-3, was reacted with 5-(4,4,5,5-tetramethyl-[1,3,2]dioxaborolan-2-yl)-pyrimidin-2-ylamine in General Procedure A. Purification on silica yielded 161. NMR (CDCl$_3$): 2.53-2.55 (m, 4H, 2×Ch2), 2.68 (s, 3H, CH3), 3.14 (m, 4H, 2×CH2), 3.64 (s, 2H, CH2), 3.70-3.73 (m, 4H, 2×CH2), 3.77-3.79 (m, 4H, 2×Ch2), 5.00 (sbr, 2H, NH2), 6.83 (s, H, ArH), 8.39 (s, 2H, 2×ArH). MS: (ESI+): MH+=491.23

Example 79

2-(4-methoxypyridin-3-yl)-4-morpholino-6-((4-N-methylsulfonylpiperazin-1-yl)methyl)thieno[3,2-d]pyrimidine 162

2-Chloro-6-(4-methanesulfonyl-piperazin-1-ylmethyl)-4-morpholin-4-yl-thieno[3,2-d]pyrimidine, prepared via General Procedure B-3, was reacted with 4-methoxy-3-pyridineboronic acid in General Procedure A. Purification on silica yielded 162. NMR (CDCl$_3$): 2.67-2.69 (m, 4H, 2×CH2), 2.81 (s 3H, CH3), 3.29-3.31 (m, 4H, 2×CH2), 3.84-3.86 (m, 4H, 2×CH2), 3.88 (s, 2H, CH2), 3.92 (s, 3H, CH3), 4.00-4.02 (m, 4H, 2×CH2), 6.91 (d, H, ArH, J=5.81 Hz), 7.33 (s, H, ArH), 8.52 (d, H, ArH, J=5.83 Hz), 8.85 (s, H, ArH). MS: (ESI+): MH+=505.17

Example 80

2-(4-((2-(6-aminopyridin-3-yl)-4-morpholinothieno[3,2-d]pyrimidin-6-yl)methyl)piperazin-1-yl)-N,N-dimethylacetamide 163

A mixture of 1-BOC-piperazine (387 mg), 2-chloro-N,N-dimethylacetamide (0.43 mL) and triethylamine (0.58 mL) in chloroform was stirred at room temperature. After stirring overnight the reaction mixture was diluted with dichloromethane, washed with brine, dried (MgSO$_4$) and the solvent removed in vacuo to yield 4-dimethylcarbamoylmethyl-piperazine-1-carboxylic acid tert-butyl ester (558 mg). Treatment of this compound with HCl in dichloromethane/methanol yielded N,N-dimethyl-2-piperazin-1-yl-acetamide, which was isolated as the hydrochloride salt.

Reaction between 2-chloro-4-morpholin-4-yl-thieno[3,2-d]pyrimidine-6-carbaldehyde 10 (Example 3) and N,N-dimethyl-2-piperazin-1-yl-acetamide using General Procedure B-3 yielded 2-[4-(2-chloro-4-morpholin-4-yl-thieno[3,2-d]pyrimidin-6-ylmethyl)-piperazin-1-yl]-N,N-dimethyl-acetamide.

2-[4-(2-Chloro-4-morpholin-4-yl-thieno[3,2-d]pyrimidin-6-ylmethyl)-piperazin-1-yl]-N,N-dimethyl-acetamide was reacted with 5-(4,4,5,5-tetramethyl-[1,3,2]dioxaborolan-2-yl)-pyridin-2-ylamine in General Procedure A. Purification on silica yielded 163. NMR 400 MHz (CDCl3): 2.61 (8H, b, CH2), 2.94 (3H, s, CH3), 3.07 (3H, s, CH3), 3.19 (2H, s, CH2), 3.82 (2H, s, CH2), 3.87-3.89 (4H, m, CH2), 4.01-4.04 (4H, m, CH2), 4.60 (2H, s, CH2), 6.56 (1H, d (J=9.03), ar), 7.26 (1H, s, ar), 8.45 (1H, dd (J=8.45, 2.29), ar), 9.15 (1H, d (J=1.78), ar). MH+=497.21

Example 81

6-((4-methylpiperazin-1-yl)methyl)-4-morpholino-2-(pyrimidin-5-yl)thieno[3,2-d]pyrimidine 164

2-Chloro-6-(4-methyl-piperazin-1-ylmethyl)-4-morpholin-4-yl-thieno[3,2-d]pyrimidine, prepared via General Procedure B-3, was reacted with pyrimidine-5-boronic acid in General Procedure A. Purification on silica yielded 164. (400 MHz CDCl3): 2.31 (3H, s, CH3), 2.50 (4H, b, CH2), 2.61 (4H, b, CH2), 3.85 (2H, s, CH2), 3.88-3.91 (4H, m, CH2), 4.06-4.08 (4H, m, CH2), 7.33 (1H, s, ar), 9.27 (1H, s, ar), 9.67 (2H, s, ar). MH+=412.27

Example 82

5-(4-morpholino-6-((4-N-methylsulfonylpiperazin-1-yl)methyl)furo[2,3-d]pyrimidin-2-yl)pyrimidin-2-amine 165

2-Chloro-6-((4-(methylsulfonyl)piperazin-1-yl)methyl)-4-morpholinofuro[2,3-d]pyrimidine (1 eq), 5-(4,4,5,5-tetramethyl-1,3,2-dioxaborolan-2-yl)pyrimidin-2-amine (1.7 eq) and bis(triphenylphosphine)palladium(II) dichloride (0.1 eq) in 1M KOAc aqueous solution (3 eq) and an equal volume of acetonitrile (3 eq) was heated to 140° C. in a sealed microwave reactor for 12 min. Upon completion, the reaction mixture was concentrated and crude mixture was purified by reverse phase HPLC to yield 34 mg of 165. MS (Q1) 476 (M)+.

Example 83

4-((2-(6-aminopyridin-3-yl)-4-morpholinothieno[3,2-d]pyrimidin-6-yl)methyl)-N,N-dimethylpiperazine-1-carboxamide 166

4-(2-Chloro-4-morpholin-4-yl-thieno[3,2-d]pyrimidin-6-ylmethyl)-piperazine-1-carboxylic acid dimethylamide (Example 45) was reacted with 5-(4,4,5,5-tetramethyl-[1,3,2]dioxaborolan-2-yl)-pyridin-2-ylamine via General Procedure A. Purification on silica yielded 166. NMR (CDCl$_3$): 2.54-2.56 (m, 4H, 2×CH2), 2.82 (s. 6H, 2×CH3), 3.28-3.30 (m, 4H, 2×CH2), 3.82 (s, 2H, CH2), 3.86-3.88 (m, 4H, 2×CH2), 4.01-4.03 (m, 4H, 2×CH2), 4.62 (sbr, 2H, NH2), 6.55 (d, H, ArH, J=8.53 Hz), 7.26 (s, H, ArH), 8.44 (dd, H, ArH, J=8.64 Hz, 2.2 Hz), 9.13 (d, H, ArH, J=1.9 Hz). MS: (ESI+): MH+ 483.36

Example 84

2-(6-methylpyridin-3-yl)-4-morpholino-6-((4-N-methylsulfonylpiperazin-1-yl)methyl)thieno[2,3-d]pyrimidine 167

2-Chloro-6-(4-methanesulfonyl-piperidin-1-ylmethyl)-4-morpholin-4-yl-thieno[2,3-d]pyrimidine, prepared via General Procedure B-3, was reacted with 2-methyl-5-(4,4,5,5-tetramethyl-[1,3,2]dioxaborolan-2-yl)-pyridine via General Procedure A. Purification on silica yielded the 167. NMR (CDCl$_3$): 2.62 (s, 3H, CH3), 2.64-2.66 (m, 4H, 2×CH2), 2.79 (s, 3H, CH3), 3.27-3.29 (m, 4H, 2×CH2), 3.81 (s, 2H, CH2), 3.87-3.89 (m, 4H, 2×CH2), 3.95-3.97 (m, 4H, 2×CH2), 7.14 (s, H, ArH), 7.22 (d, H, ArH, J=8.09 Hz), 8.55 (dd, H, ArH, J=8.01 Hz, 2.18 Hz), 9.49 (d, H, ArH, J=1.87 Hz). MS: (ESI+): MH+=489.29

Example 85

N,1-dimethyl-N-((4-morpholino-2-(pyrimidin-5-yl)thieno[2,3-d]pyrimidin-6-yl)methyl)piperidin-4-amine 168

1-Methyl-4-(methylamino)-piperidine was reacted with 2-chloro-4-morpholinothieno[2,3-d]pyrimidine-6-carbaldehyde via General Procedure B-3. Purification on silica yielded (2-chloro-4-morpholin-4-yl-thieno[2,3-d]pyrimidin-6-ylmethyl)-methyl-(1-methyl-piperidin-4-yl)-amine.

(2-Chloro-4-morpholin-4-yl-thieno[2,3-d]pyrimidin-6-ylmethyl)-methyl-(1-methyl-piperidin-4-yl)-amine was reacted with pyrimidine-5-boronic acid in General Procedure A. Purification on silica yielded 168. NMR (CDCl3): 1.59-1.81 (4H, m), 1.96-2.03 (2H, m), 2.25 (3H, s, Me), 2.28 (3H, s, Me), 2.44-2.52 (1H, m), 2.90-2.95 (2H, m), 3.80-3.88 (6H, m, CH$_2$), 3.90-3.94 (4H, m, CH$_2$), 7.10 (1H, s, Ar), 9.16 (1H, s, Ar) and 9.60 (2H, s, Ar). MS: (ESI+): MH+ 440.22

Example 86

6-((4-methylpiperazin-1-yl)methyl)-4-morpholino-2-(pyrimidin-5-yl)thieno[2,3-d]pyrimidine 169

N-Methylpiperazine was reacted with 2-chloro-4-morpholinothieno[2,3-d]pyrimidine-6-carbaldehyde via General Procedure B-3. Purification on silica yielded 2-chloro-6-(4-methyl-piperazin-1-ylmethyl)-4-morpholin-4-yl-thieno[2,3-d]pyrimidine.

2-Chloro-6-(4-methyl-piperazin-1-ylmethyl)-4-morpholin-4-yl-thieno[2,3-d]pyrimidine was reacted with pyrimidine-5-boronic acid in General Procedure A. Purification on silica yielded 169. NMR (CDCl$_3$): 2.30 (3H, s, Me), 2.48-2.64 (8H, m, CH$_2$), 3.71 (2H, s, CH$_2$), 3.88-3.93 (4H, m, CH$_2$), 3.98-4.03 (4H, m, CH$_2$), 7.15 (1H, s, Ar), 9.21 (1H, s, Ar) and 9.62 (2H, s, Ar). MS: (ESI+): MH+ 412.33

Example 87

5-(4-morpholino-6-((piperazin-1-yl)methyl)thieno[3,2-d]pyrimidin-2-yl)pyridine-3-carbonitrile 170

2-Chloro-6-(4-methanesulfonyl-piperazin-1-ylmethyl)-4-morpholin-4-yl-thieno[3,2-d]pyrimidine, prepared via General Procedure B-3, was reacted with 3-cyanopyridine-5-boronic acid pinacol ester via General Procedure A. Purification on silica yielded 170. (400 MHz CDCl3): 2.68-2.71 (4H, m, CH2), 2.81 (3H, s, CH3), 3.30-3.32 (4H, m, CH2), 3.90-3.92 (6H, m, CH2), 4.06-4.08 (4H, m, CH2), 7.35 (1H, s, ar), 8.92 (1H, d (J=2.09), ar), 8.96-8.97 (1H, m, ar), 9.81 (1H, d (J=2.03), ar). MH+ 500.20

Example 88

2-(4-((2-(6-aminopyridin-3-yl)-4-morpholinothieno[3,2-d]pyrimidin-6-yl)methyl)piperazin-1-yl)-N,2-dimethylpropanamide 171

To a mixture of dichloromethane (10 mL), aqueous sodium bicarbonate (2M, 10 mL), and aqueous sodium carbonate (2M, 10 mL) was added methylamine hydrochloride (300 mg) at 0° C. To this was added 2-bromoisobutyryl bromide (0.50 mL) with vigorous stirring. After 2 hours standard work up yielded 2-bromo-2,N-dimethyl-propionamide (548 mg) as an off-white solid.

A mixture of 2-bromo-2,N-dimethyl-propionamide (312 mg), 1-BOC-piperazine (323 mg) and silver oxide (800 mg) was stirred in toluene (5 mL) at reflux. After 24 hours the reaction mixture was cooled, filtered through celite, diluted with chloroform, washed with brine, dried (MgSO$_4$) and the solvent removed in vacuo to yield 4-(1-methyl-1-methylcarbamoyl-ethyl)-piperazine-1-carboxylic acid tert-butyl ester (461 mg). Removal of the BOC group with HCl yielded N-methyl-2-piperazin-1-yl-isobutyramide, which was isolated as the hydrochloride salt.

Reaction between 2-chloro-4-morpholin-4-yl-thieno[3,2-d]pyrimidine-6-carbaldehyde 10 (Example 3) and N-methyl-2-piperazin-1-yl-isobutyramide using General Procedure B-3 yielded 2-[4-(2-chloro-4-morpholin-4-yl-thieno[3,2-d]pyrimidin-6-ylmethyl)-piperazin-1-yl]-N-methyl-isobutyramide.

2-[4-(2-chloro-4-morpholin-4-yl-thieno[3,2-d]pyrimidin-6-ylmethyl)-piperazin-1-yl]-N-methyl-isobutyramide was reacted with 5-(4,4,5,5-tetramethyl-[1,3,2]dioxaborolan-2-yl)-pyridin-2-ylamine in General Procedure A. Purification on silica yielded 171. (400 MHz CDCl3): 1.21 (6H, s, ar), 2.56 (8H, b, CH2), 2.80 (3H, d (J=5.03), CH3), 3.82 (2H, s, ar), 3.87-3.89 (4H, m, CH2), 4.01-4.04 (4H, m, CH2), 4.61 (1H, s, NH), 6.56 (1H, d (J=8.40), ar), 7.15 (1H, d, ar), 8.45-8.47 (1H, m, ar), 9.15 (1H, s, ar). MH+ 511.52

Example 89

2-(4-((2-(2-aminopyrimidin-5-yl)-4-morpholinothieno[3,2-d]pyrimidin-6-yl)methyl)piperazin-1-yl)-N,N-dimethylacetamide 172

2-[4-(2-Chloro-4-morpholin-4-yl-thieno[3,2-d]pyrimidin-6-ylmethyl)-piperazin-1-yl]-N,N-dimethyl-acetamide (Example 80) was reacted with 5-(4,4,5,5-tetramethyl-[1,3,2]dioxaborolan-2-yl)-pyrimidin-2-ylamine via General Procedure A. Purification on silica yielded 172. (400 MHz CDCl3): 2.61 (8H, s, CH2), 2.94 (3H, s, CH3), 3.07 (3H, s, CH3), 3.19 (2H, s, CH2), 3.82 (2H, s, CH2), 3.87 (4H, m, CH2), 4.01 (4H, m, CH2), 5.19 (2H, s, NH), 7.26 (1H, s, ar), 9.28 (2H, s, ar). MH+ 498.37

Example 90

2-(4-((2-(2-aminopyrimidin-5-yl)-4-morpholinothieno[3,2-d]pyrimidin-6-yl)methyl)piperazin-1-yl)-N,2-dimethylpropanamide 173

2-[4-(2-Chloro-4-morpholin-4-yl-thieno[3,2-d]pyrimidin-6-ylmethyl)-piperazin-1-yl]-N-methyl-isobutyramide (Example 88) was reacted with 5-(4,4,5,5-tetramethyl-[1,3,2]dioxaborolan-2-yl)-pyrimidin-2-ylamine in General Procedure A. Purification on silica yielded 173. NMR 400 MHz (CDCl3): 2.56 (6H, b, CH3), 2.80 (3H, d (J=4.93), CH3), 3.83 (2H, s, CH2), 3.88 (4H, m, CH2), 4.03 (4H, m, CH2), 5.19 (2H, s, NH), 7.26 (1H, s, ar), 9.28 (2H, s, ar). MH+ 512.37

Example 91

N,N-dimethyl-2-(4-((2-(6-methylpyridin-3-yl)-4-morpholinothieno[3,2-d]pyrimidin-6-yl)methyl)piperazin-1-yl)acetamide 174

2-[4-(2-Chloro-4-morpholin-4-yl-thieno[3,2-d]pyrimidin-6-ylmethyl)-piperazin-1-yl]-N,N-dimethyl-acetamide (Example 80) was reacted with 2-methyl-5-(4,4,5,5-tetramethyl-[1,3,2]dioxaborolan-2-yl)-pyridine in General Procedure A. Purification on silica yielded 174. (400 MHz CDCl3): 2.54 (8H, m, CH2), 2.55 (3H, s, CH3), 2.87 (3H, s, CH3), 3.00 (3H, s, CH3), 3.12 (2H, s, CH2), 3.76 (2H, s, CH2), 3.81-3.83 (4H, m, CH2), 3.96-3.99 (4H, m, CH2), 7.16 (1H, m, ar), 7.23 (1H, s, ar), 8.48 (1 h, dd (J=8.06, 2.23), ar), 9.43 (1H, d (J=1.87), ar). MH+ 496.37

Example 92

4-((2-(2-aminopyrimidin-5-yl)-4-morpholinothieno[3,2-d]pyrimidin-6-yl)methyl)-N,N-dimethylpiperazine-1-carboxamide 175

4-(2-Chloro-4-morpholin-4-yl-thieno[3,2-d]pyrimidin-6-ylmethyl)-piperazine-1-carboxylic acid dimethylamide (Example 45) was reacted with 5-(4,4,5,5-tetramethyl-[1,3,2]dioxaborolan-2-yl)-pyrimidin-2-ylamine via General Procedure A. Purification on silica yielded 175. NMR (CDCl$_3$): 2.57-2.59 (m, 4H, 2×CH2), 2.85 (s, 6H, 2×CH3), 3.31-3.33 (m, 4H, 2×CH2), 3.86 (s, 2H, CH2), 3.89-3.92 (m, 4H, 2×CH2), 4.04-4.06 (m, 4H, 2×CH2), 5.27 (sbr, 2H, NH2), 7.29 (s, H, ArH), 9.30 (s, 2H, 2×ArH). MS: (ESI+): MH+ 484.35

Example 93

2-(2-isopropyl-1H-imidazol-1-yl)-4-morpholino-6-((piperazin-1-yl)methyl)thieno[3,2-d]pyrimidine 176

To 2-isopropylimidazole (28 mg) in dry N,N-dimethylformamide (1 ml) was added sodium hydride (10 mg, 60% dispersion in mineral oil). After 30 minutes, 2-chloro-6-(4-methanesulfonyl-piperazin-1-ylmethyl)-4-morpholin-4-yl-thieno[3,2-d]pyrimidine, prepared via General Procedure B-3, was added and the reaction mixture was heated in the microwave for 45 minutes at 120° C. The reaction mixture was diluted with ethyl acetate, washed with water, dried (MgSO$_4$) and the solvent removed in vacuo and the residue purified using flash chromatography to yield 176. NMR (400 MHz CDCl3): 1.19 (1H, s, CH), 1.30 (6H, d (J=6.84), 2.61-2.63 (4H, m, CH2), 2.74 (3H, s, CH3), 3.23-3.25 (4H, m, CH2), 3.79-3.82 (6H, m, CH2), 3.92-3.94 (4H, m, CH2), 6.92 (1H, s, ar), 7.18 (1H, s, ar), 7.66 (1H, d (J=1.49), ar). MH+ 506.30

Example 94

N,2-dimethyl-2-(4-((2-(6-methylpyridin-3-yl)-4-morpholinothieno[3,2-d]pyrimidin-6-yl)methyl)piperazin-1-yl)propanamide 177

2-[4-(2-Chloro-4-morpholin-4-yl-thieno[3,2-d]pyrimidin-6-ylmethyl)-piperazin-1-yl]-N-methyl-isobutyramide (Example 88) was reacted with 2-methyl-5-(4,4,5,5-tetramethyl-[1,3,2]dioxaborolan-2-yl)-pyridine via General Procedure A. Purification on silica yielded 177. NMR (400 MHz CDCl3): 1.27 (6H, s, CH3), 2.58 (8H, b, CH2), 2.65 (3H, s, CH3), 2.82 (3H, d (J=4.97), CH3), 3.86 (2H, s, CH2), 3.90-3.92 (4H, m, CH2), 4.06-4.09 (4H, m, CH2), 7.21 (1H, b, NH), 7.26 (1H, d (J=8.23), ar), 7.33 (1H, s, ar), 8.58 (1H, dd (J=8.07, 2.17), ar), 9.53 (1H, d (J=1.80), ar). MH+ 510.24

Example 95

1-(4-((2-(2-aminopyrimidin-5-yl)-7-methyl-4-morpholinothieno[3,2-d]pyrimidin-6-yl)methyl)piperazin-1-yl)-2-hydroxyethanone 178

1-(4-((2-Chloro-7-methyl-4-morpholinothieno[3,2-d]pyrimidin-6-yl)methyl)piperazin-1-yl)-2-hydroxyethanone (60 mg) was reacted with 34 mg of 5-(4,4,5,5-tetramethyl-1,3,2-dioxaborolan-2-yl)pyrimidin-2-amine via General Procedure A. The product was purified by reverse phase HPLC to yield 6.9 mg of 178. MS (Q1) 485.1 (M)+

Example 96

1-(4-((2-(6-aminopyridin-3-yl)-7-methyl-4-morpholinothieno[3,2-d]pyrimidin-6-yl)methyl)piperazin-1-yl)-2-hydroxyethanone 179

The HCl salt of 2-chloro-7-methyl-4-morpholino-6-((piperazin-1-yl)methyl)thieno[3,2-d]pyrimidine (300 mg) was reacted with glycolic acid via General Procedure B to give 306 mg of 1-(4-((2-chloro-7-methyl-4-morpholinothieno[3,2-d]pyrimidin-6-yl)methyl)piperazin-1-yl)-2-hydroxyethanone.

1-(4-((2-Chloro-7-methyl-4-morpholinothieno[3,2-d]pyrimidin-6-yl)methyl)piperazin-1-yl)-2-hydroxyethanone (60 mg) was reacted with 34 mg of 5-(4,4,5,5-tetramethyl-1,3,2-dioxaborolan-2-yl)pyridin-2-amine via General Procedure A. The product was purified by reverse phase HPLC to yield 23 mg of 179. MS (Q1) 484.1 (M)+.

Example 97

1-(4-((2-(2-aminopyrimidin-5-yl)-4-morpholinothieno[2,3-d]pyrimidin-6-yl)methyl)piperazin-1-yl)-2-hydroxyethanone 180

2-Chloro-4-morpholinothieno[2,3-d]pyrimidine-6-carbaldehyde from General Procedure D-2 (720 mg) was reacted with Boc-piperazine via General Procedure B-4 to generate tert-butyl 4-((2-chloro-4-morpholinothieno[2,3-d]pyrimidin-6-yl)methyl)piperazine-1-carboxylate. Tert-butyl 4-((2-chloro-4-morpholinothieno[2,3-d]pyrimidin-6-yl)methyl)piperazine-1-carboxylate (1.1 g) was converted via General Procedure D to the HCl salt of 2-chloro-4-morpholino-6-((piperazin-1-yl)methyl)thieno[2,3-d]pyrimidine. 2-Chloro-4-morpholino-6-((piperazin-1-yl)methyl)thieno[2,3-d]pyrimidine (600 mg) was reacted with glycolic acid via General Procedure B to 1-(4-((2-chloro-4-morpholinothieno[2,3-d]pyrimidin-6-yl)methyl)piperazin-1-yl)-2-hydroxyethanone. 1-(4-((2-Chloro-4-morpholinothieno[2,3-d]pyrimidin-6-yl)methyl)piperazin-1-yl)-2-hydroxyethanone (265 mg) was reacted with 5-(4,4,5,5-tetramethyl-1,3,2-dioxaborolan-2-yl)pyrimidin-2-amine via General Procedure A to give 180. MS (Q1) 471.2 (M)+.

Example 98

1-(4-((2-(6-aminopyridin-3-yl)-4-morpholinothieno[2,3-d]pyrimidin-6-yl)methyl)piperazin-1-yl)-2-hydroxyethanone 181

1-(4-((2-Chloro-4-morpholinothieno[2,3-d]pyrimidin-6-yl)methyl)piperazin-1-yl)-2-hydroxyethanone (265 mg) was reacted with 5-(4,4,5,5-tetramethyl-1,3,2-dioxaborolan-2-yl)pyridin-2-amine via General Procedure A to give 16.5 mg of 181. MS (Q1) 470.2 (M)+

Example 99

(S)-1-(4-((2-(2-aminopyrimidin-5-yl)-4-morpholinothieno[2,3-d]pyrimidin-6-yl)methyl)piperazin-1-yl)-2-hydroxypropan-1-one 182

2-Chloro-4-morpholino-6-((piperazin-1-yl)methyl)thieno[2,3-d]pyrimidine (600 mg) was reacted with lactic acid via General Procedure B to give (S)-1-(4-((2-chloro-4-morpholinothieno[2,3-d]pyrimidin-6-yl)methyl)piperazin-1-yl)-2-hydroxypropan-1-one.

(S)-1-(4-((2-Chloro-4-morpholinothieno[2,3-d]pyrimidin-6-yl)methyl)piperazin-1-yl)-2-hydroxypropan-1-one (265 mg) was reacted with 5-(4,4,5,5-tetramethyl-1,3,2-dioxaborolan-2-yl)pyrimidin-2-amine via General Procedure A to give 64 mg of 182. MS (Q1) 485.2 (M)+.

Example 100

(S)-1-(4-((2-(6-aminopyridin-3-yl)-4-morpholinothieno[2,3-d]pyrimidin-6-yl)methyl)piperazin-1-yl)-2-hydroxypropan-1-one 183

(S)-1-(4-((2-Chloro-4-morpholinothieno[2,3-d]pyrimidin-6-yl)methyl)piperazin-1-yl)-2-hydroxypropan-1-one (265 mg) was reacted with 5-(4,4,5,5-tetramethyl-1,3,2-dioxaborolan-2-yl)pyridin-2-amine via General Procedure A to give 113 mg of 183. MS (Q1) 484.3 (M)+.

Example 101

N-(5-(6-((4-(2-hydroxyacetyl)piperazin-1-yl)methyl)-4-morpholinothieno[3,2-d]pyrimidin-2-yl)pyridin-2-yl)acetamide 184

1-(4-((2-(6-Aminopyridin-3-yl)-4-morpholinothieno[3,2-d]pyrimidin-6-yl)methyl)piperazin-1-yl)-2-(tetrahydro-2H-pyran-2-yloxy)ethanone (110 mg) was reacted with 80 µL acetic anhydride in 500 µL pyridine overnight at 40° C. to give N-(5-(4-morpholino-6-((4-(2-(tetrahydro-2H-pyran-2-yloxy)acetyl)piperazin-1-yl)methyl)thieno[3,2-d]pyrimidin-2-yl)pyridin-2-yl)acetamide. This intermediate was subjected to Procedure D to remove the THP protecting group and give 6.3 mg of 184 after purification. MS (Q1) 512.3 (M)+.

Example 102

1-(4-((2-(2-aminopyrimidin-5-yl)-4-morpholinothieno[3,2-d]pyrimidin-6-yl)methyl)piperazin-1-yl)-2-hydroxyethanone 185

Tert-butyl 4-((2-chloro-4-morpholinothieno[3,2-d]pyrimidin-6-yl)methyl)piperazine-1-carboxylate from General Procedure B-3 (800 mg) was converted to the HCl salt of 2-chloro-4-morpholino-6-((piperazin-1-yl)methyl)thieno[3,2-d]pyrimidine via General Procedure D.

2-Chloro-4-morpholino-6-((piperazin-1-yl)methyl)thieno[3,2-d]pyrimidine (630 mg) was reacted with glycolic acid via General Procedure B to give 1-(4-((2-chloro-4-morpholinothieno[3,2-d]pyrimidin-6-yl)methyl)piperazin-1-yl)-2-hydroxyethanone.

1-(4-((2-Chloro-4-morpholinothieno[3,2-d]pyrimidin-6-yl)methyl)piperazin-1-yl)-2-hydroxyethanone (730 mg) was reacted with 17 mg para-toluenesulfonic acid and 245 µL of 3,4-dihydro-2H-pyran in ethyl acetate overnight to yield 1-(4-((2-chloro-4-morpholinothieno[3,2-d]pyrimidin-6-yl)methyl)piperazin-1-yl)-2-(tetrahydro-2H-pyran-2-yloxy)ethanone.

1-(4-((2-Chloro-4-morpholinothieno[3,2-d]pyrimidin-6-yl)methyl)piperazin-1-yl)-2-(tetrahydro-2H-pyran-2-yloxy)ethanone (250 mg) was reacted with 5-(4,4,5,5-tetramethyl-1,3,2-dioxaborolan-2-yl)pyrimidin-2-amine via General Procedure A to generate 1-(4-((2-(2-aminopyrimidin-5-yl)-4-morpholinothieno[3,2-d]pyrimidin-6-yl)methyl)piperazin-1-yl)-2-(tetrahydro-2H-pyran-2-yloxy)ethanone.

1-(4-((2-(2-Aminopyrimidin-5-yl)-4-morpholinothieno[3,2-d]pyrimidin-6-yl)methyl)piperazin-1-yl)-2-(tetrahydro-2H-pyran-2-yloxy)ethanone (75 mg) was subjected to General Procedure D to remove the protecting group and give 12.4 mg of 185 after purification. MS (Q1) 471.2 (M)+.

Example 103

1-(4-((2-(6-aminopyridin-3-yl)-4-morpholinothieno[3,2-d]pyrimidin-6-yl)methyl)piperazin-1-yl)-2-hydroxyethanone 186

1-(4-((2-Chloro-4-morpholinothieno[3,2-d]pyrimidin-6-yl)methyl)piperazin-1-yl)-2-(tetrahydro-2H-pyran-2-yloxy)ethanone prepared via General Procedure B-3 (250 mg) was reacted with 5-(4,4,5,5-tetramethyl-1,3,2-dioxaborolan-2-yl)pyridin-2-amine via General Procedure A to give 1-(4-((2-(6-aminopyridin-3-yl)-4-morpholinothieno[3,2-d]pyrimidin-6-yl)methyl)piperazin-1-yl)-2-(tetrahydro-2H-pyran-2-yloxy)ethanone.

1-(4-((2-(6-Aminopyridin-3-yl)-4-morpholinothieno[3,2-d]pyrimidin-6-yl)methyl)piperazin-1-yl)-2-(tetrahydro-2H-pyran-2-yloxy)ethanone (75 mg) was subjected to Procedure D to remove the protecting group and give 3.1 mg of 186 after purification. MS (Q1) 470.2 (M)+.

Example 104

5-(4-morpholino-6-((piperazin-1-yl)methyl)thieno[3,2-d]pyrimidin-2-yl)pyrazin-2-amine 187

2-Chloro-6-((4-methanesulfonylpiperazin-1-yl)methyl)-4-morpholinothieno[3,2-d]pyrimidine (75 mg) was reacted with 5-aminopyrazine-2-boronic acid pinacol ester following General Procedure A to give 20 mg of 187 following reversed phase HPLC purification. MS (Q1) 491 (M)+

Example 105

2-(5-(4-morpholino-6-((piperazin-1-yl)methyl)thieno[3,2-d]pyrimidin-2-yl)pyridin-2-ylamino)ethanol 188

2-Chloro-6-((4-methanesulfonylpiperazin-1-yl)methyl)-4-morpholinothieno[3,2-d]pyrimidine (100 mg) was reacted with 2-fluoropyridine-5-boronic acid following General Procedure A. One half of the crude material was heated in the microwave with excess hydroxylamine in DMF to give 188 after reversed phase HPLC purification. MS (Q1) 534 (M)+.

Example 106

5-(4-morpholino-6-((4-N-methylsulfonylpiperazin-1-yl)methyl)thieno[3,2-d]pyrimidin-2-yl)pyridin-2-ol 189

2-Chloro-6-((4-methanesulfonylpiperazin-1-yl)methyl)-4-morpholinothieno[3,2-d]pyrimidine, prepared via General Procedure B-3, (100 mg) was used in General Procedure A using 2-methoxypyridine-5-boronic acid as the boronic acid. The resulting crude (60 mg) was treated with 1 mL of 48% HBr in acetic acid and heated to 125° C. for 6 min in the microwave. The 2-hydroxy pyridine was extracted into ethylacetate and washed with water. After evaporation of the organic layer the crude was purified by reversed phase HPLC purification to yield 17 mg of 189. NMR (CDCl$_3$): 2.67 (m, 4H, 2×CH2), 2.80 (s, 3H, CH3), 3.30 (m, 4H, 2×CH2), 3.87-3.89 (m, 6H, 3×CH2), 3.98-4.00 (m, 4H, 2×CH2), 6.65 (d, H, ArH, J=10.27 Hz), 7.25 (s, H, ArH) 8.50-8.53 (m, 2H, 2×ArH), 11.6 (sbr, H, OH). MS: (ESI+): MH+ 491.22

Example 107

5-(6-((1-methylpiperidin-4-yl-N-methylamino)methyl)-7-methyl-4-morpholinothieno[3,2-d]pyrimidin-2-yl)pyrimidin-2-amine 190

N-((2-chloro-7-methyl-4-morpholinothieno[3,2-d]pyrimidin-6-yl)methyl)-N,1-dimethylpiperidin-4-amine following Example 115 (0.23 mmol) was reacted using General Procedure A: Suzuki Coupling to give 190 (TFA salt) in a 5% yield after reverse-phase HPLC purification. MS (Q1) 469 (M)+.

Example 108

5-(7-methyl-4-morpholino-6-((4-N-methylsulfonylpiperazin-1-yl)methyl)thieno[3,2-d]pyrimidin-2-yl)pyrimidin-2-amine 191

2-Chloro-6-((4-methylsulfonylpiperazin-1-yl)methyl)-4-morpholinothieno[3,2-d]pyrimidine from Example 133 (2.24 mmol) was reacted using General Procedure A: Suzuki Coupling which was worked up by filtering off precipitate, dissolving it in 1M HCl, basification of the resulting aqueous layer with NaHCO$_3$, extraction with EtOAc and DCM, drying over MgSO$_4$, and concentrating in vacuo to give 191 in 88% yield (no further purification necessary). MS (Q1) 505 (M)+.

Example 109

7-methyl-4-morpholino-6-((4-N-methylsulfonylpiperazin-1-yl)methyl)-2-(pyrimidin-5-yl)thieno[3,2-d]pyrimidine 192

2-Chloro-6-((4-methylsulfonylpiperazin-1-yl)methyl)-4-morpholinothieno[3,2-d]pyrimidine from Example 133 (0.24 mmol) was reacted using General Procedure A: Suzuki Coupling to give 192 (TFA salt) in 12% yield after reverse-phase HPLC purification. MS (Q1) 490 (M)+.

Example 110

(S)-1-((S)-4-((2-(6-aminopyridin-3-yl)-4-morpholinothieno[3,2-d]pyrimidin-6-yl)methyl)-3-methylpiperazin-1-yl)-2-hydroxypropan-1-one 193

2-Chloro-4-morpholinothieno[3,2-d]pyrimidine-6-carbaldehyde 10 from Example 3 (200 mg) was used according to General Procedure B-3 with (S)-4-N-trityl-2-methyl-piperazine. The crude product was then dissolved in 10 mL of methanol and reacted with 0.5 mL of concentrated HCl for several hours before basifying with NaOH and extracting into EtOAc. After evaporation the crude reaction mixture containing 200 mg of 2-chloro-6-(((S)-2-methylpiperazin-1-yl)methyl-4-morpholinothieno[3,2-d]pyrimidine was reacted with lactic acid via General Procedure B-2. 120 mg of (S)-1-((S)-4-((2-chloro-4-morpholinothieno[3,2-d]pyrimidin-6-yl)methyl)-3-methylpiperazin-1-yl)-2-hydroxypropan-1-one was reacted with 88 mg of 5-(4,4,5,5-tetramethyl-1,3,2-dioxaborolan-2-yl)pyridin-2-amine via General Procedure A to give 19.6 mg of 193. MS (Q1) 498.3 (M)+.

Example 111

2-(6-methylpyridin-3-yl)-4-morpholino-6-((4-N-methylsulfonylpiperazin-1-yl)methyl)thieno[3,2-d]pyrimidine 194

2-Chloro-6-((4-methanesulfonylpiperazin-1-yl)methyl)-4-morpholinothieno[3,2-d]pyrimidine, prepared via General Procedure B-3, was reacted with 2-picoline-5-boronic acid pinacol ester in General Procedure A. Purification on silica and ether trituration gave 194. NMR (CDCl3): 2.63 (3H, s), 2.67-2.71 (4H, m), 2.81 (3H, s), 3.29-3.33 (4H, m), 3.89 (2H, s), 3.89-3.93 (4H, m), 4.08-4.12 (4H, m), 7.23 (1H, d, J=8.1), 7.35 (1H, s), 8.55 (1H, dd, J=8.1, 2.1), 9.50 (1 h, d, J=2.1). MS (ESI+): MH+ 489.24 (95%)

Example 112

N-methyl-5-(4-morpholino-6-((4-N-methylsulfonylpiperazin-1-yl)methyl)thieno[3,2-d]pyrimidin-2-yl)pyridin-2-amine 195

2-Chloro-6-((4-methanesulfonyl-piperazin-1-yl)methyl)-4-morpholin-4-yl-thieno[3,2-d]pyrimidine, prepared via General Procedure B-3, was reacted with tert-butyl 5-(5,5-dimethyl-1,3,2-dioxaborinan-2-yl)pyridin-2-yl(methyl)carbamate (Kumar et al (2003) J. Label Compd. Radiopharm., 46:1055-1065) via General Procedure A. Purification on silica yielded 195 (note BOC group cleaved during Suzuki reaction). NMR (CDCl$_3$): 2.66-2.68 (m, 4H, 2×CH2), 2.80 (s, 3H, CH3), 3.00 (s, 3H, CH3), 3.28-3.30 (m, 4H, 2×CH2), 3.86-3.88 (m, 6H, 3×CH2), 4.00-4.02 (m, 4H, 2×CH2), 4.12 (s, H, NH), 6.57 (d, H, ArH, J=9.03 Hz), 7.26 (s, H, ArH), 8.62 (d, H, ArH, J=9.04 Hz), 9.00 (s, H, ArH). MS: (ESI+): MH+ 504.33

Example 113

N-methyl-N-(5-(4-morpholino-6-((piperazin-1-yl)methyl)thieno[3,2-d]pyrimidin-2-yl)pyridin-2-yl)acetamide 196

N-methyl-5-(4-morpholino-6-((4-N-methylsulfonylpiperazin-1-yl)methyl)thieno[3,2-d]pyrimidin-2-yl)pyridin-2-amine 195 (1 eq.) was stirred with acetyl chloride (1 eq.) and NEt$_3$ (1 eq.) in dry CH$_2$Cl$_2$ (10 mL) at R.T. overnight. Water/CH$_2$Cl$_2$ work up then purification on silica yielded 196 (28%). NMR (CDCl$_3$): 2.17 (s, 3H, CH3), 2.69-2.70 (m, 4H, 2×CH2), 2.81 (s, 3H, CH3), 3.31 (m, 4H, 2×CH2), 3.44 (s, 3H, CH3), 3.88-3.90 (m, 6H, 3×CH2), 4.04-4.07 (m, 4H, 2×CH2), 7.33 (s, H, ArH), 7.39 (m, H, ArH), 8.70 (dd, H, ArH, J=6.08 Hz, 2.3 Hz), 9.47 (d, H, ArH, J=2.12 Hz). MS: (ESI+): MH+ 546.34

Example 114

5-(6-((1-methylpiperidin-4-ylamino)N-methylaminomethyl)-7-methyl-4-morpholinothieno[3,2-d]pyrimidin-2-yl)pyridin-2-amine 197

N-((2-chloro-7-methyl-4-morpholinothieno[3,2-d]pyrimidin-6-yl)methyl)-N,1-dimethylpiperidin-4-amine following Example 115 (0.23 mmol) was reacted using General

Example 115

N,1-dimethyl-N-((7-methyl-4-morpholino-2-(pyridin-3-yl)thieno[3,2-d]pyrimidin-6-yl)methyl)piperidin-4-amine 198

2-Chloro-7-methyl-4-morpholinothieno[3,2-d]pyrimidine-6-carbaldehyde (0.5 g) was dissolved in 10 mL of 1,2-DCE and 1.0 eq. AcOH and 1.3 eq. of 1-methyl-4-(methylamino)piperidine was added and the reaction was stirred 15 minutes followed by the addition of sodium triacetoxyborohydride. The reaction was stirred for 24 hours and product formation was confirmed by LCMS. The reaction was diluted with sat. NaHCO$_3$, extracted with dichloromethane, dried over MgSO$_4$ and concentrated in vacuo. The crude product was purified by flash chromatography (EtOAc/hexanes) to give 0.61 g N-((2-chloro-7-methyl-4-morpholinothieno[3,2-d]pyrimidin-6-yl)methyl)-N,1-dimethylpiperidin-4-amine (88% yield). MS (Q1) 411 (M)+.

N-((2-chloro-7-methyl-4-morpholinothieno[3,2-d]pyrimidin-6-yl)methyl)-N,1-dimethylpiperidin-4-amine (0.23 mmol) was reacted using General Procedure A: Suzuki Coupling to give 198 (TFA salt) in a 67% yield after reverse-phase HPLC purification. MS (Q1) 453 (M)+.

Example 116

N-(5-(4-morpholino-6-((4-N-methylsulfonylpiperazin-1-yl)methyl)furo[3,2-d]pyrimidin-2-yl)pyridin-2-yl)formamide 199

To a solution of 236 (1.0 eq) in formic acid 96% (0.07M) at 0° C. was added 60 eq of acetic anhydride. The reaction mixture was allowed to warm up to r.t. and stirred for 60 h. Water/methanol (1:1) were added and the mixture was concentrated to yield the crude intermediate. This intermediate was purified by reverse phase HPLC to yield 5 mg of 199. MS (Q1) 502 (M+).

Example 117

N-(5-(4-morpholino-6-((4-N-methylsulfonylpiperazin-1-yl)methyl)thieno[3,2-d]pyrimidin-2-yl)pyridin-2-yl)formamide 200

A solution of 221 from Example 138 (1.0 eq) in formic acid 96% (0.01 M) at 0° C. was added 60 eq of acetic anhydride. The reaction mixture was allowed to warm up to r.t. and stirred for 60 h. Water/methanol (1:1) were added and the mixture was concentrated to yield the crude intermediate. This intermediate was purified by reverse phase HPLC to yield 3 mg of 200. MS (Q1) 519 (M+).

Example 118

(S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one 201

2-Chloro-7-methyl-4-morpholinothieno[3,2-d]pyrimidine-6-carbaldehyde (495 mg) was reacted with Boc-piperazine via General Procedure B-3 to give tert-butyl 44(2-chloro-7-methyl-4-morpholinothieno[3,2-d]pyrimidin-6-yl)methyl)piperazine-1-carboxylate.

Tert-butyl 4-((2-chloro-7-methyl-4-morpholinothieno[3,2-d]pyrimidin-6-yl)methyl)piperazine-1-carboxylate (777 mg) was subjected to General Procedure E to give the HCl salt of 2-chloro-7-methyl-4-morpholino-6-((piperazin-1-yl)methyl)thieno[3,2-d]pyrimidine. The HCl salt of 2-chloro-7-methyl-4-morpholino-6-((piperazin-1-yl)methyl)thieno[3,2-d]pyrimidine (590 mg) was reacted with lactic acid via General Procedure B-2 to give (S)-1-(4-((2-chloro-7-methyl-4-morpholinothieno[3,2-d]pyrimidin-6-yl)methyl)piperazin-1-yl)-2-hydroxypropan-1-one.

(S)-1-(4-((2-Chloro-7-methyl-4-morpholinothieno[3,2-d]pyrimidin-6-yl)methyl)piperazin-1-yl)-2-hydroxypropan-1-one (60 mg) was reacted with 50 mg of 5-(4,4,5,5-tetramethyl-1,3,2-dioxaborolan-2-yl)pyrimidin-2-amine via General Procedure A to give 10 mg of 201. MS (Q1) 499.3 (M)+.

Example 119

(S)-1-(4-((2-(6-aminopyridin-3-yl)-7-methyl-4-morpholinothieno[3,2-d]pyrimidin-6-yl)methyl)piperazin-1-yl)-2-hydroxypropan-1-one 202

(S)-1-(4-((2-Chloro-7-methyl-4-morpholinothieno[3,2-d]pyrimidin-6-yl)methyl)piperazin-1-yl)-2-hydroxypropan-1-one (60 mg) was reacted with 50 mg of 5-(4,4,5,5-tetramethyl-1,3,2-dioxaborolan-2-yl)pyridin-2-amine via General Procedure A to give 67.3 mg of 202. MS (Q1) 498.3 (M)+.

Example 120

(S)-2-hydroxy-1-(4-((2-(2-methoxypyrimidin-5-yl)-7-methyl-4-morpholinothieno[3,2-d]pyrimidin-6-yl)methyl)piperazin-1-yl)propan-1-one 203

(S)-1-(4-((2-Chloro-7-methyl-4-morpholinothieno[3,2-d]pyrimidin-6-yl)methyl)piperazin-1-yl)-2-hydroxypropan-1-one (60 mg) was reacted with 35 mg of 2-methoxypyrimidin-5-yl-5-boronic acid via General Procedure A to give 7.2 mg of 203. MS (Q1) 514.3 (M)+.

Example 121

(S)-2-hydroxy-1-(4-((2-(6-methoxypyridin-3-yl)-7-methyl-4-morpholinothieno[3,2-d]pyrimidin-6-yl)methyl)piperazin-1-yl)propan-1-one 204

(S)-1-(4-((2-Chloro-7-methyl-4-morpholinothieno[3,2-d]pyrimidin-6-yl)methyl)piperazin-1-yl)-2-hydroxypropan-1-one (60 mg) was reacted with 35 mg of 6-methoxypyridin-3-yl-3-boronic acid via General Procedure A to give 51.7 mg of 204. MS (Q1) 513.3 (M)+.

Example 122

(S)-2-hydroxy-1-(4-((7-methyl-4-morpholino-2-(pyrimidin-5-yl)thieno[3,2-d]pyrimidin-6-yl)methyl)piperazin-1-yl)propan-1-one 205

(S)-1-(4-((2-Chloro-7-methyl-4-morpholinothieno[3,2-d]pyrimidin-6-yl)methyl)piperazin-1-yl)-2-hydroxypropan-1-one (60 mg) was reacted with 28 mg of pyrimidin-5-yl-5-boronic acid via General Procedure A to give 45.7 mg of 205. MS (Q1) 484.3 (M)+.

Example 123

(S)-2-hydroxy-1-(4-((7-methyl-4-morpholino-2-(pyridin-3-yl)thieno[3,2-d]pyrimidin-6-yl)methyl)piperazin-1-yl)propan-1-one 206

(S)-1-(4-((2-Chloro-7-methyl-4-morpholinothieno[3,2-d]pyrimidin-6-yl)methyl)piperazin-1-yl)-2-hydroxypropan-1-one (60 mg) was reacted with 27 mg of pyridin-3-yl-3-boronic acid via General Procedure A to give 56.2 mg of 206. MS (Q1) 483.3 (M)+.

Example 124

(S)-1-(4-((2-(2-aminopyrimidin-5-yl)-4-morpholinothieno[3,2-d]pyrimidin-6-yl)methyl)piperazin-1-yl)-2-hydroxypropan-1-one 207

2-Chloro-4-morpholino-6-((piperazin-1-yl)methyl)thieno[3,2-d]pyrimidine (600 mg) was reacted with lactic acid via General Procedure B to give (S)-1-(4-((2-chloro-4 morpholinothieno[3,2-d]pyrimidin-6-yl)methyl)piperazin-1-yl)-2-hydroxypropan-1-one.

(S)-1-(4-((2-Chloro-4-morpholinothieno[3,2-d]pyrimidin-6-yl)methyl)piperazin-1-yl)-2-hydroxypropan-1-one (61 mg) was reacted with 51 mg of 5-(4,4,5,5-tetramethyl-1,3,2-dioxaborolan-2-yl)pyrimidin-2-amine via General Procedure A to give 34.2 mg of 207. MS (Q1) 485.3 (M)+.

Example 125

(S)-1-(4-((2-(6-aminopyridin-3-yl)-4-morpholinothieno[3,2-d]pyrimidin-6-yl)methyl)piperazin-1-yl)-2-hydroxypropan-1-one 208

(S)-1-(4-((2-Chloro-4-morpholinothieno[3,2-d]pyrimidin-6-yl)methyl)piperazin-1-yl)-2-hydroxypropan-1-one (61 mg) was reacted with 50 mg of 5-(4,4,5,5-tetramethyl-1,3,2-dioxaborolan-2-yl)pyridin-2-amine via General Procedure A to give 63.4 mg of 208. MS (Q1) 484.3 (M)+.

Example 126

(S)-2-hydroxy-1-(4-((2-(2-methoxypyrimidin-5-yl)-4-morpholinothieno[3,2-d]pyrimidin-6-yl)methyl)piperazin-1-yl)propan-1-one 209

(S)-1-(4-((2-Chloro-4-morpholinothieno[3,2-d]pyrimidin-6-yl)methyl)piperazin-1-yl)-2-hydroxypropan-1-one (61 mg) was reacted with 35 mg of 2-methoxypyrimidin-5-yl-5-boronic acid via General Procedure A to give 33.3 mg of 209. MS (Q1) 500.3 (M)+

Example 127

(S)-2-hydroxy-1-(4-((2-(6-methoxypyridin-3-yl)-4-morpholinothieno[3,2-d]pyrimidin-6-yl)methyl)piperazin-1-yl)propan-1-one 210

(S)-1-(4-((2-Chloro-4-morpholinothieno[3,2-d]pyrimidin-6-yl)methyl)piperazin-1-yl)-2-hydroxypropan-1-one (61 mg) was reacted with 35 mg of 6-methoxypyridin-3-yl-3-boronic acid via General Procedure A to give 39.4 mg of 210. MS (Q1) 499.3 (M)+

Example 128

(S)-2-hydroxy-1-(4-((4-morpholino-2-(pyrimidin-5-yl)thieno[3,2-d]pyrimidin-6-yl)methyl)piperazin-1-yl)propan-1-one 211

(S)-1-(4-((2-Chloro-4-morpholinothieno[3,2-d]pyrimidin-6-yl)methyl)piperazin-1-yl)-2-hydroxypropan-1-one (61 mg) was reacted with 29 mg of pyrimidin-5-yl-5-boronic acid via General Procedure A to give 20.9 mg of 211. MS (Q1) 470.3 (M)+.

Example 129

(S)-2-hydroxy-1-(4-((4-morpholino-2-(pyridin-3-yl)thieno[3,2-d]pyrimidin-6-yl)methyl)piperazin-1-yl)propan-1-one 212

(S)-1-(4-((2-Chloro-4-morpholinothieno[3,2-d]pyrimidin-6-yl)methyl)piperazin-1-yl)-2-hydroxypropan-1-one (61 mg) was reacted with 28 mg of pyridin-3-yl-3-boronic acid via General Procedure A to give 18.1 mg of 212. MS (Q1) 469.3 (M)+.

Example 130

N,1-dimethyl-N-((4-morpholino-2-(pyridin-3-yl)thieno[3,2-d]pyrimidin-6-yl)methyl)piperidin-4-amine 213

To a solution of 2-chloro-4-morpholinothieno[3,2-d]pyrimidine-6-carbaldehyde (0.5 g, 1.8 mmol) in 1,2-dichloroethane (10 mL) was added N,1-dimethylpiperidin-4-amine (0.3 g, 2.3 mmol) and AcOH (100 μL, 1.8 mmol). After stirring 10 min at room temperature, Na(OAc)$_3$BH (0.5 g, 2.1 mmol) was added and the resulting mixture stirred overnight. The reaction was quenched by the addition of saturated aqueous NaHCO$_3$ and the organic layer was separated. The aqueous layer was extracted with CH$_2$Cl$_2$ and the combined organics were dried over Na$_2$SO$_4$, filtered, and concentrated in vacuo. The crude reaction mixture was purified by silica gel chromatography (95:5; CH$_2$Cl$_2$: 2 M NH$_3$ in MeOH). A portion of the purified intermediate (0.3 mmol) was coupled following General Procedure A with 3-(4,4,5,5-tetramethyl-1,3,2-dioxaborolan-2-yl)pyridine to provide 213 after reverse phase HPLC purification (27 mg). MS (Q1) 439 (M)+.

Example 131

N,1-dimethyl-N-((4-morpholino-2-(6-aminopyridin-3-yl)thieno[3,2-d]pyrimidin-6-yl)methyl)piperidin-4-amine 214

To a solution of 2-chloro-4-morpholinothieno[3,2-d]pyrimidine-6-carbaldehyde (0.5 g, 1.8 mmol) in 1,2-dichloroethane (10 mL) was added N,1-dimethylpiperidin-4-amine (0.3 g, 2.3 mmol) and AcOH (100 μL, 1.8 mmol). After stirring 10 min at room temperature, Na(OAc)$_3$BH (0.5 g, 2.1 mmol) was added and the resulting mixture stirred overnight. The reaction was quenched by the addition of saturated aqueous NaHCO$_3$ and the organic layer was separated. The aqueous layer was extracted with CH$_2$Cl$_2$ and the combined organics were dried over Na$_2$SO$_4$, filtered, and concentrated in vacuo.

The crude reaction mixture was purified by silica gel chromatography (95:5; $CH_2Cl_2$: 2 M $NH_3$ in MeOH). A portion of the purified intermediate (0.3 mmol) was coupled following General Procedure A with 5-(4,4,5,5-tetramethyl-1,3,2-dioxaborolan-2-yl)pyridin-2-amine to provide 214 after reverse phase HPLC purification (25 mg). MS (Q1) 454 (M)+.

Example 132

N-(5-(4-morpholino-6-((4-N-methylsulfonylpiperazin-1-yl)methyl)thieno[3,2-d]pyrimidin-2-yl)pyrimidin-2-yl)acetamide 215

Compound 221 from Example 138 (1.0 eq) was treated with 60 eq of acetyl chloride in pyridine (~0.1M) at 80° C. The reaction was stirred until complete. Water/methanol (1:1) were added and the mixture was concentrated to yield the crude intermediate. This intermediate was purified by reverse phase HPLC to yield 13 mg of 215. MS (Q1) 533 ($M^+$)

Example 133

5-(6-((4-N-methylsulfonylpiperazin-1-yl)methyl)-7-methyl-4-morpholinothieno[3,2-d]pyrimidin-2-yl)pyridin-2-amine 216

2-Chloro-7-methyl-4-morpholinothieno[3,2-d]pyrimidine-6-carbaldehyde (0.58 g) and 1.3 eq. BOC-piperazine were dissolved in 10 mL of 1,2-DCE and 1.0 eq. of AcOH was added. After stirring the reaction mixture for 15 minutes 1.2 eq. of sodium triacetoxyborohydride was added and the solution stirred 24 hours at room temperature. Complete reaction was confirmed by LCMS and the solution diluted with sat. $NaHCO_3$, extracted with dichloromethane, and concentrated in vacuo. The crude material was purified by flash chromatography (EtOAc/hexanes) to give 880 mg compound A (97% yield). Compound A was dissolved in 8 mL dichloromethane and 2 mL MeOH followed by the addition of 10 mL 4N HCl/Dioxane and allowed to stir at room temperature for 1 hour at which point BOC deprotection was confirmed by LCMS and the solvents removed in vacuo. This material was dissolved in 20 mL dichloromethane and 1.3 eq. $Et_3N$ and cooled to 0° before adding 1.2 eq. $MeO_2SCl$ and allowed to stir at room temp for 1 hour followed by the addition of another 5.2 eq. $Et_3N$ and 1.2 eq. $MeO_2SCl$ and stirred for another 2 hours. The reaction was deemed complete by LCMS and the reaction was diluted with $H_2O$, extracted with dichloromethane, washed with brine, and concentrated in vacuo. The crude product was purified by flash chromatography to give 0.84 g of 2-chloro-6-((4-methylsulfonylpiperazin-1-yl)methyl)-4-morpholinothieno[3,2-d]pyrimidine (97% overall yield). MS (Q1) 447 (M)+.

2-Chloro-6-((4-methylsulfonylpiperazin-1-yl)methyl)-4-morpholinothieno[3,2-d]pyrimidine (0.24 mmol) was reacted using General Procedure A: Suzuki Coupling to give 216 (TFA salt) in 42% yield after reverse-phase HPLC purification. MS (Q1) 504 (M)+.

Example 134

7-methyl-4-morpholino-6-((4-N-methylsulfonylpiperazin-1-yl)methyl)-2-(pyridin-3-yl)thieno[3,2-d]pyrimidine 217

2-Chloro-6-((4-methylsulfonylpiperazin-1-yl)methyl)-4-morpholinothieno[3,2-d]pyrimidine from Example 133 (0.24 mmol) was reacted using General Procedure A: Suzuki Coupling to give 217 (TFA salt) in 25% yield after reverse-phase HPLC purification. MS (Q1) 489 (M)+.

Example 135

N-((2-(2-aminopyridin-5-yl)-4-morpholinothieno[3,2-d]pyrimidin-6-yl)methyl)-N-methyl(N-1-methylsulfonyl)piperidin-4-amine 218

(2-Chloro-4-morpholin-4-yl-thieno[3,2-d]pyrimidin-6-ylmethyl)-(1-methanesulfonyl-piperidin-4-yl)-methyl-amine (Example 137) was reacted with 2-aminopyridine-5-boronic acid pinacol ester via General Procedure A. Purification on silica yielded 218. NMR (CDCl3): 1.60-1.70 (2H, br), 1.71-1.81 (2H, m), 1.94-1.98 (2H, br m), 2.39 (3H, s), 2.61-2.73 (2H+1H, m), 2.79 (3H, s), 3.86-3.90 (4H, m), 3.86-3.90 (2H, m), 3.94 (2H, s), 4.03-4.07 (4H, m), 4.65 (2H, br), 6.58 (1H, d, J=8.6), 7.28 (1H, s, under $CHCl_3$ peak), 8.48 (1H, d, J=8.6), 9.17 (1H, s). MS (ESI+): MH+ 518.4 (33%)

Example 136

N-((2-(2,4-dimethoxypyrimidin-5-yl)-4-morpholinothieno[3,2-d]pyrimidin-6-yl)methyl)-N-methyl(N-1-methylsulfonyl)piperidin-4-amine 219

(2-Chloro-4-morpholin-4-yl-thieno[3,2-d]pyrimidin-6-ylmethyl)-(1-methanesulfonyl-piperidin-4-yl)-methyl-amine (Example 137) was reacted with 2,4-dimethoxypyrimidine-5-boronic acid via General Procedure A. Purification on silica yielded 219. NMR (CDCl3): 1.60-1.70 (2H, br), 1.71-1.81 (2H, m), 1.94-1.98 (2H, br m), 2.39 (3H, s), 2.61-2.73 (2H+1H, m), 2.79 (3H, s), 3.86-3.90 (4H, m), 3.86-3.94 (2H, m), 3.94 (2H, s), 4.03-4.07 (4H, m), 7.31 (1H, s), 8.94 (1H, s). MS (ESI+): MH+ 564.38 (100%)

Example 137

N-((2-(2-aminopyrimidin-5-yl)-4-morpholinothieno[3,2-d]pyrimidin-6-yl)methyl)-N-methyl(N-1-methylsulfonyl)piperidin-4-amine 220

Reductive amination of 1-methanesulfonyl-piperidin-4-one (331 mg) with (2-chloro-4-morpholin-4-yl-thieno[3,2-d]pyrimidin-6-ylmethyl)-methyl-amine (430 mg) under standard conditions followed by aqueous work-up and purification on silica gave (2-chloro-4-morpholin-4-yl-thieno[3,2-d]pyrimidin-6-ylmethyl)-(1-methanesulfonyl-piperidin-4-yl)-methyl-amine (520 mg).

(2-Chloro-4-morpholin-4-yl-thieno[3,2-d]pyrimidin-6-ylmethyl)-(1-methanesulfonyl-piperidin-4-yl)-methyl-amine was reacted with 2-aminopyrimidine-5-boronic acid via General Procedure A. Purification on silica yielded 220. NMR (CDCl3): 1.60-1.70 (2H, br), 1.71-1.81 (2H, m), 1.94-1.98 (2H, br m), 2.39 (3H, s), 2.61-2.73 (2H+1H, m), 2.79 (3H, s), 3.86-3.90 (4H, m), 3.86-3.90 (2H, m), 3.94 (2H, s), 4.03-4.07 (4H, m), 5.23 (2H, br), 7.28 (1H, s, under $CHCl_3$ peak), 9.30 (1H, s). MS (ESI+): MH+ 519.41

Example 138

5-(4-morpholino-6-((4-N-methylsulfonylpiperazin-1-yl)methyl)thieno[3,2-d]pyrimidin-2-yl)pyrimidin-2-amine 221

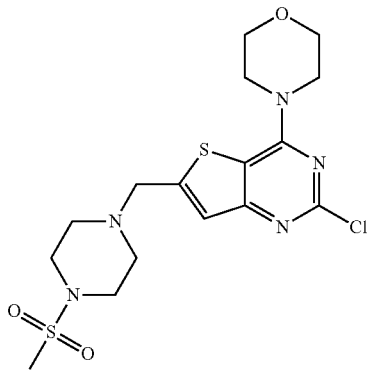 [SMILES: CS(=O)(=O)N1CCN(Cc2cc3nc(Cl)nc(N4CCOCC4)c3s2)CC1]

2-Chloro-6-((4-methylsulfonylpiperazin-1-yl)methyl)-4-morpholinothieno[3,2-d]pyrimidine was reacted with 5-(4,4,5,5-tetramethyl-1,3,2-dioxaborolan-2-yl)pyrimidin-2-amine via General Procedure B to give, after purification by reverse HPLC, 10 mg of 221. MS (Q1) 491 (M+).

Example 139

5-(4-morpholino-6-((4-N-methylsulfonylpiperazin-1-yl)methyl)furo[3,2-d]pyrimidin-2-yl)pyrimidin-2-amine 222

2-Chloro-6-((4-(methylsulfonyl)piperazin-1-yl)methyl)-4-morpholinofuro[3,2-d]pyrimidine, prepared in Example 153) was reacted with 5-(4,4,5,5-tetramethyl-1,3,2-dioxaborolan-2-yl)pyrimidin-2-amine via General Procedure E to give, after purification by reverse HPLC, 4 mg of 5-(6-((4-methylsulfonylpiperazin-1-yl)methyl)-4-morpholinofuro[3,2-d]pyrimidin-2-yl)pyrimidin-2-amine. MS (Q1) 475 (M+)

Example 140

N-(5-(4-morpholino-6-((4-N-methylsulfonylpiperazin-1-yl)methyl)furo[3,2-d]pyrimidin-2-yl)pyridin-2-yl)acetamide 223

Compound 236 (1.0 eq) is treated with 10 eq of pyridine in acetyl chloride (~0.1M) at 80° C. The reaction is stirred until complete. Water/methanol (1:1) were added and the mixture was concentrated to yield the crude intermediate. This intermediate was purified by reverse phase HPLC to yield 14 mg of 223. MS (Q1) 516 (M+)

Example 141

4-morpholino-6-((4-N-methylsulfonylpiperazin-1-yl)methyl)-2-(pyridin-3-yl)furo[3,2-d]pyrimidine 224

2-Chloro-6-((4-(methylsulfonyl)piperazin-1-ylmethyl)-4-morpholinofuro[3,2-d]pyrimidine (Example 153) was reacted with pyridine-3-boronic acid via General Procedure E to give, after purification by reverse HPLC, 14 mg of 224. MS (Q1) 459 (M+).

Example 142

2-(2,4-dimethoxypyrimidin-5-yl)-4-morpholino-6-((4-N-methylsulfonylpiperazin-1-yl)methyl)thieno[3,2-d]pyrimidine 225

2-Chloro-6-(4-methanesulfonyl-piperazin-1-ylmethyl)-4-morpholin-4-yl-thieno[3,2-d]pyrimidine, prepared via General Procedure B-3, was reacted with 2,4-dimethoxy-5-(4,4,5,5-tetramethyl-[1,3,2]dioxaborolan-2-yl)-pyrimidine in General Procedure A. Purification on silica yielded 225. NMR (400 MHz CDCl3): 2.68 (4H, m, CH2), 2.81 (3H, s, CH3), 3.30 (4H, m, CH2), 3.85-3.88 (6H, m, CH2), 4.00-4.03 (4H, m, CH2), 4.06 (3H, s, CH3), 4.09 (3H, s, CH3), 7.33 (1H, s, ar), 8.93 (1H, s, ar). MH+=536.30

Example 143

(5-(4-morpholino-6-((4-N-methylsulfonylpiperazin-1-yl)methyl)thieno[3,2-d]pyrimidin-2-yl)furan-2-yl)methanol 226

2-Chloro-6-(4-methanesulfonyl-piperazin-1-ylmethyl)-4-morpholin-4-yl-thieno[3,2-d]pyrimidine, prepared via General Procedure B-3, was reacted with 5-formyl-2-furanboronic acid in General Procedure A. Purification on silica yielded 5-[6-(4-methanesulfonyl-piperazin-1-ylmethyl)-4-morpholin-4-yl-thieno[3,2-d]pyrimidin-2-yl]-furan-2-carbaldehyde.

Treatment of 5-[6-(4-methanesulfonyl-piperazin-1-ylmethyl)-4-morpholin-4-yl-thieno[3,2-d]pyrimidin-2-yl]-furan-2-carbaldehyde with sodium borohydride in methanol yielded 226. NMR (400 MHz CDCl3): 2.67 (4H, t (J=4.81), CH2), 2.81 (3H, s, CH3), 3.30 (4H, t (J=4.72), CH2), 3.87-3.89 (6H, m, CH2), 4.00-4.03 (4H, m, CH2), 4.74 (2H, d (J=6.11), CH2), 6.46 (1H, d (J=3.32), ar), 7.18 (1H, d (J=3.29), ar), 7.36 (1H, s, ar). MH+ 494.16

Example 144

2-(6-methoxypyridin-3-yl)-4-morpholino-6-((piperazin-1-yl)methyl)thieno[3,2-d]pyrimidine 227

2-Chloro-6-(4-methanesulfonyl-piperazin-1-ylmethyl)-4-morpholin-4-yl-thieno[3,2-d]pyrimidine, prepared via General Procedure B-3, was reacted with 2-methoxy-5-pyridineboronic acid in General Procedure A. Purification on silica yielded 227. NMR (CDCl$_3$): 2.67-2.69 (m, 4H, 2×CH2), 2.80 (s, 3H, CH3), 3.29-3.31 (m, 4H, 2×CH2), 3.86-3.89 (m, 6H, 3×CH2), 4.01-4.05 (m, 7H, 2×CH2+CH3), 6.80 (d, H, ArH, J=8.56 Hz), 7.30 (s, H, ArH), 8.57 (dd, H, ArH, J=8.64 Hz, 2.31 Hz), 9.23 (d, H, ArH, J=2.22 Hz). MS: (ESI+): MH+ 505.15

Example 145

4-morpholino-6-((piperazin-1-yl)methyl)-2-(4-N-methylpyridin-4-yl)thieno[3,2-d]pyrimidine 228

2-Chloro-6-(4-methanesulfonyl-piperazin-1-ylmethyl)-4-morpholin-4-yl-thieno[3,2-d]pyrimidine, prepared via General Procedure B-3, was reacted with 4-pyridineboronic acid in General Procedure A. Purification on silica yielded 228. NMR (CDCl$_3$): 2.68-2.70 (m, 4H, 2×CH2), 2.81 (s, 3H, CH3), 3.29-3.32 (m, 4H, 2×CH2), 3.89-3.91 (m, 6H, 3×CH2), 4.06-4.08 (m, 4H, 2×CH2), 7.35 (s, H, ArH), 8.26

(dd, 2H, 2×ArH, J=4.53 Hz, 3 Hz), 8.72 (dd, 2H, 2×ArH, J=4.66 Hz, 3 Hz). MS: (ESI+): MH+=475.15

Example 146

(5-(4-morpholino-6-((4-N-methylsulfonylpiperazin-1-yl)methyl)thieno[3,2-d]pyrimidin-2-yl)thiophen-2-yl)methanol 229

2-Chloro-6-(4-methanesulfonyl-piperazin-1-ylmethyl)-4-morpholin-4-yl-thieno[3,2-d]pyrimidine, prepared via General Procedure B-3, was reacted with 5-formyl-2-thiopheneboronic acid in General Procedure A. Purification on silica yielded 5-[6-(4-methanesulfonyl-piperazin-1-ylmethyl)-4-morpholin-4-yl-thieno[3,2-d]pyrimidin-2-yl]-thiophene-2-carbaldehyde.
Treatment of 5-[6-(4-methanesulfonyl-piperazin-1-ylmethyl)-4-morpholin-4-yl-thieno[3,2-d]pyrimidin-2-yl]-thiophene-2-carbaldehyde with sodium borohydride in methanol yielded 229. NMR (400 MHz CDCl3): 2.67 (4H, t (J=4.81), CH2) 2.81 (3H, s, CH3), 3.30 (4H, t (J=3.78), CH2), 3.86-3.89 (6H, m, CH2), 4.01-4.03 (4H, m, CH2), 4.86 (2H, s, CH2), 7.02 (1H, d (J=3.77), ar), 7.30 (1H, b, ar), 7.82 (1H, b, ar). MH+ 510.24

Example 147

2-(5-methoxypyridin-3-yl)-4-morpholino-6-((4-N-methylsulfonylpiperazin-1-yl)methyl)thieno[2,3-d]pyrimidine 230

2-Chloro-6-(4-methanesulfonyl-piperidin-1-ylmethyl)-4-morpholin-4-yl-thieno[2,3-d]pyrimidine, prepared via General Procedure B-3, was reacted with 3-methoxypyridine-5-boronic acid pinacol ester in General Procedure A. Purification on silica yielded 230. NMR (CDCl$_3$): 2.65-2.67 (m, 4H, 2×CH2), 2.80 (s, 3H, CH3), 3.27-3.30 (m, 4H, 2×CH2), 3.82 (s, 2H, CH2), 3.88-3.90 (m, 4H, 2×CH2), 3.96-3.99 (m, 4H, 2×CH2), 7.16 (s, H, ArH), 8.20 (m, H, ArH), 8.37 (m, H, ArH), 9.23 (s, H, ArH). MS: (ESI+): MH+ 505.17

Example 148

2-(furan-3-yl)-4-morpholino-6-((4-N-methylsulfonylpiperazin-1-yl)methyl)thieno[3,2-d]pyrimidine 231

2-Chloro-6-(4-methanesulfonyl-piperazin-1-ylmethyl)-4-morpholin-4-yl-thieno[3,2-d]pyrimidine, prepared via General Procedure B-3, was reacted with 3-furanboronic acid in General Procedure A. Purification on silica yielded 231. NMR (CDCl$_3$): 2.66-2.68 (m, 4H, 2×CH2), 2.80 (s, 3H, CH3), 3.28-3.31 (m, 4H, 2×CH2), 3.86-3.88 (m, 6H, 3×CH2), 3.98-4.01 (m, 4H, 2×CH2), 7.04 (d, H, ArH, J=1.65 Hz), 7.26 (ms, H, ArH-part under CDCl3), 7.46 (ms, H, ArH), 8.18 (s, H, ArH). MS: (ESI+): MH+ 464.16

Example 149

(5-(4-morpholino-6-((4-N-methylsulfonylpiperazin-1-yl)methyl)thieno[2,3-d]pyrimidin-2-yl)pyridin-3-yl)methanol 232

2-Chloro-6-(4-methanesulfonyl-piperidin-1-ylmethyl)-4-morpholin-4-yl-thieno[2,3-d]pyrimidine, prepared via General Procedure B-3, was reacted with 5-formylpyridineboronic acid in General Procedure A. Purification on silica yielded 5-(6-((4-(methylsulfonyl)piperazin-1-yl)methyl)-4-morpholinothieno[2,3-d]pyrimidin-2-yl)nicotinaldehyde in 80% purity.
5-(6-((4-(Methylsulfonyl)piperazin-1-yl)methyl)-4-morpholinothieno[2,3-d]pyrimidin-2-yl)nicotinaldehyde (95 mg) and sodium triacetoxyborohydride (55 mg) in dry 1,2-dichloroethane (10 mL) was heated at 40° C. overnight. A further portion of sodium triacetoxyborohydride (49 mg) was then added and heating continued for another 4 h. Water/CH$_2$Cl$_2$ work up then purification on silica yielded 232 (37 mg). NMR (CDCl$_3$): 2.65-2.67 (m, 4H, 2×CH2), 2.80 (s, 3H, CH3), 3.27-3.30 (m, 4H, 2×CH2), 3.82 (s, 2H, CH2), 3.88-3.91 (m, 4H, 2×CH2), 3.97-4.0 (m, 4H, 2×CH2), 4.84 (s, 2H, CH2), 7.17 (s, H, ArH), 8.67 (s, H, ArH), 8.69 (s, H, ArH), 9.55 (s, H, ArH). MS: (ESI+): MH+ 505.18

Example 150

N-(5-(4-morpholino-6-((4-N-methylsulfonylpiperazin-1-yl)methyl)thieno[3,2-d]pyrimidin-2-yl)pyridin-2-yl)acetamide 233

To 2-amino-5-(4,4,5,5-tetramethyl-1,3,2-dioxaborolan-2-yl)pyridine (120 mg) in dry DCM (3 ml) and triethylamine (1.5 equiv., 114 uL) was added acetic anhydride (1.1 equiv., 57ul) and the reaction mixture was stirred at room temperature overnight. Dichloromethane/brine extraction and purification on silica gave 66 mg of N-[5-(4,4,5,5-tetramethyl-1,3,2-dioxaborolan-2-yl)pyridine-2-yl]-acetamide.
2-Chloro-6-(4-methanesulfonyl-piperazin-1-ylmethyl)-4-morpholin-4-yl-thieno[3,2-d]pyrimidine, prepared via General Procedure B-3, was reacted with N-[5-(4,4,5,5-tetramethyl-1,3,2-dioxaborolan-2-yl)pyridine-2-yl]-acetamide via General Procedure A. Purification on silica and ether trituration gave 233. NMR (CDCl3): 2.25 (3H, s), 2.67-2.71 (4H, m), 2.81 (3H, s), 3.29-3.33 (4H, m), 3.89 (2H, s), 3.89-3.93 (4H, m), 4.08-4.12 (4H, m), 7.35 (1H, s), 7.97 (1H, br. s), 8.28 (1H, d), 8.71 (1H, d), 9.30 (1H, s). MS (ESI+): MH$^+$ 532.28 (100%)

Example 151

5-(4-morpholino-6-((4-N-methylsulfonylpiperazin-1-yl)methyl)thieno[2,3-d]pyrimidin-2-yl)pyridin-2-amine 234

2-Chloro-6-(4-methanesulfonyl-piperidin-1-ylmethyl)-4-morpholin-4-yl-thieno[2,3-d]pyrimidine, prepared via General Procedure B-3, was reacted with 5-(4,4,5,5-tetramethyl-[1,3,2]dioxaborolan-2-yl)-pyridin-2-ylamine in General Procedure A. Purification on silica yielded 234. NMR (CDCl$_3$): 2.63-2.66 (m, 4H, 2×CH2), 2.79 (s, 3H, CH3), 3.26-3.29 (m, 4H, 2×CH2), 3.79 (s, 2H, CH2), 3.86-3.89 (m, 4H, 2×CH2), 3.92-3.95 (m, 4H, 2×CH2), 4.63 (sbr, 2H, NH2), 6.55 (d, H, ArH, J=8.71 Hz), 7.11 (s, H, ArH), 8.44 (dd, H, ArH, J=8.64 Hz, J=2.25 Hz), 9.14 (d, H, ArH, J=2.13 Hz). MS: (ESI+): MH$^+$=490.16

Example 152

(5-(4-morpholino-6-((4-N-methylsulfonylpiperazin-1-yl)methyl)thieno[3,2-d]pyrimidin-2-yl)pyridin-3-yl)methanol 235

To 60 mg of 5-[6-(4-methanesulfonyl-piperazin-1-ylmethyl)-4-morpholin-4-yl-thieno[3,2-d]pyrimidin-2-yl]-pyridine-3-carbaldehyde 241 (Example 158) in dry DMF was added sodium triacetoxyborohydride (66 mg) and the reaction mixture was heated at 40° C. overnight. After the SCX-2 cartridge work-up, purification on silica and recrystallization from DCM/hexane gave 235 (45 mg). NMR (CDCl3): 1.80-1.90 (1H, br, OH), 2.67-2.71 (4H, m), 2.81 (3H, s), 3.29-3.33 (4H, m), 3.89 (2H, s), 3.89-3.93 (4H, m), 4.08-4.12 (4H, m), 4.86 (2H, s), 7.35 (1H, s), 8.70 (1H, s), 8.71 (1H, s), 9.56 (1H, s). MS (ESI+): MH+ 505.17 (100%)

Example 153

5-(4-morpholino-6-((4-N-methylsulfonylpiperazin-1-yl)methyl)furo[3,2-d]pyrimidin-2-yl)pyridin-2-amine 236

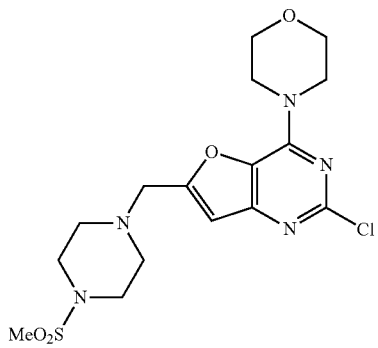 [SMILES: CS(=O)(=O)N1CCN(Cc2cc3nc(Cl)nc(N4CCOCC4)c3o2)CC1]

2-Chloro-4-morpholinofuro[3,2-d]pyrimidine-6-carbaldehyde 39 prepared following Example 20 (65 mg, 1.0 eq) was dissolved in 1,2-dichloroethane (9.7 ml) and treated with hydrochloride salt of 1-methanesulfonylpiperazine (69 mg, 1.4 eq), sodium acetate (28 mg, 1.4 eq) and trimethyl orthoformate (0.27 ml, 10 eq). Reaction mixture was stirred at r.t. for 12 h. Sodium triacetoxyborohydride (62 mg, 1.2 eq) was added and reaction mixture was stirred at r.t. for 8 h. Reaction mixture was quenched with saturated aq. NaHCO$_3$ and extracted with dichloromethane. The combined organic layers were dried (Na$_2$SO$_4$) and concentrated. The crude reaction mixture was purified by flash chromatography to yield 2-chloro-6-((4-(methylsulfonyl)piperazin-1-yl)methyl)-4-morpholinofuro[3,2-d]pyrimidine (70 mg, 68%): MS (Q1) 416 (M)$^+$.

2-Chloro-6-((4-(methylsulfonyl)piperazin-1-yl)methyl)-4-morpholinofuro[3,2-d]pyrimidine was reacted with 5-(4,4,5,5-tetramethyl-1,3,2-dioxaborolan-2-yl)pyridin-2-amine via General Procedure E to give, after purification by reverse HPLC, 22 mg of 236. MS (Q1) 474 (M$^+$).

Example 154

2-(2-methoxypyrimidin-5-yl)-4-morpholino-6-((4-N-methylsulfonylpiperazin-1-yl)methyl)furo[3,2-d]pyrimidine 237

2-Chloro-6-((4-(methylsulfonyl)piperazin-1-yl)methyl)-4-morpholinofuro[3,2-d]pyrimidine (Example 153) was reacted with 2-methoxypyrimidine-5-boronic acid via General Procedure E to give, after purification by reverse HPLC, 4 mg of 237. MS (Q1) 490 (M$^+$).

Example 155

5-(4-morpholino-6-((4-N-methylsulfonylpiperazin-1-yl)methyl)furo[3,2-d]pyrimidin-2-yl)pyridine-3-carbaldehyde 238

2-Chloro-6-((4-(methylsulfonyl)piperazin-1-yl)methyl)-4-morpholinofuro[3,2-d]pyrimidine (Example 153) was reacted with 5-(4,4,5,5-tetramethyl-[1,3,2]dioxaborolan-2-yl)-pyridine-3-carbaldehyde via General Procedure E to give, after purification by reverse HPLC, 11 mg of 238. MS (Q1) 487 (M$^+$).

Example 156

2-(5-methoxypyridin-3-yl)-4-morpholino-6-((4-N-methylsulfonylpiperazin-1-yl)methyl)furo[3,2-d]pyrimidine 239

2-Chloro-6-((4-(methylsulfonyl)piperazin-1-yl)methyl)-4-morpholinofuro[3,2-d]pyrimidine (Example 153) was reacted with 3-methoxy-5-(4,4,5,5-tetramethyl-[1,3,2]dioxaborolan-2-yl)-pyridine via General Procedure E to give, after purification by reverse HPLC, 29 mg of 239. MS (Q1) 489 (M$^+$).

Example 157

5-(4-morpholino-6-((4-N-methylsulfonylpiperazin-1-yl)methyl)thieno[3,2-d]pyrimidin-2-yl)pyridin-2-amine 240

2-Chloro-6-(4-methanesulfonyl-piperazin-1-ylmethyl)-4-morpholin-4-yl-thieno[3,2-d]pyrimidine, prepared via General Procedure B-3, was reacted with 2-amino-pyridine-5-boronic acid pinacol ester in General Procedure A. Purification on silica and ether trituration gave 240. NMR (CDCl3): 2.67-2.71 (4H, m), 2.81 (3H, s), 3.29-3.33 (4H, m), 3.89 (2H, s), 3.89-3.93 (4H, m), 4.08-4.12 (4H, m), 4.60-4.65 (2H, br. s), 6.57 (1H, d, J=8.6), 7.40 (1H, s), 8.45 (1H, dd, J=8.6, 2.2), 9.17 (1H, d, J=2.2). MS (ESI+): MH+490.18 (100%)

Example 158

5-(4-morpholino-6-((4-N-methylsulfonylpiperazin-1-yl)methyl)thieno[3,2-d]pyrimidin-2-yl)pyridine-3-carbaldehyde 241

2-Chloro-6-(4-methanesulfonyl-piperazin-1-ylmethyl)-4-morpholin-4-yl-thieno[3,2-d]pyrimidine, prepared via General Procedure B-3, was reacted with 5-formylpyridine-3-boronic acid pinacol ester in General Procedure A. Purification on silica and ether trituration gave 241. NMR (CDCl3): 2.67-2.71 (4H, m), 2.81 (3H, s), 3.29-3.33 (4H, m), 3.89 (2H, s), 3.89-3.93 (4H, m), 4.08-4.12 (4H, m), 7.38 (1H, s), 9.18 (2H, m), 9.37 (1H, s), 10.25 (1H, s). MS (ESI+): MH+ 503.17 (100%)

Example 160

2-(5-methoxypyridin-3-yl)-4-morpholino-6-((4-N-methylsulfonylpiperazin-1-yl)methyl)thieno[3,2-d]pyrimidine 243

2-Chloro-6-(4-methanesulfonyl-piperazin-1-ylmethyl)-4-morpholin-4-yl-thieno[3,2-d]pyrimidine, prepared via General Procedure B-3, was reacted with 3-methoxypyridine-5-boronic acid pinacol ester in General Procedure A. Purification on silica and ether trituration gave 243. NMR (CDCl3): 2.68-2.72 (4H, m), 2.82 (3H, s), 3.29-3.33 (4H, m), 3.90 (2H, s), 3.90-3.94 (4H, m), 4.00 (3H, s), 4.05-4.10 (4H, m), 7.35 (1H, s), 8.23 (1H, s), 8.38 (1H, s), 9.26 (1H, s). MS (ESI+): MH+ 505.19 (100%)

Example 161

N,N-dimethyl-5-(4-morpholino-6-((4-N-methylsulfonylpiperazin-1-yl)methyl)thieno[3,2-d]pyrimidin-2-yl)pyrimidin-2-amine 244

2-Chloro-6-(4-methanesulfonyl-piperazin-1-ylmethyl)-4-morpholin-4-yl-thieno[3,2-d]pyrimidine, prepared via General Procedure B-3, was reacted with 2-dimethylamino-pyrimidine-5-boronic acid pinacol ester in General Procedure A. Purification on silica and ether trituration gave 244. NMR (CDCl3): 2.68-2.72 (4H, m), 2.82 (3H, s), 3.29 (6H, s), 3.29-3.33 (4H, m), 3.90 (2H, s), 3.90-3.94 (4H, m), 4.05-4.10 (4H, m), 7.31 (1H, br. s), 9.30 (2H, s). MS (ESI+): 519.3 (100%)

Example 162

4-morpholino-6-((4-N-methylsulfonylpiperazin-1-yl)methyl)-2-(pyrimidin-5-yl)furo[3,2-d]pyrimidine 245

2-Chloro-6-((4-(methylsulfonyl)piperazin-1-yl)methyl)-4-morpholinofuro[3,2-d]pyrimidine (Example 153) was reacted with pyrimidine-5-boronic acid via General Procedure E to give, after purification by reverse HPLC, 30 mg of 6-((4-methylsulfonylpiperazin-1-yl)methyl)-4-morpholino-2-(pyrimidin-5-yl)furo[3,2-d]pyrimidine. MS (Q1) 460 (M$^+$).

Example 163

2-(2-methoxypyrimidin-5-yl)-4-morpholino-6-((4-N-methylsulfonylpiperazin-1-yl)methyl)thieno[3,2-d]pyrimidine 246

2-Chloro-6-(4-methanesulfonyl-piperazin-1-ylmethyl)-4-morpholin-4-yl-thieno[3,2-d]pyrimidine, prepared via General Procedure B-3, was reacted with 2-methoxy-5-pyrimidine-boronic acid in General Procedure A. Purification on silica and ether trituration gave 246. NMR (CDCl3): 2.68-2.72 (4H, m), 2.82 (3H, s), 3.29-3.33 (4H, m), 3.90 (2H, s), 3.90-3.94 (4H, m), 4.05-4.10 (4H, m), 4.12 (3H, s), 7.32 (1H, br. s), 9.48 (2H, s). MS (ESI+): MH+ 506.2 (100%)

Example 164

1-(5-(4-morpholino-6-((4-N-methylsulfonylpiperazin-1-yl)methyl)furo[3,2-d]pyrimidin-2-yl)pyridin-2-yl)urea 247

To a solution of 236 (1.0 eq) in acetonitrile (0.1M) at r.t. was added chlorosulfonyl isocyanate (10 eq) dropwise. The reaction was stirred for 40 minutes, then concentrated. To the residue was added 2N HCl and mixture was heated to 80° C. for 20 minutes. Reaction mixture was allowed to cool down to room temperature, and was neutralized with NaOH 6M. Mixture was then concentrated. The crude product was purified by reverse phase HPLC to give 6 mg of 247. MS (Q1) 517 (M$^+$ Example 174

5-(4-morpholino-6-((4-N-methylsulfonylpiperazin-1-yl)methyl)thieno[3,2-d]pyrimidin-2-yl)pyridin-2-methylsulfonylamine 257

To 5-[6-(4-methanesulfonyl-piperazin-1-ylmethyl)-4-morpholin-4-yl-thieno[3,2-d]pyrimidin-2-yl]-pyridin-2-ylamine 240 (100 mg) in pyridine (2 ml) was added methanesulfonyl chloride (4 equiv., 60 μl) and the reaction mixture was heated at 80° C. for 4 hours. Dichloromethane/brine extraction, purification on silica and DCM/ether trituration gave 257 (23 mg). NMR (CDCl3/MeOD): 2.56-2.59 (4H, m), 2.72 (3H, s), 3.10 (3H, s), 3.17-3.20 (4H, m), 3.74-3.79 (4H, m), 3.79 (2H, s), 3.92-3.95 (4H, m), 7.10 (1H, d, J=8.9), 7.19 (1H, s), 8.49 (1H, d, J=8.9), 8.90 (1H, s). MS (ESI+): MH+ 568.27

Example 175

6-methyl-5-(4-morpholino-6-((4-N-methylsulfonylpiperazin-1-yl)methyl)thieno[3,2-d]pyrimidin-2-yl)pyridin-2-amine 258

6-Amino-3-bromo-2-methylpyridine (1 eq.) was stirred with BOC anyhydride (1.14 eq.) and DMAP (1 eq.) in dry CH$_2$Cl$_2$ at R.T. overnight. Water/CH$_2$Cl$_2$ work up then purification on silica yielded the desired compound (51%) to yield tert-butyl 5-bromo-6-methylpyridin-2-ylcarbamate.

tert-Butyl 5-(5,5-dimethyl-1,3,2-dioxaborinan-2-yl)-6-methylpyridin-2-ylcarbamate was prepared from tert-butyl 5-bromo-6-methylpyridin-2-ylcarbamate following a procedure in Kumar et al (2003) J. Label Compd. Radiopharm. 46:1055-1065.

2-Chloro-6-(4-methanesulfonyl-piperazin-1-ylmethyl)-4-morpholin-4-yl-thieno[3,2-d]pyrimidine, prepared via General Procedure B-3, was reacted with tert-butyl 5-(5,5-dimethyl-1,3,2-dioxaborinan-2-yl)-6-methylpyridin-2-ylcarbamate via General Procedure A. Purification on silica yielded 258. NMR (CDCl$_3$): 2.60-2.63 (m, 4H, 2×CH2), 2.65 (s, 3H, CH3), 2.74 (s, 3H, CH3), 3.22-3.24 (m, 4H, 2×CH2), 3.78-3.81 (m, 6H, 3×CH2), 3.91-3.94 (m, 4H, 2×CH2), 4.43 (s, 2H, NH2), 6.36 (d, H, ArH, J=8.38 Hz), 7.22 (s, H, ArH), 7.98 (d, H, ArH, J=8.41 Hz). MS: (ESI+): MH+ 504.22

Example 176

5-(4-morpholino-6-((4-N-isobutylsulfonylpiperazin-1-yl)methyl)thieno[3,2-d]pyrimidin-2-yl)pyridin-2-amine 259

NMR (400 MHz, CDCl3): 1.14 (6H, (J=6.74), CH3), 2.31-2.34 (1H, m, CH), 2.66-2.68 (4H, m, CH2), 2.79 (2H, d (J=6.55), CH2), 3.35-3.36 (4H, m, CH2), 3.88 (2H, s, CH2), 3.89-3.92 (4H, m, CH2), 4.04-4.06 (4H, m, CH2), 4.68 (2H, b, NH2), 6.59 (1H, d (J=8.05), ar), 7.28 (1H, s, ar), 8.49 (1H, d (J=8.64), ar), 9.17 (1H, d (J=1.86), ar). (M+H)+ 532.35

Example 177

2-(2,4-dimethoxypyrimidin-5-yl)-4-morpholino-6-((4-N-phenylsulfonylpiperazin-1-yl)methyl)thieno[3,2-d]pyrimidine 260

6-(4-Benzenesulfonyl-piperazin-1-ylmethyl)-2-chloro-4-morpholin-4-yl-thieno[3,2-d]pyrimidine (described above) was reacted with 2,4-dimethoxy-5-(4,4,5,5-tetramethyl-[1,3, 2]dioxaborolan-2-yl)-pyrimidine in General Procedure A. Purification on silica yielded 260. NMR (400 MHz, CDCl3): 2.56-2.58 (4H, m, $CH_2$), 3.04 (4H, m, CH2), 3.74-3.77 (6H, m, CH2), 3.88-3.91 (4H, m, CH2), 3.98 (3H, s, CH3), 4.01 (3H, s, CH3), 7.21 (1H, s, ar), 7.47-7.51 (2H, m, ar), 7.54-7.58 (1H, m, ar), 7.71 (2H, d (J=7.13), ar), 8.84 (1H, s, ar). (M+H)+ 598.28

Example 178

2-(2,4-dimethoxypyrimidin-5-yl)-4-morpholino-6-((4-N-cyclopropylsulfonylpiperazin-1-yl)methyl)thieno[3,2-d]pyrimidine 261

2-Chloro-6-(4-cyclopropanesulfonyl-piperazin-1-ylmethyl)-4-morpholin-4-yl-thieno[3,2-d]pyrimidine (Example 39) was reacted with 2,4-dimethoxy-5-(4,4,5,5-tetramethyl-[1,3,2]dioxaborolan-2-yl)-pyrimidine via General Procedure A. Purification on silica yielded the desired compound. NMR (400 MHz, CDCl3): 1.01-1.04 (2H, m, CH2), 1.20-1.25 (2H, m, CH2), 2.30 (1H, m, CH), 2.67-2.70 (4H, m, CH2), 3.39-3.41 (4H, m, CH2), 2.87-3.88 (4H, m, CH2), 3.90 (2H, s, CH2), 4.03-4.05 (4H, m, CH2), 4.08 (3H, s, CH3), 4.11 (3H, s, CH3), 7.36 (1H, s, ar), 8.95 (1H, s, ar).

Example 179

5-(6-(((S)-3-methyl-(4-N-methylsulfonyl)piperazin-1-yl)methyl)-4-morpholinothieno[3,2-d]pyrimidin-2-yl)pyridin-2-amine 262

To a solution of (S)-methylpiperazine (400 mg) in dichloromethane (20 mL) at 0° C. was added di-tert-butyl dicarbonate (871 mg). The reaction was stirred at room temperature for 4 h and then quenched with water (20 mL) and extracted into dichloromethane (2×40 mL). The combined organics were washed with saturated aqueous brine solution (40 mL), dried ($MgSO_4$) and concentrated to give (S)-3-methyl-piperazine-1-carboxylic acid tert-butyl ester as a white solid (669 mg, 84%).

To a solution of (S)-3-methyl-piperazine-1-carboxylic acid (669 mg) and triethylamine (0.56 mL) in dichloromethane (10 mL) at 0° C. was added dropwise methanesulfonyl chloride (0.28 mL). The reaction mixture was stirred at room temperature for 16 h and then quenched with water (10 mL) and extracted into dichloromethane (2×20 mL). The combined organic layers were washed with saturated aqueous brine solution (2×20 mL), dried ($MgSO_4$) and concentrated to give (S)-4-methanesulfonyl-3-methyl-piperazine-1-carboxylic acid tert-butyl ester as a pale yellow solid (924 mg, 99%).

To a solution of (S)-4-methanesulfonyl-3-methyl-piperazine-1-carboxylic acid tert-butyl ester (924 mg) in dichloromethane (20 mL) at 0° C. was added dropwise HCl (6.65 mL of a 2 M solution in diethyl ether). The reaction mixture was stirred at room temperature for 2 h. The precipitate formed was then collected by filtration and dried to afford (S)-1-methanesulfonyl-2-methyl-piperazine hydrochloride salt as a white solid (583 mg, 82%).

(S)-1-Methanesulfonyl-2-methyl-piperazine hydrochloride salt was reacted with 10 (Example 3) via General Procedure B-3. Purification on silica yielded 2-chloro-6-((S)-4-methanesulfonyl-3-methyl-piperazin-1-ylmethyl)-4-morpholin-4-yl-thieno[3,2-d]pyrimidine.

2-Chloro-6-((S)-4-methanesulfonyl-3-methyl-piperazin-1-ylmethyl)-4-morpholin-4-yl-thieno[3,2-d]pyrimidine was reacted with 2-amino-5-(4,4,5,5-tetramethyl-1,3,2-dioxaborolan-2-yl)pyridine in General Procedure A. Purification on silica yielded 262. NMR ($CDCl_3$): 1.34 (3H, d, J 6.8, Me), 2.18-2.24 (1H, m), 2.32-2.38 (1H, m), 2.66-2.69 (1 H, m), 2.77 (3H, s, Me), 2.80-2.84 (1H, m), 3.19-3.23 (1H, m), 3.50-3.53 (1H, m), 3.64 (1 H, d, J 14.8, CH), 3.70 (1H, d, J 14.8, CH), 3.80-3.84 (4H, m, $CH_2$), 3.91-3.95 (4H, m, $CH_2$), 4.01-4.05 (1H, m), 4.58 (2H, br s, $NH_2$), 6.49 (1H, d, J 8.0, Ar), 7.20 (1H, s, Ar), 8.38 (1H, dd, J 8.0 and 2.3, Ar) and 9.07 (1H, d, J 2.3, Ar). MS: (ESI+): MH+ 504.25

Example 180

5-(6-(((S)-3-methyl-(4-N-methylsulfonyl)piperazin-1-yl)methyl)-4-morpholinothieno[3,2-d]pyrimidin-2-yl)pyrimidin-2-amine 263

2-Chloro-6-((S)-4-methanesulfonyl-3-methyl-piperazin-1-ylmethyl)-4-morpholin-4-yl-thieno[3,2-d]pyrimidine (Example 179) was reacted with 2-aminopyrimidine-5-boronic acid pinacol ester via General Procedure A. Purification on silica yielded the desired compound. NMR ($CDCl_3$): 1.44 (3H, d, J 6.8, Me), 2.28-2.34 (1H, m), 2.41-2.44 (1H, m), 2.75-2.80 (1H, m), 2.89 (3H, s, Me), 2.91-2.94 (1H, m), 3.32-3.39 (1H, m), 3.60-3.66 (1H, m), 3.78 (1H, d, J 14.8, CH), 3.82 (1H, d, J 14.8, CH), 3.90-3.94 (4H, m, $CH_2$), 4.00-4.05 (4H, m, $CH_2$), 4.07-4.09 (1H, m), 5.29 (2H, br s, $NH_2$), 7.30 (1H, s, Ar) and 9.29 (2H, s, Ar). MS: (ESI+): MH+=505.12

Example 181

5-(6-(((2R,6S)-2,6-dimethyl-(4-N-methylsulfonyl)piperazin-1-yl)methyl)-4-morpholinothieno[3,2-d]pyrimidin-2-yl)pyridin-2-amine 264

To 2-chloro-4-morpholin-4-yl-thieno[3,2-d]pyrimidine-6-carbaldehyde 10 (1.5 g) in ethanol (30 mL) was added sodium borohydride (1 g). After 4 hours the reaction mixture was quenched with brine and the resulting solid was collected by filtration and air dried to yield (2-chloro-4-morpholin-4-yl-thieno[3,2-d]pyrimidin-6-yl)-methanol (1.42 g).

To (2-chloro-4-morpholin-4-yl-thieno[3,2-d]pyrimidin-6-yl)-methanol (1.42 g) in toluene (14 ml) warmed to 40° C. was added phosphorous tribromide (0.16 ml) and the mixture was then heated to 100° C. After heating for 6 hours the reaction mixture was cooled, diluted with chloroform, washed with brine, dried ($MgSO_4$) and the solvent removed in vacuo to yield 6-bromomethyl-2-chloro-4-morpholin-4-yl-thieno[3,2-d]pyrimidine (1.40 g).

To a solution of cis-2,6-dimethyl-piperazine (600 mg) and triethylamine (0.80 mL) in dichloromethane (10 mL) at 0° C. was added dropwise methanesulfonyl chloride (0.43 mL). The reaction mixture was stirred at room temperature for 16 h and then quenched with water (10 mL) and extracted into dichloromethane (2×20 mL). The combined organic layers were washed with saturated aqueous brine solution (2×20 mL), dried ($MgSO_4$) and concentrated to afford (3S,5R)-1-methanesulfonyl-3,5-dimethyl-piperazine as a white solid (817 mg, 81%).

To a mixture of 6-bromomethyl-2-chloro-4-morpholin-4-yl-thieno[3,2-d]pyrimidine (380 mg) and (3S,5R)-1-methanesulfonyl-3,5-dimethyl-piperazine (314 mg) in acetonitrile (10 mL) was added potassium carbonate (620 mg). The reaction mixture was heated at 80° C. for 16 h and then allowed to cool to room temperature. The reaction mixture was then partitioned between dichloromethane (20 mL) and saturated aqueous sodium bicarbonate solution (20 mL). The combined organics were washed with brine (30 mL), dried (MgSO$_4$), reduced in vacuo and purified by column chromatography to give 2-chloro-6-((2S,6R)-4-methanesulfonyl-2,6-dimethyl-piperazin-1-ylmethyl)-4-morpholin-4-yl-thieno[3,2-d]pyrimidine.

2-Chloro-6-((2S,6R)-4-methanesulfonyl-2,6-dimethyl-piperazin-1-ylmethyl)-4-morpholin-4-yl-thieno[3,2-d]pyrimidine was reacted with 2-amino-5-(4,4,5,5-tetramethyl-1,3,2-dioxaborolan-2-yl)pyridine in General Procedure A. Purification on silica yielded 264. NMR (CDCl$_3$): 1.12 (6H, d, J 7.0, Me), 2.49-2.52 (2H, m), 2.71 (3H, s, Me), 2.68-2.72 (2 H, m), 3.47-3.49 (2H, m), 3.80-3.83 (4H, m, CH$_2$), 3.94-3.97 (4H, m, CH$_2$), 4.08 (2H, s, CH$_2$), 6.48 (1H, d, J 8.0, Ar), 7.19 (1H, s, Ar), 8.38 (1H, dd, J 8.0 and 2.2, Ar) and 9.07 (1 H, d, J 2.2, Ar). MS: (ESI+): MH+=518.26

Example 182

5-(6-(((2R,6S)-2,6-dimethyl-(4-N-methylsulfonyl) piperazin-1-yl)methyl)-4-morpholinothieno[3,2-d] pyrimidin-2-yl)pyrimidin-2-amine 265

2-Chloro-6-((2S,6R)-4-methanesulfonyl-2,6-dimethyl-piperazin-1-ylmethyl)-4-morpholin-4-yl-thieno[3,2-d]pyrimidine (Example 181) was reacted with 2-aminopyrimidine-5-boronic acid pinacol ester in General Procedure A. Purification on silica yielded 265. NMR (CDCl$_3$): 1.13 (6H, d, J 7.0, Me), 2.48-2.53 (2H, m), 2.71 (3H, s, Me), 2.79-2.81 (2H, m), 3.51-3.54 (2H, m), 3.81-3.84 (4H, m, CH$_2$), 3.94-3.97 (4H, m, CH$_2$), 4.09 (2H, s, CH$_2$), 5.19 (2H, br s, NH$_2$), 7.20 (1H, s, Ar) and 9.20 (2H, s, Ar). MS: (ESI+): MH+=519.34

Example 183

5-(4-morpholino-6-((1-O,O—S-thiomorpholin-4-yl) methyl)thieno[3,2-d]pyrimidin-2-yl)pyridin-2-amine 266

2-Chloro-6-((1-O,O—S-thiomorpholin-4-yl)methyl)-4-morpholin-4-yl-thieno[3,2-d]pyrimidine (Example 193) was reacted with 2-amino-5-(4,4,5,5-tetramethyl-1,3,2-dioxaborolan-2-yl)pyridine in General Procedure A. Purification on silica yielded 266. NMR: (DMSO) 2.90-2.99 (8H, m), 3.62-3.70 (4H, m), 3.82 (2H, s, CH$_2$), 3.83-3.88 (4H, m), 5.13 (2H, br s, NH$_2$), 6.57 (1H, d, J 8.1, Ar), 7.07 (1H, s, Ar), 8.13 (1H, dd, J 8.1 and 2.0, Ar) and 8.72 (1H, d, J 2.0, Ar). MS: (ESI+): MH+=461.27

Example 184

N,N-dimethyl-1-((4-morpholino-2-(pyrimidin-5-yl) thieno[2,3-d]pyrimidin-6-yl)methyl)piperidine-4-carboxamide 267

Reaction between 2-chloro-4-morpholin-4-yl-thieno[2,3-d]pyrimidine-6-carbaldehyde (General Procedure D-2) and piperidine-4-carboxylic acid dimethylamide (Example 42) using General Procedure B-3 yielded 1-(2-chloro-4-morpholin-4-yl-thieno[2,3-d]pyrimidin-6-ylmethyl)-piperidine-4-carboxylic acid dimethylamide.

1-((2-Chloro-4-morpholinothieno[2,3-d]pyrimidin-6-yl)methyl)-N,N-dimethylpiperidine-4-carboxamide was reacted with pyrimidine-5-boronic acid in General Procedure A. Purification on silica yielded 267. NMR (CDCl$_3$): 1.71-1.4 (m, 2H, CH2), 1.9-1.99 (m, 2H, CH2), 2.14-2.20 (m, 2H, CH2), 2.52-2.57 (m, H, CH), 2.97 (s, H, CH3), 3.04-3.07 (m, 5H, CH3+CH2), 3.80 (s, 2H, CH2), 3.91-3.93 (m, 4H, 2×CH2), 3.98-4.02 (m, 4H, 2×CH2), 7.19 (s, H, ArH), 9.29 (s, H, ArH), 9.70 (s, 2H, 2×ArH). MS: (ESI+): MH+=468.26

Example 185

N,N-dimethyl-4-((4-morpholino-2-(pyrimidin-5-yl) thieno[2,3-d]pyrimidin-6-yl)methyl)piperazine-1-carboxamide 268

Reaction between 2-chloro-4-morpholin-4-yl-thieno[2,3-d]pyrimidine-6-carbaldehyde (General Procedure D-2) and piperazine-1-carboxylic acid dimethylamide (Example 26) using General Procedure B-3 yielded 4-((2-chloro-4-morpholinothieno[2,3-d]pyrimidin-6-yl)methyl)-N,N-dimethylpiperazine-1-carboxamide.

4-((2-Chloro-4-morpholinothieno[2,3-d]pyrimidin-6-yl) methyl)-N,N-dimethylpiperazine-1-carboxamide was reacted with pyrimidine-5-boronic acid in General Procedure A. Purification on silica yielded 268. NMR (CDCl$_3$): 2.55-2.57 (m, 4H, 2×CH2), 2.84 (s, 6H, 2×CH3), 3.31-3.33 (m, 4H, 2×CH2), 3.80 (s, 2H, CH2), 3.90-3.92 (m, 4H, 2×CH2), 3.99-4.02 (m, 4H, 2×CH2), 7.19 (s, H, ArH), 9.28 (s, H, ArH), 9.69 (s, 2H, 2×ArH). MS: (ESI+): MH+=469.24

Example 186

N-methyl-1-((4-morpholino-2-(pyrimidin-5-yl) thieno[2,3-d]pyrimidin-6-yl)methyl)piperidine-4-carboxamide 269

Reaction between 2-chloro-4-morpholin-4-yl-thieno[2,3-d]pyrimidine-6-carbaldehyde (General Procedure D-2) and piperidine-4-carboxylic acid methylamide (Example 25) using General Procedure B-3 yielded 1-((2-chloro-4-morpholinothieno[2,3-d]pyrimidin-6-yl)methyl)-N-methylpiperidine-4-carboxamide.

1-((2-Chloro-4-morpholinothieno[2,3-d]pyrimidin-6-yl) methyl)-N-methylpiperidine-4-carboxamide was reacted with pyrimidine-5-boronic acid in General Procedure A. Purification on silica yielded 269. NMR (CDCl$_3$): 1.71 (s, 3H, CH3), 1.77-1.90 (m, 4H, 2×CH2), 2.10-2.17 (m, 3H, CH2+CH), 2.85 (d, 3H, CH3, J=4.81 Hz), 3.02-3.05 (m, 2H, CH2), 3.78 (s, 2H, CH2), 3.90-3.94 (m, 4H, 2×CH2), 3.97-4.01 (m, 4H, 2×CH2), 5.54 (s, H, NH), 7.18 (s, H, ArH), 9.28 (s, H, ArH), 9.69 (s, 2H, 2×ArH). MS: (ESI+): MH+=454.21

Example 187

N-(2-methoxyethyl)-N-methyl-1-((4-morpholino-2-(pyrimidin-5-yl)thieno[2,3-d]pyrimidin-6-yl)methyl) piperidin-4-amine 270

A mixture of N—BOC-4-piperidine (500 mg), N-(2-methoxyethyl)methylamine (335 mg), acetic acid (0.15 mL) and sodium triacetoxyborohydride (797 mg) was stirred at room temperature in 1,2-dichloroethane (5 mL). After stirring overnight, the reaction mixture was diluted with chloroform, washed with sodium bicarbonate solution, dried (MgSO$_4$) and the solvent removed in vacuo. The residue was purified using flash chromatography to yield 4-[(2-methoxy-ethyl)-methyl-amino]-piperidine-1-carboxylic acid tert-butyl ester. Treatment of this compound with HCl in dichloromethane/methanol yielded (2-methoxy-ethyl)-methyl-piperidin-4-yl-amine, which was isolated as the hydrochloride salt.

Reaction between 2-chloro-4-morpholin-4-yl-thieno[2,3-d]pyrimidine-6-carbaldehyde (General Procedure D-2) and (2-methoxy-ethyl)-methyl-piperidin-4-yl-amine using General Procedure B-3 yielded 1-((2-chloro-4-morpholinothieno[2,3-d]pyrimidin-6-yl)methyl)-N-(2-methoxyethyl)-N-methylpiperidin-4-amine.

1-((2-Chloro-4-morpholinothieno[2,3-d]pyrimidin-6-yl)methyl)-N-(2-methoxyethyl)-N-methylpiperidin-4-amine was reacted with pyrimidine-5-boronic acid in General Procedure A. Purification on silica yielded 270. NMR (CDCl$_3$): 1.60-1.68 (m, 2H, CH2), 1.77-1.79 (m, 2H, Ch2), 2.06-2.11 (m, 2H, CH2), 2.34 (s, 3H, CH3), 2.42-2.48 (m, H, CH), 2.67-2.70 (m, 2H, CH2), 3.03-3.06 (m, 2H, CH2), 3.37 (s, 3H, CH3), 3.47-3.50 (m, 2H, CH2), 3.77 (s, 2H, CH2), 3.90-3.92 (m, 4H, 2×CH2), 3.99-4.01 (m, 4H, 2×CH2), 7.16 (s, H, ArH), 9.28 (s, H, ArH), 9.69 (s, 2H, 2×ArH). MS: (ESI+): MH+=484.26

Example 188

5-(7-methyl-4-morpholino-6-((4-N-cyclopropylsulfonylpiperazin-1-yl)methyl)thieno[3,2-d]pyrimidin-2-yl)pyrimidin-2-amine 271

To 2-chloro-7-methyl-4-morpholin-4-yl-6-piperazin-1-ylmethyl-thieno[3,2-d]pyrimidine (100 mg) in anhydrous DCM (2 ml) and triethylamine (1.5 equiv., 60 µl) at 0° C. was added cyclopropanesulfonyl chloride (1.1 equiv., 31 µl) and the reaction mixture was allowed to warm up to room temperature overnight. DCM/brine extraction and purification on silica gave 2-chloro-6-(4-cyclopropanesulfonyl-piperazin-1-ylmethyl)-7-methyl-4-morpholin-4-yl-thieno[3,2-d]pyrimidine (101 mg).

2-Chloro-6-(4-cyclopropanesulfonyl-piperazin-1-ylmethyl)-7-methyl-4-morpholin-4-yl-thieno[3,2-d]pyrimidine was reacted with 2-aminopyrimidine-5-boronic acid in General Procedure A. Purification on silica and recrystallization from hot DCM/hexane gave 271. NMR (CDCl3): 1.00-1.04 (2H, m), 1.18-1.22 (2H, m), 2.27-2.33 (1H, m), 2.45 (3H, s), 2.67-2.70 (4H, m), 3.38-3.41 (4H, m), 3.86 (2H, s), 3.39-3.41 (4H, m), 4.03-4.05 (4H, m), 5.23 (2H, br), 9.35 (2H, s). MS (ESI+): MH+ 531.29 (70%)

Example 189

5-(7-methyl-4-morpholino-6-((4-N-phenylsulfonylpiperazin-1-yl)methyl)thieno[3,2-d]pyrimidin-2-yl)pyrimidin-2-amine 272

To 2-Chloro-7-methyl-4-morpholin-4-yl-6-piperazin-1-ylmethyl-thieno[3,2-d]pyrimidine (100 mg) in anhydrous DCM (2 ml) and triethylamine (1.5 equiv., 60 µl) at 0° C. was added benzenesulfonyl chloride (1.3 equiv., 45.5 µl) and the reaction mixture was allowed to warm up to room temperature overnight. Chloroform/brine extraction and purification on silica gave 2-chloro-6-(4-benzenesulfonyl-piperazin-1-ylmethyl)-7-methyl-4-morpholin-4-yl-thieno[3,2-d]pyrimidine (104 mg).

2-Chloro-6-(4-benzenesulfonyl-piperazin-1-ylmethyl)-7-methyl-4-morpholin-4-yl-thieno[3,2-d]pyrimidine was reacted with 2-aminopyrimidine-5-boronic acid in General Procedure A. Purification on silica and ether trituration gave 272. NMR (CDCl3): 2.45 (3H, s), 2.67-2.70 (4H, m), 3.10-3.15 (4H, br), 3.86 (2H, s), 3.39-3.41 (4H, m), 4.03-4.05 (4H, m), 5.23 (2H, br), 7.55-7.60 (2H, m), 7.62-7.65 (1H, m), 7.79 (2H, d, J=8.6), 9.35 (2H, s). MS (ESI+): MH+ 567.27 (35%)

Example 190

5-(7-methyl-4-morpholino-6-((4-N-isopropylsulfonylpiperazin-1-yl)methyl)thieno[3,2-d]pyrimidin-2-yl)pyrimidin-2-amine 273

To 2-Chloro-7-methyl-4-morpholin-4-yl-6-piperazin-1-ylmethyl-thieno[3,2-d]pyrimidine (100 mg) in anhydrous DCM (2 ml) and triethylamine (1.5 equiv., 60 µL) at 0° C. was added isopropylsulfonyl chloride (1.3 equiv., 45.5 µl) and the reaction mixture was allowed to warm up to room temperature overnight. Chloroform/brine extraction and purification on silica gave 2-chloro-7-methyl-4-morpholin-4-yl-6-[4-(propane-2-sulfonyl)-piperazin-1-ylmethyl]-thieno[3,2-d]pyrimidine (105 mg).

2-Chloro-7-methyl-4-morpholin-4-yl-6-((4-(propane-2-sulfonyl)-piperazin-1-ylmethylFthieno[3,2-d]pyrimidine (105 mg) was reacted with 2-aminopyrimidine-5-boronic acid in General Procedure A. Purification on silica and recrystallization from hot DCM/hexane gave 273. NMR (CDCl3): 1.37 (6H, d, J=6.8), 2.44 (3H, s), 2.63-2.66 (4H, m), 3.18-3.25 (1H, m), 3.43-3.46 (4H, m), 3.86 (2H, s), 3.89-3.91 (4H, m), 4.03-4.05 (4H, m), 5.23 (2H, br), 9.35 (2H, s). MS (ESI+): MH+ 533.31 (40%)

Example 191

N,1-dimethyl-N-((4-morpholino-2-(pyrimidin-5-yl)thieno[3,2-d]-2-amino-pyrimidin-6-yl)methyl)piperidin-4-amine 274

Reaction between 2-chloro-4-morpholin-4-yl-thieno[3,2-d]pyrimidine-6-carbaldehyde 10 (Example 3) and 1-methyl-4-(methylamino)piperidine using General Procedure B-3 yielded (2-chloro-4-morpholin-4-yl-thieno[3,2-d]pyrimidin-6-ylmethyl)-methyl-(1-methyl-piperidin-4-yl)-amine.

(2-Chloro-4-morpholin-4-yl-thieno[3,2-d]pyrimidin-6-ylmethyl)-methyl-(1-methyl-piperidin-4-yl)-amine was reacted with 2-aminopyrimidine-5-boronic acid in General Procedure A. Purification on silica gave 274. NMR (400 MHz, CDCl3): 1.62-1.69 (2H, m), 1.80-1.83 (2H, m), 1.95-2.00 (2H, m), 2.25 (3H, s), 2.31 (3H, s) 2.45-2.55 (1H, m), 2.93-3.01 (2H, m), 3.88-3.90 (4H, m), 3.91 (2H, s), 4.00-4.02 (4H, m), 5.25 (2H, br, s), 7.24 (1H, s), 9.37 (1H, s). (M+H)+ 455

Example 192

5-(4-morpholino-6-((4-N-methylsulfonylpiperazin-1-yl)methyl)thieno[3,2-d]pyrimidin-2-yl)pyridine-2-carboxamide 275

2-Chloro-6-(4-methanesulfonyl-piperazin-1-ylmethyl)-4-morpholin-4-yl-thieno[3,2-d]pyrimidine, prepared via General Procedure B-3, was reacted with 2-cyanopyridine-5-boronic acid pinacol ester in General Procedure A. Purification on silica gave 275 as a minor component. NMR (CDCl3): 2.68-2.72 (4H, m), 2.82 (3H, s), 3.29-3.33 (4H, m), 3.90 (2H, s), 3.90-3.94 (4H, m), 4.05-4.10 (4H, m), 5.59 (1H, br), 7.38 (1H, s), 7.94 (1H, br), 8.30 (1H, d, J=8.1), 8.86 (1H, d, J=8.2), 9.60 (1H, s). MS (ESI+): MH+ 518.24 (100%)

Example 193

5-(4-morpholino-6-((1-O,O—S-thiomorpholin-4-yl)methyl)thieno[3,2-d]pyrimidin-2-yl)pyrimidin-2-amine 276

Thiomorpholine 1,1-dioxide was reacted with 10 (Example 3) via General Procedure B-3. Purification on silica yielded 2-chloro-6-((1-O,O—S-thiomorpholin-4-yl)methyl)-4-morpholin-4-yl-thieno[3,2-d]pyrimidine.

2-Chloro-6-((1-O,O—S-thiomorpholin-4-yl)methyl)-4-morpholin-4-yl-thieno[3,2-d]pyrimidine was reacted with 2-aminopyrimidine-5-boronic acid pinacol ester in General Procedure A. Purification on silica yielded 276. NMR (DMSO): 3.01-3.03 (4H, m), 3.14-3.18 (4H, m), 3.77-3.80 (4H, m), 3.94-3.97 (4H, m), 4.08 (2H, s, CH$_2$), 7.08 (2H, s, NH$_2$), 7.37 (1H, s, Ar) and 9.11 (2H, s, Ar). MS: (ESI+): MH+ 462.16

Example 194

5-(6-(((R)-3-methyl-(4-N-methylsulfonyl)piperazin-1-yl)methyl)-4-morpholinothieno[3,2-d]pyrimidin-2-yl)pyridin-2-amine 277

2-Chloro-6-((R)-4-methanesulfonyl-3-methyl-piperazin-1-ylmethyl)-4-morpholin-4-yl-thieno[3,2-d]pyrimidine (Example 195) was reacted with 2-amino-5-(4,4,5,5-tetramethyl-1,3,2-dioxaborolan-2-yl)pyridine via General Procedure A. Purification on silica yielded 277. NMR (CDCl$_3$): 1.34 (3H, d, J 6.8, Me), 2.18-2.24 (1H, m), 2.32-2.38 (1H, m), 2.66-2.69 (1H, m), 2.77 (3H, s, Me), 2.80-2.84 (1H, m), 3.19-3.23 (1H, m), 3.50-3.53 (1H, m), 3.64 (1H, d, J 14.8, CH), 3.70 (1H, d, J 14.8, CH), 3.80-3.84 (4H, m, CH$_2$), 3.91-3.95 (4 H, m, CH$_2$), 4.01-4.05 (1H, m), 4.58 (2H, br s, NH$_2$), 6.49 (1H, d, J 8.0, Ar), 7.20 (1H, s, Ar), 8.38 (1H, dd, J 8.0 and 2.3, Ar) and 9.07 (1H, d, J 2.3, Ar). MS: (ESI+): MH+ 504.23

Example 195

5-(6-(((R)-3-methyl-(4-N-methylsulfonyl)piperazin-1-yl)methyl)-4-morpholinothieno[3,2-d]pyrimidin-2-yl)pyrimidin-2-amine 278

To a solution of (R)-methylpiperazine (400 mg) in dichloromethane (20 mL) at 0° C. was added di-tert-butyl dicarbonate (871 mg). The reaction was stirred at room temperature for 4 h and then quenched with water (20 mL) and extracted into dichloromethane (2×40 mL). The combined organics were washed with saturated aqueous brine solution (40 mL), dried (MgSO$_4$) and concentrated to give (R)-3-methyl-piperazine-1-carboxylic acid tert-butyl ester as a white solid (669 mg, 84%).

To a solution of (R)-3-methyl-piperazine-1-carboxylic acid (669 mg) and triethylamine (0.56 mL) in dichloromethane (10 mL) at 0° C. was added dropwise methanesulfonyl chloride (0.28 mL). The reaction mixture was stirred at room temperature for 16 h and then quenched with water (10 mL) and extracted into dichloromethane (2×20 mL). The combined organic layers were washed with saturated aqueous brine solution (2×20 mL), dried (MgSO$_4$) and concentrated to give (R)-4-methanesulfonyl-3-methyl-piperazine-1-carboxylic acid tert-butyl ester as a pale yellow solid (924 mg, 99%).

To a solution of (R)-4-methanesulfonyl-3-methyl-piperazine-1-carboxylic acid tert-butyl ester (924 mg) in dichloromethane (20 mL) at 0° C. was added dropwise HCl (6.65 mL of a 2 M solution in diethyl ether). The reaction mixture was stirred at room temperature for 2 h. The precipitate formed was then collected by filtration and dried to afford (R)-1-methanesulfonyl-2-methyl-piperazine hydrochloride salt as a white solid (520 mg, 73%).

(R)-1-Methanesulfonyl-2-methyl-piperazine hydrochloride salt was reacted with 10 (Example 3) via General Procedure B-3. Purification on silica yielded 2-chloro-6-((R)-4-methanesulfonyl-3-methyl-piperazin-1-ylmethyl)-4-morpholin-4-yl-thieno[3,2-d]pyrimidine.

2-Chloro-6-((R)-4-methanesulfonyl-3-methyl-piperazin-1-ylmethyl)-4-morpholin-4-yl-thieno[3,2-d]pyrimidine was reacted with 2-aminopyrimidine-5-boronic acid pinacol ester in General Procedure A. Purification on silica yielded 278. NMR (CDCl$_3$): 1.44 (3H, d, J 6.8, Me), 2.28-2.34 (1H, m), 2.41-2.44 (1H, m), 2.75-2.80 (1H, m), 2.89 (3 H, s, Me), 2.91-2.94 (1H, m), 3.32-3.39 (1H, m), 3.60-3.66 (1H, m), 3.78 (1H, d, J 14.8, CH), 3.82 (1H, d, J 14.8, CH), 3.90-3.94 (4H, m, CH$_2$), 4.00-4.05 (4H, m, CH$_2$), 4.07-4.09 (1H, m), 5.29 (2H, br s, NH$_2$), 7.30 (1H, s, Ar) and 9.29 (2H, s, Ar). MS: (ESI+): MH+ 505.15

Example 196

4-(4-morpholino-6-((4-N-methylsulfonylpiperazin-1-yl)methyl)thieno[3,2-d]pyrimidin-2-yl)pyridine-2,6-diamine 279

2-Chloro-7-methyl-4-morpholino-6-((4-N-methylsulfonylpiperazin-1-yl)methyl)thieno[3,2-d]pyrimidine (2.38 mM) was added to sodium thiomethoxide dissolved in 50 mL toluene under N$_2$ and heated to reflux. The reaction was stirred at reflux 24 hours and there was very little product by LCMS. To this reaction mixture was added 50 mL DMF to dissolve the starting material and again heated to reflux for two hours. Complete product formation was confirmed by LCMS. The reaction was poured onto ice water, extracted with ether, dried over MgSO$_4$, and concentrated in vacuo. This crude product waspurified by flash chromatography (MeOH/DCM) giving 7-methyl-2-(methylthio)-4-morpholino-6-((4-N-methylsulfonylpiperazin-1-yl)methyl)thieno[3,2-d]pyrimidine. MS (Q1) 445 (M+)

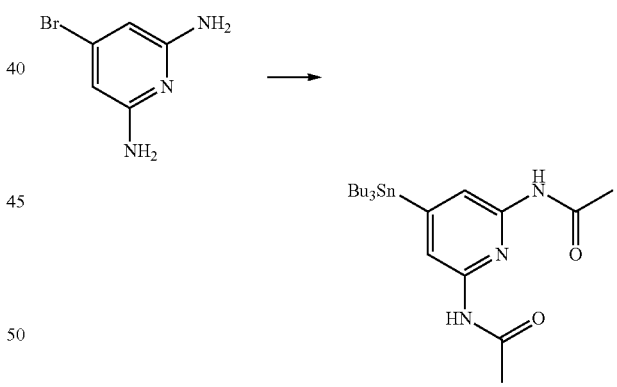

To 4-bromo-2,6-diaminopyridine in 20 mL acetic anhydride was added a few drops of sulfuric acid and the reaction mixture heated to reflux for 72 hours at which time the reaction was complete by LCMS. The reaction was cooled to room temperature and the resulting precipitate was dissolved in water and further diluted with Sat. NaHCO$_3$, extracted with EtOAc, dried over MgSO$_4$, and concentrated in vacuo. To this was added 3.0 eq. of bis (tributyltin), 0.02 eq. of dichlorobis (PPh$_3$) Palladium II and 20 mL toluene. This reaction mixture was heated to reflux under N$_2$ for 1.5 hours and complete reaction confirmed by LCMS. This was loaded onto silica column and purified by flash chromatography (EtOAc/Hexanes) to give 0.28 g of 4-tributylstannyl-2,6-diacetylaminopyridine.

7-Methyl-2-(methylthio)-4-morpholino-6-((4-N-methylsulfonylpiperazin-1-yl)methyl)thieno[3,2-d]pyrimidine (0.29 mM) was added to 4-tributylstannyl-2,6-diacetylaminopyridine dissolved in 10 mL 1,2-DME followed by the addition of Cu(I)Br-dimethylsulfide and stirred at room temperature for ten minutes. Finally, Pd(PPH$_3$)$_4$ was added and the reaction mixture was heated to reflux under N$_2$ for 2 hours. Complete product formation was confirmed by LCMS. The reaction was diluted with EtOAc, extracted 1× with water and 1× with 1 M HCl. The combined aqueous layers were basified with 10% w/w KOH and extracted the product with EtOAc, dried over MgSO$_4$, and concentrated in vacuo. This crude product was dissolved in 2 N HCl and heated to reflux for 12 hours to remove the acetyl groups and after concentrating in vacuo and HPLC purification gave 279. MS (Q1) 506 (M+)

Example 197

5-(4-morpholino-6-((4-N-methylsulfonylpiperazin-1-yl)methyl)thieno[3,2-d]pyrimidin-2-yl)pyridine-2-carbonitrile 280

2-Chloro-6-(4-methanesulfonyl-piperazin-1-ylmethyl)-4-morpholin-4-yl-thieno[3,2-d]pyrimidine, prepared via General Procedure B-3, was reacted with 2-cyanopyridine-5-boronic acid pinacol ester in General Procedure A. Purification on silica gave 280. NMR (CDCL3): 2.68-2.72 (4H, m), 2.82 (3H, s), 3.29-3.33 (4H, m), 3.90 (2H, s), 3.90-3.94 (4H, m), 4.05-4.10 (4H, m), 7.38 (1H, s), 7.80 (1H, d, J=8.1), 8.84 (1H, d, J=8.2), 9.75 (1H, s). MS (ESI+): MH+ 541.30 (50%)

Example 198

5-(4-morpholino-6-((4-N-(thiophen-2-yl)sulfonyl)piperazin-1-yl)methyl)thieno[3,2-d]pyrimidin-2-yl)pyrimidin-2-amine 281

To N-Boc-piperazine (500 mg) in DCM (10 ml) was added triethylamine (450 µl) and 2-thiophenesulfonyl chloride (530 mg). The reaction mixture was stirred at room temperature overnight, then partitioned between dichloromethane and water, washed with brine, organics were dried over MgSO$_4$, filtered and volatiles removed in vacuo to give 4-(2-thiophenesulfonyl)-piperazine-1-carboxylic acid tert-butyl ester (759 mg).

4-(2-Thiophenesulfonyl)-piperazine-1-carboxylic acid tert-butyl ester (759 mg) was dissolved in methanol (10 ml) and dichloromethane (5 ml), 2M HCl in diethyl ether (11.4 ml) was added and the reaction mixture was stirred at room temperature overnight, then cooled in ice bath, the resulted precipitate was filtered, washed with ether to yield 4-(2-thiophenesulfonyl)-piperazine hydrochloride salt (529 mg).

4-(2-Thiophenesulfonyl)-piperazine hydrochloride salt was reacted with 10 (Example 3) via General Procedure B-3. Chloroform/brine extraction and hot ethyl acetate trituration gave 2-chloro-6-[4-(2-thiopenesulfonyl)-piperazin-1-ylmethyl]-4-morpholin-4-yl-thieno[3,2-d]pyrimidine (224 mg).

2-Chloro-6-[4-(2-thiophenesulfonyl)-piperazin-1-ylmethyl]-4-morpholin-4-yl-thieno[3,2-d]pyrimidine was reacted with 2-aminopyrimidine-5-boronic acid in General Procedure A. Purification on silica and recrystallization from hot DCM/hexane gave 281. NMR (CDCl3): 2.68-2.72 (4H, m), 3.15-3.20 (4H, m), 3.85 (2H, s), 3.85-3.90 (4H, m), 4.00-4.04 (4H, m), 5.24 (2H, br), 7.18-7.20 (1H, m), 7.28 (1H, s), 7.57 (1H, m), 7.67 (1H, m), 9.29 (2H, s). MS (ESI+): MH+ 559.21 (100%)

Example 199

5-(4-morpholino-6-((4-N-2-fluorophenylsulfonylpiperazin-1-yl)methyl)thieno[3,2-d]pyrimidin-2-yl)pyrimidin-2-amine 282

To N-Boc-piperazine (500 mg) in DCM (10 ml) was added triethylamine (450 µl) and 2-fluorobenzenesulfonyl chloride (380 µl). The reaction mixture was stirred at room temperature overnight, then partitioned between dichloromethane and water, washed with brine, organics were dried over MgSO$_4$, filtered and volatiles removed in vacuo to give 4-(2-fluoro-benzenesulfonyl)-piperazine-1-carboxylic acid tert-butyl ester (891 mg).

4-(2-Fluoro-benzenesulfonyl)-piperazine-1-carboxylic acid tert-butyl ester (891 mg) was dissolved in methanol (10 ml) and dichloromethane (5 ml), 2M HCl in diethyl ether (12.9 ml) was added and the reaction mixture was stirred at room temperature overnight, then cooled in ice bath, the resulted precipitate was filtered, washed with ether to yield 4-(2-fluoro-benzenesulfonyl)-piperazine hydrochloride salt (600 mg).

4-(2-Fluoro-benzenesulfonyl)-piperazine hydrochloride salt was reacted with 10 (Example 3) in General Procedure B-3. Chloroform/brine extraction and hot ethyl acetate trituration gave 2-chloro-6-[4-(2-fluoro-benzenesulfonyl)-piperazin-1-ylmethyl]-4-morpholin-4-yl-thieno[3,2-d]pyrimidine (277 mg).

2-Chloro-6-[4-(2-fluoro-benzenesulfonyl)-piperazin-1-ylmethyl]-4-morpholin-4-yl-thieno[3,2-d]pyrimidine was reacted with 2-aminopyrimidine-5-boronic acid in General Procedure A. Purification on silica and recrystallization from hot DCM/hexane gave 282. NMR (CDCl3/MeOD): 2.53-2.56 (4H, m), 3.15-3.20 (4H, m), 3.75 (2H, s), 3.75-3.81 (4H, m), 3.89-3.93 (4H, m), 7.15 (1H, s), 7.14-7.25 (2H, m), 7.51-7.58 (1H, m), 7.71-7.77 (1H, m), 9.08 (2H, s). MS (ESI+): MH+ 571.22 (80%)

Example 200

5-(6-((4-(methylsulfonyl)piperidin-1-yl)methyl)-4-morpholinothieno[2,3-d]pyrimidin-2-yl)pyrimidin-2-amine 283

Reaction between 2-chloro-4-morpholin-4-yl-thieno[2,3-d]pyrimidine-6-carbaldehyde (General Procedure D-2) and 4-methanesulfonyl-piperidine (Example 34) using General Procedure B-3 yielded 2-chloro-6-(4-methanesulfonyl-piperidin-1-ylmethyl)-4-morpholin-4-yl-thieno[2,3-d]pyrimidine.

2-Chloro-6-(4-methanesulfonyl-piperidin-1-ylmethyl)-4-morpholin-4-yl-thieno[2,3-d]pyrimidine was reacted with 2-aminopyrimidine-5-boronic acid in General Procedure A. Purification on silica gave 283. NMR (400 MHz, CDCl3): 1.88-2.00 (2H, m), 2.04-2.20 (4H, m), 2.83-2.86 (4H, m), 3.13-3.20 (2H, m), 3.81 (2H, s), 3.88-3.90 (4H, m), 3.92-3.96 (4H, m), 5.25 (2H, br, s), 7.18 (1H, s), 9.37 (1H, s). (M+H)+ 490

Example 201

5-(4-morpholino-6-((4-N-3-fluorophenylsulfonylpiperazin-1-yl)methyl)thieno[3,2-d]pyrimidin-2-yl)pyrimidin-2-amine 284

To N-Boc-piperazine (500 mg) in DCM (10 ml) was added triethylamine (450 µl) and 3-fluorobenzenesulfonyl chloride (390 μl). The reaction mixture was stirred at room temperature overnight, then partitioned between dichloromethane and water, washed with brine, organics were dried over MgSO$_4$, filtered and volatiles removed in vacuo to give 4-(3-fluoro-benzenesulfonyl)-piperazine-1-carboxylic acid tert-butyl ester (919 mg).

4-(3-Fluoro-benzenesulfonyl)-piperazine-1-carboxylic acid tert-butyl ester (919 mg) was dissolved in methanol (10 ml) and dichloromethane (5 ml), 2M HCl in diethyl ether (12 ml) was added and the reaction mixture was stirred at room temperature overnight. Volatiles were removed in vacuo to yield 4-(3-fluoro-benzenesulfonyl)-piperazine hydrochloride salt (807 mg).

4-(3-Fluoro-benzenesulfonyl)-piperazine hydrochloride salt was reacted with 10 (Example 3) in General Procedure B-3. Chloroform/brine extraction and hot ethyl acetate trituration gave 2-chloro-6-[4-(3-fluoro-benzenesulfonyl)-piperazin-1-ylmethyl]-4-morpholin-4-yl-thieno[3,2-d]pyrimidine (100 mg).

2-Chloro-6-[4-(3-fluoro-benzenesulfonyl)-piperazin-1-ylmethyl]-4-morpholin-4-yl-thieno[3,2-d]pyrimidine was reacted with 2-aminopyrimidine-5-boronic acid via General Procedure A. Purification on silica and recrystallization from hot DCM/hexane gave 284. NMR (DMSO): 2.55-2.58 (4H, m), 2.98-3.03 (4H, m), 3.73-3.77 (4H, m), 3.88 (2H, s), 3.90-3.94 (4H, m), 7.06 (2H, br. s), 7.32 (1H, s), 7.55-7.65 (2H, m), 7.70-7.75 (1H, m), 9.10 (2H, s). MS (ESI+): MH+ 571.20 (100%)

Example 202

5-(4-morpholino-6-((4-N-(1-methylimidazol-4-yl)piperazin-1-yl)methyl)thieno[3,2-d]pyrimidin-2-yl)pyrimidin-2-amine 285

To N-Boc-piperazine (500 mg) in DCM (10 ml) was added triethylamine (450 μl) and 1-methylimidazole-4-sulfonyl chloride (524 mg). The reaction mixture was stirred at room temperature overnight, then partitioned between dichloromethane and water, washed with brine, organics were dried over MgSO$_4$, filtered and volatiles removed in vacuo to give 4-(1-methylimidazole-4-sulfonyl)-piperazine-1-carboxylic acid tert-butyl ester (730 mg).

4-(1-Methylimidazole-4-sulfonyl)-piperazine-1-carboxylic acid tert-butyl ester (730 mg) was dissolved in methanol (10 ml) and dichloromethane (5 ml), 2M HCl in diethyl ether (11 ml) was added and the reaction mixture was stirred at room temperature overnight. Volatiles were removed in vacuo to yield 4-(1-methylimidazole-4-sulfonyl)-piperazine hydrochloride salt (704 mg).

4-(1-Methylimidazole-4-sulfonyl)-piperazine hydrochloride salt was reacted with 10 (Example 3) via General Procedure B-3. Chloroform/brine extraction and hot ethyl acetate trituration gave 2-chloro-6-[4-(1-methylimidazole-4-sulfonyl)-piperazin-1-ylmethyl]-4-morpholin-4-yl-thieno[3,2-d]pyrimidine (93 mg).

2-Chloro-6-[4-(1-methylimidazole-4-sulfonyl)-piperazin-1-ylmethyl]-4-morpholin-4-yl-thieno[3,2-d]pyrimidine was reacted with 2-aminopyrimidine-5-boronic acid via General Procedure A. Purification on silica and recrystallization from hot DCM/hexane gave 285. NMR (DMSO): 2.55-2.58 (4H, m), 2.98-3.03 (4H, m), 3.72 (3H, s), 3.73-3.77 (4H, m), 3.88 (2H, s), 3.90-3.94 (4H, m), 7.06 (2H, br. s), 7.32 (1H, s), 7.83 (1H, d, J=1.3), 7.89 (1H, d, J=1.3), 9.10 (2H, s). MS (ESI+): MH+ 557.24 (100%)

Example 203

5-(4-morpholino-6-((4-N-4-fluorophenylsulfonylpiperazin-1-yl)methyl)thieno[3,2-d]pyrimidin-2-yl)pyrimidin-2-amine 286

To N-Boc-piperazine (500 mg) in DCM (10 ml) was added triethylamine (450 μl) and 4-fluorobenzenesulfonyl chloride (564 mg). The reaction mixture was stirred at room temperature overnight, then partitioned between dichloromethane and water, washed with brine, organics were dried over MgSO$_4$, filtered and volatiles removed in vacuo to give 4-(4-fluoro-benzenesulfonyl)-piperazine-1-carboxylic acid tert-butyl ester (937 mg).

4-(4-Fluoro-benzenesulfonyl)-piperazine-1-carboxylic acid tert-butyl ester (937 mg) was dissolved in methanol (10 ml) and dichloromethane (5 ml), 2M HCl in diethyl ether (13.6 ml) was added and the reaction mixture was stirred at room temperature overnight. Volatiles were removed in vacuo to yield 4-(4-fluoro-benzenesulfonyl)-piperazine hydrochloride salt (819 mg).

4-(4-Fluoro-benzenesulfonyl)-piperazine hydrochloride salt was reacted with 10 (Example 3) in General Procedure B-3. Chloroform/brine extraction and hot ethyl acetate trituration gave 2-chloro-6-[4-(4-fluoro-benzenesulfonyl)-piperazin-1-ylmethyl]-4-morpholin-4-yl-thieno[3,2-d]pyrimidine (85 mg).

2-Chloro-6-[4-(4-fluoro-benzenesulfonyl)-piperazin-1-ylmethyl]-4-morpholin-4-yl-thieno[3,2-d]pyrimidine was reacted with 2-aminopyrimidine-5-boronic acid in General Procedure A. Purification on silica and recrystallization from hot DCM/hexane gave 286. NMR (DMSO): 2.55-2.58 (4H, m), 2.98-3.03 (4H, m), 3.73-3.77 (4H, m), 3.88 (2H, s), 3.90-3.94 (4H, m), 7.06 (2H, br. s), 7.32 (1H, s), 7.50-7.55 (211, t), 7.80-7.84 (2H, m), 9.10 (2H, s). MS (ESI+): MH+ 570.23 (100%)

Example 204

5-(4-morpholino-6-((4-(dimethylaminosulfonyl)piperidin-1-yl)methyl)thieno[3,2-d]pyrimidin-2-yl)pyrimidin-2-amine 287

To 4-hydroxy-piperidine-1-carboxylic acid tert-butyl ester (9.2 g) in dichloromethane (170 ml), stirring at 0° C. was added methanesulfonyl chloride (5.33 ml) and triethylamine (10.24 ml). The reaction mixture was slowly warmed to room temperature and stirred overnight. The reaction mixture was partitioned between chloroform and water. The combined organics were washed with brine and dried (MgSO$_4$). The solvent was removed in vacuo to yield 14 g of 4-methanesulfonyl-piperidine-carboxylic acid tert-butyl ester.

A mixture of 4-methanesulfonyl-piperidine-carboxylic acid tert-butyl ester (2.82 g), sodium thioacetate (2.31 g) and DMF (40 ml) was stirred at 60° C. After 4 hours the reaction mixture was cooled and partitioned between ethyl acetate and brine. The combined organics were dried (MgSO$_4$) and the solvents removed in vacuo. The resulting crude mixture was purified by flash chromatography to yield 4-acetylsulfanyl-piperidine-1-carboxylic acid tert-butyl ester (1.8 g).

4-acetylsulfanyl-piperidine-1-carboxylic acid tert-butyl ester (400 mg) was stirred in acetic acid (3 ml) and water (3 ml) at 0° C. Chlorine gas was bubbled through the reaction mixture. The reaction mixture was stirred for 1.5 hours. The reaction mixture was then diluted with water to yield a precipitate which was collected by filtration to yield 4-chlorosulfonyl-piperidine-1-carboxylic acid tert-butyl ester (295 mg).

To a solution of 4-chlorosulfonyl-piperidine-1-carboxylic acid tert-butyl ester (310 mg) in dichloromethane stirring at 0° C. was added triethylamine (610 μl) and dimethylamine HCl salt (268 mg)). The reaction mixture was stirred overnight then quenched with water and extracted into dichloromethane. The combined organics were washed with brine and dried (MgSO$_4$). The solvent was removed in vacuo to yield 4-(morpholine-4-sulfonyl)-piperidine-1-carboxylic acid tert-butyl ester (250 mg).

To a solution of 4-(dimethylamine-4-sulfonyl)-piperidine-1-carboxylic acid tert-butyl ester in dichloromethane (10 ml) and methanol (10 ml) was added 2M hydrogen chloride in ether (2 μL). The reaction mixture was stirred overnight. The solvents were removed in vacuo to yield 4-(piperidine-4-sulfonyl)-dimethylamide hydrochloride salt.

4-(Piperidine-4-sulfonyl)-dimethylamide hydrochloride salt was reacted with 10 (Example 3) in General Procedure B-3. Chloroform/brine extraction and hot ethyl acetate trituration gave 1-(2-chloro-4-morpholin-4-yl-thieno[3,2-d]pyrimidine-4-sulfonic acid dimethylamide.

1-(2-Chloro-4-morpholin-4-yl-thieno[3,2-d]pyrimidine-4-sulfonic acid dimethylamide was reacted with 2-aminopyrimidine-5-boronic acid in General Procedure A. Purification on silica and ether trituration gave 287. NMR (DMSO): 1.62-1.72 (2H, m), 1.90-1.98 (2H, m), 2.10-2.18 (2H, m), 2.83 (6H, s), 3.20-3.26 (1H, m), 3.77-3.81 (4H, m), 3.85 (2H, s), 3.94-3.98 (4H, m), 7.05 (2H, s), 7.34 (1H, s), 9.11 (2H, s). MS (ESI+): MH+ 519.35 (100%)

Example 205

5-(4-morpholino-6-((4-(dimethylaminosulfonyl)piperidin-1-yl)methyl)thieno[3,2-d]pyrimidin-2-yl)pyridin-2-amine 288

1-(2-Chloro-4-morpholin-4-yl-thieno[3,2-d]pyrimidine-4-sulfonic acid dimethylamide (Example 204) was reacted with 2-aminopyridine-5-boronic acid pinacol ester via General Procedure A. Purification on silica and ether trituration gave 288. NMR (DMSO): 1.62-1.72 (2H, m), 1.90-1.98 (2H, m), 2.10-2.18 (2H, m), 2.83 (6H, s), 3.20-3.26 (1H, m), 3.77-3.81 (4H, m), 3.85 (2H, s), 3.94-3.98 (4H, m), 6.31 (2H, br), 6.52 (1H, d), 7.33 (1H, s), 8.29 (1H, dd), 8.94 (1H, d). MS (ESI+): MH+ 518.37 (45%)

Example 206

1-((2-(2-aminopyrimidin-5-yl)-4-morpholinothieno[3,2-d]pyrimidin-6-yl)methyl)-4-phenylpiperidin-4-ol 289

Reaction between 2-chloro-4-morpholin-4-yl-thieno[3,2-d]pyrimidine-6-carbaldehyde 10 (Example 3) and 4-hydroxy-4-phenylpiperidine via General Procedure B-3 yielded 1-(2-chloro-4-morpholin-4-yl-thieno[3,2-d]pyrimidin-6-yl-methyl)-4-phenyl-piperidin-4-ol.

1-(2-Chloro-4-morpholin-4-yl-thieno[3,2-d]pyrimidin-6-ylmethyl)-4-phenyl-piperidin-4-ol was reacted with 2-aminopyrimidine-5-boronic acid in General Procedure A. Purification on silica gave 289, purity 95%. NMR (400 MHz 1H DMSO): 9.12 (s, 2H); 7.50 (d, 2H, J=7.26); 7.34 (d, 2H, J=11.96); 7.32 (d, 1H, J=15.36); 7.21 (t, 1H, J=7.28); 7.04 (s, 2H); 3.96 (t, 4H, J=4.70); 3.89 (s, 2H); 3.79 (t, 4H, J=4.67); 2.74 (d, 2H, J=10.55); 2.58 (t, 2H, J=10.65); 2.97 (m, 2H); 1.65, (d, 2H, J=12.40). LC-MS (m+1)=503.63

Example 207

5-(6-((4-(N-(2-methoxyethyl)-N-methylamino)piperidin-1-yl)methyl)-4-morpholinothieno[3,2-d]pyrimidin-2-yl)pyrimidin-2-amine 290

Reaction between 2-chloro-4-morpholin-4-yl-thieno[3,2-d]pyrimidine-6-carbaldehyde 10 (Example 3) and (2-methoxy-ethyl)-methyl-piperidin-4-yl-amine (Example 187) using General Procedure B-3 yielded 1-((2-chloro-4-morpholinothieno[3,2-d]pyrimidin-6-yl)methyl)-N-(2-methoxyethyl)-N-methylpiperidin-4-amine.

1-((2-Chloro-4-morpholinothieno[3,2-d]pyrimidin-6-yl)methyl)-N-(2-methoxyethyl)-N-methylpiperidin-4-amine was reacted with 5-(4,4,5,5-tetramethyl-[1,3,2]dioxaborolan-2-yl)-pyrimidin-2-ylamine in General Procedure A. Purification on silica yielded 290. NMR (CDCl$_3$): 1.63-1.70 (m, 2H, CH2), 1.78 (m, 2H, CH2), 2.09-2.15 (m, 2H, CH2), 2.36 (s, 3H, CH3), 2.50 (m, H, CH), 2.69 (m, 2H, CH2), 3.04-3.06 (m, 2H, CH2), 3.38 (s, 3H, CH3), 3.49 (m, 2H, CH2), 3.82 (s, 2H, CH2), 389-3.91 (m, 4H, 2×CH2), 4.04-4.06 (m, 4H, 2×CH2), 5.23 (s, 2H, NH2), 7.27 (s, H, ArH), 9.30 (s, 2H, 2×ArH). MS: (ESI+): MH+=499.29

Example 208

5-(4-morpholino-6-((4-N-ethylsulfonylpiperazin-1-yl)methyl)thieno[3,2-d]pyrimidin-2-yl)pyrimidin-2-amine 291

To 2-Chloro-4-morpholin-4-yl-6-piperazin-1-ylmethyl-thieno[3,2-d]pyrimidine HCl salt from General Procedure B-3 (50 mg) in dry DCM (3 ml) and triethylamine (3.5 equiv., 60 ul) was added ethanesulfonyl chloride (1.1 equiv., 10 ul) at 0° C. and the reaction mixture was allowed to warm up to room temperature overnight. Extraction with DCM/brine gave 2-chloro-6-(4-ethanesulfonyl-piperazin-1-ylmethyl)-4-morpholin-4-yl-thieno[3,2-d]pyrimidine as a crude product (67 mg), which was reacted with 2-aminopyrimidine-5-boronic acid in General Procedure A. Purification on silica and ether trituration gave 291. NMR (CDCl3): 1.40 (3H, t, J=7.4), 2.65-2.69 (4H, m), 3.00 (2H, q, J=7.4), 3.37-3.41 (4H, m), 3.86 (2H, s), 3.89-3.91 (4H, m), 4.03-4.05 (4H, m), 5.23 (2H, br), 9.35 (2H, s). MS (ESI+): MH+ 505.15 (100%)

Example 209

5-(6-((4-(N-methyl,N-methylsulfonylamino)piperidin-1-yl)methyl)-4-morpholinothieno[3,2-d]pyrimidin-2-yl)pyridin-2-amine 292

To a solution of 1-BOC-4-piperidone (3.5 g, 17.5 mmol) in methanol (10 mL) was added a solution of 2M methylamine in methanol (13 mL, 26 mmol). The reaction mixture was stirred for 16 hours and then sodium cyanoborohydride (1.1 g, 17.5 mmol) was added. After stirring for 2 hours the reaction mixture was then diluted with dichloromethane, washed with sodium bicarbonate solution, dried (MgSO$_4$) and the solvent removed in vacuo. The residue was purified by flash chromatography using 10% methanol in dichloromethane as the eluent to yield 4-methylamino-piperidine-1-carboxylic acid tert-butyl ester (1.72 g, 46%).

To a solution of 4-methylamino-piperidine-1-carboxylic acid tert-butyl ester (1.72 g, 8 mmol) in dichloromethane (10 mL) was added triethylamine (1.30 mL, 8.8 mmol) followed by methanesulphonyl chloride (0.68 mL, 8.8 mmol). After stirring for 16 hours the reaction mixture was then diluted with dichloromethane, washed with sodium bicarbonate solution, dried (MgSO$_4$) and the solvent removed in vacuo. The residue was purified by flash chromatography using 50% ethyl acetate in petroleum ether as the eluent to yield 4-(methanesulfonyl-methyl-amino)-piperidine-1-carboxylic acid tert-butyl ester as a white solid (1.85 g, 75%). Treatment of this compound with trifluoroacetic acid in dichloromethane yielded N-methyl-N-piperidin-4-yl-methanesulfonamide, which was isolated as the TFA salt.

N-[1-(2-Chloro-4-morpholin-4-yl-thieno[3,2-d]pyrimidin-6-ylmethyl)-piperidin-4-yl]-N-methyl-methanesulfonamide was made by treating 2-chloro-4-morpholin-4-yl-thieno[3,2-d]pyrimidine-6-carbaldehyde 10 and N-methyl-N-piperidin-4-yl-methanesulfonamide according to the General Procedure B-3.

A suspension of N-[1-(2-chloro-4-morpholin-4-yl-thieno[3,2-d]pyrimidin-6-ylmethyl)-piperidin-4-yl]-N-methyl-methanesulfonamide (148 mg, 0.32 mmol), 5-(4,4,5,5-tetramethyl-[1,3,2]dioxaborolan-2-yl)-pyridin-2-ylamine (86 mg, 0.39 mmol), 1M Na$_2$CO$_3$ (1 ml, 1 mmol) and Pd(PPh$_3$)$_2$Cl$_2$ (21 mg, 0.03 mmol) in acetonitrile was heated in a microwave at 140° C. for 25 mins. The reaction was then acidified with 2N HCl (aq) extracted with ethyl acetate, the water layer separated and basified with K$_2$CO$_3$ (sat. aq) resulting in a white precipitate as 292 which was filtered and dried (120 mg, 72%). NMR (DMSO, 400 MHz), 1.62-1.67 (2H, m), 1.74-1.82 (2H, m), 2.18-2.24 (2H, m), 2.77 (3H, s), 2.95 (3H, s), 2.97-3.03 (2H, m), 3.57-3.66 (1H, m), 3.85 (4H, t, J=4.4), 3.89 (2H, s), 4.00 (4H, t, J=4.4), 6.37 (2H, s), 6.56 (1H, d, J=8.8), 7.36 (1H, s), 8.34 (1H, dd, J=8.8, 2.4), 8.99 (1H, d, J=2.4). MS: (ESI+): MH+ 518

Example 210

4-methoxy-5-(4-morpholino-6-((4-N-methylsulfonylpiperazin-1-yl)methyl)thieno[3,2-d]pyrimidin-2-yl)pyrimidin-2-amine 293

A mixture of 2,4-dichloropyrimidine (5 g) in ammonium hydroxide (28% solution, 100 ml) was stirred at room temperature for 16 h. The resulting solid was filtered, washed with diethyl ether and air dried. To the crude product in methanol (20 mL) was added sodium methoxide (28% solution, 3.38 mL) and the mixture was heated at reflux for 16 h. After cooling to room temperature the solvent was reduced in vacuo and the residue purified by column chromatography to give 4-methoxy-pyrimidin-2-ylamine as a white solid.

To a solution of 4-methoxy-pyrimidin-2-ylamine (405 mg) in acetic acid (10 mL) was added N-iodosuccinimide (950 mg) and the mixture was heated at 80° C. for 4 h. After cooling to room temperature, the reaction was quenched with 5% aqueous sodium thiosulphate solution (20 mL) and the solvent removed in vacuo. The product was then extracted into dicholoromethane (3×20 mL) and the combined organics were washed with brine (40 mL), dried (MgSO$_4$) and reduced in vacuo to give 5-iodo-4-methoxy-pyrimidin-2-ylamine as a white solid.

To a solution of 5-iodo-4-methoxy-pyrimidin-2-ylamine (320 mg) in 1,4-dioxane (10 mL) was added bis(tributyltin) (1.29 mL), tetrakis(triphenylphosphine)palladium (0) (74 mg) and lithium chloride (162 mg) and the reaction mixture was heated at reflux for 16 h. After cooling to room temperature, the mixture was filtered through Celite, washing with ethyl acetate. The filtrate was washed with water (2×20 mL), brine (20 mL), dried (MgSO$_4$), reduced in vacuo and purifed by column chromatography to give 4-methoxy-5-tributyl-stannanyl-pyrimidin-2-ylamine as a yellow oil.

To a solution of 6-(4-methanesulfonyl-piperazin-1-ylmethyl)-2-methylsulfanyl-4-morpholin-4-yl-thieno[3,2-d]pyrimidine (70 mg) in 1,2-dimethoxyethane (10 mL) was added 4-methoxy-5-tributylstannyl-pyrimidin-2-ylamine (131 mg) and copper(I)bromide-dimethyl sulfide (65 mg) and the reaction mixture was stirred at room temperature for 10 minutes. Tetrakis(triphenylphosphine)palladium (0) (9 mg) was then added and the reaction mixture was heated at reflux for 16 h. After cooling to room temperature, the mixture was diluted with ethyl acetate (20 mL) and washed with water (2×20 mL) and brine (2×20 mL) The organic phase was dried (MgSO$_4$), reduced in vacuo and purified by column chromatography to give 293. NMR: (CDCl$_3$) 2.58-2.62 (4 H, m), 2.73 (3 H, s, Me), 3.18-3.22 (4 H, m), 3.76-3.80 (6 H, m), 3.89-3.94 (7 H, m), 4.98 (2 H, br s, NH), 7.24 (1 H, s, Ar) and 8.72 (1 H, s, Ar). MS: (ESI+): MH+ 521.25

Example 211

5-(6-((4-(N-methyl,N-methylsulfonylamino)piperidin-1-yl)methyl)-4-morpholinothieno[3,2-d]pyrimidin-2-yl)pyrimidin-2-amine 294

A suspension of N-[1-(2-chloro-4-morpholin-4-yl-thieno[3,2-d]pyrimidin-6-ylmethyl)-piperidin-4-yl]-N-methyl-methanesulfonamide (137 mg, 0.3 mmol), 5-(4,4,5,5-tetramethyl-[1,3,2]dioxaborolan-2-yl)-pyrimidin-2-ylamine (76 mg, 0.36 mmol), 1M Na$_2$CO$_3$ (1 ml, 1 mmol) and Pd(PPh$_3$)$_2$Cl$_2$ (21 mg, 0.03 mmol) in acetonitrile was heated in a microwave at 140° C. for 25 mins. The reaction was then acidified with 2N HCl (aq) extracted with ethyl acetate, the water layer separated and basified with K$_2$CO$_3$ (sat. aq) resulting in 294 as a white precipitate which was filtered and dried (128 mg, 83%). NMR (DMSO, 400 MHz), 1.55-1.63 (2H, m), 1.68-1.79 (2H, m), 2.11-2.18 (2H, m), 2.70 (3H, s), 2.89 (3H, s), 2.94-2.98 (2H, m), 3.53-3.61 (1H, m), 3.79 (4H, t, J=5.2), 3.84 (2H, s), 3.95 (4H, t, J=4.4), 7.04 (2H, s), 7.32 (1H, s), 9.11 (2H, s). MS: (ESI+): MH+=519

Example 212

5-(6-((methyl((1-methyl-1H-imidazol-4-yl)methyl)amino)methyl)-4-morpholinothieno[3,2-d]pyrimidin-2-yl)pyrimidin-2-amine 295

(2-Chloro-4-morpholin-4-yl-thieno[3,2-d]pyrimidin-6-ylmethyl)methylamine was reacted with 1-methyl-1H-imidazole-4-carbaldehyde using standard reductive amination conditions. The resulting crude material was triturated with diethyl ether and methanol to give (2-chloro-4-morpholin-4-yl-thieno[3,2-d]pyrimidin-6-ylmethyl)-methyl-(1-methyl-1H-imidazol-4-ylmethyl)-amine as a solid (93% yield).

(2-Chloro-4-morpholin-4-yl-thieno[3,2-d]pyrimidin-6-ylmethyl)-methyl-(1-methyl-1H-imidazol-4-ylmethyl)-amine was reacted with 5-(4,4,5,5-tetramethyl-[1,3,2]dioxaborolan-2-yl)-pyrimidin-2-ylamine according to General Procedure A. The resulting solid was purified by flash column chromatography using 10% methanol/ethyl acetate as the eluent to give 295 as a solid (49% yield). NMR (DMSO, 400 MHz), 2.19 (3H, s), 3.62 (2H, s), 3.68 (3H, s), 3.75-3.78 (4H, m), 3.85 (2H, s), 3.93-3.97 (4H, m), 6.85 (1H, s), 7.04 (2H, s), 7.36 (1H, s), 7.58 (1H, s), 9.11 (2H, s). MS: (ESI+): MH+=452

Example 213

5-(4-morpholino-6-((4-N-isobutyrylsulfonylpiperazin-1-yl)methyl)thieno[3,2-d]pyrimidin-2-yl)pyrimidin-2-amine 296

To 2-chloro-6-[4-piperazin-1-ylmethyl]-4-morpholine-4-yl-thieno[3,2-d]pirimidine (115 mg) in DCM (3 ml) and triethylamine (91 ul) was added isobutanesulfonyl chloride (63 ul) at 0° C. The reaction mixture was allowed to warm up to room temperature over 4 hours. Aqueous work-up and purification on silica gave 2-chloro-6-[4-(2-methyl-propane-1-sulfonyl)-piperazin-1-ylmethyl]-4-morpholine-4-yl-thieno[3,2-d]pyrimidine (86 mg).

2-Chloro-6-[4-(2-methyl-propane-1-sulfonyl)-piperazin-1-ylmethyl]-4-morpholine-4-yl-thieno[3,2-d]pyrimidine was reacted with 2-aminopyrimidine-5-boronic acid via General Procedure A. Purification on silica yielded 296. NMR (CDCl3): 1.14 (6H, d, J=6.7), 2.28-2.38 (1H, m), 2.66-2.69 (4H, m), 2.79 (2H, d, J=6.6), 3.33-3.36 (4H, m), 3.86 (2H, s), 3.89-3.91 (4H, m), 4.03-4.05 (4H, m), 5.23 (2H, br), 7.31 (1H, s), 9.35 (2H, s). MS (ESI+): MH+ 533.31 (100%)

Example 214

6-(4-morpholino-6-((4-N-methylsulfonylpiperazin-1-yl)methyl)thieno[2,3-d]pyrimidin-2-yl)pyridin-2-amine 297

2-Chloro-4-morpholino-6-((4-N-methylsulfonylpiperazin-1-yl)methyl)thieno[2,3-d]pyrimidine (0.44 mM) and 6-aminopyridine-2-boronic acid pinacol ester were coupled using General Procedure A to give 297 (TFA salt) after reverse-phase HPLC purification. MS (Q1) 491 (M+)

Example 215

1-((2-(2-aminopyrimidin-5-yl)-4-morpholinothieno[2,3-d]pyrimidin-6-yl)methyl)pyrrolidin-3-ol 298

To a solution of 2-chloro-4-morpholinothieno[2,3-d]pyrimidine-6-carbaldehyde, from General Procedure D-2, (200 mg, 0.7 mmol) in 1,2-dichloroethane (4 mL) was added 3-pyrrolidinol (1 mmol), and AcOH (0.7 mmol). After the reaction mixture stirred for 10 min at room temperature Na(OAc)₃BH (0.8 mmol) was added. The mixture was stirred overnight at room temperature. The reaction was quenched by the addition of saturated (aq) NaHCO₃. The organic layer was separated and the aqueous layer was extracted with EtOAc and CH₂Cl₂. The combined organics were dried over Na₂SO₄ and concentrated in vacuo. The crude material was coupled following General Procedure A with 5-(4,4,5,5-tetramethyl-1,3,2-dioxaborolan-2-yl)pyrimidin-2-amine to provide 298 after reverse phase HPLC purification (7 mg). MS (Q1) 414 (M)+

Example 216

5-(4-morpholino-6-(1-(4-N-methylsulfonylpiperazin-1-yl)ethyl)thieno[3,2-d]pyrimidin-2-yl)pyridin-2-amine 299

2-Chloro-6-[1-(4-methanesulfonyl-piperazin-1-yl)-ethyl]-4-morpholin-4-yl-thieno[3,2-d]pyrimidine was reacted with 2-amino-5-(4,4,5,5-tetramethyl-1,3,2-dioxaborolan-2-yl)pyridine in General Procedure A. Purification on silica yielded 299. NMR: (CDCl₃): 1.43 (3 H, d, J 7.2, Me), 2.56-2.68 (4 H, m, CH₂), 2.73 (3 H, s, Me), 3.18-3.29 (4 H, m, CH₂), 3.80-3.83 (4 H, m, CH₂), 3.94-3.99 (5 H, m), 4.58 (2 H, br s, NH2), 6.48 (1 H, d, J 8.1, Ar), 7.19 (1 H, s, Ar), 8.38 (1 H, dd, J 8.1 and 2.0, Ar) and 9.07 (1 H, d, J 2.0, Ar). MS: (ESI+): MH+=504.26

Example 217

5-(4-morpholino-6-(1-(4-N-methylsulfonylpiperazin-1-yl)ethyl)thieno[3,2-d]pyrimidin-2-yl)pyrimidin-2-amine 300

To a solution of 2-chloro-4-morpholinothieno[3,2-d]pyrimidine 4 in THF (General Procedure D-1, 10 mL) at −78° C. was added n-butyllithium (0.94 mL of a 2.5 M solution in hexanes). After stirring for 1 h at −78° C., acetaldehyde (0.33 mL) was added and the mixture was allowed to warm to room temperature over 16 h. The reaction was then quenched with water and extracted into dichloromethane. The combined organics were washed with brine, dried (MgSO₄) and reduced in vacuo to yield 1-(2-chloro-4-morpholin-4-yl-thieno[3,2-d]pyrimidin-6-yl)-ethanol (540 mg).

To a solution of 1-(2-chloro-4-morpholin-4-yl-thieno[3,2-d]pyrimidin-6-yl)-ethanol (509 mg) in dichloromethane (20 mL) at 0° C. was added triethylamine (0.28 mL) and then methanesulfonyl chloride (0.14 mL). The reaction mixture was stirred at room temperature for 16 h and then quenched with water and extracted into dichloromethane. The combined organics were washed with brine, dried (MgSO₄) and reduced in vacuo to yield methanesulfonic acid 1-(2-chloro-4-morpholin-4-yl-thieno[3,2-d]pyrimidin-6-yl)-ethyl ester (640 mg).

To solution of methanesulfonic acid 1-(2-chloro-4-morpholin-4-yl-thieno[3,2-d]pyrimidin-6-yl)-ethyl ester (640 mg) and 1-methanesulfonyl-piperazine hydrochloride salt (described above) (511 mg) in acetonitrile (50 mL) was added potassium carbonate (1.170 g) and the reaction mixture was stirred at reflux for 16 h. After cooling to room temperature the reaction mixture was reduced in vacuo, redissolved into dichloromethane and washed with saturated aqueous sodium hydrogencarbonate solution and then brine. The organics were dried (MgSO₄), reduced in vacuo and purified on silica to yield 2-chloro-6-[1-(4-methanesulfonyl-piperazin-1-yl)-ethyl]-4-morpholin-4-yl-thieno[3,2-d]pyrimidine.

2-Chloro-6-[1-(4-methanesulfonyl-piperazin-1-yl)-ethyl]-4-morpholin-4-yl-thieno[3,2-d]pyrimidine was reacted with 2-aminopyrimidine-5-boronic acid pinacol ester in General Procedure A. Purification on silica yielded 300. NMR: (CDCl₃): 1.44 (3 H, d, J 7.1, Me), 2.52-2.64 (4 H, m, CH₂), 2.73 (3 H, s, Me), 3.21-3.23 (4 H, m, CH₂), 3.80-3.83 (4 H, m, CH₂), 3.94-4.06 (5 H, m), 5.16 (2 H, s, NH₂) and 9.20 (2 H, s, Ar). MS: (ESI+): MH+=505.20

Example 218

(R)-1-((2-(2-aminopyrimidin-5-yl)-4-morpholinothieno[2,3-d]pyrimidin-6-yl)methyl)piperidin-3-ol 301

To a solution of 2-chloro-4-morpholinothieno[2,3-d]pyrimidine-6-carbaldehyde, from General Procedure D-2, (200 mg, 0.7 mmol) in 1,2-dichloroethane (4 mL) was added (R)-(+)-3-hydroxypiperidine hydrochloride (1 mmol), and AcOH (0.7 mmol). After the reaction mixture stirred for 10 min at room temperature Na(OAc)₃BH (0.8 mmol) was added. The mixture was stirred overnight at room temperature. The reaction was quenched by the addition of saturated (aq) NaHCO₃.

The organic layer was separated and the aqueous layer was extracted with EtOAc and $CH_2Cl_2$. The combined organics were dried over $Na_2SO_4$ and concentrated in vacuo. The crude material was coupled following General Procedure A with 5-(4,4,5,5-tetramethyl-1,3,2-dioxaborolan-2-yl)pyrimidin-2-amine to provide 301 after reverse phase HPLC purification (5 mg). MS (Q1) 428 (M)+

Example 219

1-((2-(2-aminopyrimidin-5-yl)-4-morpholinothieno [2,3-d]pyrimidin-6-yl)methyl)piperidin-4-ol 302

To a solution of 2-chloro-4-morpholinothieno[2,3-d]pyrimidine-6-carbaldehyde, from General Procedure D-2, (200 mg, 0.7 mmol) in 1,2-dichloroethane (4 mL) was added 4-hydroxypiperidine (1 mmol), and AcOH (0.7 mmol). After the reaction mixture stirred for 10 min at room temperature $Na(OAc)_3BH$ (0.8 mmol) was added. The mixture was stirred overnight at room temperature. The reaction was quenched by the addition of saturated (aq) $NaHCO_3$. The organic layer was separated and the aqueous layer was extracted with EtOAc and $CH_2Cl_2$. The combined organics were dried over $Na_2SO_4$ and concentrated in vacuo. The crude material was coupled following General Procedure A with 5-(4,4,5,5-tetramethyl-1,3,2-dioxaborolan-2-yl)pyrimidin-2-amine to provide 302 after reverse phase HPLC purification (12 mg). MS (Q1) 428 (M)+

Example 220

5-(6-((3-(methylsulfonyl)pyrrolidin-1-yl)methyl)-4-morpholinothieno[2,3-d]pyrimidin-2-yl)pyrimidin-2-amine 303

To a solution of 2-chloro-4-morpholinothieno[2,3-d]pyrimidine-6-carbaldehyde, from General Procedure D-2, (200 mg, 0.7 mmol) in 1,2-dichloroethane (4 mL) was added 3-(methylsulfonyl)pyrrolidine (1 mmol), and AcOH (0.7 mmol). After the reaction mixture stirred for 10 min at room temperature $Na(OAc)_3BH$ (0.8 mmol) was added. The mixture was stirred overnight at room temperature. The reaction was quenched by the addition of saturated (aq) $NaHCO_3$. The organic layer was separated and the aqueous layer was extracted with EtOAc and $CH_2Cl_2$. The combined organics were dried over $Na_2SO_4$ and concentrated in vacuo. The crude material was coupled following General Procedure A with 5-(4,4,5,5-tetramethyl-1,3,2-dioxaborolan-2-yl)pyrimidin-2-amine to provide 303 after reverse phase HPLC purification (148 mg). MS (Q1) 476 (M)+

Example 221

2-(2-methylpyrimidin-5-yl)-morpholino-6-(4-N-methylsulfonyl(piperazin-1-yl)methyl)thieno[2,3-d] pyrimidine 304

To a solution of 6-(4-methanesulfonyl-piperazin-1-ylmethyl)-2-methylsulfanyl-4-morpholin-4-yl-thieno[2,3-d]pyrimidine (104 mg) in 1,2-dimethoxyethane (10 mL) was added 2-methyl-5-tributylstannanyl-pyrimidine (180 mg) (prepared as above) and copper(I)bromide-dimethyl sulfide (96 mg) and the reaction mixture was stirred at room temperature for 10 minutes. Tetrakis(triphenylphosphine)palladium (0) (14 mg) was then added and the reaction mixture was heated at reflux for 16 h. After cooling to room temperature, the mixture was diluted with ethyl acetate (20 mL) and washed with water (2×20 mL) and brine (2×20 mL). The organic phase was dried ($MgSO_4$), reduced in vacuo and purified by column chromatography to give 304. NMR: ($CDCl_3$) 2.67-2.70 (4 H, m), 2.82 (3 H, s, Me), 2.84 (3 H, s, Me), 3.30-3.32 (4 H, m), 3.85 (2 H, s, CH2), 3.91-3.92 (4 H, m), 3.98-4.01 (4 H, m), 7.01 (1 H, s, Ar) and 9.58 (2 H, s, Ar). MS: (ESI+): MH+=490.14

Example 222

2-(2-methylaminopyrimidin-5-yl)-morpholino-6-(4-N-methylsulfonyl(piperazin-1-yl)methyl)thieno[2,3-d]pyrimidine 305

To a solution of 6-(4-methanesulfonyl-piperazin-1-ylmethyl)-2-methylsulfanyl-4-morpholin-4-yl-thieno[2,3-d]pyrimidine (80 mg) in 1,2-dimethoxyethane (10 mL) was added methyl-(5-tributylstannanyl-pyrimidin-2-yl)-amine (143 mg) (prepared as above) and copper(I)bromide-dimethyl sulfide (74 mg) and the reaction mixture was stirred at room temperature for 10 minutes. Tetrakis(triphenylphosphine) palladium (0) (10 mg) was then added and the reaction mixture was heated at reflux for 16 h. After cooling to room temperature, the mixture was diluted with ethyl acetate (20 mL) and washed with water (2×20 mL) and brine (2×20 mL). The organic phase was dried ($MgSO_4$), reduced in vacuo and purified by column chromatography to give 305. NMR: ($CDCl_3$): 2.65-2.68 (4 H, m), 2.82 (3 H, s, Me), 3.12 (3 H, d, J 5.1, Me), 3.29-3.31 (4 H, m), 3.82 (2 H, s, CH2), 3.89-3.90 (4 H, m), 3.94-3.96 (4 H, m), 5.30 (1 H, q, J 5.1, NH), 7.14 (1 H, s, Ar) and 9.30 (2 H, s, Ar). MS: (ESI+): MH+=505.19

Example 223

2-(2-methylpyrimidin-5-yl)-4-morpholino-6-(4-N-methylsulfonyl(piperazin-1-yl)methyl)thieno[3,2-d] pyrimidine 306

To a solution of acetamidine hydrochloride (6.0 g) in ethanol (20 mL) was added sodium ethoxide (20 mL of a 21% solution in ethanol) and the reaction mixture was heated at 50° C. and mucobromic acid (6.82 g) in ethanol (10 mL) was added. After stirring at 50° C. for 1 h, a further portion of sodium ethoxide (10 mL of a 21% solution in ethanol) was added and the mixture was stirred at room temperature for 16 h. The mixture was then filtered and the filtrate reduced in vacuo. The residue was then treated with 2 M aqueous hydrochloric acid (30 mL) and stirred vigorously for 30 minutes. The resulting solid was filtered, washed with water and air dried to give 5-bromo-2-methyl-pyrimidine-4-carboxylic acid (1.46 g). This was then heated at 175° C. for 16 h. After cooling to room temperature the mixture was purified by Kugelrohr distillation to give 5-bromo-2-methyl-pyrimidine as a white solid (746 mg).

To a solution of 5-bromo-2-methyl-pyrimidine (300 mg) in 1,4-dioxane (10 mL) was added bis(tributyltin) (1.75 mL), tetrakis(triphenylphosphine)palladium (0) (100 mg) and lithium chloride (221 mg) and the reaction mixture was heated at reflux for 16 h. After cooling to room temperature, the mixture was filtered through Celite, washing with ethyl acetate. The filtrate was washed with water (2×20 mL), brine (20 mL), dried ($MgSO_4$), reduced in vacuo and purifed by column chromatography to give 2-methyl-5-tributylstannanyl-pyrimidine as a yellow oil.

To a solution of 6-(4-methanesulfonyl-piperazin-1-ylmethyl)-2-methylsulfanyl-4-morpholin-4-yl-thieno[3,2-d]pyrimidine (100 mg) in 1,2-dimethoxyethane (10 mL) was added 2-methyl-5-tributylstannanyl-pyrimidine (176 mg) and copper(I)bromide-dimethyl sulfide (94 mg) and the reaction mixture was stirred at room temperature for 10 minutes. Tetrakis(triphenylphosphine)palladium (0) (13 mg) was then added and the reaction mixture was heated at reflux for 16 h. After cooling to room temperature, the mixture was diluted with ethyl acetate (20 mL) and washed with water (2×20 mL) and brine (2×20 mL). The organic phase was dried (MgSO$_4$), reduced in vacuo and purified by column chromatography to give 306. NMR: (CDCl$_3$) 2.69-2.72 (4 H, m), 2.83 (3 H, s, Me), 2.84 (3 H, s, Me), 3.31-3.34 (4 H, m), 3.90-3.93 (6 H, m), 4.06-4.08 (4 H, m), 7.37 (1 H, Ar) and 9.58 (1 H, Ar). MS: (ESI+): MH+=490.15

Example 224

5-(4-morpholino-6-(4-N-(thiophen-2-yl)sulfonyl (piperazin-1-yl)methyl)thieno[2,3-d]pyrimidin-2-yl) pyrimidin-2-amine 307

To 2-chloro-4-morpholin-4-yl-6-piperazin-1-ylmethyl-thieno[2,3-d]pyrimidine (150 mg) in anhydrous DCM (4 ml) and triethylamine (90 ul) was added 2-thiophenesulfonyl chloride (101 ul) at 0° C. The reaction mixture was allowed to warm up to room temperature over 4 hours. Aqueous work-up and purification on silica gave 2-chloro-4-morpholin-4-yl-6-[4-(thiophene-2-sulfonyl)-piperazin-1-ylmethyl]-thieno[2,3-d]pyrimidine (208 mg).
2-Chloro-4-morpholin-4-yl-6-[4-(thiophene-2-sulfonyl)-piperazin-1-ylmethyl]-thieno[2,3-d]pyrimidine was reacted with 2-aminopyrimidine-5-boronic acid in General Procedure A. Purification on silica yielded 307. NMR (DMSO): 2.53-2.58 (4H, m), 3.20-3.23 (4H, m), 3.74-3.77 (4H, m), 3.80 (2H, s), 3.88-3.91 (4H, m), 7.08 (2H, br), 7.30-7.32 (1H, m), 7.52 (1H, s), 7.65-7.67 (1H, m), 8.08-8.10 (1H, m), 9.08 (2H, s). MS (ESI+): MH+ 559.15 (15%)

Example 225

5-(4-morpholino-6-((4-N-cyclopropylsulfonylpiperazin-1-yl)methyl)thieno[2,3-d]pyrimidin-2-yl)pyrimidin-2-amine 308

2-chloro-4-morpholinothieno[2,3-d]pyrimidine-6-carbaldehyde from General Procedure B-3 (1.00 g) was reacted with tert-butyl-1-piperazine carboxylate (0.85 g) in General Procedure Z. Aqueous work-up and purification on silica gave 4-(2-chloro-4-morpholin-4-yl-thieno[2,3-d]pyrimidine-6-ylmethyl0-piperazine-1-carboxylic acid tert-butyl ester (1.61 g).
4-(2-Chloro-4-morpholin-4-yl-thieno[2,3-d]pyrimidine-6-ylmethyl0-piperazine-1-carboxylic acid tert-butyl ester (1.61 g) was treated with an excess of hydrogen chloride in diethyl ether at room temperature overnight. Removal of volatiles and basification with aqueous sodium hydrogen chloride afforded 2-chloro-4-morpholin-4-yl-6-piperazin-1-ylmethyl-thieno[2,3-d]pyrimidine (0.90 g).
To 2-chloro-4-morpholin-4-yl-6-piperazin-1-ylmethyl-thieno[2,3-d]pyrimidine (187 mg) in anhydrous DCM (5 ml) and triethylamine (111 ul) was added cyclopropanesulfonyl chloride (65 ul) at 0° C. The reaction mixture was allowed to warm up to room temperature over 4 hours. Aqueous work-up and purification on silica gave 2-chloro-4-morpholin-4-yl-6-[4-(cyclopropane-2-sulfonyl)-piperazin-1-ylmethyl]-thieno[2,3-d]pyrimidine (159 mg).
2-Chloro-4-morpholin-4-yl-6-[4-(cyclopropane-2-sulfonyl)-piperazin-1-ylmethyl]-thieno[2,3-d]pyrimidine was reacted with 2-aminopyrimidine-5-boronic acid in General Procedure A. Purification on silica yielded 308. NMR (DMSO): 0.90-0.92 (2H, m), 0.97-1.00 (2H, m), 2.53-2.58 (4H, m), 2.60-2.64 (1H, m), 3.20-3.23 (4H, m), 3.74-3.77 (4H, m), 3.80 (2H, s), 3.88-3.91 (4H, m), 7.08 (2H, br), 7.52 (1H, s), 9.08 (2H, s). MS (ESI+): MH+ 517.22 (50%)

Example 226

2-(1-((2-(2-aminopyrimidin-5-yl)-4-morpholinothieno[3,2-d]pyrimidin-6-yl)methyl)piperidin-4-ylsulfonyl)-N,N-dimethylacetamide 309

To sodium chloride (60% wt. suspension in mineral oil, 108 mg) in dry DMF (5 ml) was added methyl thioglycolate (160ul) dropwise at 0° C. After 30 minutes added 4-methanesulfonyl-piperidine-carboxylic acid tert-butyl ester (500 mg) as a solution in DMF (1.5 ml) and the reaction mixture was warmed up to room temperature over 5 hours. Aqueous work-up and purification on silica yielded 4-methoxycarbonylmethylsulfanyl-piperidine-1-carboxylic acid tert-butyl ester (414 mg).
To 4-methoxycarbonylmethylsulfanyl-piperidine-1-carboxylic acid tert-butyl ester (414 mg) in chloroform (5 ml) was added meta-chloroperbenzoic acid (MCPBA, 796 mg) and the reaction mixture was stirred at room temperature overnight. Aqueous work-up and purification on silica gave 4-methoxycarbonylmethylsulfonyl-piperidine-1-carboxylic acid tert-butyl ester (254 mg). 4-Methoxycarbonylmethylsulfonyl-piperidine-1-carboxylic acid tert-butyl ester (238 mg) was reacted with excess of dimethylamine solution in MeOH (2.0M, 7 ml) at room temperature overnight. Removal of volatiles afforded 4-N,N-dimethylamino-carbonylmethylsulfonyl-piperidine-1-carboxylic acid tert-butyl ester (280 mg), which was treated with excess of hydrogen chloride solution in diethyl ether (2.0M, 3 ml) at room temperature overnight to give 4-N,N-dimethylamino-carbonylmethylsulfonyl-piperidine HCl salt (209 mg).
4-N,N-dimethylamino-carbonylmethylsulfonyl-piperidine HCl salt (101 mg) was reacted with Intermediate D (120 mg) in General Procedure Z. Aqueous work-up and purification on silica yielded 2-[1-(chloro-4-morpholin-4-yl-thieno[3,2-d]pyrimidin-6-ylmethyl)piperidine-4-sulfonyl]-N,N-dimethyl-acetamide (110 mg).
2-[1-(Chloro-4-morpholin-4-yl-thieno[3,2-d]pyrimidin-6-ylmethyl)piperidine-4-sulfony]-N,N-dimethyl-acetamide was reacted with 2-aminopyrimidine-5-boronic acid in General Procedure A. Purification on silica yielded 309. NMR (CDCl3): 1.98-2.08 (2H, m), 2.18-2.28 (4H, m), 3.04 (3H, s), 3.13-3.17 (2H, m), 3.22 (3H, s), 3.45-3.53 (1H, m), 3.85 (2H, s), 3.90-3.93 (4H, m), 4.03-4.06 (4H, m), 4.08 (2H, s), 5.20 (2H, br), 7.27 (1H, s), 9.30 (2H, s). MS (ESI+): MH+ 561.20 (100%)

Example 227

5-(4-morpholino-6-((4-(thiazol-2-ylsulfonyl)piperidin-1-yl)methyl)thieno[3,2-d]pyrimidin-2-yl)pyrimidin-2-amine 310

To 4-hydroxy-piperidine-1-carboxylic acid tert-butyl ester (9.2 g) in dichloromethane (170 ml), stirring at 0° C. was added methane sulphonyl chloride (5.33 ml) and triethylamine (0.24 ml). The reaction mixture was slowly warmed to room temperature and stirred overnight. The reaction mixture was partitioned between chloroform and water. The combined organics were washed with brine and dried (MgSO$_4$).

The solvent was removed in vacuo to yield 14 g of 4-methanesulfonyl-piperidine-carboxylic acid tert-butyl ester.

To sodium chloride (60% wt. suspension in mineral oil, 108 mg) in dry DMF (5 ml) was added 1,3-thiazole-2-thiol (315 mg) at 0° C. After 30 minutes added 4-methanesulfonyl-piperidine-carboxylic acid tert-butyl ester (500 mg) as a solution in DMF (2 ml) and the reaction mixture was warmed up to room temperature overnight, then heated at 50° C. for 3 hours. Aqueous work-up and purification on silica yielded 4-(thiazol-2-ylsulfanyl)-piperidine-1-carboxylic acid tert-butyl ester (174 mg).

4-(Thiazol-2-ylsulfanyl)-piperidine-1-carboxylic acid tert-butyl ester (172 mg) was treated with MCPBA (311 mg) in chloroform (5 ml) at room temperature for 7 hours. DCM/aqueous NaHCO$_3$ extraction and purification on silica gave 4-(thiazol-2-ylsulfonyl)-piperidine-1-carboxylic acid tert-butyl ester (166 mg), which was treated with excess of hydrogen chloride solution in diethyl ether (2.0M, 3 ml) at room temperature overnight to give 4-(thiazole-2-sulfonyl)-piperidine HCl salt (126 mg).

4-(Thiazole-2-sulfonyl)-piperidine HCl salt (124 mg) was reacted with Intermediate D (130 mg) in General Procedure Z. Aqueous work-up, purification on silica and trituration with hot ethyl acetate yielded 2-chloro-4-morpholin-4-yl-6-[4(thiazole-2-sulfonyl)-piperidin-1-ylmethyl]-thieno[3,2-d]pyrimidine (73 mg).

2-Chloro-4-morpholin-4-yl-6-[4(thiazole-2-sulfonyl)-piperidin-1-ylmethyl]-thieno[3,2-d]pyrimidine was reacted with 2-aminopyrimidine-5-boronic acid in General Procedure A. Purification on silica yielded 310. NMR (CDCl3): 2.03-2.18 (4H, m), 2.18-2.22 (2H, m), 3.12-3.16 (2H, m), 3.39-3.46 (1H, m), 3.84 (2H, s), 3.90-3.93 (4H, m), 4.03-4.06 (4H, m), 5.20 (2H, br), 7.26 (1H, s), 7.79 (1H, d, J=3.0), 8.11 (1H, d, J=3.0), 9.29 (2H, s). MS (ESI+): MH+ 559.13 (100%)

Example 228

4-(4-morpholino-6-((4-N-methylsulfonylpiperazin-1-yl)methyl)thieno[3,2-d]pyrimidin-2-yl)pyridine-2,6-diamine 311

2-Chloro-4-morpholino-6-((4-N-methylsulfonylpiperazin-1-yl)methyl)thieno[3,2-d]pyrimidine was reacted with 2,6-difluoropyridine-4-boronic acid in General Procedure A. Purification on silica yielded 2-(2,6-difluoro-pyridin-4-yl)-6-(4-methanesulfonyl-piperazin-1-ylmethyl)-4-morpholin-4-yl-thieno[3,2-d]pyrimidine.

2-(2,6-Difluoro-pyridin-4-yl)-6-(4-methanesulfonyl-piperazin-1-ylmethyl)-4-morpholin-4-yl-thieno[3,2-d]pyrimidine (107 mg) was heated in ammonia hydroxide (90 ml) in a sealed stainless steel pressurized vessel at 150° C. for 6 days. Extraction into chloroform and purification on reversed phase silica HPLC afforded 311. NMR (CDCl3): 2.67-2.71 (4H, m), 2.81 (3H, s), 3.29-3.33 (4H, m), 3.89 (2H, s), 3.89-3.93 (4H, m), 4.08-4.12 (4H, m), 4.35 (4H, br s), 6.93 (2H, s), 7.35 (1H, s). MS (ESI+): MH+ 505.15 (70%)

Example 229

5-(6-((4-((methylsulfonyl)methylsulfonyl)piperidin-1-yl)methyl)-4-morpholinothieno[3,2-d]pyrimidin-2-yl)pyrimidin-2-amine 312

To 2-chloro-4-morpholino-6-((piperazin-1-yl)methyl)thieno[3,2-d]pyrimidine (54 mg) in DCM (2 ml) and triethylamine (44 ul) was added methylsulfonylmethylsulfonyl chloride (45 ul) at 0° C. The reaction mixture was allowed to warm up to room temperature overnight. Aqueous work-up and purification on silica gave 2-chloro-6-(4-methanesulfonylmethanesulfonyl-piperazin-1-ylmethyl)-4-morpholin-4-yl-thieno[3,2-d]pyrimidine (35 mg).

2-Chloro-6-(4-methanesulfonylmethanesulfonyl-piperazin-1-ylmethyl)-4-morpholin-4-yl-thieno[3,2-d]pyrimidine was reacted with 2-aminopyrimidine-5-boronic acid in General Procedure A. Purification on silica yielded 312. NMR (CDCl3): 2.67-2.70 (4H, m), 3.24 (3H, s), 3.49-3.54 (4H, m), 3.90 (2H, s), 3.90-3.93 (4H, m), 4.03-4.06 (4H, m), 4.42 (2H, s), 5.24 (2H, br s), 7.30 (1H, s), 9.30 (2H, s). MS (ESI+): MH+ 569.17 (100%)

Example 230

2-(2-methylaminopyrimidin-5-yl)-morpholino-6-(4-N-methylsulfonyl(piperazin-1-yl)methyl)thieno[3,2-d]pyrimidine 313

To a solution of 5-bromo-2-(methylamino)pyrimidine (200 mg) in 1,4-dioxane (10 mL) was added bis(tributyltin) (1.07 mL), tetrakis(triphenylphosphine)palladium (0) (61 mg) and lithium chloride (135 mg) and the reaction mixture was heated at reflux for 16 h. After cooling to room temperature, the mixture was filtered through Celite, washing with ethyl acetate. The filtrate was washed with water (2×20 mL), brine (20 mL), dried (MgSO$_4$), reduced in vacuo and purifed by column chromatography to give methyl-(5-tributylstannanyl-pyrimidin-2-yl)-amine as a yellow oil.

To a solution of 6-(4-methanesulfonyl-piperazin-1-ylmethyl)-2-methylsulfanyl-4-morpholin-4-yl-thieno[3,2-d]pyrimidine (80 mg) in 1,2-dimethoxyethane (10 mL) was added methyl-(5-tributylstannanyl-pyrimidin-2-yl)-amine (143 mg) and copper(I)bromide-dimethyl sulfide (74 mg) and the reaction mixture was stirred at room temperature for 10 minutes. Tetrakis(triphenylphosphine)palladium (0) (10 mg) was then added and the reaction mixture was heated at reflux for 16 h. After cooling to room temperature, the mixture was diluted with ethyl acetate (20 mL) and washed with water (2×20 mL) and brine (2×20 mL). The organic phase was dried (MgSO$_4$), reduced in vacuo and purified by column chromatography to give 313. NMR: (CDCl$_3$): 2.59-2.61 (4 H, m), 2.73 (3 H, s, Me), 3.01 (3 H, d, J 5.1, Me), 3.21-3.24 (4 H, m), 3.78-3.81 (6 H, m), 3.93-3.96 (4 H, m), 7.22 (1 H, s, Ar) and 9.21 (2 H, s, Ar). MS: (ESI+): MH+ 505.20

Example 231

4-(4-morpholino-6-((4-N-methylsulfonylpiperazin-1-yl)methyl)thieno[3,2-d]pyrimidin-2-yl)pyridin-2-amine 314

2-Chloro-4-morpholino-6-((4-N-methylsulfonylpiperazin-1-yl)methyl)thieno[3,2-d]pyrimidine was reacted with 2-fluoropyridine-4-boronic acid in General Procedure A. Purification on silica yielded 2-(2-fluoro-pyridin-4-yl)-6-(4-methanesulfonyl-piperazin-1-ylmethyl)-4-morpholin-4-yl-thieno[3,2-d]pyrimidine.

2-(2-Fluoro-pyridin-4-yl)-6-(4-methanesulfonyl-piperazin-1-ylmethyl)-4-morpholin-4-yl-thieno[3,2-d]pyrimidine (107 mg) was heated in ammonia hydroxide (90 ml) in a sealed stainless steel pressurized vessel at 150° C. for 5 days. Extraction into chloroform and purification on silica afforded 314 (57 mg). NMR (CDCl3): 2.67-2.71 (4H, m), 2.81 (3H, s), 3.29-3.33 (4H, m), 3.89 (2H, s), 3.89-3.93 (4H, m), 4.08-4.12

(4H, m), 4.55 (2H, br s), 7.36 (1H, s), 7.54 (1H, s), 7.65 (1H, d, J=5.3), 8.21 (1H, d, J=5.3). MS (ESI+): MH+ 490.16 (74%)

Example 232

N-((2-(2-aminopyrimidin-5-yl)-4-morpholinothieno [3,2-d]pyrimidin-6-yl)methyl)-N-methyl(N-1-isopropyl)piperidin-4-amine 315

(2-Chloro-4-morpholin-4-yl-thieno[3,2-d]pyrimidin-6-ylmethyl)-methylamine was made by treating 2-chloro-4-morpholin-4-yl-thieno[3,2-d]pyrimidine-6-carbaldehyde 10 (Example 3) and 40% methylamine in water according to the General Procedure B-4.

(2-Chloro-4-morpholin-4-yl-thieno[3,2-d]pyrimidin-6-ylmethyl)-(1-isopropyl-piperidin-4-yl)-methyl-amine was made in an analogous manner by treating (2-chloro-4-morpholin-4-yl-thieno[3,2-d]pyrimidin-6-ylmethyl)-methyl-amine and 1-isopropyl-4-piperidone according to the General Procedure B-4.

A suspension of (2-chloro-4-morpholin-4-ylthieno[3,2-d] pyrimidin-6-ylmethyl)-(1-isopropyl-piperidin-4-yl)-methylamine (61 mg, 0.144 mmol), 5-(4,4,5,5-tetramethyl-[1,3,2] dioxaborolan-2-yl)-pyrimidin-2-ylamine (37 mg, 0.17 mmol), 1M Na$_2$CO$_3$ (0.5 ml, 0.5 mmol) and Pd(PPh$_3$)$_2$Cl$_2$ (10 mg, 0.014 mmol) in acetonitrile was heated in a microwave at 140° C. for 25 mins. The reaction was then acidified with 2N HCl (aq) extracted with ethyl acetate, the water layer separated and basified with K$_2$CO$_3$ (sat. aq) resulting in an impure precipitate which was purified on alumina using 5% methanol in dichloromethane as the eluent to give 315 (11 mg, 16%). NMR (CDCl3, 400 MHz), 1.05 (6H, d, J=6.8), 1.60-1.69 (2H, m), 1.72-1.76 (2H, m), 2.08-2.15 (2H, m), 2.37 (3H, s), 2.48-2.54 (1H, m), 2.71-2.76 (1H, m), 2.95-3.00 (2H, m), 3.89 (4H, t, J=4.4), 3.99 (2H, s), 4.05 (4H, t, J=4.8), 5.2 (2H, s), 7.27 (1H, s), 9.30 (2H, s). MS: (ESI+): MH+=483.

Example 233

5-(7-Methyl-6-4(2R,6S)-2,6-dimethyl-(4-N-methylsulfonyl)piperazin-1-yl)methyl)-4-morpholinothieno [3,2-d]pyrimidin-2-yl)pyrimidin-2-amine 316

To a mixture of cis-2,6-dimethylpiperazine and triethylamine in DCM at 0° C. was added dropwise methanesulphonyl chloride and the reaction mixture stirred at room temperature overnight. After quenching with water, extraction into DCM and being washed with brine, the organics were dried and the solvent removed under reduced pressure to yield 1-Methanesulfonyl-piperazine as a pale yellow solid.

To a suspension of 2-chloro-7-methyl-4-morpholinothieno [3,2-d]pyrimidine-6-carbaldehyde (400 mg, 1.34 mmol) in methanol at 0° C. was added sodium borohydride. After stirring for 2 hours, the mixture was quenched with 50:50 H$_2$O: NaHCO$_3$ (sat. aq). The methanol was removed under reduced pressure to give a suspension which was filtered and washed with H$_2$O followed by ether to give (2-Chloro-7-methyl-4-morpholin-4-yl-thieno[3,2-d]pyrimidin-6-yl)-methanol.

To a stirring suspension (2-chloro-7-methyl-4-morpholin-4-yl-thieno[3,2-d]pyrimidin-6-yl)-methanol in toluene at 40° C. was added PBr$_3$ and the reaction mixture stirred at 100° C. overnight. DCM/saturated aqueous NaHCO$_3$ extraction of the cooled mixture gave 6-Bromomethyl-2-chloro-7-methyl-4-morpholin-4-yl-thieno[3,2-d]pyrimidine.

To a mixture of 1-methanesulfonyl-piperazine and 6-bromomethyl-2-chloro-7-methyl-4-morpholin-4-yl-thieno[3,2-d]pyrimidine in acetonitrile was added potassium carbonate and the mixture refluxed overnight. After cooling to room temperature, the acetonitrile was removed under reduced pressure. DCM/sat. aq. NaHCO$_3$ extraction and purification on silica gave 2-Chloro-6-((2S,6R)-4-methanesulfonyl-2,6-dimethyl-piperazin-1-ylmethyl)-7-methyl-4-morpholin-4-yl-thieno[3,2-d]pyrimidine.

2-Chloro-6-((2S,6R)-4-methanesulfonyl-2,6-dimethyl-piperazin-1-ylmethyl)-7-methyl-4-morpholin-4-yl-thieno[3,2-d]pyrimidine (135 mg, 0.29 mmol) was reacted with 2-amino-pyrimidine-5-boronic acid pinacol ester (88 mg, 0.4 mmol) in General Procedure A. After extraction into 2M HCl, the mixture was washed with ethyl acetate then basified and the precipitate collected by filtration. Purification using a thiourea SPE cartridge gave 316 as a cream solid (90 mg, 0.17 mmol) NMR (CDCl3, 400 MHz), 9.25 (s, 2H); 5.12 (s, 2H); 3.95 (t, 4H, J=4.6 Hz); 3.95 (s, 2H); 3.82 (t, 4H, J=4.8 Hz); 3.51 (d, 2H, J=11.3 Hz); 2.82 (m, 2H); 2.74 (s, 3H); 2.55 (t, 2H, J=10.8 Hz); 2.33 (s, 3H); 1.06 (d, 6H, J=6.3 Hz). MS: (ESI+): MH+ 533.30

Example 234

1-((2-(2-aminopyrimidin-5-yl)-4-morpholinothieno [3,2-d]pyrimidin-6-yl)methyl)-4-(4-chlorophenyl) piperidin-4-ol 317

To 4-(4-chlorophenyl)-4-hydroxypiperidine (368 mg, 1.74 mmol) in dichloroethane was added 2-chloro-4-morpholin-4-yl-thieno[3,2-d]pyrimidine-6-carbaldehyde 10 from Example 3 (400 mg, 1.41 mmol) and trimethylorthoformate. After stirring for 1 hour at room temperature, sodium triacetoxyborohydride was added and the reaction mixture stirred overnight. The mixture was quenched with saturated aqueous Na$_2$CO$_3$. Chloroform/brine extraction gave crude material which was then triturated with hot ethyl acetate to give 1-(2-Chloro-4-morpholin-4-yl-thieno[3,2-d]pyrimidin-6-ylmethyl)-4-(4-chloro-phenyl)-piperidin-4-ol. (272 mg, 0.56 mmol).

1-(2-Chloro-4-morpholin-4-yl-thieno[3,2-d]pyrimidin-6-ylmethyl)-4-(4-chloro-phenyl)-piperidin-4-ol (146 mg, 0.3 0 mmol) was reacted with 2-amino-pyrimidine-5-boronic acid pinacol ester (94 mg, 0.45 mmol) in General Procedure A. After extraction into 2M HCl, the mixture was washed with EtOAc then basified and the precipitate collected by filtration. Purification on silica gave 317 as a pale yellow solid (75 mg, 0.14 mmol). NMR (CD$_3$OD, 400 MHz), 9.19 (s, 2H); 7.52 (m, 2H); 7.39 (s, 1H), 7.35 (m, 2H); 4.08 (t, 411, J=4.1 Hz); 3.97 (s, 2H); 3.89 (t, 4H, J=4.8 Hz); 2.87 (d, 2H); 2.70 (t, 2H, J=11.2 Hz); 2.18 (m, 2H); 1.77 (d, 2H, J=13.2 Hz). MS: (ESI+): MH+=538.27

Example 235

2-(2-(methylthio)pyrimidin-5-yl)-4-morpholino-6-((4-N-methylsulfonylpiperazin-1-yl)methyl)thieno[3, 2-d]pyrimidine 318

Following the General Procedures herein, 318 was prepared. MS: (ESI+): MH+

Example 236

5-(6-((4-(methylsulfonyl)piperazin-1-yl)methyl)-4-morpholinothieno[2,3-d]pyrimidin-2-yl)-4-(trifluoromethyl)pyrimidin-2-amine 319

A mixture of 2-chloro-6-(4-methanesulfonyl-piperidin-1-ylmethyl)-4-morpholin-4-yl-thieno[2,3-d]pyrimidine (100 mg), 1M Na₂CO₃ (0.7 mL), 5-(4,4,5,5-tetramethyl-[1,3,2]dioxaborolan-2-yl)-4-trifluoromethyl-pyrimidin-2-ylamin (1.5 eq.) [WO 2007/084786] and bis(triphenylphosphine)palladium (II) chloride (0.05 eq.) in MeCN (1.5 mL) was heated at 140° C. for 25 min. in microwave. The resulting mixture was diluted with water then extracted with ethyl acetate. Combined extracts were dried (Na₂SO₄), filtered and concentrated then purified by preparative HPLC to give 319 (19 mg). NMR: (CDCl₃): 2.58-2.60 (m, 4H, 2×CH2), 2.73 (s, 3H, CH3), 3.21-3.22 (m, 4H, 2×CH), 3.75 (s, 2H, CH2), 3.76-3.78 (m, 4H, 2×CH2), 3.85-3.88 (m, 4H, 2×CH2), 5.34 (sbr, 2H, NH2), 7.10 (s, H, ArH), 8.90 (s, H, ArH). MS: (ESI+): MH+=559.28

Example 237

5-(6-((methyl(piperidin-4-ylmethyl)amino)methyl)-4-morpholinothieno[3,2-d]pyrimidin-2-yl)pyrimidin-2-amine 320

Reaction between (2-chloro-4-morpholin-4-yl-thieno[3,2-d]pyrimidin-6-ylmethyl)-methyl-amine (described above) and 4-formyl-piperidine-1-carboxylic acid tert-butyl ester using standard reductive amination conditions yielded 4-{[(2-chloro-4-morpholin-4-yl-thieno[3,2-d]pyrimidin-6-ylmethyl)-methyl-amino]-methyl}-piperidine-1-carboxylic acid tert-butyl ester, which was reacted with 2-aminopyrimidine-5-boronic acid in General Procedure A, followed by treatment with HCl to cleave the BOC group to yield 320. 400 MHz 1H NMR CDCl3: 9.21 (s, 2H); 7.18 (s, 1H); 5.18 (brs, NH2); 3.96 (t, 4H, J=4.7 HZ); 3.81 (t, 4H, J=4.7 Hz); 3.71 (s, 2H, CH2); 3.01 (d, 2H, J=12.2 Hz); 2.56-1.50 (m, 2H); 2.23 (m, 5H, CH2&Me); 1.73 (d, 2H, J=12.8 Hz); 1.65-1.50 (m, 1H); 1.07-0.97 (m, 2H). LC-MS (m+1)=455.34

Example 238

5-(6-((methyl(1-methylpiperidin-4-yl)amino)methyl)-4-morpholinothieno[2,3-d]pyrimidin-2-yl)-4-(trifluoromethyl)pyrimidin-2-amine 321

(2-Chloro-4-morpholin-4-yl-thieno[2,3-d]pyrimidin-6-ylmethyl)-methyl-(1-methyl-piperidin-4-yl)-amine (100 mg), 1M Na₂CO₃ (0.7 mL), 5-(4,4,5,5-tetramethyl-[1,3,2]dioxaborolan-2-yl)-4-trifluoromethyl-pyrimidin-2-ylamin (1.5 eq.) [WO 2007/084786] and bis(triphenylphosphine)palladium (II) chloride (0.05 eq.) in MeCN (15 mL) was heated at 140° C. for 25 min. in microwave. The resulting mixture was diluted with water then extracted with ethyl acetate. Combined extracts were dried (Na₂SO₄), filtered and concentrated then purified by preparative HPLC to give 321 (45 mg). NMR: (CDCl₃): 1.2 (s, 2H, CH2), 1.57-1.65 (m, 2H, CH2), 1.72-1.74 (m, 2H, CH2), 1.87-1.92 (m, 2H, CH2), 2.21 (s, 3H, CH3), 2.26 (s, 3H, CH3), 2.54 (m, H, CH), 2.85-2.87 (m, 2H, CH2), 3.76-3.78 (m, 4H, 2×CH2), 3.84-3.86 (m, 4H, 2×CH2), 5.34 (sbr, 2H, NH2), 7.06 (s, H, ArH), 8.91 (s, H, ArH). MS: (ESI+): MH+=523.35

Example 239 tert-butyl 4-((2-(2-aminopyrimidin-5-yl)-7-methyl-4-morpholinothieno[3,2-d]pyrimidin-6-yl)methyl)piperazine-1-carboxylate 322

Following the General Procedures herein, 322 was prepared. MS: (ESI+): MH+=527

Example 240

5-(7-methyl-4-morpholino-6-(piperazin-1-ylmethyl)thieno[3,2-d]pyrimidin-2-yl)-4-(trifluoromethyl)pyrimidin-2-amine 323

4-(2-Chloro-7-methyl-4-morpholin-4-yl-thieno[3,2-d]pyrimidin-6-ylmethyl)-piperazine-1-carboxylic acid tert-butyl ester (200 mg), prepared as in Example 118, was coupled to 5-(4, 4,5,5-tetramethyl-[1,3,2]dioxaborolan-2-yl)-4-trifluoromethyl-pyrimidin-2-ylamine via General Procedure A to yield 30 mg of 4-[2-(2-Amino-4-trifluoromethyl-pyrimidin-5-yl)-7-methyl-4-morpholin-4-yl-thieno[3,2-d]pyrimidin-6-ylmethyl]-piperazine-1-carboxylic acid tert-butyl ester.

A mixture of 30 mg of 4-[2-(2-Amino-4-trifluoromethyl-pyrimidin-5-yl)-7-methyl-4-morpholin-4-yl-thieno[3,2-d]pyrimidin-6-ylmethyl]-piperazine-1-carboxylic acid tert-butyl ester in 4.0 M of hydrogen chloride in 1,4-dioxane was stirred for 1 h. The mixture was evaporated. The product was purified by reverse phase HPLC to yield 6 mg of 323. MS (Q1) 495.2 (M)⁺.

Example 241

(S)-1-(4-((2-(2-Amino-4-methylpyrimidin-5-yl)-4-morpholinothieno[3,2-d]pyrimidin-6-yl)methyl)piperazin-1-yl)-2-hydroxypropan-1-one 324

4-methyl-5-(4,4,5,5-tetramethyl (1,3,2-dioxaborolan-2-yl))pyrimidine-2-ylamine was prepared according to WO2007/084786. 110 mg of 1-[4-(2-Chloro-4-morpholin-4-yl-thieno[3,2-d]pyrimidin-6-ylmethyl)-piperazin-1-yl]-2-hydroxypropan-1-one was coupled to 4-methyl-5-(4,4,5,5-tetramethyl (1,3,2-dioxaborolan-2-yl))pyrimidine-2-ylamine via General Procedure A to yield 50 mg of 324. MS (Q1) 499.2 (M)⁺.

Example 242

(S)-1-(4-((2-(2-Amino-4-(trifluoromethyl)pyrimidin-5-yl)-7-methyl-4-morpholinothieno[3,2-d]pyrimidin-6-yl)methyl)piperazin-1-yl)-2-hydroxypropan-1-one 325

5-(4,4,5,5-Tetramethyl-[1,3,2]dioxaborolan-2-yl)-4-trifluoromethyl-pyrimidin-2-ylamine was prepared according to WO2007/084786. 110 mg of 1-[4-(2-Chloro-7-methyl-4-morpholin-4-yl-thieno[3,2-d]pyrimidin-6-ylmethyl)-piperazin-1-yl]-2-hydroxy-propan-1-one, prepared as in Example 118, was coupled to 5-(4, 4,5,5-Tetramethyl-[1,3,2]dioxaborolan-2-yl)-4-trifluoromethyl-pyrimidin-2-ylamine via General Procedure A to yield 20 mg of 325 MS (Q1) 567.2 (M)⁺.

Example 243

1-(4-((2-(2-Amino-4-methylpyrimidin-5-yl)-7-methyl-4-morpholinothieno[3,2-d]pyrimidin-6-yl)methyl)piperazin-1-yl)-2-hydroxy-2-methylpropan-1-one 326

1-[4-(2-Chloro-4-morpholin-4-yl-thieno[3,2-d]pyrimidin-6-ylmethyl)-piperazin-1-yl]-2-hydroxy-2-methyl-propan-1-one (200 mg), prepared as in Example 118, was coupled to 4-methyl-5-(4,4,5,5-tetramethyl (1,3,2-dioxaborolan-2-yl))pyrimidine-2-ylamine via General Procedure A to yield 133 mg of 326. MS (Q1) 527.2 (M)+.

Example 244

5-(6-((4-(methylsulfonyl)piperazin-1-yl)methyl)-4-morpholinothieno[3,2-d]pyrimidin-2-yl)-4-(trifluoromethyl)pyrimidin-2-amine 327

2-Chloro-6-(4-methanesulfonyl-piperazin-1-ylmethyl)-4-morpholin-4-yl-thieno[3,2-d]pyrimidine (200 mg), prepared via General Procedure B-3, was coupled to 5-(4,4,5,5-tetramethyl-[1,3,2]dioxaborolan-2-yl)-4-trifluoromethyl-pyrimidin-2-ylamine via General Procedure A to yield 20 mg of 327. MS (Q1) 559.2 (M)+.

Example 245

5-(6-((4-((2-methyl-1H-imidazol-1-yl)methyl)piperidin-1-yl)methyl)-4-morpholinothieno[3,2-d]pyrimidin-2-yl)pyrimidin-2-amine 328

2-Chloro-4-morpholin-4-yl-thieno[3,2-d]pyrimidine-6-carboxaldehyde 10 was reacted with 4-(2-methyl-imidazol-1-ylmethyl)-piperidine, dihydrochloride salt using standard reductive amination conditions. The resulting crude solid was purified on silica using a gradient of 0%-40% methanol in ethyl acetate as the eluent to give 2-chloro-6-[4-(2-methyl-imidazol-1-ylmethyl)-piperidin-1-ylmethyl]-4-morpholin-4-yl-thieno[3,2-d]pyrimidine as a pure white solid (27% yield), which was reacted with 5-(4,4,5,5-tetramethyl-[1,3,2]dioxaborolan-2-yl)-pyrimidin-2-ylamine according to General Procedure A. The resulting solid was triturated with methanol to give 328 as an off white solid (62% yield). NMR (CDCl3, 400 MHz), 1.32-1.46 (2H, m), 1.65 (2H, d, J=11.6), 1.69-1.75 (1H, m), 2.08 (2H, t, J=11.2), 2.39 (3H, s), 3.01 (2H, d, J=11.2), 3.75 (2H, d, J=7.2), 3.82 (2H, s), 3.89-3.91 (4H, m), 4.03-4.06 (4H, m), 5.22 (2H, br s), 6.80 (1H, s), 6.93 (1H, s), 9.30 (2H, s). MS: (ESI+): MH+=506

Example 246

5-(4-morpholino-6-((4-(morpholinomethyl)piperidin-1-yl)methyl)thieno[3,2-d]pyrimidin-2-yl)pyrimidin-2-amine 329

2-Chloro-4-morpholin-4-yl-thieno[3,2-d]pyrimidine-6-carboxaldehyde 10 was reacted with 4-piperidin-4-ylmethyl-morpholine, dihydrochloride salt using standard reductive amination conditions. The resulting crude solid was purified on silica using a gradient of 0%-40% methanol in ethyl acetate as the eluent to give 2-chloro-4-morpholin-4-yl-6-(4-morpholin-4-ylmethyl-piperidin-1-ylmethyl)-thieno[3,2-d]pyrimidine as a white solid (43% yield), which was reacted with 5-(4,4,5,5-tetramethyl-[1,3,2]dioxaborolan-2-yl)-pyrimidin-2-ylamine according to General Procedure A. The resulting solid was triturated with methanol to give 329 as an off white solid (88% yield). NMR (CDCl3, 400 MHz), 1.26-1.34 (2H, m), 1.78 (2H, d, J=11.9), 2.09 (2H, t, J=10.8), 2.21 (2H, d, J 7.2), 2.38-2.43 (4H, m), 2.99 (2H, d, J=11.3), 3.70-3.73 (4H, m), 3.82 (2H, s), 3.88-3.90 (4H, m), 4.03-4.06 (4H, m), 5.21 (2H, br s), 7.28 (1H, s), 9.30 (2H, s). MS: (ESI+): MH+=511

Example 247

5-(4-morpholino-6-((4-(piperidin-1-ylmethyl)piperidin-1-yl)methyl)thieno[3,2-d]pyrimidin-2-yl)pyrimidin-2-amine 330

2-Chloro-4-morpholin-4-yl-thieno[3,2-d]pyrimidine-6-carboxaldehyde 10 was reacted with 1-(piperidin-4-ylmethyl)piperidine using standard reductive amination conditions. The resulting crude solid was triturated with methanol to give 2-chloro-4-morpholin-4-yl-6-(4-piperidin-1-ylmethyl-piperidin-1-ylmethyl)-thieno[3,2-d]pyrimidine, which was reacted with 5-(4,4,5,5-tetramethyl-[1,3,2]dioxaborolan-2-yl)-pyrimidin-2-ylamine according to General Procedure A. The resulting solid was triturated with methanol to give 330 as an off white solid (23% yield). NMR (CDCl3, 400 MHz), 1.27-1.31 (3H, m), 1.42-1.46 (2H, m), 1.50-1.56 (4H, m), 1.77 (2H, d, J=13.1), 2.09 (2H, t, J=11.2), 2.15 (2H, d, J=7.1), 2.30-2.35 (4H, m), 2.97 (2H, d, J=10.9), 3.82 (2H, s), 3.88-3.91 (4H, m), 4.03-4.06 (4H, m), 5.21 (1H, br s), 7.27 (1H, s), 9.30 (2H, s). MS: (ESI+): MH+=509

Example 248

5-(4-morpholino-6-((4-(pyrrolidin-1-ylmethyl)piperidin-1-yl)methyl)thieno[3,2-d]pyrimidin-2-yl)pyrimidin-2-amine 331

2-Chloro-4-morpholin-4-yl-thieno[3,2-d]pyrimidine-6-carboxaldehyde 10 was reacted with 4-pyrrolidin-1-ylmethyl-piperidine, dihydrochloride salt using standard reductive amination conditions. The resulting crude solid was triturated with methanol to give 2-chloro-4-morpholin-4-yl-6-(4-pyrrolidin-1-ylmethyl-piperidin-1-ylmethyl)-thieno[3,2-d]pyrimidine as an off white solid (63% yield), which was reacted with 5-(4,4,5,5-tetramethyl-[1,3,2]dioxaborolan-2-yl)-pyrimidin-2-ylamine according to General Procedure A. The resulting solid was triturated with methanol to give 331 as an off white solid (84% yield). NMR (CDCl3, 400 MHz), 1.28-1.36 (2H, m), 1.48-1.52 (1H, m), 1.77-1.82 (6H, m), 2.10 (2H, t, J=11.0), 2.34 (2H, d, J=7.0), 2.44-2.49 (4H, m), 2.99 (2H, d, J 11.0), 3.82 (2H, s), 3.88-3.91 (4H, m), 4.03-4.06 (4H, m), 5.21 (2H, br s), 7.27 (1H, s), 9.30 (2H, s). MS: (ESI+): MH+=495

Example 249

5-(6-((4-((dimethylamino)methyl)piperidin-1-yl)methyl)-4-morpholinothieno[3,2-d]pyrimidin-2-yl)pyrimidin-2-amine 332

2-Chloro-4-morpholin-4-yl-thieno[3,2-d]pyrimidine-6-carboxaldehyde 10 was reacted with dimethyl-piperidin-4-ylmethyl-amine using standard reductive amination conditions. The resulting crude solid was triturated with methanol to give [1-(2-chloro-4-morpholin-4-yl-thieno[3,2-d]pyrimidin-6-ylmethyl)-piperidin-4-ylmethyl]-dimethyl-amine as an off white solid (51% yield), which was reacted with 5-(4,4,5,5-tetramethyl-[1,3,2]dioxaborolan-2-yl)-pyrimidin-2-ylamine according to General Procedure A. The resulting solid was triturated with methanol to give 332 as an off white solid (36% yield). NMR (CDCl3, 400 MHz), 1.29-1.35 (2H, m), 1.46-1.51 (1H, m), 1.77 (2H, d, J=11.8), 2.08-2.15 (4H, m), 2.22 (6H, s), 2.99 (2H, d, J=11.5), 3.82 (2H, s), 3.88-3.91 (4H, m), 4.03-4.06 (4H, m), 5.21 (2H, br s), 7.27 (1H, s), 9.30 (2H, s). MS: (ESI+): MH+=469

Example 250

5-(6-((1-methylpiperidin-4-ylamino)methyl)-4-morpholinothieno[3,2-d]pyrimidin-2-yl)pyrimidin-2-amine 333

2-Chloro-4-morpholin-4-yl-thieno[3,2-d]pyrimidine-6-carboxaldehyde 10 was reacted with 1-methyl-piperidin-4-ylamine using standard reductive amination conditions. The resulting crude solid was purified on silica using a gradient of 0-20% methanol in ethyl acetate as the eluent to give (2-chloro-4-morpholin-4-yl-thieno[3,2-d]pyrimidin-6-ylmethyl)-(1-methyl-piperidin-4-yl)-amine as an off white solid (34% yield), which was reacted with 5-(4,4,5,5-tetramethyl-[1,3,2]dioxaborolan-2-yl)-pyrimidin-2-ylamine according to General Procedure A. The resulting solid was triturated with methanol to give 333 as an off white solid (35% yield). NMR (CDCl3, 400 MHz), 1.42-1.50 (3H, m), 1.94-2.02 (4H, m), 2.28 (3H, s), 2.54-2.60 (1H, m), 2.84 (2H, d, J=11.9), 3.88-3.91 (4H, m), 4.04-4.06 (4H, m), 4.18 (2H, s), 5.23 (2H, br s), 7.27 (1H, s), 9.30 (2H, s). MS: (ESI+): MH+=441

Example 251

5-(6-(((1-isopropylpiperidin-4-yl)(2-methoxyethyl)amino)methyl)-4-morpholinothieno[3,2-d]pyrimidin-2-yl)pyrimidin-2-amine 334

Reaction of 2-methoxyethylamine with 2-chloro-4-morpholin-4-yl-thieno[3,2-d]pyrimidine-6-carbaldehyde 10 using standard reductive amination conditions yielded (2-chloro-4-morpholin-4-yl-thieno[3,2-d]pyrimidin-6-ylmethyl)-(2-methoxy-ethyl)-amine, which was reacted with 1-isopropyl-4-piperidone using the standard reductive amination conditions to yield (2-chloro-4-morpholin-4-yl-thieno[3,2-d]pyrimidin-6-ylmethyl)-(1-isopropyl-piperidin-4-yl)-(2-methoxyethyl)amine.

(2-Chloro-4-morpholin-4-yl-thieno[3,2-d]pyrimidin-6-ylmethyl)-(1-isopropyl-piperidin-4-yl)-(2-methoxy-ethyl)-amine was reacted with 2-aminopyrimidine-5-boronic acid in General Procedure A. Acid/base work-up and trituration with ether yielded 334. 400 MHz, 1H NMR CDCl3: 9.30 (s, 2H), 7.26 (s, 1H), 5.22 (br s, 2H, NH2), 4.06 (s, 2H), 4.05 (t, 4H, J 4.4), 3.90 (t, 4H, J4.6), 3.50 (t, 2H, J6.0), 3.32 (s, 3H), 2.94 (d, 2H, J 11.2), 2.85 (t, 2H, J 6.1), 2.75-2.68 (m, 1H), 2.61-2.55 (m, 1H), 2.10 (t, 2H, J 11.4), 1.85 (d, 2H, J12.0), 1.65-1.53 (m, 2H), 1.03 (d, 6H, J 6.4). LC-MS (m+1)=527.41

Example 252

5-(6-((methyl((1-methylpiperidin-4-yl)methyl)amino)methyl)-4-morpholinothieno[3,2-d]pyrimidin-2-yl)pyrimidin-2-amine 335

Reaction between (2-chloro-4-morpholin-4-yl-thieno[3,2-d]pyrimidin-6-ylmethyl)-methyl-amine and 1-methylpiperidine-4-carbaldehyde using standard reductive amination conditions yielded (2-chloro-4-morpholin-4-yl-thieno[3,2-d]pyrimidin-6-ylmethyl)-methyl-(1-methyl-piperidin-4-ylmethyl)-amine, which was reacted with 2-aminopyrimidine-5-boronic acid in General Procedure A. Acid/base work-up and trituration with ether yielded 335. 400 MHz 1H NMR CDCl3: 9.30 (s, 2H), 7.26 (s, 1H), 5.30 (br s, 2H, NH2), 4.04 (t, 4H, J4.5), 3.90 (t, 4H, J4.5), 3.80 (s, 2H), 2.87 (d, 2H, J11.5), 2.33 (d, 2H, J7.1), 2.30 (s, 3H), 2.28 (s, 3H), 1.93 (t, 2H, J11.7), 1.83 (d, 2H, J13.1), 1.57-1.51 (m, 1H), 1.32-1.22 (m, 2H). LC-MS (m+1)=469.35

Example 253

5-(4-morpholino-6-((4-morpholinopiperidin-1-yl)methyl)thieno[3,2-d]pyrimidin-2-yl)pyrimidin-2-amine 336

2-Chloro-4-morpholin-4-yl-thieno[3,2-d]pyrimidine-6-carboxaldehyde 10 was reacted with 4-piperidin-4-yl-morpholine using standard reductive amination conditions. The resulting crude solid was triturated with methanol to give 2-chloro-4-morpholin-4-yl-6-(4-morpholin-4-yl-piperidin-1-ylmethyl)-thieno[3,2-d]pyrimidine as an off white solid (50% yield), which was reacted with 5-(4,4,5,5-tetramethyl-[1,3,2]dioxaborolan-2-yl)-pyrimidin-2-ylamine according to General Procedure A. The resulting solid was purified by mass directed chromatography to give 336 as an off white solid (21% yield). NMR (CDCl3, 400 MHz), 1.60-1.67 (2H, m), 1.86 (2H, d, J=12.2), 2.14 (2H, t, J=10.6), 2.17-2.23 (1H, m), 2.57-2.59 (4H, m), 3.05 (2H, d, J=11.7), 3.73-3.75 (4H, m), 3.83 (2H, s), 3.88-3.91 (4H, m), 4.03-4.06 (4H, m), 5.21 (br s), 7.27 (1H, s), 9.30 (2H, s). MS: (ESI+): MH+=497

Example 254

5-(6-((4-(dimethylamino)piperidin-1-yl)methyl)-4-morpholinothieno[3,2-d]pyrimidin-2-yl)pyrimidin-2-amine 337

2-Chloro-4-morpholin-4-yl-thieno[3,2-d]pyrimidine-6-carboxaldehyde 10 was reacted with dimethyl-piperidin-4-yl-amine using standard reductive amination conditions. The resulting crude solid was triturated with diethyl ether to give [1-(2-chloro-4-morpholin-4-yl-thieno[3,2-d]pyrimidin-6-ylmethyl)-piperidin-4-yl]-dimethyl-amine as an off white solid (45% yield), which was reacted with 5-(4,4,5,5-tetramethyl-[1,3,2]dioxaborolan-2-yl)-pyrimidin-2-ylamine according to General Procedure A. The resulting solid was purified by mass directed chromatography (20% yield) to give 337. NMR (CDCl3, 400 MHz), 1.60-1.65 (2H, m), 1.83-1.86 (2H, d, J 12.2), 2.11-2.17 (3H, m), 2.32 (6H, s), 3.04 (2H, d, J 11.4), 3.83 (2H, s), 3.88-3.91 (4H, m), 4.03-4.06 (4H, m), 5.24 (2H, br s), 7.27 (1H, br s), 7.27 (1H, s), 9.30 (2H, s). MS: (ESI+): MH+=455

Example 255

5-(6-((methyl(1-methylpyrrolidin-3-yl)amino)methyl)-4-morpholinothieno[3,2-d]pyrimidin-2-yl)pyrimidin-2-amine 338

2-Chloro-4-morpholin-4-yl-thieno[3,2-d]pyrimidine-6-carboxaldehyde 10 was reacted with N,N-dimethyl-3-aminopyrrolidine using standard reductive amination conditions. The resulting crude oil (2-chloro-4-morpholin-4-yl-thieno[3,2-d]pyrimidin-6-ylmethyl)-methyl-(1-methyl-pyrrolidin-3-yl)-amine was reacted with 5-(4,4,5,5-tetramethyl-[1,3,2]dioxaborolan-2-yl)-pyrimidin-2-ylamine according to General Procedure A. The resulting solid was purified by mass directed chromatography (14% yield) to give 338. NMR (CDCl3, 400 MHz), 1.83-1.90 (1H, m), 2.06-2.12 (1H, m), 2.30 (3H, s), 2.31 (3H, s), 2.57-2.62 (2H, m), 2.58-2.65 (1H, m), 2.72 (1H, t, J=9.2), 3.30-3.35 (1H, m), 3.80-3.88 (2H, m), 3.88-3.94 (4H, m), 4.03-4.09 (4H, m), 5.22 (2H, br s), 7.28 (1H, s), 9.30 (2H, s). MS: (ESI+): MH+=441

Example 256

5-(6-(((1-cyclopropylpiperidin-4-yl)(methyl)amino)methyl)-4-morpholinothieno[3,2-d]pyrimidin-2-yl)pyrimidin-2-amine 339

(2-Chloro-4-morpholin-4-yl-thieno[3,2-d]pyrimidin-6-ylmethyl)methylamine was reacted with 1-cyclopropyltetrahydro-4(1H)-pyridinone using standard reductive amination conditions. The resulting crude solid was triturated with diethyl ether and methanol to give (2-chloro-4-morpholin-4-yl-thieno[3,2-d]pyrimidin-6-ylmethyl)-(1-cyclopropyl-piperidin-4-yl)methyl-amine as a solid (57% yield), which was reacted with 5-(4,4,5,5-tetramethyl-[1,3,2]dioxaborolan-2-yl)-pyrimidin-2-ylamine according to General Procedure A. The resulting solid was purified by mass directed chromatography (18% yield) to give 339. NMR (CDCl3, 400 MHz), 0.39-0.47 (4H, m), 1.58-1.66 (3H, m), 1.83 (2H, d, J=12.1), 2.19 (2H, t, J=9.9), 2.36 (3H, s), 2.54-2.58 (1H, m), 3.13 (2H, d, J=11.5), 3.88-3.92 (6H, m), 4.03-4.06 (4H, m), 5.22 (2H, br s), 7.27 (1H, s), 9.30 (2H, s). MS: (ESI+): MH+=481

Example 257

5-(6-((4-aminopiperidin-1-yl)methyl)-4-morpholinothieno[3,2-d]pyrimidin-2-yl)pyrimidin-2-amine 340

2-Chloro-4-morpholin-4-yl-thieno[3,2-d]pyrimidine-6-carboxaldehyde 10 was reacted with 4-(N—BOC-amino)-piperidine using standard reductive amination conditions. The resulting crude oil was triturated with diethyl ether and methanol to give [1-(2-chloro-4-morpholin-4-yl-thieno[3,2-d]pyrimidin-6-ylmethyl)-piperidin-4-yl]-carbamic acid tert-butyl ester as a solid (71% yield), which was reacted with 5-(4,4,5,5-tetramethyl-[1,3,2]dioxaborolan-2-yl)-pyrimidin-2-ylamine according to General Procedure A. The resulting solid was triturated with diethyl ether and methanol to give 340 as an off white solid (18% yield). NMR (CDCl3, 400 MHz), 1.43-1.48 (2H, m), 1.84 (2H, d, J=10.3), 2.19 (2H, t, J=11.3), 2.70-2.73 (1H, m), 2.93-2.96 (2H, m), 3.83 (2H, s), 3.88-3.91 (4H, m), 4.03-4.06 (4H, m), 5.21 (2H, br s), 7.27 (1H, s), 9.30 (2H, s). MS: (ESI+): MH+=427

Example 258

5-(6-((3-(dimethylamino)pyrrolidin-1-yl)methyl)-4-morpholinothieno[3,2-d]pyrimidin-2-yl)pyrimidin-2-amine 341

2-Chloro-4-morpholin-4-yl-thieno[3,2-d]pyrimidine-6-carboxaldehyde 10 was reacted with 3-(dimethylamino) pyrrolidine using standard reductive amination conditions. The resulting crude oil was triturated with diethyl ether and methanol to give [1-(2-chloro-4-morpholin-4-yl-thieno[3,2-d]pyrimidin-6-ylmethyl)-pyrrolidin-3-yl]dimethyl-amine as a solid (61% yield), which was reacted with 5-(4,4,5,5-tetramethyl-[1,3,2]dioxaborolan-2-yl)-pyrimidin-2-ylamine according to General Procedure A. The resulting solid was triturated with diethyl ether and methanol to give 341 as an off white solid (86% yield). NMR (CDCl3, 400 MHz), 1.76-1.82 (1H, m), 2.20-2.10 (1H, m), 2.23 (6H, s), 2.48 (2H, dd, J=7.4 and 8.5), 2.66-2.17 (2H, m), 2.81-2.95 (3H, m), 3.88-3.90 (4H, m), 3.90-3.99 (2H, m), 4.03-4.06 (4H, m), 5.23 (2H, br s), 7.28 (1H, s), 9.30 (2H, s). MS: (ESI+): MH+=441

Example 259

5-(6-((methyl(piperidin-4-yl)amino)methyl)-4-morpholinothieno[3,2-d]pyrimidin-2-yl)pyrimidin-2-amine 342

(2-Chloro-4-morpholin-4-yl-thieno[3,2-d]pyrimidin-6-ylmethyl)-methylamine was reacted with 1-tert-butyl 4-oxo-1-piperidinecarboxylate using standard reductive amination conditions. The resulting crude solid was triturated with diethylether to give 4-[(2-chloro-4-morpholin-4-yl-thieno[3,2-d]pyrimidin-6-ylmethyl)-methyl-amino]-piperidine-1-carboxylic acid tert-butyl ester as an off white solid (72% yield), which was reacted with 5-(4,4,5,5-tetramethyl-[1,3,2]dioxaborolan-2-yl)-pyrimidin-2-ylamine according to General Procedure A. The resulting solid was stirred in a solution of 2N HCl (5 ml) and methanol (5 ml) overnight, before the solution was evaporated in vacuo to remove the methanol and the acidic solution made basic with sat. aq. K2CO3. The resulting solid was filtered and washed with diethyl ether to give 342 as a solid (52% yield). NMR (CDCl3, 400 MHz), 1.48-1.55 (3H, m), 1.86 (2H, d, J=12.7), 2.38 (3H, s), 2.58-2.64 (3H, m), 3.18 (2H, d, J=12.2), 3.88-3.91 (4H, m), 3.94 (2H, s), 4.03-4.06 (4H, m), 5.23 (2H, br s), 7.28 (1H, s), 9.30 (2H, s). MS: (ESI+): MH+=441

Example 260

5-(6-(((1-(2-methoxyethyl)piperidin-4-yl)(methyl)amino)methyl)-4-morpholinothieno[3,2-d]pyrimidin-2-yl)pyrimidin-2-amine 343

To a solution of 4-piperidone monohydrate hydrochloride salt (2.2 g, 14.32 mmol, 1 eq) in acetonitrile, 2-bromoethyl methyl ether (5.9 ml, 28.6 mmol, 2 eq), and K2CO3 (2 eq) was added and heated at reflux overnight. Reaction extracted into dichloromethane (50 ml), washed with water (2×50 ml), dried (MgSO4), and evaporated in vacuo to give 1-(2-methoxyethyl)piperidin-4-one as a yellow oil.

(2-Chloro-4-morpholin-4-yl-thieno[3,2-d]pyrimidin-6-ylmethyl)methylamine was reacted with 1-(2-methoxyethyl)piperidin-4-one using standard reductive amination conditions. The resulting crude solid was triturated with diethyl ether and methanol to give (2-chloro-4-morpholin-4-yl-thieno[3,2-d]pyrimidin-6-ylmethyl)-[1-(2-methoxyethyl)-piperidin-4-yl]-methyl-amine as an off white solid (32% yield), which was reacted with 5-(4,4,5,5-tetramethyl-[1,3,2]dioxaborolan-2-yl)-pyrimidin-2-ylamine according to General Procedure A. The resulting solid was triturated with diethyl ether and methanol to give 343 as a solid (43% yield). NMR (CDCl3, 400 MHz), 0.95-0.99 (2H, m), 1.68-1.77 (2H, m), 1.81-1.84 (2H, m), 2.02 (2H, t, J=10.3), 2.37 (3H, s), 2.50-2.59 (3H, m), 3.06 (2H, d, J=11.5), 3.37 (3H, s), 3.88-3.91 (4H, m), 3.93 (2H, s), 4.03-4.06 (4H, m), 5.23 (2H, br s), 7.26 (1H, s), 9.30 (2H, s). MS: (ESI+): MH+=499

Example 261

5-(6-((methyl(1-propylpiperidin-4-yl)amino)methyl)-4-morpholinothieno[3,2-d]pyrimidin-2-yl)pyrimidin-2-amine 344

(2-Chloro-4-morpholin-4-yl-thieno[3,2-d]pyrimidin-6-ylmethyl)-methylamine was reacted with 1-propyl-piperidin- 4-one using standard reductive amination conditions. The resulting crude solid was triturated was with diethyl ether and methanol to give (2-chloro-4-morpholin-4-yl-thieno[3,2-d]pyrimidin-6-ylmethyl)-methyl-(1-propyl-piperidin-4-yl)amine as a solid (30% yield), which was reacted with 5-(4,4,5,5-tetramethyl-[1,3,2]dioxaborolan-2-yl)-pyrimidin-2-ylamine according to General Procedure A. The resulting solid was triturated with diethylether and methanol to give 344 as a solid (77% yield). NMR (CDCl3, 400 MHz), 0.92 (3H, t, J=7.3), 1.49-1.56 (2H, m), 1.64-1.72 (2H, m), 1.82-1.86 (2H, m), 1.93 (2H, t, J=11.3), 2.29 (2H, dd, J=7.7 and 7.9), 2.37 (3H, s), 2.50-2.56 (1H, m), 3.03 (2H, d, J=11.6), 3.88-3.91 (4H, m), 3.93 (2H, s), 4.03-4.06 (4H, m), 5.22 (2H, br s), 7.27 (1H, s), 9.30 (2H, s). MS: (ESI+): MH+=483

Example 262

5-(6-(((1-cyclohexylpiperidin-4-yl)(methyl)amino)methyl)-4-morpholinothieno[3,2-d]pyrimidin-2-yl)pyrimidin-2-amine 345

(2-Chloro-4-morpholin-4-yl-thieno[3,2-d]pyrimidin-6-ylmethyl)methylamine was reacted with 1-cyclohexyltetrahydro-4(1H)-pyridinone using standard reductive amination conditions. The resulting crude solid was triturated with diethyl ether and methanol to give (2-chloro-4-morpholin-4-yl-thieno[3,2-d]pyrimidin-6-ylmethyl)-(1-cyclohexyl-piperidin-4-yl)-methyl-amine as a solid (72% yield), which was reacted with 5-(4,4,5,5-tetramethyl-[1,3,2]dioxaborolan-2-yl)-pyrimidin-2-ylamine according to General Procedure A. The resulting solid was triturated with diethylether and methanol to give 345 as a solid (76% yield). NMR (CDCl3, 400 MHz), 1.06-1.21 (5H, m), 1.51-1.57 (3H, m), 1.74-1.81 (6H, m), 2.12-2.18 (3H, m), 2.24 (3H, s), 2.41-2.47 (1H, m), 2.94-2.96 (2H, m), 3.84 (4H, t, J=4.4), 3.87 (2H, s), 3.99 (4H, t, J=4.4), 5.26 (2H, s), 7.21 (1H, s), 9.25 (2H, s). MS: (ESI+): MH+=523

Example 263

5-(6-(((1-isobutylpiperidin-4-yl)(methyl)amino)methyl)-4-morpholinothieno[3,2-d]pyrimidin-2-yl)pyrimidin-2-amine 346

(2-Chloro-4-morpholin-4-yl-thieno[3,2-d]pyrimidin-6-ylmethyl)-methylamine was reacted with 1-(2-methylpropyl)-4-piperidone using standard reductive amination conditions. The resulting crude solid was triturated with diethyl ether and methanol to give (2-chloro-4-morpholin-4-yl-thieno[3,2-d]pyrimidin-6-ylmethyl)-(1-isobutyl-piperidin-4-yl)-methyl-amine as a solid (48% yield), which was reacted with 5-(4,4,5,5-tetramethyl-[1,3,2]dioxaborolan-2-yl)-pyrimidin-2-ylamine according to General Procedure A. The resulting solid was triturated with diethylether and methanol to give 346 as a solid (60% yield). NMR (CDCl3, 400 MHz), 0.91 (6H, d, J=6.6), 1.587-1.70 (2H, m), 1.71-1.79 (3H, m), 1.89 (2H, t, J=11.7), 2.07 (2H, d, J=7.3), 2.37 (3H, s), 2.48-2.54 (1H, m), 2.96 (2H, d, J 11.6), 3.88-3.90 (4H, m), 3.93 (2H, s), 4.03-4.06 (4H, m), 5.22 (2H, br s), 7.27 (1H, s), 9.30 (2H, s). MS: (ESI+): MH+=497

Example 264

5-(6-(((1-ethylpiperidin-4-yl)(methyl)amino)methyl)-4-morpholinothieno[3,2-d]pyrimidin-2-yl)pyrimidin-2-amine 347

(2-Chloro-4-morpholin-4-yl-thieno[3,2-d]pyrimidin-6-ylmethyl)methylamine was reacted with 1-ethyl-4-piperidone using standard reductive amination conditions. The resulting crude solid was triturated with a small amount of diethyl ether and methanol to give (2-chloro-4-morpholin-4-yl-thieno[3,2-d]pyrimidin-6-ylmethyl)-(1-ethyl-piperidin-4-yl)-methyl-amine as a solid (50% yield), which was reacted with 5-(4,4,5,5-tetramethyl-[1,3,2]dioxaborolan-2-yl)-pyrimidin-2-ylamine according to General Procedure A. The resulting solid was triturated with diethylether and methanol to give 347 as a solid (75% yield). NMR (CDCl3, 400 MHz), 1.10 (3H, t, J=7.2), 1.56-1.73 (2H, m), 1.84-1.95 (4H, m), 2.38 (3H, s), 2.42 (2H, q, J=7.0), 2.51-2.58 (1H, m), 3.06 (2H, d, J=11.8), 3.88-3.91 (4H, m), 3.93 (2H, s), 4.03-4.06 (4H, m), 5.21 (2H, br s), 7.27 (1H, s), 9.30 (2H, s). MS: (ESI+): MH+=469

Example 265

4-Methyl-5-(6-((4-(methylsulfonyl)piperazin-1-yl)methyl)-4-morpholinothieno[2,3-d]pyrimidin-2-yl)pyrimidin-2-amine 348

2-Chloro-6-(4-methanesulfonyl-piperazin-1-ylmethyl)-4-morpholin-4-yl-thieno[2,3-d]pyrimidine (300 mg), prepared according to General Procedure B-3, was coupled to 4-methyl-5-(4,4,5,5-tetramethyl (1,3,2-dioxaborolan-2-yl))pyrimidine-2-ylamine via General Procedure A to yield 36.1 mg of 348. MS (Q1) 505.2 (M)$^+$.

Example 266

(S)-1-(4-((2-(2-amino-4-methylpyrimidin-5-yl)-7-methyl-4-morpholinothieno[3,2-d]pyrimidin-6-yl)methyl)piperazin-1-yl)-2-hydroxypropan-1-one 349

1-[4-(2-Chloro-7-methyl-4-morpholin-4-yl-thieno[3,2-d]pyrimidin-6-ylmethyl)-piperazin-1-yl]-2-hydroxy-propan-1-one (200 mg) was coupled to 4-methyl-5-(4,4,5,5-tetramethyl (1,3,2-dioxaborolan-2-yl))pyrimidine-2-ylamine via General Procedure A to yield 20 mg of 349. MS (Q1) 513.2 (M)$^+$.

Example 267

1-(4-((2-(2-aminopyrimidin-5-yl)-7-methyl-4-morpholinothieno[3,2-d]pyrimidin-6-yl)methyl)piperazin-1-yl)-2-(methylsulfonyl)ethanone 350

Crude HCl salt of 5-(7-methyl-4-morpholino-6-(piperazin-1-ylmethyl)thieno[3,2-d]pyrimidin-2-yl)pyrimidin-2-amine (74 mg) was reacted with 50 mg 2-(methylsulfonyl)acetic acid via General Procedure B to give 54.6 mg of 350 after reverse phase HPLC purification. MS (Q1) 547.2 (M)+.

Example 268

(1-aminocyclopropyl)(4-((2-(2-aminopyrimidin-5-yl)-7-methyl-4-morpholinothieno[3,2-d]pyrimidin-6-yl)methyl)piperazin-1-yl)methanone 351

Crude HCl salt of 5-(7-methyl-4-morpholino-6-(piperazin-1-ylmethyl)thieno[3,2-d]pyrimidin-2-yl)pyrimidin-2-amine (74 mg) was reacted with 70 mg 1-(tert-butoxycarbonylamino)cyclopropanecarboxylic acid via General Procedure B, treated with TFA and purified via reverse phase HPLC to yield 89.1 mg of 351 after reverse phase HPLC purification. MS (Q1) 510.3 (M)+.

Example 269

2-amino-1-(4-((2-(2-aminopyrimidin-5-yl)-7-methyl-4-morpholinothieno[3,2-d]pyrimidin-6-yl)methyl)piperazin-1-yl)-2-methylpropan-1-one 352

Crude HCl salt of 5-(7-methyl-4-morpholino-6-(piperazin-1-ylmethyl)thieno[3,2-d]pyrimidin-2-yl)pyrimidin-2-amine (74 mg) was reacted with 70 mg 2-(tert-butoxycarbonylamino)-2-methylpropanoic acid via General Procedure B, treated with TFA and purified via reverse phase HPLC to yield 71.3 mg of 352 after reverse phase HPLC purification. MS (Q1) 512.3 (M)+

Example 270

(R)-2-amino-1-(4-((2-(2-aminopyrimidin-5-yl)-7-methyl-4-morpholinothieno[3,2-d]pyrimidin-6-yl)methyl)piperazin-1-yl)propan-1-one 353

Crude HCl salt of 5-(7-methyl-4-morpholino-6-(piperazin-1-ylmethyl)thieno[3,2-d]pyrimidin-2-yl)pyrimidin-2-amine (74 mg) was reacted with 60 mg Boc-D-Alanine via General Procedure B, treated with TFA and purified via reverse phase HPLC to yield 33.7 mg of 353 after reverse phase HPLC purification. MS (Q1) 498.3 (M)+

Example 271

(S)-2-amino-1-(4-((2-(2-aminopyrimidin-5-yl)-7-methyl-4-morpholinothieno[3,2-d]pyrimidin-6-yl)methyl)piperazin-1-yl)propan-1-one 354

Crude HCl salt of 5-(7-methyl-4-morpholino-6-(piperazin-1-ylmethyl)thieno[3,2-d]pyrimidin-2-yl)pyrimidin-2-amine (74 mg) was reacted with 60 mg Boc-L-Alanine via General Procedure B, treated with TFA and purified via reverse phase HPLC to yield 52.7 mg of 354 after reverse phase HPLC purification. MS (Q1) 498.3 (M)+

Example 272

1-(4-((2-(2-aminopyrimidin-5-yl)-7-methyl-4-morpholinothieno[3,2-d]pyrimidin-6-yl)methyl)piperazin-1-yl)-2-(dimethylamino)ethanone Crude HCl salt of 5-(7-methyl-4-morpholino-6-(piperazin-1-ylmethyl)thieno[3,2-d]pyrimidin-2-yl)pyrimidin-2-amine (74 mg) was reacted with 40 mg 2-(dimethylamino)acetic acid via Procedure B to give 38.2 mg of 355 after reverse phase HPLC purification. MS (Q1) 512.3 (M)+.

Example 273

2-amino-1-(4-((2-(2-aminopyrimidin-5-yl)-7-methyl-4-morpholinothieno[3,2-d]pyrimidin-6-yl)methyl)piperazin-1-yl)ethanone 356

Crude HCl salt of 5-(7-methyl-4-morpholino-6-(piperazin-1-ylmethyl)thieno[3,2-d]pyrimidin-2-yl)pyrimidin-2-amine (74 mg) was reacted with 60 mg Boc-Glycine via General Procedure B, treated with TFA and purified via reverse phase HPLC to yield 45.3 mg of 356 after reverse phase HPLC purification. MS (Q1) 484.3 (M)+.

Example 274

1-(4-((2-(2-aminopyrimidin-5-yl)-7-methyl-4-morpholinothieno[3,2-d]pyrimidin-6-yl)methyl)piperazin-1-yl)-2-hydroxy-2-methylpropan-1-one 357

Crude HCl salt of 5-(7-methyl-4-morpholino-6-(piperazin-1-ylmethyl)thieno[3,2-d]pyrimidin-2-yl)pyrimidin-2-amine (74 mg) was reacted with 40 mg 2-hydroxy-2-methylpropanoic acid via General Procedure B to give 58.3 mg of 357 after reverse phase HPLC purification. MS (Q1) 513.3 (M)+.

Example 275

5-(7-methyl-4-morpholino-6-(piperazin-1-ylmethyl)thieno[3,2-d]pyrimidin-2-yl)pyrimidin-2-amine 358

Tert-butyl 4-((2-(2-aminopyrimidin-5-yl)-7-methyl-4-morpholinothieno[3,2-d]pyrimidin-6-yl)methyl)piperazine-1-carboxylate (75 mg) was treated with TFA and purified via reverse phase HPLC to give 74.4 mg of 358. MS (Q1) 427.2 (M)+.

Example 276

5-(6-((4-(methylsulfonyl)piperazin-1-yl)methyl)-4-morpholinothieno[2,3-d]pyrimidin-2-yl)pyridin-3-amine 359

To a solution of 3-amino-5-bromopyridine (300 mg) in dichloromethane (20 mL) was added di-tertbutyl dicarbonate (832 mg) and dimethylaminopyridine (11 mg) and the reaction was stirred at room temperature for 16 h. The mixture was partitioned between dichloromethane (30 mL) and water (30 mL). The organic layer was washed with brine (2×40 mL), dried (MgSO$_4$) and reduced in vacuo to give di-tert-butyl (5-bromopyridin-3-yl)imidodicarbonate.

To a solution of di-tert-butyl (5-bromopyridin-3-yl)imidodicarbonate (413 mg) in DMSO (8 mL) was added bispinacolatodiboron (450 mg), potassium acetate (326 mg) and Pd(dppO$_2$Cl$_2$ (45 mg) and the reaction was stirred at 80° C. for 16 h. After cooling to room temperature, the reaction was quenched with water (20 mL) and extracted into ethylacetate (3×30 mL). The organic layers were dried (MgSO$_4$) and reduced in vacuo to give 3-di-tert-butylimidodicarbonate-5-(4,4,5,5-tetramethyl-[1,3,2]dioxaborolan-2-yl)-pyridine.

3-Di-tert-butylimidodicarbonate-5-(4,4,5,5-tetramethyl-[1,3,2]dioxaborolan-2-yl)-pyridine was reacted with 2-chloro-6-(4-methanesulfonyl-piperazin-1-ylmethyl)-4-morpholin-4-yl-thieno[2,3-d]pyrimidine in General Procedure A. Purification on silica yielded 359.

Example 277

5-(6-((4-(methylsulfonyl)piperazin-1-yl)methyl)-4-morpholinothieno[2,3-d]pyrimidin-2-yl)-3-nitropyridin-2-amine 360

4-(2-Chloro-6-((4-(methylsulfonyl)piperazin-1-yl)methyl)thieno[2,3-d]pyrimidin-4-yl)morpholine (100 mg, 0.2 mmol) was reacted with 3-nitro-5-(4,4,5,5-tetramethyl-1,3,2-dioxaborolan-2-yl)pyridin-2-amine (0.24 g, 0.9 mmol)

according to General Procedure Suzuki to afford 360 (18 mg) following reverse phase HPLC purification. MS (Q1) 535 (M)+

Example 278

N,3-dimethyl-5-(6-((4-(methylsulfonyl)piperazin-1-yl)methyl)-4-morpholinothieno[2,3-d]pyrimidin-2-yl)pyridin-2-amine 361

To a solution of 2-amino-5-bromo-3-methylpyridine (500 mg) in THF (5 mL) was added sodium bis(trimethylsilyl) amide (5.35 mL of a 1 M solution in THF) and the reaction stirred at room temperature for 15 min. Then, di-tert-butyldicarbonate (554 mg) was added and the reaction stirred at room temperature for 16 h. The reaction was quenched with water (30 mL) and extracted into dichloromethane (3×20 mL). The organic layers were washed with brine (2×40 mL), dried ($MgSO_4$), reduced in vacuo and purified on silica to give (5-bromo-3-methyl-pyridin-2-yl)-carbamic acid tert-butyl ester.

To a solution of (5-bromo-3-methyl-pyridin-2-yl)-carbamic acid tert-butyl ester (409 mg) in THF (20 mL) was added sodium hydride (68 mg) and the reaction was stirred at room temperature for 20 min. Then, iodomethane (0.11 mL) was added and the reaction was stirred at room temperature for 16 h. The reaction was quenched with water (30 mL) and extracted into ethylacetate (2×20 mL). The organic layers were washed with brine (2×40 mL), dried ($MgSO_4$) and reduced in vacuo to give (5-bromo-3-methyl-pyridin-2-yl)-methyl-carbamic acid tert-butyl ester as a yellow oil.

To a solution of (5-bromo-3-methyl-pyridin-2-yl)-methyl-carbamic acid tert-butyl ester as a yellow oil (354 mg) in DMSO (5 mL) was added bispinacolatodiboron (476 mg), potassium acetate (345 mg) and $Pd(dppf)_2Cl_2$ (48 mg) and the reaction was stirred at 80° C. for 16 h. After cooling to room temperature, the reaction was quenched with water (20 mL) and extracted into ethylacetate (3×30 mL). The organic layers were dried ($MgSO_4$), reduced in vacuo and purified on silica to give methyl-[3-methyl-5-(4,4,5,5-tetramethyl-[1,3,2]dioxaborolan-2-yl)-pyridin-2-yl]-carbamic acid tert-butyl ester as a white solid.

Methyl-[3-methyl-5-(4,4,5,5-tetramethyl-[1,3,2]dioxaborolan-2-yl)-pyridin-2-yl]-carbamic acid tert-butyl ester was reacted with 2-chloro-6-(4-methanesulfonyl-piperazin-1-ylmethyl)-4-morpholin-4-yl-thieno[2,3-d]pyrimidine in General Procedure A. Purification on silica yielded 361. NMR: ($CDCl_3$): 2.54-2.58 (4 H, m), 2.72 (3 H, s), 3.04-3.07 (3 H, m), 3.18-3.21 (4 H, m), 3.72 (2 H, s), 3.78-3.80 (4 H, m), 3.85-3.88 (4 H, m), 4.40 (1 H, s, NH), 7.031 (1 H, s, Ar), 8.16 (1 H, s, Ar) and 9.09 (1 H, s, Ar). MS: (ESI+): MH+=518.24

Example 279

(5-(6-((4-(methylsulfonyl)piperazin-1-yl)methyl)-4-morpholinothieno[2,3-d]pyrimidin-2-yl)pyridin-2-yl)methanol 362

To a solution of 5-bromopyridine-2-carbaldehyde (300 mg) in methanol (10 mL) was added sodium borohydride (61 mg) and the reaction stirred at room temperature for 72 h. The reaction was quenched with saturated aqueous sodium carbonate solution (20 mL) and water (20 mL) and extracted into dichloromethane (3×30 mL). The organic layers were dried ($MgSO_4$) and reduced in vacuo to give (5-bromo-pyridin-2-yl)-methanol as a white solid.

To a solution of (5-bromo-pyridin-2-yl)-methanol (300 mg) in dichloromethane (20 mL) was added imidazole (217 mg) and tert-butyldiphenylsilyl chloride (0.41 mL) and the reaction stirred at room temperature for 16 h. the reaction was quenched with water (20 mL) and extracted into dichloromethane (2×30 mL). The organic layers were dried ($MgSO_4$) and reduced in vacuo to give 5-bromo-2-(tert-butyl-diphenylsilanyloxymethyl)-pyridine as an oil.

To a solution of 5-bromo-2-(tert-butyl-diphenylsilanyloxymethyl)-pyridine (640 mg) in DMSO (5 mL) was added bispinacolatodiboron (610 mg), potassium acetate (442 mg) and $Pd(dppf)_2Cl_2$ (61 mg) and the reaction was stirred at 80° C. for 16 h. After cooling to room temperature, the reaction was quenched with water (20 mL) and extracted into ethylacetate (3×30 mL). The organic layers were dried ($MgSO_4$), reduced in vacuo and purified on silica to give 2-(tert-butyl-diphenyl-silanyloxymethyl)-5-(4,4,5,5-tetramethyl-[1,3,2]dioxaborolan-2-yl)-pyridine as a colourless oil.

2-(tert-Butyl-diphenyl-silanyloxymethyl)-5-(4,4,5,5-tetramethyl-[1,3,2]dioxaborolan-2-yl)-pyridine was reacted with 2-chloro-6-(4-methanesulfonyl-piperazin-1-ylmethyl)-4-morpholin-4-yl-thieno[2,3-d]pyrimidine in General Procedure A. Purification on silica yielded 362. NMR: ($CDCl_3$): 2.58-2.60 (4 H, m), 2.73 (3 H, s, Me), 3.20-3.22 (4 H, m), 3.75 (2 H, s), 3.81-3.84 (4 H, m), 3.90-3.92 (4 H, m), 4.76 (2 H, s, NH2), 6.92 (1 H, s, Ar), 7.25 (1 H, d, J 8.3, Ar), 8.61 (1 H, d, J 8.3, Ar) and 9.51 (1 H, s, Ar). MS: (ESI+): MH+=505.14

Example 280

4-(2-(4-methylpyridin-3-yl)-6-((4-(methylsulfonyl)piperazin-1-yl)methyl)thieno[2,3-d]pyrimidin-4-yl)morpholine 363

2-Chloro-6-(4-methanesulfonyl-piperazin-1-ylmethyl)-4-morpholin-4-yl-thieno[2,3-d]pyrimidine was reacted with 4-methyl-3-boronic acid in General Procedure A. Purification on silica yielded 363. NMR: ($CDCl_3$): 2.63 (3 H, s, Me), 2.65-2.69 (4 H, m), 2.82 (3 H, s, Me), 3.29-3.31 (4 H, m), 3.85 (2 H, s, CH2), 3.88-3.90 (4 H, m), 3.95-3.97 (4 H, m), 7.20 (2 H, s, Ar), 8.50-8.51 (1 H, m, Ar) and 9.10 (1 H, s, Ar). MS: (ESI+): MH+=489.12

Example 281

4-(2-(5-methylpyridin-3-yl)-6-((4-(methylsulfonyl)piperazin-1-yl)methyl)thieno[2,3-d]pyrimidin-4-yl)morpholine 364

2-Chloro-6-(4-methanesulfonyl-piperazin-1-ylmethyl)-4-morpholin-4-yl-thieno[2,3-d]pyrimidine was reacted with 5-methyl-3-boronic acid in General Procedure A. Purification on silica yielded 364. NMR: ($CDCl_3$): 2.36 (3 H, s, Me), 2.57-2.60 (4 H, m), 2.73 (3 H, s, Me), 3.20-3.23 (4 H, m), 3.75 (2 H, s), 3.81-3.85 (4 H, m), 3.90-3.92 (4 H, m), 7.09 (1 H, s, Ar), 8.41 (1 H, s, Ar), 8.43 (1 H, s, Ar) and 9.36 (1 H, s, Ar). MS: (ESI+): MH+=489.09

Example 282

N-ethyl-5-(6-((4-(methylsulfonyl)piperazin-1-yl)methyl)-4-morpholinothieno[2,3-d]pyrimidin-2-yl)pyridin-2-amine 365

To a solution of 2-(BOC-amino)-5-bromopyridine (500 mg) in THF (20 mL) at 0° C. was added sodium hydride (88 mg) and the reaction stirred for 20 min. Then, iodoethane (0.18 mL) was added and the reaction stirred at room temperature for 16 h. The reaction was quenched with water (20 mL) and extracted into ethylacetate (3×20 mL). The organic layers were dried (MgSO$_4$) and reduced in vacuo to give (5-bromo-pyridin-2-yl)-ethyl-carbamic acid tert-butyl ester as a white solid.

To a solution of (5-bromo-pyridin-2-yl)-ethyl-carbamic acid tert-butyl ester as a white solid (706 mg) in DMSO (8 mL) was added bispinacolatodiboron (953 mg), potassium acetate (691 mg) and Pd(dppf)$_2$Cl$_2$ (96 mg) and the reaction was stirred at 80° C. for 16 h. After cooling to room temperature, the reaction was quenched with water (20 mL) and extracted into ethylacetate (3×30 mL). The organic layers were dried (MgSO$_4$), reduced in vacuo and purified on silica to give ethyl-[5-(4,4,5,5-tetramethyl-[1,3,2]dioxaborolan-2-yl)-pyridin-2-yl]-carbamic acid tert-butyl ester as a colourless oil.

2-Chloro-6-(4-methanesulfonyl-piperazin-1-ylmethyl)-4-morpholin-4-yl-thieno[2,3-d]pyrimidine was reacted with ethyl-[5-(4,4,5,5-tetramethyl-[1,3,2]dioxaborolan-2-yl)-pyridin-2-yl]-carbamic acid tert-butyl ester in General Procedure A. Purification on silica yielded 365. NMR: (CDCl$_3$): 1.31 (3 H, t, J 7.2, Me), 2.65-2.68 (4 H, m), 2.82 (3 H, s, Me), 3.28-3.31 (4 H, m), 3.38-3.44 (2 H, m, CH$_2$), 3.81 (2 H, s, CH$_2$), 3.88-3.90 (4 H, m), 3.94-3.97 (4 H, m), 4.71-4.74 (1 H, m, NH), 6.45 (1 H, d, J 8.7, Ar), 7.12 (1 H, s, Ar), 8.46 (1 H, dd, J 8.7 and 2.3, Ar) and 9.19 (1 H, d, J 2.3, Ar). MS: (ESI+): MH+=518.22

Example 283

5-(6-((4-((2-methoxyethyl)(methyl)amino)piperidin-1-yl)methyl)-4-morpholinothieno[2,3-d]pyrimidin-2-yl)pyridin-2-amine 366

(2-Chloro-4-morpholin-4-yl-thieno[2,3-d]pyrimidine-6-carboxaldehyde) was reacted with (2-methoxy-ethyl)-methyl-piperidin-4-yl-amine using standard reductive amination conditions to give [1-(2-chloro-4-morpholin-4-yl-thieno[2,3-d]pyrimidin-6-ylmethyl)-piperidin-4-yl]-(2-methoxyethyl)-methyl amine as a solid, which was reacted with 5-(4,4,5,5-tetramethyl-[1,3,2]dioxaborolan-2-yl)-pyridin-2-ylamine according to General Procedure A. The resulting solid was triturated with diethyl ether and methanol to give 366 as an off white solid (53% yield). NMR (CDCl3, 400 MHz), 1.59-1.70 (2H, m), 1.78-1.81 (2H, m), 2.10 (2H, t, J=12.3), 2.37 (3H, s), 2.42-2.48 (1H, m), 2.70 (2H, t, J=5.9), 3.07 (2H, d, J=11.3), 3.41 (3H, s), 3.49-3.54 (2H, m), 3.78 (2H, s), 3.92-3.94 (4H, m), 3.97-4.00 (4H, m), 4.67 (2H, br s), 6.60 (1H, d, J=8.9), 7.13 (1H, s), 8.51 (1H, dd, J=8.6 and 2.2), 9.20 (1H, d, J=1.6). MS: (ESI+): MH+=498

Example 284

5-(6-((4-((2-methoxyethyl)(methyl)amino)piperidin-1-yl)methyl)-4-morpholinothieno[2,3-d]pyrimidin-2-yl)-N-methylpyridin-2-amine 367

To a solution of 2-(BOC-amino)-5-bromopyridine (3.06 g) in THF (50 mL) was added sodium hydride (538 mg) and the reaction stirred at room temperature for 20 min. Then, iodomethane (0.84 mL) was added and the reaction stirred at room temperature for 16 h. The reaction was quenched with water (30 mL) and extracted into dichloromethane (3×30 mL). The organic layers were dried (MgSO$_4$) and reduced in vacuo to give (5-bromo-pyridin-2-yl)-methyl-carbamic acid tert-butyl ester as an oil.

To a solution of (5-bromo-pyridin-2-yl)-methyl-carbamic acid tert-butyl ester (3.286 g) in THF (50 mL) at −78° C. was added n-butyllithium (5.15 mL of a 2.5 M solution in hexanes). After stirring at −78° C. for 20 min, triisopropyl borate (5.31 mL) was added. The reaction was warmed to −45° C. over 4 h, then, neopentyl glycol (1.19 g) was added. The reaction was warmed to room temperature over 16 h and then quenched with ice/water (70 mL) and extracted into dichloromethane (3×40 mL). The organic layers were dried (MgSO$_4$), reduced in vacuo and purified on silica to give methyl-[5-(4,4,5,5-tetramethyl-[1,3,2]dioxaborolan-2-yl)-pyridin-2-yl]-carbamic acid tert-butyl ester as an off-white solid.

2-Chloro-4-morpholin-4-yl-thieno[2,3-d]pyrimidine-6-carboxaldehyde was reacted with (2-methoxy-ethyl)-methyl-piperidin-4-yl-amine using standard reductive amination conditions to give [1-(2-chloro-4-morpholin-4-yl-thieno[2,3-d]pyrimidin-6-ylmethyl)-piperidin-4-yl]-(2-methoxyethyl)-methyl amine as a solid, which was reacted with methyl-[5-(4,4,5,5-tetramethyl-[1,3,2]dioxaborolan-2-yl)-pyridin-2-yl]-carbamic acid tert-butyl ester according to General Procedure A. The resulting solid was triturated with diethyl ether to give 367 as an off white solid (35% yield). NMR (DMSO, 400 MHz), 1.38-1.50 (2H, m), 1.60-1.66 (2H, m), 1.97-2.03 (2H, m), 2.09 (2H, s), 2.19 (3H, s), 2.24-2.33 (1H, m), 2.55 (2H, dd, J=7.8 and 6.2), 2.84 (3H, d, J=4.8), 2.88-2.94 (2H, m), 3.31-3.36 (2H, m), 3.71 (2H, s), 3.75-3.79 (4H, m), 3.86-3.89 (4H, m), 6.50 (1H, d, J=8.8), 6.90-6.94 (1H, m), 7.43 (1H, s), 8.26 (1H, dd, J=8.8 and 2.3), 9.00 (1H, d, J=2.1). MS: (ESI+): MH+=512

Example 285

5-(6-((4-((2-methoxyethyl)(methyl)amino)piperidin-1-yl)methyl)-4-morpholinothieno[2,3-d]pyrimidin-2-yl)-N-methylpyrimidin-2-amine 368

To a solution [5-(4,4,5,5-tetramethyl-[1,3,2]dioxaborolan-2-yl)-pyrimidin-2-yl]-carbamic acid tert-butyl ester (457 mg, 1.43 mmol, 1 eq) in anhydrous tetrahydrofuran at 0° C., sodium hydride (60% in mineral oil, 69 mg, 1.7 mmol, 1.3 eq) was added and stirred for 20 mins at 0° C., before iodomethane (134 ul, 2.1 mmol, 1.5 eq) was added and stirred at room temperature overnight. The solution was extracted into ethyl acetate (20 ml) washing with water (20×20 ml), before drying over MgSO$_4$ and evaporation. The resulting orange solid (methyl-[5-(4,4,5,5-tetramethyl-[1,3,2]dioxaborolan-2-yl)-pyrimidin-2-yl]-carbamic acid tert-butyl ester) was used crude.

2-Chloro-4-morpholin-4-yl-thieno[2,3-d]pyrimidine-6-carboxaldehyde was reacted with (2-methoxy-ethyl)-methyl-piperidin-4-yl-amine using standard reductive amination conditions to give [1-(2-chloro-4-morpholin-4-yl-thieno[2,3-d]pyrimidin-6-ylmethyl)-piperidin-4-yl]-(2-methoxyethyl)-methyl amine as a solid, which was reacted with methyl-[5-(4,4,5,5-tetramethyl-[1,3,2]dioxaborolan-2-yl)-pyrimidin-2-yl]-carbamic acid tert-butyl ester according to General Procedure A. The resulting solid was purified by mass directed chromatography to give 368 as an off white solid (14% yield). NMR (CDCl3, 400 MHz), 1.59-1.62 (2H, m), 1.64-1.67 (2H, m), 2.04-2.07 (2H, m), 2.34 (3H, s), 2.37-2.42 (1H, m), 2.66-2.69 (2H, m), 3.02-3.05 (2H, m), 3.10 (3H, d, J=4.8), 3.37 (3H, s), 3.48-3.51 (2H, m), 3.74 (2H, s), 3.87-3.89 (4H, m), 3.93-3.95 (4H, m), 5.33-5.34 (1H, m), 7.10 (1H, s), 9.30 (2H, s). MS: (ESI+): MH+=513

Example 286

N-methyl-5-(6-((methyl(1-methylpiperidin-4-yl)amino)methyl)-4-morpholinothieno[2,3-d]pyrimidin-2-yl)pyrimidin-2-amine 369

Following the General Procedures herein, 369 was prepared. MS: (ESI+): MH+=469.6

Example 287

4-methyl-5-(6-((4-(methylsulfonyl)piperazin-1-yl)methyl)-4-morpholinothieno[2,3-d]pyrimidin-2-yl)pyridin-2-amine 370

To a solution of 2-amino-5-bromo-4-methylpyridine (300 mg) in dichloromethane (10 ml) was added dimethylaminopyridine (10 mg) and di-tert-butyldicarbonate (770 mg) and the reaction was stirred at room temperature for 16 h. The reaction was quenched with water (20 mL) and extracted into dichloromethane (3×20 ml). The organic layers were dired (MgSO$_4$), reduced in vacuo and purified on silica to give di-tert-butyl (5-bromo-4-methylpyridin-2-yl)imidodicarbonate as a yellow oil which solidified on standing.

To a solution of di-tert-butyl (5-bromo-4-methylpyridin-2-yl)imidodicarbonate (564 mg) in DMSO (8 mL) was added bis-pinacolatodiboron (592 mg), potassium acetate (429 mg) and Pd(dppf)$_2$Cl$_2$ (60 mg) and the reaction was heated at 80° C. for 16 h. After cooling to room temperature, the mixture was poured onto water and the product extracted into ethylacetate (3×20 mL). The organic layers were dried (MgSO$_4$), reduced in vacuo and purified on silica to give 2-di-tert-butyl imidodicarbonate-4-methyl-5-(4,4,5,5-tetramethyl-[1,3,2]dioxaborolan-2-yl)-pyridine as an oil.

2-Di-tert-butyl imidodicarbonate-4-methyl-5-(4,4,5,5-tetramethyl-[1,3,2]dioxaborolan-2-yl)-pyridine was reacted with 2-chloro-6-(4-methanesulfonyl-piperazin-1-ylmethyl)-4-morpholin-4-yl-thieno[2,3-d]pyrimidine in General Procedure A. Purification on silica yielded 370. NMR: (CDCl$_3$): (400 MHz, CDCl3): 2.51 (3 H, s, Me), 2.57-2.59 (4 H, m), 2.72 (3 H, s, Me), 3.19-3.20 (4 H, m), 3.73 (2 H, s, CH2), 3.78-3.80 (4 H, m), 3.82-3.84 (4 H, m), 2.21 (2 H, s, NH2), 6.31 (1 H, s, Ar), 7.06 (1 H, s, Ar) and 8.65 (1 H, s, Ar). MS: (ESI+): MH+ 504.18

Example 288

4-(2-(5,6-dimethylpyridin-3-yl)-6-((4-(methylsulfonyl)piperazin-1-yl)methyl)thieno[2,3-d]pyrimidin-4-yl)morpholine 371

To a solution of 2,3-lutidine (0.51 mL) in fuming sulfuric acid (10 mL) at 155° C. was added bromine (0.3 mL) dropwise over 2 h. The reaction mixture was then heated at 155° C. for 16 h. After cooling to room temperature, the mixture was poured onto ice and the ph adjusted to 10 with aqueous sodium hydroxide solution. The product was extracted into ethylacetate (3×40 mL) and the organic layers were dried (MgSO$_4$), reduced in vacuo and purified on silica to give 5-bromo-2,3-dimethyl-pyridine as a yellow oil.

To a solution of 5-bromo-2,3-dimethyl-pyridine (170 mg) in DMSO (5 mL) was added bis-pinacolatodiboron (371 mg), potassium acetate (269 mg) and Pd(dppf)$_2$Cl$_2$ (37 mg) and the reaction was heated at 80° C. for 16 h. After cooling to room temperature, the mixture was poured onto water and the product extracted into ethylacetate (3×20 mL). The organic layers were dried (MgSO$_4$) and reduced in vacuo to give 2,3-dimethyl-5-(4,4,5,5-tetramethyl-[1,3,2]dioxaborolan-2-yl)-pyridine as an oil.

2,3-Dimethyl-5-(4,4,5,5-tetramethyl-[1,3,2]dioxaborolan-2-yl)-pyridine was reacted with 2-chloro-6-(4-methanesulfonyl-piperazin-1-ylmethyl)-4-morpholin-4-yl-thieno[2,3-d]pyrimidine in General Procedure A. Purification on silica yielded 371. NMR: (CDCl$_3$): (400 MHz, CDCl3): 2.40 (3 H, s, Me), 2.59 (3 H, s, Me), 2.63-2.68 (4 H, m), 2.82 (3 H, s, Me), 3.29-3.31 (4 H, m), 3.84 (2 H, s, CH2), 3.90-3.92 (4 H, m), 3.98-4.00 (4 H, m), 7.17 (1 H, s, Ar), 8.41 (1 H, s, Ar) and 9.35 (1 H, s, Ar). MS: (ESI+): MH+ 503.15

Example 289

3,4-dimethyl-5-(6-((4-(methylsulfonyl)piperazin-1-yl)methyl)-4-morpholinothieno[2,3-d]pyrimidin-2-yl)pyridin-2-amine 372

To a solution of 2-amino-5-bromo-3,4-dimethylpyridine (300 mg) in dichloromethane (10 mL) was added dimethylaminopyridine (9 mg) and di-tert-butyldicarbonate (717 mg) and the reaction was stirred at room temperature for 16 h. The reaction was quenched with water (20 mL) and extracted into dichlormethane (2×20 mL). The organic layers were dried (MgSO$_4$), reduced in vacuo and purified on silica to give di-tert-butyl (5-bromo-3,4-dimethylpyridin-2-yl)imidodicarbonate as a white solid.

To a solution of di-tert-butyl (5-bromo-3,4-dimethylpyridin-2-yl)imidodicarbonate (597 mg) in DMSO (8 mL) was added bispinacolatodiboron (605 mg), potassium acetate (438 mg) and Pd(dppf)$_2$Cl$_2$ (61 mg) and the reaction was stirred at 80° C. for 16 h. After cooling to room temperature, the reaction was quenched with water (20 mL) and extracted into ethylacetate (3×30 mL). The organic layers were dried (MgSO$_4$), reduced in vacuo and purified on silica to give 2-di-tert-butylimidodicarbonate-3,4-dimethyl-5-(4,4,5,5-tetramethyl-[1,3,2]dioxaborolan-2-yl)-pyridine.

2-Di-tert-butylimidodicarbonate-3,4-dimethyl-5-(4,4,5,5-tetramethyl-[1,3,2]dioxaborolan-2-yl)-pyridine was reacted with 2-chloro-6-(4-methanesulfonyl-piperazin-1-ylmethyl)-4-morpholin-4-yl-thieno[2,3-d]pyrimidine in General Procedure A. Purification on silica yielded 372. NMR: (CDCl3): (400 MHz, CDCl3): 2.02 (3 H, s, Me), 2.51 (3 H, s, Me), 2.66-2.69 (4 H, m), 2.82 (3 H, s, Me), 3.29-3.32 (4 H, m), 3.81 (2 H, s, CH2), 3.81-3.88 (4 H, m), 3.92-3.95 (4 H, m), 4.53 (2 H, s, NH2), 7.17 (1 H, s, Ar) and 8.45 (1 H, s, Ar). MS: (ESI+): MH+ 518.23

Example 290

(S)-2-hydroxy-1-(4-((2-(6-(methylamino)pyridin-3-yl)-4-morpholinothieno[3,2-d]pyrimidin-6-yl)methyl)piperazin-1-yl)propan-1-one 373

Tert-butyl 4-((2-chloro-4-morpholinothieno[3,2-d]pyrimidin-6-yl)methyl)piperazine-1-carboxylate (75 mg) was reacted with 83 mg tert-butyl methyl(5-(4,4,5,5-tetramethyl-1,3,2-dioxaborolan-2-yl)pyridin-2-yl)carbamate via General Procedure A. The crude intermediate was extracted with ethyl acetate and saturated sodium bicarbonate solution. The organic layer was concentrated to dryness then treated with TFA to remove the t-butoxycarbonyl groups. The crude TFA salt of N-methyl-5-(4-morpholino-6-(piperazin-1-ylmethyl)thieno[3,2-d]pyrimidin-2-yl)pyridin-2-amine was reacted with L-Lactic acid via General Procedure B to give 44.2 mg of 373 after reverse phase HPLC purification. MS (Q1) 498.3 (M)+.

Example 291

(S)-2-hydroxy-1-(4-((2-(6-(methylamino)pyridin-3-yl)-4-morpholinothieno[2,3-d]pyrimidin-6-yl)methyl)piperazin-1-yl)propan-1-one 374

Tert-butyl 4-((2-chloro-4-morpholinothieno[2,3-d]pyrimidin-6-yl)methyl)piperazine-1-carboxylate (75 mg) was reacted with 83 mg tert-butyl methyl(5-(4,4,5,5-tetramethyl-1,3,2-dioxaborolan-2-yl)pyridin-2-yl)carbamate via General Procedure A. The crude intermediate was extracted with ethyl acetate and saturated sodium bicarbonate solution. The organic layer was concentrated to dryness then treated with TFA to remove the t-butoxycarbonyl groups. The crude TFA salt of N-methyl-5-(4-morpholino-6-(piperazin-1-ylmethyl)thieno[2,3-d]pyrimidin-2-yl)pyridin-2-amine was reacted with L-Lactic acid via General Procedure B to give 46 mg of 374 after reverse phase HPLC purification. MS (Q1) 498.3 (M)+.

Example 292

(S)-2-hydroxy-1-(4-((7-methyl-2-(6-(methylamino)pyridin-3-yl)-4-morpholinothieno[3,2-d]pyrimidin-6-yl)methyl)piperazin-1-yl)propan-1-one 375

Tert-butyl 4-((2-chloro-7-methyl-4-morpholinothieno[3,2-d]pyrimidin-6-yl)methyl)piperazine-1-carboxylate (84 mg) was reacted with 90 mg tert-butyl methyl(5-(4,4,5,5-tetramethyl-1,3,2-dioxaborolan-2-yl)pyridin-2-yl)carbamate via General Procedure A. The crude intermediate was extracted with ethyl acetate and saturated sodium bicarbonate solution. The organic layer was concentrated to dryness then treated with TFA to remove the t-butoxycarbonyl groups.

The crude TFA salt of N-methyl-5-(7-methyl-4-morpholino-6-(piperazin-1-ylmethyl)thieno[3,2-d]pyrimidin-2-yl)pyridin-2-amine was reacted with L-lactic acid via General Procedure B to give 56 mg of 375 after reverse phase HPLC purification. MS (Q1) 512.3 (M)+

Example 293

3-chloro-5-(6-((4-(methylsulfonyl)piperazin-1-yl)methyl)-4-morpholinothieno[2,3-d]pyrimidin-2-yl)pyridin-2-amine 376

4-(2-chloro-6-((4-(methylsulfonyl)piperazin-1-yl)methyl)thieno[2,3-d]pyrimidin-4-yl)morpholine (0.8 g, 1.7 mmol) was reacted with 3-chloro-5-(4,4,5,5-tetramethyl-1,3,2-dioxaborolan-2-yl)pyridin-2-amine (0.6 g) according to General Procedure Suzuki to provide 376 (0.8 g) following silica gel purification (0-15% MeOH in CH$_2$Cl$_2$) MS (Q1) 524 (M)+.

Example 294

3-chloro-5-(6-((4-(methylsulfonyl)piperazin-1-yl)methyl)-4-morpholinothieno[3,2-d]pyrimidin-2-yl)pyridin-2-amine 377

4-(2-Chloro-6-((4-(methylsulfonyl)piperazin-1-yl)methyl)thieno[3,2-d]pyrimidin-4-yl)morpholine (100 mg) was reacted with 3-chloro-5-(4,4,5,5-tetramethyl-1,3,2-dioxaborolan-2-yl)pyridin-2-amine (83 mg) according to General Procedure Suzuki to afford 377 (22 mg) following reverse phase HPLC purification. MS (Q1) 524 (M)+

Example 295

3-methyl-5-(6-((4-(methylsulfonyl)piperazin-1-yl)methyl)-4-morpholinothieno[2,3-d]pyrimidin-2-yl)pyridin-2-amine 378

2-Chloro-6-((4-(methylsulfonyl)piperazin-1-yl)methyl)-4-morpholinothieno[2,3-d]pyrimidine and 3-methyl-2-aminopyridine boronic acid were reacted in General Procedure A Suzuki Coupling to produce 378 in 80% yield after RP-HPLC purification. MS (Q1) 504.2 (M)+, purity 100% by UV 254 nm, 1H NMR (DMSO).

Example 296

4-methyl-5-(6-((4-(methylsulfonyl)piperazin-1-yl)methyl)-4-morpholinothieno[3,2-d]pyrimidin-2-yl)pyrimidin-2-amine 379

2-Chloro-6-(4-methanesulfonyl-piperazin-1-ylmethyl)-4-morpholin-4-yl-thieno[3,2-d]pyrimidine (225 mg) was coupled to 4-methyl-5-(4,4,5,5-tetramethyl (1,3,2-dioxaborolan-2-yl))pyrimidine-2-ylamine via General Procedure A to yield 42 mg of 379. MS (Q1) 505.2 (M)$^+$.

Example 297

1-((2-(2-(methylamino)pyrimidin-5-yl)-4-morpholinothieno[2,3-d]pyrimidin-6-yl)methyl)pyrrolidin-3-ol 380

To a solution of 2-chloro-4-morpholinothieno[2,3-d]pyrimidine-6-carbaldehyde (1.1 g, 3.9 mmol) in 1,2-dichloroethane (20 mL) was added pyrrolidin-3-ol (5.4 mmol), and AcOH (3.9 mmol). After the reaction mixture stirred 10 min at room temperature, Na(OAc)$_3$BH (4.6 mmol) was added then the mixture stirred 72 h at room temperature. The reaction was quenched by the addition of saturated aqueous NaHCO$_3$. The organic layer was separated and the aqueous layer was extracted with CH$_2$Cl$_2$. The combined organics were dried over Na$_2$SO$_4$ and concentrated in vacuo. The crude material was purified by silica gel chromatography (0-20% MeOH in CH$_2$Cl$_2$) to afford 1-((2-chloro-4-morpholinothieno[2,3-d]pyrimidin-6-yl)methyl)pyrrolidin-3-ol (0.5 g). MS (Q1) 355 (M)+

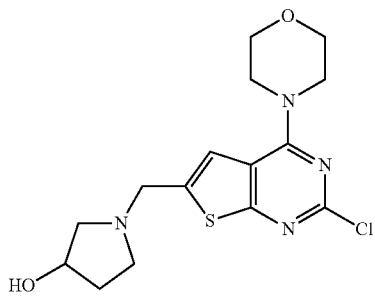 [SMILES: OC1CCN(Cc2cc3c(N4CCOCC4)nc(Cl)nc3s2)C1]

1-((2-chloro-4-morpholinothieno[2,3-d]pyrimidin-6-yl)methyl)pyrrolidin-3-ol (235 mg, 0.67 mmol) was utilized in a Suzuki coupling with tert-butyl methyl(5-(4,4,5,5-tetramethyl-1,3,2-dioxaborolan-2-yl)pyrimidin-2-yl)carbamate (311 mg, 0.93 mmol) according to General Procedure Suzuki to provide 380 (83 mg) after reverse phase HPLC purification. MS (Q1) 428 (M)+

Example 298

1-((2-(2-(methylamino)pyrimidin-5-yl)-4-morpholinothieno[2,3-d]pyrimidin-6-yl)methyl)piperidin-4-ol 381

To a solution of 2-chloro-4-morpholinothieno[2,3-d]pyrimidine-6-carbaldehyde (1.1 g, 3.9 mmol) in 1,2-dichloroethane (20 mL) was added piperidin-4-ol (5.4 mmol), and AcOH (3.9 mmol). After the reaction mixture stirred 10 min at room temperature, Na(OAc)$_3$BH (4.6 mmol) was added and the mixture stirred 72 h at room temperature. The reaction was quenched by the addition of saturated aqueous NaHCO$_3$. The organic layer was separated and the aqueous layer was extracted with CH$_2$Cl$_2$. The combined organics were dried over Na$_2$SO$_4$ and concentrated in vacuo. The crude reaction was purified by silica gel chromatography (0-20% MeOH in CH$_2$Cl$_2$) to afford 1-((2-chloro-4-morpholinothieno[2,3-d]pyrimidin-6-yl)methyl)piperidin-4-ol (0.6 g). MS (Q1) 369 (M)+

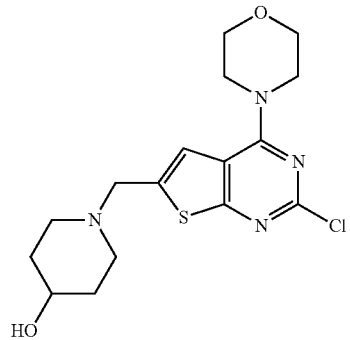 [SMILES: OC1CCN(Cc2cc3c(N4CCOCC4)nc(Cl)nc3s2)CC1]

1-((2-chloro-4-morpholinothieno[2,3-d]pyrimidin-6-yl)methyl)piperidin-4-ol (187 mg, 0.5 mmol) was utilized in a Suzuki coupling with tert-butyl methyl(5-(4,4,5,5-tetramethyl-1,3,2-dioxaborolan-2-yl)pyrimidin-2-yl)carbamate (238 mg, 0.7 mmol) according to General Procedure Suzuki to provide 381 (53 mg) after reverse phase HPLC purification. MS (Q1) 442 (M)+

Example 299

1-((2-(2-aminopyrimidin-5-yl)-4-morpholinothieno[3,2-d]pyrimidin-6-yl)methyl)-4-methylpiperidin-4-ol 382

To BOC piperidone (2.5 g) on dry ether (50 mL) was slowly added methyl magnesium bromide (3.0M solution in ether, 4.4.mL). The reaction mixture was heated to reflux for 16 hours, cooled, and 15 mL of 2M HCl was added. The ether layer was collected, washed with water, dried (MgSO$_4$) and the solvent removed in vacuo. The residue was purified using flash chromatography to yield 4-hydroxy-4-methyl-piperidine-1-carboxylic acid tert-butyl ester. Cleavage of the BOC group was achieved with 2M HCl in ether to yield 4-methyl-piperidin-4-ol.

Reaction of 4-methyl-piperidin-4-ol with 2-chloro-4-morpholin-4-yl-thieno[3,2-d]pyrimidine-6-carbaldehyde 10 using standard reductive amination conditions yielded 1-(2-chloro-4-morpholin-4-yl-thieno[3,2-d]pyrimidin-6-ylmethyl)-4-methyl-piperidin-4-ol, which was reacted with 2-aminopyrimidine-5-boronic acid in General Procedure A. Purification on silica yielded 382. 400 MHz 1H NMR CDCl3: 9.21 (s, 2H, 2×Ar): 7.19 (s, 1H, ArH); 5.17 (brs, NH2): 3.95 (t, 4H, 2×CH2, J=4.7 Hz); 3.80 (t, 4H, 2×CH2, J=4.7 Hz); 3.76 (s, 2H, CH2); 2.60-2.54 (m, 2H, CH2); 2.44 (t, 2H, CH2, J=10.9 Hz); 1.69-1.62 (m, 2H, CH2); 1.55 (d, 2H, CH2, J=16.1 Hz); 1.20 (s, 3H, Me); 1.12 (s, 1H, OH). LC-MS (m+1)=442.13

Example 300

N-(5-(6-((4-(methylsulfonyl)piperazin-1-yl)methyl)-4-morpholinothieno[2,3-d]pyrimidin-2-yl)pyridin-2-yl)acetamide 383

5-[6-(4-Methanesulfonyl-piperazin-1-ylmethyl)-4-morpholin-4-yl-thieno[2,3-]pyrimidin-2-yl]-pyridin-2-ylamine was reacted with excess of acetic anhydride in DCM and triethylamine at room temperature overnight to give 383. (CDCl3): 2.17 (3H, s), 2.56-2.59 (4H, m), 2.73 (3H, s), 3.20-3.23 (4H, m), 3.74 (2H, s), 3.81-3.84 (4H, m), 3.87-3.90 (4H, m), 7.08 (1H, s), 7.89 (1H, s), 8.19 (1H, d), 8.62 (1H, d), 9.22 (1H, s). (ESI+): MH+ 532.22 (30%)

Example 301

N-methyl-5-(6-((4-(methylsulfonyl)piperazin-1-yl)methyl)-4-morpholinothieno[2,3-d]pyrimidin-2-yl)pyridin-2-amine 384

To a solution of 2-(BOC-amino)-5-bromopyridine (3.06 g) in THF (50 mL) was added sodium hydride (538 mg) and the reaction stirred at room temperature for 20 min. Then, iodomethane (0.84 mL) was added and the reaction stirred at room temperature for 16 h. The reaction was quenched with water (30 mL) and extracted into dichloromethane (3×30 mL). The organic layers were dried (MgSO$_4$) and reduced in vacuo to give (5-bromo-pyridin-2-yl)-methyl-carbamic acid tert-butyl ester as an oil.

To a solution of (5-bromo-pyridin-2-yl)-methyl-carbamic acid tert-butyl ester (3.286 g) in THF (50 mL) at −78° C. was added n-butyllithium (5.15 mL of a 2.5 M solution in hexanes). After stirring at −78° C. for 20 min, triisopropyl borate (5.31 mL) was added. The reaction was warmed to −45° C. over 4 h, then, neopentyl glycol (1.19 g) was added. The reaction was warmed to room temperature over 16 h and then quenched with ice/water (70 mL) and extracted into dichloromethane (3×40 mL). The organic layers were dried (MgSO$_4$), reduced in vacuo and purfied on silica to give [5-(4,4,5,5-tetramethyl-[1,3,2]dioxaborinan-2-yl)-pyridin-2-yl]-methyl-carbamic acid tert-butyl ester as an off-white solid, which was reacted with 2-chloro-6-(4-methanesulfonyl-piperazin-1-ylmethyl)-4-morpholin-4-yl-thieno[2,3-d] pyrimidine in General Procedure A. Purification on silica yielded 384. NMR: (CDCl$_3$): 2.65-2.68 (4 H, m), 2.81 (3 H, s, Me), 3.02 (3 H, d, J 5.2, NMe), 3.28-3.30 (4 H, m), 3.81 (2 H, s), 3.88-3.90 (4 H, m), 3.94-3.97 (4 H, m), 4.78-4.80 (1 H, m, NH), 6.46 (1 H, d, J 8.8, Ar), 7.12 (1 H, s, Ar), 8.48 (1 H, dd, J 2.0 and 8.8, Ar) and 9.21 (1 H, d, J 2.0, Ar). MS: (ESI+): MH+ 504.14

Example 302

2-(4-((2-(2-aminopyrimidin-5-yl)-4-morpholinothieno[2,3-d]pyrimidin-6-yl)methyl)piperazin-1-yl)ethanol 385

To a solution of 2-chloro-4-morpholinothieno[2,3-d]pyrimidine-6-carbaldehyde (1.1 g, 3.9 mmol) in 1,2-dichloroethane (20 mL) was added 1-(2-hydroxyethyl)piperazine (0.7 mL, 5.4 mmol), and AcOH (3.9 mmol). After the reaction mixture stirred 10 min at room temperature, Na(OAc)$_3$BH (4.6 mmol) was added then the mixture stirred 72 h at room temperature. The reaction was quenched by the addition of saturated aqueous NaHCO$_3$. The organic layer was separated and the aqueous layer was extracted with CH$_2$Cl$_2$. The combined organics were dried over Na$_2$SO$_4$ and concentrated in vacuo. 2-(4-((2-chloro-4-morpholinothieno[2,3-d]pyrimidin-6-yl)methyl)piperazin-1-yl)ethanol was purified by silica gel chromatography (0-20% MeOH in CH$_2$Cl$_2$) to afford 2-(4-((2-chloro-4-morpholinothieno[2,3-d]pyrimidin-6-yl)methyl)piperazin-1-yl)ethanol (0.8 g). MS (Q1) 398 (M)+

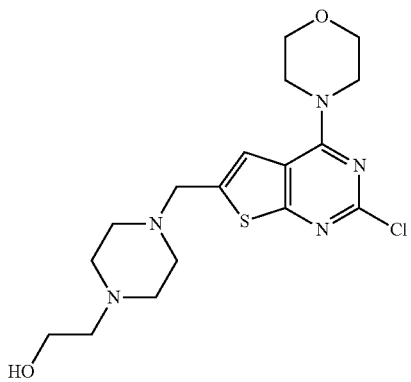 [SMILES: OCCN1CCN(Cc2cc3c(N4CCOCC4)nc(Cl)nc3s2)CC1]

2-(4-((2-chloro-4-morpholinothieno[2,3-d]pyrimidin-6-yl)methyl)piperazin-1-yl)ethanol (175 mg) was utilized in a Suzuki coupling with 5-(4,4,5,5-tetramethyl-1,3,2-dioxaborolan-2-yl)pyrimidin-2-amine according to General Procedure Suzuki to provide 385 (20 mg) after reverse phase HPLC purification. MS (Q1) 457 (M)+

Example 303

N,N-dimethyl-2-(5-(6-((4-(methylsulfonyl)piperazin-1-yl)methyl)-4-morpholinothieno[2,3-d]pyrimidin-2-yl)pyrimidin-2-yloxy)ethanamine 386

To a solution of N,N-dimethylethanolamine (0.36 mL) in THF (15 mL) was added sodium hydride (145 mg). After stirring at room temperature for 10 minutes, 5-bromo-2-chloropyrimidine (500 mg) was added and the mixture heated at reflux for 16 h. After cooling to room temperature, the mixture was extracted into 2 M aqueous HCl solution (30 mL) and washed with ethyl acetate (30 mL). The aqueous layer was made basic with sodium carbonate and the produt extracted into ethylacetate (3×30 mL). The organic layers were dried (MgSO$_4$) and reduced in vacuo to give [2-(5-bromo-pyridin-2-yloxy)-ethyl]-dimethylamine as a white solid.

To a solution of [2-(5-bromo-pyridin-2-yloxy)-ethyl]dimethylamine (260 mg) in 1,4-dioxane (10 mL) was added bis(tributyltin) (1.07 mL), tetrakis(triphenylphosphine) palladium(0) (61 mg) and lithium chloride (134 mg) and the reaction mixture was heated at reflux for 16 h. After cooling to room temperature, the mixture was filtered through Celite, washing with ethyl acetate. The filtrate was washed with water (2×20 mL), brine (20 mL), dried (MgSO$_4$), reduced in vacuo and purified by column chromatography to give dimethyl-[2-(5-tributylstannanyl-pyridin-2-yloxy)-ethyl]amine as a yellow oil.

To a solution of 6-(4-methanesulfonyl-piperazin-1-ylmethyl)-2-methylsulfanyl-4-morpholin-4-yl-thieno[2,3-d]pyrimidine (90 mg) in 1,2-dimethoxyethane (10 mL) was added dimethyl-[2-(5-tributylstannanyl-pyridin-2-yloxy)-ethyl]-amine (184 mg) and copper(I)bromide-dimethyl sulfide (83 mg) and the reaction mixture was stirred at room temperature for 10 minutes. Tetrakis(triphenylphosphine)palladium(0) (12 mg) was then added and the reaction mixture was heated at reflux for 16 h. After cooling to room temperature, the mixture was diluted with ethyl acetate (20 mL) and washed with water (2×20 mL) and brine (2×20 mL) The organic phase was dried (MgSO$_4$), reduced in vacuo and purified by column chromatography to give 386. NMR: (CDCl$_3$): 2.22 (6 H, s, Me), 2.50-2.52 (4 H, m), 2.66-2.69 (5 H, m), 3.13-3.15 (4 H, m), 3.68 (2 H, s, CH$_2$), 3.73-3.76 (4 H, m), 3.81-3.84 (4 H, m), 4.40-4.44 (2 H, m), 7.01 (1 H, s, Ar) and 9.31 (2 H, s, Ar). MS: (ESI+): MH+ 563.18

Example 304

4-(6-((4-(methylsulfonyl)piperazin-1-yl)methyl)-2-(6-phenylpyridin-3-yl)thieno[2,3-d]pyrimidin-4-yl)morpholine 387

To a solution of 2,5-dibromopyridine (1.00 g) in toluene (10 mL) and ethanol (5 mL) was added phenylboronic acid (515 mg), sodium carbonate (1.34 g) and tetrakis (triphenylphosphine)palladium(0) (24 mg) and the reaction mixture was heated at reflux for 16 h. After cooling to room temperature, the reaction was quenched with water (30 mL) and extracted into ethylacetate (2×30 mL). The organic layers were washed with brine (40 mL), dried (MgSO$_4$), reduced in vacuo and purified on silica to give 5-bromo-2-phenyl-pyridine as a white solid.

To a solution of 5-bromo-2-phenyl-pyridine (500 mg) in 1,4-dioxane (10 mL) was added bis(tributyltin) (2.16 mL), tetrakis(triphenylphosphine) palladium(0) (123 mg) and lithium chloride (272 mg) and the reaction mixture was heated at reflux for 16 h. After cooling to room temperature, the mixture was filtered through Celite, washing with ethyl acetate. The filtrate was washed with water (2×20 mL), brine (20 mL), dried (MgSO$_4$), reduced in vacuo and purified by column chromatography to give 2-phenyl-5-tributylstannanyl-pyridine as a yellow oil.

To a solution of 6-(4-methanesulfonyl-piperazin-1-ylmethyl)-2-methylsulfanyl-4-morpholin-4-yl-thieno[2,3-d]pyrimidine (90 mg) in 1,2-dimethoxyethane (10 mL) was added 2-phenyl-5-tributylstannanyl-pyridine (180 mg) and copper(I)bromide-dimethyl sulfide (84 mg) and the reaction mixture was stirred at room temperature for 10 minutes. Tetrakis (triphenylphosphine)palladium(0) (12 mg) was then added and the reaction mixture was heated at reflux for 16 h. After cooling to room temperature, the mixture was diluted with ethyl acetate (20 mL) and washed with water (2×20 mL) and brine (2×20 mL). The organic phase was dried (MgSO$_4$), reduced in vacuo and purified by column chromatography to give 387. NMR: (CDCl$_3$): 2.65-2.69 (4 H, m), 2.82 (3 H, s, Me), 3.28-3.32 (4 H, m), 3.84 (2 H, s, CH$_2$), 3.90-3.93 (4 H, m), 4.00-4.02 (4 H, m), 7.18 (1 H, s, Ar), 7.45-7.53 (3 H, m, Ar), 7.85 (1 H, d, J 8.5, Ar), 8.09-8.12 (2 H, m, Ar), 8.76 (1 H, d, J 8.5, Ar) and 9.72 (1 H, d, J 1.2, Ar). MS: (ESI+): MH+ 551.14

Example 305

(S)-2-hydroxy-1-(4-((2-(2-(methylamino)pyrimidin-5-yl)-4-morpholinothieno[2,3-d]pyrimidin-6-yl)methyl)piperazin-1-yl)propan-1-one 388

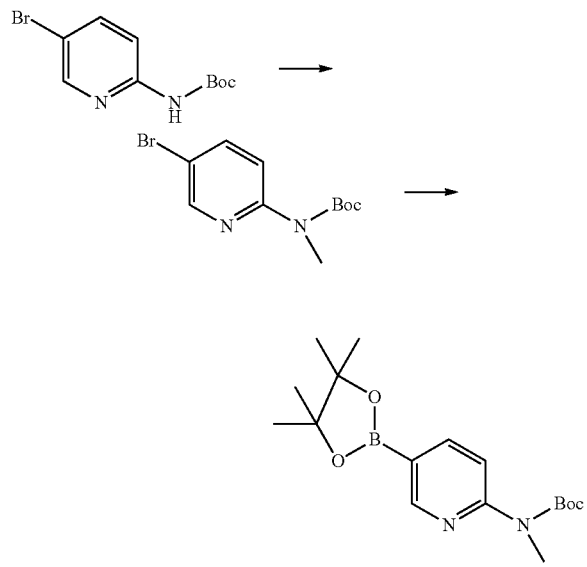

To 10 g of tert-butyl 5-bromopyridin-2-ylcarbamate was added 50 mL DMF and 20 g of cesium carbonate. Slowly 4 mL of methyl iodide was added to the stirring reaction mixture at room temperature. Monitor reaction by TLC until complete, about 30 minutes. The majority of the DMF was concentrated under hi-vacuum and the reaction mixture was subsequently extracted with ethyl acetate and water. The organic layer was concentrated and purified by isco using a 0-30% gradient (H/E) over 25 mins. The fractions containing product are concentrated to get 9.85 g of clear oil. To a solution of 9.5 g tert-butyl 5-bromopyridin-2-yl(methyl)carbamate in 60 mL DMSO was added 13 g bispinacolatodiboron, 9.7 g KOAc and 1.4 g [1,1'-bis(diphenylphosphi no)ferrocene]dichloropalladium(II), complex with dichloromethane (1:1) and the reaction was heated at 80° C. overnight. The reaction mixture was cooled to room temperature, water was added and extracted with ethyl acetate. The organic layer was dried, filtered and concentrated to give a black oil. Mixture was purified via ISCO; product elutes at 12% EtOAc. Pure fractions were concentrated to get 11.94 g of tert-butyl methyl(5-(4,4,5,5-tetramethyl-1,3,2-dioxaborolan-2-yl)pyridin-2-yl)carbamate as crystalline white solid. NMR indicates the presence of 30% by weight of residual bispinnacolatodiboron reagent.

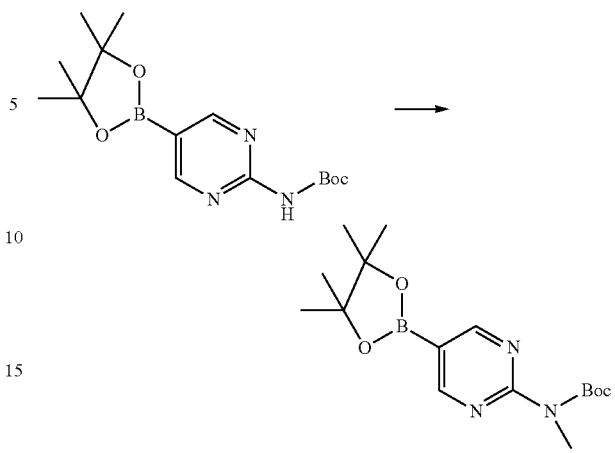

Tert-butyl 5-(4,4,5,5-tetramethyl-1,3,2-dioxaborolan-2-yl)pyrimidin-2-ylcarbamate (250 mg) was treated with 3 equivalents methyl iodide and cesium carbonate at room temperature for one hour. The crude reaction mixture was extracted with ethyl acetate and water. The initial organic layer was discarded. The aqueous layer was acidified to pH 5 and the product was extracted out of the aqueous with ethyl acetate. This organic layer was dried with magnesium sulfate, filtered and concentrated to give 150 mg crude tert-butyl methyl 5-(4,4,5,5-tetramethyl-1,3,2-dioxaborolan-2-yl)pyrimidin-2-ylcarbamate.

Tert-butyl 4-((2-chloro-4-morpholinothieno[2,3-d]pyrimidin-6-yl)methyl)piperazine-1-carboxylate (50 mg) was reacted with tert-butyl methyl 5-(4,4,5,5-tetramethyl-1,3,2-dioxaborolan-2-yl)pyrimidin-2-ylcarbamate via General Procedure A. This crude intermediate was treated with TFA for 30 minutes then evaporated to dryness.

The crude TFA salt of N-methyl-5-(4-morpholino-6-((piperazin-1-yl)methyl)thieno[2,3-d]pyrimidin-2-yl)pyrimidin-2-amine was reacted with L-lactic acid via General Procedure B to give 28.3 mg of 388 after reverse phase HPLC purification. MS (Q1) 499.3 (M)+

Example 306

(S)-2-hydroxy-1-(4-((7-methyl-2-(2-(methylamino)pyrimidin-5-yl)-4-morpholinothieno[3,2-d]pyrimidin-6-yl)methyl)piperazin-1-yl)propan-1-one 389

Tert-butyl 5-(4,4,5,5-tetramethyl-1,3,2-dioxaborolan-2-yl)pyrimidin-2-ylcarbamate (250 mg) was treated with 3 equivalents methyl iodide and cesium carbonate at room temperature for one hour. The crude reaction mixture was extracted with ethyl acetate and water. The initial organic layer is discarded. The aqueous layer was acidified to pH 5 and the product was extracted out of the aqueous with ethyl acetate. This organic layer was dried with magnesium sulfate, filtered and concentrated to give 150 mg crude tert-butyl methyl5-(4,4,5,5-tetramethyl-1,3,2-dioxaborolan-2-yl)pyrimidin-2-ylcarbamate.

Tert-butyl 4-((2-chloro-7-methyl-4-morpholinothieno[3,2-d]pyrimidin-6-yl)methyl)piperazine-1-carboxylate (50 mg) was reacted with tert-butyl methyl5-(4,4,5,5-tetramethyl-1,3,2-dioxaborolan-2-yl)pyrimidin-2-ylcarbamate via General Procedure A. This crude intermediate was treated with TFA for 30 minutes then evaporated to dryness.

The crude TFA salt of N-methyl-5-(7-methyl-4-morpholino-6-((piperazin-1-yl)methyl)thieno[3,2-d]pyrimidin-2-yl)pyrimidin-2-amine was reacted with L-lactic acid via General Procedure B to give 24.5 mg of 389 after reverse phase HPLC purification. MS (Q1) 513.3 (M)+.

Example 307

5-(6-(1,4'-bipiperidin-1'-ylmethyl)-4-morpholinothieno[2,3-d]pyrimidin-2-yl)pyrimidin-2-amine 390

2-Chloro-4-morpholin-4-yl-thieno[2,3-d]pyrimidine-6-carbaldehyde was reacted with 4-piperidinopiperidine using the general reductive amination General Procedure to yield 1'-(2-chloro-4-morpholin-4-yl-thieno[2,3-d]pyrimidin-6-ylmethyl)-[1,4]bipiperidinyl, which was reacted with 2-aminopyrimidine-5-boronic acid, pinacol ester in General Procedure A. Purification on silica yielded 390. NMR: (CDCl$_3$): 1.45-1.48 (2H, m), 1.52-1.56 (6H, m), 1.79-1.81 (2H, m), 2.02-2.05 (2H, m), 2.25-2.27 (1H, m), 2.53-2.56 (4H, m), (3.06 (2H, d), 3.72 (2H, s), 3.86-3.90 (4H, m), 3.95-3.99 (4H, m), 5.25 (2H, s, br.), 7.10 (1H, s), 9.30 (1H, s). MS ESI m/z 495 (MH+, 100%)

Example 308

N-isopropyl-5-(6-((4-(methylsulfonyl)piperazin-1-yl)methyl)-4-morpholinothieno[3,2-d]pyrimidin-2-yl)pyrimidin-2-amine 391

To a solution of 5-bromo-2-chloropyrimidine (600 mg) in THF (10 mL) was added isopropylamine (5.30 mL) and the reaction heated at 65° C. for 16 h. After cooling to room temperature the mixture was poured into 2 M aqueous HCl (30 mL) and washed with dichloromethane (30 mL). The aqueous layer was made basic with sodium carbonate and the product extracted into dichloromethane (3×20 mL). The organic layers were dried (MgSO$_4$) and reduced in vacuo to give (5-bromo-pyridin-2-yl)-isopropylamine as an off-white solid.

To a solution of (5-bromo-pyridin-2-yl)-isopropylamine (490 mg) in 1,4-dioxane (10 mL) was added bis(tributyltin) (2.29 mL), tetrakis(triphenylphosphine) palladium(0) (131 mg) and lithium chloride (288 mg) and the reaction mixture was heated at reflux for 16 h. After cooling to room temperature, the mixture was filtered through Celite, washing with ethyl acetate. The filtrate was washed with water (2×20 mL), brine (20 mL), dried (MgSO$_4$), reduced in vacuo and purified by column chromatography to give isopropyl-(5-tributylstannanyl-pyridin-2-yl)-amine as a yellow oil.

To a solution of 6-(4-methanesulfonyl-piperazin-1-ylmethyl)-2-methylsulfanyl-4-morpholin-4-yl-thieno[3,2-d]pyrimidine (90 mg) in 1,2-dimethoxyethane (10 mL) was added isopropyl-(5-tributylstannanyl-pyridin-2-yl)-amine (173 mg) and copper(I)bromide-dimethyl sulfide (84 mg) and the reaction mixture was stirred at room temperature for 10 minutes. Tetrakis(triphenylphosphine)palladium(0) (12 mg) was then added and the reaction mixture was heated at reflux for 16 h. After cooling to room temperature, the mixture was diluted with ethyl acetate (20 mL) and washed with water (2×20 mL) and brine (2×20 mL). The organic phase was dried (MgSO$_4$), reduced in vacuo and purified by column chromatography to give 391. NMR: (CDCl$_3$): 1.24 (6 H, d, J 7.0, Me), 2.59-2.62 (4 H, m), 2.73 (3 H, s, Me), 3.21-3.24 (4 H, m), 3.78-3.81 (6 H, m), 3.92-3.95 (4 H, m), 4.14-4.19 (1 H, m, CH), 5.19 (1 H, d, J 7.5, NH), 7.21 (1 H, s, Ar) and 9.19 (2 H, s, Ar). MS: (ESI+): MH+ 533.48

Example 309

N-ethyl-5-(6-((4-(methylsulfonyl)piperazin-1-yl)methyl)-4-morpholinothieno[2,3-d]pyrimidin-2-yl)pyrimidin-2-amine 392

A solution of 5-bromo-2-chloropyrimidine (300 mg) in ethylamine (10 mL of a 2 M solution in THF) was heated at reflux for 16 h. After cooling to room temperature the mixture was poured into 2 M aqueous HCl (30 mL) and washed with dichloromethane (30 mL). The aqueous layer was made basic with sodium carbonate and the product extracted into dichloromethane (3×20 mL). The organic layers were dried (MgSO$_4$) and reduced in vacuo to give (5-bromo-pyridin-2-yl)-ethyl-amine as an off-white solid.

To a solution of (5-bromo-pyridin-2-yl)-ethyl-amine (364 mg) in 1,4-dioxane (10 mL) was added bis(tributyltin) (1.82 mL), tetrakis(triphenylphosphine) palladium(0) (104 mg) and lithium chloride (229 mg) and the reaction mixture was heated at reflux for 16 h. After cooling to room temperature, the mixture was filtered through Celite, washing with ethyl acetate. The filtrate was washed with water (2×20 mL), brine (20 mL), dried (MgSO$_4$), reduced in vacuo and purified by column chromatography to give ethyl-(5-tributylstannanyl-pyridin-2-yl)-amine as a yellow oil.

To a solution of 6-(4-methanesulfonyl-piperazin-1-ylmethyl)-2-methylsulfanyl-4-morpholin-4-yl-thieno[2,3-d]pyrimidine (90 mg) in 1,2-dimethoxyethane (10 mL) was added ethyl-(5-tributylstannanyl-pyridin-2-yl)-amine (167 mg) and copper(I)bromide-dimethyl sulfide (84 mg) and the reaction mixture was stirred at room temperature for 10 minutes. Tetrakis(triphenylphosphine) palladium(0) (12 mg) was then added and the reaction mixture was heated at reflux for 16 h. After cooling to room temperature, the mixture was diluted with ethyl acetate (20 mL) and washed with water (2×20 mL) and brine (2×20 mL). The organic phase was dried (MgSO$_4$), reduced in vacuo and purified by column chromatography to give 392. NMR: (CDCl$_3$): 1.16 (3 H, t, J 7.0, Me), 2.56-2.59 (4 H, m), 2.72 (3 H, s, Me), 3.19-3.22 (4 H, m), 3.39-3.50 (2 H, m, CH2), 3.72 (2 H, s, CH2), 3.80-3.87 (4 H, m), 4.02-4.08 (4 H, m), 5.23-5.26 (1 H, m), 7.04 (1 H, s, Ar) and 9.19 (2 H, s, Ar). MS: (ESI+): MH+ 519.27

Example 310

5-(6-((methyl(1-methylpiperidin-4-yl)amino)methyl)-4-morpholinothieno[2,3-d]pyrimidin-2-yl)pyrimidin-2-amine 393

2-Chloro-4-morpholin-4-yl-thieno[2,3-d]pyrimidine-6-carbaldehyde was reacted with 1-methyl-4-(methylamino) piperidine using the general reductive amination procedure to yield (2-chloro-4-morpholin-4-yl-thieno[2,3-d]pyrimidin-6-ylmethyl)-methyl-(1-methyl-piperidin-4-yl)-amine, which was reacted with 2-aminopyrimidine-5-boronic acid, pinacol ester in General Procedure A. Purification on silica yielded 393 NMR: (CDCl$_3$): 1.61-1.64 (2H, m), 1.79-1.86 (2H, m), 1.91-1.96 (2H, m), 2.27 (3H, s), 2.31 (3H, s), 2.48-2.52 (1H, m), 2.92 (2H, d), 3.81 (2H, s), 3.85-3.89 (4H, m), 3.92-3.96 (4H, m), 5.23 (2H, s, br.), 7.12 (1H, s), 9.30 (2H, s). MS ESI m/z 455 (MH+, 100%)

Example 311

N-isopropyl-5-(6-((4-(methylsulfonyl)piperazin-1-yl)methyl)-4-morpholinothieno[2,3-d]pyrimidin-2-yl)pyrimidin-2-amine 394

To a solution of 6-(4-methanesulfonyl-piperazin-1-ylmethyl)-2-methylsulfanyl-4-morpholin-4-yl-thieno[2,3-d]pyrimidine (90 mg) in 1,2-dimethoxyethane (10 mL) was added isopropyl-(5-tributylstannanyl-pyridin-2-yl)-amine (173 mg) and copper(I)bromide-dimethyl sulfide (84 mg) and the reaction mixture was stirred at room temperature for 10 minutes. Tetrakis(triphenylphosphine)palladium(0) (12 mg) was then added and the reaction mixture was heated at reflux for 16 h. After cooling to room temperature, the mixture was diluted with ethyl acetate (20 mL) and washed with water (2×20 mL) and brine (2×20 mL). The organic phase was dried (MgSO$_4$), reduced in vacuo and purified by column chromatography to give 394. NMR: (CDCl$_3$): 1.21 (6 H, d, J 6.5, Me), 2.56-2.59 (4 H, m), 2.73 (3 H, s, Me), 3.19-3.22 (4 H, m), 3.73 (2 H, s), 3.78-3.80 (4 H, m), 3.85-3.87 (4 H, m), 4.08-4.18 (1 H, m), 5.15 (1 H, d, J 7.0, NH), 7.05 (1 H, s, Ar) and 9.19 (2 H, s, Ar). MS: (ESI+): MH+ 533.28

Example 312

N-ethyl-5-(6-((4-(methylsulfonyl)piperazin-1-yl)methyl)-4-morpholinothieno[3,2-d]pyrimidin-2-yl)pyrimidin-2-amine 395

To a solution of 6-(4-methanesulfonyl-piperazin-1-ylmethyl)-2-methylsulfanyl-4-morpholin-4-yl-thieno[3,2-d]pyrimidine (152 mg) in 1,2-dimethoxyethane (10 mL) was added ethyl-(5-tributylstannanyl-pyridin-2-yl)-amine (283 mg) and copper(I)bromide-dimethyl sulfide (142 mg) and the reaction mixture was stirred at room temperature for 10 minutes. Tetrakis(triphenylphosphine)palladium(0) (20 mg) was then added and the reaction mixture was heated at reflux for 16 h. After cooling to room temperature, the mixture was diluted with ethyl acetate (20 mL) and washed with water (2×20 mL) and brine (2×20 mL). The organic phase was dried (MgSO$_4$), reduced in vacuo and purified by column chromatography to give 395. NMR: (CDCl$_3$): 1.21 (3 H, t, J 7.2, Me), 2.59-2.62 (4 H, m), 2.74 (1 H, s, Me), 3.21-3.24 (4 H, m), 3.41-3.50 (2 H, m, CH2), 3.79 (2 H, s), 3.80-3.81 (4 H, m), 3.93-3.96 (4 H, m), 5.23-5.25 (1 H, m, NH), 7.22 (1 H, s, Ar) and 9.20 (2 H, s, Ar). MS: (ESI+): MH+ 519.26

Example 313

5-(6-((4-(benzyl(methyl)amino)piperidin-1-yl)methyl)-4-morpholinothieno[2,3-d]pyrimidin-2-yl)pyrimidin-2-amine 396

To a mixture of 1-BOC-4-piperidone (505 mg) in 1,2-dichloroethane (10 mL) was added N-benzylmethylamine (0.39 ml) followed by trimethylorthoformate (0.83 mL). After 1 hour sodium triacetoxyborohydride (805 mg) was added. The reaction mixture was stirred for 2 days at room temperature. The reaction mixture was then diluted with dichloromethane, washed with aqueous sodium bicarbonate solution, dried (MgSO$_4$) and the solvent removed in vacuo to yield 4-(benzyl-methyl-amino)-piperidine-1-carboxylic acid tert-butyl ester.

4-(Benzyl-methyl-amino)-piperidine-1-carboxylic acid tert-butyl ester was dissolved in DCM and methanol and 2.0M HCl in ether was added. After 3 hours the solvent was removed in vacuo and the residue was recrystallised from ethyl acetate/methanol to yield benzyl-methyl-piperidin-4-yl-amine (hydrochloride salt).

2-Chloro-4-morpholin-4-yl-thieno[2,3-d]pyrimidine-6-carbaldehyde was reacted with benzyl-methyl-piperidin-4-yl-amine (hydrochloride salt) using the general reductive amination procedure to yield benzyl-[1-(2-chloro-4-morpholin-4-yl-thieno[2,3-d]pyrimidin-6-ylmethyl)-piperidin-4-yl]-methyl-amine, which was reacted with 2-aminopyrimidine-5-boronic acid, pinacol ester in General Procedure A. Purification on silica yielded 396. NMR (CDCl$_3$); 1.65-1.73 (2H, m), 1.79-1.83 (2H, m), 2.05-2.09 (2H, m), 2.20 (3H, s), 2.45-2.47 (1H, m); 3.02 (2H, d), 3.60 (2H, s), 3.78 (2H, s), 3.85-3.89 (4H, m), 3.92-3.96 (4H, m), 5.23 (2H, s, br.), 7.12 (1H, s), 7.23-7.24 (1H, m), 7.31-7.33 (4H, m), 9.30 (2H, s). MS ESI m/z 531 (MH+, 100%)

Example 314

5-(6-((4-((2-methoxyethyl)(methyl)amino)piperidin-1-yl)methyl)-4-morpholinothieno[2,3-d]pyrimidin-2-yl)pyrimidin-2-amine 397

2-Chloro-4-morpholin-4-yl-thieno[2,3-d]pyrimidine-6-carbaldehyde was reacted with (2-methoxy-ethyl)-methyl-piperidin-4-yl-amine using the general reductive amination procedure to yield [1-(2-chloro-4-morpholin-4-yl-thieno[2,3-d]pyrimidin-6-ylmethyl)-piperidin-4-yl]-(2-methoxy-ethyl)-methyl-amine, which was reacted with 2-aminopyrimidine-5-boronic acid, pinacol ester in General Procedure A. Purification on silica yielded 397. NMR (CDCl$_3$); 1.55-1.58 (2H, m), 1.71-1.74 (2H, m), 2.02-2.05 (2H, m), 2.30 (3H, s), 2.41-2.43 (1H, m), 2.62 (2H, t), 3.00 (2H, d), 3.39 (3H, s), 3.46 (2H, t), 3.75 (2H, s), 3.85-3.89 (4H, m), 3.92-3.96 (4H, m), 5.23 (2H, s, br.), 7.12 (1H, s), 9.30 (2H, s). MS ESI m/z 499 (MH+, 100%)

Example 315

(R)-1-(4-((2-(2-aminopyrimidin-5-yl)-4-morpholinothieno[2,3-d]pyrimidin-6-yl)methyl)piperazin-1-yl)-2-hydroxypropan-1-one 398

Tert-butyl 4-((2-chloro-4-morpholinothieno[2,3-d]pyrimidin-6 yl)methyl)piperazine-1-carboxylate (4.08 gm) was reacted with 2.79 g 5-(4,4,5,5-tetramethyl-1,3,2-dioxaborolan-2-yl)pyrimidin-2-amine via General Procedure A to yield 4.38 g tert-butyl 4-((2-(2-aminopyrimidin-5-yl)-4-morpholinothieno[2,3-d]pyrimidin-6-yl)methyl)piperazine-1-carboxylate. 150 mg of this crude intermediate was subjected to General Procedure D and subsequently reacted with 84 mg D-lactic Acid via General Procedure B to give 28 mg of 398 after reverse phase HPLC purification. MS (Q1) 485.3 (M)+.

Example 316

(R)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one 399

Tert-butyl 4-((2-chloro-7-methyl-4-morpholinothieno[3,2-d]pyrimidin-6-yl)methyl)piperazine-1-carboxylate (1.49 gm) was reacted with 985 mg 5-(4,4,5,5-tetramethyl-1,3,2-dioxaborolan-2-yl)pyrimidin-2-amine via General Procedure A to yield 1.62 g tert-butyl 4-((2-(2-aminopyrimidin-5-yl)-7-methyl-4-morpholinothieno[3,2-d]pyrimidin-6-yl)methyl)piperazine-1-carboxylate. 150 mg of this crude intermediate was subjected to General Procedure D and subsequently reacted with 84 mg D-lactic Acid via General Procedure B to give 106.3 mg of 399 after reverse phase HPLC purification. MS (Q1) 499.3 (M)+

Example 317

(R)-1-(4-((2-(2-aminopyrimidin-5-yl)-4-morpholinothieno[3,2-d]pyrimidin-6-yl)methyl)piperazin-1-yl)-2-hydroxypropan-1-one 400

Tert-butyl 4-((2-chloro-4-morpholinothieno[3,2-d]pyrimidin-6-yl)methyl)piperazine-1-carboxylate (2.4 gm) was reacted with 1.64 gm 5-(4,4,5,5-tetramethyl-1,3,2-dioxaborolan-2-yl)pyrimidin-2-amine via General Procedure A to yield 2.4 g tert-butyl 4-((2-(2-aminopyrimidin-5-yl)-4-morpholinothieno[3,2-d]pyrimidin-6-yl)methyl)piperazine-1-carboxylate. 150 mg of this crude intermediate was subjected to procedure D and subsequently reacted with 84 mg D-lactic Acid via General Procedure B to give 102.5 mg of 400 after reverse phase HPLC purification. MS (Q1) 485.2 (M)+.

Example 318

N-(5-(6-((4-(methylsulfonyl)piperazin-1-yl)methyl)-4-morpholinothieno[3,2-d]pyrimidin-2-yl)thiazol-2-yl)acetamide 401

A suspension of 2-chloro-6-(4-methanesulphonyl-piperazin-1-ylmethyl)-4-morpholin-4-yl-thieno[3,2-d]pyrimidine (201 mg, 0.465 mmol), (5-tributylstannyl-thiazol-2-yl)-carbamic acid tert-butyl ester (341 mg, 0.7 mmol), and Pd(PPh$_3$)$_4$ (27 mg, 0.023 mmol) in anhydrous DMA was heated in a microwave at 150° C. for 10 mins. Ethyl acetate/water extraction and purification on silica using 10% methanol in ethyl acetate as the eluent to give 5-[6-(4-methanesulphonyl-piperazin-1-ylmethyl)-4-morpholin-4-yl-thieno[3,2-d]pyrimidin-2-yl]-thiazol-2-ylamine as an off-white solid (84 mg, 36%).

To a solution of 5-[6-(4-methanesulphonyl-piperazin-1-ylmethyl)-4-morpholin-4-yl-thieno[3,2-d]pyrimidin-2-yl]-thiazol-2-ylamine (12 mg, 0.024 mmol) in THF (1 ml) at RT triethylamine (8 ul, 0.053 mmol, 2 eq) and acetyl chloride (2ul, 0.026 mmol, 1.1 eq) was added and the reaction allowed to stir at RT overnight. The solution was extracted into ethyl acetate (10 ml) washing with water (2×10 ml), and dried over MgSO$_4$. The crude material was triturated with diethyl ether to give 401 as a yellow solid (7 mg, 54% yield). NMR (CDCl3, 400 MHz), 2.34 (3H, s), 2.69 (4H, t, J=4.8), 2.83 (3H, s), 3.22 (4H, t, J=4.8), 3.89-3.91 (6H, m), 4.03 (4H, t, J=4.8), 7.33 (1H, s), 8.23 (1H, s), 9.44 (1H, br s). MS: (ESI+): MH+=538

Example 319

1-((2-(2-aminopyrimidin-5-yl)-4-morpholinothieno[3,2-d]pyrimidin-6-yl)methyl)-4-(pyridin-2-yl)piperidin-4-ol 402

To a solution of nBuLi (2.5 m in hexanes, 2.00 mL) at −50° C. was added 2-bromopyridine (780 mg) in dry ether (10 mL). After 10 minutes an ethereal solution of BOC-piperidone (1.16 g) was added and the reaction mixture was gradually warmed to room temperature. After 1 hour, the reaction mixture was quenched with ammonium chloride solution, extracted with ether, dried (MgSO$_4$) and the solvent removed in vacuo to yield an oil which was purified using flash chromatography to yield 4'-Hydroxy-3',4',5',6'-tetrahydro-2'H-[2, 4']bipyridinyl-1'-carboxylic acid tert-butyl ester. Cleavage of the BOC group with HCl yielded 2',3',5',6'-tetrahydro-1'H-[2,4]bipyridinyl-4'-ol.

Reaction of 2',3',5',6'-tetrahydro-1'H-[2,4]bipyridinyl-4'-ol with 2-chloro-4-morpholin-4-yl-thieno[3,2-d]pyrimidine-6-carbaldehyde 10 using standard reductive amination conditions yielded 1'-(2-chloro-4-morpholin-4-yl-thieno[3,2-d]pyrimidin-6-ylmethyl)-2',3',5',6'-tetrahydro-1'H-[2,4']bipyridinyl-4'-ol, which was reacted with 2-aminopyrimidine-5-boronic acid in General Procedure A. Purification on silica yielded 402. 400 MHz 1H NMR CDCl3 9.16 (s, 2H); 8.47 (d, 1H, J=4.8 Hz); 7.70 (t, 1H, J=7.7 Hz); 7.45 (d, 1H, J=7.9 Hz); 7.26 (s, 1H); 7.19 (t, 1H, J=6.2 Hz); 4.00 (t, 4H, J=4.6 Hz); 3.87 (s, 2H); 3.85 (t, 4H, J=4.7 Hz); 2.875 (d, 2H, J=11.0 Hz); 2.63 (t, 2H, J=11.2 Hz); 2.16 (m, 2H); 1.63 (d, 2H, J=12.6 Hz). LC-MS (m+1)=505.18

Example 320

4-(6-((4-(methylsulfonyl)piperazin-1-yl)methyl)-2-(5-phenylpyridin-3-yl)thieno[2,3-d]pyrimidin-4-yl)morpholine 403

To a solution of 3,5-dibromopyridine (1.00 g) in toluene (10 mL) and ethanol (5 mL) was added phenylboronic acid (515 mg), sodium carbonate (1.34 g) and tetrakis (triphenylphosphine)palladium(0) (24 mg) and the reaction mixture was heated at reflux for 16 h. After cooling to room temperature, the reaction was quenched with water (30 mL) and extracted into ethylacetate (2×30 mL). The organic layers were washed with brine (40 mL), dried (MgSO$_4$), reduced in vacuo and purified on silica to give 3-bromo-5-phenyl-pyridine as a white solid.

To a solution of 3-bromo-5-phenyl-pyridine (300 mg) in 1,4-dioxane (10 mL) was added bis(tributyltin) (1.30 mL), tetrakis(triphenylphosphine) palladium(0) (74 mg) and lithium chloride (163 mg) and the reaction mixture was heated at reflux for 16 h. After cooling to room temperature, the mixture was filtered through Celite, washing with ethyl acetate. The filtrate was washed with water (2×20 mL), brine (20 mL), dried (MgSO$_4$), reduced in vacuo and purified by column chromatography to give 3-phenyl-5-tributylstannanly-pyridine as a yellow oil.

To a solution of 6-(4-methanesulfonyl-piperazin-1-ylmethyl)-2-methylsulfanyl-4-morpholin-4-yl-thieno[2,3-d]pyrimidine (135 mg) in 1,2-dimethoxyethane (10 mL) was added 3-phenyl-5-tributylstannanyl-pyridine (270 mg) and copper(I)bromide-dimethyl sulfide (125 mg) and the reaction mixture was stirred at room temperature for 10 minutes. Tetrakis(triphenylphosphine)palladium(0) (18 mg) was then added and the reaction mixture was heated at reflux for 16 h. After cooling to room temperature, the mixture was diluted with ethyl acetate (20 mL) and washed with water (2×20 mL) and brine (2×20 mL). The organic phase was dried (MgSO$_4$), reduced in vacuo and purified by column chromatography to give 403. NMR: (CDCl$_3$): 3.17 (3 H, s, Me), 3.93-3.95 (4 H, m), 4.13-4.16 (4 H, m), 5.28 (2 H, s, NH), 7.83 (1 H, t, J 7.0, Ar), 7.92 (1 H, s, Ar), 8.26 (2 H, td, J 7.7 and 1.5, Ar), 8.53-8.54 (1 H, m, Ar) and 9.30 (2 H, s, Ar). MS: (ESI+): MH+ 497.08

Example 321

(S)-5-(6-((4-(2-hydroxypropanoyl)piperazin-1-yl)methyl)-4-morpholinothieno[2,3-d]pyrimidin-2-yl)picolinonitrile 404

Tert-butyl 4-((2-chloro-4-morpholinothieno[2,3-d]pyrimidin-6-yl)methyl)piperazine-1-carboxylate (75 mg) was reacted with 6-cyanopyridin-3-yl-3-boronic ester via General Procedure A. This crude intermediate was subjected to General Procedure D in which the crude HCl salt of 5-(4-morpholino-6-((piperazin-1-yl)methyl)thieno[2,3-d]pyrimidin-2-yl)pyridine-2-carbonitrile was reacted with L-Lactic acid via General Procedure B to give 7 mg of 404 after reverse phase HPLC purification. MS (Q1) 494.2 (M)+

Example 322

(S)-5-(6-((4-(2-hydroxypropanoyl)piperazin-1-yl) methyl)-7-methyl-4-morpholinothieno[3,2-d]pyrimidin-2-yl)picolinonitrile 405

Tert-butyl 4-((2-chloro-7-methyl-4-morpholinothieno[3,2-d]pyrimidin-6-yl)methyl)piperazine-1-carboxylate (75 mg) was reacted with 6-cyanopyridin-3-yl-3-boronic ester via General Procedure A. This crude intermediate was subjected to General Procedure D in which the crude HCl salt of 5-(7-methyl-4-morpholino-6-((piperazin-1-yl)methyl) thieno[3,2-d]pyrimidin-2-yl)pyridine-2-carbonitrile was reacted with L-Lactic acid via General Procedure B to give 8.6 mg of 405 after reverse phase HPLC purification. MS (Q1) 508.2 (M)+.

Example 323

(S)-1-(4-((2-(2,4-dimethoxypyrimidin-5-yl)-7-methyl-4-morpholinothieno[3,2-d]pyrimidin-6-yl)methyl)piperazin-1-yl)-2-hydroxypropan-1-one 406

Tert-butyl 4-((2-chloro-7-methyl-4-morpholinothieno[3,2-d]pyrimidin-6-yl)methyl)piperazine-1-carboxylate (75 mg) was reacted with 2,4-dimethoxypyrimidin-5-yl-5-boronic acid via General Procedure A. This crude intermediate was subjected to General Procedure D in which the crude HCl salt of 2-(2,4-dimethoxypyrimidin-5-yl)-7-methyl-4-morpholino-6-((piperazin-1-yl)methyl)thieno[3,2-d]pyrimidine was reacted with L-Lactic acid via General Procedure B to give 17.2 mg of 406 after reverse phase HPLC purification. MS (Q1) 544.2 (M)+.

Example 324

(S)-1-(4-((2-(2-(dimethylamino)pyrimidin-5-yl)-7-methyl-4-morpholinothieno[3,2-d]pyrimidin-6-yl) methyl)piperazin-1-yl)-2-hydroxypropan-1-one 407

Tert-butyl 4-((2-chloro-7-methyl-4-morpholinothieno[3,2-d]pyrimidin-6-yl)methyl)piperazine-1-carboxylate (100 mg) was reacted with 70 mg 2-(dimethylamino)pyrimidin-5-yl-5-boronic pinacol ester via General Procedure A. This crude intermediate was subjected to General Procedure D in which 100 mg of the crude HCl salt of N,N-dimethyl-5-(7-methyl-4-morpholino-6-((piperazin-1-yl)methyl)thieno[3,2-d]pyrimidin-2-yl)pyrimidin-2-amine was reacted with 60 mg L-lactic Acid via General Procedure B to give 25.5 mg of 407 after reverse phase HPLC purification. MS (Q1) 527.3 (M)+.

Example 325

1-((2-(2-aminopyrimidin-5-yl)-4-morpholinothieno[3,2-d]pyrimidin-6-yl)methyl)-4-(thiazol-2-yl)piperidin-4-ol 408

To a solution of thiazole (470 mg) in dry THF (10 mL) at −78° C. was added nBuLi (2.5 m in hexanes, 2.21 mL). After 30 minutes BOC-piperidone (1 g) was added and the reaction mixture was gradually warmed to room temperature. After stirring overnight, the reaction mixture was quenched with water, extracted with ethyl acetate, dried (MgSO$_4$) and the solvent removed in vacuo to yield an oil which was purified using flash chromatography to yield 4-hydroxy-4-thiazol-2-yl-piperidine-1-carboxylic acid tert-butyl ester. Cleavage of the BOC group with HCl yielded 4-thiazol-2-yl-piperidin-4-ol.

Reaction of 4-thiazol-2-yl-piperidin-4-ol with 2-chloro-4-morpholin-4-yl-thieno[3,2-d]pyrimidine-6-carbaldehyde 10 using standard reductive amination conditions yielded 1-(2-chloro-4-morpholin-4-yl-thieno[3,2-d]pyrimidin-6-ylmethyl)-4-thiazol-2-yl-piperidin-4-ol, which was reacted with 2-aminopyrimidine-5-boronic acid in General Procedure A. Purification on silica yielded 408. 400 MHz 1H NMR CDCl3 9.30 (s, 2H); 7.76 (d, 1H, J=3.3 Hz); 7.325 (d, 1H, J=3.3 Hz); 7.31 (s, 1H); 5.23 (s, NH2); 4.07-3.90 (m, 8H); 2.92 (d, 2H, J=11.7 Hz); 2.66 (t, 2H); 2.36 (m, 2H); 1.95 (d, 2H, J=11.6 Hz). LC-MS (m+1)=511.14

Example 326

4-(2-(2-methylpyrimidin-5-yl)-6-((4-(methylsulfonyl)piperazin-1-yl)methyl)thieno[2,3-d]pyrimidin-4-yl)morpholine 409

To a solution of 6-(4-methanesulfonyl-piperazin-1-ylmethyl)-2-methylsulfanyl-4-morpholin-4-yl-thieno[2,3-d]pyrimidine (104 mg) in 1,2-dimethoxyethane (10 mL) was added 2-methyl-5-tributylstannanyl-pyrimidine (180 mg) and copper(I)bromide-dimethyl sulfide (96 mg) and the reaction mixture was stirred at room temperature for 10 minutes. Tetrakis(triphenylphosphine)palladium (0) (14 mg) was then added and the reaction mixture was heated at reflux for 16 h. After cooling to room temperature, the mixture was diluted with ethyl acetate (20 mL) and washed with water (2×20 mL) and brine (2×20 mL). The organic phase was dried (MgSO$_4$), reduced in vacuo and purified by column chromatography to give 409. NMR: (CDCl$_3$): 2.67-2.70 (4 H, m), 2.82 (3 H, s, Me), 2.84 (3 H, s, Me), 3.30-3.32 (4 H, m), 3.85 (2 H, s, CH2), 3.91-3.92 (4 H, m), 3.98-4.01 (4 H, m), 7.01 (1 H, s, Ar) and 9.58 (2 H, s, Ar). MS: (ESI+): MH+=490.14

Example 327

N-methyl-5-(6-((4-(methylsulfonyl)piperazin-1-yl) methyl)-4-morpholinothieno[2,3-d]pyrimidin-2-yl) pyrimidin-2-amine 410

To a solution of 6-(4-methanesulfonyl-piperazin-1-ylmethyl)-2-methylsulfanyl-4-morpholin-4-yl-thieno[2,3-d]pyrimidine (80 mg) in 1,2-dimethoxyethane (10 mL) was added methyl-(5-tributylstannanyl-pyrimidin-2-yl)-amine (143 mg) (prepared as above) and copper(I)bromide-dimethyl sulfide (74 mg) and the reaction mixture was stirred at room temperature for 10 minutes. Tetrakis(triphenylphosphine) palladium (0) (10 mg) was then added and the reaction mixture was heated at reflux for 16 h. After cooling to room temperature, the mixture was diluted with ethyl acetate (20 mL) and washed with water (2×20 mL) and brine (2×20 mL). The organic phase was dried (MgSO$_4$), reduced in vacuo and purified by column chromatography to give 410. NMR: (CDCl$_3$): 2.65-2.68 (4 H, m), 2.82 (3 H, s, Me), 3.12 (3 H, d, J 5.1, Me), 3.29-3.31 (4 H, m), 3.82 (2 H, s, CH2), 3.89-3.90

(4 H, m), 3.94-3.96 (4 H, m), 5.30 (1 H, q, J 5.1, NH), 7.14 (1 H, s, Ar) and 9.30 (2 H, s, Ar). MS: (ESI+): MH+=505.19

Example 328

4-(2-(2-methylpyrimidin-5-yl)-6-((4-(methylsulfonyl)piperazin-1-yl)methyl)thieno[3,2-d]pyrimidin-4-yl)morpholine 411

To a solution of acetamidine hydrochloride (6.0 g) in ethanol (20 mL) was added sodium ethoxide (20 mL of a 21% solution in ethanol) and the reaction mixture was heated at 50° C. and mucobromic acid (6.82 g) in ethanol (10 mL) was added. After stirring at 50° C. for 1 h, a further portion of sodium ethoxide (10 mL of a 21% solution in ethanol) was added and the mixture was stirred at room temperature for 16 h. The mixture was then filtered and the filtrate reduced in vacuo. The residue was then treated with 2 M aqueous hydrochloric acid (30 mL) and stirred vigorously for 30 minutes. The resulting solid was filtered, washed with water and air dried to give 5-bromo-2-methyl-pyrimidine-4-carboxylic acid (1.46 g). This was then heated at 175° C. for 16 h. After cooling to room temperature the mixture was purified by Kugelrohr distillation to give 5-bromo-2-methyl-pyrimidine as a white solid (746 mg).

To a solution of 5-bromo-2-methyl-pyrimidine (300 mg) in 1,4-dioxane (10 mL) was added bis(tributyltin) (1.75 mL), tetrakis(triphenylphosphine)palladium (0) (100 mg) and lithium chloride (221 mg) and the reaction mixture was heated at reflux for 16 h. After cooling to room temperature, the mixture was filtered through Celite, washing with ethyl acetate. The filtrate was washed with water (2×20 mL), brine (20 mL), dried (MgSO$_4$), reduced in vacuo and purifed by column chromatography to give 2-methyl-5-tributylstannanyl-pyrimidine as a yellow oil.

To a solution of 6-(4-methanesulfonyl-piperazin-1-ylmethyl)-2-methylsulfanyl-4-morpholin-4-yl-thieno[3,2-d]pyrimidine (100 mg) in 1,2-dimethoxyethane (10 mL) was added 2-methyl-5-tributylstannanyl-pyrimidine (176 mg) and copper(I)bromide-dimethyl sulfide (94 mg) and the reaction mixture was stirred at room temperature for 10 minutes. Tetrakis(triphenylphosphine)palladium (0) (13 mg) was then added and the reaction mixture was heated at reflux for 16 h. After cooling to room temperature, the mixture was diluted with ethyl acetate (20 mL) and washed with water (2×20 mL) and brine (2×20 mL). The organic phase was dried (MgSO$_4$), reduced in vacuo and purified by column chromatography to give 411. NMR: (CDCl$_3$): 2.69-2.72 (4 H, m), 2.83 (3 H, s, Me), 2.84 (3 H, s, Me), 3.31-3.34 (4 H, m), 3.90-3.93 (6 H, m), 4.06-4.08 (4 H, m), 7.37 (1 H, Ar) and 9.58 (1 H, Ar). MS: (ESI+): MH+=490.15

Example 329

5-(4-morpholino-6-((4-(thiophen-2-ylsulfonyl)piperazin-1-yl)methyl)thieno[2,3-d]pyrimidin-2-yl)pyrimidin-2-amine 412

To 2-chloro-4-morpholin-4-yl-6-piperazin-1-ylmethyl-thieno[2,3-d]pyrimidine (150 mg) in anhydrous DCM (4 ml) and triethylamine (90 ul) was added 2-thiophenesulfonyl chloride (101 ul) at 0° C. The reaction mixture was allowed to warm up to room temperature over 4 hours. Aqueous work-up and purification on silica gave 2-chloro-4-morpholin-4-yl-6-[4-(thiophene-2-sulfonyl)-piperazin-1-ylmethyl]-thieno[2,3-d]pyrimidine (208 mg), which was reacted with 2-aminopyrimidine-5-boronic acid in General Procedure A. Purification on silica yielded 412. NMR (DMSO): 2.53-2.58 (4H, m), 3.20-3.23 (4H, m), 3.74-3.77 (4H, m), 3.80 (2H, s), 3.88-3.91 (4H, m), 7.08 (2H, br), 7.30-7.32 (1H, m), 7.52 (1H, s), 7.65-7.67 (1H, m), 8.08-8.10 (1H, m), 9.08 (2H, s) MS (ESI+): MH+ 559.15 (15%)

Example 330

5-(6-((4-(cyclopropylsulfonyl)piperazin-1-yl)methyl)-4-morpholinothieno[2,3-d]pyrimidin-2-yl)pyrimidin-2-amine 413

2-Chloro-4-morpholin-4-yl-thieno[2,3-d]pyrimidine-6-carbaldehyde (1.00 g) was reacted with tert-butyl-1-piperazine carboxylate (0.85 g) using standard reductive amination conditions. Aqueous work-up and purification on silica gave 4-(2-chloro-4-morpholin-4-yl-thieno[2,3-d]pyrimidine-6-ylmethyl-piperazine-1-carboxylic acid tert-butyl ester (1.61 g).

4-(2-Chloro-4-morpholin-4-yl-thieno[2,3-d]pyrimidine-6-ylmethyl0-piperazine-1-carboxylic acid tert-butyl ester (1.61 g) was treated with an excess of hydrogen chloride in diethyl ether at room temperature overnight. Removal of volatiles and basification with aqueous sodium hydrogen chloride afforded 2-chloro-4-morpholin-4-yl-6-piperazin-1-ylmethyl-thieno[2,3-d]pyrimidine (0.90 g).

To 2-chloro-4-morpholin-4-yl-6-piperazin-1-ylmethyl-thieno[2,3-d]pyrimidine (187 mg) in anhydrous DCM (5 ml) and triethylamine (111 ul) was added cyclopropanesulfonyl chloride (65 ul) at 0° C. The reaction mixture was allowed to warm up to room temperature over 4 hours. Aqueous work-up and purification on silica gave 2-chloro-4-morpholin-4-yl-6-[4-(cyclopropane-2-sulfonyl)-piperazin-1-ylmethyl]-thieno [2,3-d]pyrimidine (159 mg), which was reacted with 2-aminopyrimidine-5-boronic acid in General Procedure A. Purification on silica yielded 413. NMR (DMSO): 0.90-0.92 (2H, m), 0.97-1.00 (2H, m), 2.53-2.58 (4H, m), 2.60-2.64 (1H, m), 3.20-3.23 (4H, m), 3.74-3.77 (4H, m), 3.80 (2H, s), 3.88-3.91 (4H, m), 7.08 (2H, br), 7.52 (1H, s), 9.08 (2H, s) MS (ESI+): MH+ 517.22 (50%)

Example 331

2-(1-((2-(2-aminopyrimidin-5-yl)-4-morpholinothieno[3,2-d]pyrimidin-6-yl)methyl)piperidin-4-ylsulfonyl)-N,N-dimethylacetamide 414

To sodium hydride (60% wt. suspension in mineral oil, 108 mg) in dry DMF (5 ml) was added methyl thioglycolate (160 ul) dropwise at 0° C. After 30 minutes added 4-methanesulfonyl-piperidine-carboxylic acid tert-butyl ester (500 mg) as a solution in DMF (1.5 ml) and the reaction mixture was warmed up to room temperature over 5 hours. Aqueous work-up and purification on silica yielded 4-methoxycarbonylmethylsulfanyl-piperidine-1-carboxylic acid tert-butyl ester (414 mg).

To 4-methoxycarbonylmethylsulfanyl-piperidine-1-carboxylic acid tert-butyl ester (414 mg) in chloroform (5 ml) was added mCPBA (796 mg) and the reaction mixture was stirred at room temperature overnight. Aqueous work-up and purification on silica gave 4-methoxycarbonylmethylsulfonyl-piperidine-1-carboxylic acid tert-butyl ester (254 mg). 4-Methoxycarbonylmethylsulfonyl-piperidine-1-carboxylic acid tert-butyl ester (238 mg) was reacted with excess of dimethylamine solution in MeOH (2.0M, 7 ml) at room temperature overnight. Removal of volatiles afforded 4-N,N-dimethylamino-carbonylmethylsulfonyl-piperidine-1-carboxylic acid tert-butyl ester (280 mg), which was treated with excess of hydrogen chloride solution in diethyl ether (2.0M, 3 ml) at room temperature overnight to give 4-N,N-dimethylamino-carbonylmethylsulfonyl-piperidine HCl salt (209 mg).

4-N,N-Dimethylamino-carbonylmethylsulfonyl-piperidine HCl salt (101 mg) was reacted with 2-Chloro-4-morpholin-4-yl-thieno[3,2-d]pyrimidine-6-carbaldehyde 10 (120 mg) using standard reductive amination conditions. Aqueous work-up and purification on silica yielded 2-[1-(chloro-4-morpholin-4-yl-thieno[3,2-d]pyrimidin-6-ylmethyl)piperidine-4-sulfonyl]-N,N-dimethyl-acetamide (110 mg), which was reacted with 2-aminopyrimidine-5-boronic acid in General Procedure A. Purification on silica yielded 414. NMR (CDCl3): 1.98-2.08 (2H, m), 2.18-2.28 (4H, m), 3.04 (3H, s), 3.13-3.17 (2H, m), 3.22 (3H, s), 3.45-3.53 (1H, m), 3.85 (2H, s), 3.90-3.93 (4H, m), 4.03-4.06 (4H, m), 4.08 (2H, s), 5.20 (2H, br), 7.27 (1H, s), 9.30 (2H, s) MS (ESI+): MH+ 561.20 (100%

Example 332

5-(4-morpholino-6-((4-(thiazol-2-ylsulfonyl)piperidin-1-yl)methyl)thieno[3,2-d]pyrimidin-2-yl)pyrimidin-2-amine 415

To 4-hydroxy-piperidine-1-carboxylic acid tert-butyl ester (9.2 g) in dichloromethane (170 ml), stirring at 0° C. was added methane sulphonyl chloride (5.33 ml) and triethylamine (0.24 ml). The reaction mixture was slowly warmed to room temperature and stirred overnight. The reaction mixture was partitioned between chloroform and water. The combined organics were washed with brine and dried (MgSO$_4$). The solvent was removed in vacuo to yield 14 g of 4-methanesulfonyl-piperidine-carboxylic acid tert-butyl ester.

To sodium hydride (60% wt. suspension in mineral oil, 108 mg) in dry DMF (5 ml) was added 1,3-thiazole-2-thiol (315 mg) at 0° C. After 30 minutes, 4-methanesulfonyl-piperidine-carboxylic acid tert-butyl ester (500 mg) was added as a solution in DMF (2 ml) and the reaction mixture was warmed up to room temperature overnight, then heated at 50° C. for 3 hours. Aqueous work-up and purification on silica yielded 4-(thiazol-2-ylsulfanyl)-piperidine-1-carboxylic acid tert-butyl ester (174 mg).

4-(Thiazol-2-ylsulfanyl)-piperidine-1-carboxylic acid tert-butyl ester (172 mg) was treated with mCPBA (311 mg) in chloroform (5 ml) at room temperature for 7 hours. DCM/aqueous NaHCO$_3$ extraction and purification on silica gave 4-(thiazol-2-ylsulfonyl)-piperidine-1-carboxylic acid tert-butyl ester (166 mg), which was treated with excess of hydrogen chloride solution in diethyl ether (2.0M, 3 ml) at room temperature overnight to give 4-(thiazole-2-sulfonyl)-piperidine HCl salt (126 mg).

4-(Thiazole-2-sulfonyl)-piperidine HCl salt (124 mg) was reacted with 2-chloro-4-morpholin-4-yl-thieno[3,2-d]ppimidine-6-carbaldehyde 10 (130 mg) using standard reductive amination conditions. Aqueous work-up, purification on silica and trituration with hot ethyl acetate yielded 2-chloro-4-morpholin-4-yl-6-[4(thiazole-2-sulfonyl)-piperidin-1-yl-methyl]-thieno[3,2-d]pyrimidine (73 mg), which was reacted with 2-aminopyrimidine-5-boronic acid in General Procedure A. Purification on silica yielded 415. NMR (CDCl3): 2.03-2.18 (4H, m), 2.18-2.22 (2H, m), 3.12-3.16 (2H, m), 3.39-3.46 (1H, m), 3.84 (2H, s), 3.90-3.93 (4H, m), 4.03-4.06 (4H, m), 5.20 (2H, br), 7.26 (1H, s), 7.79 (1H, d, J=3.0), 8.11 (1H, d, J=3.0), 9.29 (2H, s) MS (ESI+): MH+ 559.13 (100%)

Example 333

5-(6-((4-(methylsulfonylmethylsulfonyl)piperazin-1-yl)methyl)-4-morpholinothieno[3,2-d]pyrimidin-2-yl)pyrimidin-2-amine 416

To 2-chloro-4-morpholin-4-yl-6-piperazin-1-ylmethyl-thieno[3,2-d]pyrimidine (54 mg) in DCM (2 ml) and triethylamine (44 ul) was added methylsulfonylmethylsulfonyl chloride (45 ul) at 0° C. The reaction mixture was allowed to warm up to room temperature overnight. Aqueous work-up and purification on silica gave 2-chloro-6-(4-methanesulfonylmethanesulfonyl-piperazin-1-ylmethyl)-4-morpholin-4-yl-thieno[3,2-d]pyrimidine (35 mg).

2-Chloro-6-(4-methanesulfonylmethanesulfonyl-piperazin-1-ylmethyl)-4-morpholin-4-yl-thieno[3,2-d]pyrimidine was reacted with 2-aminopyrimidine-5-boronic acid in General Procedure A. Purification on silica yielded 416. NMR (CDCl3): 2.67-2.70 (4H, m), 3.24 (3H, s), 3.49-3.54 (4H, m), 3.90 (2H, s), 3.90-3.93 (4H, m), 4.03-4.06 (4H, m), 4.42 (2H, s), 5.24 (2H, br s), 7.30 (1H, s), 9.30 (2H, s). MS (ESI+): MH+ 569.17 (100%)

Example 334

N-methyl-5-(6-((4-(methylsulfonyl)piperazin-1-yl)methyl)-4-morpholinothieno[3,2-d]pyrimidin-2-yl)pyrimidin-2-amine 417

To a solution of 5-bromo-2-(methylamino)pyrimidine (200 mg) in 1,4-dioxane (10 mL) was added bis(tributyltin) (1.07 mL), tetrakis(triphenylphosphine)palladium (0) (61 mg) and lithium chloride (135 mg) and the reaction mixture was heated at reflux for 16 hf. After cooling to room temperature, the mixture was filtered through Celite, washing with ethyl acetate. The filtrate was washed with water (2×20 mL), brine (20 mL), dried (MgSO$_4$), reduced in vacuo and purifed by column chromatography to give methyl-(5-tributylstannyl-pyrimidin-2-yl)-amine as a yellow oil.

To a solution of 6-(4-methanesulfonyl-piperazin-1-ylmethyl)-2-methylsulfanyl-4-morpholin-4-yl-thieno[3,2-d]pyrimidine (80 mg) in 1,2-dimethoxyethane (10 mL) was added methyl-(5-tributylstannyl-pyrimidin-2-yl)-amine (143 mg) and copper(I)bromide-dimethyl sulfide (74 mg) and the reaction mixture was stirred at room temperature for 10 minutes. Tetrakis(triphenylphosphine)palladium (0) (10 mg) was then added and the reaction mixture was heated at reflux for 16 h. After cooling to room temperature, the mixture was diluted with ethyl acetate (20 mL) and washed with water (2×20 mL) and brine (2×20 mL). The organic phase was dried (MgSO$_4$), reduced in vacuo and purified by column chromatography to give 417. NMR: (CDCl$_3$): 2.59-2.61 (4 H, m), 2.73 (3 H, s, Me), 3.01 (3 H, d, J 5.1, Me), 3.21-3.24 (4 H, m), 3.78-3.81 (6 H, m), 3.93-3.96 (4 H, m), 7.22 (1 H, s, Ar) and 9.21 (2 H, s, Ar) MS: (ESI+): MH+=505.20

Example 335

4-(6-((4-(methylsulfonyl)piperazin-1-yl)methyl)-4-morpholinothieno[3,2-d]pyrimidin-2-yl)pyridin-2-amine 418

2-Chloro-6-(4-methanesulfonyl-piperazin-1-ylmethyl)-4-morpholin-4-yl-thieno[3,2-d]pyrimidine was reacted with 2-fluoropyridine-4-boronic acid in General Procedure A. Purification on silica yielded 2-(2-fluoro-pyridin-4-yl)-6-(4-methanesulfonyl-piperazin-1-ylmethyl)-4-morpholin-4-yl-thieno[3,2-d]pyrimidine.

2-(2-Fluoro-pyridin-4-yl)-6-(4-methanesulfonyl-piperazin-1-ylmethyl)-4-morpholin-4-yl-thieno[3,2-d]pyrimidine (107 mg) was heated in ammonia hydroxide (90 ml) in a sealed stainless steel pressurized vessel at 150° C. for 5 days. Extraction into chloroform and purification on silica afforded 418 (57 mg). NMR (CDCl3): 2.67-2.71 (4H, m), 2.81 (3H, s), 3.29-3.33 (4H, m), 3.89 (2H, s), 3.89-3.93 (4H, m), 4.08-4.12 (4H, m), 4.55 (2H, br s), 7.36 (1H, s), 7.54 (1H, s), 7.65 (1H, d, J=5.3), 8.21 (1H, d, J=5.3) MS (ESI+): MH+ 490.16 (74%)

Example 336

5-(6-(((1-isopropylpiperidin-4-yl)(methyl)amino) methyl)-4-morpholinothieno[3,2-d]pyrimidin-2-yl) pyrimidin-2-amine 419

(2-Chloro-4-morpholin-4-yl-thieno[3,2-d]pyrimidin-6-ylmethyl)methylamine was made by treating 2-chloro-4-morpholin-4-yl-thieno[3,2-d]pyrimidine-6-carbaldehyde 10 and 40% methylamine in water according to the General Procedure B-4.

(2-Chloro-4-morpholin-4-yl-thieno[3,2-d]pyrimidin-6-ylmethyl)-(1-isopropyl-piperidin-4-yl)-methyl-amine was made by treating (2-chloro-4-morpholin-4-yl-thieno[3,2-d]pyrimidin-6-ylmethyl)-methyl-amine andl-isopropyl-4-piperidone according to the General Procedure B-4.

A suspension of (2-chloro-4-morpholin-4-ylthieno[3,2-d]pyrimidin-6-ylmethyl)-(1-isopropyl-piperidin-4-yl)-methyl-amine (61 mg, 0.144 mmol), 5-(4,4,5,5-tetramethyl-[1,3,2] dioxaborolan-2-yl)-pyrimidin-2-ylamine (37 mg, 0.17 mmol), 1M Na$_2$CO$_3$ (0.5 ml, 0.5 mmol) and Pd(PPh$_3$)$_2$Cl$_2$ (10 mg, 0.014 mmol) in acetonitrile was heated in a microwave at 140° C. for 25 mins. The reaction was then acidified with 2N HCl (aq) extracted with ethyl acetate, the water layer separated and made basic with K$_2$CO$_3$ (sat. aq) resulting in a precipitate, purified on alumina using 5% methanol in dichloromethane as the eluent to give 419 (11 mg, 16%). NMR (CDCl3, 400 MHz), 1.05 (6H, d, J=6.8), 1.60-1.69 (2H, m), 1.72-1.76 (2H, m), 2.08-2.15 (2H, m), 2.37 (3H, s), 2.48-2.54 (1H, m), 2.71-2.76 (1H, m), 2.95-3.00 (2H, m), 3.89 (4H, t, J=4.4), 3.99 (2H, s), 4.05 (4H, t, J=4.8), 5.2 (2H, s), 7.27 (1H, s), 9.30 (2H, s). MS: (ESI+): MH+=483.

Example 337

5-(6-(((2R,6S)-2,6-dimethyl-4-(methylsulfonyl)piperazin-1-yl)methyl)-7-methyl-4-morpholinothieno[3, 2-d]pyrimidin-2-yl)pyrimidin-2-amine 420

To a mixture of cis-2,6-dimethylpiperazine and triethylamine in DCM at 0° C. was added dropwise methanesulphonyl chloride and the reaction mixture stirred at room temperature overnight. After quenching with water, extraction into DCM and being washed with brine, the organics were dried and the solvent removed under reduced pressure to yield 1-methanesulfonyl-3,5-dimethylpiperazine as a pale yellow solid.

To a suspension of 2-chloro-7-methyl-4-morpholin-4-yl-thieno[3,2-d]pyrimidine-6-carbaldehyde (400 mg, 1.34 mmol) in methanol at 0° C. was added sodium borohydride and. After stirring for 2 hours, the mixture was quenched with 50:50 H$_2$O:NaHCO$_3$ (sat. aq). The methanol was removed under reduced pressure to give a suspension which was filtered and washed with H$_2$O followed by ether to give (2-chloro-7-methyl-4-morpholin-4-yl-thieno[3,2-d]pyrimidin-6-yl)-methanol.

To a stirring suspension (2-chloro-7-methyl-4-morpholin-4-yl-thieno[3,2-d]pyrimidin-6-yl)-methanol in toluene at 40° C. was added PBr$_3$ and the reaction mixture stirred at 100° C. overnight. DCM/saturated aqueous NaHCO$_3$ extraction of the cooled mixture gave 6-bromomethyl-2-chloro-7-methyl-4-morpholin-4-yl-thieno[3,2-d]pyrimidine.

To a mixture of 1-methanesulfonyl-3,5-dimethylpiperazine and 6-bromomethyl-2-chloro-7-methyl-4-morpholin-4-yl-thieno[3,2-d]pyrimidine in acetonitrile was added potassium carbonate and the mixture refluxed overnight. After cooling to room temperature, the acetonitrile was removed under reduced pressure. DCM/sat. aq. NaHCO$_3$ extraction and purification on silica gave 2-chloro-6-((2S,6R)-4-methanesulfonyl-2,6-dimethyl-piperazin-1-ylmethyl)-7-methyl-4-morpholin-4-yl-thieno[3,2-d]pyrimidine.

2-Chloro-6-((2S,6R)-4-methanesulfonyl-2,6-dimethyl-piperazin-1-ylmethyl)-7-methyl-4-morpholin-4-yl-thieno[3, 2-d]pyrimidine (135 mg, 0.29 mmol) was reacted with 2-amino-pyrimidine-5-boronic acid pinacol ester (88 mg, 0.4 mmol) in General Procedure A. After extraction into 2M HCl, the mixture was washed with ethyl acetate then made basic and the precipitate collected by filtration. Purification using a thiourea SPE cartridge gave 420 as a cream solid (90 mg, 0.17 mmol) NMR (CDCl3, 400 MHz), 9.25 (s, 2H); 5.12 (s, 2H); 3.95 (t, 4H, J=4.6 Hz); 3.95 (s, 2H); 3.82 (t, 4H, J=4.8 Hz); 3.51 (d, 2H, J=11.3 Hz); 2.82 (m, 2H); 2.74 (s, 3H); 2.55 (t, 2H, J=10.8 Hz); 2.33 (s, 3H); 1.06 (d, 6H, J=6.3 Hz) MS: (ESI+): MH+=533.30

Example 338

1-((2-(2-aminopyrimidin-5-yl)-4-morpholinothieno [3,2-d]pyrimidin-6-yl)methyl)-4-(4-chlorophenyl) piperidin-4-ol 421

To 4-(4-chlorophenyl)-4-hydroxypiperidine (368 mg, 1.74 mmol) in dichloroethane was added 2-chloro-4-morpholin-4-yl-thieno[3,2-d]pyrimidine-6-carbaldehyde 10 (400 mg, 1.41 mmol) and trimethylorthoformate. After stirring for 1 hour at room temperature, sodium triacetoxyborohydride was added and the reaction mixture stirred overnight. The mixture was quenched with saturated aqueous Na$_2$CO$_3$. Chloroform/brine extraction gave crude material which was then triturated with hot ethyl acetate to give 1-(2-chloro-4-morpholin-4-yl-thieno[3,2-d]pyrimidin-6-ylmethyl)-4-(4-chloro-phenyl)-piperidin-4-ol. (272 mg, 0.56 mmol)

1-(2-Chloro-4-morpholin-4-yl-thieno[3,2-d]pyrimidin-6-ylmethyl)-4-(4-chloro-phenyl)-piperidin-4-ol (146 mg, 0.30 mmol) was reacted with 2-amino-pyrimidine-5-boronic acid pinacol ester (94 mg, 0.45 mmol) in General Procedure A. After extraction into 2M HCl, the mixture was washed with EtOAc then made basic and the precipitate collected by filtration. Purification on silica gave 421 as a pale yellow solid (75 mg, 0.14 mmol). NMR (CD$_3$OD, 400 MHz), 9.19 (s, 2H); 7.52 (m, 2H); 7.39 (s, 1H), 7.35 (m, 2H); 4.08 (t, 4H, J=4.1 Hz); 3.97 (s, 2H); 3.89 (t, 4H, J=4.8 Hz); 2.87 (d, 2H); 2.70 (t, 2H, J=11.2 Hz); 2.18 (m, 2H); 1.77 (d, 2H, J=13.2 Hz) MS: (ESI+): MH+=538.27

Example 339

(S)-3-methyl-4-(6-((4-methylpiperazin-1-yl)methyl)-2-(pyrimidin-5-yl)thieno[3,2-d]pyrimidin-4-yl)morpholine 422

Following General Procedure D, (S)-2-chloro-4-(3-methylmorpholino)thieno[3,2-d]pyrimidine-6-carbaldehyde (100 mg, 0.34 mmol), HOAc (25 mg), NaBH(OAc)$_3$ (80 mg, 0.37 mmol), N-methylpiperazine (41 mg, 0.40 mmol), 1,2-dichloroethane (1.0 mL), trimethylorthoformate were reacted at room temperature. The crude product was used in the next step without purification. MS (Q1) 382 (M)+. Following General Procedure A, crude product from above, pyrimidine-5-boronic acid (27 mg), Pd(PPh₃)₄ (20 mg), MeCN (1 mL) and 1M KOAc in H₂O (1 mL) were irradiated at 150° C. for 30 min. The reaction mixture was diluted with CH₂Cl₂, and filtered. The filtrate was concentrated to give crude 422 which was purified by reverse phase HPLC. (14 mg) MS (Q1) 426 (M)+

Example 340

(S)-5-(6-((methyl(1-methylpiperidin-4-yl)amino)methyl)-4-(3-methylmorpholino)thieno[2,3-d]pyrimidin-2-yl)pyrimidin-2-amine 423

To a solution of 2-chloro-4-morpholinothieno[2,3-d]pyrimidine-6-carbaldehyde (0.3 g, 1.0 mmol) in 1,2-dichloroethane (3.6 mL) was added N,1-dimethylpiperidin-4-amine (1.4 mmol), and AcOH (1.0 mmol). After the reaction mixture stirred 10 min at room temperature, Na(OAc)₃BH (1.1 mmol) was added then the mixture stirred 72 h at room temperature. The reaction was quenched by the addition of saturated aqueous NaHCO₃. The organic layer was separated and the aqueous layer was extracted with CH₂Cl₂. The combined organics were dried over Na₂SO₄ and concentrated in vacuo. The crude material was purified by silica gel chromatography (0-20% MeOH in CH₂Cl₂) to afford pure N-((2-chloro-4-morpholinothieno[2,3-d]pyrimidin-6-yl)methyl)-N,1-dimethylpiperidin-4-amine (0.2 g). MS (Q1) 410 (M)+

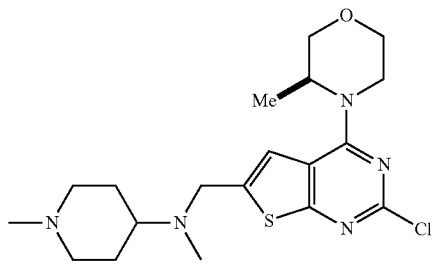 [SMILES: C[C@H]1COCCN1c1nc(Cl)nc2sc(CN(C)C3CCN(C)CC3)cc12]

N-((2-chloro-4-morpholinothieno[2,3-d]pyrimidin-6-yl)methyl)-N,1-dimethylpiperidin-4-amine (80 mg) was utilized in a Suzuki coupling with 5-(4,4,5,5-tetramethyl-1,3,2-dioxaborolan-2-yl)pyrimidin-2-amine according to General Procedure Suzuki to provide 423 after reverse phase HPLC purification. MS (Q1) 469 (M)+

Example 341

(S)-5-(4-(3-methylmorpholino)-6-((4-(methylsulfonyl)piperazin-1-yl)methyl)thieno[3,2-d]pyrimidin-2-yl)pyrimidin-2-amine 424

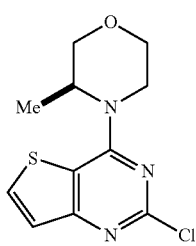 [SMILES: C[C@H]1COCCN1c1nc(Cl)nc2ccsc12]

Following General Procedure B, 3-(S)-methylmorpholine (2.2 eq), 2,4-Dichlorothieno[2,3-d]pyrimidine (400 mg, 1.95 mmol) in 5 mL of MeOH at rt for 3 h. The mixture was concentrated to dryness, diluted with sat. NaHCO₃ and extracted with CH₂Cl₂. The combined extracts were concentrated and purified by silica-gel chromatography to give (S)-4-(2-chlorothieno[3,2-d]pyrimidin-4-yl)-3-methylmorpholine (286 mg, 54%). MS (Q1) 270 (M)+.

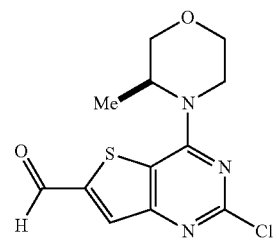 [SMILES: C[C@H]1COCCN1c1nc(Cl)nc2cc(C=O)sc12]

Following General Procedure C: (S)-4-(2-chlorothieno[3,2-d]pyrimidin-4-yl)-3-methylmorpholine (670 mg, 2.48 mmol) in THF (20 mL), was treated with nBuLi (1.48 mL, 2.5 M in hexanes, 3.7 mmol) and then dimethylformamide (DMF, 0.58 mL). Crude (S)-2-chloro-4-(3-methylmorpholino)thieno[3,2-d]pyrimidine-6-carbaldehyde was pure enough to use in subsequent manipulations without purification. MS (Q1) 298 (M)+

Following General Procedure D: (S)-2-chloro-4-(3-methylmorpholino)thieno[3,2-d]pyrimidine-6-carbaldehyde (110 mg, 0.37 mmol), HOAc (22 mg), NaBH(OAc)₃ (94 mg, 0.44 mmol), 1-methanesulfonyl piperazine (70 mg, 0.43 mmol), 1,2-dichloroethane (1.0 mL), trimethylorthoformate at room temperature for 1 h. The crude product was used in the next step without purification. MS (Q1) 445 (M)+. Following general procedure A: crude product from above, 2-aminopyrimidine-5-boronic acid pinacol ester (106 mg, 0.48 mmol), Pd(PPh₃)₄ (30 mg), MeCN (1.5 mL) and 1M KOAc in H₂O (1.5 mL) were irradiated at 140° C. for 30 min. The reaction mixture was diluted with CH₂Cl₂, and filtered. The filtrate was concentrated to give 424, purified by reverse phase HPLC. (28 mg) MS (Q1) 505 (M).

Example 342

(S)-1-(4-((2-(2-aminopyrimidin-5-yl)-4-(3-methylmorpholino)thieno[3,2-d]pyrimidin-6-yl)methyl)-1,4-diazepan-1-yl)ethanone 425

Following General Procedure D, (S)-2-chloro-4-(3-methylmorpholino)thieno[3,2-d]pyrimidine-6-carbaldehyde (110 mg, 0.37 mmol), HOAc (22 mg), NaBH(OAc)₃ (101 mg, 0.48 mmol), N-acetylhomopiperazine (63 mg, 0.44 mmol), 1,2-dichloroethane (1.0 mL), trimethylorthoformate were reacted at room temperature for 2 h. The crude product was used in the next step without purification. MS (Q1) 424 (M)+. Following general procedure A: crude product from above, 2-aminopyrimidine-5-boronic acid pinacol ester (106 mg, 0.48 mmol), Pd(PPh₃)₄ (30 mg), MeCN (1.5 mL) and 1M KOAc in H₂O (1.5 mL) were irradiated at 140° C. for 30 min. The reaction mixture was diluted with CH₂Cl₂, and filtered. The filtrate was concentrated to give crude 425 which was purified by reverse phase HPLC (68 mg). MS (Q1) 483 (M)+

Example 343

5-(6-((methyl(pyridin-4-ylmethyl)amino)methyl)-4-morpholinothieno[3,2-d]pyrimidin-2-yl)pyrimidin-2-amine 426

(2-Chloro-4-morpholin-4-yl-thieno[3,2-d]pyrimidin-6-ylmethyl)-methylamine was reacted with pyridine-4-carbaldehyde using standard reductive amination conditions. The resulting crude solid was triturated with diethyl ether to give (2-chloro-4-morpholin-4-yl-thieno[3,2-d]pyrimidin-6-ylmethyl)methylpyridin-4-ylmethylamine as a solid (93% yield), which was reacted with 5-(4,4,5,5-tetramethyl-[1,3,2]dioxaborolan-2-yl)-pyrimidin-2-ylamine according to General Procedure A. The resulting solid was triturated with diethyl ether and methanol to give 426 as a solid (80% yield). NMR (CDCl3, 400 MHz), 2.35 (3H, s), 3.66 (2H, s), 3.88 (2H, s), 3.91 (4H, t, J=5.2), 4.07 (4H, t, J=5.2), 5.27 (2H, s), 7.32 (1H, s), 7.36 (2H, d, J=6), 8.61-8.62 (2H, m), 9.30 (2H, s). MS: (ESI+): MH+=449

Example 344

5-(6-((methyl(pyridin-3-ylmethyl)amino)methyl)-4-morpholinothieno[3,2-d]pyrimidin-2-yl)pyrimidin-2-amine 427

(2-Chloro-4-morpholin-4-yl-thieno[3,2-d]pyrimidin-6-ylmethyl)-methylamine was reacted with pyridine-3-carbaldehyde using standard reductive amination conditions. The resulting crude solid was triturated with diethyl ether to give (2-chloro-4-morpholin-4-yl-thieno[3,2-d]pyrimidin-6-ylmethyl)-methyl-pyridin-3-ylmethyl-amine as a solid (71% yield), which was reacted with 5-(4,4,5,5-tetramethyl-[1,3,2]dioxaborolan-2-yl)-pyrimidin-2-ylamine according to General Procedure A. The resulting solid was triturated with diethyl ether and methanol to give 427 as a solid (99% yield). NMR (CDCl3, 400 MHz), 2.34 (3H, s), 3.67 (2H, s), 3.88 (2H, s), 3.92 (414, t, J=5.2), 4.06 (4H, t, J=5.2), 5.25 (2H, s), 7.30-7.33 (2H, m), 7.73-7.75 (2H, m), 8.55-8.57 (1H, m), 8.66-8.67 (1H, m), 9.30 (2H, s). MS: (ESI+): MH+=449

Example 345

5-(6-((methyl(pyridin-2-ylmethyl)amino)methyl)-4-morpholinothieno[3,2-d]pyrimidin-2-yl)pyrimidin-2-amine 428

(2-Chloro-4-morpholin-4-yl-thieno[3,2-d]pyrimidin-6-ylmethyl)-methylamine was reacted with pyridine-2-carbaldehyde using standard reductive amination conditions. The resulting crude solid was triturated with a small amount of diethyl ether to give (2-chloro-4-morpholin-4-yl-thieno[3,2-d]pyrimidin-6-ylmethyl)-methyl-pyridin-2-ylmethyl-amine as a solid (71% yield), which was reacted with 5-(4,4,5,5-tetramethyl-[1,3,2]dioxaborolan-2-yl)-pyrimidin-2-ylamine according to General Procedure A. The resulting solid was triturated with diethyl ether and methanol to give 428 as a solid (93% yield). NMR (CDCl3, 400 MHz), 2.41 (3H, s), 3.84 (2H, s), 3.91 (4H, t, J=5.2), 3.94 (2H, s), 4.06 (4H, t, J=5.2), 5.24 (2H, s), 7.20-7.23 (1H, m), 7.32 (1H, s), 7.54 (1H, d, J=4.8), 7.70-7.74 (1H, m), 8.59-8.60 (1H, m), 9.30 (2H, s). MS: (ESI+): MH+=449

Example 346

5-(6-((methyl((4-methylthiazol-2-yl)methyl)amino) methyl)-4-morpholinothieno[3,2-d]pyrimidin-2-yl) pyrimidin-2-amine 429

(2-Chloro-4-morpholin-4-yl-thieno[3,2-d]pyrimidin-6-ylmethyl)methylamine was reacted with 4-methyl-2-thiazole-carboxaldehyde using standard reductive amination conditions. The resulting crude solid was triturated with diethyl ether to give (2-chloro-4-morpholin-4-yl-thieno[3,2-d]pyrimidin-6-ylmethyl)-methyl-(4-methyl-thiazol-2-ylmethyl)-amine as a solid (62% yield), which was reacted with 5-(4,4,5,5-tetramethyl-[1,3,2]dioxaborolan-2-yl)-pyrimidin-2-ylamine according to General Procedure A. The resulting solid was triturated with diethyl ether and methanol to give 429 as a solid (95% yield). NMR (CDCl3, 400 MHz), 2.46 (3H, s), 2.47 (3H, s), 3.91 (4H, t, J=4.4), 3.97 (2H, s), 3.99 (2H, s), 4.07 (4H, t, J=5.2), 5.24 (2H, s), 6.90 (1H, d, J=0.8), 7.34 (1H, s), 9.30 (2H, s). MS: (ESI+): MH+=469

Example 347 p110α (Alpha) PI3K Binding Assay

Binding Assays: Initial polarization experiments were performed on an Analyst HT 96-384 (Molecular Devices Corp, Sunnyvale, Calif.). Samples for fluorescence polarization affinity measurements were prepared by addition of 1:3 serial dilutions of p110alpha PI3K (Upstate Cell Signaling Solutions, Charlottesville, Va.) starting at a final concentration of 20 ug/mL in polarization buffer (10 mM Tris pH 7.5, 50 mM NaCl, 4 mM $MgCl_2$, 0.05% Chaps, and 1 mM DTT) to 10 mM $PIP_2$ (Echelon-Inc., Salt Lake City, Utah) final concentration. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore ($\lambda$ex=530 nm; $\lambda$em=590 nm) in 384-well black low volume Proxiplates (PerkinElmer, Wellesley, Mass.) Fluorescence polarization values were plotted as a function of the protein concentration, and the $EC_{50}$ values were obtained by fitting the data to a 4-parameter equation using KaleidaGraph software (Synergy software, Reading, Pa.). This experiment also establishes the appropriate protein concentration to use in subsequent competition experiments with inhibitors.

Inhibitor $IC_{50}$ values were determined by addition of the 0.04 mg/mL p110alpha PI3K (final concentration) combined with $PIP_2$ (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore ($\lambda$ex=530 nm; $\lambda$em=590 nm) in 384-well black low volume proxi plates (PerkinElmer, Wellesley, Mass.) Fluorescence polarization values were plotted as a function of the antagonist concentration, and the $IC_{50}$ values were obtained by fitting the data to a 4-parameter equation in Assay Explorer software (MDL, San Ramon, Calif.).

Alternatively, inhibition of PI3K was determined in a radiometric assay using purified, recombinant enzyme and ATP at a concentration of 1 uM. The compound was serially diluted in 100% DMSO. The kinase reaction was incubated for 1 h at room temperature, and the reaction was terminated by the addition of PBS. $IC_{50}$ values were subsequently determined using sigmoidal dose-response curve fit (variable slope).

Example 348

In Vitro Cell Proliferation Assay

Efficacy of Formula Ia-d compounds were measured by a cell proliferation assay employing the following protocol (Promega Corp. Technical Bulletin TB288; Mendoza et al (2002) Cancer Res. 62:5485-5488):

1. An aliquot of 100 μl of cell culture containing about $10^4$ cells (PC3, Detroit562, or MDAMB361.1) in medium was deposited in each well of a 384-well, opaque-walled plate.
2. Control wells were prepared containing medium and without cells.
3. The compound was added to the experimental wells and incubated for 3-5 days.
4. The plates were equilibrated to room temperature for approximately 30 minutes.
5. A volume of CellTiter-Glo Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Alternatively, cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $EC_{50}$ values were calculated using a sigmoidal dose response curve fit.

Example 349

Caco-2 Permeability

Caco-2 cells were seeded onto Millipore Multiscreen plates at $1 \times 10^5$ cells/cm$^2$, and were cultured for 20 days. Assessment of compound permeability was subsequently conducted. The compounds were applied to the apical surface (A) of cell monolayers and compound permeation into the basolateral (B) compartment was measured. This was performed in the reverse direction (B–A) to investigate active transport. A permeability coefficient value, $P_{app}$, for each compound, a measure of the rate of permeation of the compound across the membrane, was calculated. Compounds were grouped into low ($P_{app} </= 1.0 \times 10^6$ cm/s) or high ($P_{app} >/= 1.0 \times 10^6$ cm/s) absorption potential based on comparison with control compounds with established human absorption.

For assessment of a compound's ability to undergo active efflux, the ratio of basolateral (B) to apical (A) transport compared with A to B was determined. Values of B–A/A–B >/=1.0 indicated the occurrence of active cellular efflux. The had $P_{app}$ values >/=$1.0 \times 10^6$ cm/s.

Example 350

Hepatocyte Clearance

Suspensions of cryopreserved human hepatocytes were used. Incubations were performed at compound concentration of 1 mM or 3 μM at a cell density of $0.5 \times 10^6$ viable cells/mL. The final DMSO concentration in the incubation was 0.25%. Control incubations were also performed in the absence of cells to reveal any non-enzymatic degradation. Duplicate samples (50 μL) were removed from the incubation mixture at 0, 5, 10, 20, 40 and 60 minutes (control sample at 60 minutes only) and added to MeOH—containing internal standard (100 μL)—to terminate the reaction. Tolbutamide, 7-hydroxycoumarin, and testosterone were used as control compounds. Samples were centrifuged and the supernatants at each time point pooled for analysis by LC-MSMS. From a plot of ln peak area ratio (parent compound peak area/internal standard peak area) against time, intrinsic clearance ($CL_{int}$) was calculated as follows: $CL_{int}$ (μl/min/million cells)=V×k, where k is the elimination rate constant, obtained from the gradient of ln concentration plotted against time; V is a volume term derived from the incubation volume and is expressed as uL $10^6$ cells$^{-1}$.

On the basis of low ($CL </=4.64$/min/$10^6$ cells), medium ($CL >/=4.6$; $</=25.2$ μl/min/$10^6$ cells) and high ($>/=25.2$ μl/min/$10^6$ cells) clearance, the compound of the invention was determined to have low hepatocyte clearance.

Example 351

Cytochrome P450 Inhibition

Certain compound of the invention was screened against five CYP450 targets (1A2, 2C9, 2C19, 2D6, 3A4) at 10 concentrations in duplicate, with a top concentration of 100 uM being used. Standard inhibitors (furafylline, sulfaphenazole, tranylcypromine, quinidine, ketoconazole) were used as controls. Plates were read using a BMG LabTechnologies PolarStar in fluorescence mode. The compound displayed weak activity ($IC_{50} >/= 5$ uM) against all isoforms of CYP450.

Example 352

Cytochrome P450 Induction

Freshly isolated human hepatocytes from a single donor were cultured for 48 h prior to addition of test compound at three concentrations and were incubated for 72 h. Probe substrates for CYP3A4 and CYP1A2 were added for 30 minutes and 1 h before the end of the incubation. At 72 h, cells and media were removed and the extent of metabolism of each probe substrate quantified by LC-MS/MS. The experiment was controlled by using inducers of the individual P450s incubated at one concentration in triplicate. The compound of the invention showed negligible effects on induction of cytochrome P450 enzymes.

Example 353

Plasma Protein Binding

Solutions of test compound (5 um, 0.5% final DMSO concentration) were prepared in buffer and 10% plasma (v/v in buffer). A 96 well HT dialysis plate was assembled so that each well was divided in two by a semi-permeable cellulose membrane. The buffer solution was added to one side of the membrane and the plasma solution to the other side; incubations were then conducted at 37° C. over 2 h in triplicate. The cells were subsequently emptied, and the solutions for each batch of compounds were combined into two groups (plasma-free and plasma-containing) then analysed by LC-MSMS using two sets of calibration standards for plasma-free (6 points) and plasma-containing solutions (7 points). The fraction unbound value for the compound was calculated: highly protein bound compounds ($>/=90%$ bound) had an Fu $</=0.1$. The compound of the invention had an Fu value $>/=0.1$.

Example 354 hERG Channel Blockage

The compound of the invention was evaluated for its ability to modulate rubidium efflux from HEK-294 cells stably expressing hERG potassium channels using established flux methodology. Cells were prepared in medium containing RbCl and were plated into 96-well plates and grown overnight to form monolayers. The efflux experiment was initiated by aspirating the media and washing each well with 3×100 μL of pre-incubation buffer (containing low [K+]) at room temperature. Following the final aspiration, 50 μL of working stock (2×) compound was added to each well and incubated at room temperature for 10 minutes. 50 μL of stimulation buffer (containing high [K+]) was then added to each well giving the final test compound concentrations. Cell plates were then incubated at room temperature for a further 10 minutes. 80 μL of supernatant from each well was then transferred to equivalent wells of a 96-well plate and analysed via atomic emission spectroscopy. The compound was screened as 10 pt duplicate $IC_{50}$ curves, n=2, from a top concentration of 100 μM.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

We claim:

1. A method of therapeutically treating cancer in a mammal in need of such treatment which is comprised of administering to said mammal a therapeutically effective amount of a compound selected from Formula Ic and Formula Id:

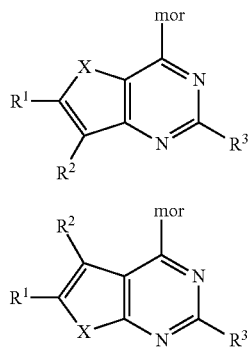

and stereoisomers, geometric isomers, tautomers, and pharmaceutically acceptable salts thereof, wherein:
X is O or S;
$R^1$ is a group of formula:

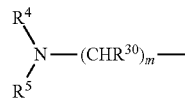

$R^2$ is selected from H, F, Cl, Br, I, $C_6$-$C_{20}$ aryl, $C_1$-$C_{20}$ heteroaryl, $C_1$-$C_6$ alkyl, $C_2$-$C_8$ alkenyl, and $C_2$-$C_8$ alkynyl;

$R^3$ is a monocyclic heteroaryl group selected from pyridyl, isoxazolyl, imidazolyl, pyrrolyl, thiazolyl, pyridazinyl, pyrimidinyl, pyrazinyl, oxazolyl, furanyl, thienyl, triazolyl, and tetrazolyl, where the monocyclic heteroaryl group is optionally substituted with one or more groups selected from F, Cl, Br, I, —CN, —$NR^{10}R^{11}$, —$OR^{10}$, —C(O)$R^{10}$, —$NR^{10}$C(O)$R^{11}$, —N(C(O)$R^{11}$)$_2$, —$NR^{10}$C(O)$NR^{10}R^{11}$, —$NR^{12}SO_2R^{10}$, —$NO_2$, —$SR^{10}$, —C(=O)$OR^{10}$, —C(=O)$NR^{10}R^{11}$, $C_6$-$C_{20}$ aryl, $C_1$-$C_{12}$ alkyl and ($C_1$-$C_{12}$ alkyl)-$OR^{10}$;

$R^4$ and $R^5$ form, together with the N atom to which they are attached, a group selected from piperazine, piperidine, pyrrolidine, oxazolidinone, morpholine, thiomorpholine, diazepan and 2,5-diaza-bicyclo[2,2,1]-heptane, which group is optionally substituted with one or more groups independently selected from F, Cl, Br, I, —CN, $CF_3$, —$NO_2$, oxo, —C(=Y)$R^{10}$, —C(=Y)$OR^{10}$, —C(=Y)$NR^{10}R^{11}$, —($CR^{14}R^{15}$)$_n$$NR^{10}R^{11}$, —($CR^{14}R^{15}$)$_n$$NR^{12}SO_2R^{10}$, —($CR^{14}R^{15}$)$_n$$OR^{10}$, —$NR^{10}R^{11}$, —$NR^{12}C$(=Y)$R^{10}$, —$NR^{12}C$(=Y)$OR^{11}$, —$NR^{12}C$(=Y)$NR^{10}R^{11}$, —$NR^{12}SO_2R^{10}$, =$NR^{12}$, $OR^{10}$, —OC(=Y)$R^{10}$, —OC(=Y)$OR^{10}$, —OC(=Y)$NR^{10}R^{11}$, —OS(O)$_2$($OR^{10}$), —OP(=Y)($OR^{10}$)($OR^{11}$), —OP($OR^{10}$)($OR^{11}$), $SR^{10}$, —S(O)$R^{10}$, —S(O)$_2$—($C_1$-$C_6$ alkyl)-S(O)$_2R^{10}$, —S(O)$_2R^{10}$, —S(O)$_2NR^{10}R^{11}$, —S(O)($OR^{10}$), —S(O)$_2$($OR^{10}$), —SC(=Y)$R^{10}$, —SC(=Y)$OR^{10}$, —SC(=Y)$NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

or one of $R^4$ and $R^5$ is $C_1$-$C_6$ alkyl, —($C_1$-$C_6$ alkyl)$_q$-($C_2$-$C_{20}$) heterocyclyl, or —($C_1$-$C_6$ alkyl)$_q$-$OR^{10}$ and the other is a piperazine, piperidine, pyrrolidine, sulfonylpyran, —($C_1$-$C_6$alkyl)-($C_2$-$C_{20}$) heterocyclyl group, or —($C_1$-$C_6$alkyl)-($C_1$-$C_{20}$) heteroaryl group, wherein said piperazine, piperidine, pyrrolidine, sulfonylpyran, heterocyclyl, or heteroaryl group is unsubstituted or substituted by $C_1$-$C_6$ alkyl, —($C_1$-$C_6$ alkyl)$_q$-$OR^{10}$ or —S(O)$_2R^{10}$;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a $C_3$-$C_{20}$ heterocyclic ring optionally containing one or more additional ring atoms selected from N, O or S, wherein said heterocyclic ring is optionally substituted with one or more groups independently selected from oxo, ($CH_2$)$_n$$OR^{10}$, $NR^{10}R^{11}$, $CF_3$, F, Cl, Br, I, $SO_2R^{10}$, C(=O)$R^{10}$, $NR^{12}C$(=Y)$R^{11}$, C(=Y)$NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —($CH_2$)$_n$-aryl, or $R^{14}$ and $R^{15}$ together with the atoms to which they are attached form a saturated or partially unsaturated $C_3$-$C_{12}$ carbocyclic ring, $R^{30}$ is H or $C_1$-$C_6$ alkyl;

mor is a morpholine group optionally substituted with one or more groups selected from F, Cl, Br, I, —C($C_1$-$C_6$ alkyl)$_2NR^{10}R^{11}$, —($CR^{14}R^{15}$)$_n$$NR^{10}R^{11}$, —C($R^{14}$$R^{15}$)$_n$$NR^{12}C$(=Y)$R^{10}$, —($CR^{14}R^{15}$)$_n$$NR^{12}S$(O)$_2R^{10}$, —CH($OR^{10}$)$R^{10}$, —($CR^{14}R^{15}$)$_n$$OR^{10}$, —($CR^{14}R^{15}$)$_n$S(O)$_2R^{10}$, —($CR^{14}R^{15}$)$_n$S(O)$_2NR^{10}R^{11}$, —C(=Y)$R^{10}$, —C(=Y)$OR^{10}$, —C(=Y)$NR^{10}R^{11}$, —C(=Y)$NR^{12}OR^{10}$, —C(=O)$NR^{12}S$(O)$_2R^{10}$, —C(=O)$NR^{12}$($CR^{14}R^{15}$)$_m$$NR^{10}R^{11}$, —$NO_2$, —$NR^{10}R^{11}$, —$NR^{12}C$(=Y)$R^{11}$, —$NR^{12}C$(=Y)$OR^{11}$, —$NR^{12}C$(=Y)

NR$^{10}$R$^{11}$, —NR$^{12}$S(O)$_2$R$^{10}$, —NR$^{12}$SO$_2$NR$^{10}$R$^{11}$, —S(O)$_2$R$^{10}$, —S(O)$_2$NR$^{10}$R$^{11}$, —SC(=Y)R$^{10}$, —SC(=Y)OR$^{10}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl;

where said alkyl, alkenyl, alkynyl, carbocyclyl, heterocyclyl, aryl and heteroaryl are optionally substituted with one or more groups independently selected from F, Cl, Br, I, —CN, CF$_3$, —NO$_2$, oxo, —C(=Y)R$^{10}$, —C(=Y)OR$^{10}$, —C(=Y)NR$^{10}$R$^{11}$, —(CR$^{14}$R$^{15}$)$_n$NR$^{10}$R$^{11}$, —(CR$^{14}$R$^{15}$)$_n$NR$^{12}$SO$_2$R$^{10}$, —(CR$^{14}$R$^{15}$)$_n$OR$^{10}$, —NR$^{10}$R$^{11}$, —NR$^{12}$C(=Y)R$^{10}$, —NR$^{12}$C(=Y)OR$^{11}$, —NR$^{12}$C(=Y)NR$^{10}$R$^{11}$, —NR$^{12}$SO$_2$R$^{10}$, =NR$^{12}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, optionally substituted C$_1$-C$_{12}$ alkyl, optionally substituted C$_2$-C$_8$ alkenyl, optionally substituted C$_2$-C$_8$ alkynyl, optionally substituted C$_3$-C$_{12}$ carbocyclyl, optionally substituted C$_2$-C$_{20}$ heterocyclyl, optionally substituted C$_6$-C$_{20}$ aryl, and optionally substituted C$_1$-C$_{20}$ heteroaryl;

Y is O, S, or NR$^{12}$;

each q is independently 0 or 1;

m is 0 or 1; and n is 1, 2, 3, 4, 5, or 6;

with the provisos that:

(i) when in Formula (Ic) mor is unsubstituted morpholino, X is S, R$^1$ is a (4-methylsulfonylpiperazin-1-yl)methyl group and R$^2$ is H, then R$^3$ is not a group selected from imidazolyl which is unsubstituted or substituted with one CH$_3$ group, pyrimidinyl which is unsubstituted and pyridinyl which is unsubstituted or substituted with one F group;

(ii) when in Formula (Ic) mor is unsubstituted morpholino, X is S, R$^1$ is a (4-methylpiperazin-1-yl)methyl group and R$^2$ is H, then R$^3$ is not pyridinyl which is substituted by one OH group; and (iii) when in Formula (Id) mor is unsubstituted morpholino, X is S, R$^1$ is a (4-methylsulfonylpiperazin-1-yl)methyl group and R$^2$ is H, then R$^3$ is not a group selected from pyridinyl which is unsubstituted and pyrimidinyl which is unsubstituted or substituted by one —OCH$_3$ or —N(CH$_3$)$_2$ group;

wherein the cancer is selected from prostate cancer, non-small cell lung cancer, and breast cancer.

2. The method of claim 1 wherein the compound is selected from Formula Ia and Formula Ib:

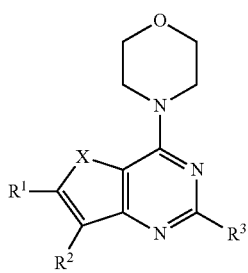

Ia

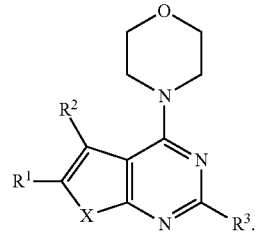

Ib

3. The method of claim 1 wherein mor is selected from the structures:

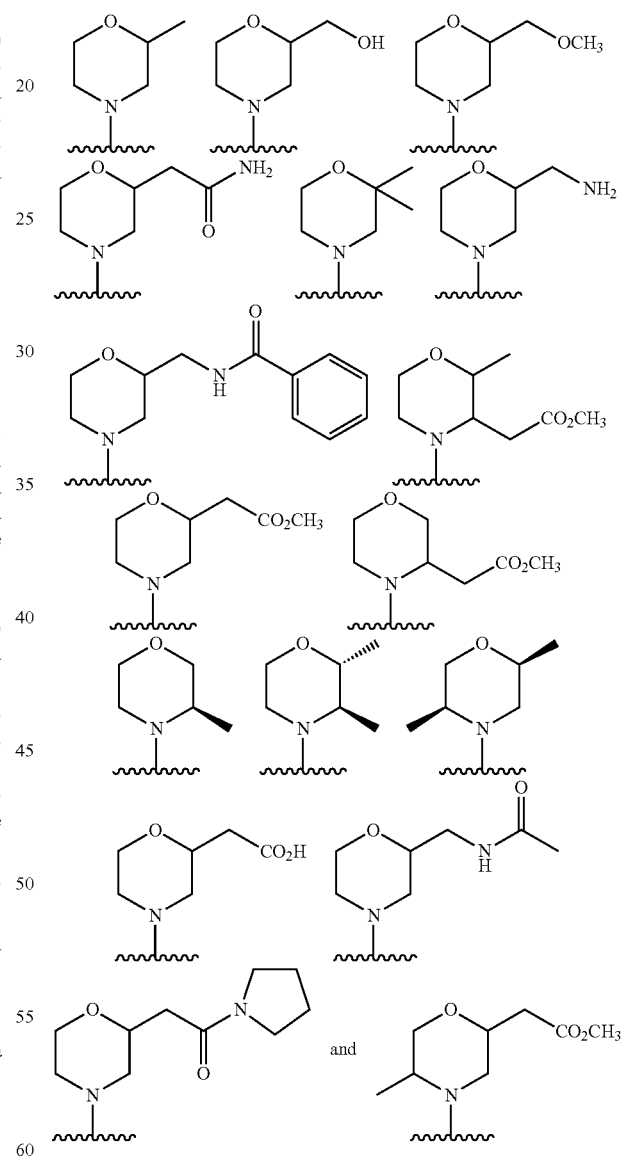

and where the wavy line indicates the attachment to the 4-position of the pyrimidine ring.

4. The method of claim 2 wherein the compound is Formula Ia, wherein X is S and having the formula:

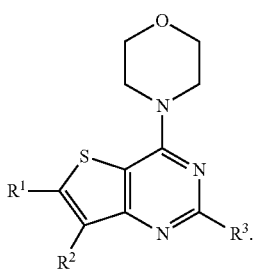

5. The method of claim 2 wherein the compound is Formula Ib, wherein X is S and having the formula:

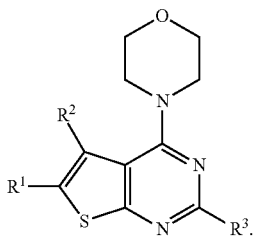

6. The method of claim 2 wherein the compound is Formula Ia, wherein X is O and having the formula:

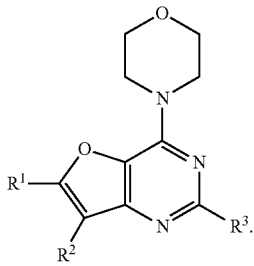

7. The method of claim 2 wherein the compound is Formula Ib, wherein X is O and having the formula:

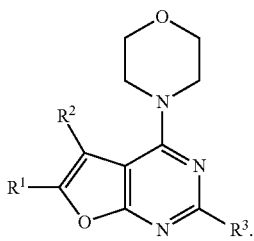

8. The method of claim 1 wherein $R^2$ is selected from H, F, Cl, Br, I, and $C_1$-$C_6$ alkyl.

9. The method of claim 1 wherein $R^3$ is selected from the structures:

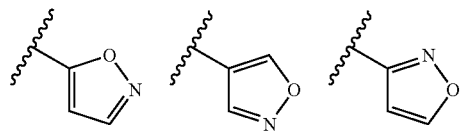

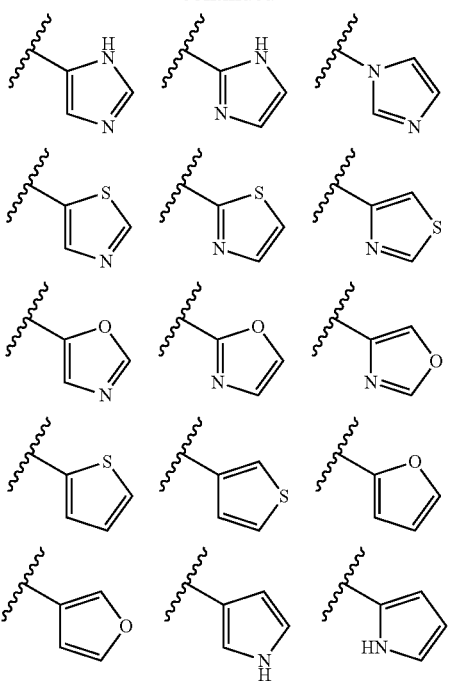

10. The method of claim 1 wherein $R^3$ is selected from the structures:

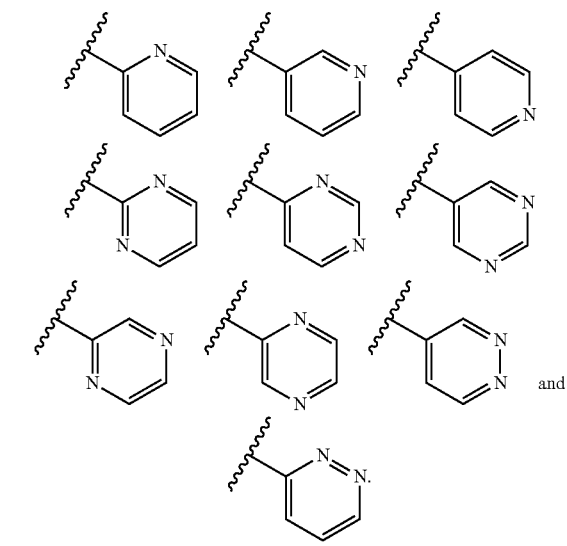

11. The method of claim 1 wherein $R^3$ is selected from the structures:

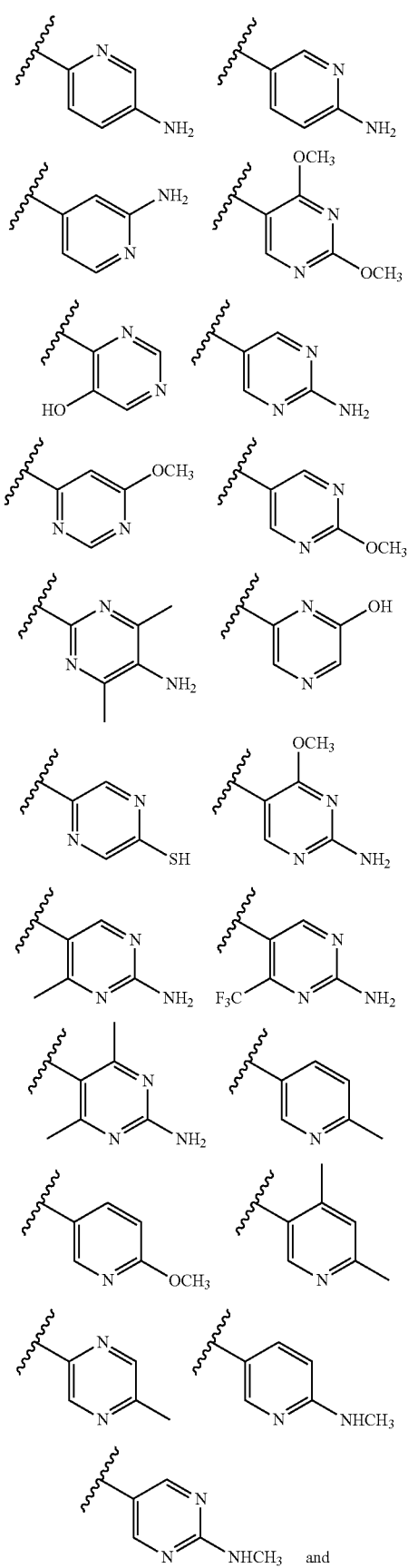
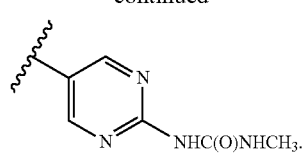
12. The method of claim 1 wherein the monocyclic heteroaryl group is substituted with one or more groups selected from F, —NH$_2$, —NHCH$_3$, —N(CH$_3$)$_2$, —OH, —OCH$_3$, —C(O)CH$_3$, —NHC(O)CH$_3$, —N(C(O)CH$_3$)$_2$, —NHC(O)NH$_2$, —CO$_2$H, —CHO, —CH$_2$OH, —C(=O)NHCH$_3$, —C(=O)NH$_2$, and —CH$_3$.
13. The method of claim 1 wherein R$^1$ is selected from the groups:
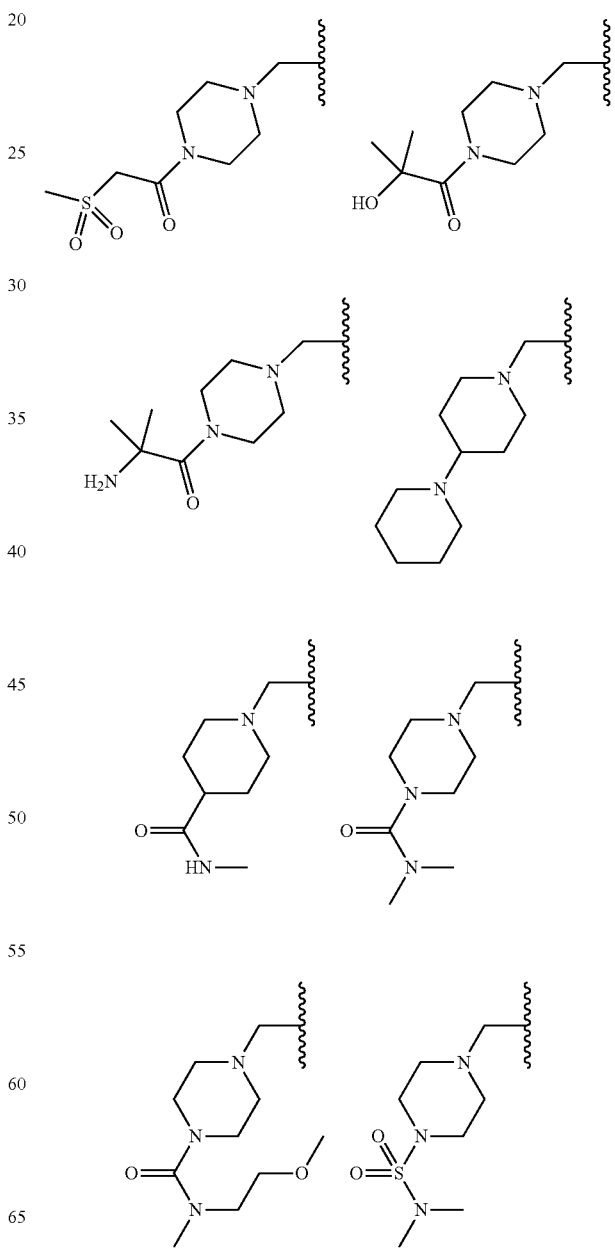

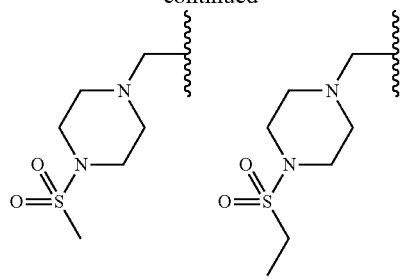
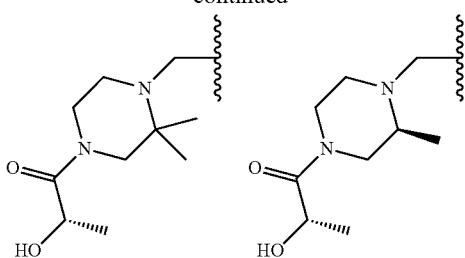
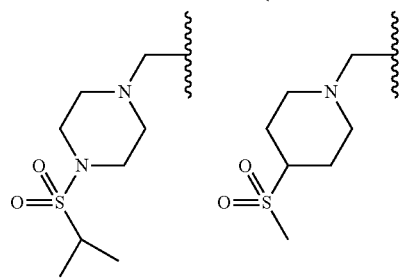
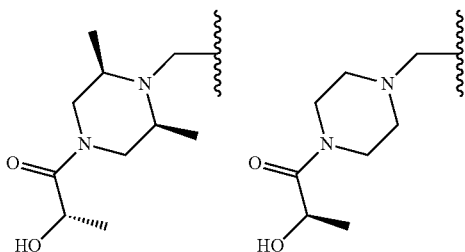
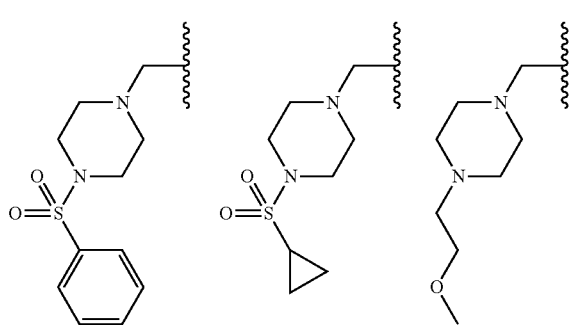
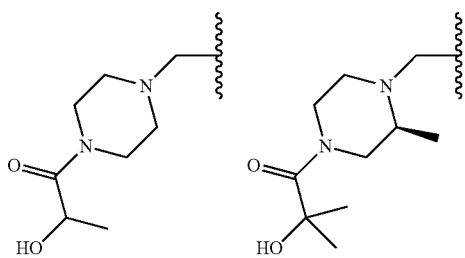
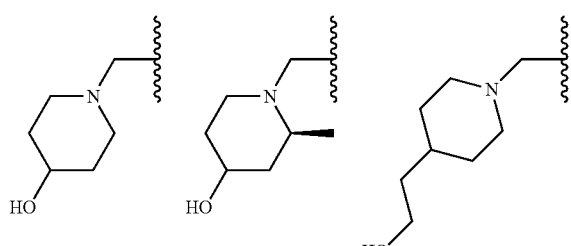
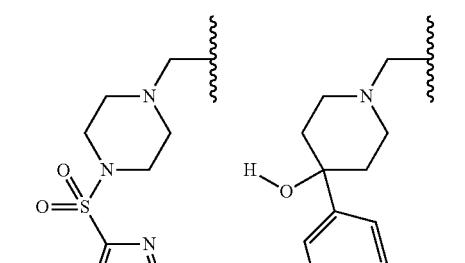
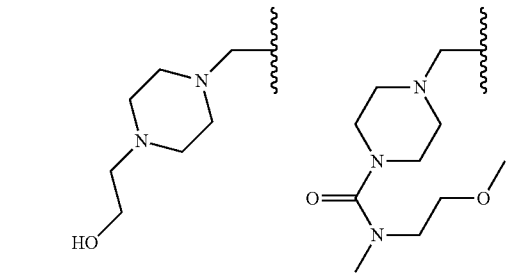
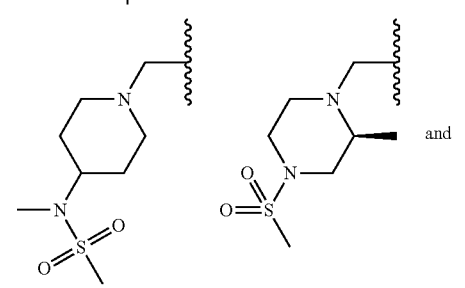

-continued

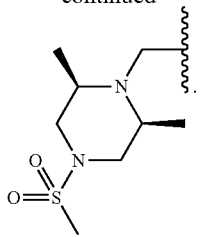

14. The method of claim 1 wherein $R^1$ is selected from the groups:

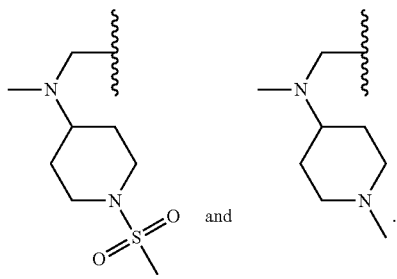

15. The method of claim 1 wherein the compound is selected from:
- 1-(4-((2-(2-aminopyrimidin-5-yl)-4-morpholinothieno[3,2-d]pyrimidin-6-yl)methyl)piperazin-1-yl)-2-(methylsulfonyl)ethanone;
- 1-(4-((2-(2-aminopyrimidin-5-yl)-4-morpholinothieno[3,2-d]pyrimidin-6-yl)methyl)piperazin-1-yl)-2-hydroxy-2-methylpropan-1-one;
- 2-amino-1-(4-((2-(2-aminopyrimidin-5-yl)-4-morpholinothieno[3,2-d]pyrimidin-6-yl)methyl)piperazin-1-yl)-2-methylpropan-1-one;
- (S)-2-amino-1-(4-((2-(2-aminopyrimidin-5-yl)-4-morpholinothieno[3,2-d]pyrimidin-6-yl)methyl)piperazin-1-yl)propan-1-one;
- 1-(4-((2-(2-aminopyrimidin-5-yl)-4-morpholinothieno[3,2-d]pyrimidin-6-yl)methyl)piperazin-1-yl)-2-(dimethylamino)ethanone;
- 2-amino-1-(4-((2-(2-aminopyrimidin-5-yl)-4-morpholinothieno[3,2-d]pyrimidin-6-yl)methyl)piperazin-1-yl)ethanone;
- 5-(4-morpholino-6-((4-(piperidin-1-yl)piperidin-1-yl)methyl)thieno[3,2-d]pyrimidin-2-yl)pyridin-2-amine;
- 1-((2-(2,4-dimethoxypyrimidin-5-yl)-4-morpholinothieno[3,2-d]pyrimidin-6-yl)methyl)-N-methylpiperidine-4-carboxamide;
- 4-((2-(2,4-dimethoxypyrimidin-5-yl)-4-morpholinothieno[3,2-d]pyrimidin-6-yl)methyl)-N,N-dimethylpiperazine-1-carboxamide;
- N-(2-methoxyethyl)-4-((2-(2,4-dimethoxypyrimidin-5-yl)-4-morpholinothieno[3,2-d]pyrimidin-6-yl)methyl)-N-methylpiperazine-1-carboxamide;
- 5-(4-morpholino-6-((4-N-dimethylaminosulfonylpiperazin-1-yl)methyl)thieno[3,2-d]pyrimidin-2-yl)pyridin-2-amine;
- 5-(4-morpholino-6-((4-N-dimethylaminosulfonylpiperazin-1-yl)methyl)thieno[3,2-d]pyrimidin-2-yl)pyrimidin-2-amine;
- 2-(2,4-dimethoxypyrimidin-5-yl)-4-morpholino-6-((4-N-dimethylaminosulfonylpiperazin-1-yl)methyl)thieno[3,2-d]pyrimidine;
- 5-(4-morpholino-6-((4-(piperidin-1-yl)piperidin-1-yl)methyl)thieno[3,2-d]pyrimidin-2-yl)pyrimidin-2-amine;
- 1-((2-(2-aminopyrimidin-5-yl)-4-morpholinothieno[3,2-d]pyrimidin-6-yl)methyl)-N-methylpiperidine-4-carboxamide;
- 5-(4-morpholino-6-((4-N-isopropylsulfonylpiperazin-1-yl)methyl)thieno[3,2-d]pyrimidin-2-yl)pyrimidin-2-amine;
- 2-(2,4-dimethoxypyrimidin-5-yl)-7-methyl-6-((4-(methylsulfonyl)piperidin-1-yl)methyl)-4-morpholinothieno[3,2-d]pyrimidine;
- 5-(7-methyl-6-((4-(methylsulfonyl)piperidin-1-yl)methyl)-4-morpholinothieno[3,2-d]pyrimidin-2-yl)pyridin-2-amine;
- 5-(7-methyl-6-((4-(methylsulfonyl)piperidin-1-yl)methyl)-4-morpholinothieno[3,2-d]pyrimidin-2-yl)pyrimidin-2-amine;
- 5-(4-morpholino-6-((4-N-phenylsulfonylpiperazin-1-yl)methyl)thieno[3,2-d]pyrimidin-2-yl)pyrimidin-2-amine;
- 5-(4-morpholino-6-((piperazin-1-yl)methyl)thieno[3,2-d]pyrimidin-2-yl)pyridin-2-amine;
- 5-(4-morpholino-6-((4-N-cyclopropylsulfonylpiperazin-1-yl)methyl)thieno[3,2-d]pyrimidin-2-yl)pyrimidin-2-amine;
- 5-(4-morpholino-6-((4-N-cyclopropylsulfonylpiperazin-1-yl)methyl)thieno[3,2-d]pyrimidin-2-yl)pyridin-2-amine;
- 1-((2-(6-aminopyridin-3-yl)-4-morpholinothieno[3,2-d]pyrimidin-6-yl)methyl)-N-methylpiperidine-4-carboxamide;
- 1-((2-(2,4-dimethoxypyrimidin-5-yl)-4-morpholinothieno[3,2-d]pyrimidin-6-yl)methyl)-N,N-dimethylpiperidine-4-carboxamide;
- 4-((2-(2-aminopyrimidin-5-yl)-7-methyl-4-morpholinothieno[3,2-d]pyrimidin-6-yl)methyl)-N,N-dimethylpiperazine-1-carboxamide;
- 1-((2-(2-aminopyrimidin-5-yl)-4-morpholinothieno[3,2-d]pyrimidin-6-yl)methyl)-N,N-dimethylpiperidine-4-carboxamide;
- 4-((2-(2-aminopyrimidin-5-yl)-4-morpholinothieno[2,3-d]pyrimidin-6-yl)methyl)-N,N-dimethylpiperazine-1-carboxamide;
- 5-(6-((4-(methylsulfonyl)piperidin-1-yl)methyl)-4-morpholinothieno[3,2-d]pyrimidin-2-yl)pyridin-2-amine;
- 5-(6-((4-(methylsulfonyl)piperidin-1-yl)methyl)-4-morpholinothieno[3,2-d]pyrimidin-2-yl)pyrimidin-2-amine;
- 2-(2,4-dimethoxypyrimidin-5-yl)-6-((4-(methylsulfonyl)piperidin-1-yl)methyl)-4-morpholinothieno[3,2-d]pyrimidine;
- 2-(6-methylpyridin-3-yl)-4-morpholino-6-((4-(piperidin-1-yl)piperidin-1-yl)methyl)thieno[3,2-d]pyrimidine;
- 1-((2-(6-aminopyridin-3-yl)-4-morpholinothieno[3,2-d]pyrimidin-6-yl)methyl)-N,N-dimethylpiperidine-4-carboxamide;
- 2-(2,4-dimethoxypyrimidin-5-yl)-4-morpholino-6-((4-(piperidin-1-yl)piperidin-1-yl)methyl)thieno[3,2-d]pyrimidine;
- 5-(4-morpholino-6-((4-N-methylsulfonylpiperazin-1-yl)methyl)thieno[2,3-d]pyrimidin-2-yl)thiazol-2-amine;
- 5-(6-((4-(1-methylpiperidin-4-yl)piperazin-1-yl)methyl)-4-morpholinothieno[3,2-d]pyrimidin-2-yl)pyrimidin-2-amine;
- 5-(6-((4-(2-methoxyethyl)piperazin-1-yl)methyl)-4-morpholinothieno[3,2-d]pyrimidin-2-yl)pyrimidin-2-amine;

5-(4-morpholino-6-((4-(pyrimidin-2-yl)piperazin-1-yl) methyl)thieno[3,2-d]pyrimidin-2-yl)pyrimidin-2-amine;
6-((4-methylpiperazin-1-yl)methyl)-4-morpholino-2-(pyridin-3-yl)thieno[3,2-d]pyrimidine;
4-morpholino-2-(pyridin-3-yl)-6-((4-(pyrrolidin-1-yl)piperidin-1-yl)methyl)thieno[3,2-d]pyrimidine;
6-((3-(methylsulfonyl)pyrrolidin-1-yl)methyl)-4-morpholino-2-(pyridin-3-yl)thieno[3,2-d]pyrimidine;
1-((4-morpholino-2-(pyridin-3-yl)thieno[3,2-d]pyrimidin-6-yl)methyl)piperidin-4-ol;
2-(1-((4-morpholino-2-(pyridin-3-yl)thieno[3,2-d]pyrimidin-6-yl)methyl)piperidin-4-yl)ethanol;
5-(6-((4-methylpiperazin-1-yl)methyl)-4-morpholinothieno[3,2-d]pyrimidin-2-yl)pyrimidin-2-amine;
5-(4-morpholino-6-((4-(pyrrolidin-1-yl)piperidin-1-yl) methyl)thieno[3,2-d]pyrimidin-2-yl)pyrimidin-2-amine;
5-(6-((3-(methylsulfonyl)pyrrolidin-1-yl)methyl)-4-morpholinothieno[3,2-d]pyrimidin-2-yl)pyrimidin-2-amine;
1-((2-(2-aminopyrimidin-5-yl)-4-morpholinothieno[3,2-d]pyrimidin-6-yl)methyl)piperidin-4-ol;
(R)-1-((2-(2-aminopyrimidin-5-yl)-4-morpholinothieno[3,2-d]pyrimidin-6-yl)methyl)piperidin-3-ol;
2-(1-((2-(2-aminopyrimidin-5-yl)-4-morpholinothieno[3,2-d]pyrimidin-6-yl)methyl)piperidin-4-yl)ethanol;
(R)-1-((2-(2-aminopyrimidin-5-yl)-4-morpholinothieno[3,2-d]pyrimidin-6-yl)methyl)pyrrolidin-3-ol;
2-(2,4-dimethoxypyrimidin-5-yl)-4-morpholino-6-((4-N-methylsulfonylpiperazin-1-yl)methyl)thieno[2,3-d]pyrimidine;
4-morpholino-6-((4-N-methylsulfonylpiperazin-1-yl)methyl)-2-(thiazol-5-yl)thieno[3,2-d]pyrimidine;
5-(4-morpholino-6-((4-N-methylsulfonylpiperazin-1-yl) methyl)thieno[3,2-d]pyrimidin-2-yl)thiazol-2-amine;
N-(2-methoxyethyl)-N-methyl-4-((2-(6-methylpyridin-3-yl)-4-morpholinothieno[3,2-d]pyrimidin-6-yl)methyl)piperazine-1-carboxamide;
4-((2-(2-aminopyrimidin-5-yl)-4-morpholinothieno[3,2-d]pyrimidin-6-yl)methyl)-N-(2-methoxyethyl)-N-methylpiperazine-1-carboxamide;
4-((2-(6-aminopyridin-3-yl)-4-morpholinothieno[3,2-d] pyrimidin-6-yl)methyl)-N-(2-methoxyethyl)-N-methylpiperazine-1-carboxamide;
2-(4-((2-(6-aminopyridin-3-yl)-4-morpholinothieno[3,2-d]pyrimidin-6-yl)methyl)piperazin-1-yl)ethanol;
2-(4-((2-(2-aminopyrimidin-5-yl)-4-morpholinothieno[3,2-d]pyrimidin-6-yl)methyl)piperazin-1-yl)ethanol;
5-(4-morpholino-6-((piperazin-1-yl)methyl)thieno[3,2-d] pyrimidin-2-yl)pyrimidin-2-amine;
5-(4-morpholino-6-((piperazin-1-yl)methyl)thieno[3,2-d] pyrimidin-2-yl)pyridin-2-amine;
5-(4-morpholino-6-((4-N-methylsulfonylpiperazin-1-yl) methyl)thieno[2,3-d]pyrimidin-2-yl)pyrimidin-2-amine;
2-(4-methoxypyridin-3-yl)-4-morpholino-6-((4-N-methylsulfonylpiperazin-1-yl)methyl)thieno[3,2-d]pyrimidine;
2-(4-((2-(6-aminopyridin-3-yl)-4-morpholinothieno[3,2-d]pyrimidin-6-yl)methyl)piperazin-1-yl)-N,N-dimethylacetamide;
6-((4-methylpiperazin-1-yl)methyl)-4-morpholino-2-(pyrimidin-5-yl)thieno[3,2-d]pyrimidine;
5-(4-morpholino-6-((4-N-methylsulfonylpiperazin-1-yl) methyl)furo[2,3-d]pyrimidin-2-yl)pyrimidin-2-amine;
4-((2-(6-aminopyridin-3-yl)-4-morpholinothieno[3,2-d] pyrimidin-6-yl)methyl)-N,N-dimethylpiperazine-1-carboxamide;
2-((6-methylpyridin-3-yl)-4-morpholino-6-((4-N-methylsulfonylpiperazin-1-yl)methyl)thieno[2,3-d]pyrimidine;
N,1-dimethyl-N-((4-morpholino-2-(pyrimidin-5-yl) thieno[2,3-d]pyrimidin-6-yl)methyl)piperidin-4-amine;
6-((4-methylpiperazin-1-yl)methyl)-4-morpholino-2-(pyrimidin-5-yl)thieno[2,3-d]pyrimidine;
5-(4-morpholino-6-((piperazin-1-yl)methyl)thieno[3,2-d] pyrimidin-2-yl)pyridine-3-carbonitrile;
2-(4-((2-(6-aminopyridin-3-yl)-4-morpholinothieno[3,2-d]pyrimidin-6-yl)methyl)piperazin-1-yl)-N,2-dimethylpropanamide;
2-(4-((2-(2-aminopyrimidin-5-yl)-4-morpholinothieno[3,2-d]pyrimidin-6-yl)methyl)piperazin-1-yl)-N,N-dimethylacetamide;
2-(4-((2-(2-aminopyrimidin-5-yl)-4-morpholinothieno[3,2-d]pyrimidin-6-yl)methyl)piperazin-1-yl)-N,2-dimethylpropanamide;
N,N-dimethyl-2-(4-((2-(6-methylpyridin-3-yl)-4-morpholinothieno[3,2-d]pyrimidin-6-yl)methyl)piperazin-1-yl)acetamide;
4-((2-(2-aminopyrimidin-5-yl)-4-morpholinothieno[3,2-d]pyrimidin-6-yl)methyl)-N,N-dimethylpiperazine-1-carboxamide;
2-(2-isopropyl-1H-imidazol-1-yl)-4-morpholino-6-((piperazin-1-yl)methyl)thieno[3,2-d]pyrimidine;
N,2-dimethyl-2-(4-((2-(6-methylpyridin-3-yl)-4-morpholinothieno[3,2-d]pyrimidin-6-yl)methyl)piperazin-1-yl)propanamide;
1-(4-((2-(2-aminopyrimidin-5-yl)-7-methyl-4-morpholinothieno[3,2-d]pyrimidin-6-yl)methyl)piperazin-1-yl)-2-hydroxyethanone;
1-(4-((2-(6-aminopyridin-3-yl)-7-methyl-4-morpholinothieno[3,2-d]pyrimidin-6-yl)methyl)piperazin-1-yl)-2-hydroxyethanone;
1-(4-((2-(2-aminopyrimidin-5-yl)-4-morpholinothieno[2,3-d]pyrimidin-6-yl)methyl)piperazin-1-yl)-2-hydroxyethanone;
1-(4-((2-(6-aminopyridin-3-yl)-4-morpholinothieno[2,3-d]pyrimidin-6-yl)methyl)piperazin-1-yl)-2-hydroxyethanone;
(S)-1-(4-((2-(2-aminopyrimidin-5-yl)-4-morpholinothieno[2,3-d]pyrimidin-6-yl)methyl)piperazin-1-yl)-2-hydroxypropan-1-one;
(S)-1-(4-((2-(6-aminopyridin-3-yl)-4-morpholinothieno[2,3-d]pyrimidin-6-yl)methyl)piperazin-1-yl)-2-hydroxypropan-1-one;
N-(5-(6-((4-(2-hydroxyacetyl)piperazin-1-yl)methyl)-4-morpholinothieno[3,2-d]pyrimidin-2-yl)pyridin-2-yl) acetamide;
1-(4-((2-(2-aminopyrimidin-5-yl)-4-morpholinothieno[3,2-d]pyrimidin-6-yl)methyl)piperazin-1-yl)-2-hydroxyethanone;
1-(4-((2-(6-aminopyridin-3-yl)-4-morpholinothieno[3,2-d]pyrimidin-6-yl)methyl)piperazin-1-yl)-2-hydroxyethanone;
5-(4-morpholino-6-((piperazin-1-yl)methyl)thieno[3,2-d] pyrimidin-2-yl)pyrazin-2-amine;
2-(5-(4-morpholino-6-((piperazin-1-yl)methyl)thieno[3,2-d]pyrimidin-2-yl)pyridin-2-ylamino)ethanol;
5-(4-morpholino-6-((4-N-methylsulfonylpiperazin-1-yl) methyl)thieno[3,2-d]primidin-2-yl)pyridin-2-ol;

5-(6-((1-methylpiperidin-4-yl-N-methylamino)methyl)-7-methyl-4-morpholinothieno[3,2-d]pyrimidin-2-yl)primidin-2-amine;

5-(7-methyl-4-morpholino-6-((4-N-methylsulfonylpiperazin-1-yl)methyl)thieno[3,2-d]pyrimidin-2-yl)pyrimidin-2-amine;

7-methyl-4-morpholino-6-((4-N-methylsulfonylpiperazin-1-yl)methyl)-2-(pyrimidin-5-yl)thieno[3,2-d]pyrimidine;

(S)-1-((S)-4-((2-(6-aminopyridin-3-yl)-4-morpholinothieno[3,2-d]pyrimidin-6-yl)methyl)-3-methylpiperazin-1-yl)-2-hydroxypropan-1-one;

2-(6-methylpyridin-3-yl)-4-morpholino-6-((4-N-methylsulfonylpiperazin-1-yl)methyl)thieno[3,2-d]pyrimidine;

N-methyl-5-(4-morpholino-6-((4-N-methylsulfonylpiperazin-1-yl)methyl)thieno[3,2-d]pyrimidin-2-yl)pyridin-2-amine;

N-methyl-N-(5-(4-morpholino-6-((piperazin-1-yl)methyl)thieno[3,2-d]pyrimidin-2-yl)pyridin-2-yl)acetamide;

5-(6-((1-methylpiperidin-4-ylamino)N-methylaminomethyl)-7-methyl-4-morpholinothieno[3,2-d]pyrimidin-2-yl)pyridin-2-amine;

N,1-dimethyl-N-((7-methyl-4-morpholino-2-(pyridin-3-yl)thieno[3,2-d]pyrimidin-6-yl)methyl)piperidin-4-amine;

N-(5-(4-morpholino-6-((4-N-methylsulfonylpiperazin-1-yl)methyl)furo[3,2-d]pyrimidin-2-yl)pyridin-2-yl)formamide;

N-(5-(4-morpholino-6-((4-N-methylsulfonylpiperazin-1-yl)methyl)thieno[3,2-d]pyrimidin-2-yl)pyridin-2-yl)formamide;

(S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one;

(S)-1-(4-((2-(6-aminopyridin-3-yl)-7-methyl-4-morpholinothieno[3,2-d]pyrimidin-6-yl)methyl)piperazin-1-yl)-2-hydroxypropan-1-one;

(S)-2-hydroxy-1-(4-((2-(2-methoxypyrimidin-5-yl)-7-methyl-4-morpholinothieno[3,2-d]pyrimidin-6-yl)methyl)piperazin-1-yl)propan-1-one;

(S)-2-hydroxy-1-(4-((2-(6-methoxypyridin-3-yl)-7-methyl-4-morpholinothieno[3,2-d]pyrimidin-6-yl)methyl)piperazin-1-yl)propan-1-one;

(S)-2-hydroxy-1-(4-((7-methyl-4-morpholino-2-(pyrimidin-5-yl)thieno[3,2-d]pyrimidin-6-yl)methyl)piperazin-1-yl)propan-1-one;

(S)-2-hydroxy-1-(4-((7-methyl-4-morpholino-2-(pyridin-3-yl)thieno[3,2-d]pyrimidin-6-yl)methyl)piperazin-1-yl)propan-1-one;

(S)-1-(4-((2-(2-aminopyrimidin-5-yl)-4-morpholinothieno[3,2-d]pyrimidin-6-yl)methyl)piperazin-1-yl)-2-hydroxypropan-1-one;

(S)-1-(4-((2-(6-aminopyridin-3-yl)-4-morpholinothieno[3,2-d]pyrimidin-6-yl)methyl)piperazin-1-yl)-2-hydroxypropan-1-one;

(S)-2-hydroxy-1-(4-((2-(2-methoxypyrimidin-5-yl)-4-morpholinothieno[3,2-d]pyrimidin-6-yl)methyl)piperazin-1-yl)propan-1-one;

(S)-2-hydroxy-1-(4-((2-(6-methoxypyridin-3-yl)-4-morpholinothieno[3,2-d]pyrimidin-6-yl)methyl)piperazin-1-yl)propan-1-one;

(S)-2-hydroxy-1-(4-((4-morpholino-2-(pyrimidin-5-yl)thieno[3,2-d]pyrimidin-6-yl)methyl)piperazin-1-yl)propan-1-one;

(S)-2-hydroxy-1-(4-((4-morpholino-2-(pyridin-3-yl)thieno[3,2-d]pyrimidin-6-yl)methyl)piperazin-1-yl)propan-1-one;

N,1-dimethyl-N-((4-morpholino-2-(pyridin-3-yl)thieno[3,2-d]pyrimidin-6-yl)methyl)piperidin-4-amine;

N,1-dimethyl-N-((4-morpholino-2-(6-aminopyridin-3-yl)thieno[3,2-d]pyrimidin-6-yl)methyl)piperidin-4-amine;

N-(5-(4-morpholino-6-((4-N-methylsulfonylpiperazin-1-yl)methyl)thieno[3,2-d]pyrimidin-2-yl)pyrimidin-2-yl)acetamide;

5-(6-((4-N-methylsulfonylpiperazin-1-yl)methyl)-7-methyl-4-morpholinothieno[3,2-d]pyrimidin-2-yl)pyridin-2-amine;

7-methyl-4-morpholino-6-((4-N-methylsulfonylpiperazin-1-yl)methyl)-2-(pyridin-3-yl)thieno[3,2-d]pyrimidine;

N-((2-(2-aminopyridin-5-yl)-4-morpholinothieno[3,2-d]pyrimidin-6-yl)methyl)-N-methyl(N-1-methylsulfonyl)piperidin-4-amine;

N-((2-(2,4-dimethoxypyrimidin-5-yl)-4-morpholinothieno[3,2-d]pyrimidin-6-yl)methyl)-N-methyl(N-1-methylsulfonyl)piperidin-4-amine;

N-((2-(2-aminopyrimidin-5-yl)-4-morpholinothieno[3,2-d]pyrimidin-6-yl)methyl)-N-methyl(N-1-methylsulfonyl)piperidin-4-amine;

5-(4-morpholino-6-((4-N-methylsulfonylpiperazin-1-yl)methyl)thieno[3,2-d]pyrimidin-2-yl)pyrimidin-2-amine;

5-(4-morpholino-6-((4-N-methylsulfonylpiperazin-1-yl)methyl)furo[3,2-d]pyrimidin-2-yl)pyrimidin-2-amine;

N-(5-(4-morpholino-6-((4-N-methylsulfonylpiperazin-1-yl)methyl)furo[3,2-d]pyrimidin-2-yl)pyridin-2-yl)acetamide;

4-morpholino-6-((4-N-methylsulfonylpiperazin-1-yl)methyl)-2-(pyridin-3-yl)furo[3,2-d]pyrimidine;

2-(2,4-dimethoxypyrimidin-5-yl)-4-morpholino-6-((4-N-methylsulfonylpiperazin-1-yl)methyl)thieno[3,2-d]pyrimidine;

(5-(4-morpholino-6-((4-N-methylsulfonylpiperazin-1-yl)methyl)thieno[3,2-d]pyrimidin-2-yl)furan-2-yl)methanol;

2-(6-methoxypyridin-3-yl)-4-morpholino-6-((piperazin-1-yl)methyl)thieno[3,2-d]pyrimidine;

4-morpholino-6-((piperazin-1-yl)methyl)-2-(4-N-methylpyridin-4-yl)thieno[3,2-d]pyrimidine;

(5-(4-morpholino-6-((4-N-methylsulfonylpiperazin-1-yl)methyl)thieno[3,2-d]pyrimidin-2-yl)thiophen-2-yl)methanol;

2-(5-methoxypyridin-3-yl)-4-morpholino-6-((4-N-methylsulfonylpiperazin-1-yl)methyl)thieno[2,3-d]pyrimidine;

2-(furan-3-yl)-4-morpholino-6-((4-N-methylsulfonylpiperazin-1-yl)methyl)thieno[3,2-d]pyrimidine;

(5-(4-morpholino-6-((4-N-methylsulfonylpiperazin-1-yl)methyl)thieno[2,3-d]pyrimidin-2-yl)pyridin-3-yl)methanol;

N-(5-(4-morpholino-6-((4-N-methylsulfonylpiperazin-1-yl)methyl)thieno[3,2-d]pyrimidin-2-yl)pyridin-2-yl)acetamide;

5-(4-morpholino-6-((4-N-methylsulfonylpiperazin-1-yl)methyl)thieno[2,3-d]pyrimidin-2-yl)pyridin-2-amine;

(5-(4-morpholino-6-((4-N-methylsulfonylpiperazin-1-yl)methyl)thieno[3,2-d]pyrimidin-2-yl)pyridin-3-yl)methanol;

5-(4-morpholino-6-((4-N-methylsulfonylpiperazin-1-yl)methyl)furo[3,2-d]pyrimidin-2-yl)pyridin-2-amine;

2-(2-methoxypyrimidin-5-yl)-4-morpholino-6-((4-N-methylsulfonylpiperazin-1-yl)methyl)furo[3,2-d]pyrimidine;

5-(4-morpholino-6-((4-N-methylsulfonylpiperazin-1-yl)methyl)furo[3,2-d]pyrimidin-2-yl)pyridine-3-carbaldehyde;

2-(5-methoxypyridin-3-yl)-4-morpholino-6-((4-N-methylsulfonylpiperazin-1-yl)methyl)furo[3,2-d]pyrimidine;

5-(4-morpholino-6-((4-N-methylsulfonylpiperazin-1-yl)methyl)thieno[3,2-d]pyrimidin-2-yl)pyridin-2-amine;

5-(4-morpholino-6-((4-N-methylsulfonylpiperazin-1-yl)methyl)thieno[3,2-d]pyrimidin-2-yl)pyridine-3-carbaldehyde;

2-(5-methoxypyridin-3-yl)-4-morpholino-6-((4-N-methylsulfonylpiperazin-1-yl)methyl)thieno[3,2-d]pyrimidine;

N,N-dimethyl-5-(4-morpholino-6-((4-N-methylsulfonylpiperazin-1-yl)methyl)thieno[3,2-d]pyrimidin-2-yl)pyrimidin-2-amine;

4-morpholino-6-((4-N-methylsulfonylpiperazin-1-yl)methyl)-2-(pyrimidin-5-yl)furo[3,2-d]pyrimidine;

2-(2-methoxypyrimidin-5-yl)-4-morpholino-6-((4-N-methylsulfonylpiperazin-1-yl)methyl)thieno[3,2-d]pyrimidine;

1-(5-(4-morpholino-6-((4-N-methylsulfonylpiperazin-1-yl)methyl)furo[3,2-d]pyrimidin-2-yl)pyridin-2-yl)urea;

5-(4-morpholino-6-((4-N-methylsulfonylpiperazin-1-yl)methyl)thieno[3,2-d]pyrimidin-2-yl)pyridin-2-methylsulfonylamine;

6-methyl-5-(4-morpholino-6-((4-N-methylsulfonylpiperazin-1-yl)methyl)thieno[3,2-d]pyrimidin-2-yl)pyridin-2-amine;

5-(4-morpholino-6-((4-N-isobutylsulfonylpiperazin-1-yl)methyl)thieno[3,2-d]pyrimidin-2-yl)pyridin-2-amine;

2-(2,4-dimethoxypyrimidin-5-yl)-4-morpholino-6-((4-N-phenylsulfonylpiperazin-1-yl)methyl)thieno[3,2-d]pyrimidine;

2-(2,4-dimethoxypyrimidin-5-yl)-4-morpholino-6-((4-N-cyclopropylsulfonylpiperazin-1-yl)methyl)thieno[3,2-d]pyrimidine;

5-(6-(((S)-3-methyl-(4-N-methylsulfonyl)piperazin-1-yl)methyl)-4-morpholinothieno[3,2-d]pyrimidin-2-yl)pyridin-2-amine;

5-(6-(((S)-3-methyl-(4-N-methylsulfonyl)piperazin-1-yl)methyl)-4-morpholinothieno[3,2-d]pyrimidin-2-yl)pyrimidin-2-amine;

5-(6-(((2R,6S)-2,6-dimethyl-(4-N-methylsulfonyl)piperazin-1-yl)methyl)-4-morpholinothieno[3,2-d]pyrimidin-2-yl)pyridin-2-amine;

5-(6-(((2R,6S)-2,6-dimethyl-(4-N-methylsulfonyl)piperazin-1-yl)methyl)-4-morpholinothieno[3,2-d]pyrimidin-2-yl)pyrimidin-2-amine;

5-(4-morpholino-6-((1-O, O—S-thiomorpholin-4-yl)methyl)thieno[3,2-d]pyrimidin-2-yl)pyridin-2-amine;

N,N-dimethyl-1-((4-morpholino-2-(pyrimidin-5-yl)thieno[2,3-d]pyrimidin-6-yl)methyl)piperidine-4-carboxamide;

N,N-dimethyl-4-((4-morpholino-2-(pyrimidin-5-yl)thieno[2,3-d]pyrimidin-6-yl)methyl)piperazine-1-carboxamide;

N-methyl-1-((4-morpholino-2-(pyrimidin-5-yl)thieno[2,3-d]pyrimidin-6-yl)methyl)piperidine-4-carboxamide;

N-(2-methoxyethyl)-N-methyl-1-((4-morpholino-2-(pyrimidin-5-yl)thieno[2,3-d]pyrimidin-6-yl)methyl)piperidin-4-amine;

5-(7-methyl-4-morpholino-6-((4-N-cyclopropylsulfonylpiperazin-1-yl)methyl)thieno[3,2-d]pyrimidin-2-yl)pyrimidin-2-amine;

5-(7-methyl-4-morpholino-6-((4-N-phenylsulfonylpiperazin-1-yl)methyl)thieno[3,2-d]pyrimidin-2-yl)pyrimidin-2-amine;

5-(7-methyl-4-morpholino-6-((4-N-isopropylsulfonylpiperazin-1-yl)methyl)thieno[3,2-d]pyrimidin-2-yl)pyrimidin-2-amine;

N, 1-dimethyl-N-((4-morpholino-2-(pyrimidin-5-yl)thieno[3,2-d]-2-amino-pyrimidin-6-yl)methyl)piperidin-4-amine;

5-(4-morpholino-6-((4-N-methylsulfonylpiperazin-1-yl)methyl)thieno[3,2-d]pyrimidin-2-yl)pyridine-2-carboxamide;

5-(4-morpholino-6-((1-O, O—S-thiomorpholin-4-yl)methyl)thieno[3,2-d]pyrimidin-2-yl)pyrimidin-2-amine;

5-(6-(((R)-3-methyl-(4-N-methylsulfonyl)piperazin-1-yl)methyl)-4-morpholinothieno[3,2-d]pyrimidin-2-yl)pyridin-2-amine;

5-(6-(((R)-3-methyl-(4-N-methylsulfonyl)piperazin-1-yl)methyl)-4-morpholinothieno[3,2-d]pyrimidin-2-yl)pyrimidin-2-amine;

4-(4-morpholino-6-((4-N-methylsulfonylpiperazin-1-yl)methyl)thieno[3,2-d]pyrimidin-2-yl)pyridine-2,6-diamine;

5-(4-morpholino-6-((4-N-methylsulfonylpiperazin-1-yl)methyl)thieno[3,2-d]pyrimidin-2-yl)pyridine-2-carbonitrile;

5-(4-morpholino-6-((4-N-(thiophen-2-yl)sulfonyl)piperazin-1-yl)methyl)thieno[3,2-d]pyrimidin-2-yl)pyrimidin-2-amine;

5-(4-morpholino-6-((4-N-2-fluorophenylsulfonylpiperazin-1-yl)methyl)thieno[3,2-d]pyrimidin-2-yl)pyrimidin-2-amine;

5-(6-((4-(methylsulfonyl)piperidin-1-yl)methyl)-4-morpholinothieno[2,3-d]pyrimidin-2-yl)pyrimidin-2-amine;

5-(4-morpholino-6-((4-N-3-fluorophenylsulfonylpiperazin-1-yl)methyl)thieno[3,2-d]pyrimidin-2-yl)pyrimidin-2-amine;

5-(4-morpholino-6-((4-N-(1-methylimidazol-4-yl)piperazin-1-yl)methyl)thieno[3,2-d]pyrimidin-2-yl)pyrimidin-2-amine;

5-(4-morpholino-6-((4-N-4-fluorophenylsulfonylpiperazin-1-yl)methyl)thieno[3,2-d]pyrimidin-2-yl)pyrimidin-2-amine;

5-(4-morpholino-6-((4-(dimethylaminosulfonyl)piperidin-1-yl)methyl)thieno[3,2-d]pyrimidin-2-yl)pyrimidin-2-amine;

5-(4-morpholino-6-((4-(dimethylaminosulfonyl)piperidin-1-yl)methyl)thieno[3,2-d]pyrimidin-2-yl)pyridin-2-amine;

1-((2-(2-aminopyrimidin-5-yl)-4-morpholinothieno[3,2-d]pyrimidin-6-yl)methyl)-4-phenylpiperidin-4-ol;

5-(6-((4-(N-(2-methoxyethyl)-N-methylamino)piperidin-1-yl)methyl)-4-morpholinothieno[3,2-d]pyrimidin-2-yl)pyrimidin-2-amine;

5-(4-morpholino-6-((4-N-ethylsulfonylpiperazin-1-yl)methyl)thieno[3,2-d]pyrimidin-2-yl)pyrimidin-2-amine;

5-(6-((4-(N-methyl,N-methylsulfonylamino)piperidin-1-yl)methyl)-4-morpholinothieno[3,2-d]pyrimidin-2-yl)pyridin-2-amine;

4-methoxy-5-(4-morpholino-6-((4-N-methylsulfonylpiperazin-1-yl)methyl)thieno[3,2-d]pyrimidin-2-yl)pyrimidin-2-amine;

5-(6-((4-(N-methyl,N-methylsulfonylamino)piperidin-1-yl)methyl)-4-morpholinothieno[3,2-d]pyrimidin-2-yl)pyrimidin-2-amine;
5-(4-morpholino-6-((4-N-isobutyrylsulfonylpiperazin-1-yl)methyl)thieno[3,2-d]pyrimidin-2-yl)pyrimidin-2-amine;
6-(4-morpholino-6-((4-N-methylsulfonylpiperazin-1-yl)methyl)thieno[2,3-d]pyrimidin-2-yl)pyridin-2-amine;
1-((2-(2-aminopyrimidin-5-yl)-4-morpholinothieno[2,3-d]pyrimidin-6-yl)methyl)pyrrolidin-3-ol;
5-(4-morpholino-6-(1-(4-N-methylsulfonylpiperazin-1-yl)ethyl)thieno[3,2-d]pyrimidin-2-yl)pyridin-2-amine;
5-(4-morpholino-6-(1-(4-N-methylsulfonylpiperazin-1-yl)ethyl)thieno[3,2-d]pyrimidin-2-yl)pyrimidin-2-amine;
(R)-1-((2-(2-aminopyrimidin-5-yl)-4-morpholinothieno[2,3-d]pyrimidin-6-yl)methyl)piperidin-3-ol;
1-((2-(2-aminopyrimidin-5-yl)-4-morpholinothieno[2,3-d]pyrimidin-6-yl)methyl)piperidin-4-ol;
5-(6-((3-(methylsulfonyl)pyrrolidin-1-yl)methyl)-4-morpholinothieno[2,3-d]pyrimidin-2-yl)pyrimidin-2-amine;
2-(2-methylpyrimidin-5-yl)-morpholino-6-(4-N-methylsulfonyl(piperazin-1-yl)methyl)thieno[2,3-d]pyrimidine;
2-(2-methylaminopyrimidin-5-yl)-morpholino-6-(4-N-methylsulfonyl(piperazin-1-yl)methyl)thieno[2,3-d]pyrimidine;
2-(2-methylpyrimidin-5-yl)-4-morpholino-6-(4-N-methylsulfonyl(piperazin-1-yl)methyl)thieno[3,2-d]pyrimidine;
5-(4-morpholino-6-(4-N-(thiophen-2-yl)sulfonyl(piperazin-1-yl)methyl)thieno[2,3-d]pyrimidin-2-yl)pyrimidin-2-amine;
5-(4-morpholino-6-((4-N-cyclopropylsulfonylpiperazin-1-yl)methyl)thieno[2,3-d]pyrimidin-2-yl)pyrimidin-2-amine;
2-(1-((2-(2-aminopyrimidin-5-yl)-4-morpholinothieno[3,2-d]pyrimidin-6-yl)methyl)piperidin-4-ylsulfonyl)-N,N-dimethylacetamide;
5-(4-morpholino-6-((4-(thiazol-2-ylsulfonyl)piperidin-1-yl)methyl)thieno[3,2-d]pyrimidin-2-yl)pyrimidin-2-amine;
4-(4-morpholino-6-((4-N-methylsulfonylpiperazin-1-yl)methyl)thieno[3,2-d]pyrimidin-2-yl)pyridine-2,6-diamine;
5-(6-((4-((methylsulfonyl)methylsulfonyl)piperidin-1-yl)methyl)-4-morpholinothieno[3,2-d]pyrimidin-2-yl)pyrimidin-2-amine;
2-(2-methylaminopyrimidin-5-yl)-morpholino-6-(4-N-methylsulfonyl(piperazin-1-yl)methyl)thieno[3,2-d]pyrimidine;
4-(4-morpholino-6-((4-N-methylsulfonylpiperazin-1-yl)methyl)thieno[3,2-d]pyrimidin-2-yl)pyridin-2-amine;
N-((2-(2-aminopyrimidin-5-yl)-4-morpholinothieno[3,2-d]pyrimidin-6-yl)methyl)-N-methyl(N-1-isopropyl)piperidin-4-amine;
5-(7-methyl-6-(((2R,6S)-2,6-dimethyl-(4-N-methylsulfonyl)piperazin-1-yl)methyl)-4-morpholinothieno[3,2-d]pyrimidin-2-yl)pyrimidin-2-amine;
1-((2-(2-aminopyrimidin-5-yl)-4-morpholinothieno[3,2-d]pyrimidin-6-yl)methyl)-4-(4-chlorophenyl)piperidin-4-ol; and
2-(2-(methylthio)pyrimidin-5-yl)-4-morpholino-6-((4-N-methylsulfonylpiperazin-1-yl)methyl)thieno[3,2-d]pyrimidine.

16. The method of claim 1 wherein the compound is selected from:
5-(6-((4-(methylsulfonyl)piperazin-1-yl)methyl)-4-morpholinothieno[2,3-d]pyrimidin-2-yl)-4-(trifluoromethyl)pyrimidin-2-amine;
5-(6-((methyl(piperidin-4-ylmethyl)amino)methyl)-4-morpholinothieno[3,2-d]pyrimidin-2-yl)pyrimidin-2-amine;
5-(6-((methyl(1-methylpiperidin-4-yl)amino)methyl)-4-morpholinothieno[2,3-d]pyrimidin-2-yl)-4-(trifluoromethyl)pyrimidin-2-amine;
tert-butyl 4-((2-(2-aminopyrimidin-5-yl)-7-methyl-4-morpholinothieno[3,2-d]pyrimidin-6-yl)methyl)piperazine-1-carboxylate;
5-(7-methyl-4-morpholino-6-(piperazin-1-ylmethyl)thieno[3,2-d]pyrimidin-2-yl)-4-(trifluoromethyl)pyrimidin-2-amine;
(S)-1-(4-((2-(2-amino-4-methylpyrimidin-5-yl)-4-morpholinothieno[3,2-d]pyrimidin-6-yl)methyl)piperazin-1-yl)-2-hydroxypropan-1-one;
(S)-1-(4-((2-(2-amino-4-(trifluoromethyl)pyrimidin-5-yl)-7-methyl-4-morpholinothieno[3,2-d]pyrimidin-6-yl)methyl)piperazin-1-yl)-2-hydroxypropan-1-one;
1-(4-((2-(2-amino-4-methylpyrimidin-5-yl)-7-methyl-4-morpholinothieno[3,2-d]pyrimidin-6-yl)methyl)piperazin-1-yl)-2-hydroxy-2-methylpropan-1-one;
5-(6-((4-(methylsulfonyl)piperazin-1-yl)methyl)-4-morpholinothieno[3,2-d]pyrimidin-2-yl)-4-(trifluoromethyl)pyrimidin-2-amine;
5-(6-((4-((2-methyl-1H-imidazol-1-yl)methyl)piperidin-1-yl)methyl)-4-morpholinothieno[3,2-d]pyrimidin-2-yl)pyrimidin-2-amine;
5-(4-morpholino-6-((4-(morpholinomethyl)piperidin-1-yl)methyl)thieno[3,2-d]pyrimidin-2-yl)pyrimidin-2-amine;
5-(4-morpholino-6-((4-(piperidin-1-ylmethyl)piperidin-1-yl)methyl)thieno[3,2-d]pyrimidin-2-yl)pyrimidin-2-amine;
5-(4-morpholino-6-((4-(pyrrolidin-1-ylmethyl)piperidin-1-yl)methyl)thieno[3,2-d]pyrimidin-2-yl)pyrimidin-2-amine;
5-(6-((4-((dimethylamino)methyl)piperidin-1-yl)methyl)-4-morpholinothieno[3,2-d]pyrimidin-2-yl)pyrimidin-2-amine;
5-(6-((1-methylpiperidin-4-ylamino)methyl)-4-morpholinothieno[3,2-d]pyrimidin-2-yl)pyrimidin-2-amine;
5-(6-(((1-isopropylpiperidin-4-yl)(2-methoxyethyl)amino)methyl)-4-morpholinothieno[3,2-d]pyrimidin-2-yl)pyrimidin-2-amine;
5-(6-((methyl((1-methylpiperidin-4-yl)methyl)amino)methyl)-4-moipholinothieno[3,2-d]pyrimidin-2-yl)pyrimidin-2-amine;
5-(4-morpholino-6-((4-morpholinopiperidin-1-yl)methyl)thieno[3,2-d]pyrimidin-2-yl)pyrimidin-2-amine;
5-(6-((4-(dimethylamino)piperidin-1-yl)methyl)-4-morpholinothieno[3,2-d]pyrimidin-2-yl)pyrimidin-2-amine;
5-(6-((methyl(1-methylpyrrolidin-3-yl)amino)methyl)-4-morpholinothieno[3,2-d]pyrimidin-2-yl)pyrimidin-2-amine;
5-(6-((((1-cyclopropylpiperidin-4-yl)(methyl)amino)methyl)-4-morpholinothieno[3,2-d]pyrimidin-2-yl)pyrimidin-2-amine;
5-(6-((4-aminopiperidin-1-yl)methyl)-4-morpholinothieno[3,2-d]pyrimidin-2-yl)pyrimidin-2-amine;

5-(6-((3-(dimethylamino)pyrrolidin-1-yl)methyl)-4-morpholinothieno[3,2-d]pyrimidin-2-yl)pyrimidin-2-amine;
5-(6-((methyl(piperidin-4-yl)amino)methyl)-4-morpholinothieno[3,2-d]pyrimidin-2-yl)pyrimidin-2-amine;
5-(6-(((1-(2-methoxyethyl)piperidin-4-yl)(methyl)amino)methyl)-4-morpholinothieno[3,2-d]pyrimidin-2-yl)pyrimidin-2-amine;
5-(6-((methyl(1-propylpiperidin-4-yl)amino)methyl)-4-morpholinothieno[3,2-d]pyrimidin-2-yl)pyrimidin-2-amine;
5-(6-(((1-cyclohexylpiperidin-4-yl)(methyl)amino)methyl)-4-morpholinothieno[3,2-d]pyrimidin-2-yl)pyrimidin-2-amine;
5-(6-(((1-isobutylpiperidin-4-yl)(methyl)amino)methyl)-4-morpholinothieno[3,2-d]pyrimidin-2-yl)pyrimidin-2-amine;
5-(6-(((1-ethylpiperidin-4-yl)(methyl)amino)methyl)-4-morpholinothieno[3,2-d]pyrimidin-2-yl)pyrimidin-2-amine;
4-methyl-5-(6-((4-(methylsulfonyl)piperazin-1-yl)methyl)-4-morpholinothieno[2,3-d]pyrimidin-2-yl)pyrimidin-2-amine;
(S)-1-(4-((2-(2-amino-4-methylpyrimidin-5-yl)-7-methyl-4-morpholinothieno[3,2-d]pyrimidin-6-yl)methyl)piperazin-1-yl)-2-hydroxypropan-1-one;
1-(4-((2-(2-aminopyrimidin-5-yl)-7-methyl-4-morpholinothieno[3,2-d]pyrimidin-6-yl)methyl)piperazin-1-yl)-2-(methylsulfonyl)ethanone;
(1-aminocyclopropyl)(4-((2-(2-aminopyrimidin-5-yl)-7-methyl-4-morpholinothieno[3,2-d]pyrimidin-6-yl)methyl)piperazin-1-yl)methanone;
2-amino-1-(4-((2-(2-aminopyrimidin-5-yl)-7-methyl-4-morpholinothieno[3,2-d]pyrimidin-6-yl)methyl)piperazin-1-yl)-2-methylpropan-1-one;
(R)-2-amino-1-(4-((2-(2-aminopyrimidin-5-yl)-7-methyl-4-morpholinothieno[3,2-d]pyrimidin-6-yl)methyl)piperazin-1-yl)propan-1-one;
(S)-2-amino-1-(4-((2-(2-aminopyrimidin-5-yl)-7-methyl-4-morpholinothieno[3,2-d]pyrimidin-6-yl)methyl)piperazin-1-yl)propan-1-one;
1-(4-2-((2-aminopyrimidin-5-yl)-7-methyl-4-morpholinothieno[3,2-d]pyrimidin-6-yl)methyl)piperazin-1-yl)-2-(dimethylamino)ethanone;
2-amino-1-(4-((2-(2-aminopyrimidin-5-yl)-7-methyl-4-morpholinothieno[3,2-d]pyrimidin-6-yl)methyl)piperazin-1-yl)ethanone;
1-(4-((2-(2-aminopyrimidin-5-yl)-7-methyl-4-morpholinothieno[3,2-d]pyrimidin-6-yl)methyl)piperazin-1-yl)-2-hydroxy-2-methylpropan-1-one;
5-(7-methyl-4-morpholino-6-(piperazin-1-ylmethyl)thieno[3,2-d]pyrimidin-2-yl)pyrimidin-2-amine;
5-(6-((4-(methylsulfonyl)piperazin-1-yl)methyl)-4-morpholinothieno[2,3-d]pyrimidin-2-yl)pyridin-3-amine;
5-(6-((4-(methylsulfonyl)piperazin-1-yl)methyl)-4-morpholinothieno[2,3-d]pyrimidin-2-yl)-3-nitropyridin-2-amine;
N,3-dimethyl-5-(6-((4-(methylsulfonyl)piperazin-1-yl)methyl)-4-morpholinothieno[2,3-d]pyrimidin-2-yl)pyridin-2-amine;
(5-(6-((4-(methylsulfonyl)piperazin-1-yl)methyl)-4-morpholinothieno[2,3-d]pyrimidin-2-yl)pyridin-2-yl)methanol;
4-(2-(4-methylpyridin-3-yl)-6-((4-(methylsulfonyl)piperazin-1-yl)methyl)thieno[2,3-d]pyrimidin-4-yl)morpholine;
4-(2-(5-methylpyridin-3-yl)-6-((4-(methylsulfonyl)piperazin-1-yl)methyl)thieno[2,3-d]pyrimidin-4-yl)morpholine;
N-ethyl-5-(6-((4-(methylsulfonyl)piperazin-1-yl)methyl)-4-morpholinothieno[2,3-d]pyrimidin-2-yl)pyridin-2-amine;
5-(6-((4-((2-methoxyethyl)(methyl)amino)piperidin-1-yl)methyl)-4-morpholinothieno[2,3-d]pyrimidin-2-yl)pyridin-2-amine;
5-(6-((4-((2-methoxyethyl)(methyl)amino)piperidin-1-yl)methyl)-4-morpholinothieno[2,3-d]pyrimidin-2-yl)-N-methylpyridin-2-amine;
5-(6-((4-((2-methoxyethyl)(methyl)amino)piperidin-1-yl)methyl)-4-morpholinothieno[2,3-d]pyrimidin-2-yl)-N-methylpyrimidin-2-amine;
N-methyl-5-(6-((methyl(1-methylpiperidin-4-yl)amino)methyl)-4-morpholinothieno[2,3-d]pyrimidin-2-yl)pyrimidin-2-amine;
4-methyl-5-(6-((4-(methylsulfonyl)piperazin-1-yl)methyl)-4-morpholinothieno[2,3-d]pyrimidin-2-yl)pyridin-2-amine;
4-(2-(5,6-dimethylpyridin-3-yl)-6-((4-(methylsulfonyl)piperazin-1-yl)methyl)thieno[2,3-d]pyrimidin-4-yl)morpholine;
3,4-dimethyl-5-(6-((4-(methylsulfonyl)piperazin-1-yl)methyl)-4-morpholinothieno[2,3-d]pyrimidin-2-yl)pyridin-2-amine;
(S)-2-hydroxy-1-(4-((2-(6-(methylamino)pyridin-3-yl)-4-morpholinothieno[3,2-d]pyrimidin-6-yl)methyl)piperazin-1-yl)propan-1-one;
(S)-2-hydroxy-1-(4-((2-(6-(methylamino)pyridin-3-yl)-4-morpholinothieno[2,3-d]pyrimidin-6-yl)methyl)piperazin-1-yl)propan-1-one;
(S)-2-hydroxy-1-(4-((7-methyl-2-(6-(methylamino)pyridin-3-yl)-4-morpholinothieno[3,2-d]pyrimidin-6-yl)methyl)piperazin-1-yl)propan-1-one;
3-chloro-5-(6-((4-(methylsulfonyl)piperazin-1-yl)methyl)-4-morpholinothieno[2,3-d]pyrimidin-2-yl)pyridin-2-amine;
3-chloro-5-(6-((4-(methylsulfonyl)piperazin-1-yl)methyl)-4-morpholinothieno[3,2-d]pyrimidin-2-yl)pyridin-2-amine;
3-methyl-5-(6-((4-(methylsulfonyl)piperazin-1-yl)methyl)-4-morpholinothieno[3,2-d]pyrimidin-2-yl)pyridin-2-amine;
4-methyl-5-(6-((4-(methylsulfonyl)piperazin-1-yl)methyl)-4-morpholinothieno[3,2-d]pyrimidin-2-yl)pyrimidin-2-amine;
1-((2-(2-(methylamino)pyrimidin-5-yl)-4-morpholinothieno[2,3-d]pyrimidin-6-yl)methyl)pyrrolidin-3-ol;
1-((2-(2-(methylamino)pyrimidin-5-yl)-4-morpholinothieno[2,3-d]pyrimidin-6-yl)methyl)piperidin-4-ol;
1-((2-(2-aminopyrimidin-5-yl)-4-morpholinothieno[3,2-d]pyrimidin-6-yl)methyl)-4-methylpiperidin-4-ol;
N-(5-(6-((4-(methylsulfonyl)piperazin-1-yl)methyl)-4-morpholinothieno[2,3-d]pyrimidin-2-yl)pyridin-2-yl)acetamide;
N-methyl-5-(6-((4-(methylsulfonyl)piperazin-1-yl)methyl)-4-morpholinothieno[2,3-d]pyrimidin-2-yl)pyridin-2-amine;
2-(4-((2-(2-aminopyrimidin-5-yl)-4-morpholinothieno[2,3-d]pyrimidin-6-yl)methyl)piperazin-1-yl)ethanol;
N,N-dimethyl-2-(5-(6-((4-(methylsulfonyl)piperazin-1-yl)methyl)-4-morpholinothieno[2,3-d]pyrimidin-2-yl)pyrimidin-2-yloxy)ethanamine;

4-(6-((4-(methylsulfonyl)piperazin-1-yl)methyl)-2-(6-phenylpyridin-3-yl)thieno[2,3-d]pyrimidin-4-yl)morpholine;

(S)-2-hydroxy-1-(4-((2-(2-(methylamino)pyrimidin-5-yl)-4-morpholinothieno[2,3-d]pyrimidin-6-yl)methyl)piperazin-1-yl)propan-1-one;

(S)-2-hydroxy-1-(4-((7-methyl-2-(2-(methylamino)pyrimidin-5-yl)-4-morpholinothieno[3,2-d]pyrimidin-6-yl)methyl)piperazin-1-yl)propan-1-one;

5-(6-(1,4'-bipiperidin-1'-ylmethyl)-4-morpholinothieno[2,3-d]pyrimidin-2-yl)pyrimidin-2-amine;

N-isopropyl-5-(6-((4-(methylsulfonyl)piperazin-1-yl)methyl)-4-morpholinothieno[3,2-d]pyrimidin-2-yl)pyrimidin-2-amine;

N-ethyl-5-(6-((4-(methylsulfonyl)piperazin-1-yl)methyl)-4-morpholinothieno[2,3-d]pyrimidin-2-yl)pyrimidin-2-amine;

5-(6-((methyl(1-methylpiperidin-4-yl)amino)methyl)-4-morpholinothieno[2,3-d]pyrimidin-2-yl)pyrimidin-2-amine;

N-isopropyl-5-(6-((4-(methylsulfonyl)piperazin-1-yl)methyl)-4-morpholinothieno[2,3-d]pyrimidin-2-yl)pyrimidin-2-amine;

N-ethyl-5-(6-((4-(methylsulfonyl)piperazin-1-yl)methyl)-4-morpholinothieno[3,2-d]pyrimidin-2-yl)pyrimidin-2-amine;

5-(6-((4-(benzyl(methyl)amino)piperidin-1-yl)methyl)-4-morpholinothieno[2,3-d]pyrimidin-2-yl)pyrimidin-2-amine;

5-(6-((4-((2-methoxyethyl)(methyl)amino)piperidin-1-yl)methyl)-4-morpholinothieno[2,3-d]pyrimidin-2-yl)pyrimidin-2-amine;

(R)-1-(4-((2-(2-aminopyrimidin-5-yl)-4-morpholinothieno[2,3-d]pyrimidin-6-yl)methyl)piperazin-1-yl)-2-hydroxypropan-1-one;

(R)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one;

(R)-1-(4-((2-(2-aminopyrimidin-5-yl)-4-morpholinothieno[3,2-d]pyrimidin-6-yl)methyl)piperazin-1-yl)-2-hydroxypropan-1-one;

N-(5-(6-((4-(methylsulfonyl)piperazin-1-yl)methyl)-4-morpholinothieno[3,2-d]pyrimidin-2-yl)thiazol-2-yl)acetamide;

1-((2-(2-aminopyrimidin-5-yl)-4-morpholinothieno[3,2-d]pyrimidin-6-yl)methyl)-4-(pyridin-2-yl)piperidin-4-ol;

4-(6-((4-(methylsulfonyl)piperazin-1-yl)methyl)-2-(5-phenylpyridin-3-yl)thieno[2,3-d]pyrimidin-4-yl)morpholine;

(S)-5-(6-((4-(2-hydroxypropanoyl)piperazin-1-yl)methyl)-4-morpholinothieno[2,3-d]pyrimidin-2-yl)picolinonitrile;

(S)-5-(6-((4-(2-hydroxypropanoyl)piperazin-1-yl)methyl)-7-methyl-4-morpholinothieno[3,2-d]pyrimidin-2-yl)picolinonitrile;

(S)-1-(4-((2-(2,4-dimethoxypyrimidin-5-yl)-7-methyl-4-morpholinothieno[3,2-d]pyrimidin-6-yl)methyl)piperazin-1-yl)-2-hydroxypropan-1-one;

(S)-1-(4-((2-(2-(dimethylamino)pyrimidin-5-yl)-7-methyl-4-morpholinothieno[3,2-d]pyrimidin-6-yl)methyl)piperazin-1-yl)-2-hydroxypropan-1-one;

1-((2-(2-aminopyrimidin-5-yl)-4-morpholinothieno[3,2-d]pyrimidin-6-yl)methyl)-4-(thiazol-2-yl)piperidin-4-ol;

4-(2-(2-methylpyrimidin-5-yl)-6-((4-(methylsulfonyl)piperazin-1-yl)methyl)thieno[2,3-d]pyrimidin-4-yl)morpholine;

N-methyl-5-(6-((4-(methylsulfonyl)piperazin-1-yl)methyl)-4-morpholinothieno[2,3-d]pyrimidin-2-yl)pyrimidin-2-amine;

4-(2-(2-methylpyrimidin-5-yl)-6-((4-(methylsulfonyl)piperazin-1-yl)methyl)thieno[3,2-d]pyrimidin-4-yl)morpholine;

5-(4-morpholino-6-((4-(thiophen-2-ylsulfonyl)piperazin-1-yl)methyl)thieno[2,3-d]pyrimidin-2-yl)pyrimidin-2-amine;

5-(6-((4-(cyclopropylsulfonyl)piperazin-1-yl)methyl)-4-morpholinothieno[2,3-d]pyrimidin-2-yl)pyrimidin-2-amine;

2-(1-((2-(2-aminopyrimidin-5-yl)-4-morpholinothieno[3,2-d]pyrimidin-6-yl)methyl)piperidin-4-ylsulfonyl)-N,N-dimethylacetamide;

5-(4-morpholino-6-((4-(thiazol-2-ylsulfonyl)piperidin-1-yl)methyl)thieno[3,2-d]pyrimidin-2-yl)pyrimidin-2-amine;

5-(6-((4-(methylsulfonylmethylsulfonyl)piperazin-1-yl)methyl)-4-morpholinothieno[3,2-d]pyrimidin-2-yl)pyrimidin-2-amine;

N-methyl-5-(6-((4-(methylsulfonyl)piperazin-1-yl)methyl)-4-morpholinothieno[3,2-d]pyrimidin-2-yl)pyrimidin-2-amine;

4-(6-((4-(methylsulfonyl)piperazin-1-yl)methyl)-4-morpholinothieno[3,2-d]pyrimidin-2-yl)pyridin-2-amine;

5-(6-(((1-isopropylpiperidin-4-yl)(methyl)amino)methyl)-4-morpholinothieno[3,2-d]pyrimidin-2-yl)pyrimidin-2-amine;

5-(6-(((2R,6S)-2,6-dimethyl-4-(methylsulfonyl)piperazin-1-yl)methyl)-7-methyl-4-morpholinothieno[3,2-d]pyrimidin-2-yl)pyrimidin-2-amine;

1-((2-(2-aminopyrimidin-5-yl)-4-morpholinothieno[3,2-d]pyrimidin-6-yl)methyl)-4-(4-chlorophenyl)piperidin-4-ol;

(S)-3-methyl-4-(6-((4-methylpiperazin-1-yl)methyl)-2-(pyrimidin-5-yl)thieno[3,2-d]pyrimidin-4-yl)morpholine;

(S)-5-(6-((methyl(1-methylpiperidin-4-yl)amino)methyl)-4-(3-methylmorpholino)thieno[2,3-d]pyrimidin-2-yl)pyrimidin-2-amine;

(S)-5-(4-(3-methylmorpholino)-6-((4-(methylsulfonyl)piperazin-1-yl)methyl)thieno[3,2-d]pyrimidin-2-yl)pyrimidin-2-amine;

(S)-1-(4-((2-(2-aminopyrimidin-5-yl)-4-(3-methylmorpholino)thieno[3,2-d]pyrimidin-6-yl)methyl)-1,4-diazepan-1-yl)ethanone;

5-(6-((methyl(pyridin-4-ylmethyl)amino)methyl)-4-morpholinothieno[3,2-d]pyrimidin-2-yl)pyrimidin-2-amine;

5-(6-((methyl(pyridin-3-ylmethyl)amino)methyl)-4-morpholinothieno[3,2-d]pyrimidin-2-yl)pyrimidin-2-amine;

5-(6-((methyl(pyridin-2-ylmethyl)amino)methyl)-4-morpholinothieno[3,2-d]pyrimidin-2-yl)pyrimidin-2-amine;

5-(6-((methyl((4-methylthiazol-2-yl)methyl)amino)methyl)-4-morpholinothieno[3,2-d]pyrimidin-2-yl)pyrimidin-2-amine; and 5-(6-((methyl((1-methyl-1H-imidazol-4-yl)methyl)amino)methyl)-4-morpholinothieno[3,2-d]pyrimidin-2-yl)pyrimidin-2-amine.

17. The method of to claim 1, further comprising administering a therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, or an agent for treating immunodeficiency disorders.

18. A method of therapeutically treating cancer in a mammal in need of such treatment which is comprised of administering to said mammal a therapeutically effective amount of (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one;
    wherein the cancer is selected from prostate cancer, non-small cell lung cancer, and breast cancer.

19. A method of therapeutically treating cancer in a mammal in need of such treatment which is comprised of administering to said mammal a therapeutically effective amount of a compound selected from (S)-1-(4-(((2-(2-aminopyrimidin-5-yl)-7-methyl-4-morpholinothieno[3,2-d]pyrimidin-6-yl)methyl)piperazin-1-yl)-2-hydroxypropan-1-one, and a stereoisomers, geometric isomers, tautomers, and pharmaceutically acceptable salts thereof;
    wherein the cancer is selected from prostate cancer, non-small cell lung cancer, and breast cancer.

20. A method of therapeutically treating cancer in a mammal in need of such treatment which is comprised of administering to said mammal a therapeutically effective amount of (S)-1-(4-(((2-(2-aminopyrimidin-5-yl)-7-methyl-4-morpholinothieno[3,2-d]pyrimidin-6-yl)methyl)piperazin-1-yl)-2-hydroxypropan-1-one, or a pharmaceutically acceptable salt thereof; wherein the cancer is selected from solid tumors of the breast, non-small cell lung cancer, and prostate cancer.

\* \* \* \* \*

UNITED STATES PATENT AND TRADEMARK OFFICE
CERTIFICATE OF CORRECTION

PATENT NO. : 8,383,620 B2
APPLICATION NO. : 12/978106
DATED : February 26, 2013
INVENTOR(S) : Bayliss et al.

It is certified that error appears in the above-identified patent and that said Letters Patent is hereby corrected as shown below:

In the Claims

In Column 330, Line 62 Claim 1:

Replace:

$-CH(OR^{10)R10}$

With:

$-CH(OR^{10})R^{10}$

In Column 346, Line 10 Claim 15:

Replace:

N,   1-dimethyl

With:

N,1-dimethyl

Signed and Sealed this
Twenty-second Day of October, 2013

Teresa Stanek Rea
*Deputy Director of the United States Patent and Trademark Office*

CERTIFICATE OF CORRECTION (continued)
U.S. Pat. No. 8,383,620 B2

In Column 348, Line 53, Claim 16:

Replace:

moipholinothieno

With:

morpholinothieno

In Column 354, Line 2, Claim 19:

Replace:

4-(((2-(

With:

4-((2-(

In Column 354, Line 12, Claim 20:

Replace:

4-(((2-(

With:

4-((2-(

UNITED STATES PATENT AND TRADEMARK OFFICE
CERTIFICATE OF CORRECTION

Page 1 of 1

PATENT NO. : 8,383,620 B2
APPLICATION NO. : 12/978106
DATED : February 26, 2013
INVENTOR(S) : Bayliss et al.

It is certified that error appears in the above-identified patent and that said Letters Patent is hereby corrected as shown below:

On the Title Page

In item (57) Abstract, Line 8:

Replace:

Formula Ia-d

With:

Formulas Ia-d

Signed and Sealed this
Seventh Day of July, 2015

Michelle K. Lee
*Director of the United States Patent and Trademark Office*